(12) United States Patent
Kim et al.

(10) Patent No.: US 9,856,243 B2
(45) Date of Patent: Jan. 2, 2018

(54) CONDENSED CYCLIC COMPOUND AND ORGANIC LIGHT-EMITTING DEVICE INCLUDING THE SAME

(71) Applicant: Samsung Display Co., Ltd., Yongin, Gyeonggi-Do (KR)

(72) Inventors: Haejin Kim, Yongin (KR); Sanghyun Han, Yongin (KR); Youngkook Kim, Yongin (KR); Jongwoo Kim, Yongin (KR); Seokhwan Hwang, Yongin (KR); Hyoungkun Kim, Yongin (KR)

(73) Assignee: Samsung Display Co., Ltd., Yongin, Gyeongi-Do (KR)

( * ) Notice: Subject to any disclaimer, the term of this patent is extended or adjusted under 35 U.S.C. 154(b) by 307 days.

(21) Appl. No.: 14/680,812

(22) Filed: Apr. 7, 2015

(65) Prior Publication Data
US 2016/0099423 A1 Apr. 7, 2016

(30) Foreign Application Priority Data
Oct. 6, 2014 (KR) .................. 10-2014-0134485

(51) Int. Cl.
| | | |
|---|---|---|
| C07D 409/12 | (2006.01) | |
| C07D 333/50 | (2006.01) | |
| C07D 409/14 | (2006.01) | |
| C07D 407/12 | (2006.01) | |
| C07D 307/77 | (2006.01) | |
| C09K 11/06 | (2006.01) | |
| H01L 51/00 | (2006.01) | |
| C07F 7/08 | (2006.01) | |
| H01L 51/50 | (2006.01) | |

(52) U.S. Cl.
CPC ......... *C07D 409/12* (2013.01); *C07D 307/77* (2013.01); *C07D 333/50* (2013.01); *C07D 407/12* (2013.01); *C07D 409/14* (2013.01); *C07F 7/0812* (2013.01); *C09K 11/06* (2013.01); *H01L 51/0061* (2013.01); *H01L 51/0073* (2013.01); *H01L 51/0074* (2013.01); *H01L 51/006* (2013.01); *H01L 51/5012* (2013.01); *H01L 51/5056* (2013.01)

(58) Field of Classification Search
CPC .. C07D 409/12; C07D 409/14; C07D 333/50; C07D 407/12; C07D 307/77; H01L 51/0061; H01L 51/0073; H01L 51/0074; H01L 51/5012; H01L 51/5056; H01L 51/006; C09K 11/06; C07F 7/0812
USPC ....................................... 428/690
See application file for complete search history.

(56) References Cited

U.S. PATENT DOCUMENTS

| 7,053,255 B2 | 5/2006 | Ikeda et al. |
| 7,233,019 B2 | 6/2007 | Ionkin et al. |
| 2005/0156164 A1 | 7/2005 | Sotoyama |
| 2007/0237984 A1 | 10/2007 | Matsuura et al. |
| 2011/0006289 A1 | 1/2011 | Mizuki et al. |
| 2011/0266526 A1 | 11/2011 | Ma et al. |
| 2012/0181520 A1* | 7/2012 | Kim ............ C07B 59/001 257/40 |
| 2013/0009137 A1* | 1/2013 | Brown ........... C08L 65/00 257/40 |
| 2013/0306958 A1 | 11/2013 | Ito et al. |
| 2014/0299851 A1 | 10/2014 | Takaku et al. |

FOREIGN PATENT DOCUMENTS

| DE | WO 2012045710 A1 * | 4/2012 | ......... C07D 307/77 |
| KR | 10-2006-0006760 A | 1/2006 | |
| KR | 10-2009-0111355 A | 10/2009 | |
| KR | 10-2010-0097182 A | 9/2010 | |
| KR | 10-2011-0077871 A | 7/2011 | |
| KR | 10-2013-0040133 A | 4/2013 | |
| KR | WO 2013055132 A2 * | 4/2013 | ............ C09K 11/06 |
| KR | 10-2013-0067274 A | 6/2013 | |
| KR | 10-2015-0145033 A | 12/2015 | |
| WO | WO 2012/045710 A1 | 4/2012 | |
| WO | WO 2012/070226 A1 | 5/2012 | |
| WO | WO 2013/006478 A1 | 1/2013 | |
| WO | WO 2013/055132 A2 | 4/2013 | |

OTHER PUBLICATIONS

Extended European Search Report dated Nov. 17, 2015, issued in corresponding EP Application No. 15188504.3.
Office Action dated Jan. 17, 2017, issued in corresponding KR Application No. 10-2014-0134485.

* cited by examiner

*Primary Examiner* — Michael M Bernshteyn
(74) *Attorney, Agent, or Firm* — Knobbe Martens Olson & Bear LLP

(57) ABSTRACT

Provided are a condensed cyclic compound of Formula 1 and an organic light-emitting device including the same

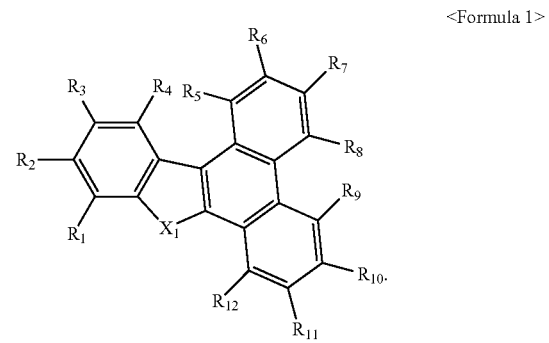
<Formula 1>

19 Claims, 4 Drawing Sheets

| 190 |
|---|
| 150 |
| 110 |

| 190 |
|-----|
| 150 |
| 110 |
| 210 |

| 220 |
|:---:|
| 190 |
| 150 |
| 110 |

| 220 |
|-----|
| 190 |
| 150 |
| 110 |
| 210 |

CONDENSED CYCLIC COMPOUND AND ORGANIC LIGHT-EMITTING DEVICE INCLUDING THE SAME

CROSS-REFERENCE TO RELATED APPLICATION

This application claims the benefit of Korean Patent Application No. 10-2014-0134485, filed on Oct. 6, 2014, in the Korean Intellectual Property Office, the disclosure of which is incorporated herein in its entirety by reference.

BACKGROUND

Field

One or more example embodiments relate to a condensed cyclic compound and an organic light-emitting device including the same.

Description of the Related Art

Organic light-emitting devices are self-emission devices that have wide viewing angles, high contrast ratios, short response times, and excellent brightness, driving voltage, and response speed characteristics, and produce multicolored images.

An organic light-emitting device may include a substrate and a first electrode on the substrate, and may have a structure of a hole transport region, an emission layer, an electron transport region, and a second electrode that are sequentially stacked in the stated order on the first electrode. Holes provided from the first electrode may move toward the emission layer through the hole transport region, and electrons provided from the second electrode may move toward the emission layer through the electron transport region. Carriers, such as holes and electrons, may be recombined in the emission layer to produce excitons. These excitons may change from an excited state to a ground state, thereby generating light.

SUMMARY

One or more example embodiments include a novel condensed cyclic compound and an organic light-emitting device including the same.

Additional aspects will be set forth in part in the description which follows and, in part, will be apparent from the description, or may be learned by practice of the presented embodiments.

According to one or more example embodiments, there is provided a condensed cyclic compound represented by Formula 1 below:

<Formula 1>

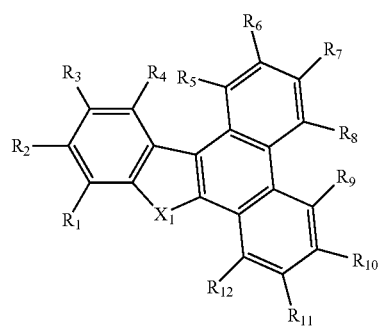

$X_1$ may be O or S;

$R_1$ to $R_{12}$ may be each independently selected from a group represented by Formula 2 below, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, and —$B(Q_4)(Q_5)$;

at least two of $R_1$ to $R_{12}$ may be each independently a group represented by Formula 2 below;

at least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, and —$B(Q_{14})(Q_{15})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), and —B($Q_{24}$)($Q_{25}$); and —Si($Q_{31}$)($Q_{32}$)($Q_{33}$) and —B($Q_{34}$)($Q_{35}$), wherein $Q_1$ to $Q_5$, $Q_{11}$ to $Q_{15}$, $Q_{21}$ to $Q_{25}$, and $Q_{31}$ to $Q_{35}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group;

stituted or unsubstituted monovalent non-aromatic condensed polycyclic group, and a substituted or unsubstituted monovalent non-aromatic condensed heteropolycyclic group;

According to one or more example embodiments, there is provided an organic light-emitting device including: a first electrode; a second electrode facing the first electrode; and an organic layer disposed between the first electrode and the second electrode and including an emission layer, wherein the organic layer includes at least one of the condensed cyclic compounds.

BRIEF DESCRIPTION OF THE DRAWINGS

These and/or other aspects will become apparent and more readily appreciated from the following description of the example embodiments, taken in conjunction with the accompanying drawings in which:

FIGS. 1 to 4 each illustrate a schematic view of an organic light-emitting according to an embodiment.

DETAILED DESCRIPTION

Reference will now be made in detail to example embodiments, examples of which are illustrated in the accompanying drawings, wherein like reference numerals refer to like elements throughout. In this regard, the present example embodiments may have different forms and should not be construed as being limited to the descriptions set forth herein. Accordingly, the example embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

There is provided a condensed cyclic compound represented by Formula 1 below:

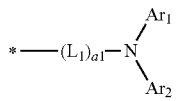

<Formula 2>

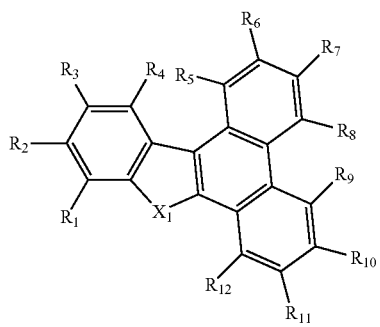

<Formula 1>

$L_1$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 may be selected from 0, 1, 2, and 3, and when a1 is 2 or more, 2 or more $L_1$s may be identical to or different from each other;

$Ar_1$ and $Ar_2$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a sub- In Formula 1, $X_1$ may be O or S. In an embodiment, $X_1$ in Formula 1 may be O, but $X_1$ is not limited thereto.

In Formula 1, $R_1$ to $R_{12}$ may be each independently selected from a group represented by Formula 2 below, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), and —B($Q_4$)($Q_5$).

In Formula 1, at least two of $R_1$ to $R_{12}$ may be each independently a group represented by Formula 2 below:

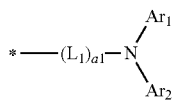

<Formula 2>

In Formula 2, $L_1$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

For example, $L_1$ in Formula 2 may be selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.
For example, $L_1$ in Formula 2 may be selected from groups represented by Formulae 3-1 to 3-35 below:
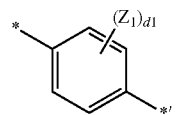
Formula 3-1
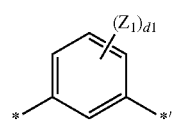
Formula 3-2
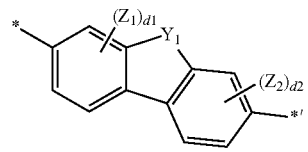
Formula 3-3
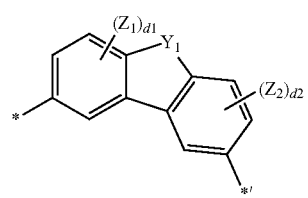
Formula 3-4
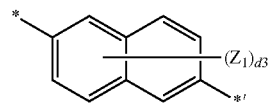
Formula 3-5
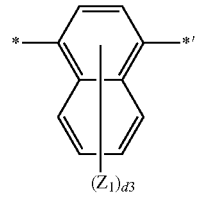
Formula 3-6
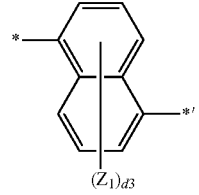
Formula 3-7
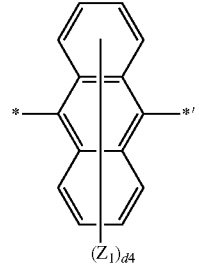
Formula 3-8
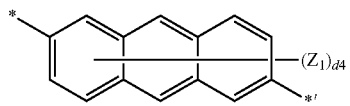
Formula 3-9
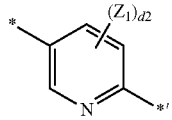
Formula 3-10
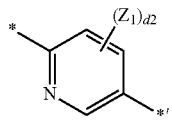
Formula 3-11
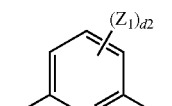
Formula 3-12
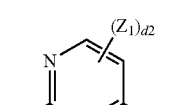
Formula 3-13
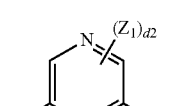
Formula 3-14
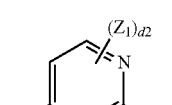
Formula 3-15
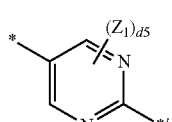
Formula 3-16
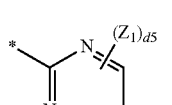
Formula 3-17
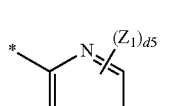
Formula 3-18
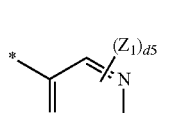
Formula 3-19
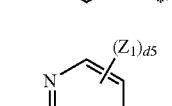
Formula 3-20

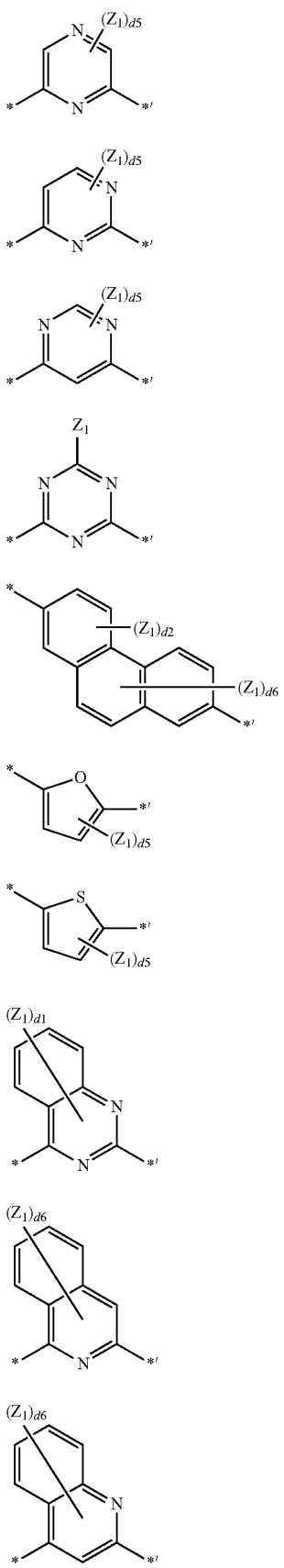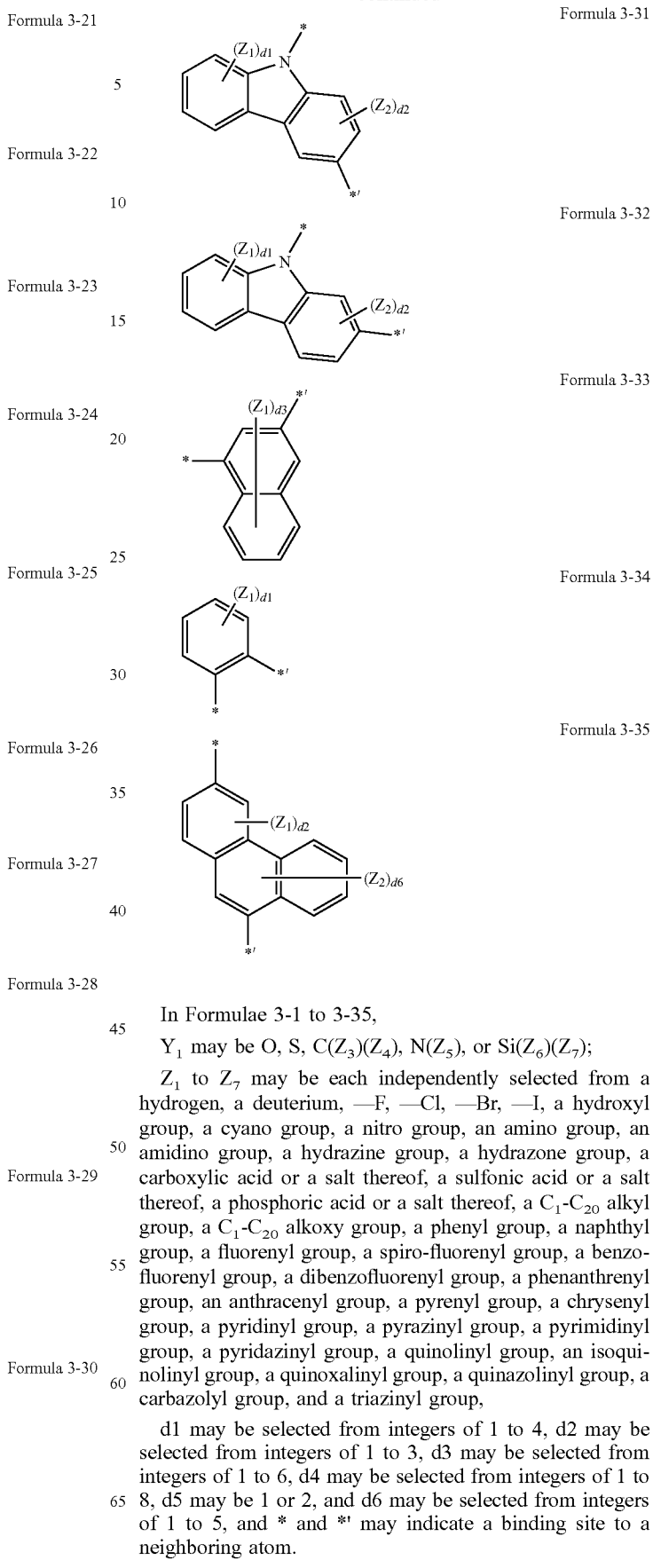

In Formulae 3-1 to 3-35, $Y_1$ may be O, S, $C(Z_3)(Z_4)$, $N(Z_5)$, or $Si(Z_6)(Z_7)$;

$Z_1$ to $Z_7$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, d1 may be selected from integers of 1 to 4, d2 may be selected from integers of 1 to 3, d3 may be selected from integers of 1 to 6, d4 may be selected from integers of 1 to 8, d5 may be 1 or 2, and d6 may be selected from integers of 1 to 5, and * and *' may indicate a binding site to a neighboring atom.

For example, L₁ in Formula 2 may be selected from a phenylene group, a naphthylene group, a pyridinylene group, a dibenzofuranylene group, and a dibenzothiophenylene group; and a phenylene group, a naphthylene group, a pyridinylene group, a dibenzofuranylene group, and a dibenzothiophenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a phenyl group, a naphthyl group, a pyridinyl group, a pyrimidinyl group, and a triazinyl group, but L₁ is not limited thereto.

In an embodiment, L₁ in Formula 2 may be selected from groups represented by Formulae 4-1 to 4-28 below, but L₁ is not limited thereto:

Formula 4-1

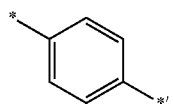

Formula 4-2

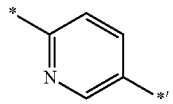

Formula 4-3

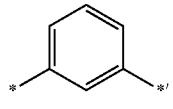

Formula 4-4

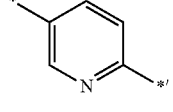

Formula 4-5

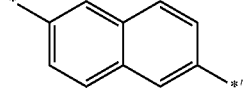

Formula 4-6

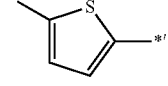

Formula 4-7

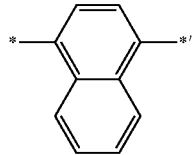

Formula 4-8

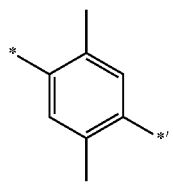

-continued

Formula 4-9

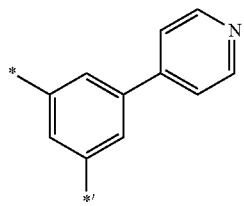

Formula 4-10

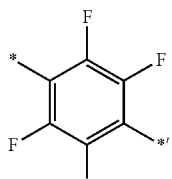

Formula 4-11

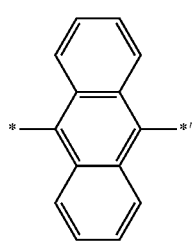

Formula 4-12

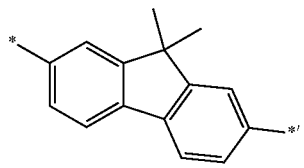

Formula 4-13

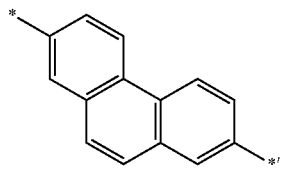

Formula 4-14

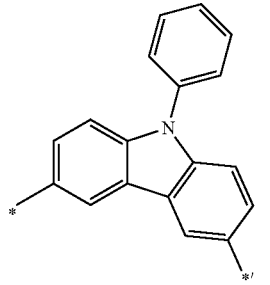

Formula 4-15

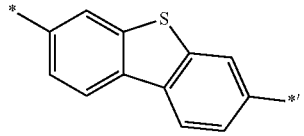

Formula 4-16

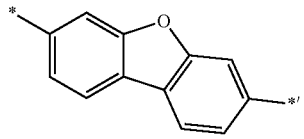

-continued

Formula 4-17 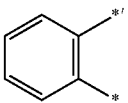

Formula 4-18

Formula 4-19 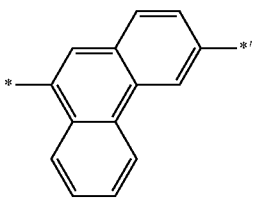

Formula 4-20

Formula 4-21 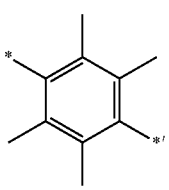

Formula 4-22

Formula 4-23

Formula 4-24

Formula 4-25

Formula 4-26

Formula 4-27

Formula 4-28

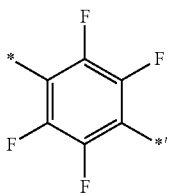
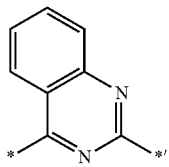
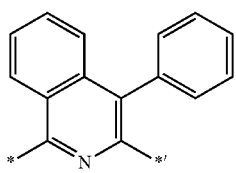
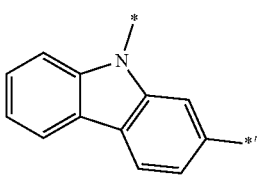
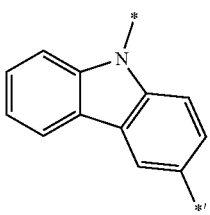
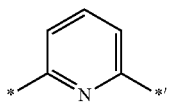
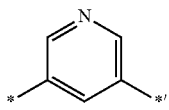
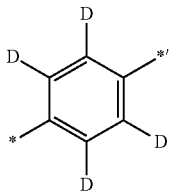
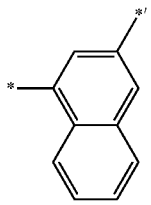

In Formulae 4-1 and 4-28, * and *' may indicate a binding site to a neighboring atom.

In Formula 2, a1 may be selected from 0, 1, 2, and 3, and may indicate the number of $L_1$ in Formula 2. When a1 is 2 or more, 2 or more $L_1$s may be identical to or different from each other. When a1 is 0, -$(L_1)_{a1}$- is a single bond. In some embodiments, a1 may be 0, 1, or 2. In some other embodiments, a1 may be 0 or 1.

In Formula 2, $Ar_1$ and $Ar_2$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, $Ar_1$ and $Ar_2$ in Formula 2 may be each independently selected from
a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ may be each independently selected from a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzooxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group.

For example, $Ar_1$ and $Ar_2$ in Formula 2 may be each independently selected from, but not limited to, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, and an imidazopyrimidinyl group; and a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$), wherein $Q_{31}$ to $Q_{33}$ may be each independently selected from a $C_1$-$C_{10}$ alkyl group, a $C_1$-$C_{10}$ alkoxy group, a phenyl group, and a naphthyl group.

In Formula 2, $Ar_1$ and $Ar_2$ may be each independently selected from a phenyl group, a naphthyl group, a fluorenyl group, a phenanthrenyl group, a pyridinyl group, a pyrimidinyl group, a triazinyl group, a dibenzofuranyl group, and a dibenzothiophenyl group; and a phenyl group, a naphthyl group, a fluorenyl group, a phenanthrenyl group, a pyridinyl group, a pyrimidinyl group, a triazinyl group, a dibenzofuranyl group, and a dibenzothiophenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a phenanthrenyl group, a pyridinyl group, a pyrimidinyl group, a triazinyl group, a dibenzofuranyl group, a dibenzothiophenyl group, and —Si($Q_{31}$)($Q_{32}$)($Q_{33}$), wherein $Q_{31}$ to $Q_{33}$ may be each independently selected from a $C_1$-$C_{10}$ alkyl group, a $C_1$-$C_{10}$ alkoxy group, a phenyl group, and a naphthyl group.

In Formula 1, $R_1$ to $R_{12}$ may be each independently selected from, but not limited to, a group represented by Formula 2, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, and an imidazopyrimidinyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a spirofluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may be each independently selected from a $C_1$-$C_{10}$ alkyl group, a $C_1$-$C_{10}$ alkoxy group, a phenyl group, and a naphthyl group.

For example, $R_1$ to $R_{12}$ in Formula 1 may be each independently selected from, but not limited to, a group represented by Formula 2, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, and a $C_1$-$C_{10}$ alkoxy group;

a phenyl group, a naphthyl group, a pyridinyl group, a pyrimidinyl group, and a triazinyl group;

a phenyl group, a naphthyl group, a pyridinyl group, a pyrimidinyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, and —Si($Q_{31}$)($Q_{32}$)($Q_{33}$); and —Si($Q_1$)($Q_2$)($Q_3$), Wherein $Q_1$ to $Q_3$ and $Q_{31}$ to $Q_{33}$ may be each independently selected from a $C_1$-$C_{10}$ alkyl group, a $C_1$-$C_{10}$ alkoxy group, a phenyl group, and a naphthyl group.

In an embodiment, in Formulae 1 and 2,

Ar₁ and Ar₂ may be each independently selected from groups represented by Formulae 5-1 to 5-43 below, and $R_1$ to $R_{12}$ may be each independently selected from a group represented by Formula 2, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_1$)($Q_2$)($Q_3$), and groups represented by Formulae 5-1 to 5-43 below, wherein $Q_1$ to $Q_3$ may be each independently selected from a $C_1$-$C_{10}$ alkyl group, a $C_1$-$C_{10}$ alkoxy group, a phenyl group, and a naphthyl group:

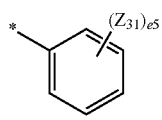
Formula 5-1

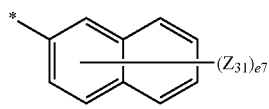
Formula 5-2

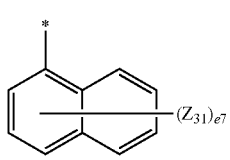
Formula 5-3

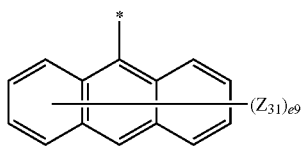
Formula 5-4

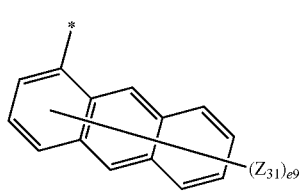
Formula 5-5

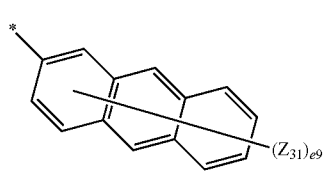
Formula 5-6

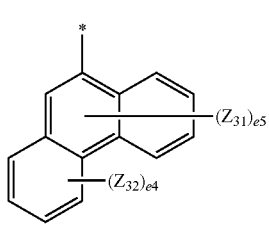
Formula 5-7

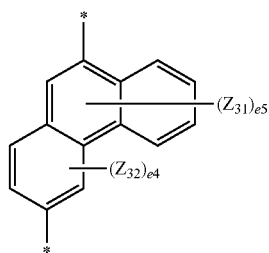
Formula 5-8

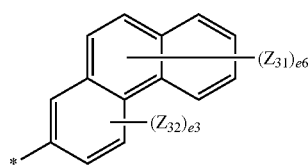
Formula 5-9

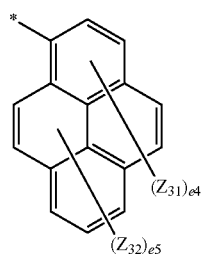
Formula 5-10

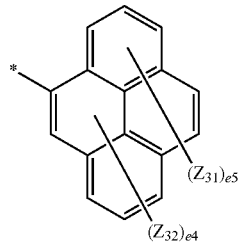
Formula 5-11

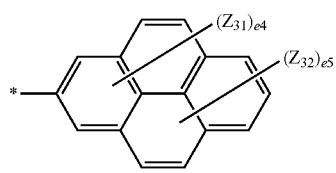
Formula 5-12

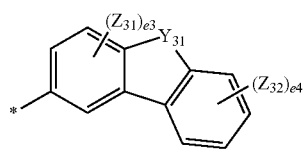
Formula 5-13

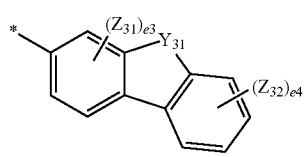
Formula 5-14

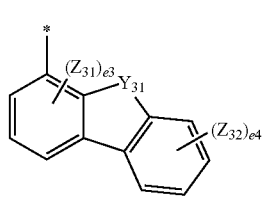
Formula 5-15

-continued
Formula 5-16
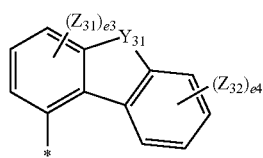
Formula 5-17
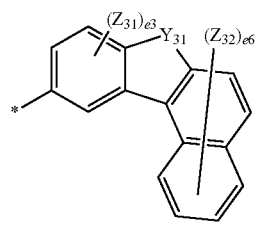
Formula 5-18
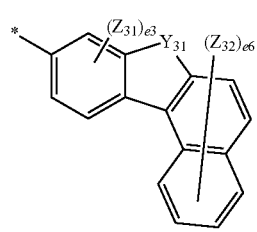
Formula 5-19
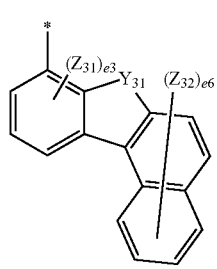
Formula 5-20
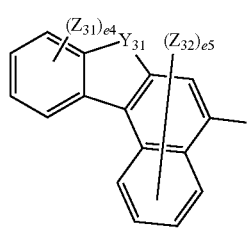
Formula 5-21
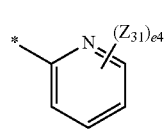
Formula 5-22
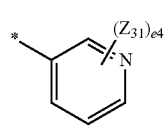
Formula 5-23
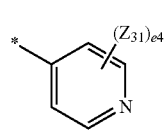
Formula 5-24
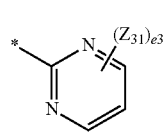
-continued
Formula 5-25
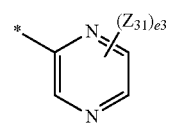
Formula 5-26
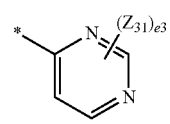
Formula 5-27
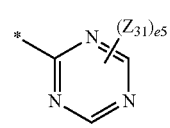
Formula 5-28
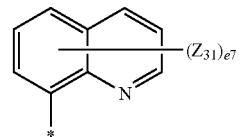
Formual 5-29
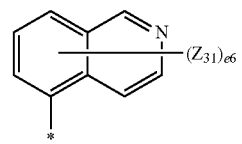
Formula 5-30
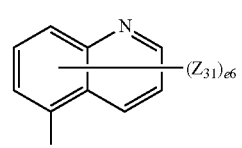
Formula 5-31
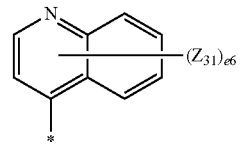
Formula 5-32
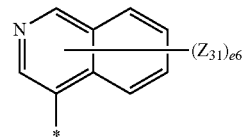
Formula 5-33
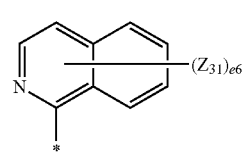
Formula 5-34
Formula 5-35

-continued

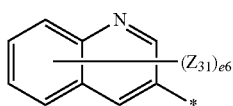
Formula 5-36

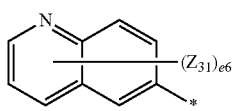
Formula 5-37

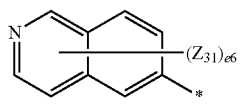
Formula 5-38

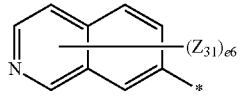
Formula 5-39

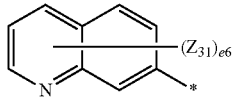
Formula 5-40

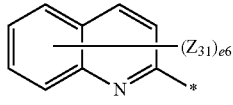
Formula 5-41

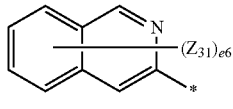
Formula 5-42

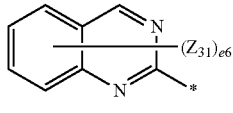
Formula 5-43

In Formulae 5-1 to 5-43, $Y_{31}$ may be O, S, $C(Z_{33})(Z_{34})$, $N(Z_{35})$, or $Si(Z_{36})(Z_{37})$;

$Z_{31}$ to $Z_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, e3 may be selected from integers of 1 to 3, e4 may be selected from integers of 1 to 4, e5 may be selected from integers of 1 to 5, e6 may be selected from integers of 1 to 6, e7 may be selected from integers of 1 to 7, e8 may be selected from integers of 1 to 8, and e9 may be selected from integers of 1 to 9, and * may indicate a bonding site to a neighboring atom.

In another embodiment, in Formulae 1 and 2, $Ar_1$ and $Ar_2$ may be each independently selected from groups represented by Formulae 6-1 to 6-41 below, and $R_1$ to $R_{12}$ may be each independently a group represented by Formula 2, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —$Si(Q_1)(Q_2)(Q_3)$, a phenyl group, a naphthyl group, a pyridinyl group, a pyrimidinyl group, and a triazinyl group, wherein $Q_1$ to $Q_3$ may be each independently selected from a $C_1$-$C_{10}$ alkyl group, a $C_1$-$C_{10}$ alkoxy group, a phenyl group, and a naphthyl group:

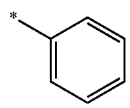
Formula 6-1

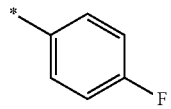
Formula 6-2

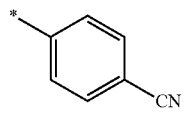
Formula 6-3

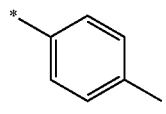
Formula 6-4

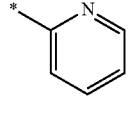
Formula 6-5

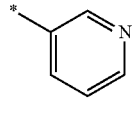
Formula 6-6

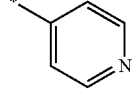
Formula 6-7

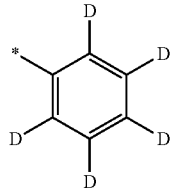
Formula 6-8

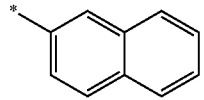
Formula 6-9

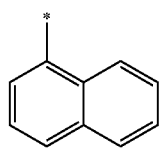
Formula 6-10

-continued
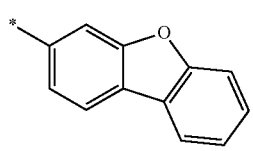
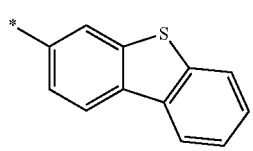
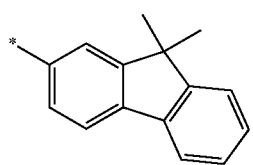
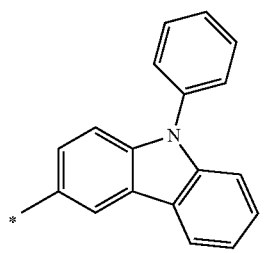
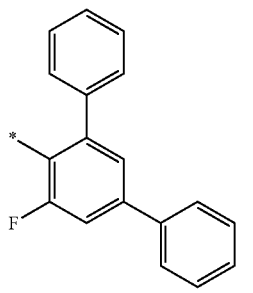
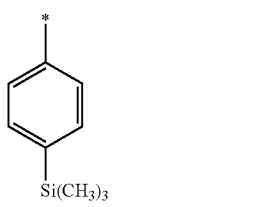
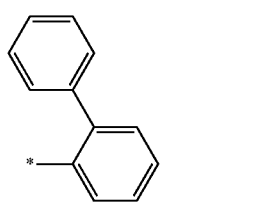
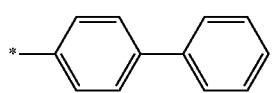
-continued
Formula 6-11
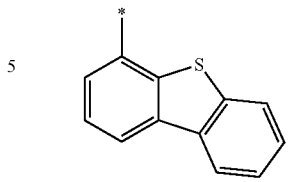
Formula 6-12
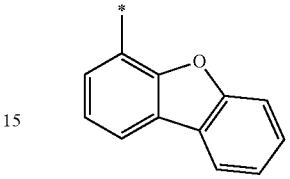
Formula 6-13
Formula 6-14
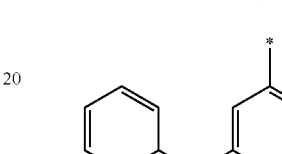
Formula 6-15
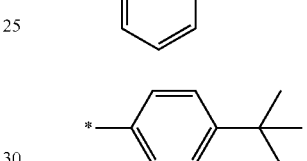
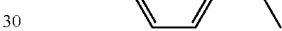
Formula 6-16
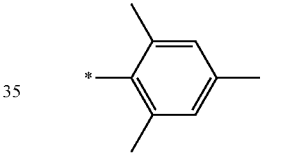
Formula 6-17
Formula 6-18
Formula 6-19
Formula 6-20
Formula 6-21
Formula 6-22
Formula 6-23
Formula 6-24
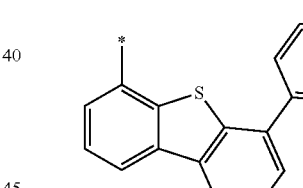
Formula 6-25
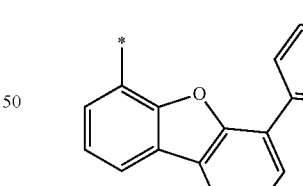
Formula 6-26
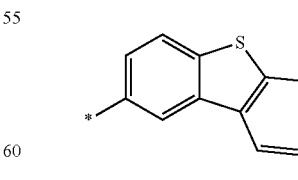
Formula 6-27
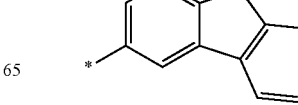

Formula 6-28
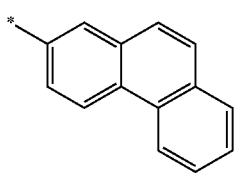

Formula 6-29
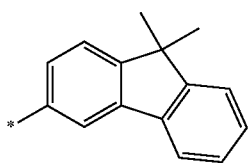

Formula 6-30
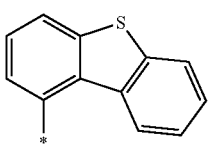

Formula 6-31
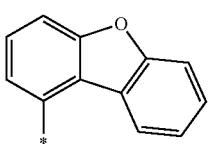

Formula 6-32
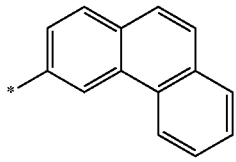

Formula 6-33
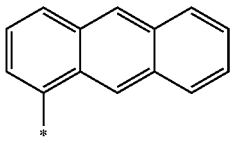

Formula 6-34
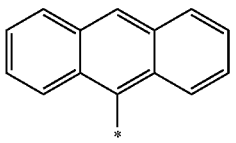

Formula 6-35
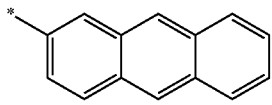

Formula 6-36
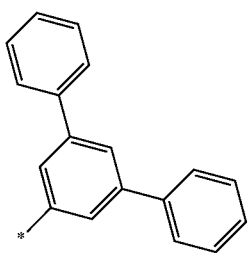

Formula 6-37
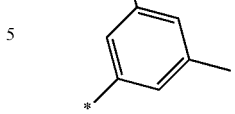

Formula 6-38
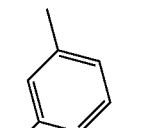

Formula 6-39
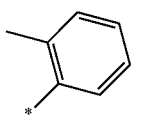

Formula 6-40
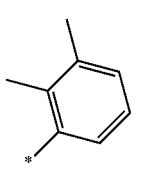

Formula 6-41
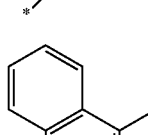

In Formulae 6-1 to 6-41, * may indicate a binding site to a neighboring atom.

In Formula 1, $R_5$ may not be a hydrogen.

In Formula 1, $R_5$ may be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group, but $R_5$ is not limited thereto.

In Formula 1, any two substituents of $R_1$ to $R_{12}$ may be each independently a group represented by Formula 2.

For example, the condensed cyclic compound of Formula 1 may be represented by one of Formulae 1-1 to 1-4 below:

<Formula 1-1>

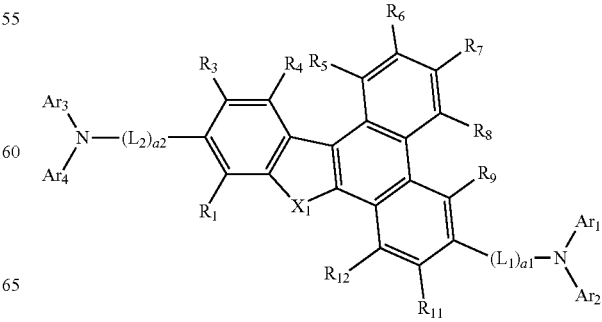

-continued

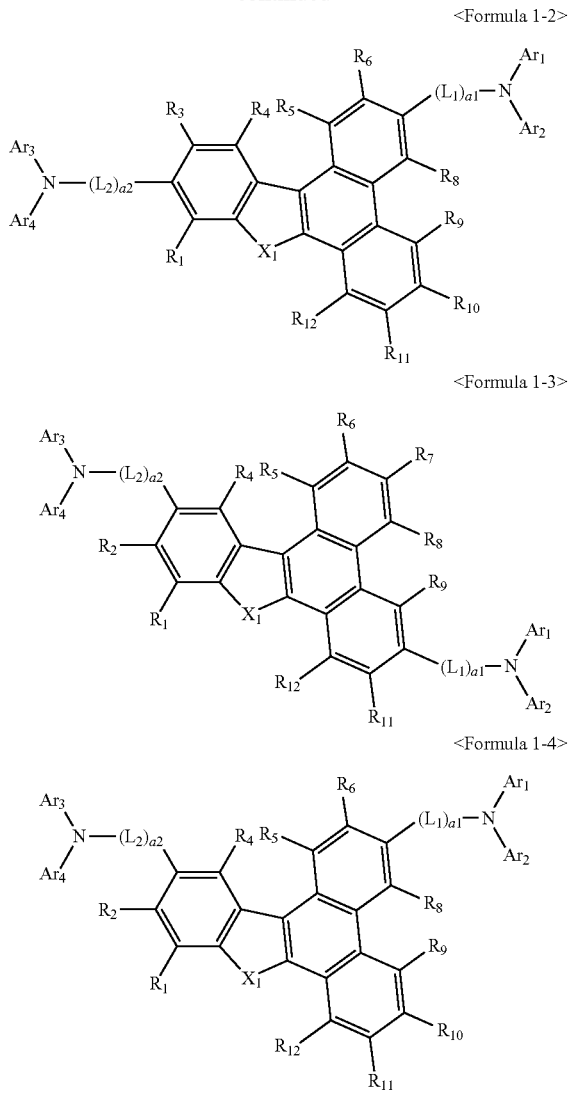

<Formula 1-2>

<Formula 1-3>

<Formula 1-4>

In Formulae 1-1 to 1-4, $X_1$, $L_1$, a1, $Ar_1$, $Ar_2$, and $R_1$ to $R_{12}$ may be understood by referring to the description provided herein, and $L_2$, $a_2$, $Ar_3$, and $Ar_4$ may be each referred to the description provided in connection with $L_1$, a1, $Ar_1$, and $Ar_2$.

In an embodiment, in Formulae 1-1 to 1-4,
a1 and a2 may be both 0;
a1 may be 0, and a2 may be 1 or 2;
a1 may be 1 or 2, and a2 may be 0;
a1 and a2 may be both 1;
a1 may be 1, and a2 may be 2;
a1 may be 2, and a2 may be 1; or
a1 and a2 may be both 2.

In another embodiment, in Formulae 1-1 to 1-4,
a1 and a2 may be both 0;
a1 may be 0, and a2 may be 1;
a1 may be 1, and a2 may be 0; or
a1 and a2 may be both 1, but a1 and a2 are not limited thereto.

In an embodiment, in Formulae 1-1 to 1-4,
$Ar_1=Ar_2=Ar_3=Ar_4$;
$Ar_1=Ar_3$, $Ar_2=Ar_4$, and $Ar_2 \neq Ar_3$;
$Ar_1=Ar_3$, $Ar_2 \neq Ar_4$, and $Ar_2 \neq Ar_3$; or
$Ar_1 \neq Ar_2 \neq Ar_3 \neq Ar_4$.

In an embodiment, in Formulae 1-1 to 1-4,
$R_1$ to $R_{12}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group, $L_1$ and $L_2$ may be each independently selected from groups represented by Formulae 3-1 to 3-35, a1 and a2 may be each independently 0, 1, or 2, and $Ar_1$ to $Ar_4$ may be each independently selected from groups represented by Formulae 5-1 to 5-43.

In another embodiment, in Formulae 1-1 to 1-4,
$R_1$ to $R_4$ and $R_6$ to $R_{12}$ may be a hydrogen, $R_5$ may be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group, $L_1$ and $L_2$ may be each independently selected from groups represented by Formulae 4-1 to 4-28, a1 and a2 may be each independently 0 or 1, and $Ar_1$ to $Ar_4$ may be each independently selected from groups represented by Formulae 6-1 to 6-41, but they are not limited thereto.

In another embodiment, the condensed cyclic compound of Formula 1 may be represented by one of Formulae 1-1(1) to 1-1(4) below, but is not limited thereto:

<Formula 1-1(1)>

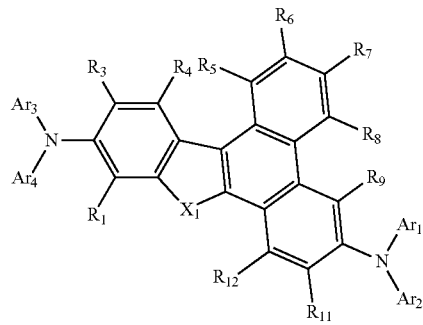

<Formula 1-1(2)>

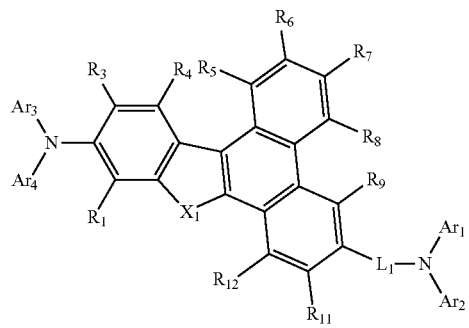

<Formula 1-1-(3)>

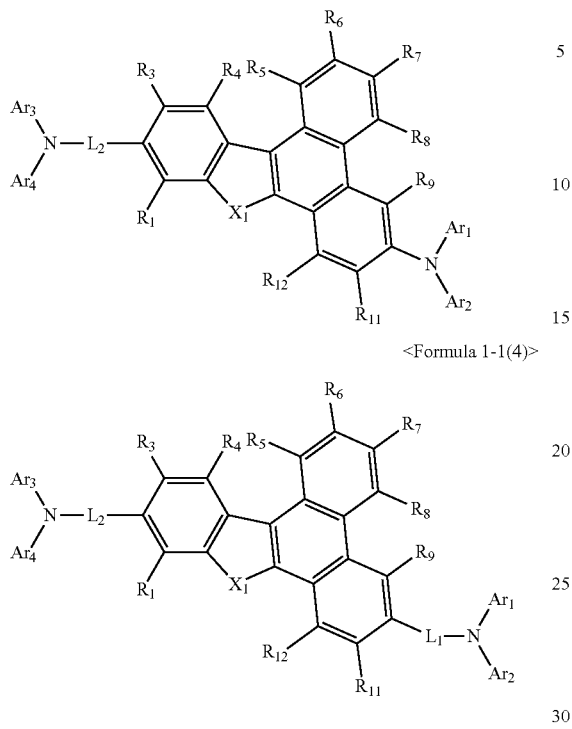

<Formula 1-1(4)>

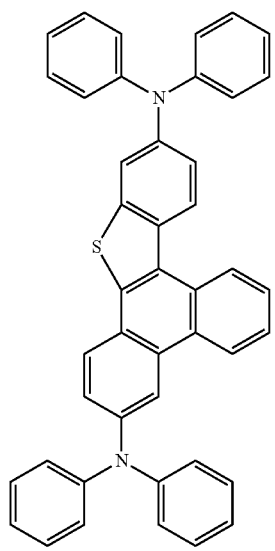

In Formulae 1-1(1) to 1-1(4), $X_1$, $L_1$, a1, $Ar_1$, $Ar_2$, $R_1$, $R_3$, $R_5$ to $R_7$, and $R_9$ to $R_{12}$ may be understood by referring to the description provided herein, and $L_2$, $a_2$, $Ar_3$, and $Ar_4$ may be each referred to the description provided in connection with $L_1$, a1, $Ar_1$, and $Ar_2$.

In an embodiment, $R_5$ in Formula 1 may not be a hydrogen. For example, $R_5$ in Formula 1 may be selected from a $C_1$-$C_{10}$ alkyl group, but is not limited thereto.

For example, the condensed cyclic compound of Formula 1 may be one of Compounds 1 to 248 and 1A to 249A below, but is not limited thereto:

1

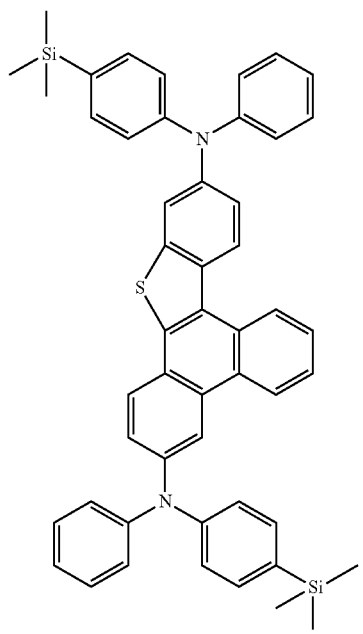

2

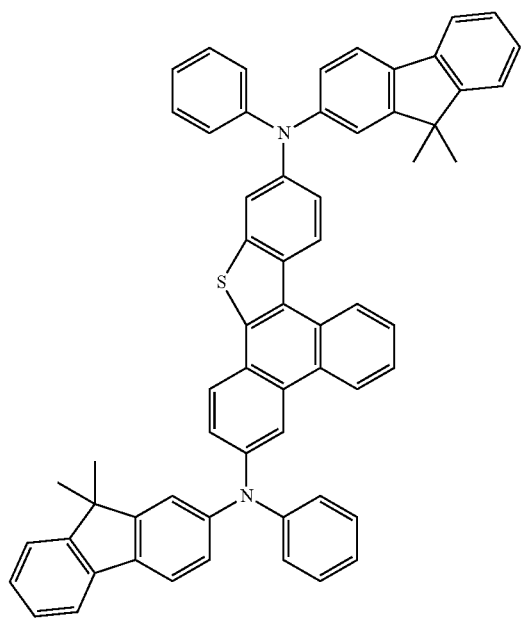

3

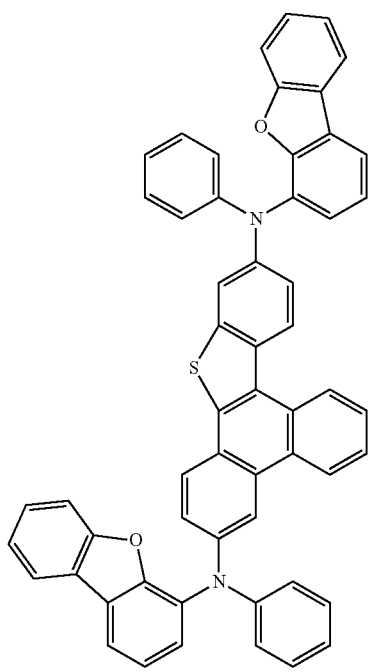
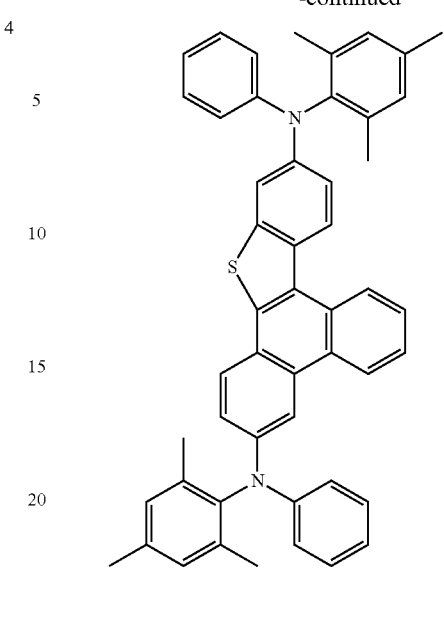
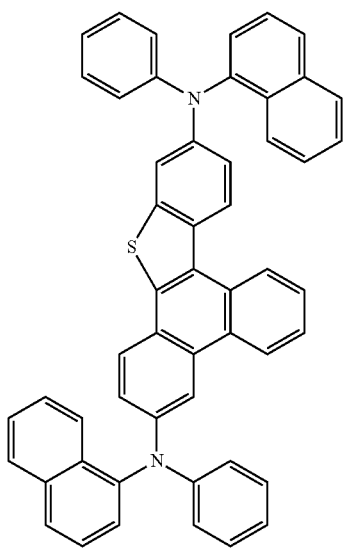
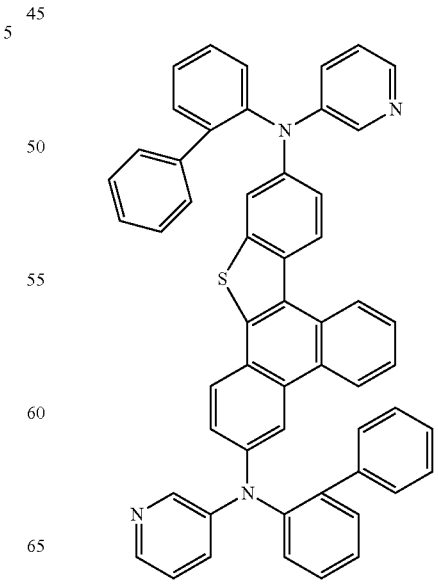

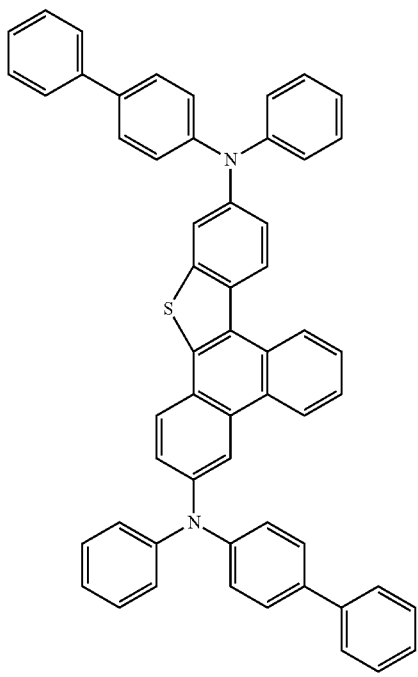
8
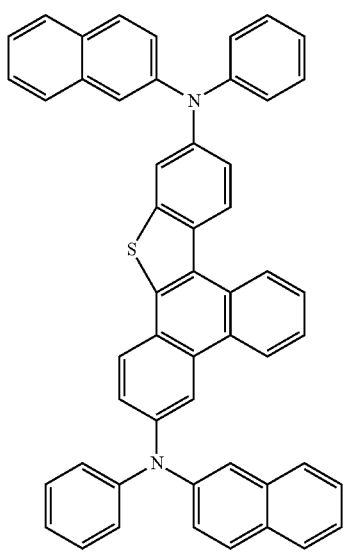
9
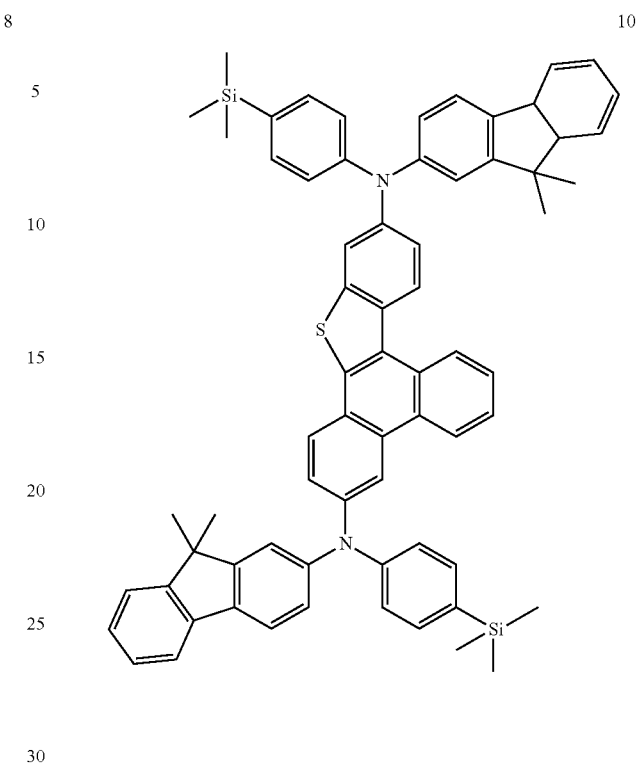
10
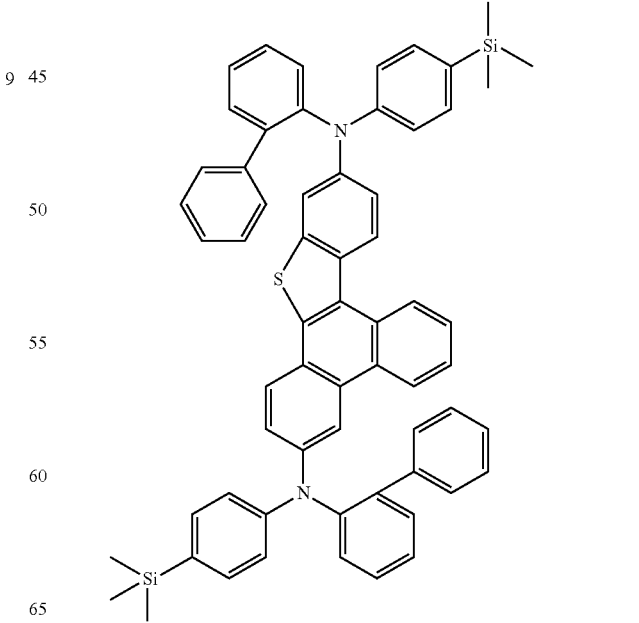
11

-continued
12
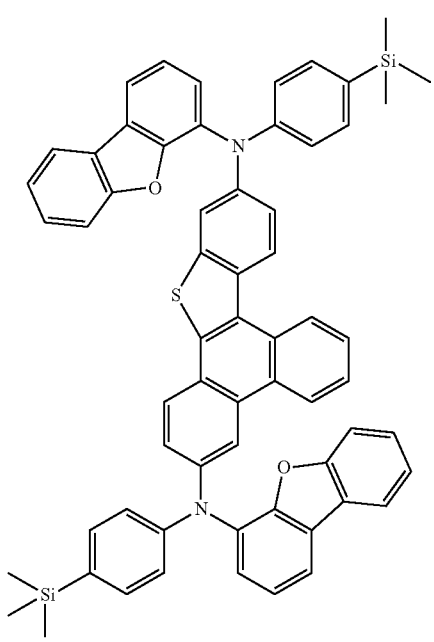
13
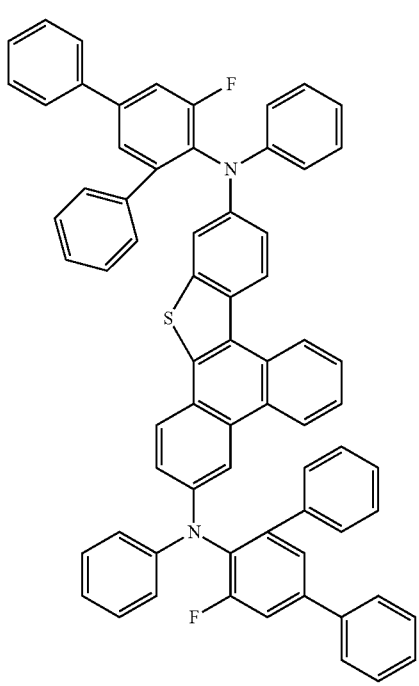
-continued
14
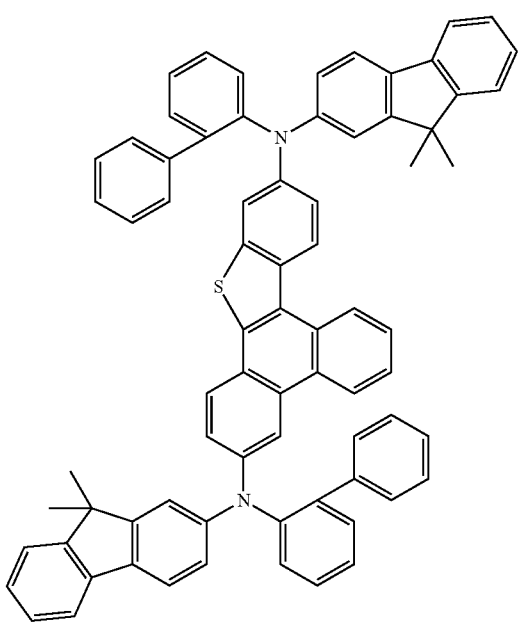
15
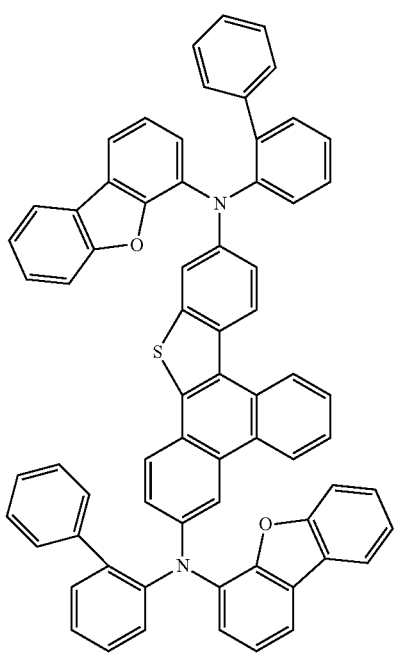

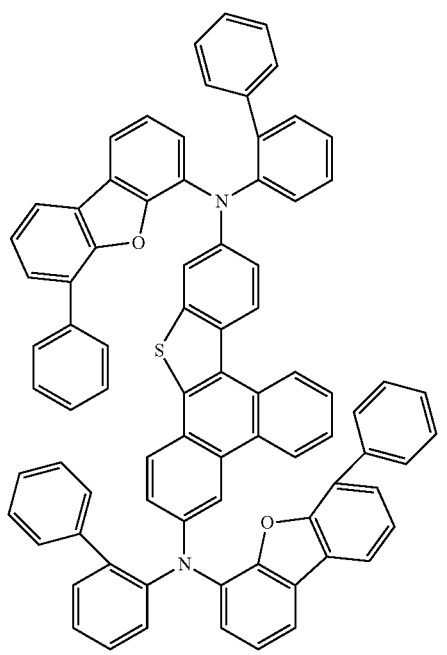
16
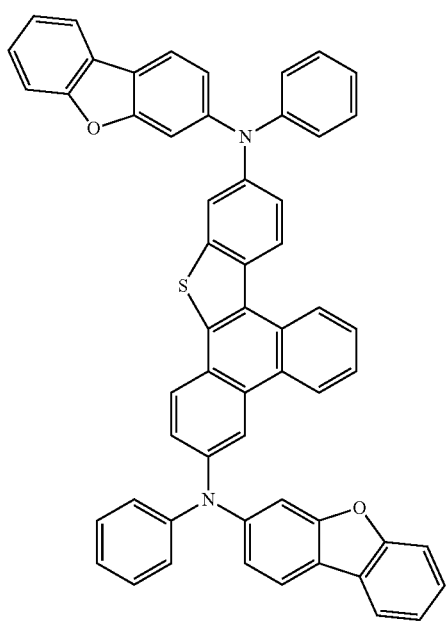
17
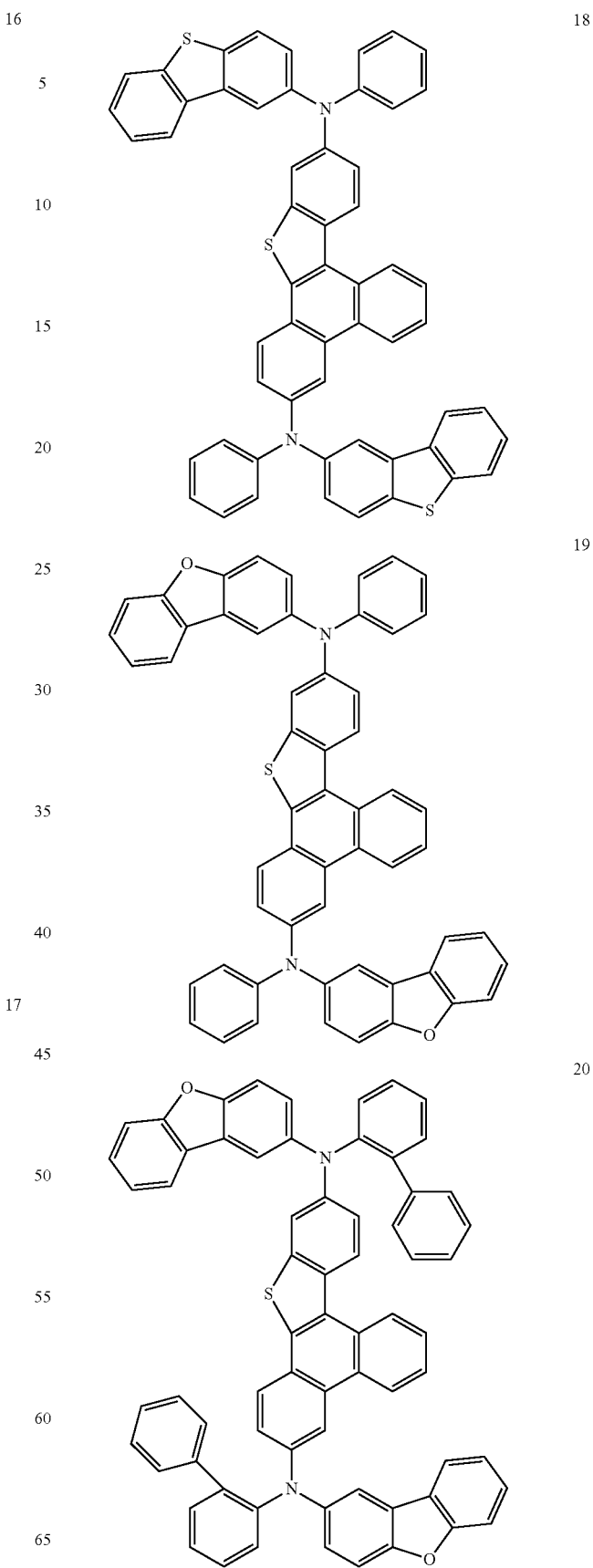

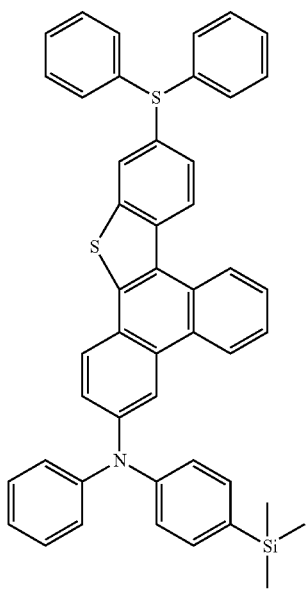
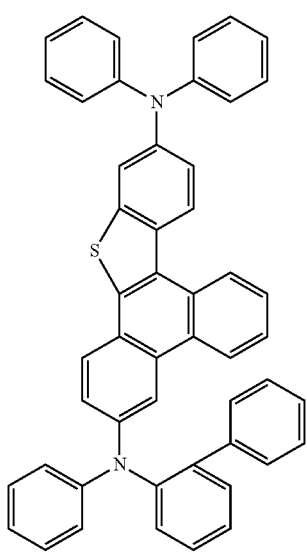
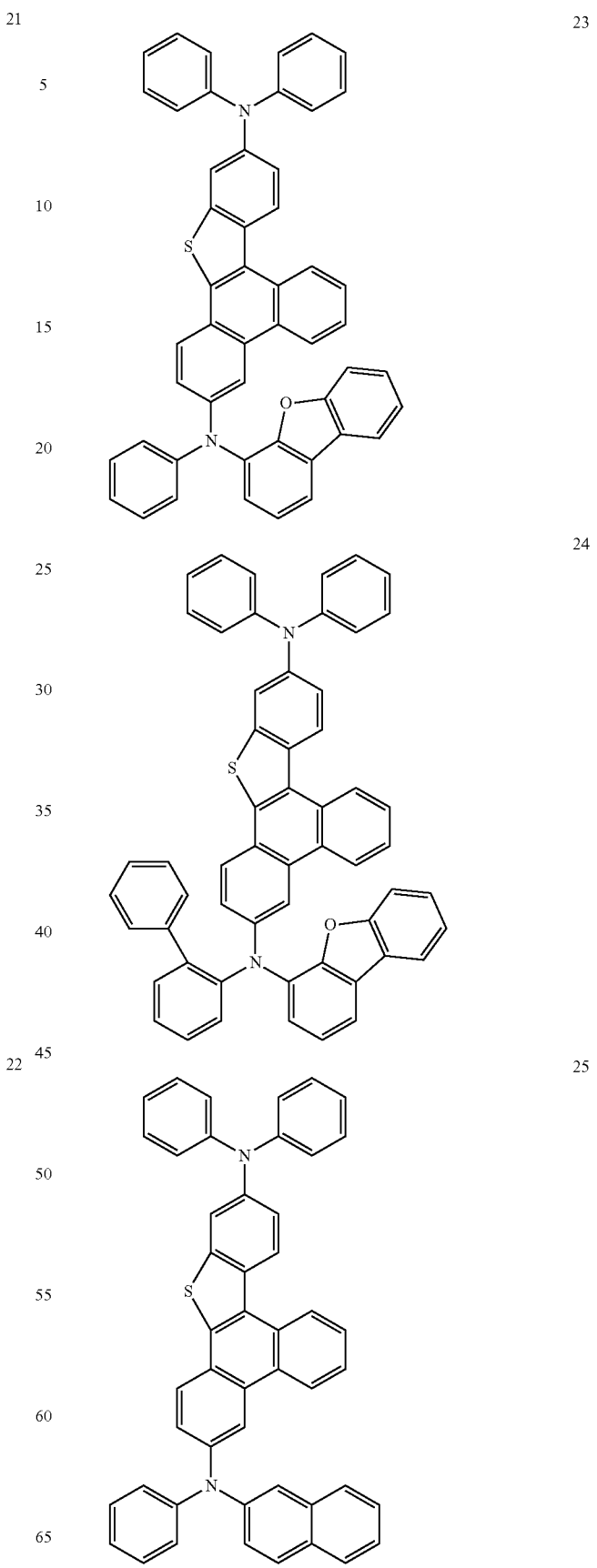

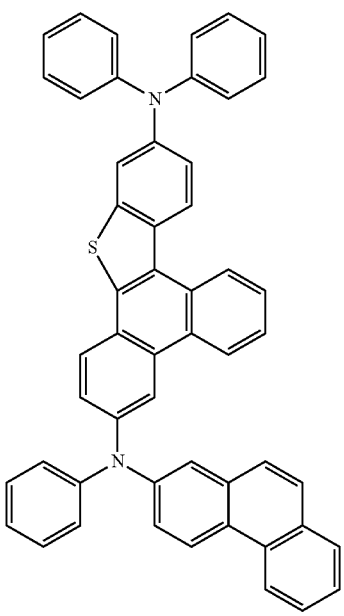
26
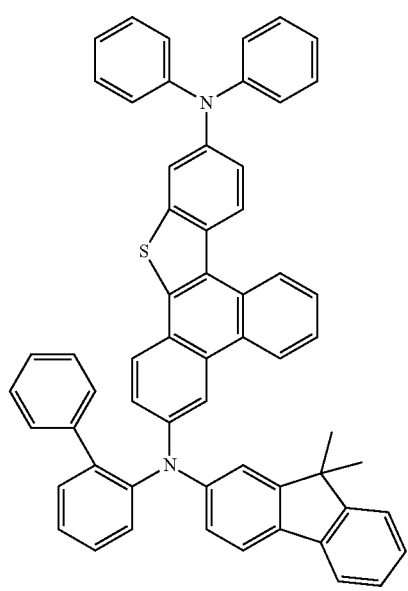
28
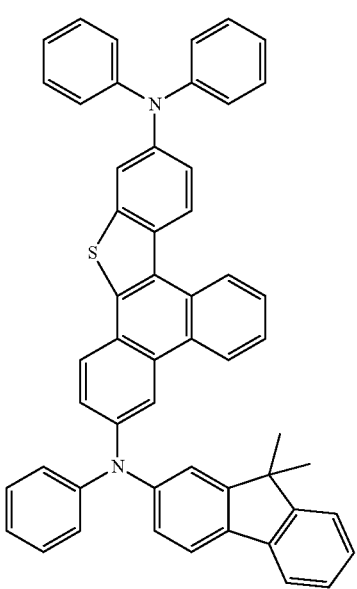
27
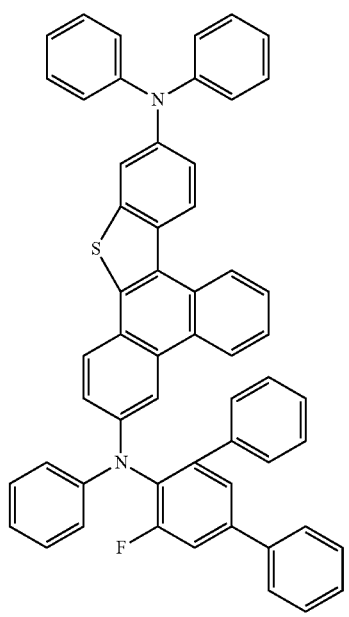
29

30
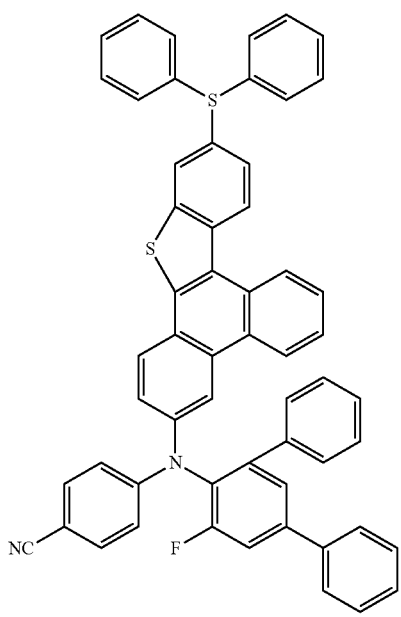
32
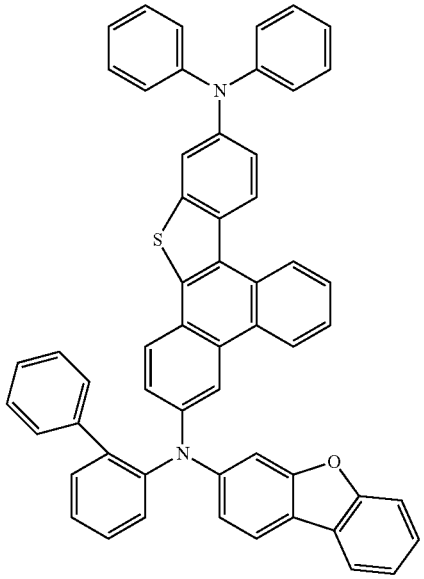
31
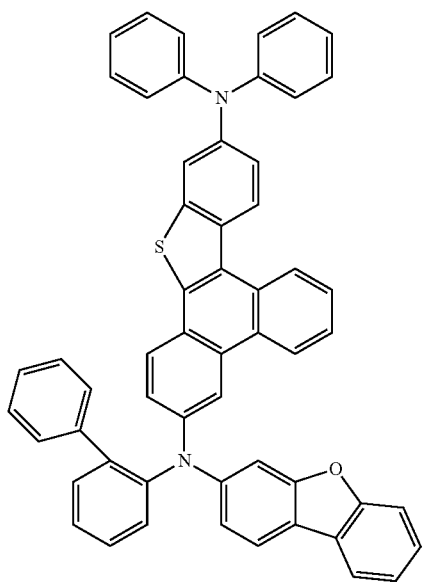
33
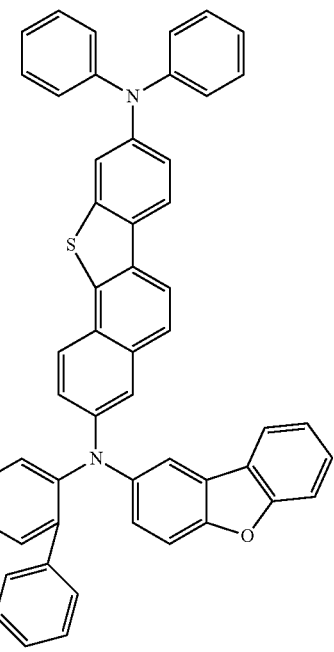

34
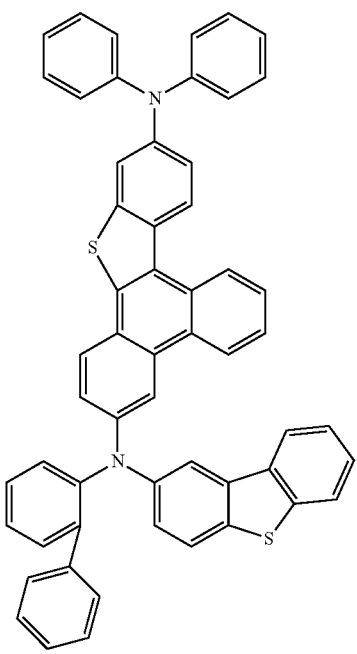
35
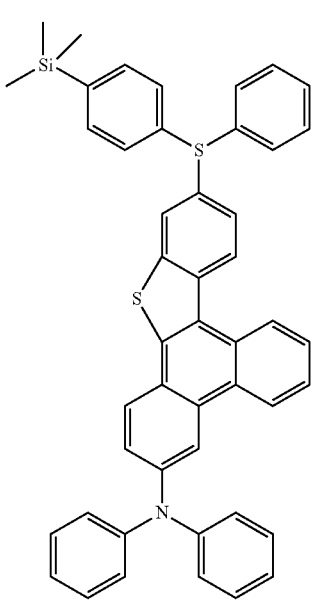
36
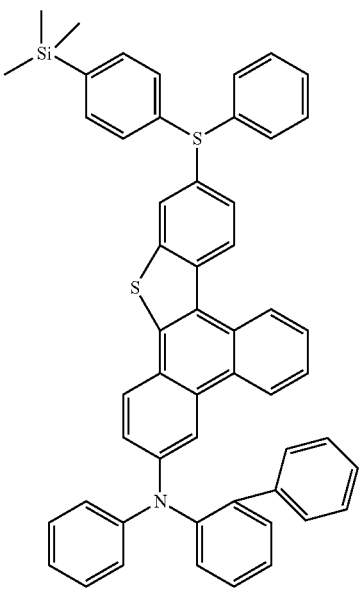
37
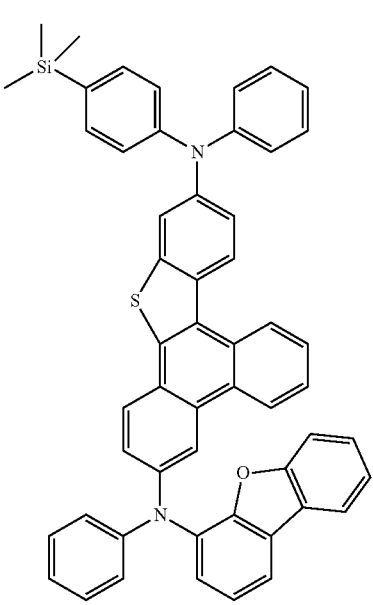

38
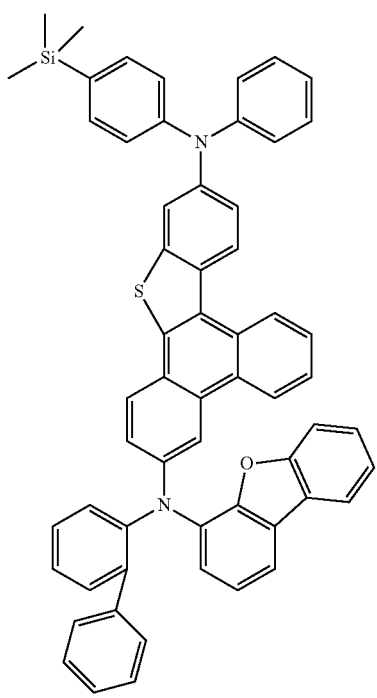
39
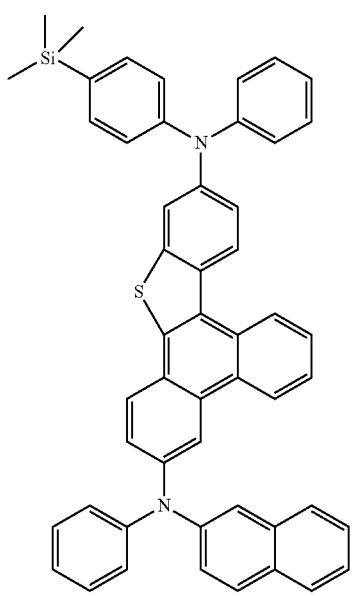
40
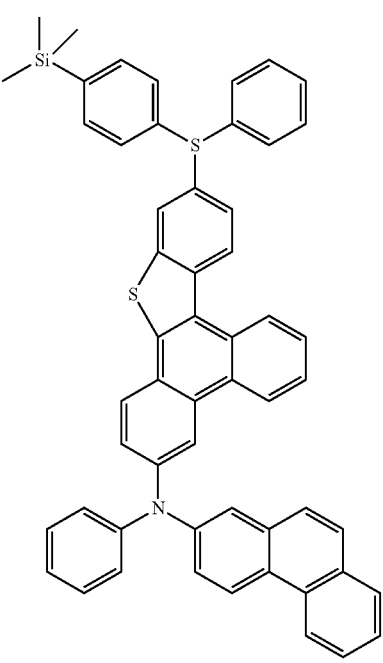
41
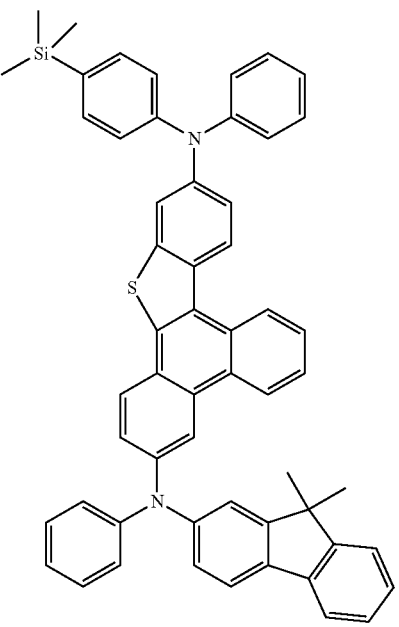

42
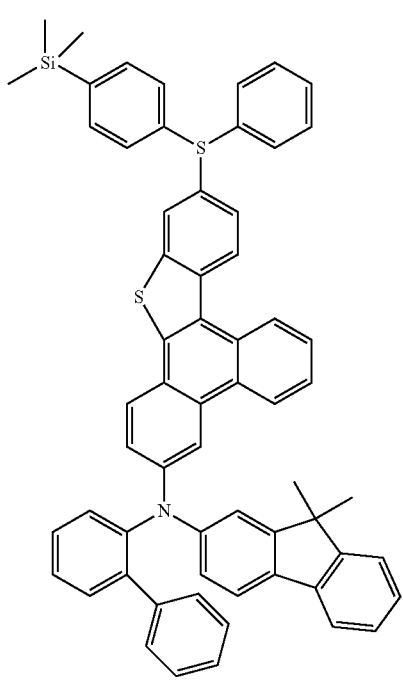
43
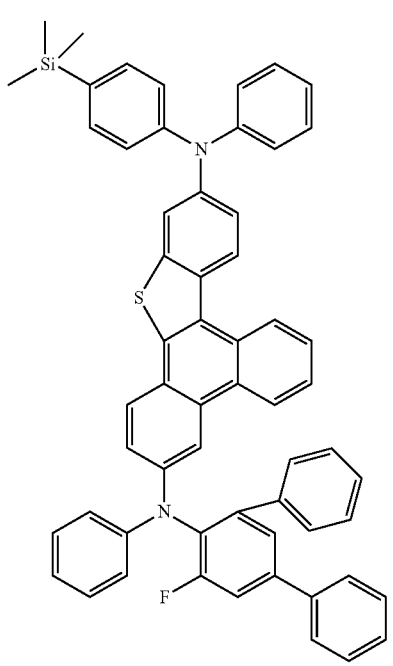
44
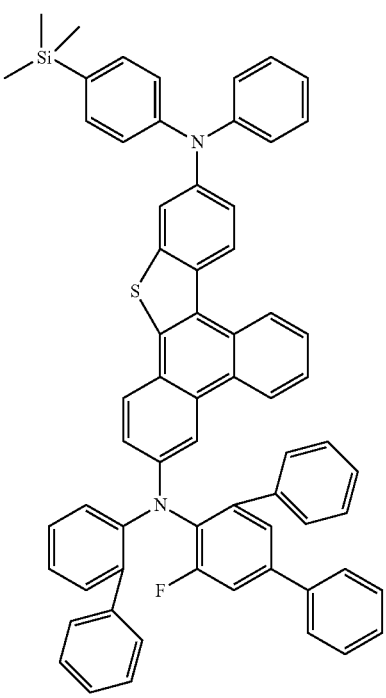
45
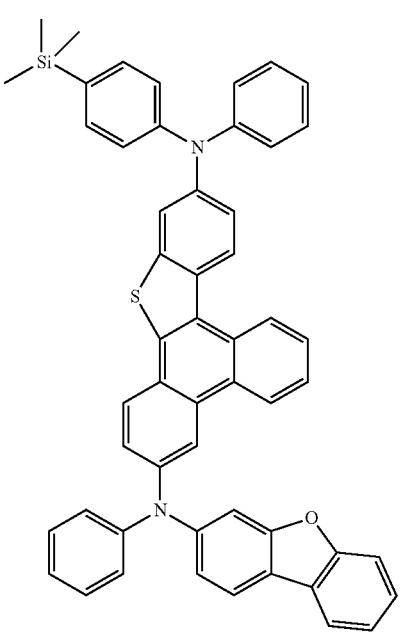

46
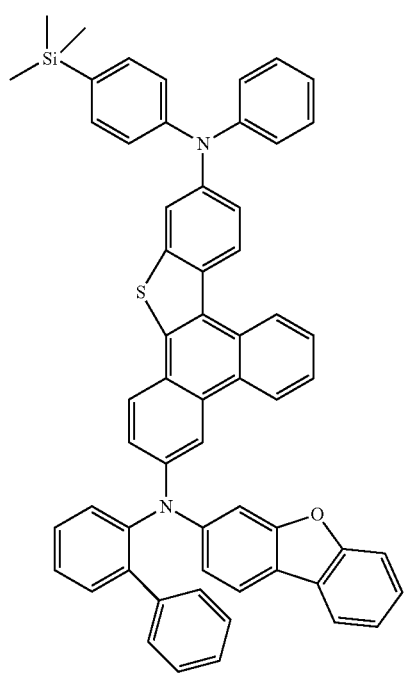
47
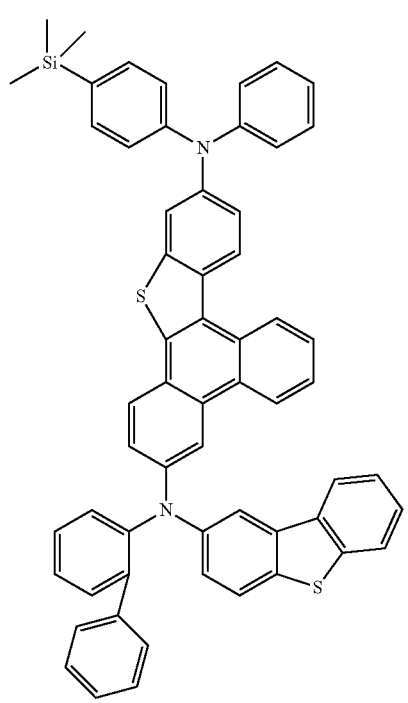
48
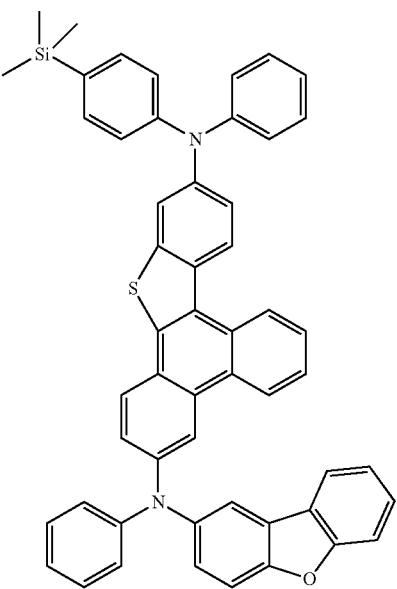
49
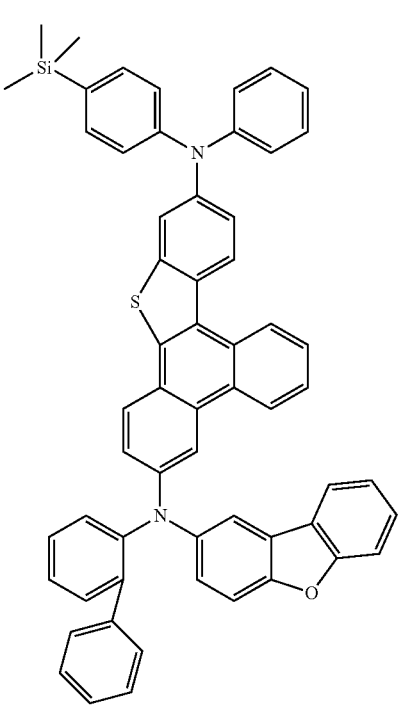

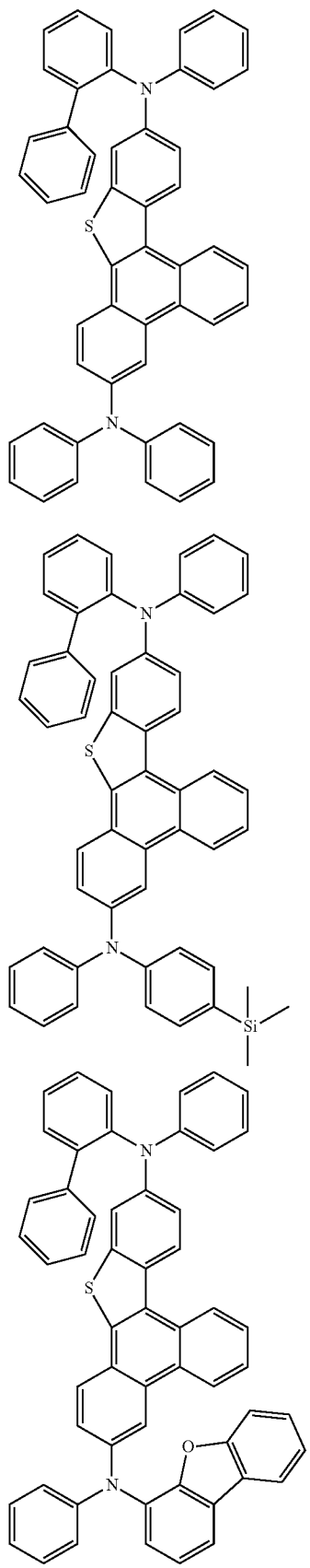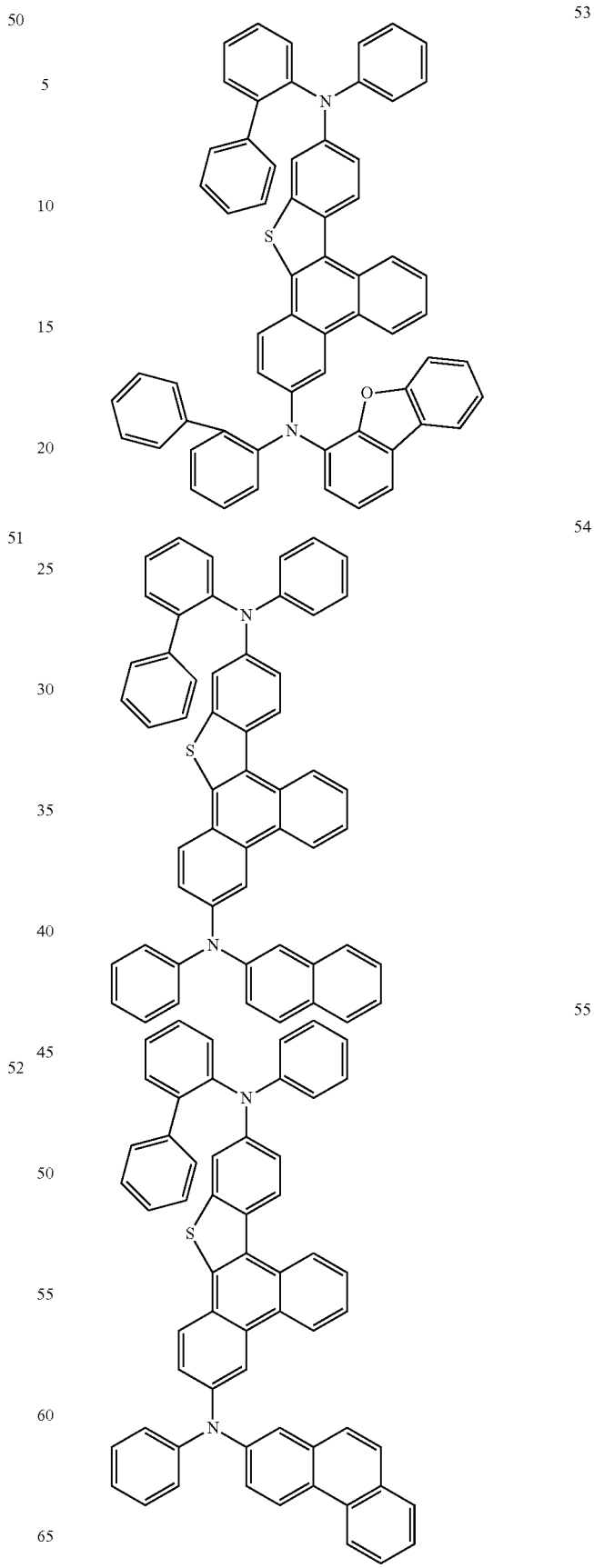

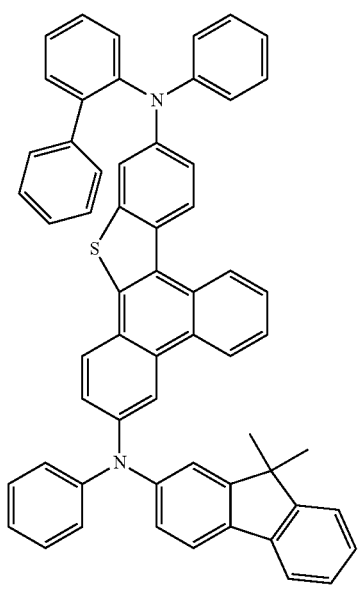
56
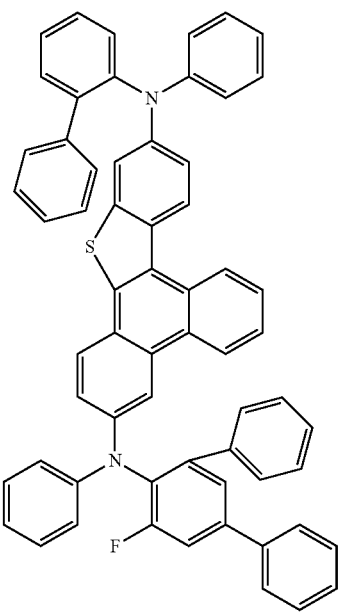
58
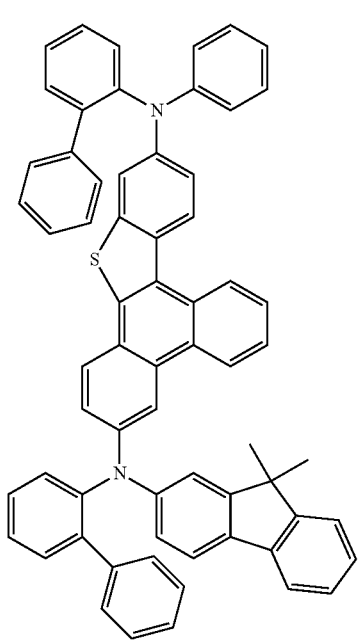
57
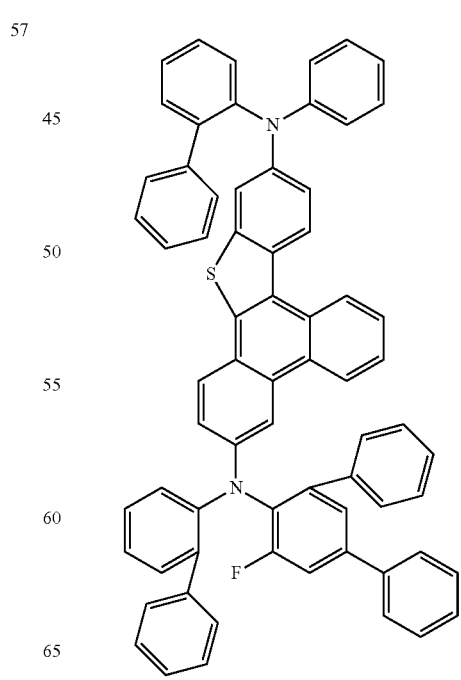
59

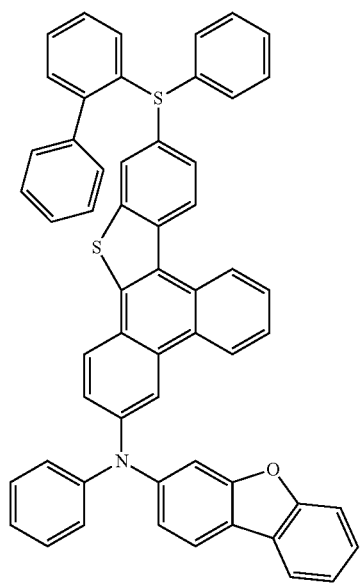
59
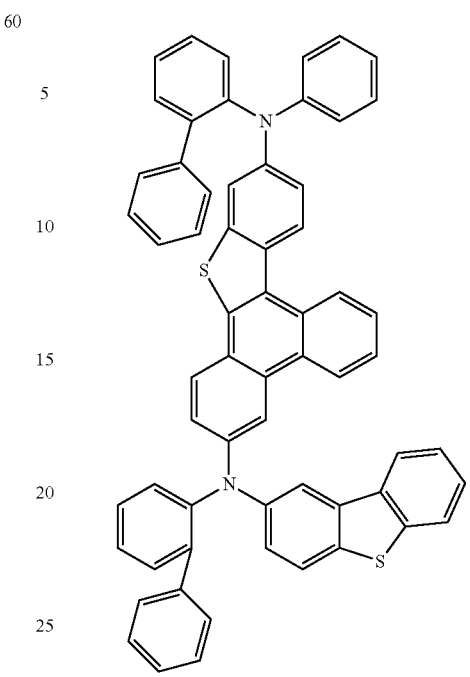
60
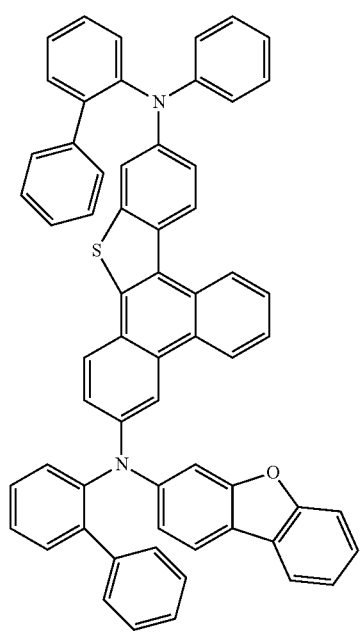
61
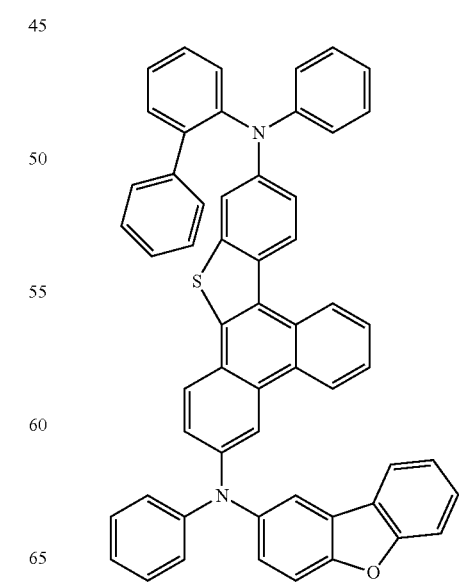
63

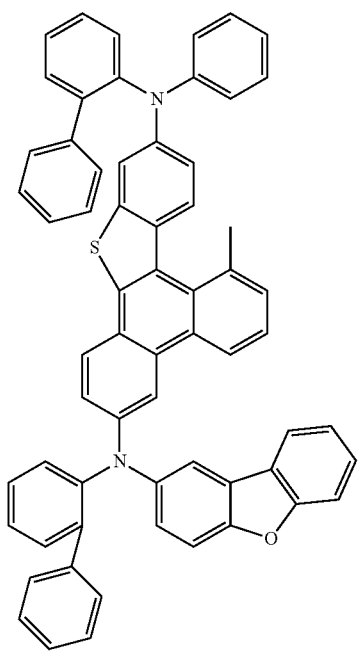
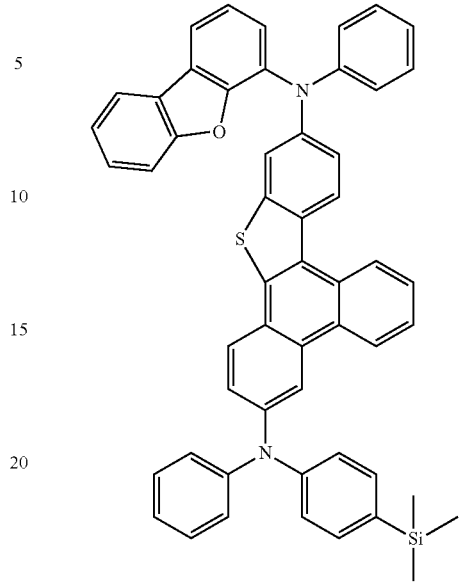
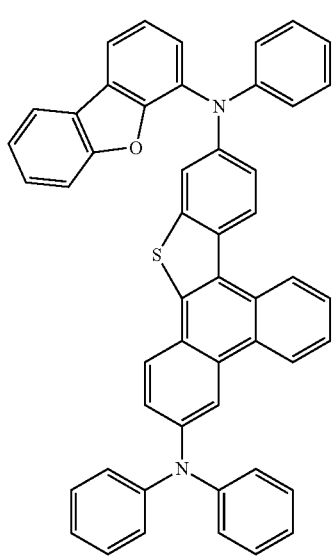
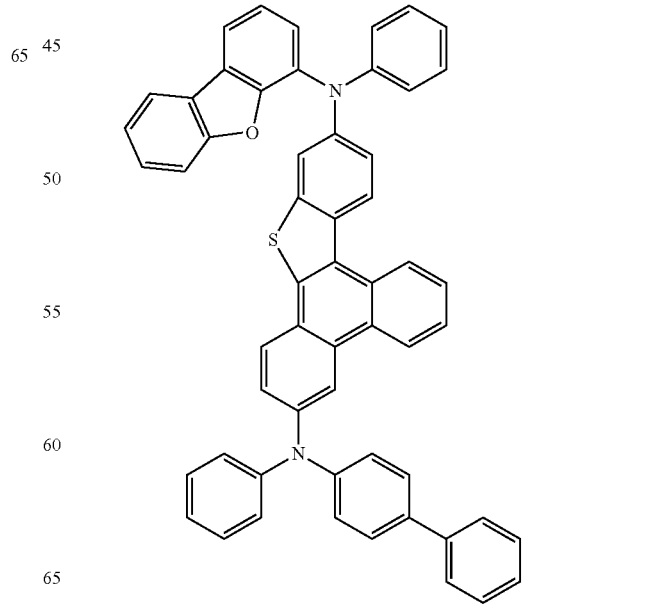

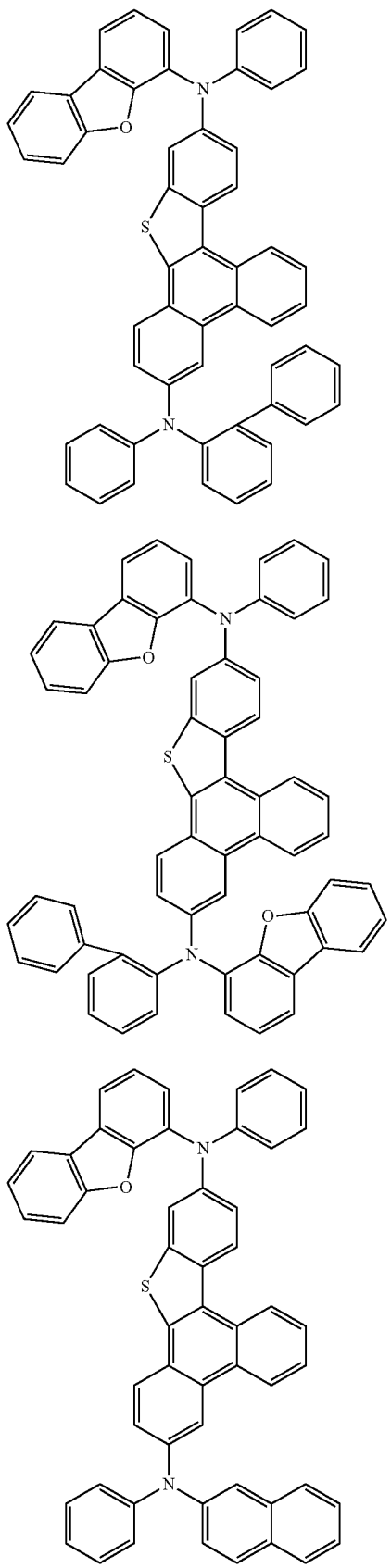
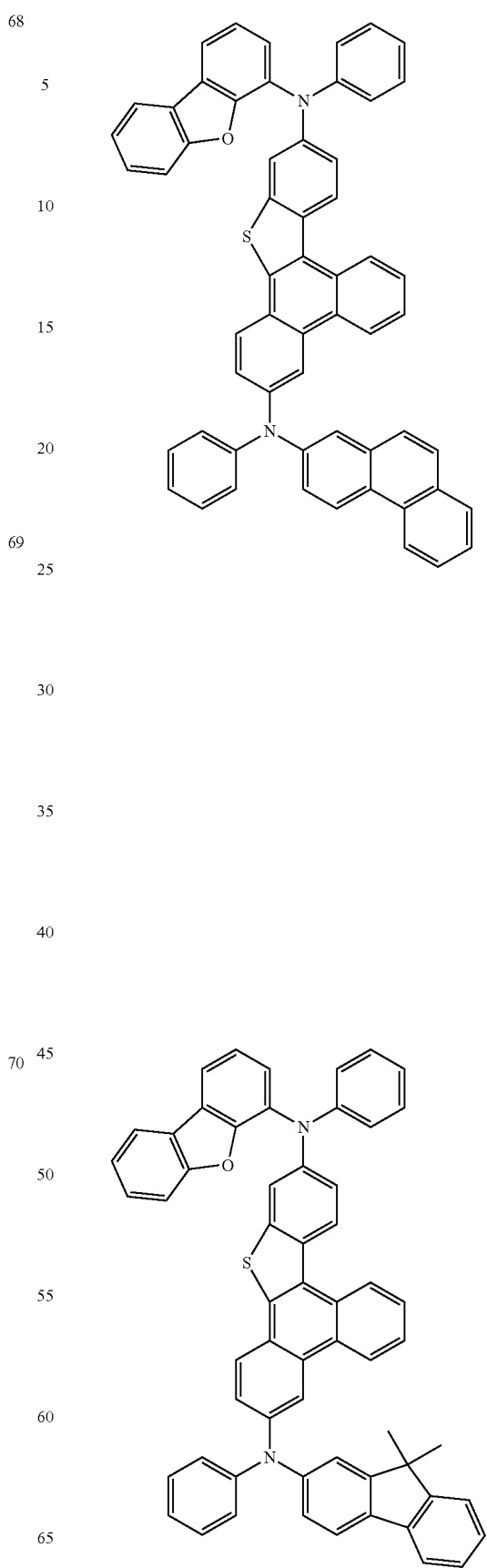

73
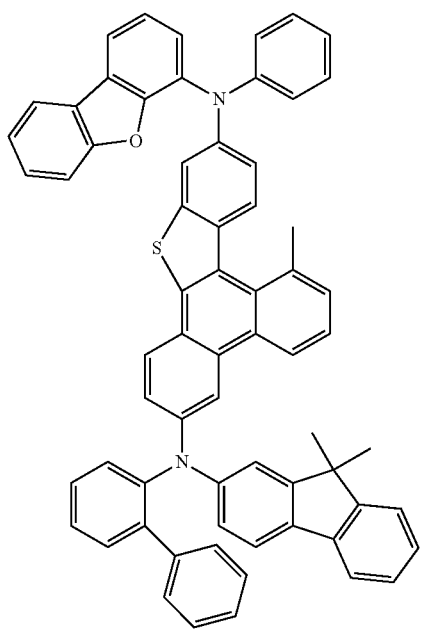
74
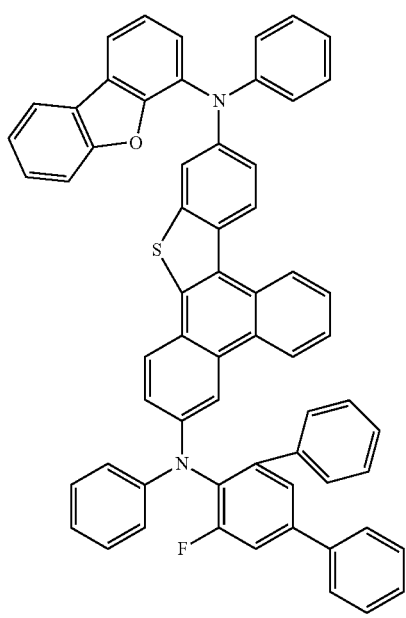
75
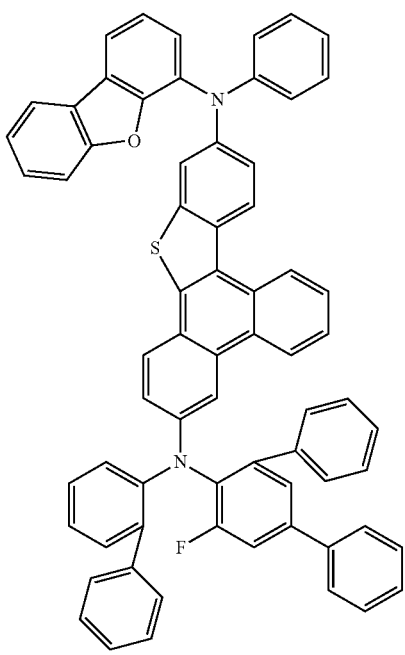
76
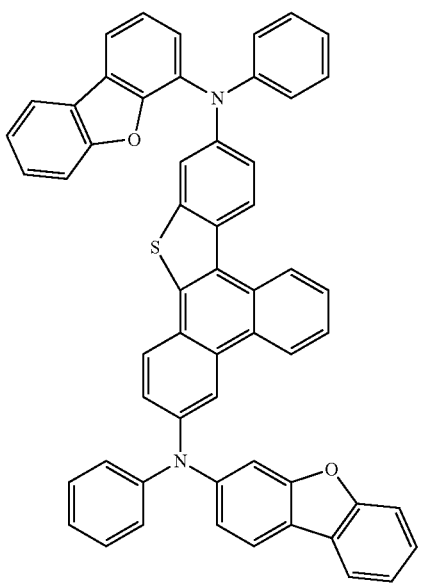

67
-continued
77
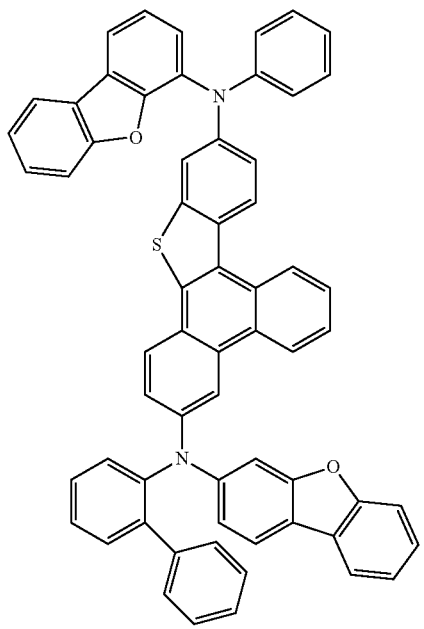
78
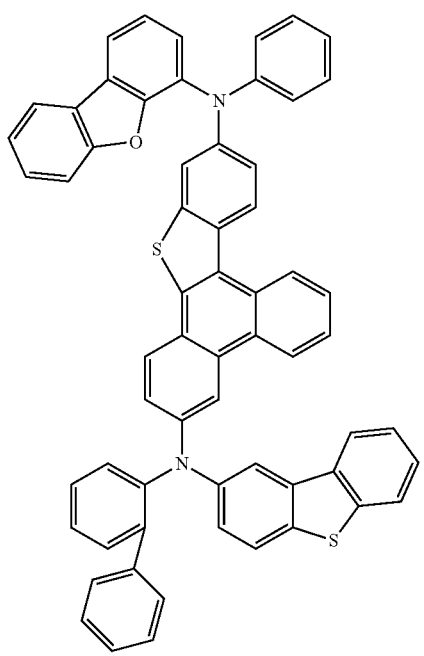
68
-continued
79
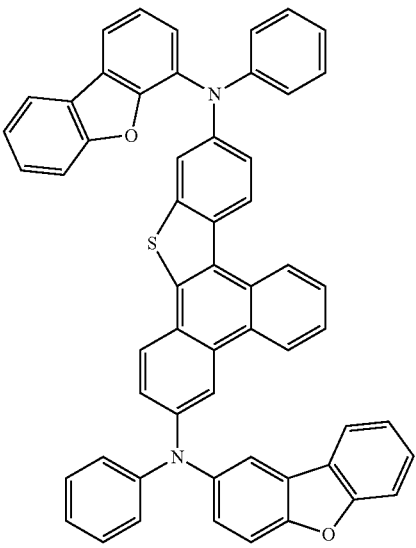
80
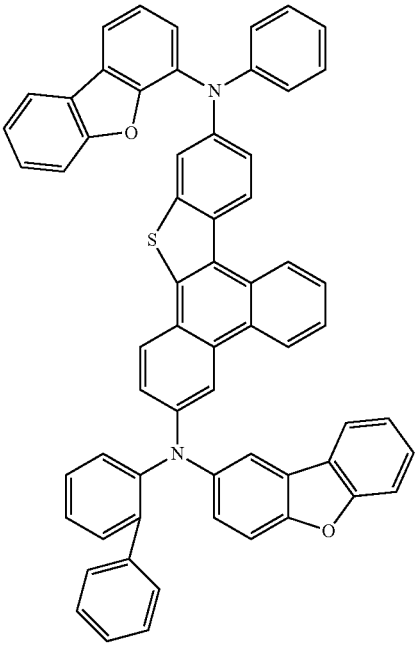

81
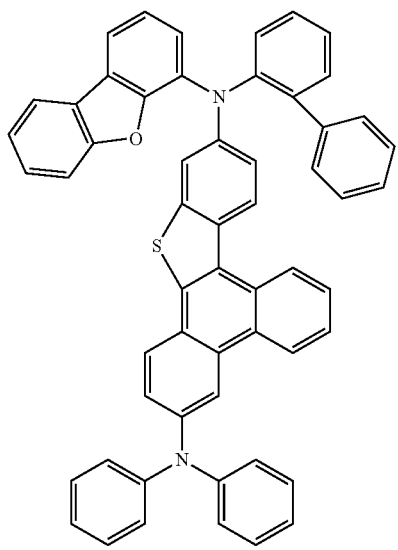
82
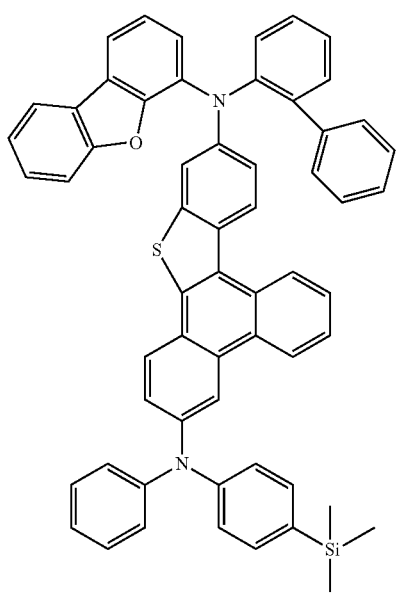
83
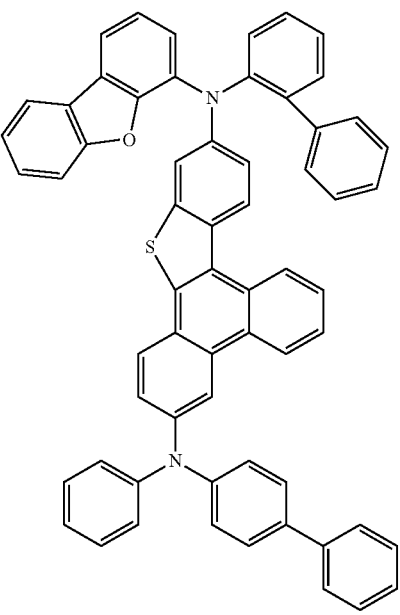
84
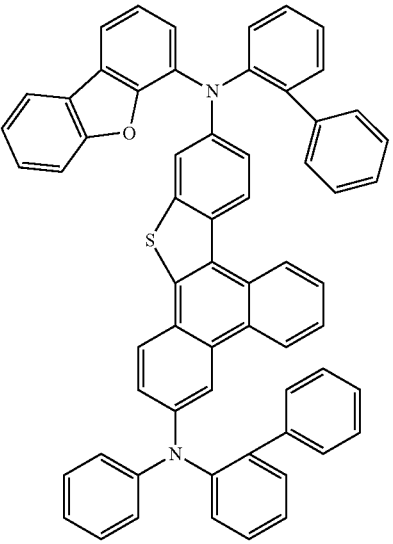

85
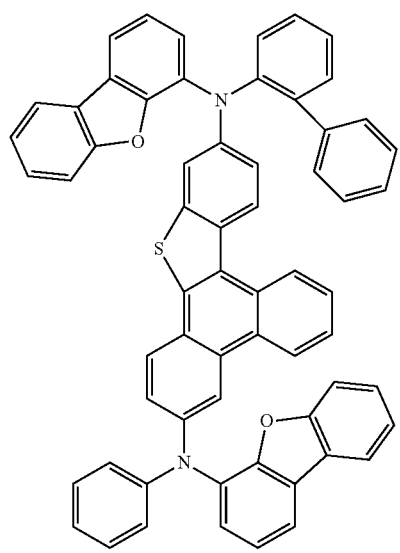
86
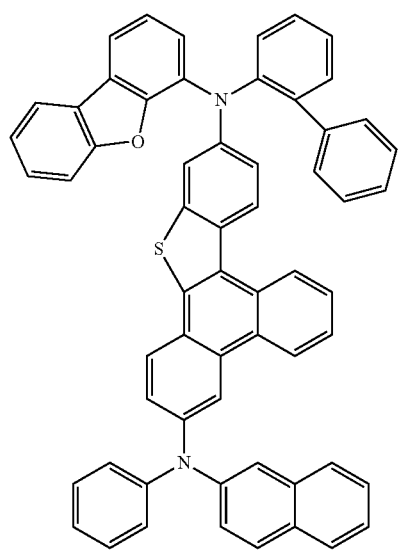
87
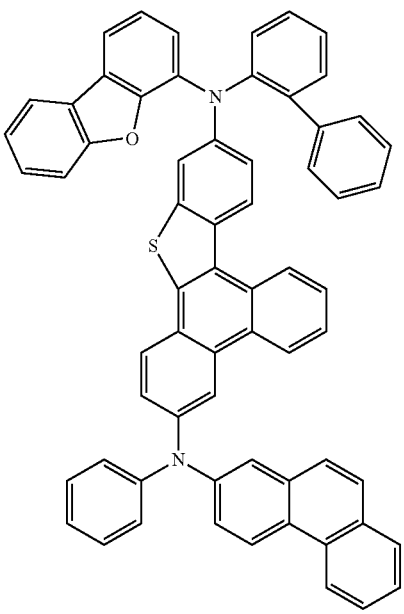
88
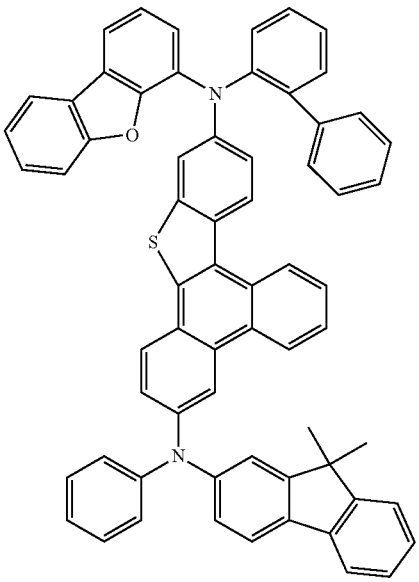

89
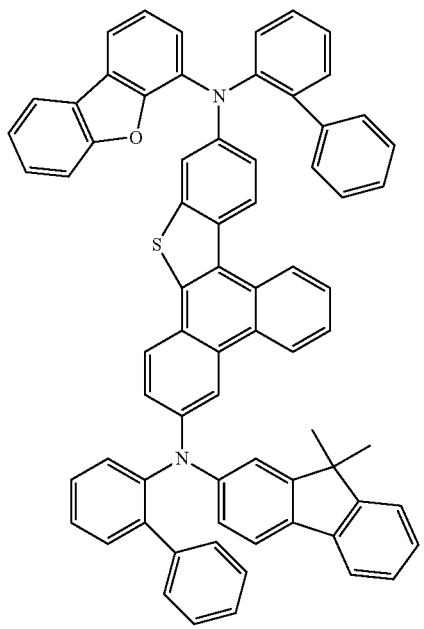
90
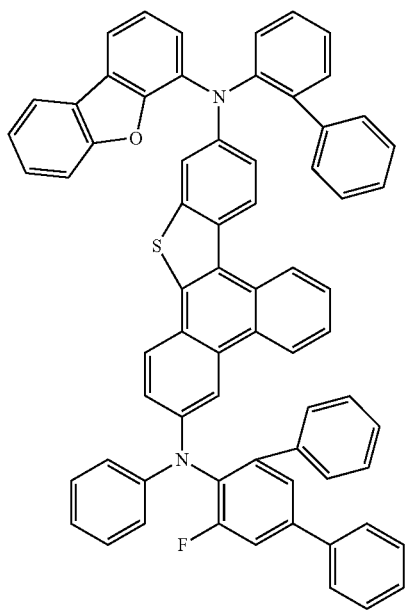
91
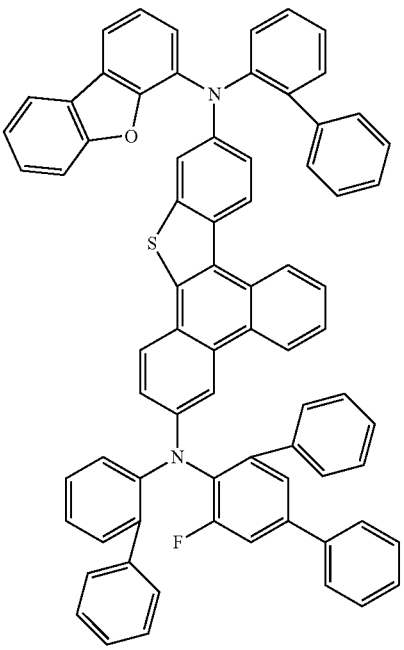
92
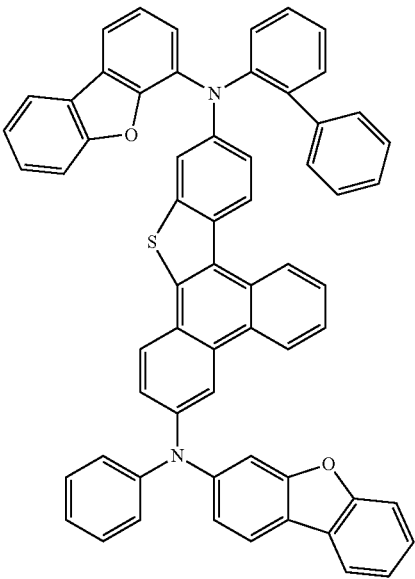

93
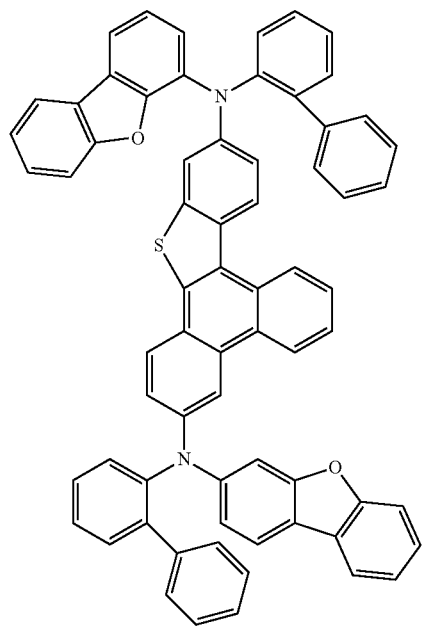
94
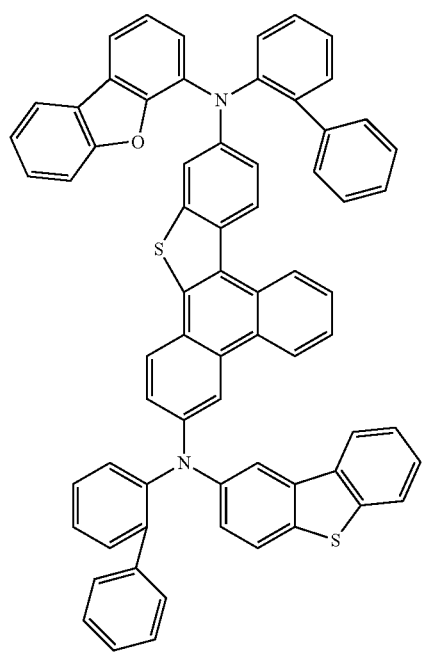
95
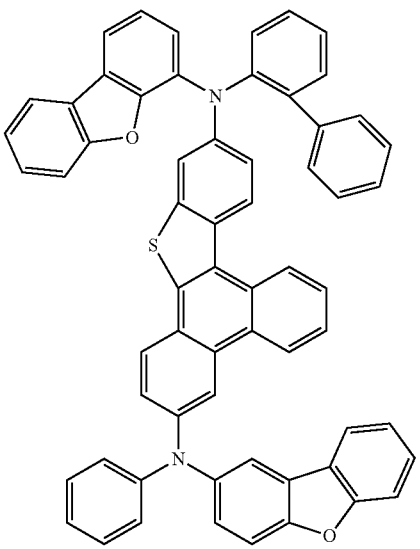
96
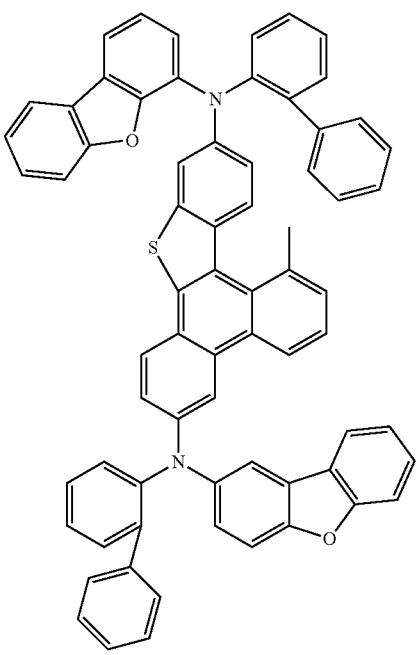

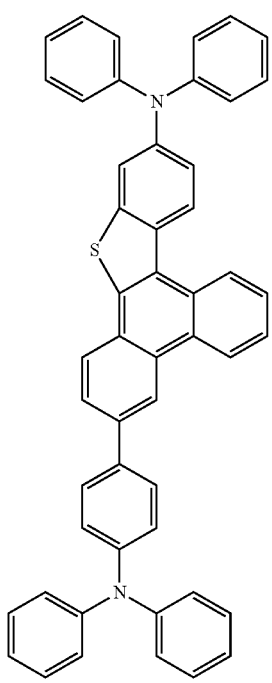
97
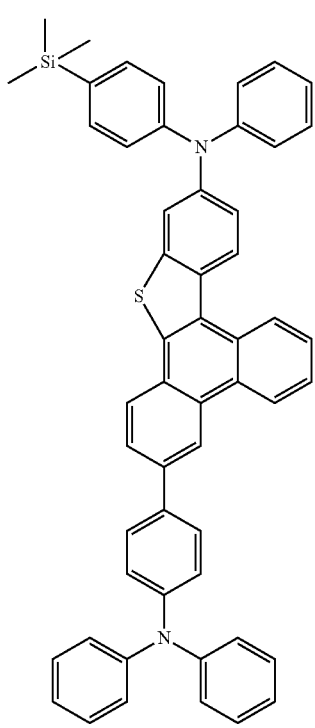
98
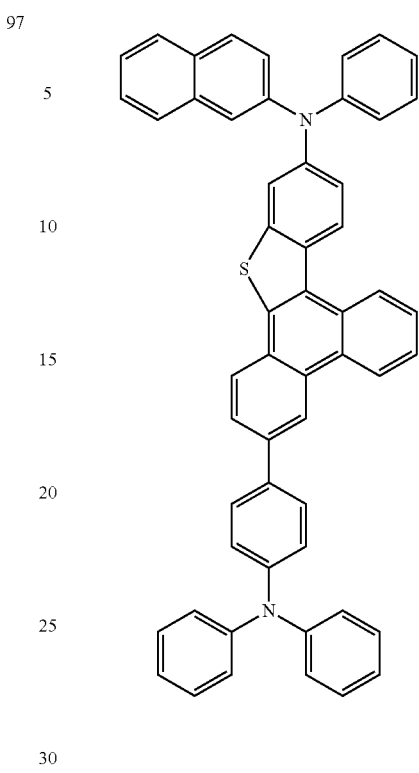
99
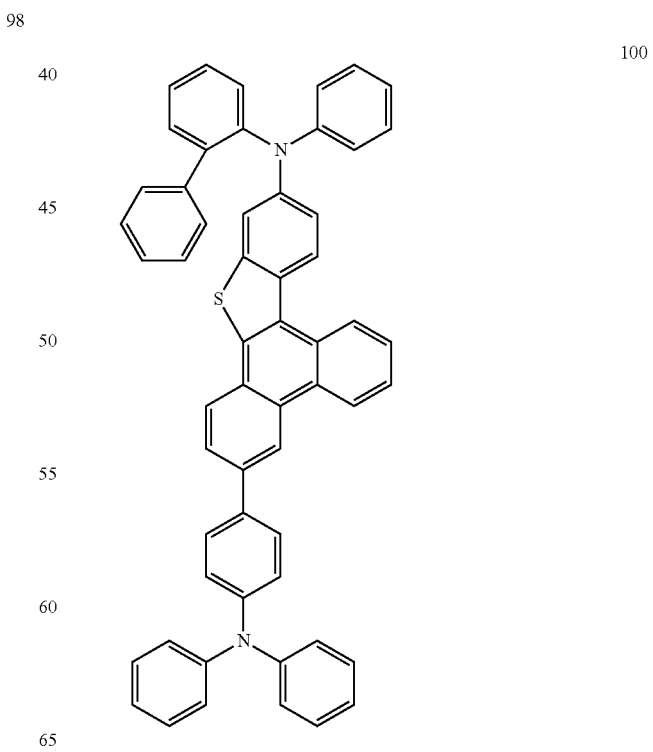
100

79
-continued
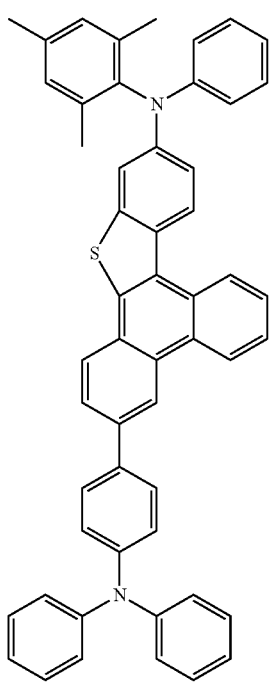
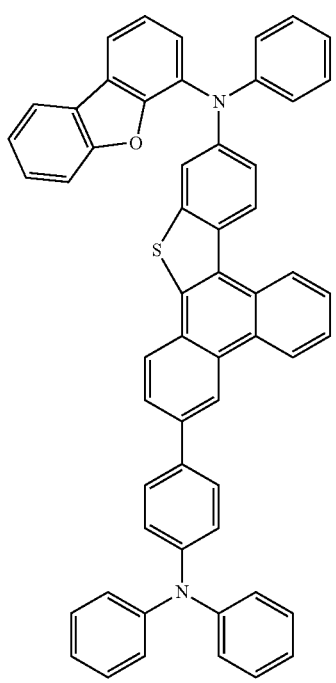
102
80
-continued
101
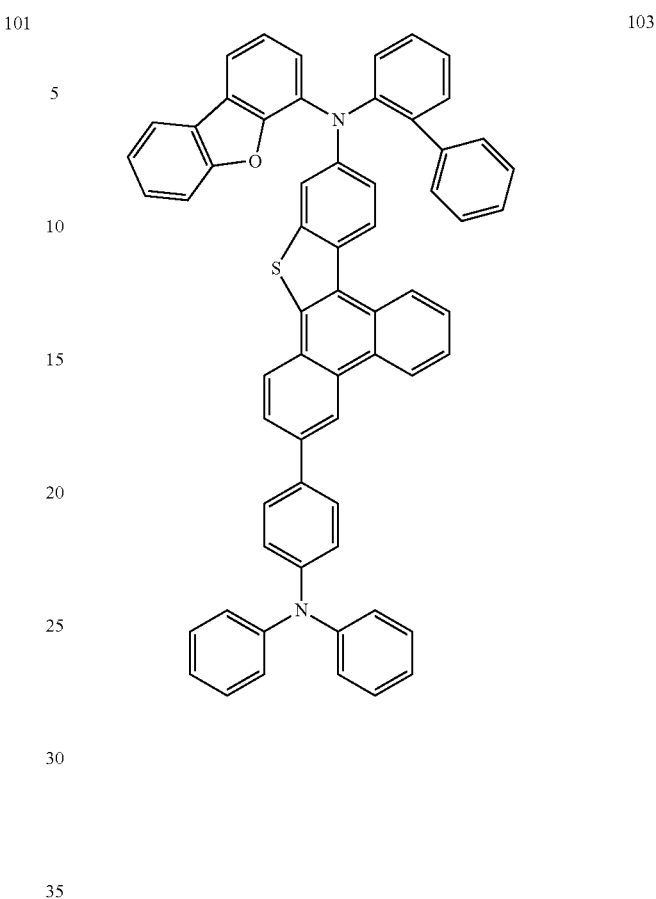
103
104
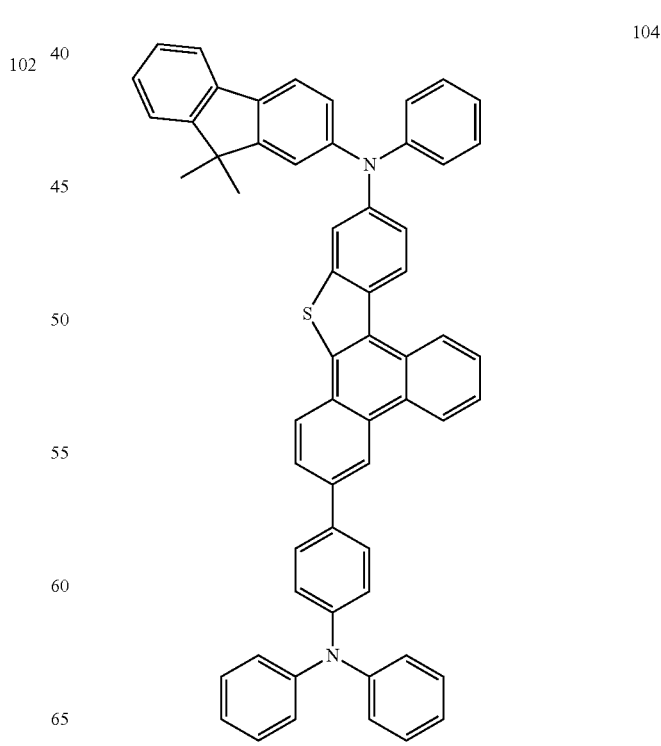

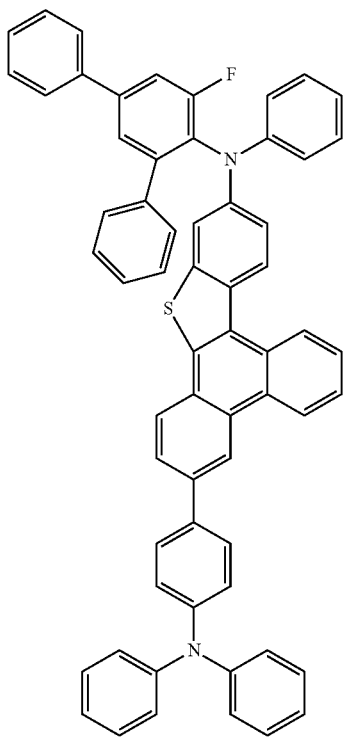
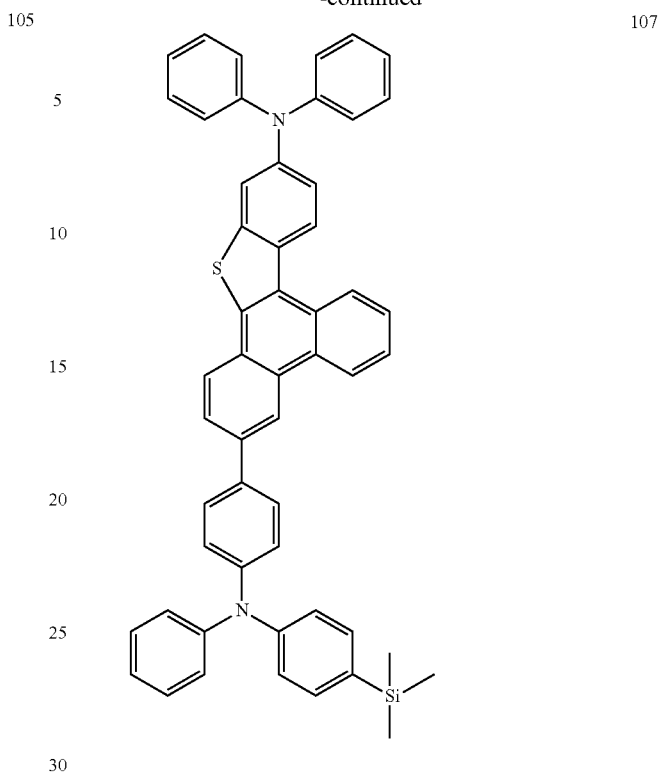
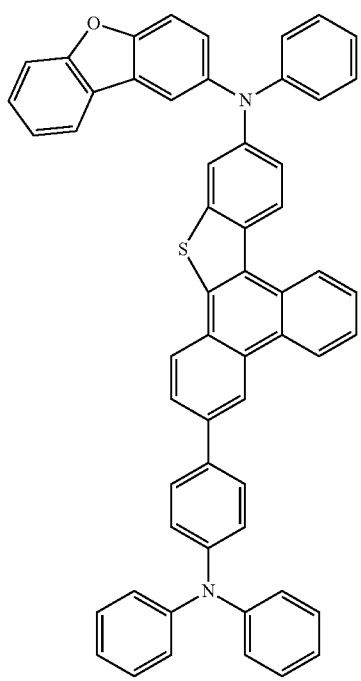
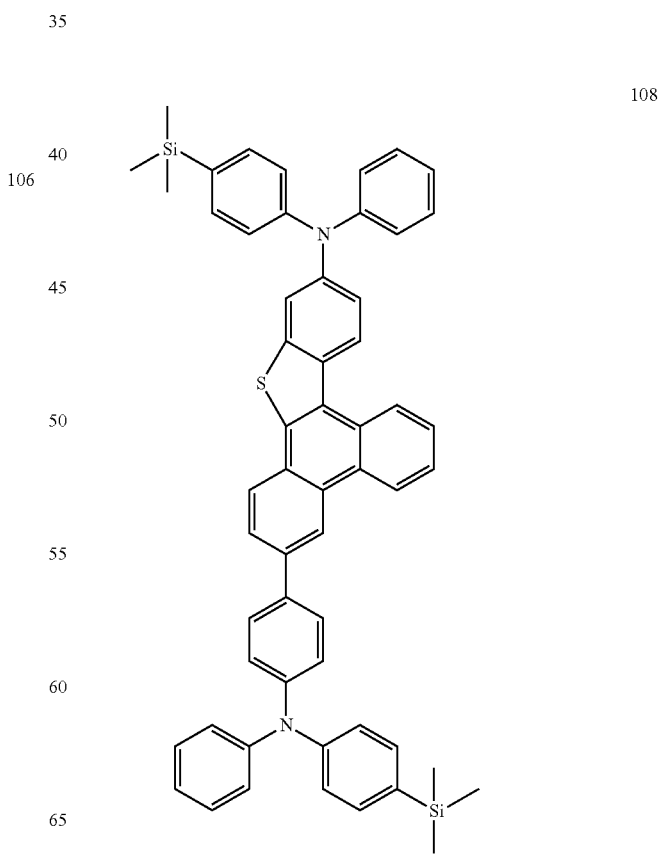

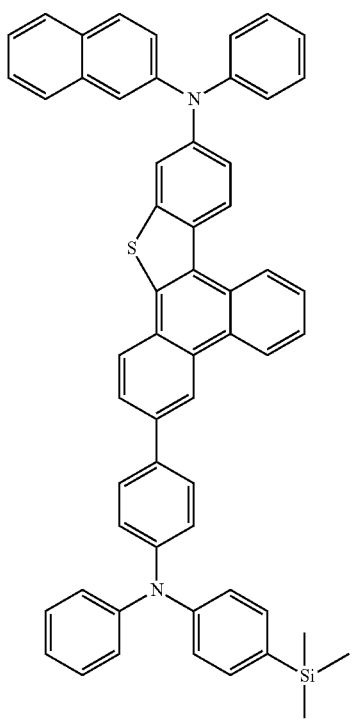
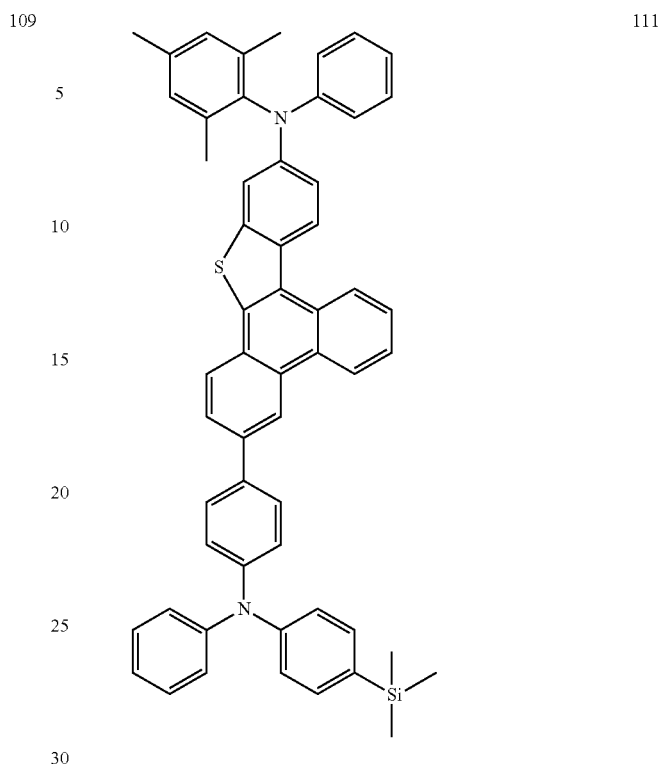
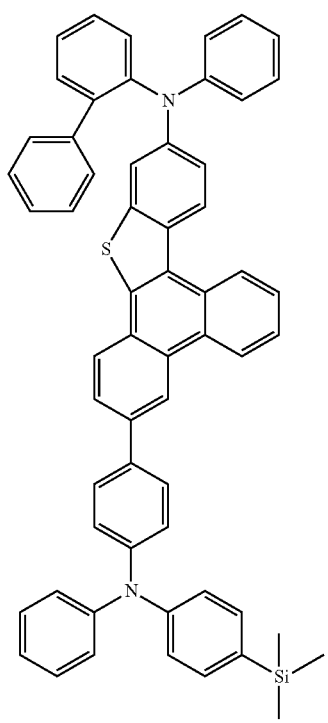
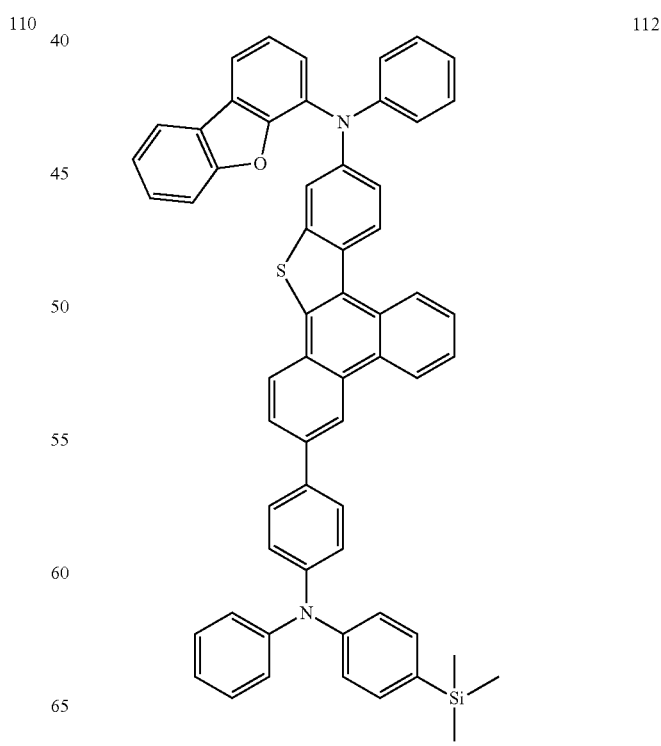

-continued
113
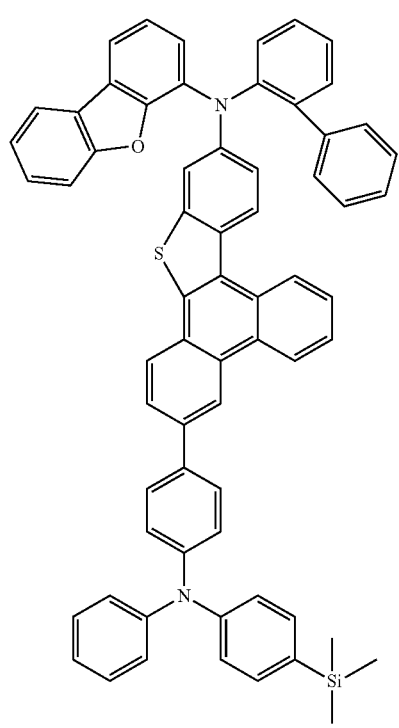
114
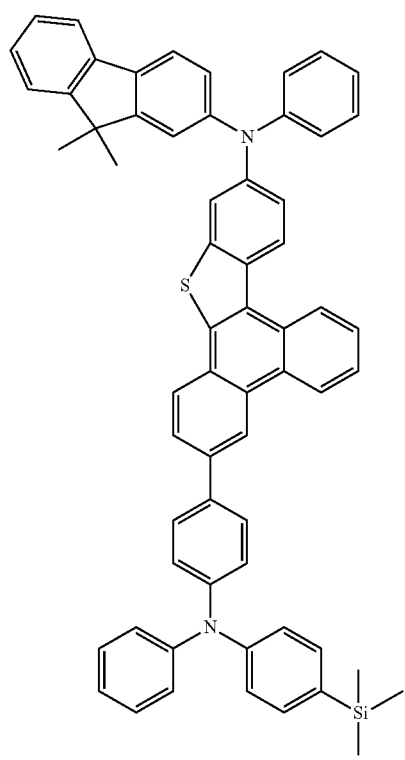
-continued
115
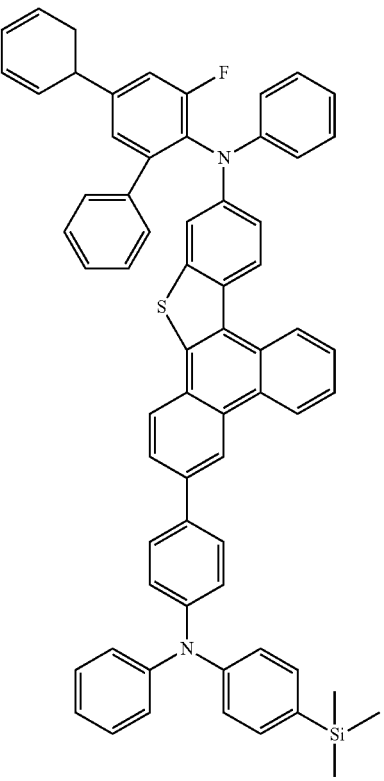
116
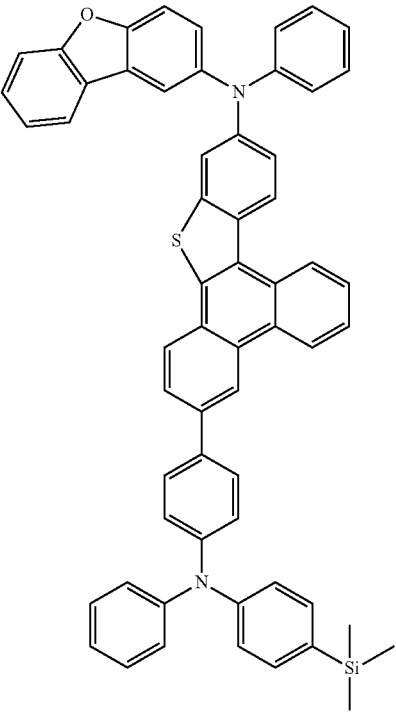

-continued
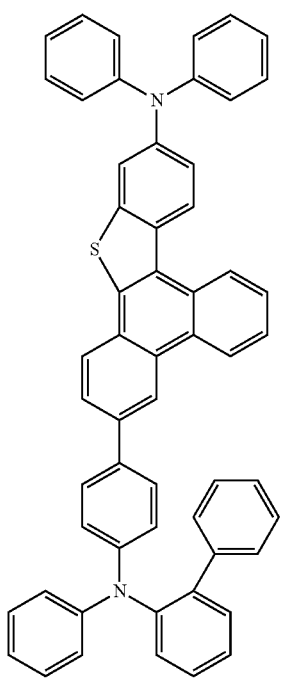
117
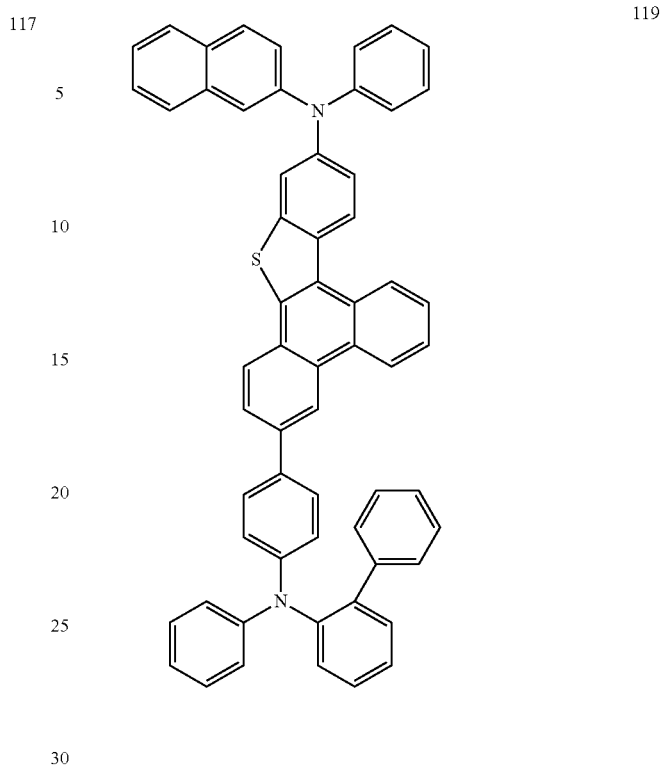
119
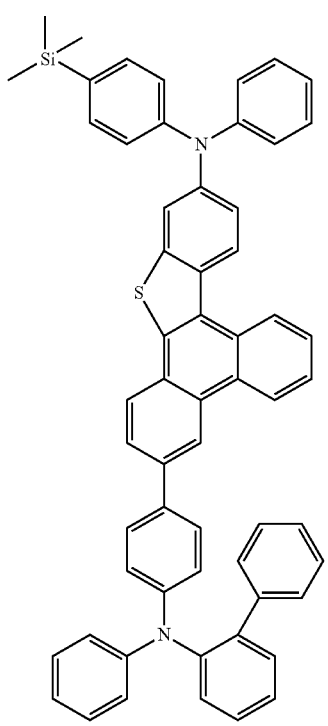
118
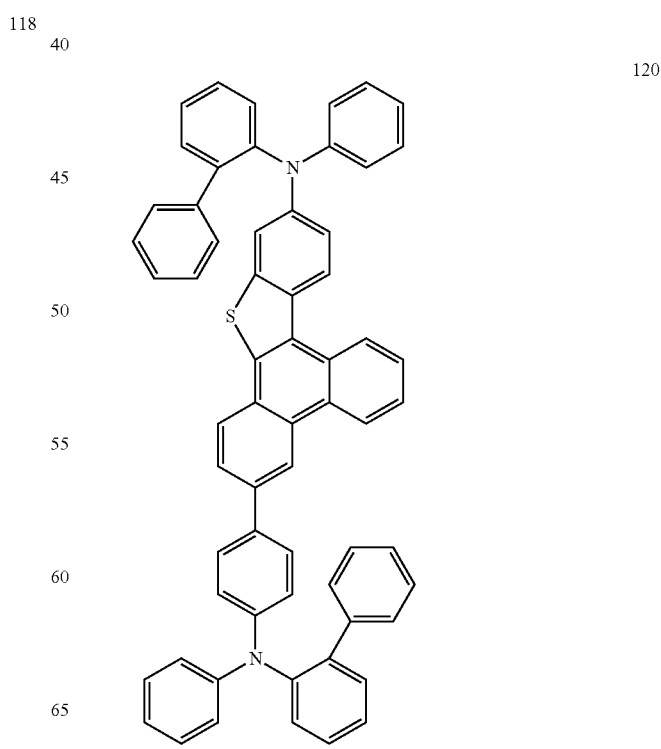
120

89
-continued
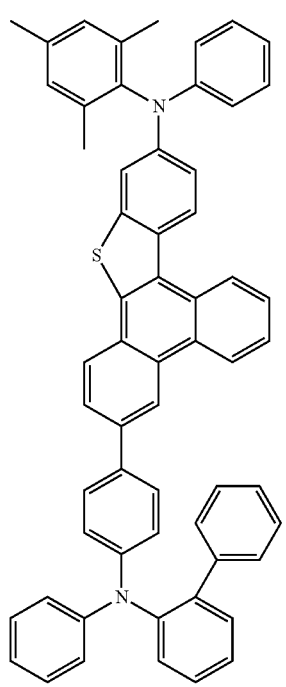
121
90
-continued
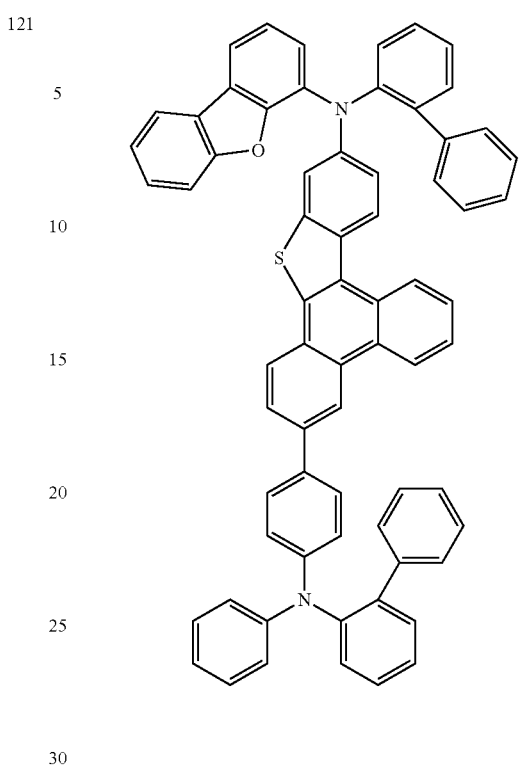
123
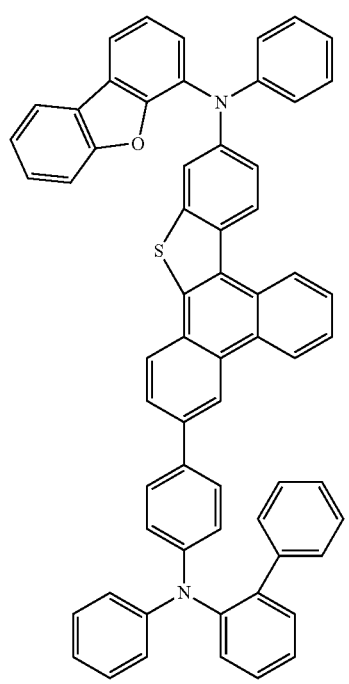
122
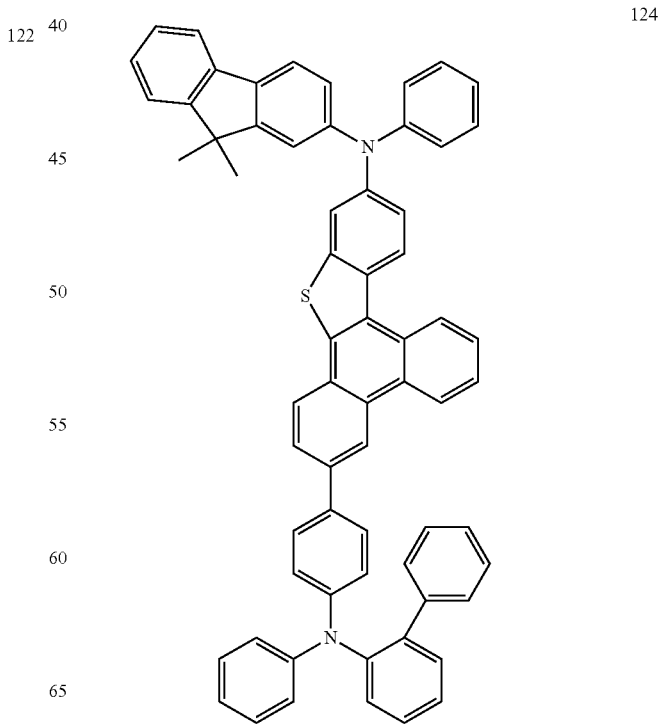
124

91
-continued
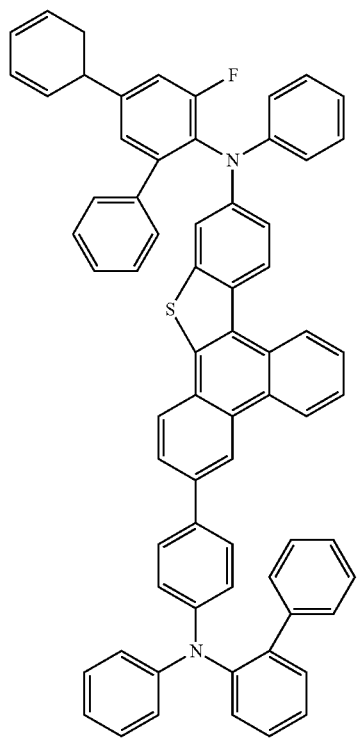
125
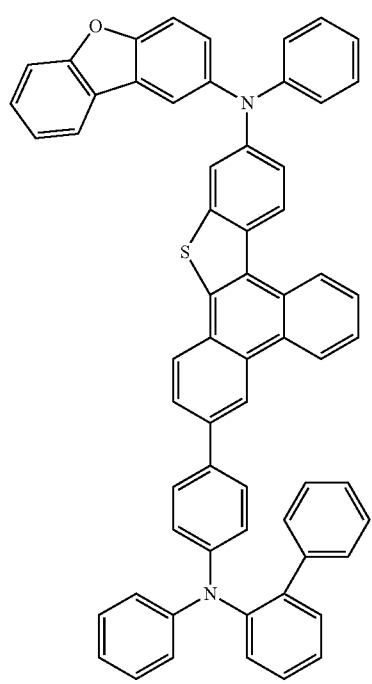
126
92
-continued
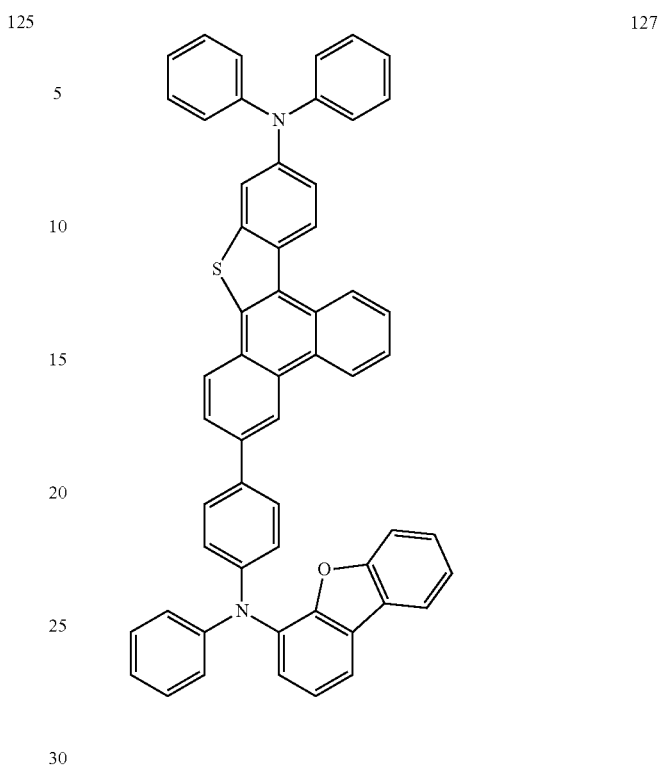
127
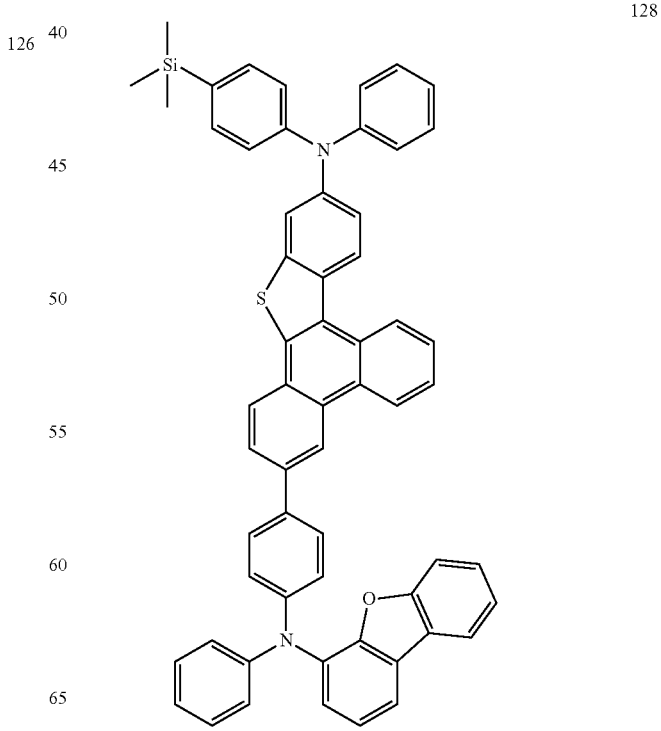
128

129
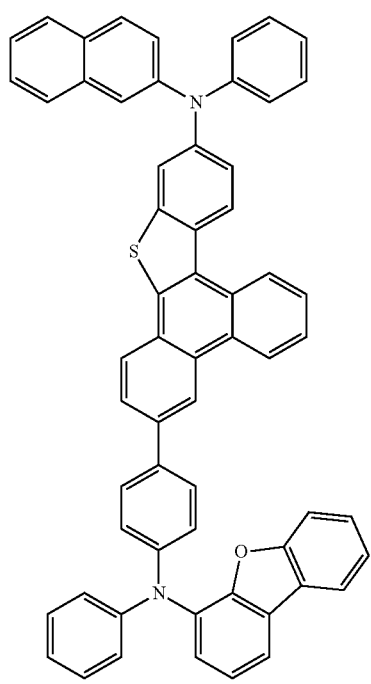
131
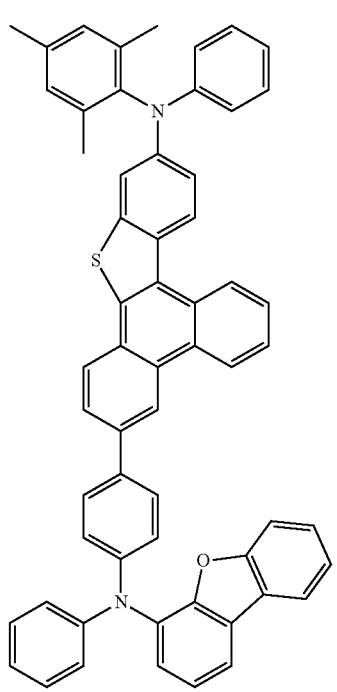
130
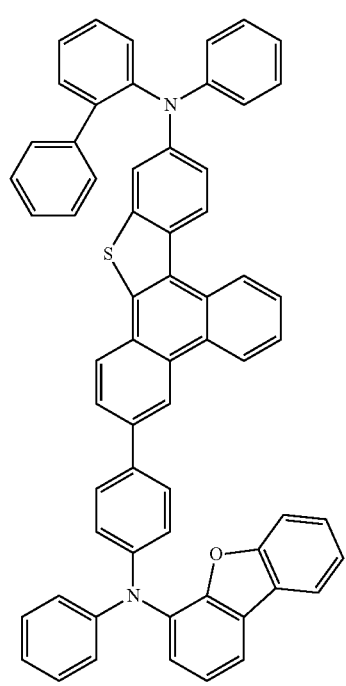
132

133
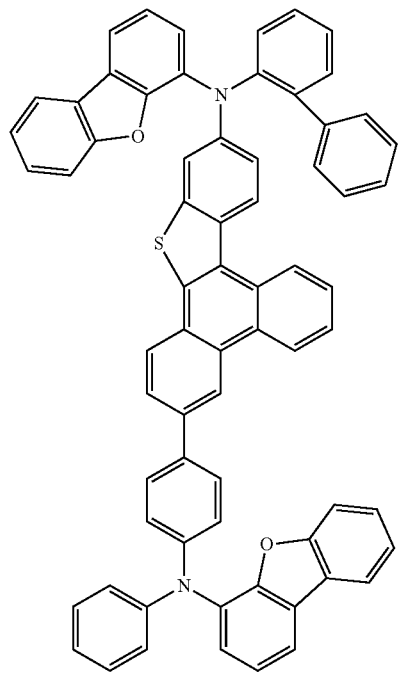
134
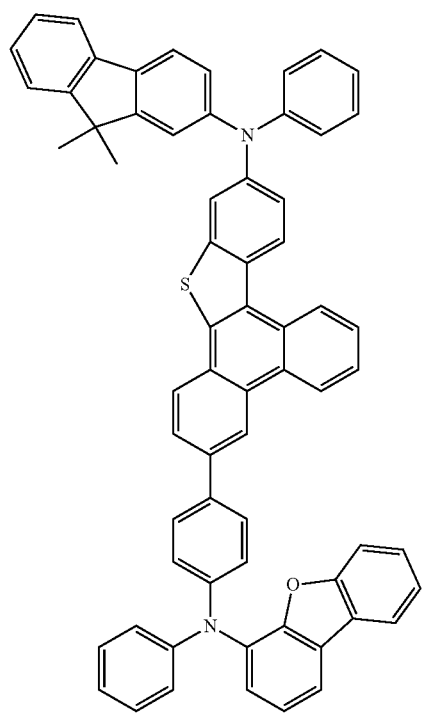
135
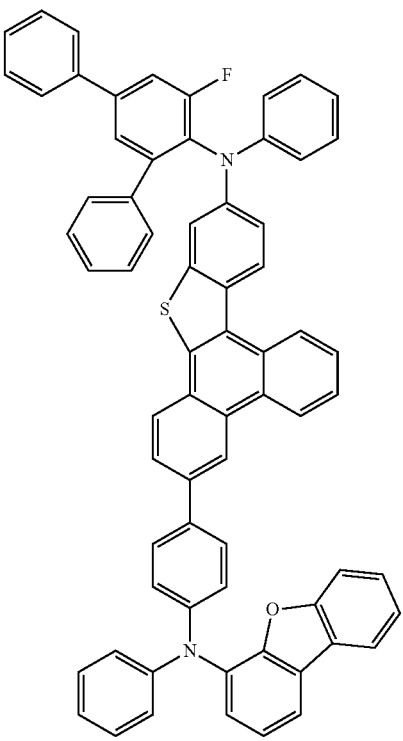
136

97
-continued
137
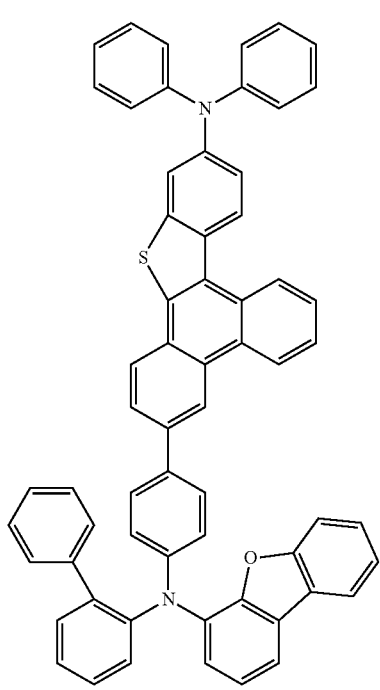
138
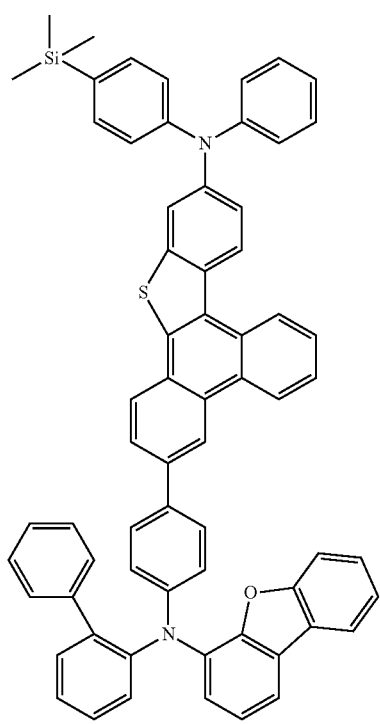
98
-continued
139
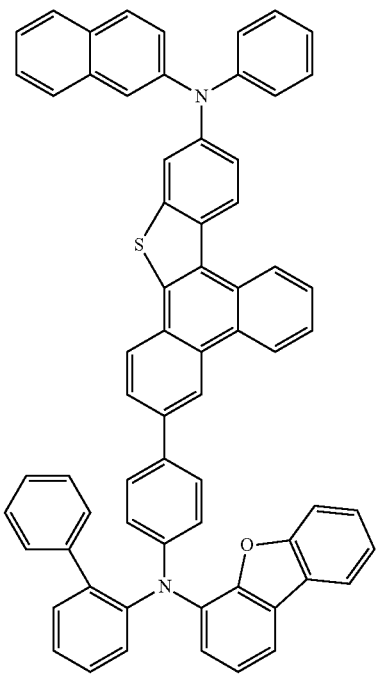
140
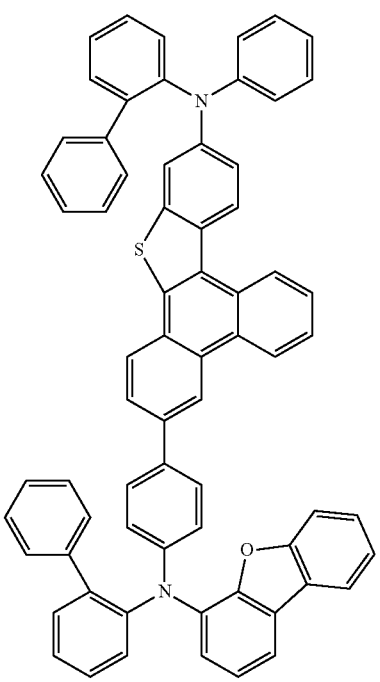

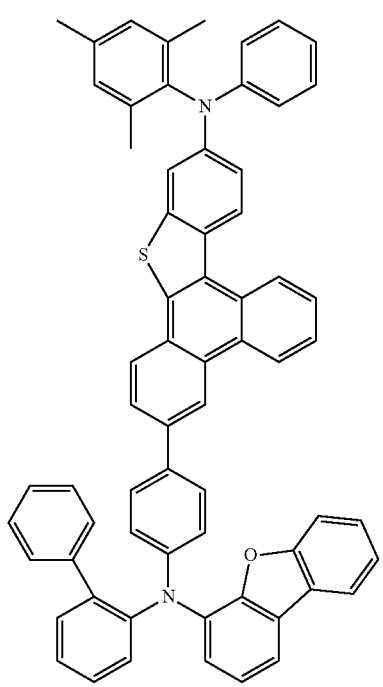
141
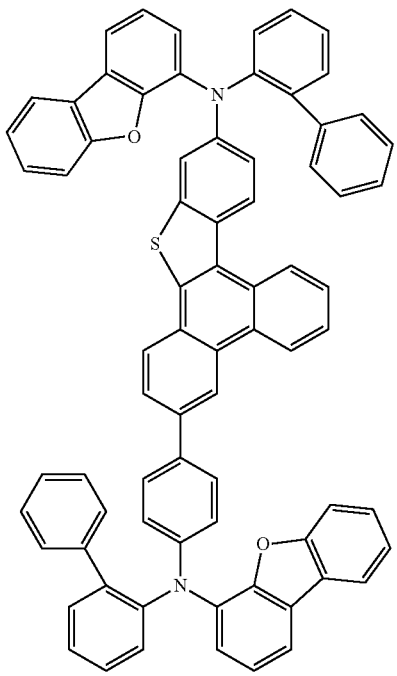
143
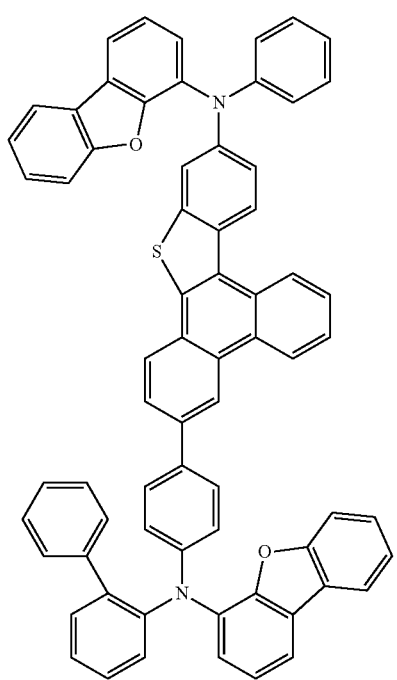
142
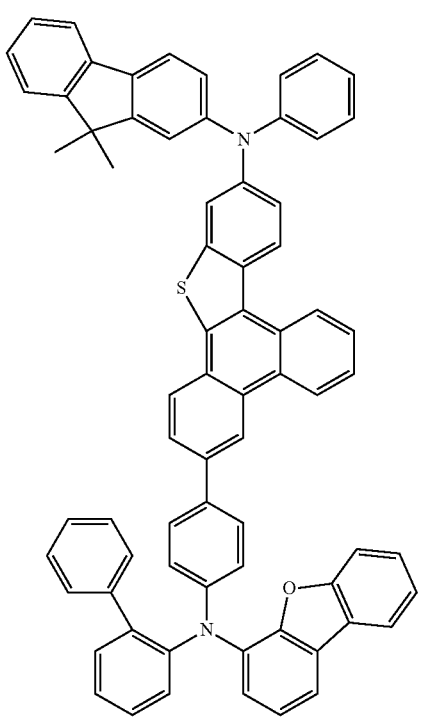
144

101
-continued
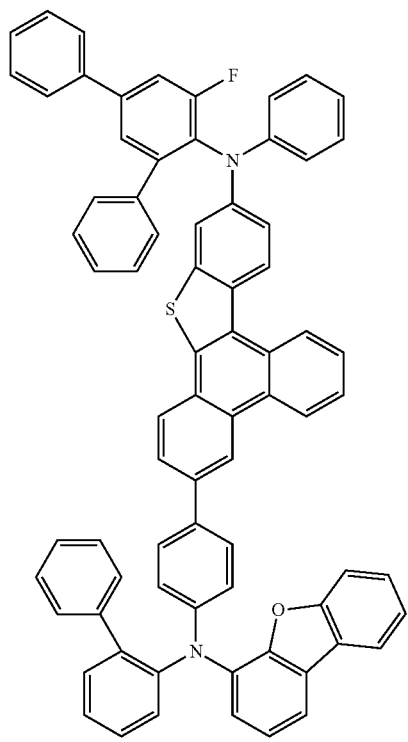
145
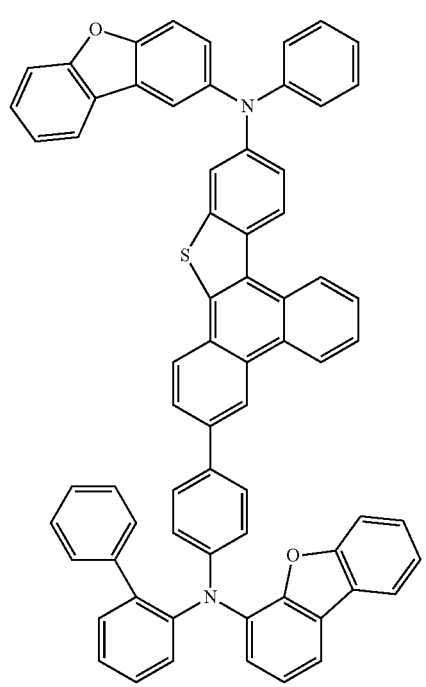
146
102
-continued
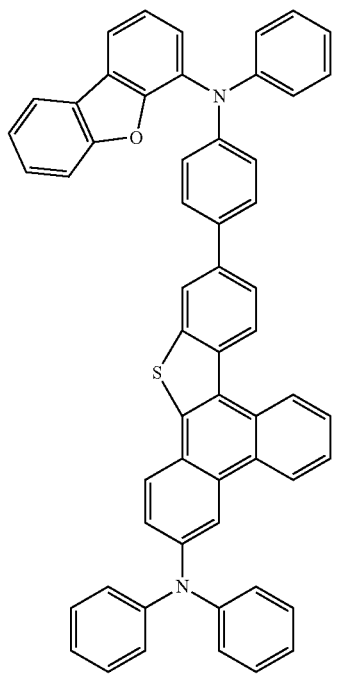
147
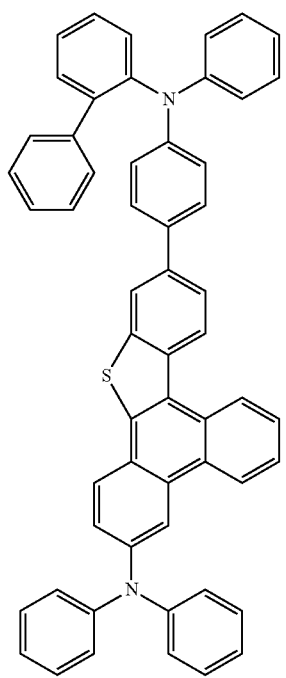
148

149
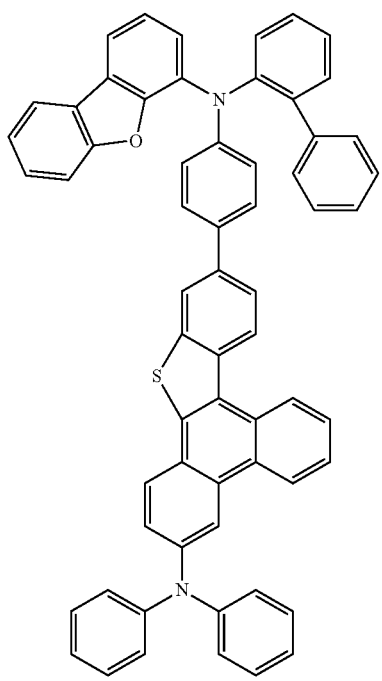
151
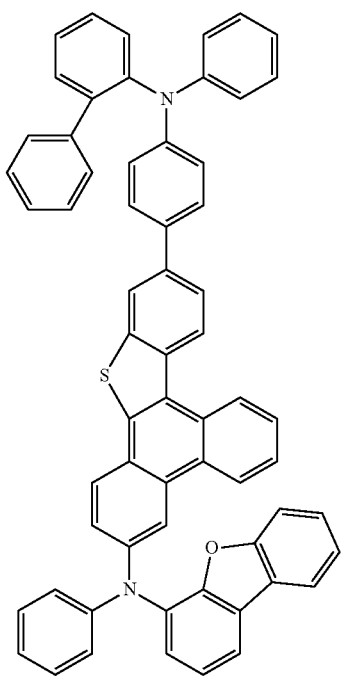
150
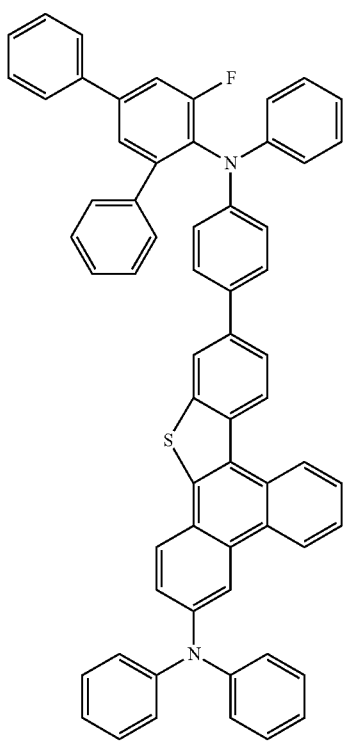
152
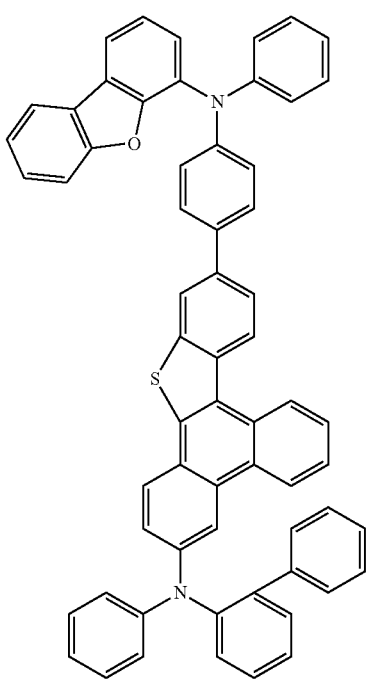

105
-continued
153
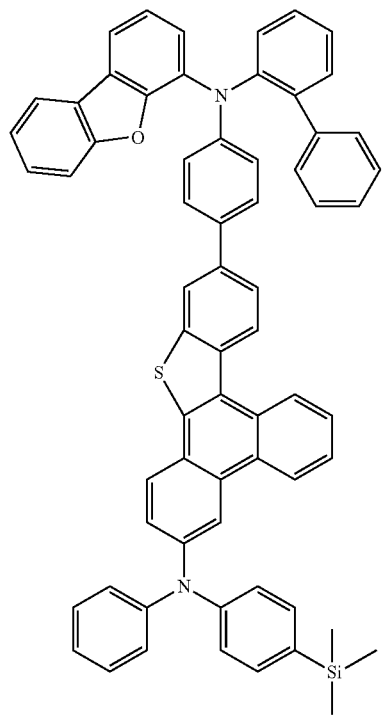
154
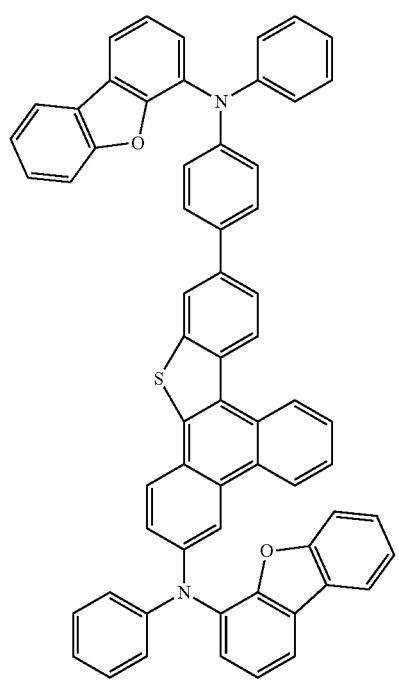
106
-continued
155
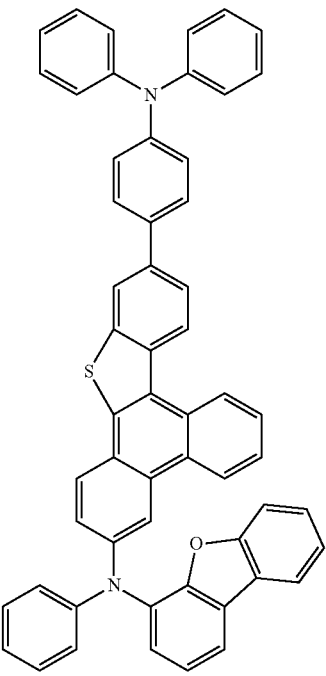
156
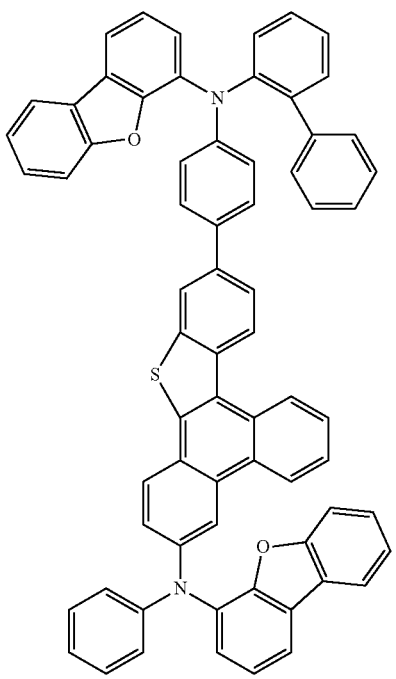

107
-continued
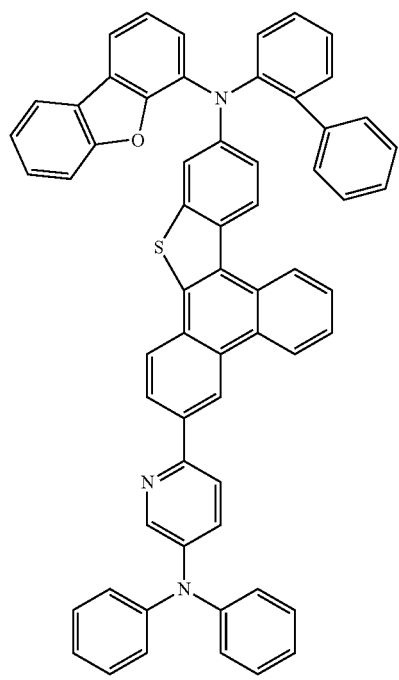
157
108
-continued
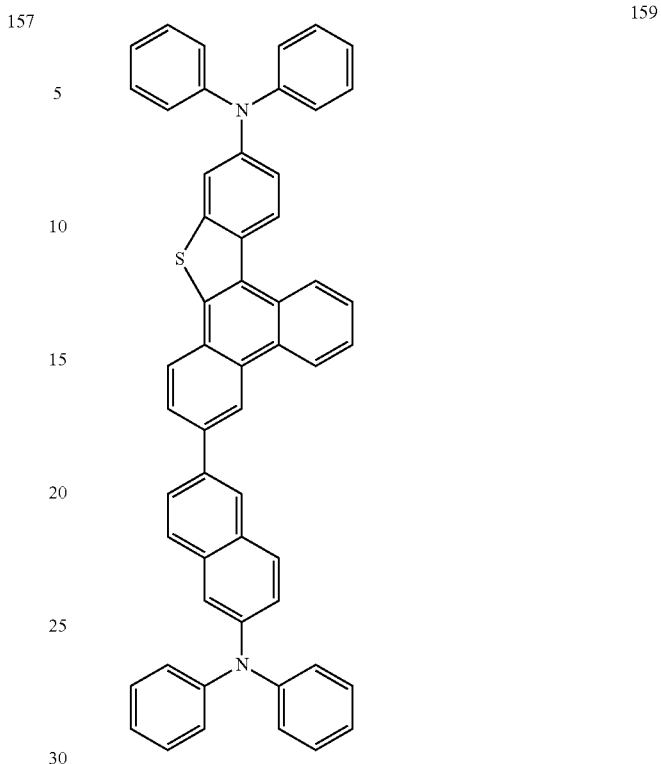
159
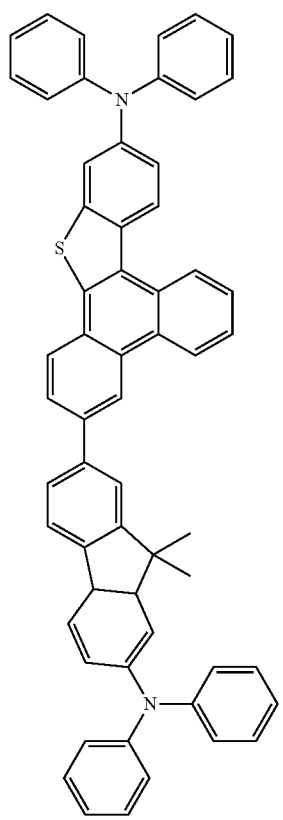
158
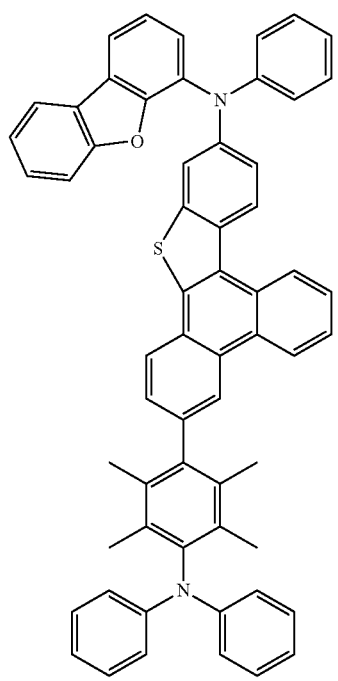
160

109
-continued
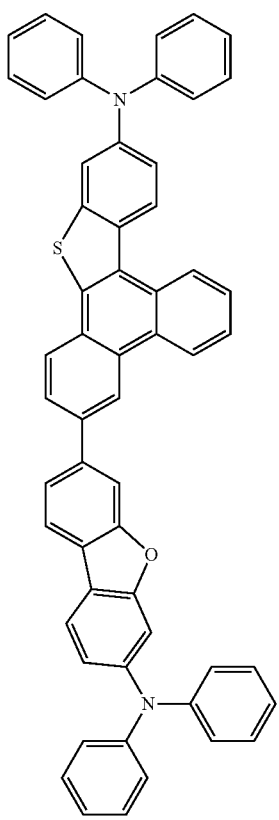
110
-continued
161
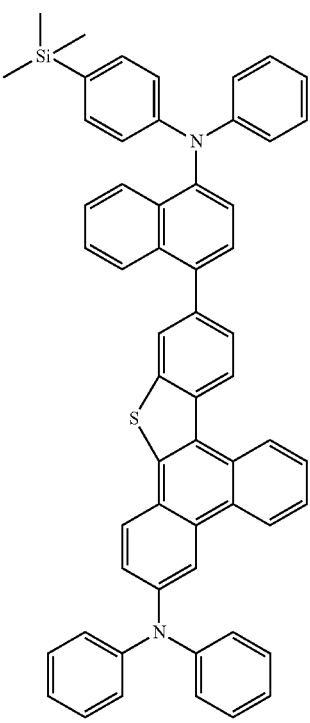
163
162
164
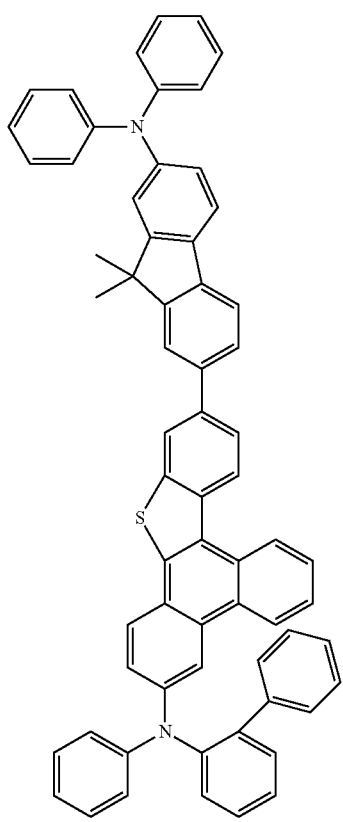
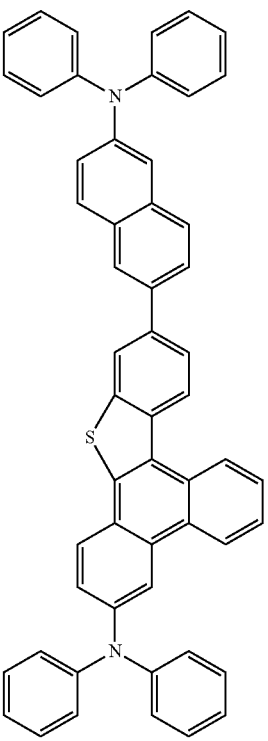

111
-continued
165
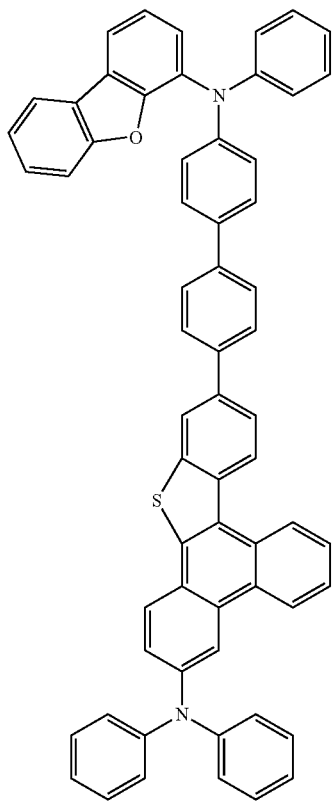
112
-continued
167
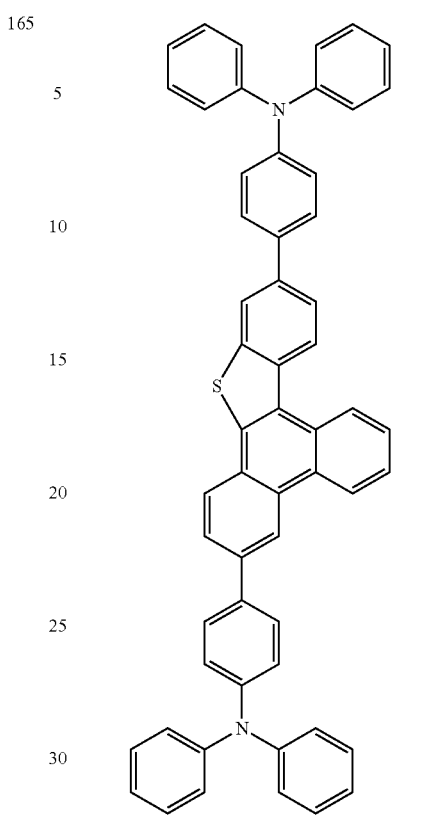
166
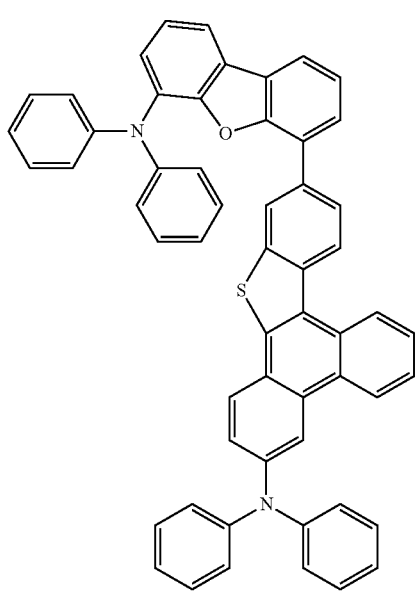
168
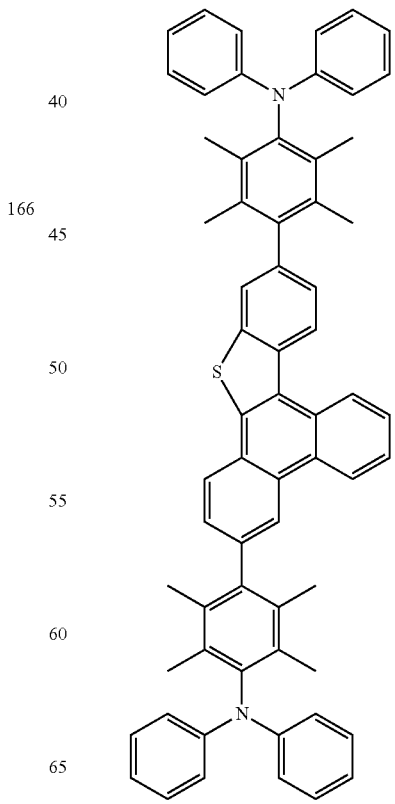

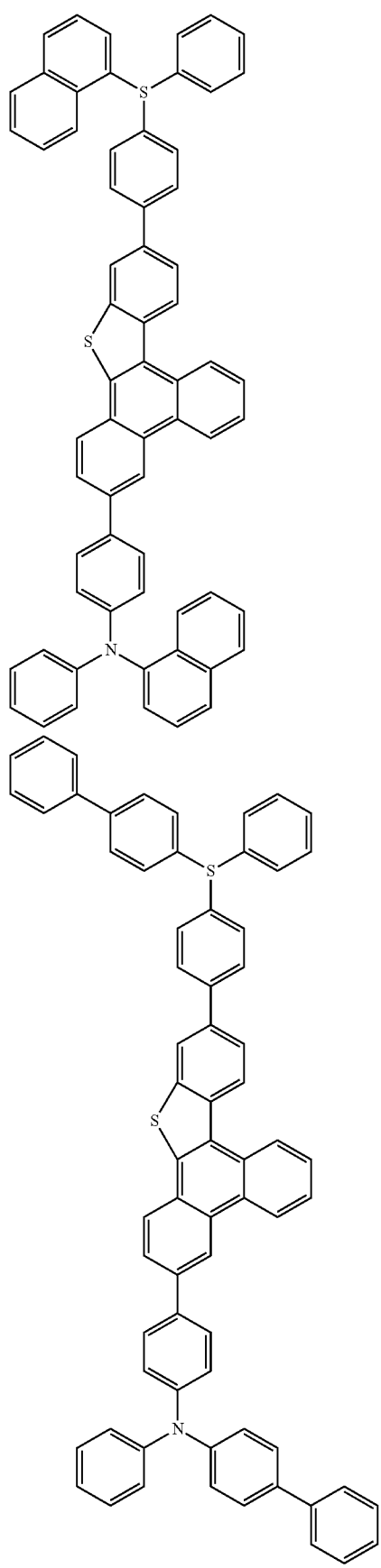
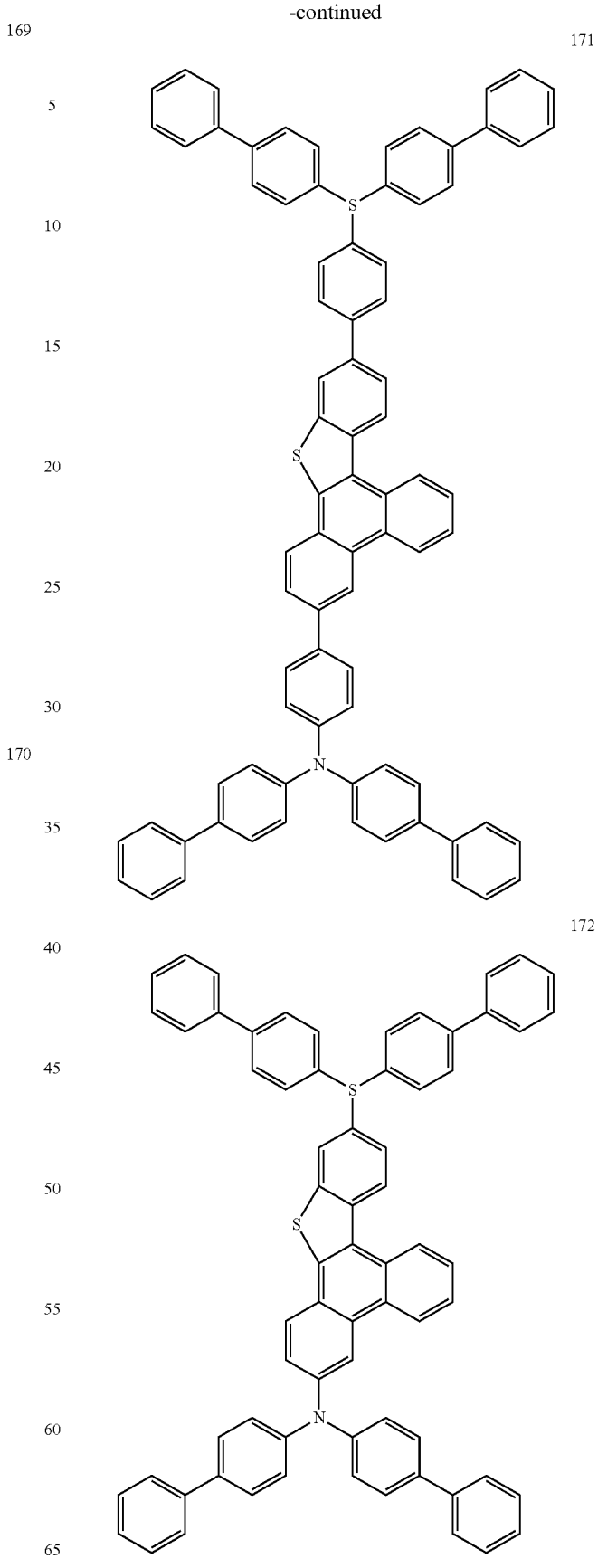

115
-continued
173
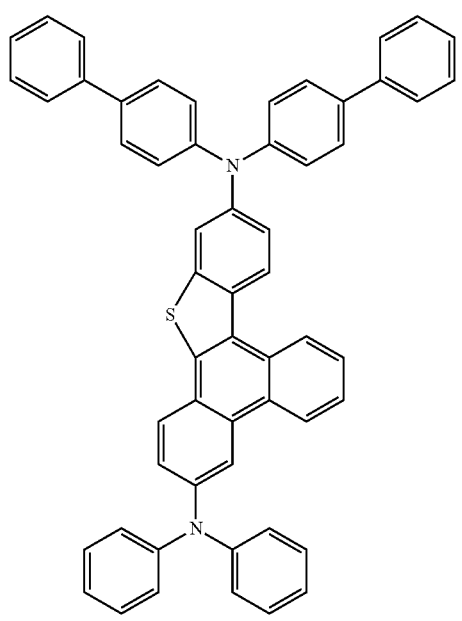
174
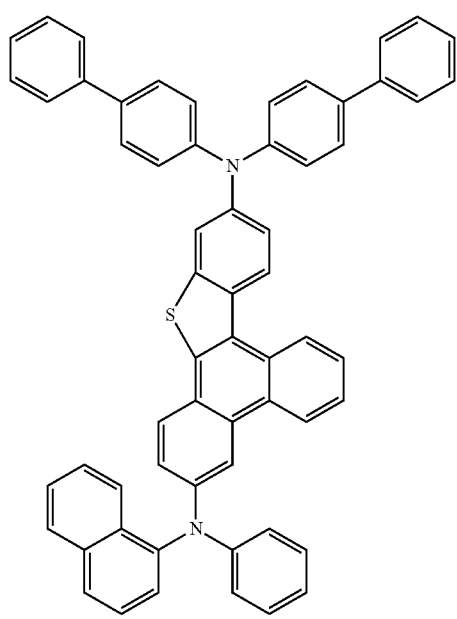
116
-continued
175
4
176
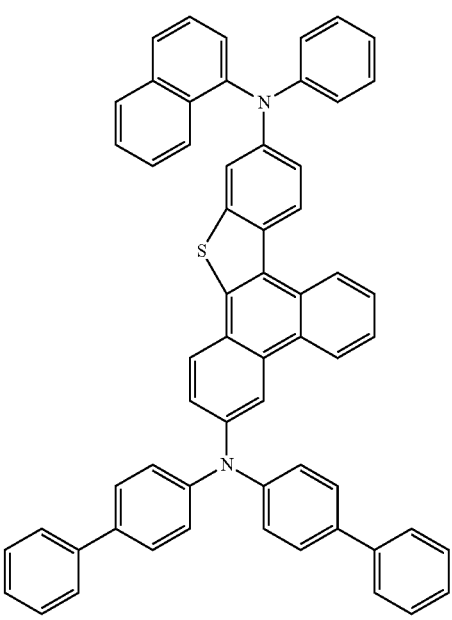

117
-continued
118
-continued
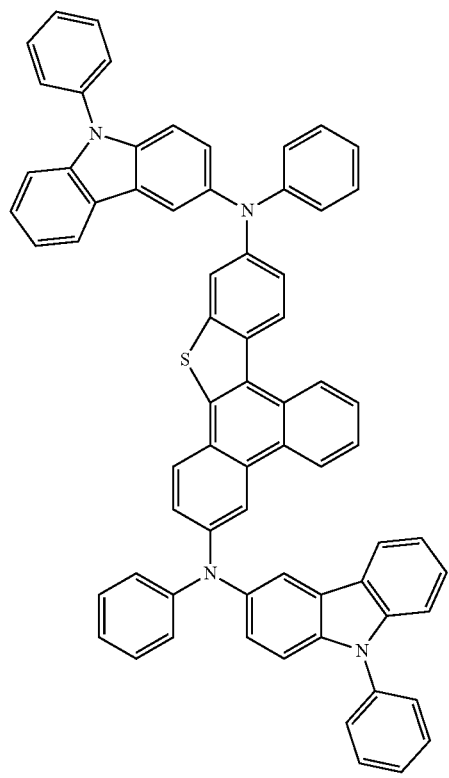
177
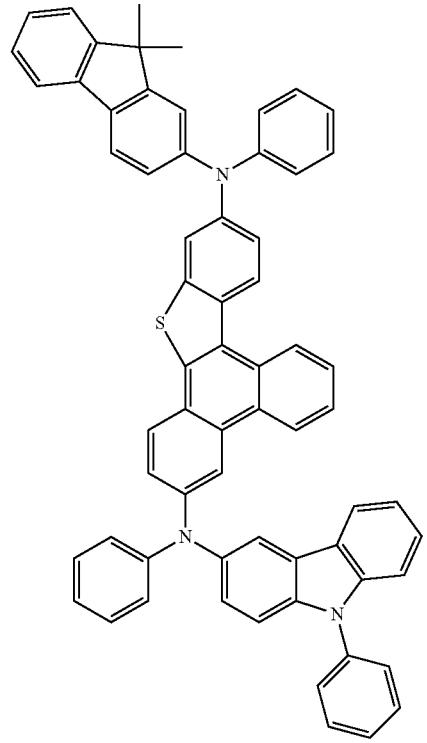
179
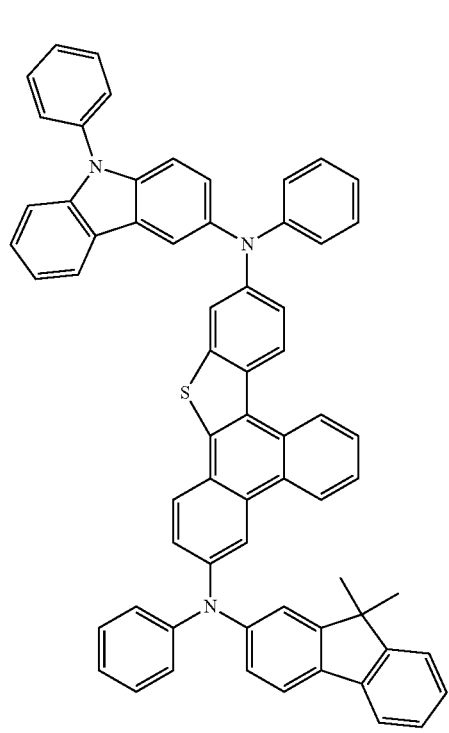
178
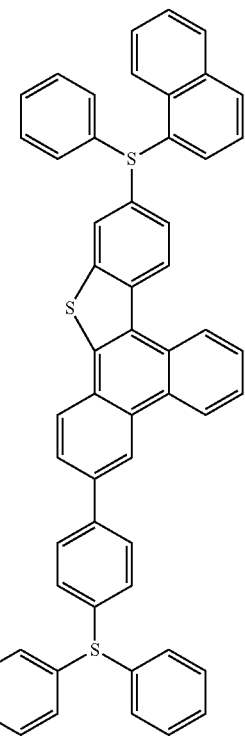
180

119
-continued
120
-continued
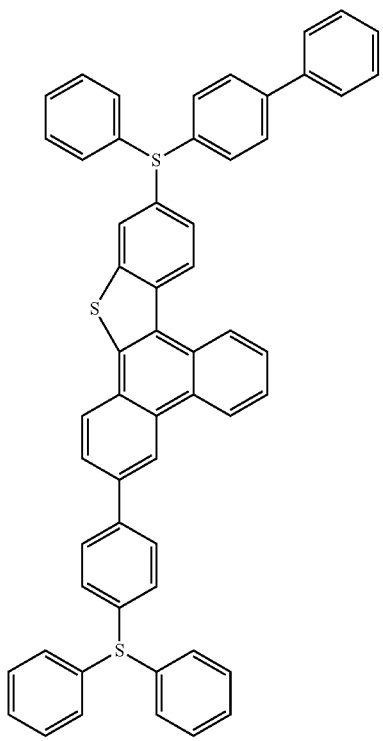
181
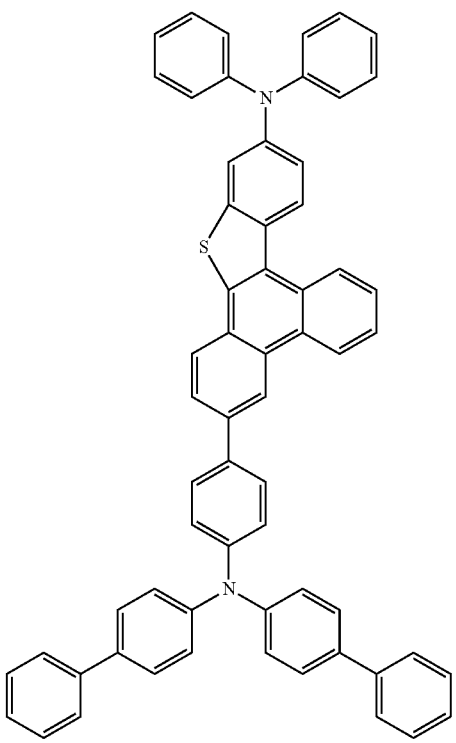
183
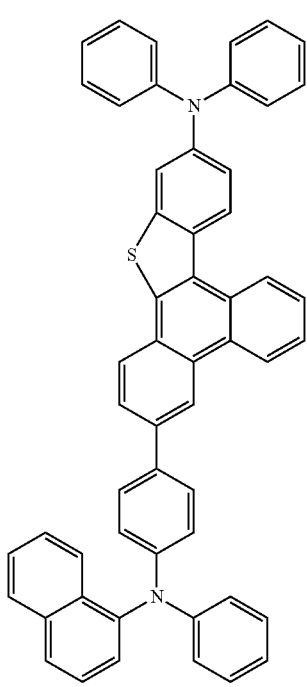
182
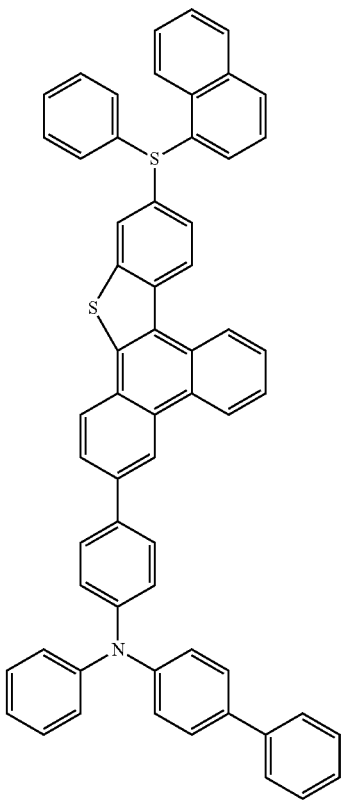
184

121
-continued
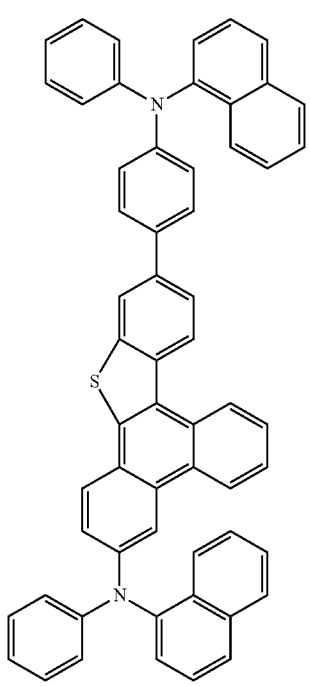
185
122
-continued
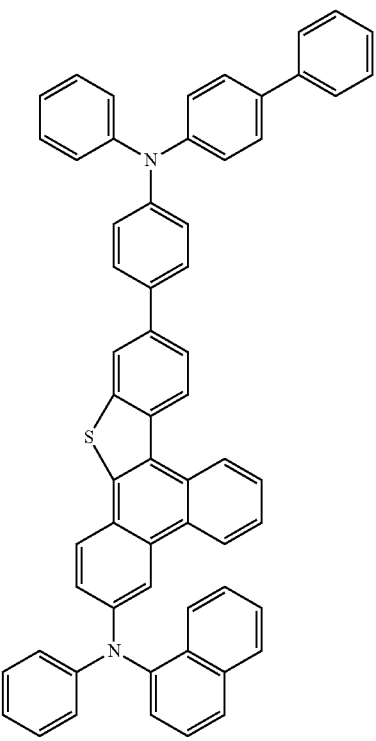
187
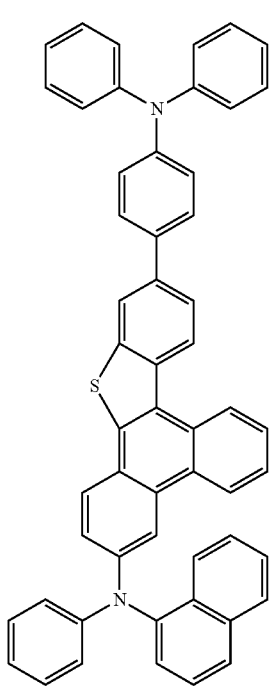
186
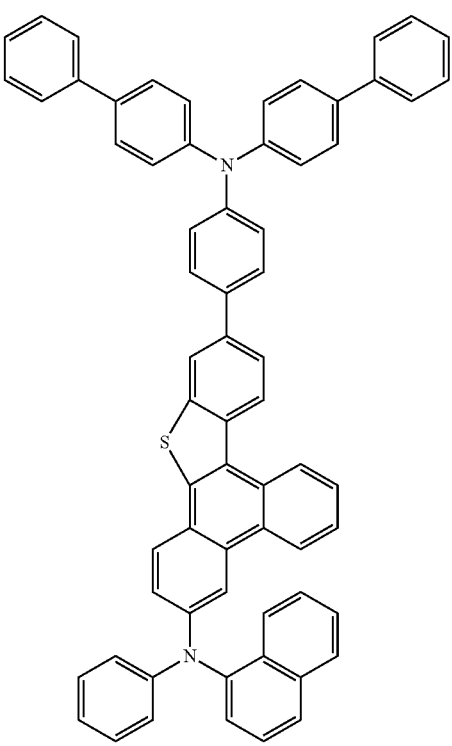
188

123
-continued
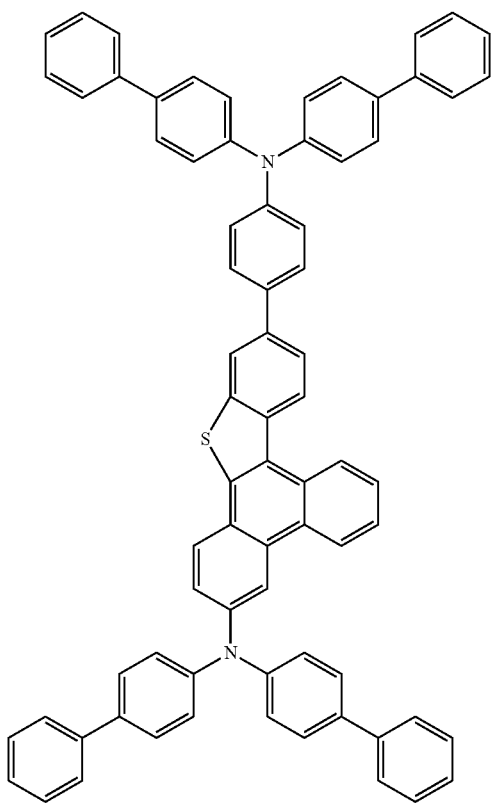
189
124
-continued
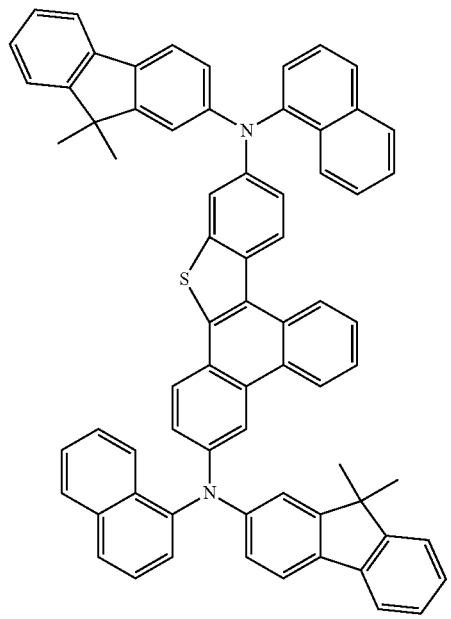
191
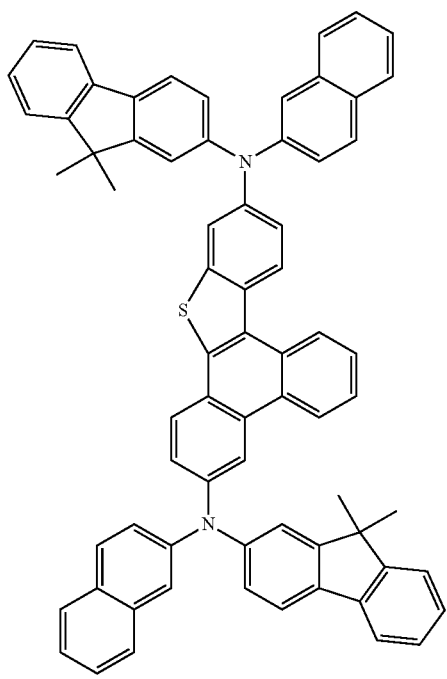
190
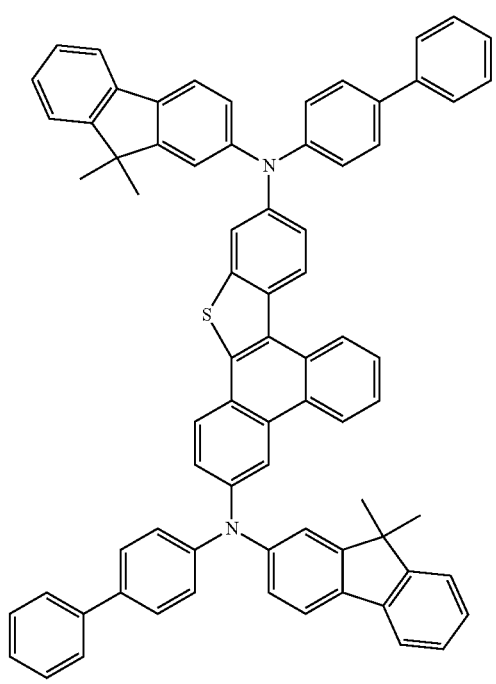
192

125
-continued
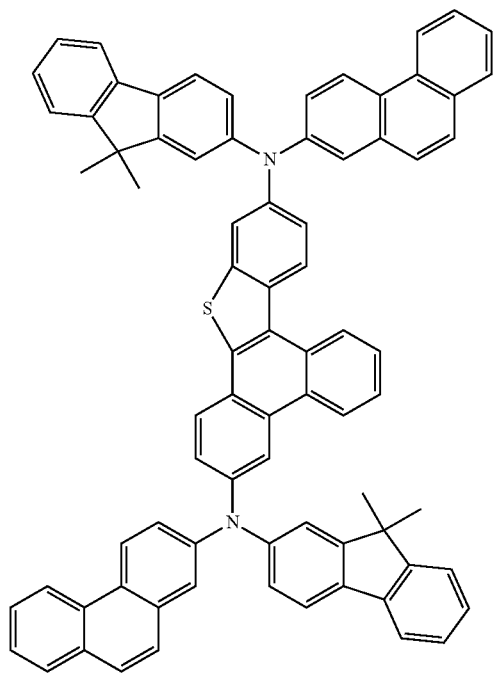
193
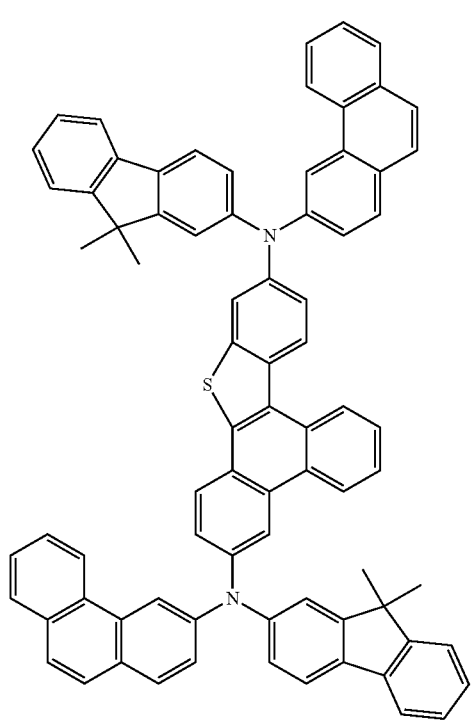
194
126
-continued
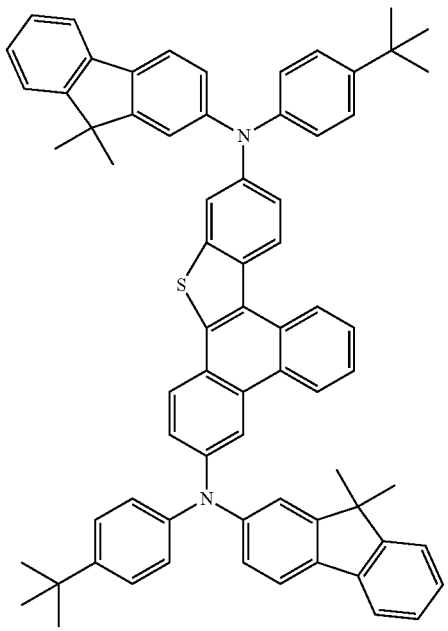
195
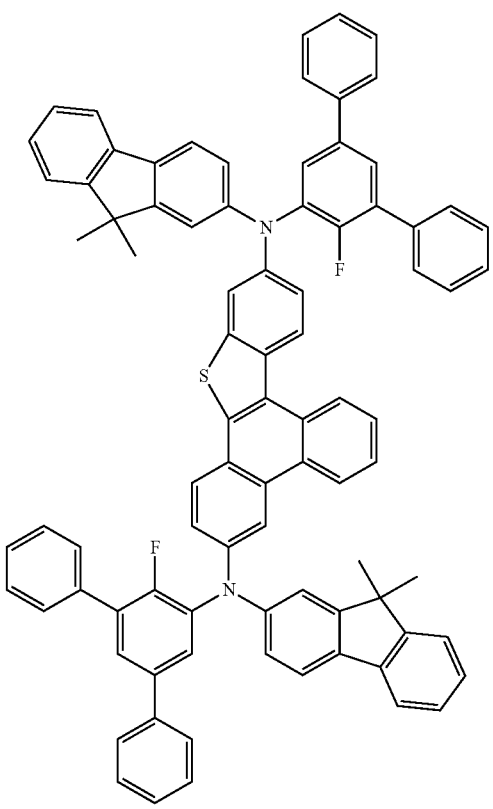
196

127-continued
197
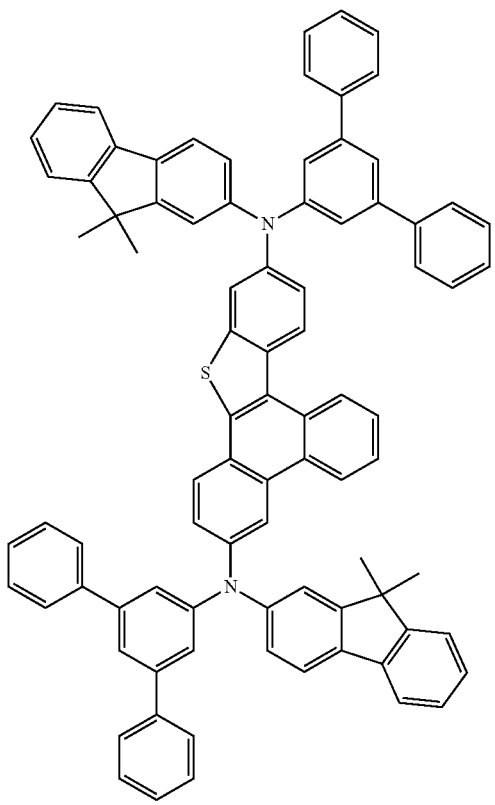
198
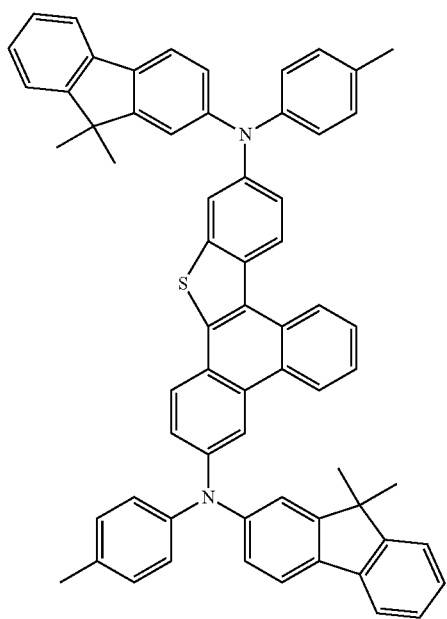
128-continued
199
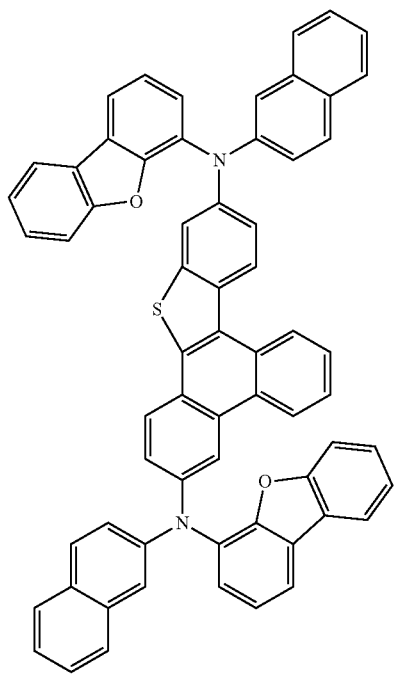
200
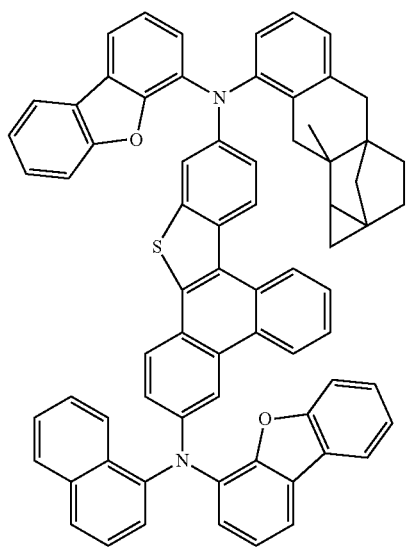

129
-continued
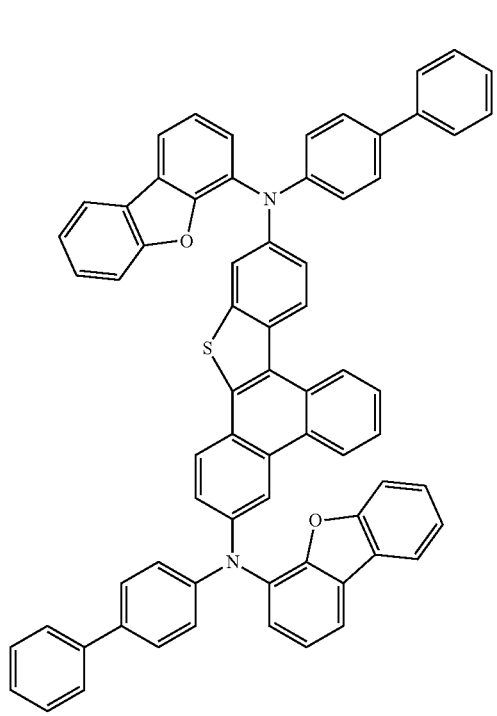
201
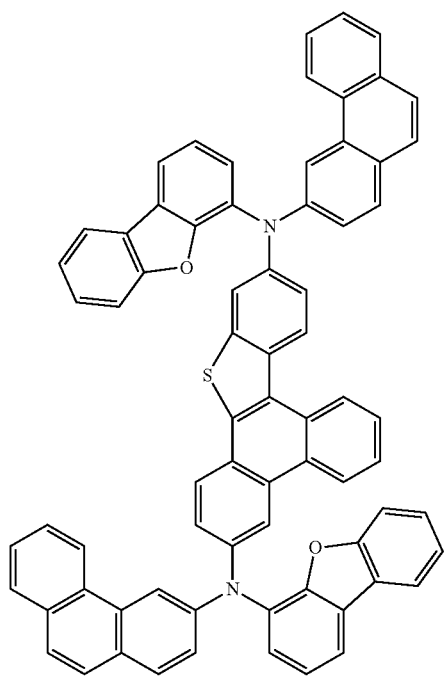
202
130
-continued
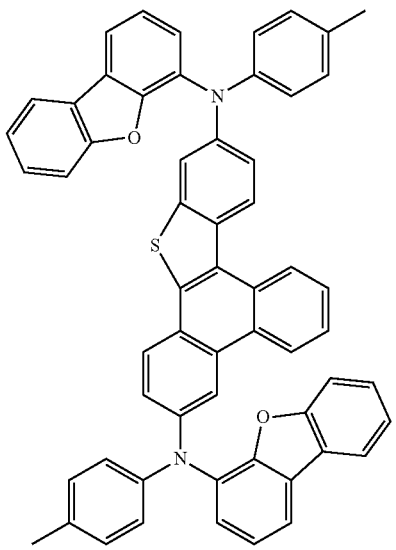
203
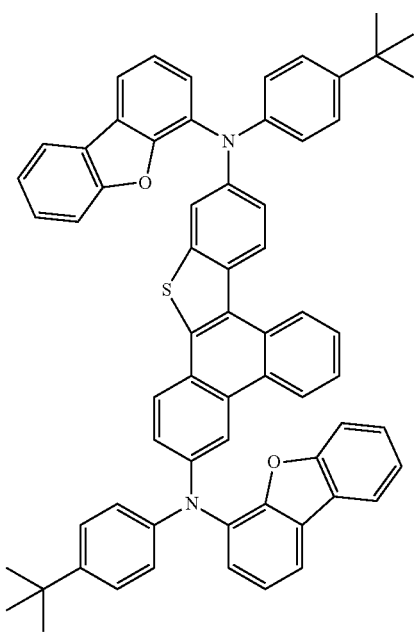
204

-continued
205
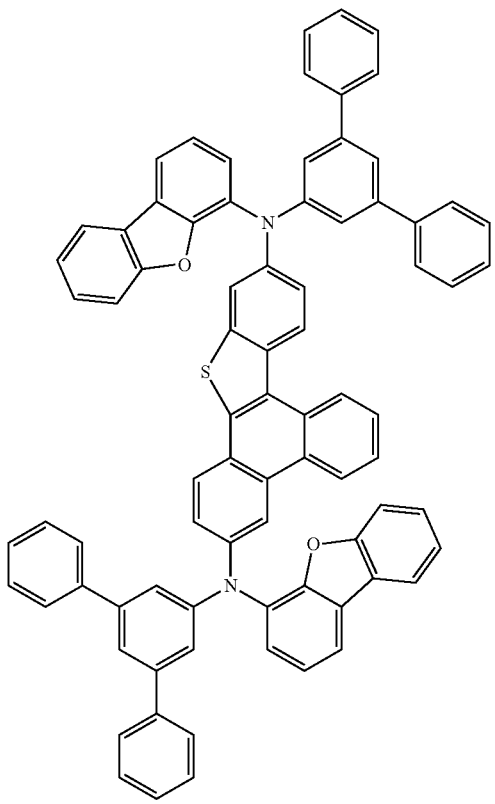
206
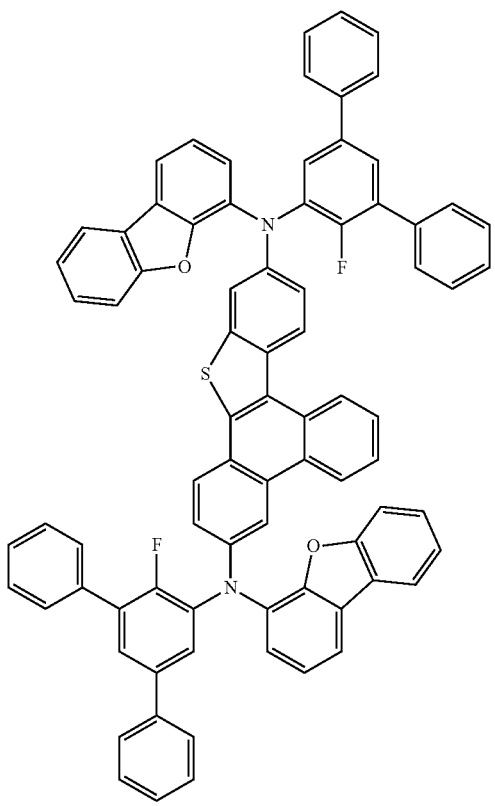
-continued
207
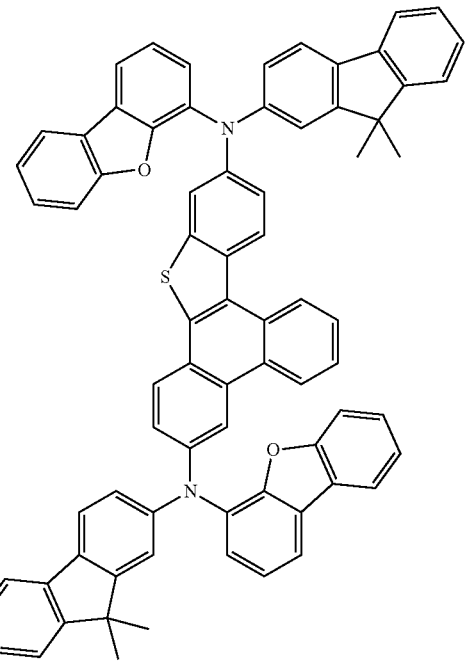
208
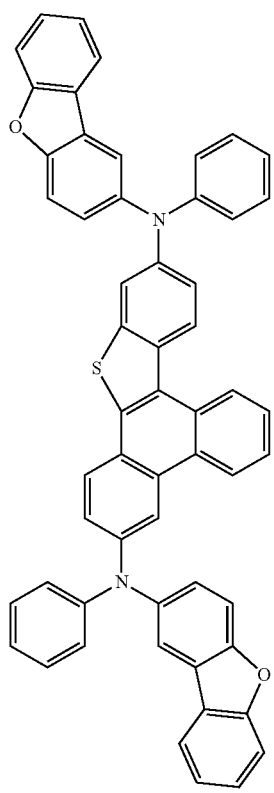

133
-continued
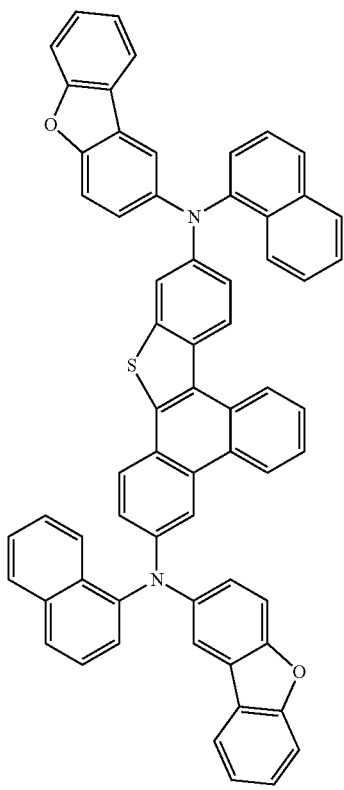
134
-continued
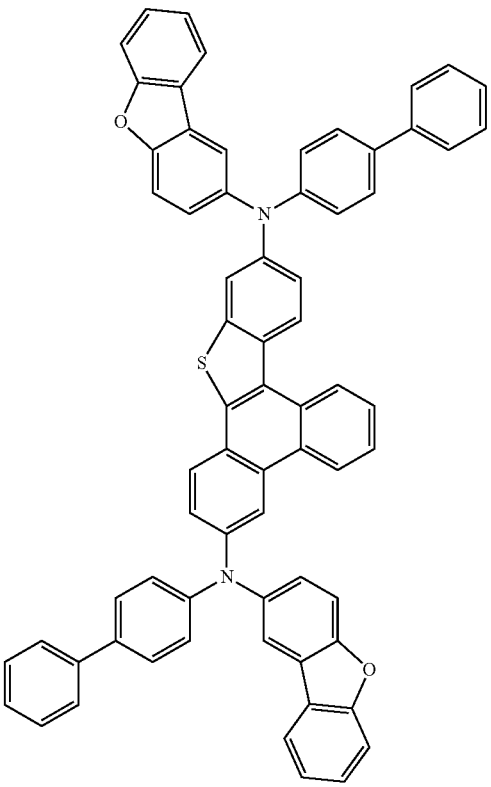
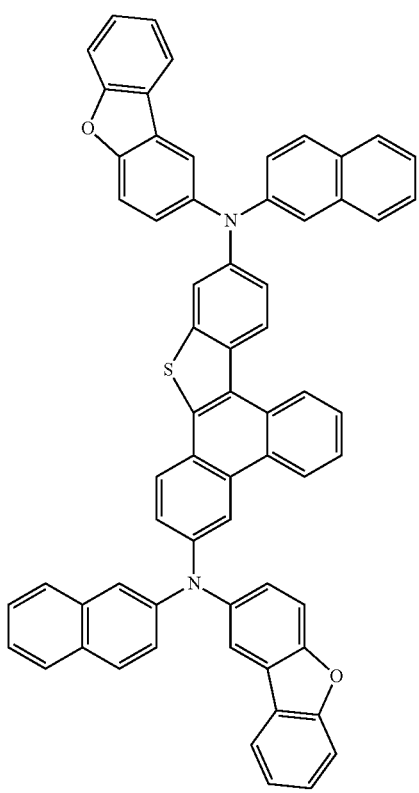
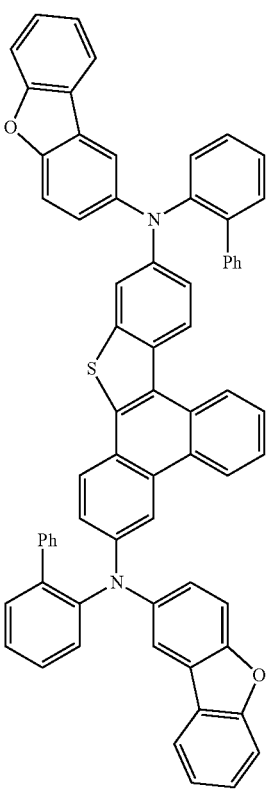

135
-continued
136
-continued
213
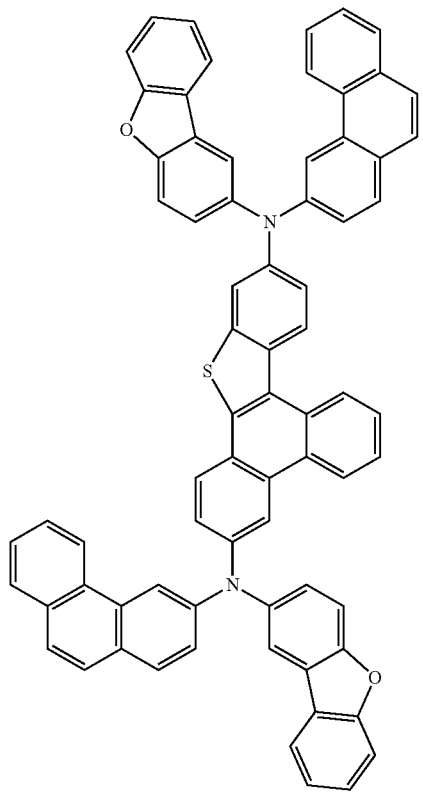
215
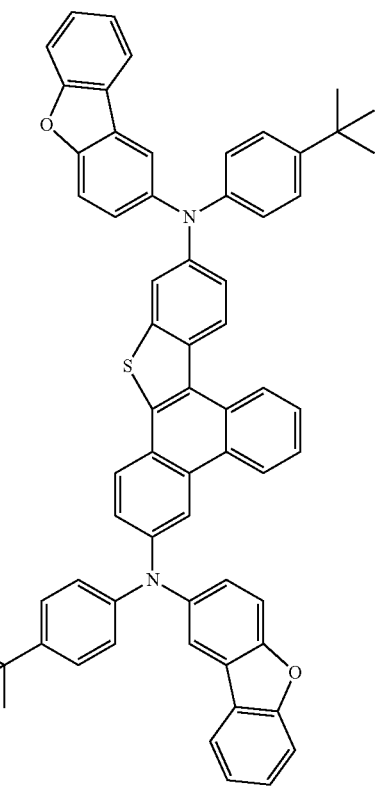
214
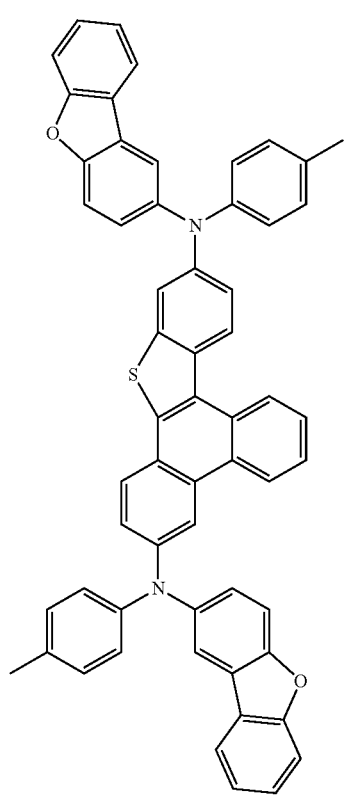
216
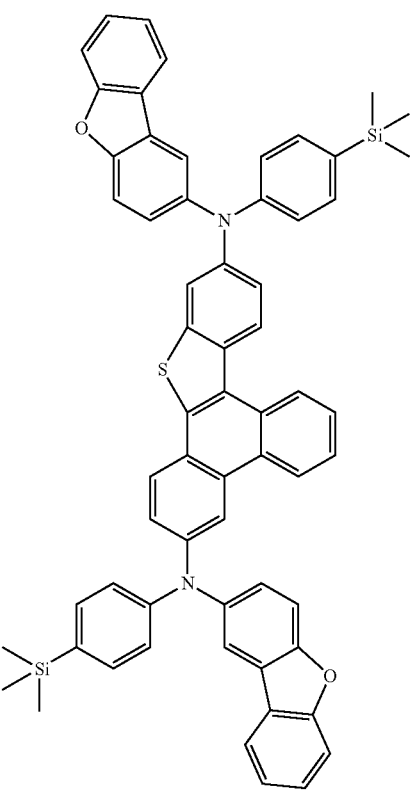

-continued
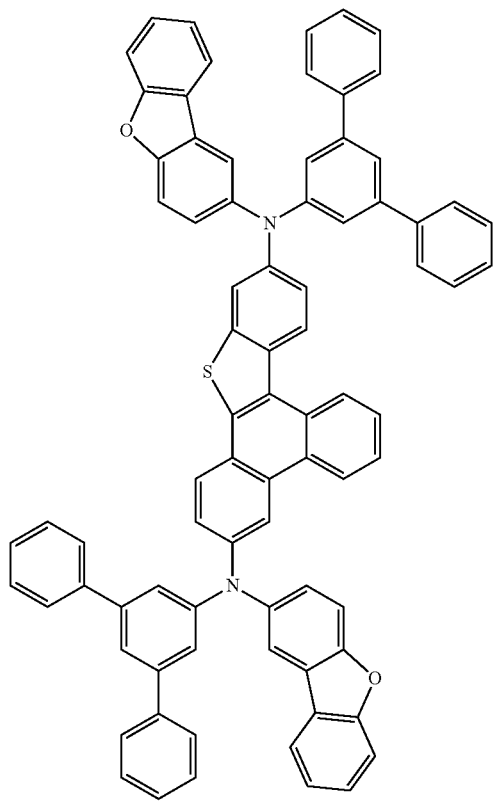
217
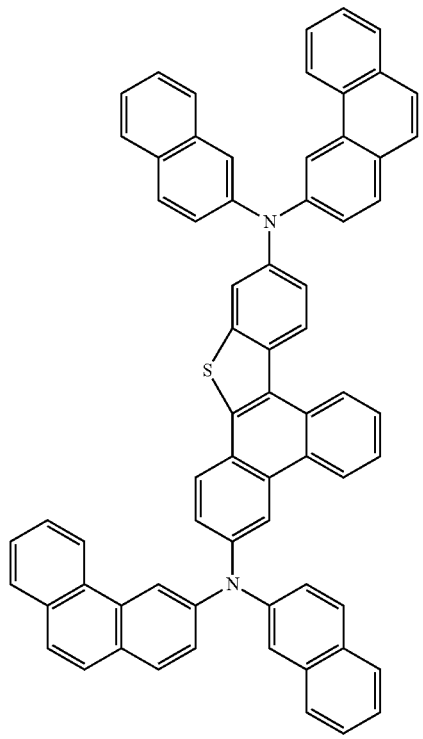
218
-continued
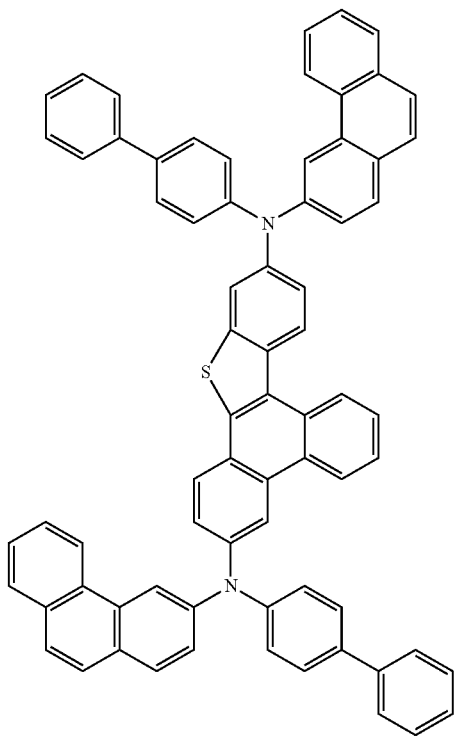
219
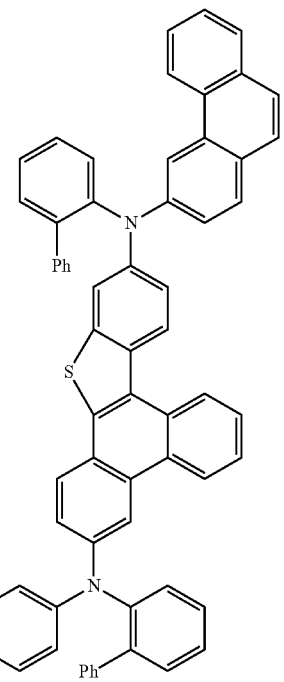
220

-continued
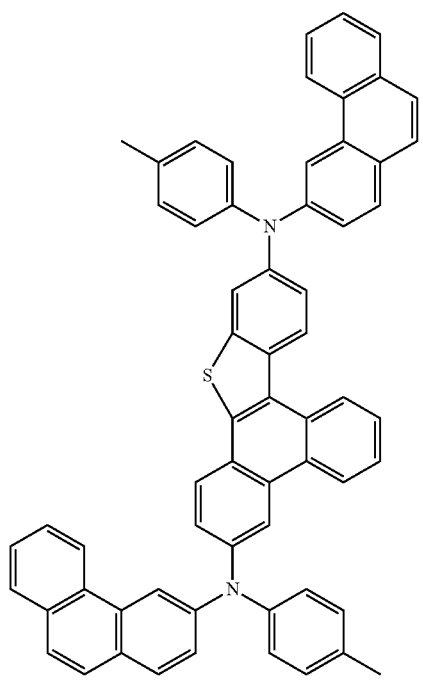
221
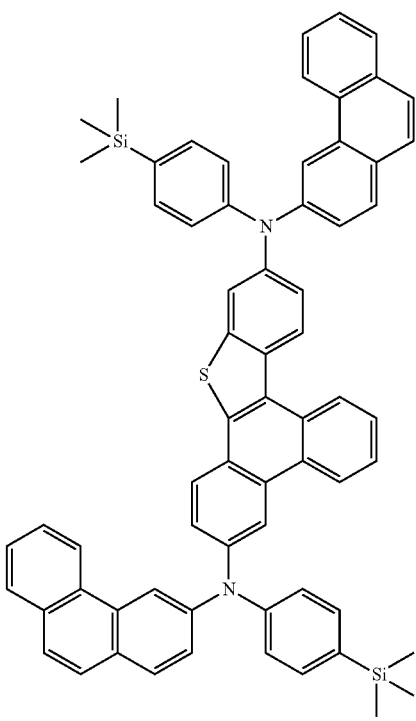
223
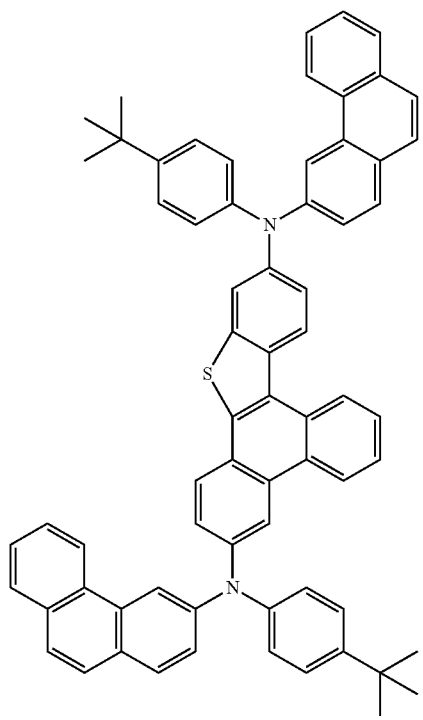
222
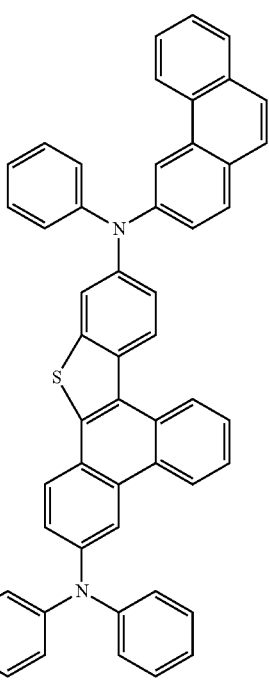
224

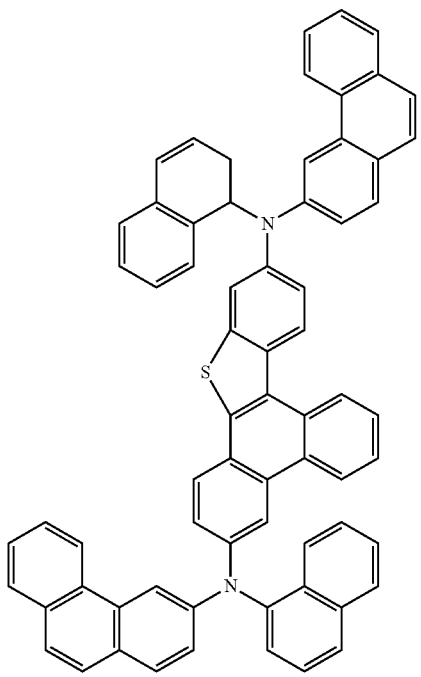
225
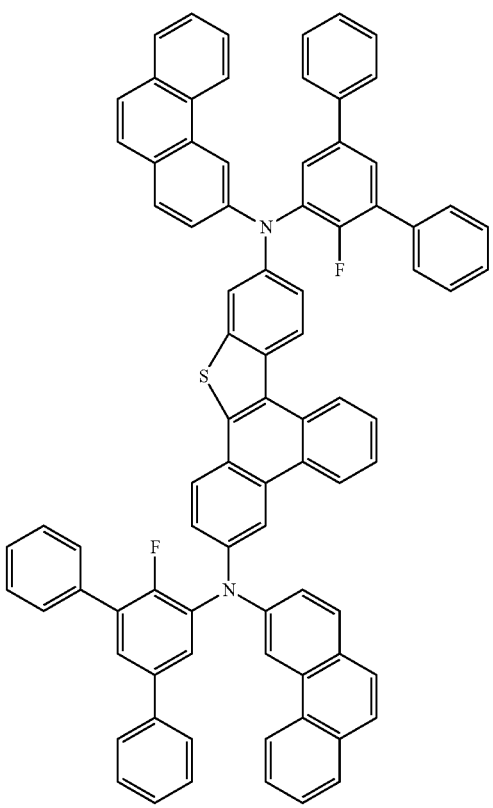
227
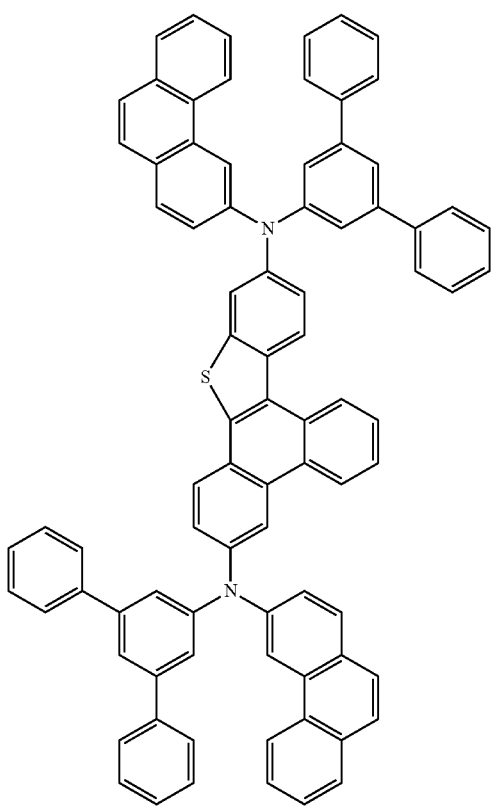
226
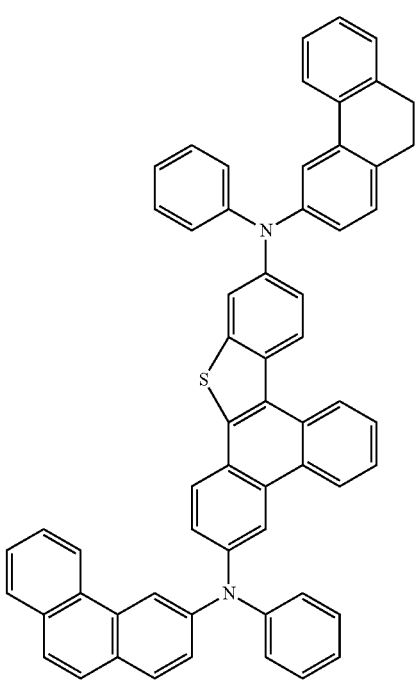
228

143
-continued
229
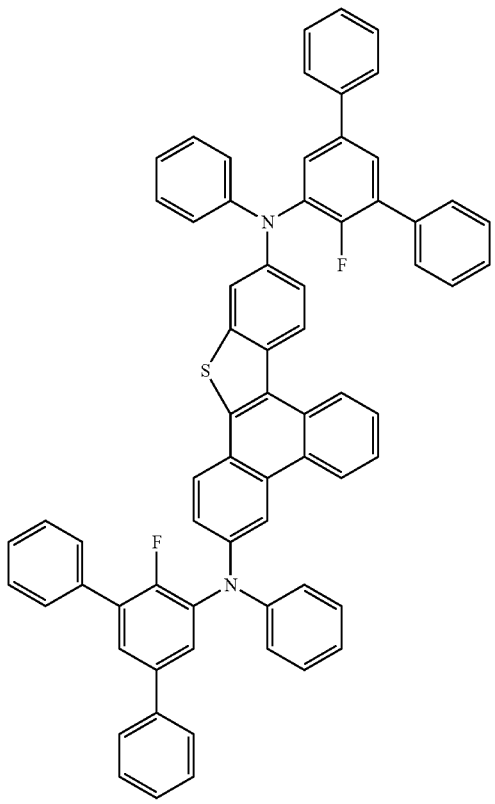
230
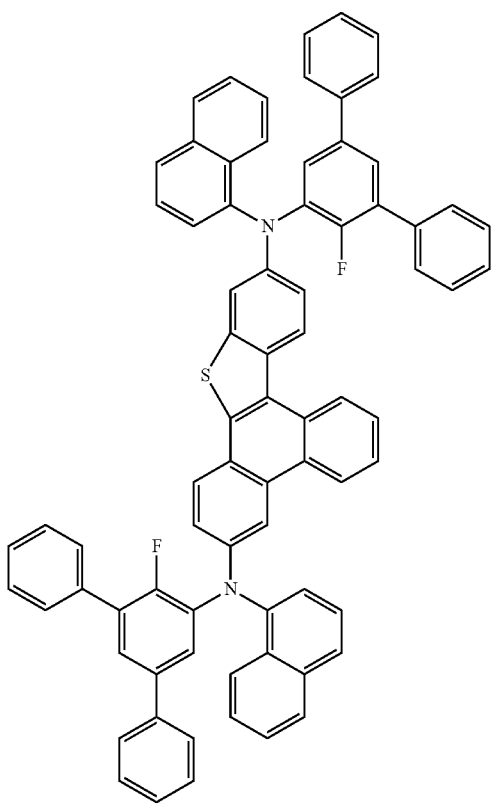
144
-continued
231
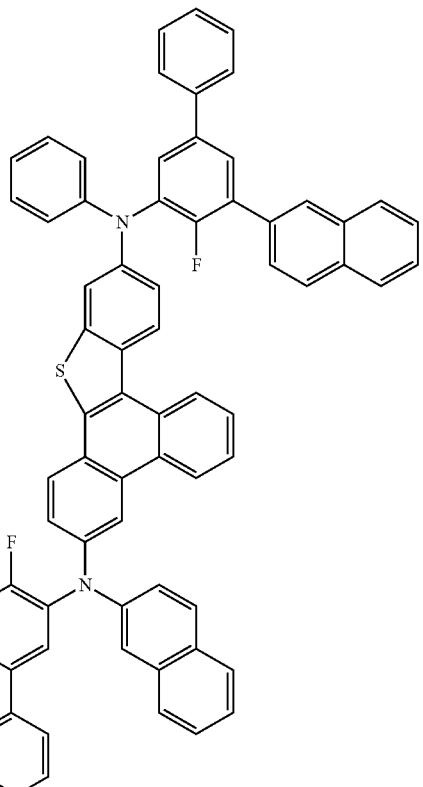
232
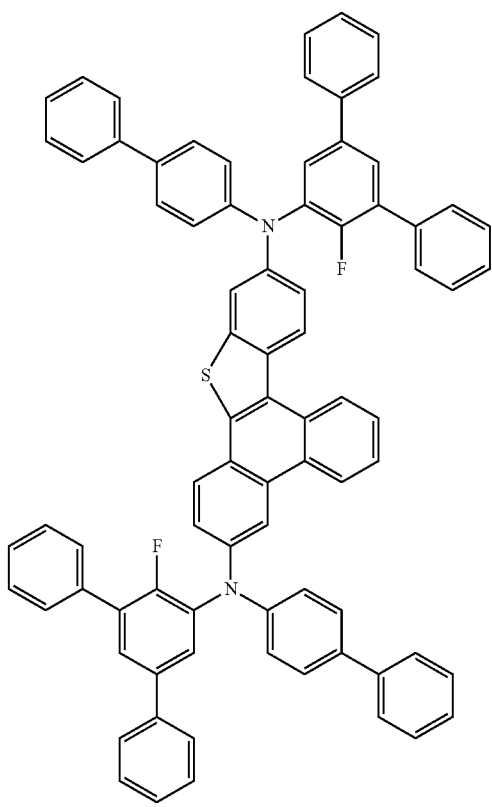

-continued
233
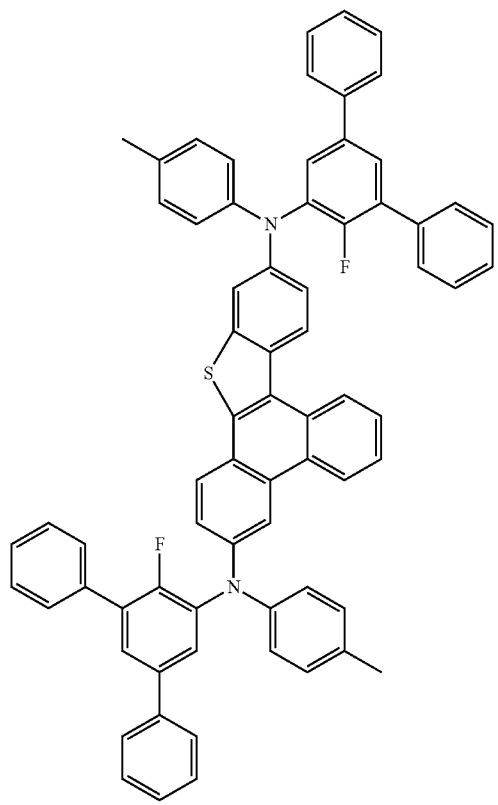
235
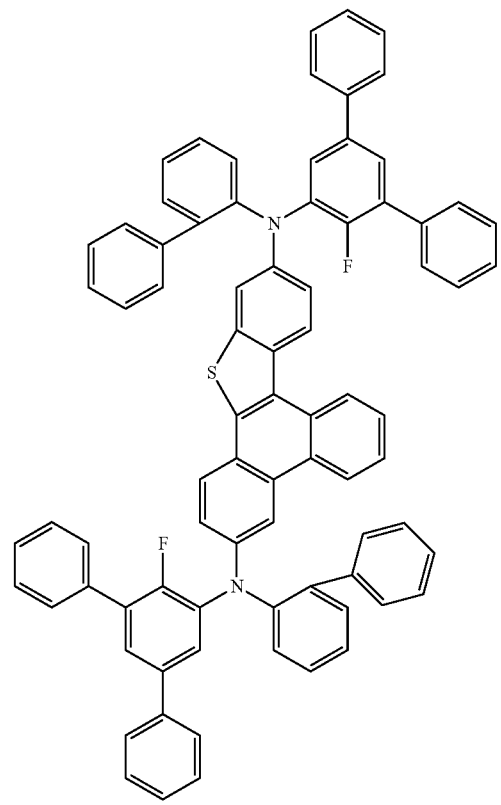
234
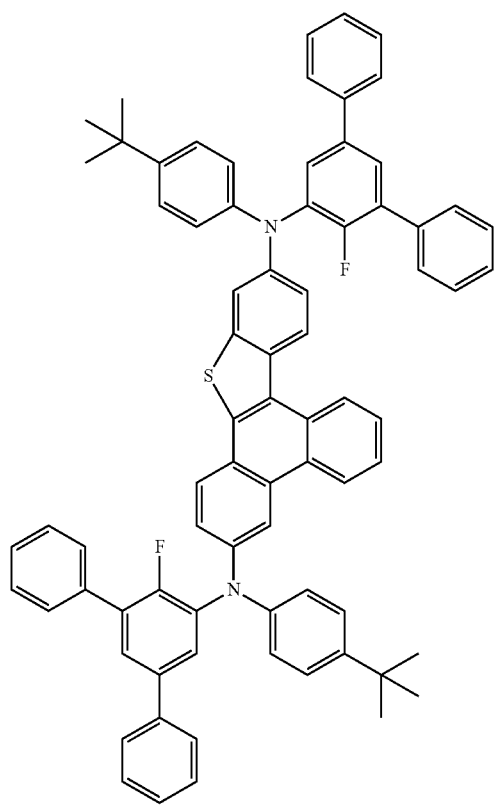
236
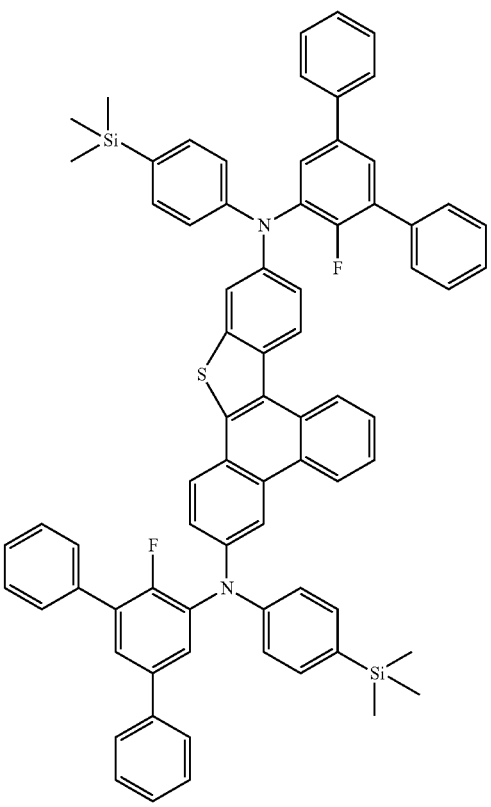

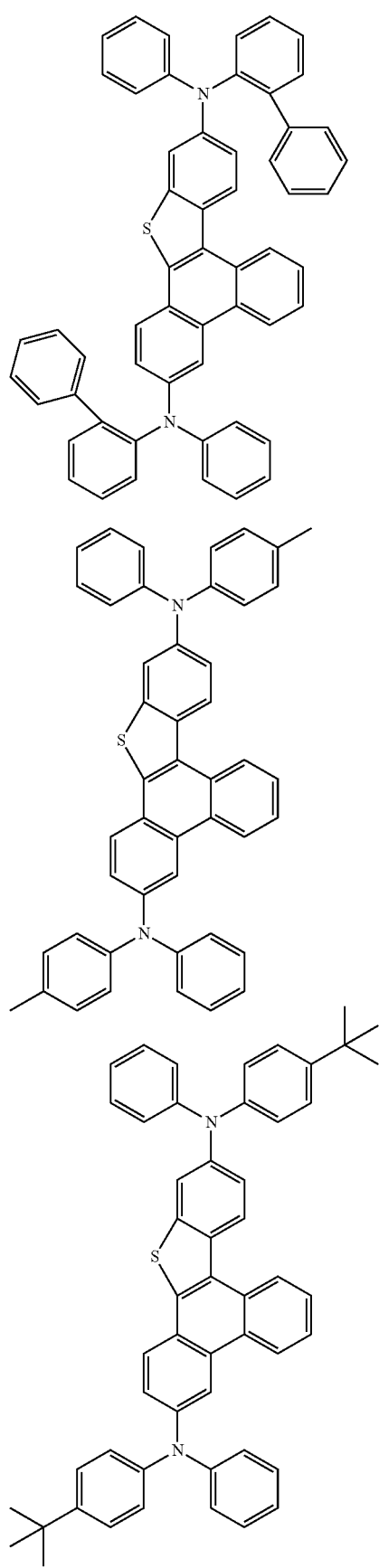
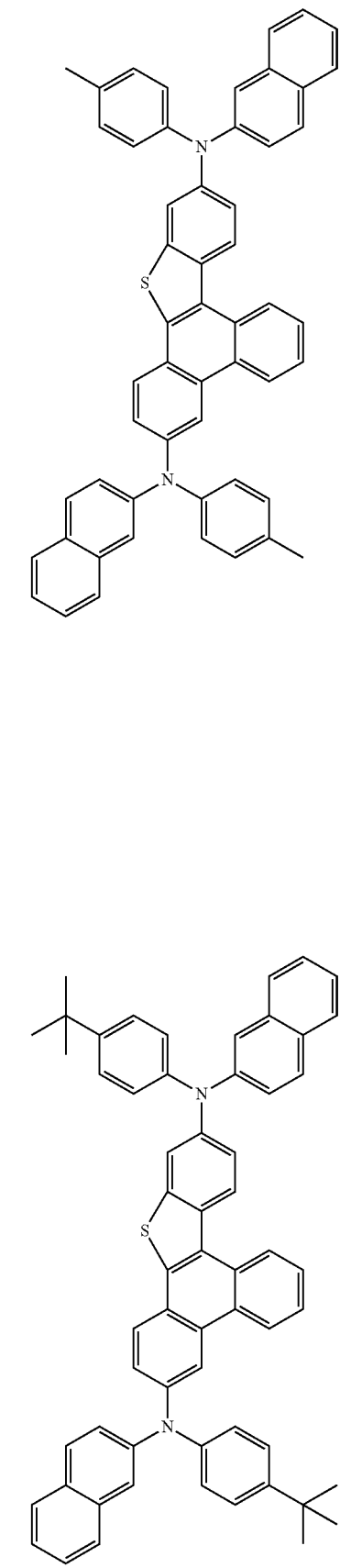

149
-continued
150
-continued
242
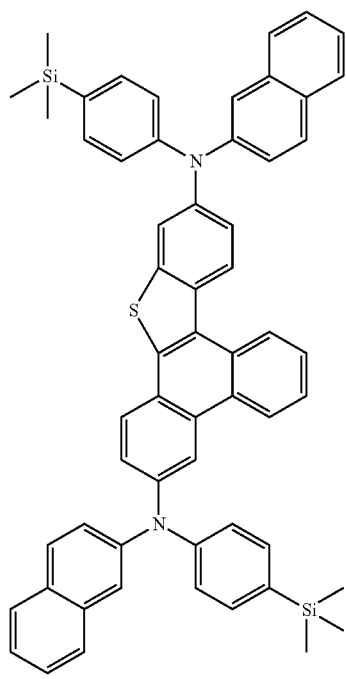
244
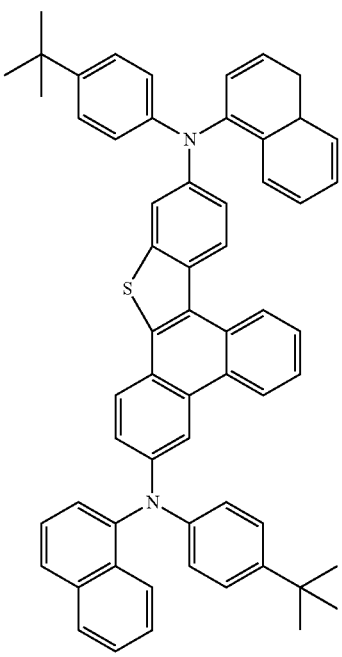
243
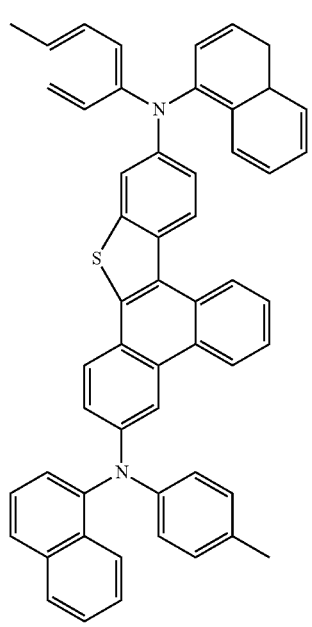
245
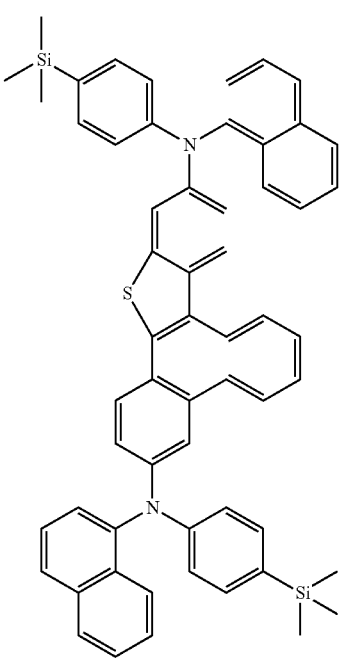

246
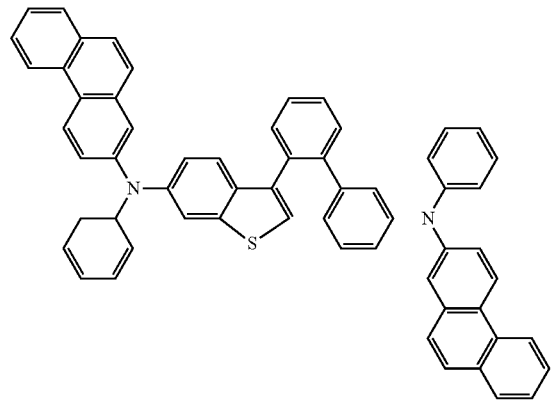
247
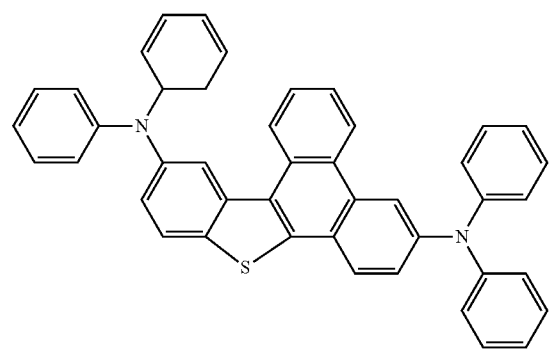
248
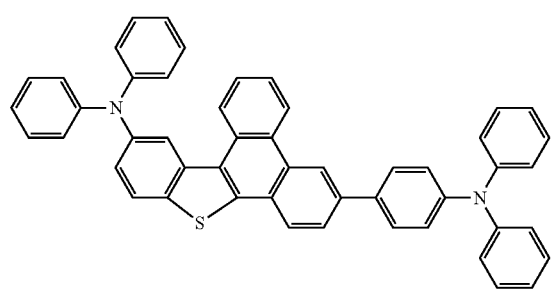
1A
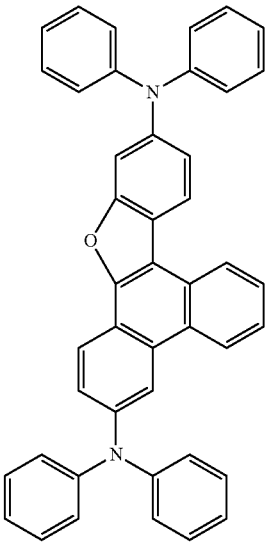
2A
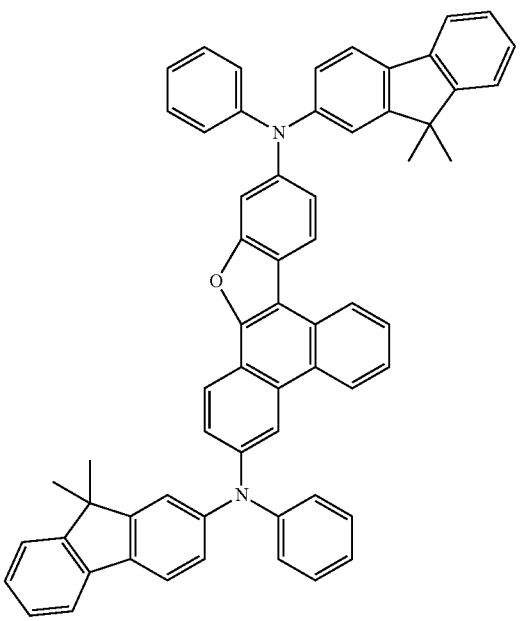

153
-continued
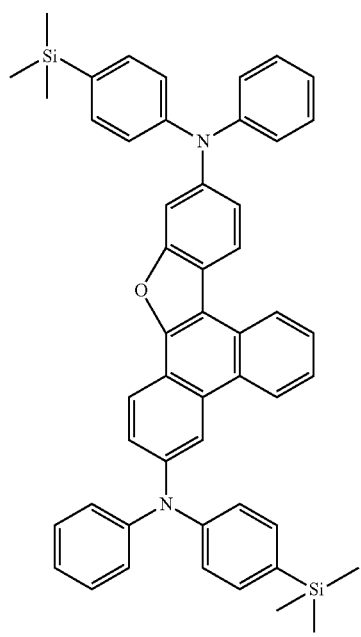
154
-continued
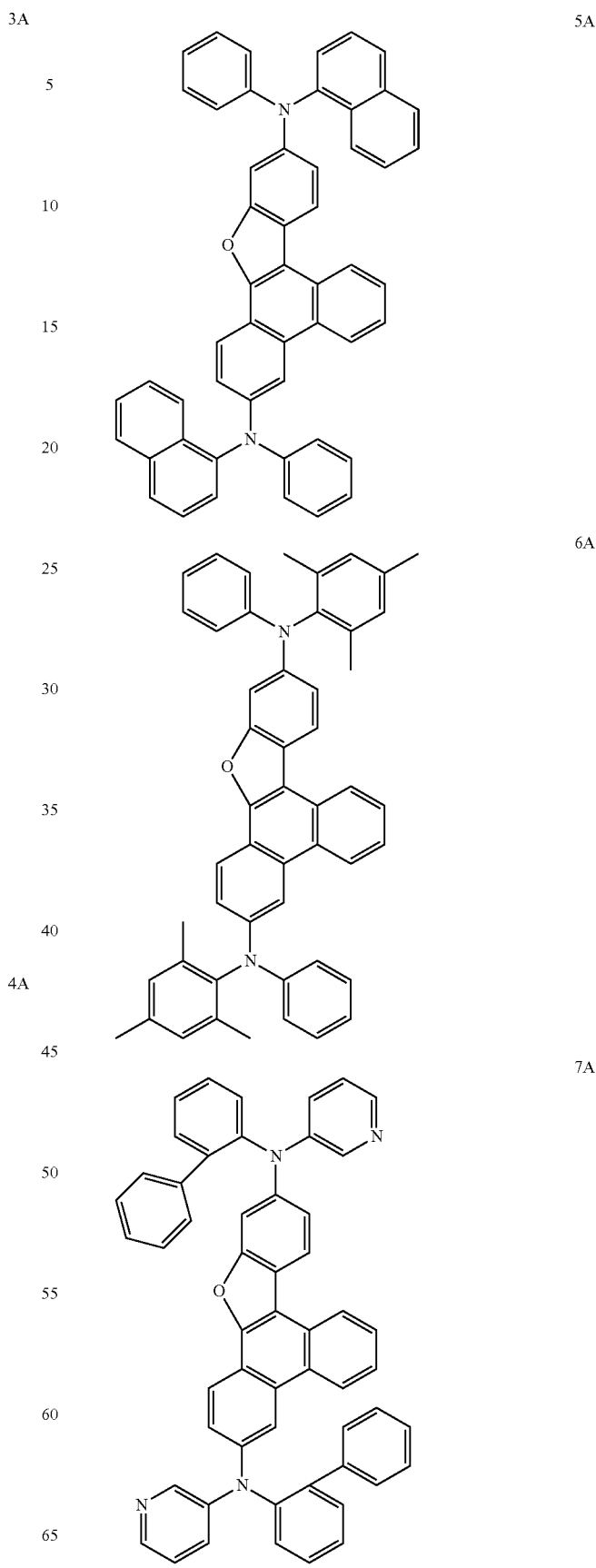
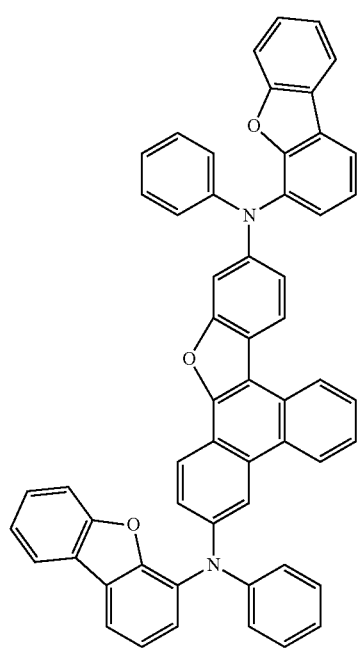

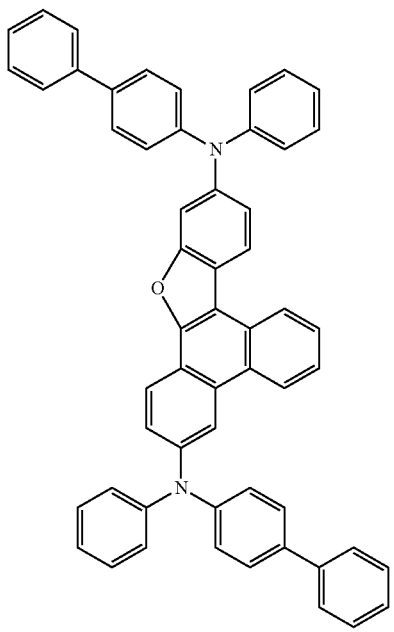
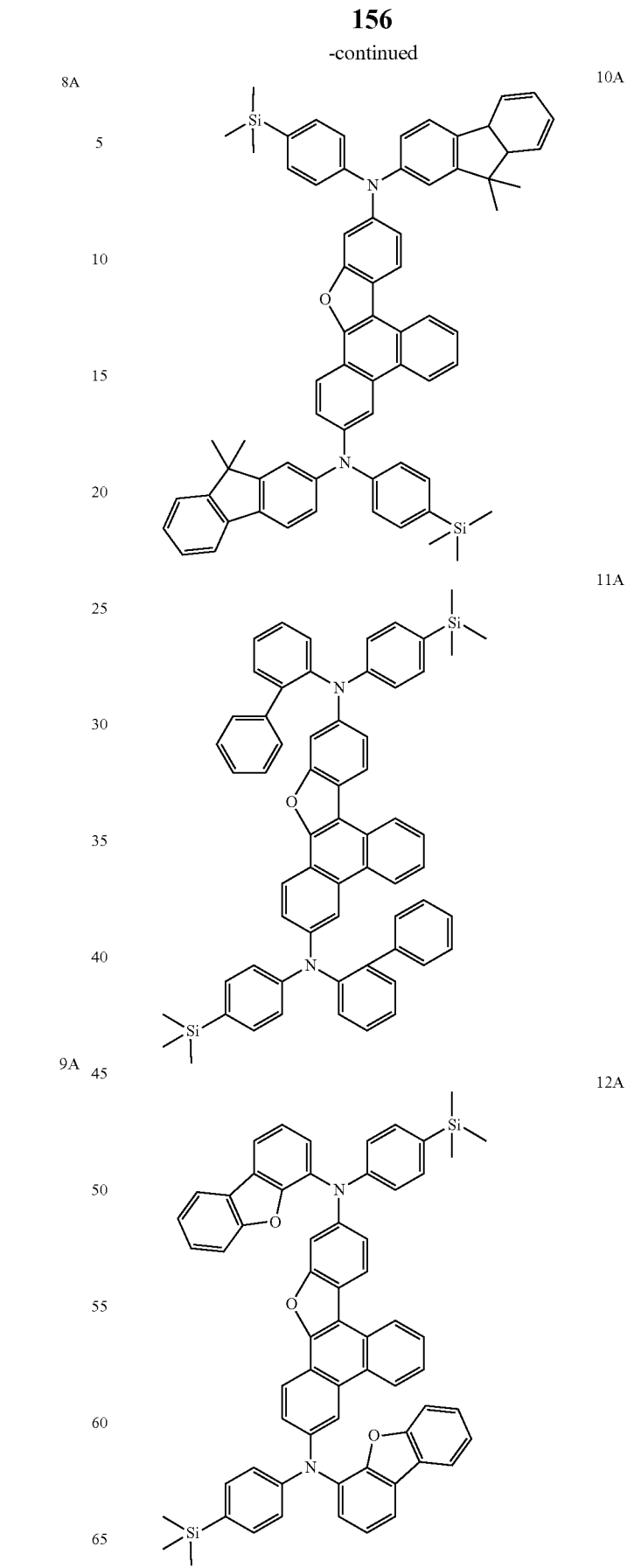

157
-continued
158
-continued
13A
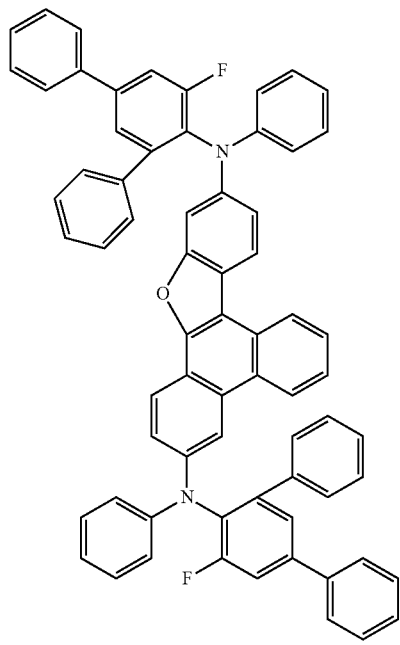
15A
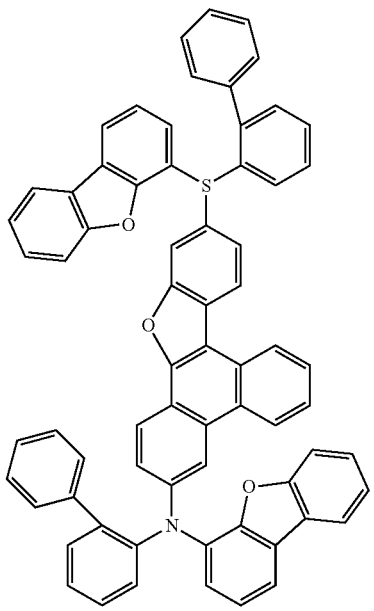
14A
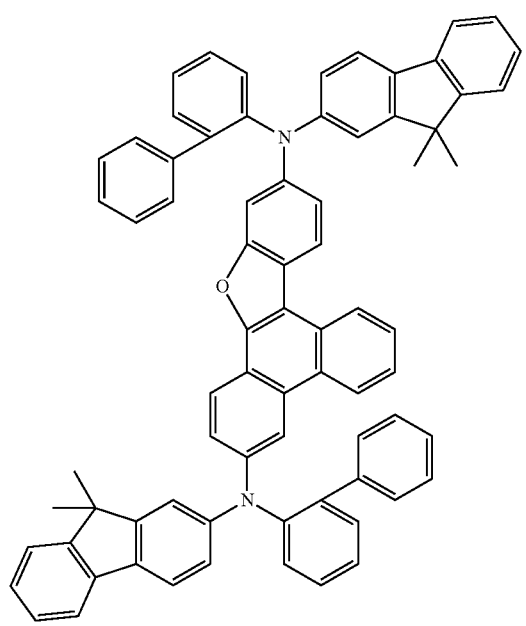
16A
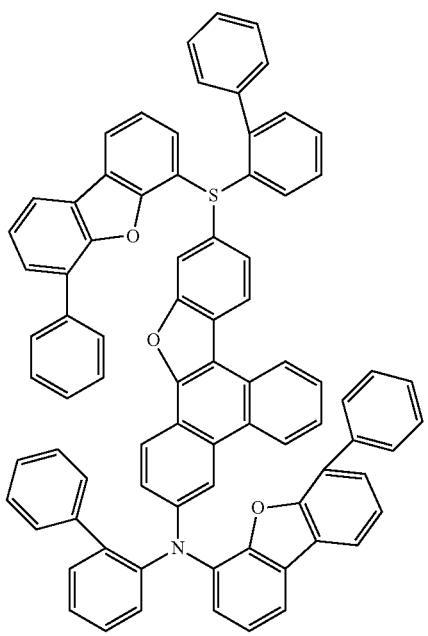

159
-continued
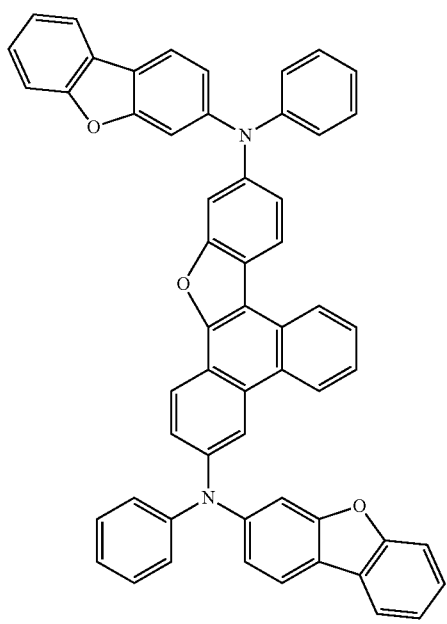
17A
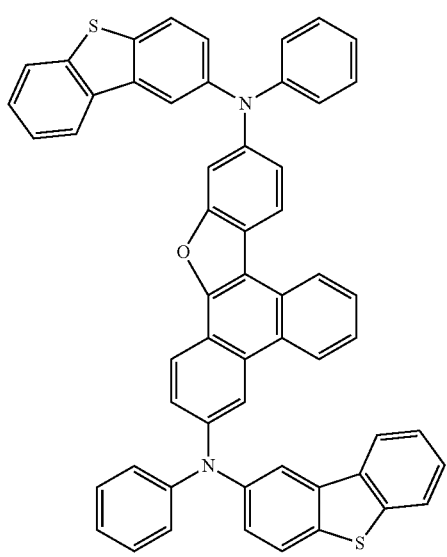
18A
160
-continued
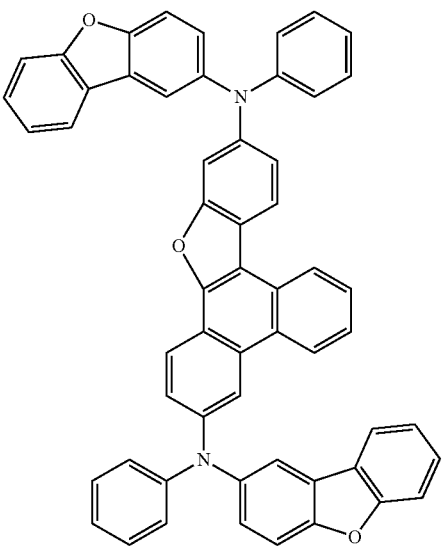
19A
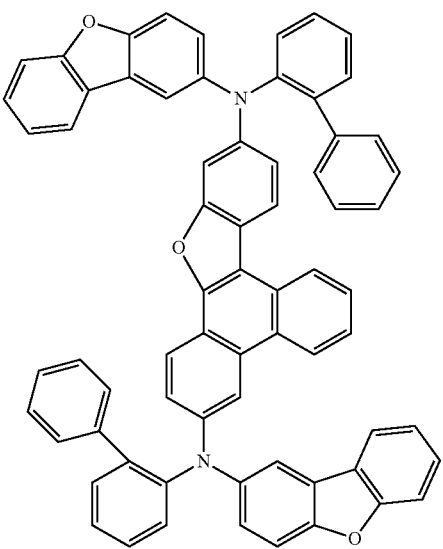
20A

161
-continued
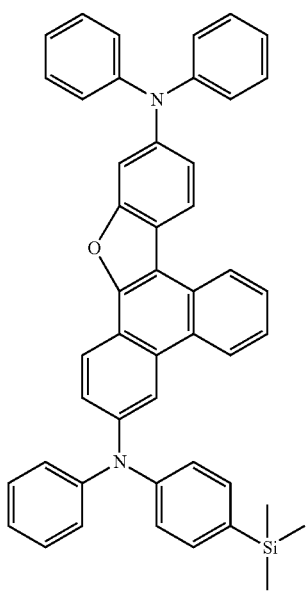
162
-continued
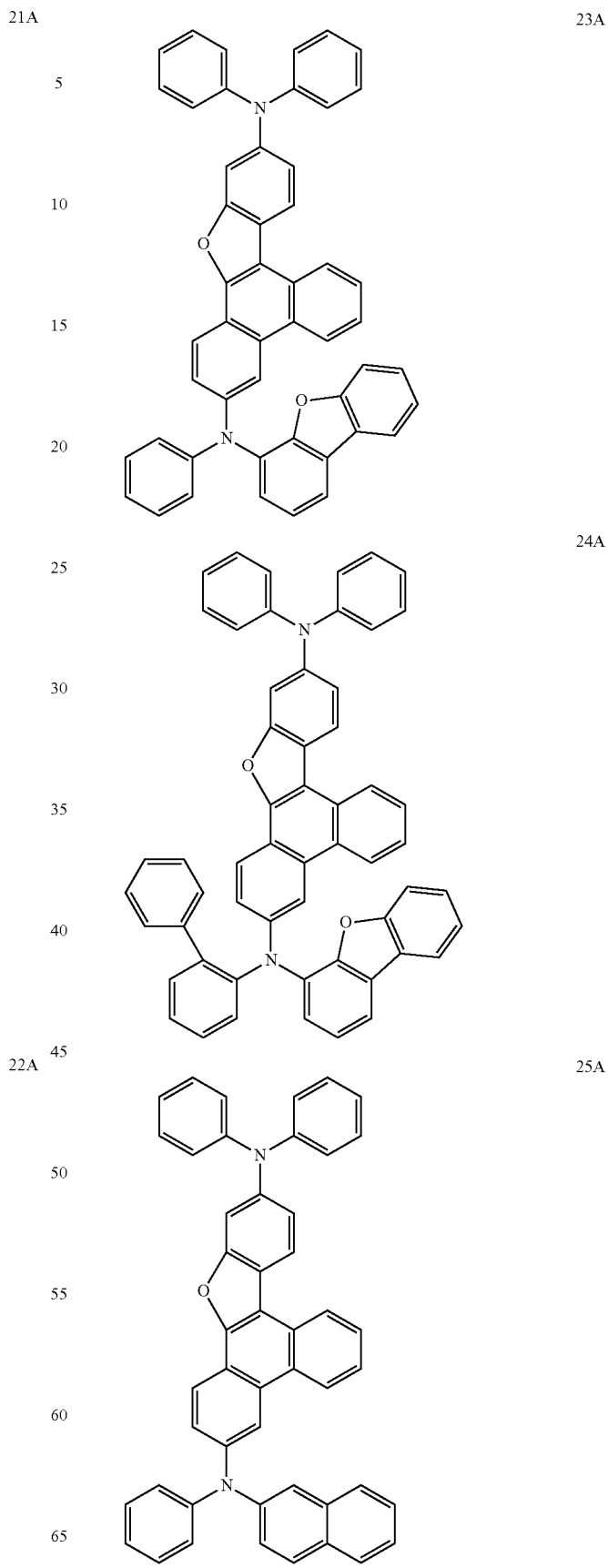
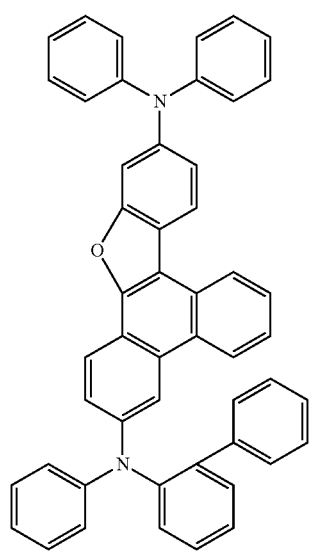

163
-continued
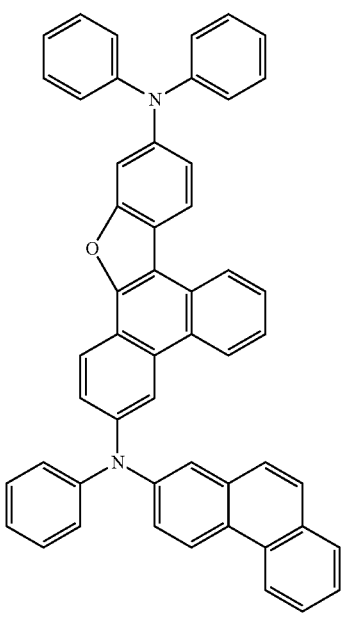
26A
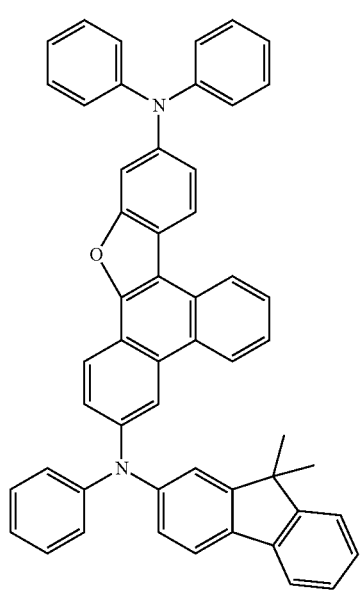
27A
164
-continued
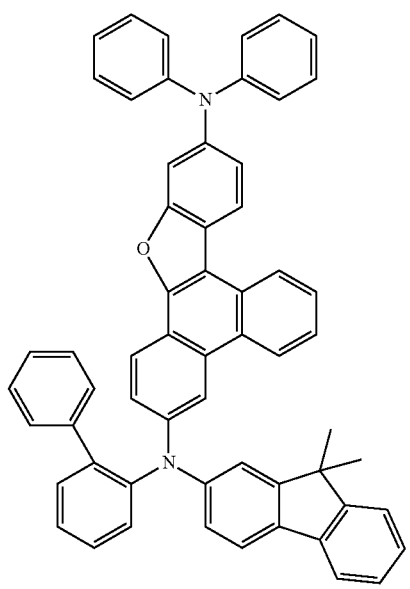
28A
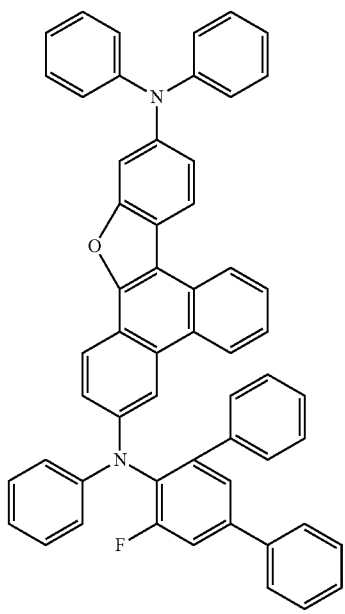
29A 165
-continued
30A
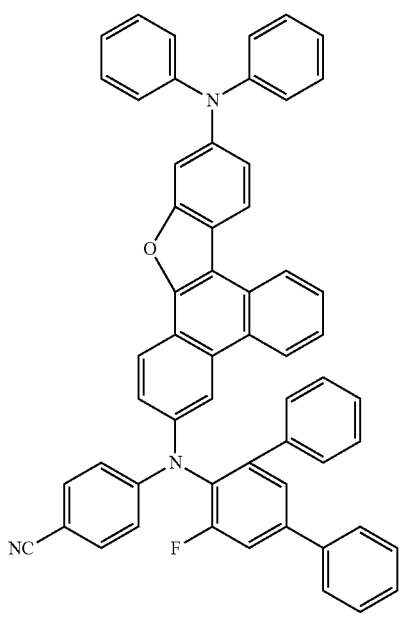
31A
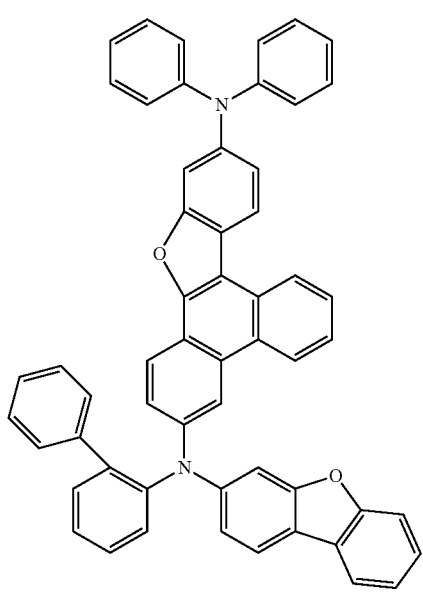
166
-continued
32A
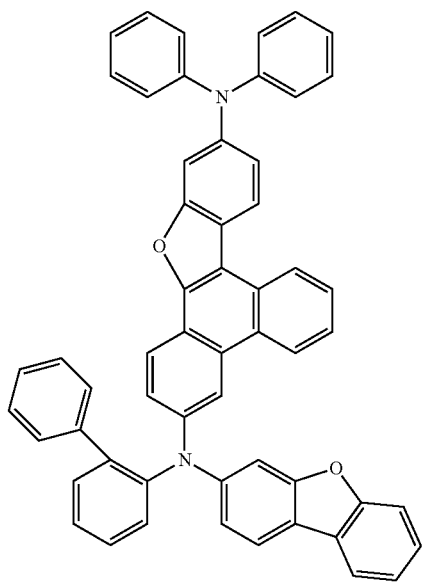
33A
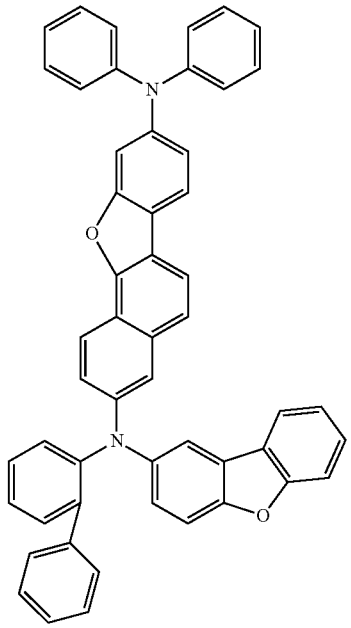

167
-continued
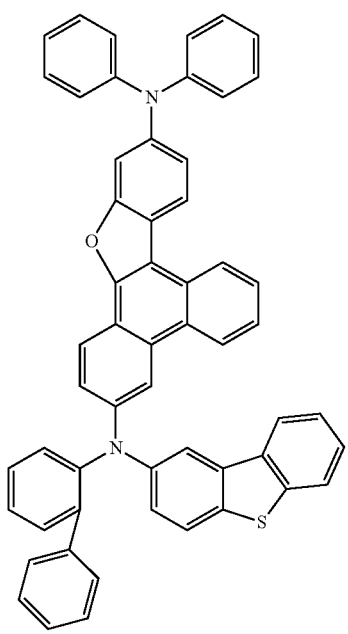
34A
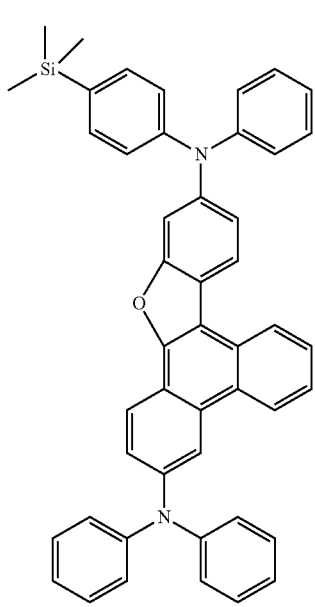
35A
168
-continued
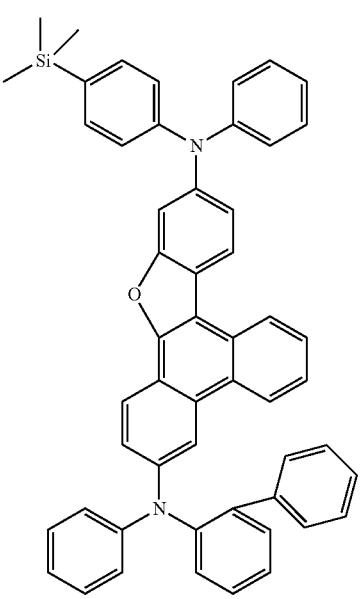
36A
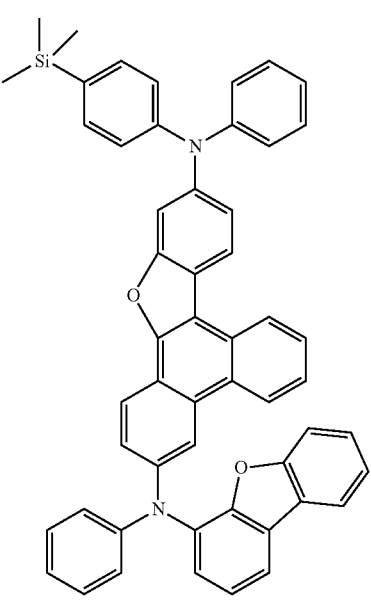
37A 169
-continued
38A
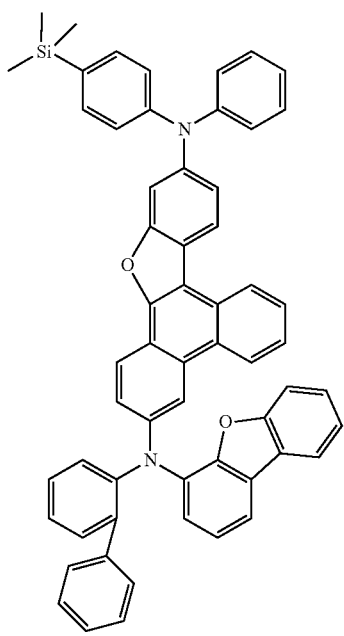
170
-continued
40A
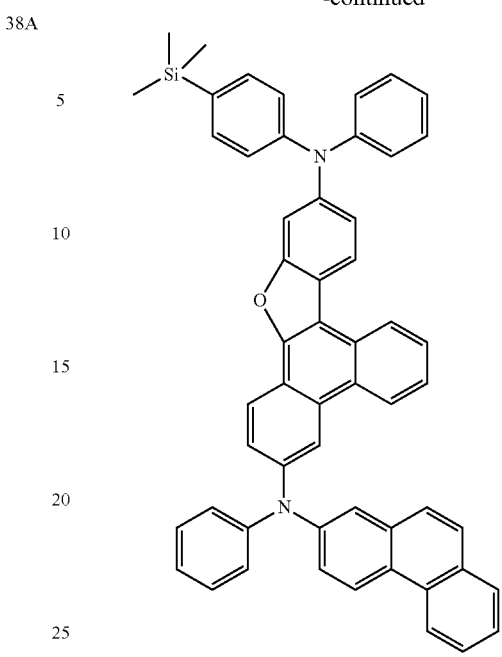
39A
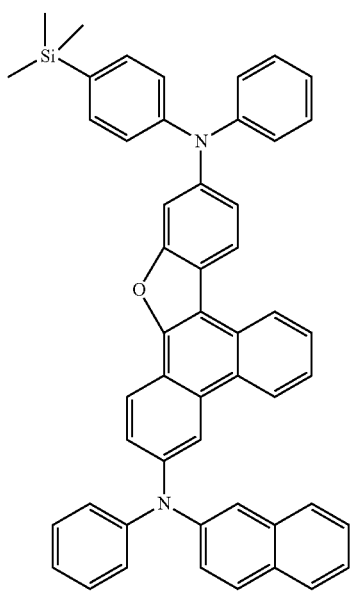
41A
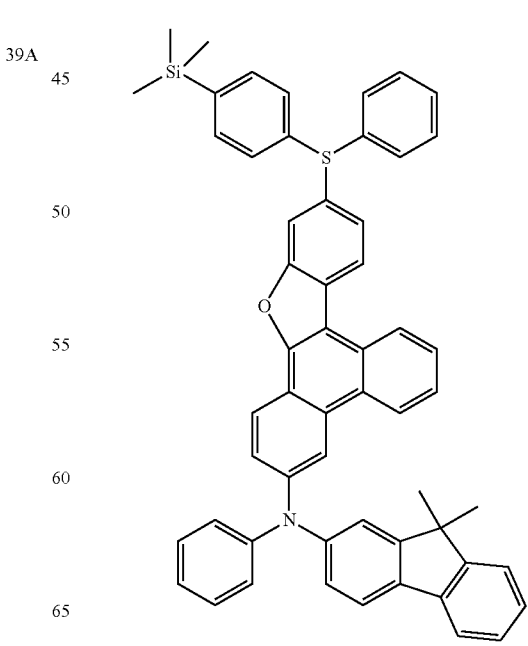

171
-continued
42A
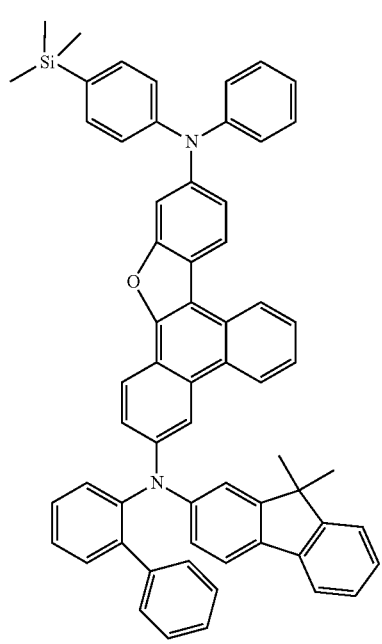
43A
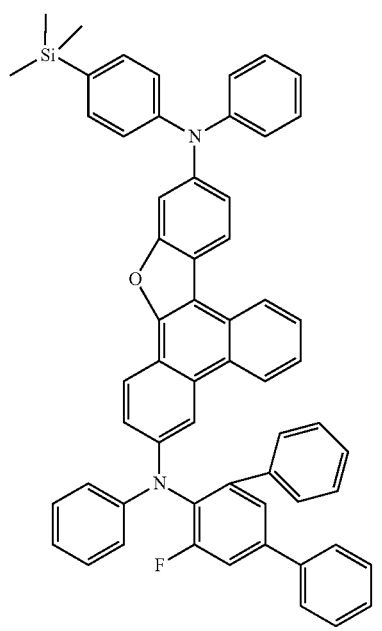
172
-continued
44A
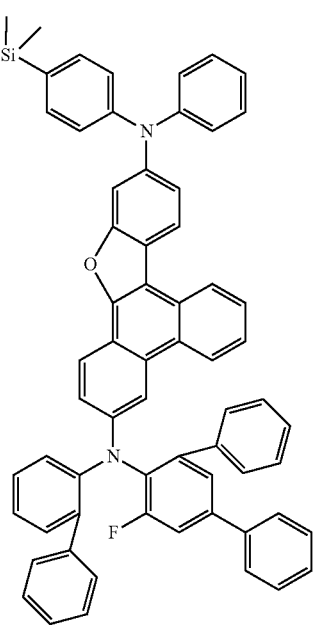
45A
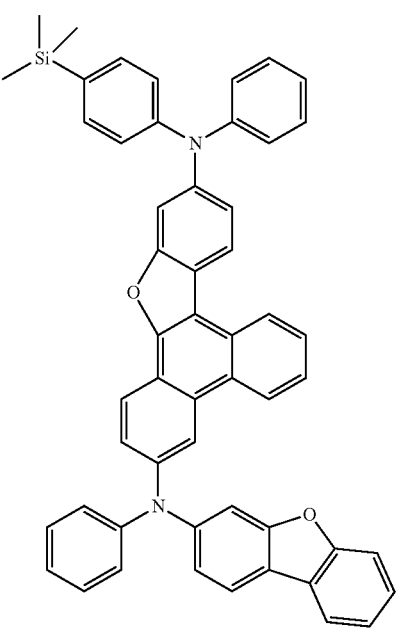

173
-continued
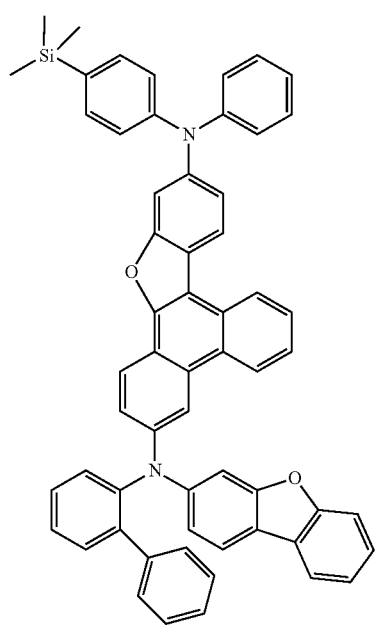
46A
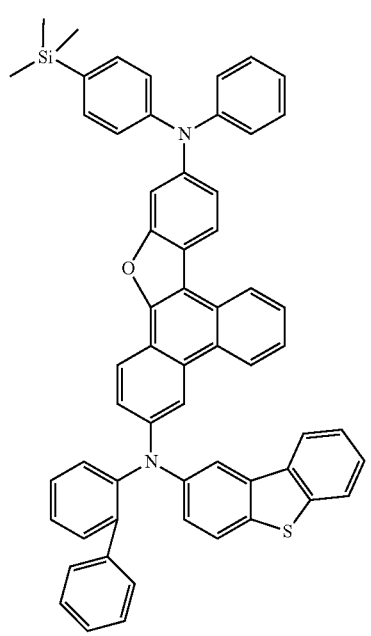
47A
174
-continued
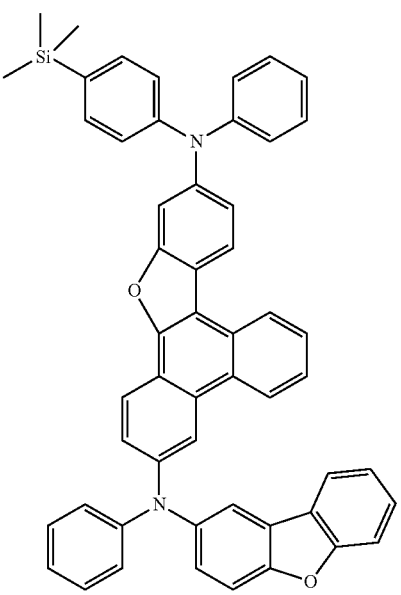
48A
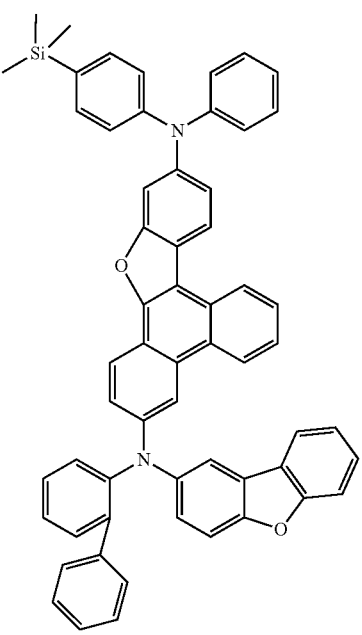
49A 175
-continued
176
-continued
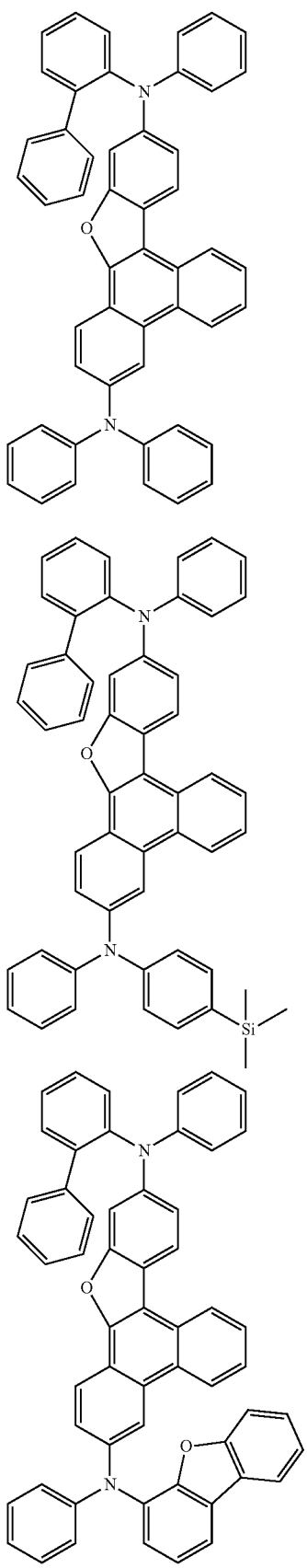
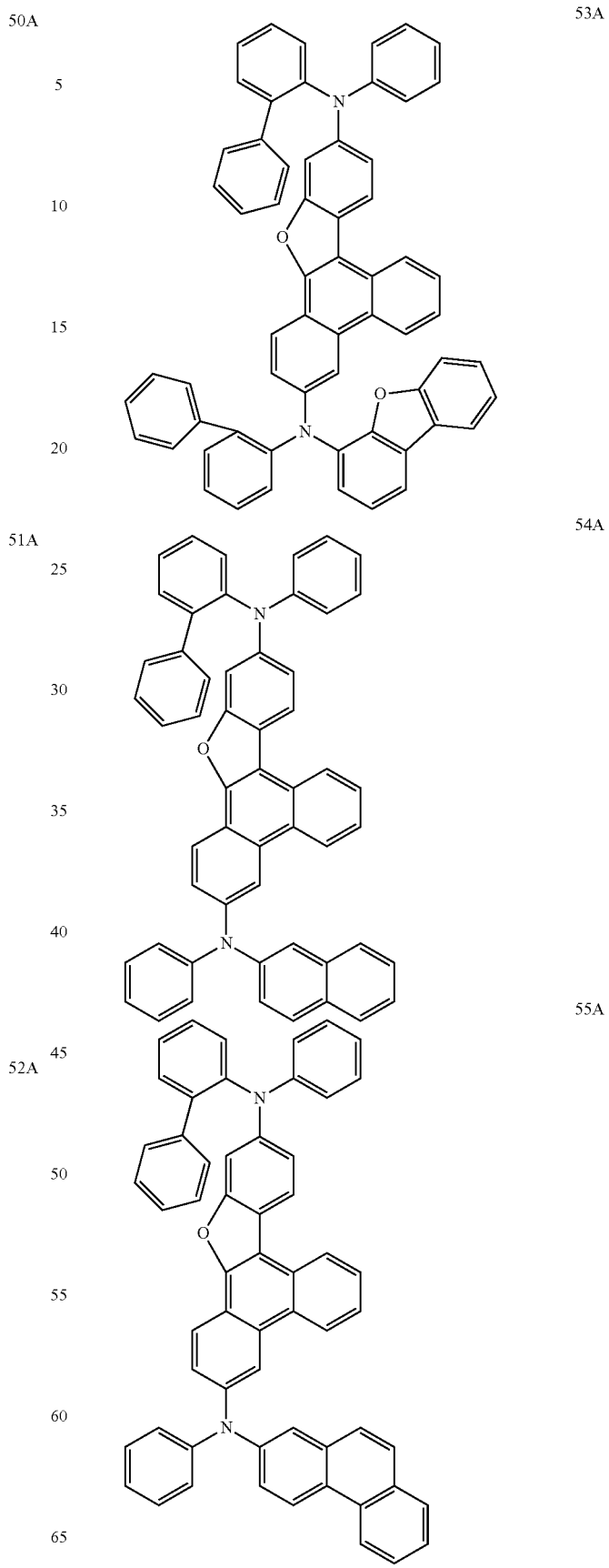

-continued
56A
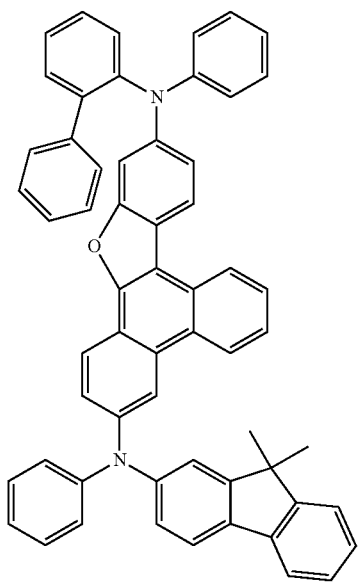
57A
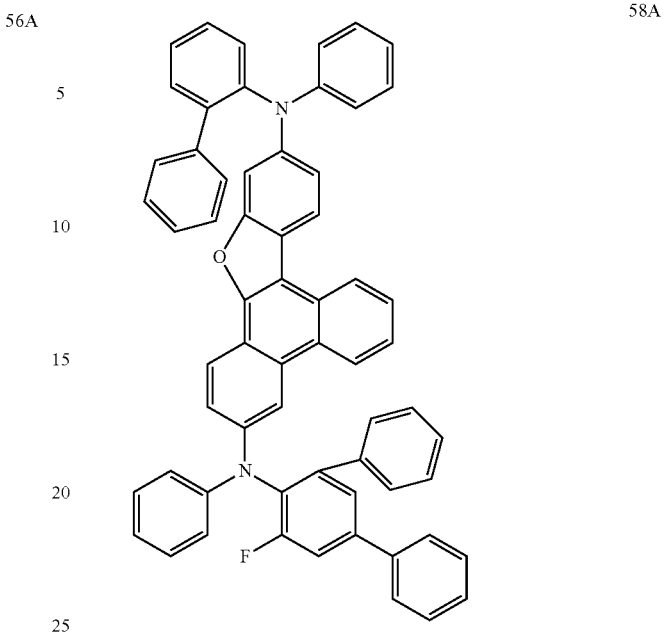
58A
59A
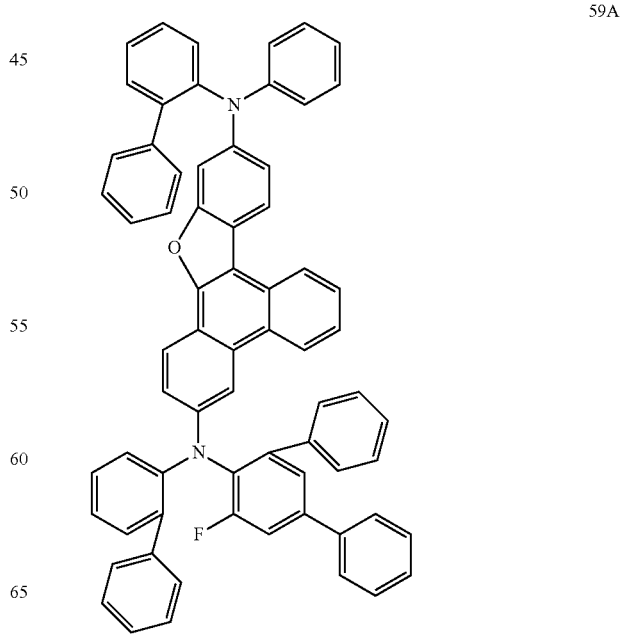

179
-continued
180
-continued
60A
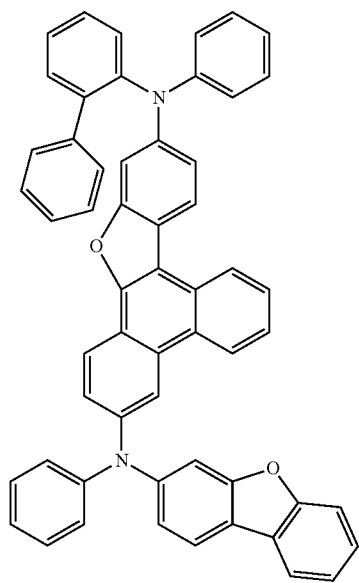
62A
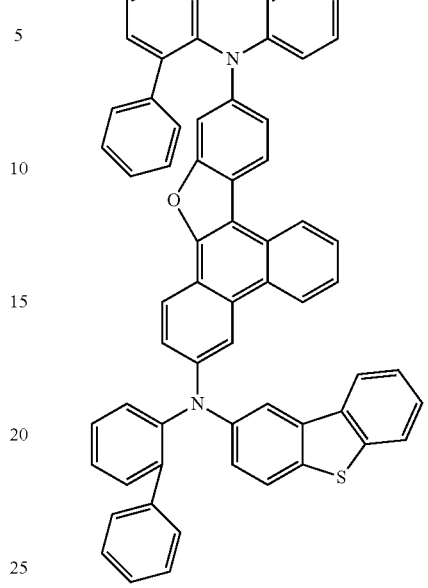
61A
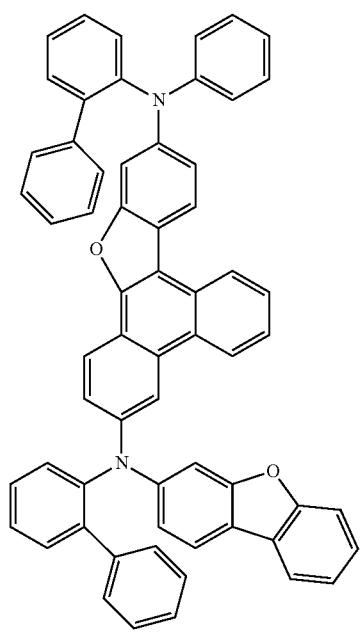
63A
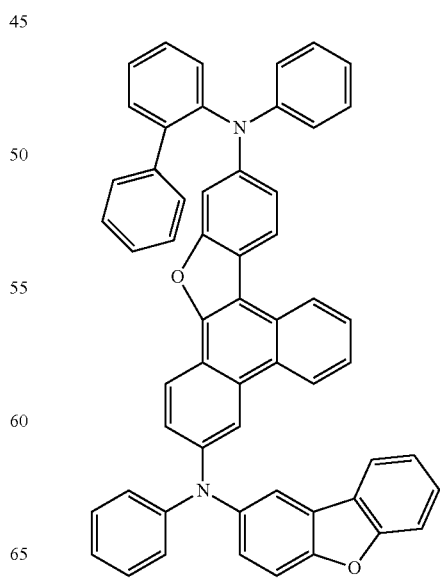

181
-continued
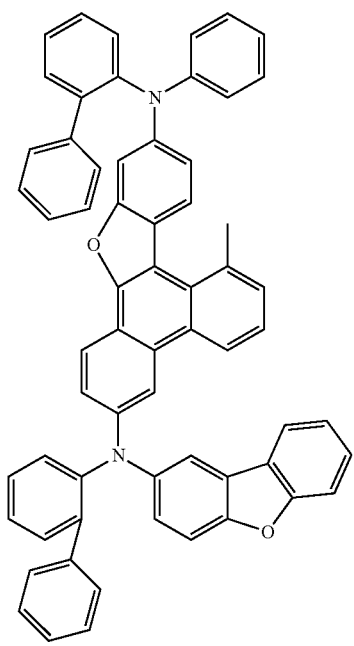
64A
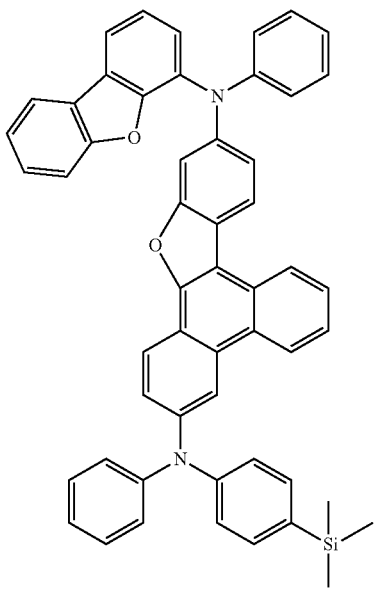
182
-continued
66A
65A
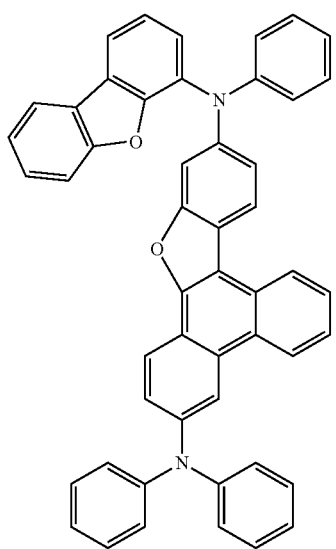
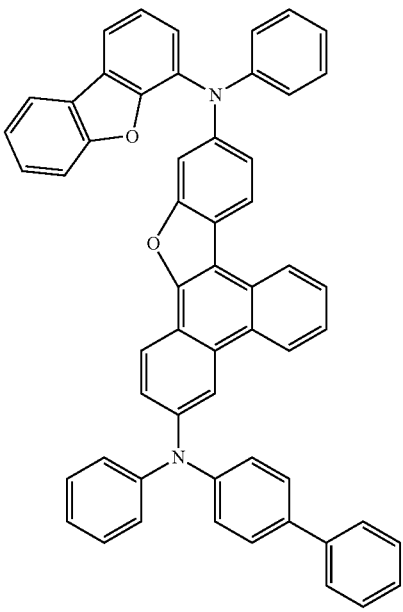
67A 183
-continued
184
-continued
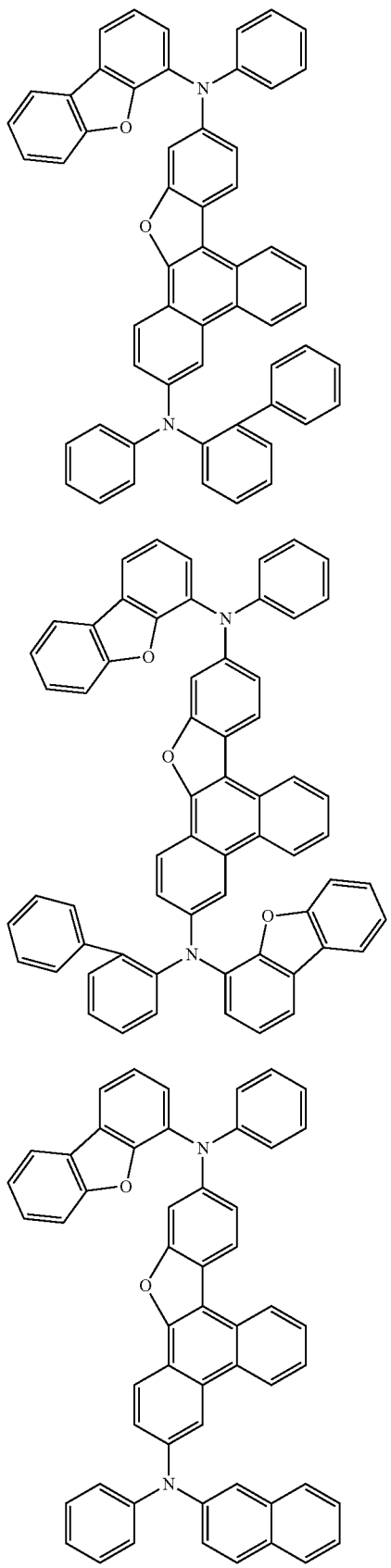
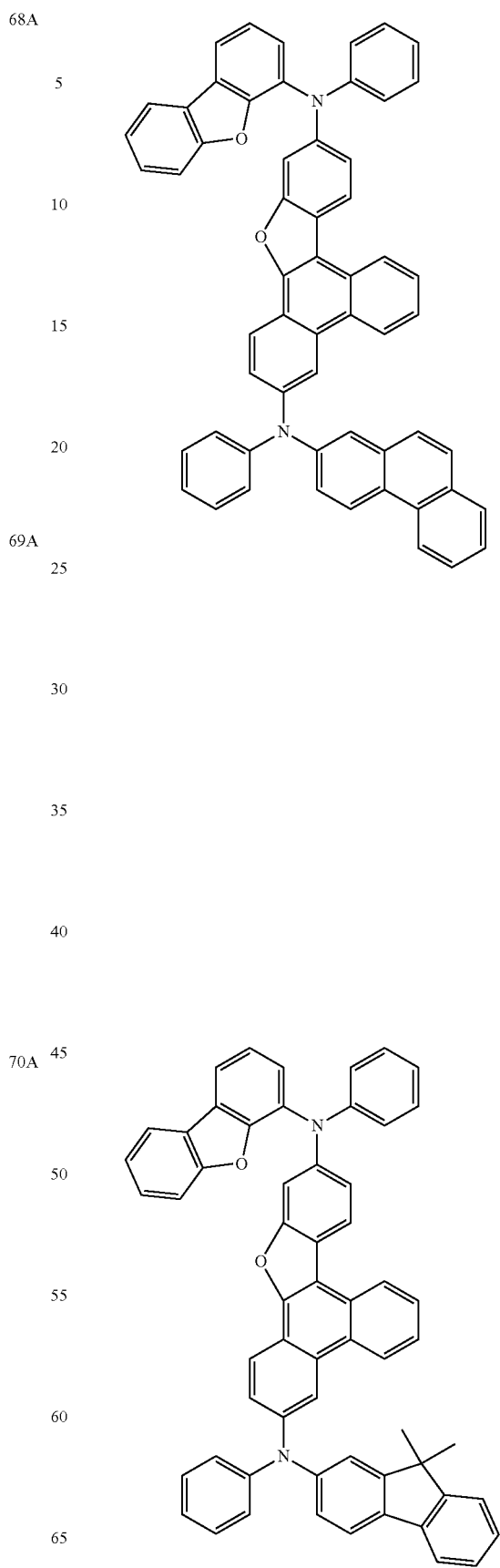
68A
69A
70A
71A
72A 185
-continued
186
-continued
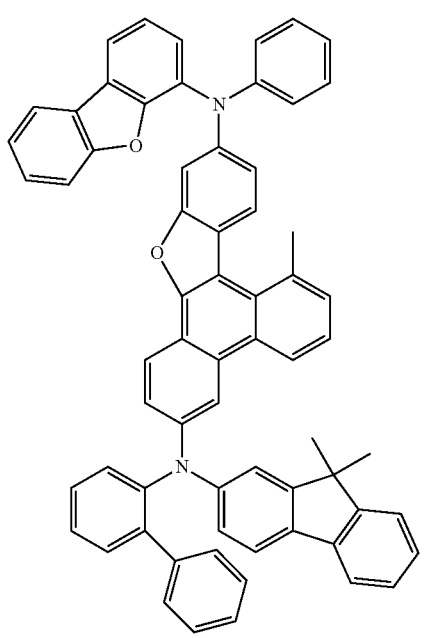
73A
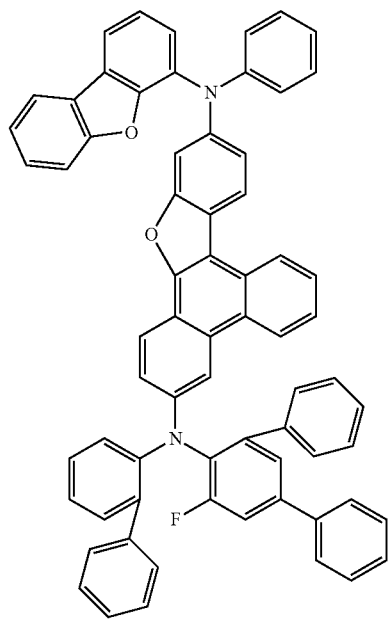
75A
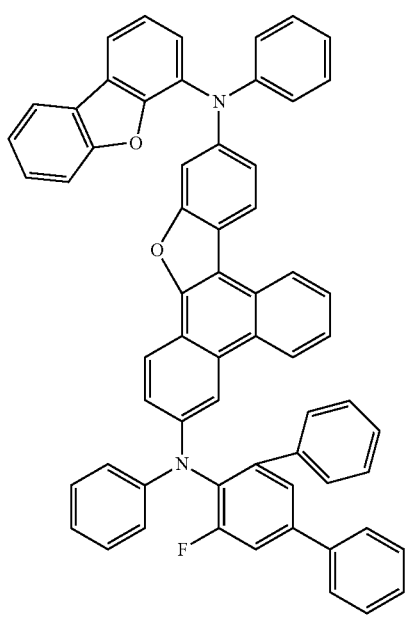
74A
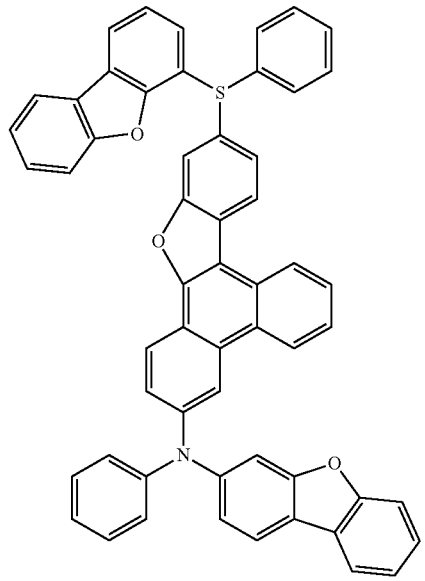
76A 187
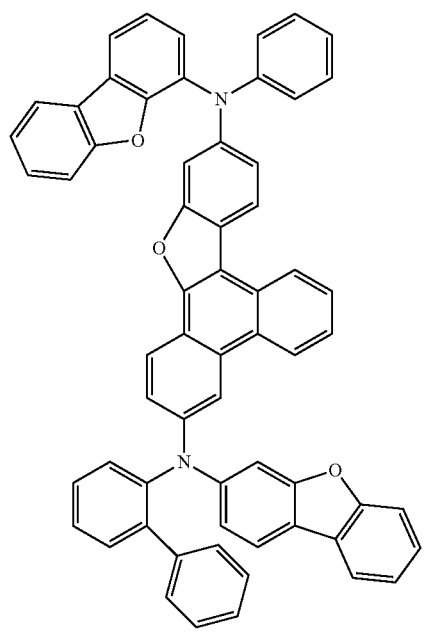
77A
188
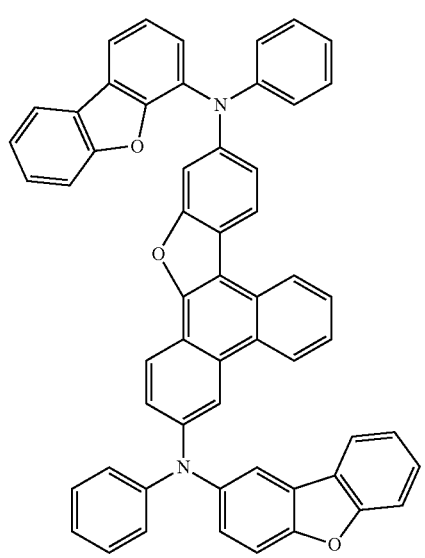
79A
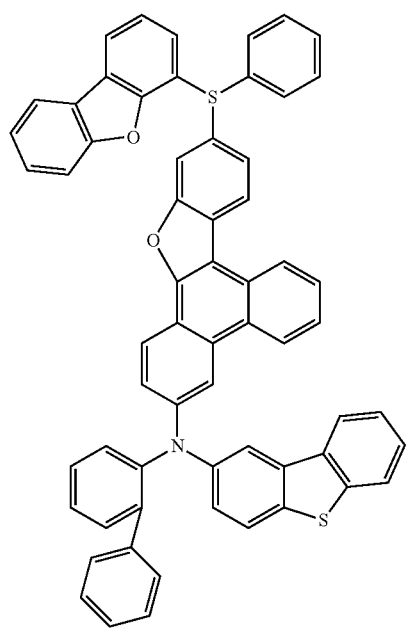
78A
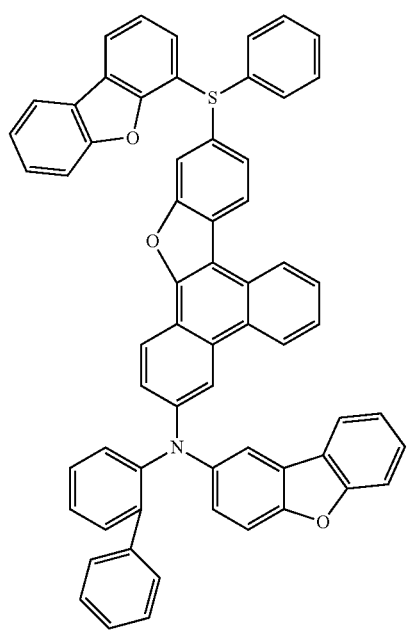
80A 189
-continued
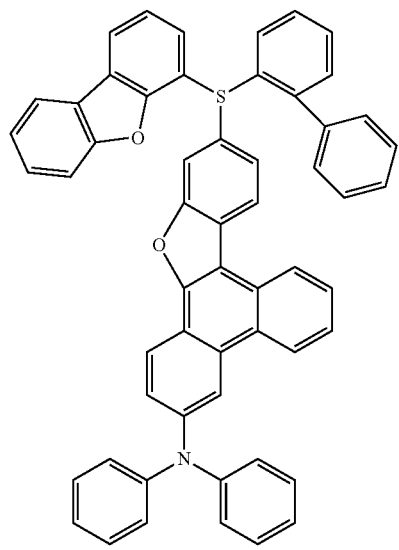
81A
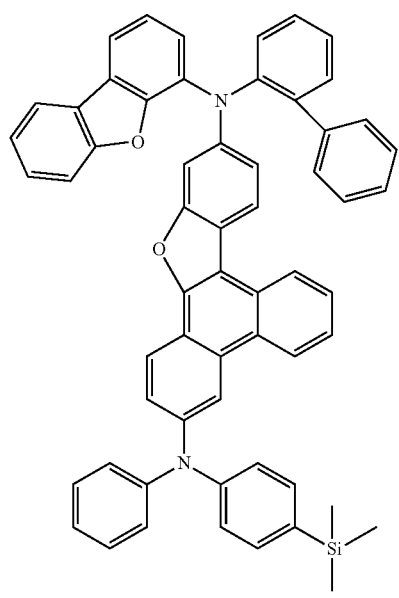
82A
190
-continued
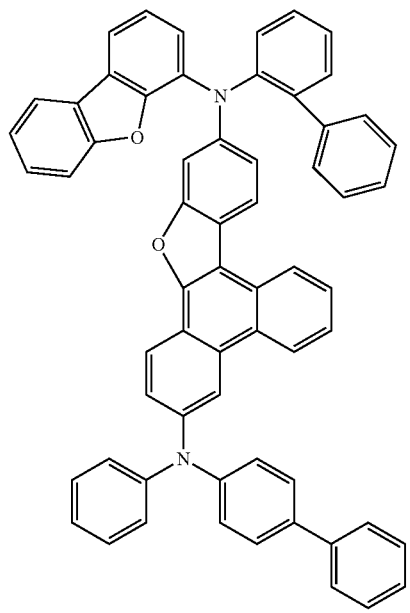
83A
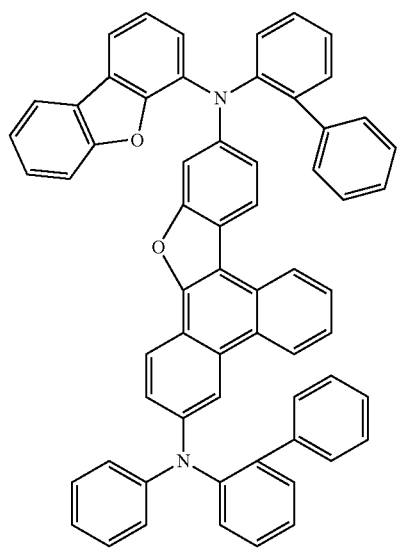
84A 191
-continued
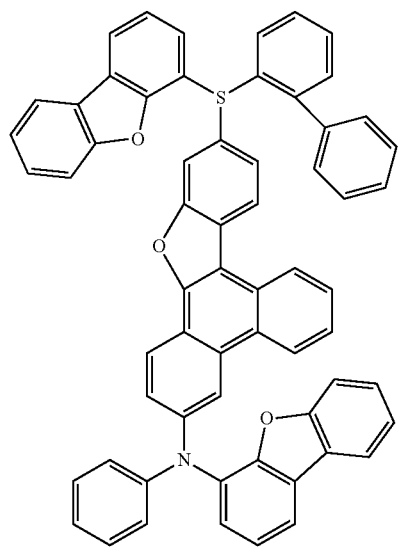
85A
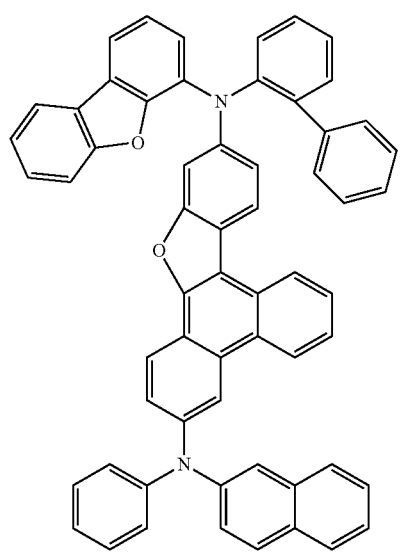
86A
192
-continued
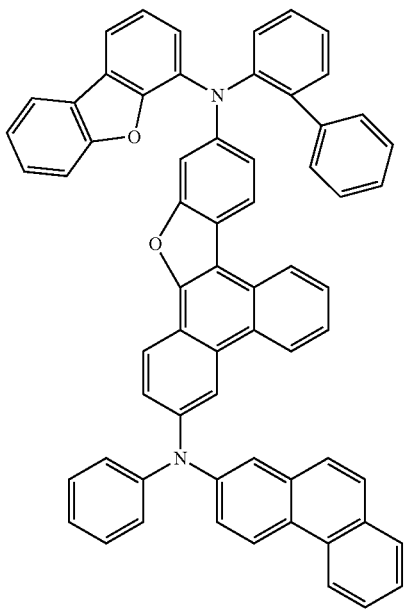
87A
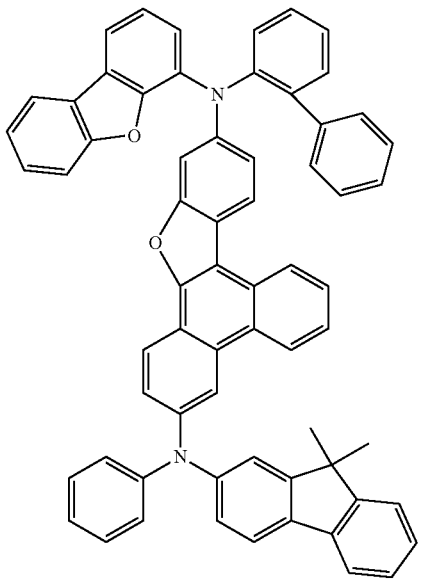
88A 193
-continued
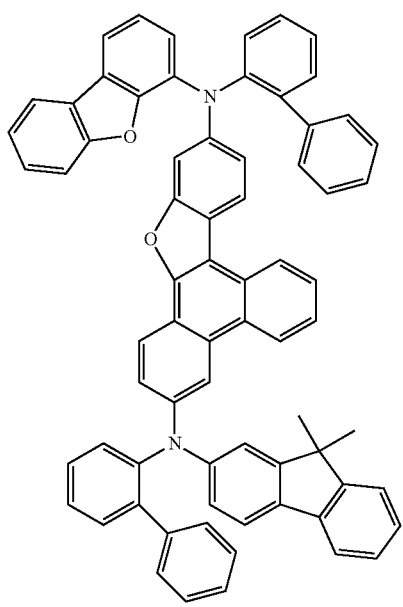
89A
194
-continued
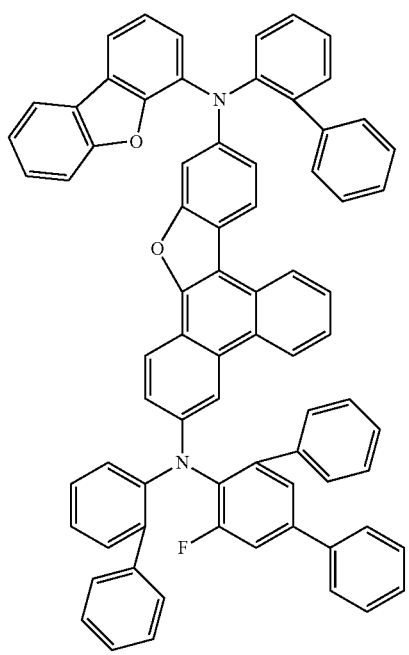
91A
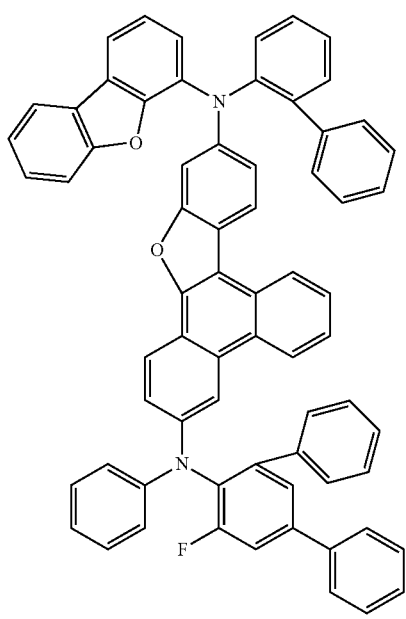
90A
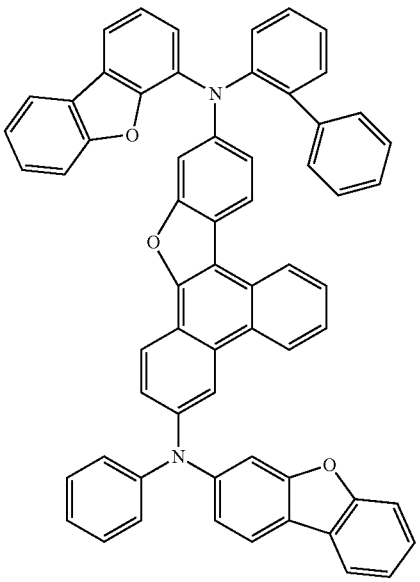
92A 195
-continued
93A
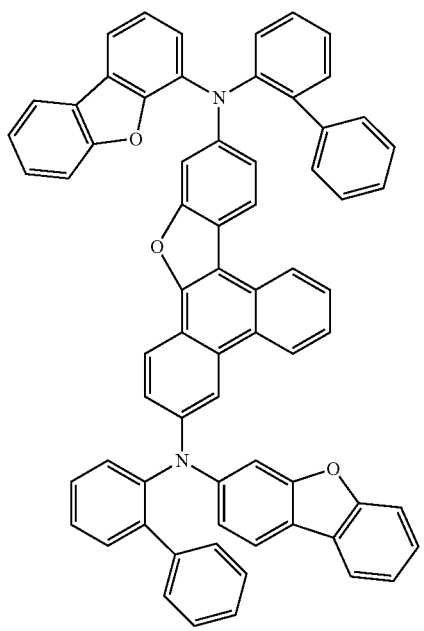
94A
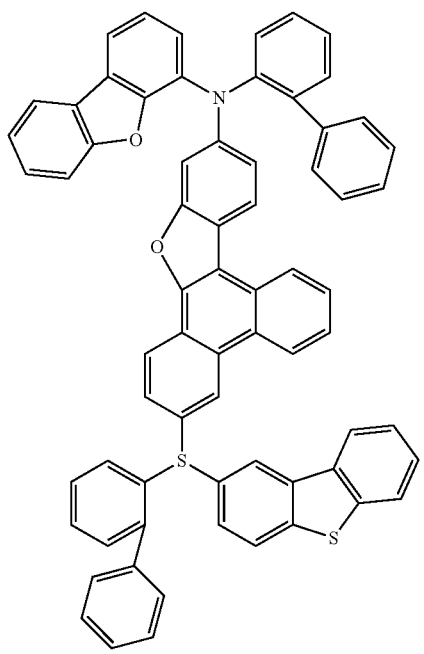
196
-continued
95A
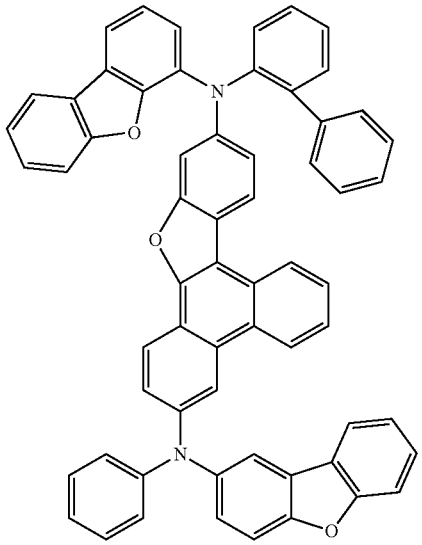
96A
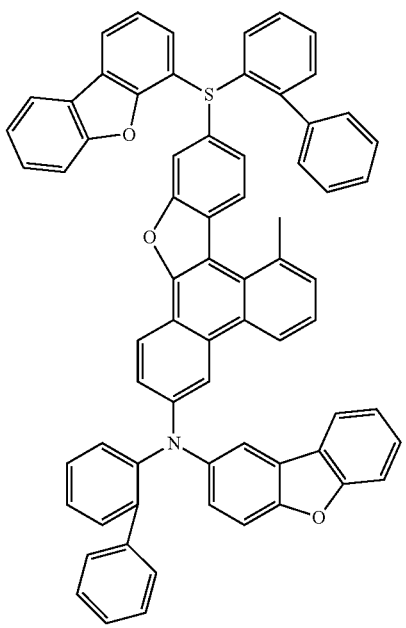

197
-continued
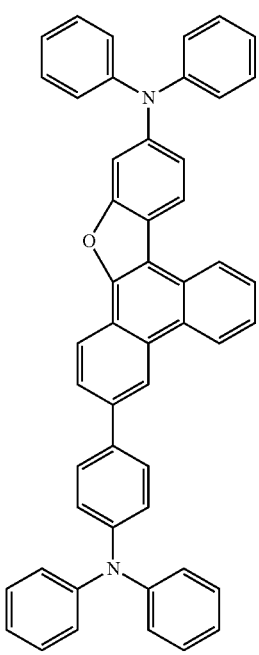
97A
198
-continued
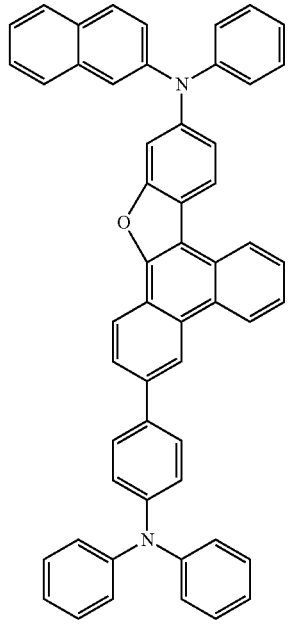
99A
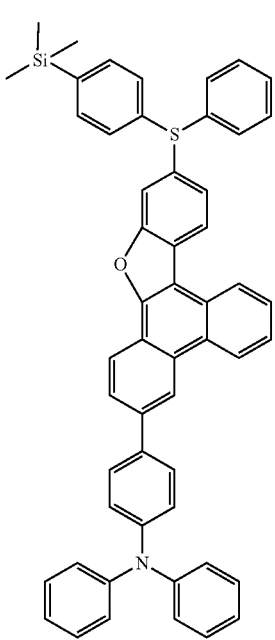
98A
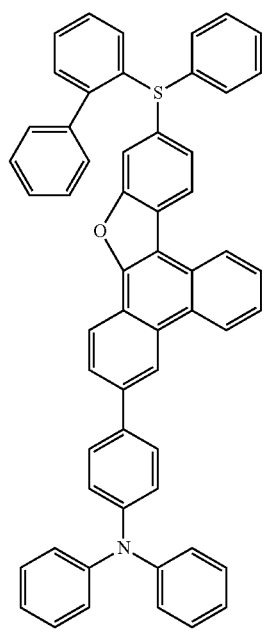
100A

199
-continued
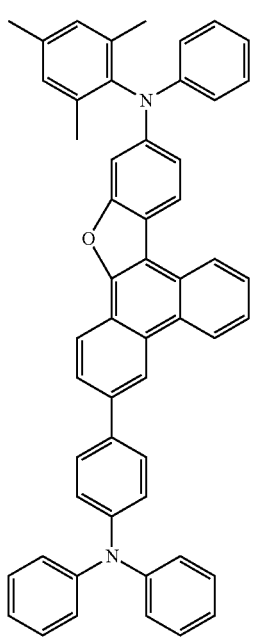
200
-continued
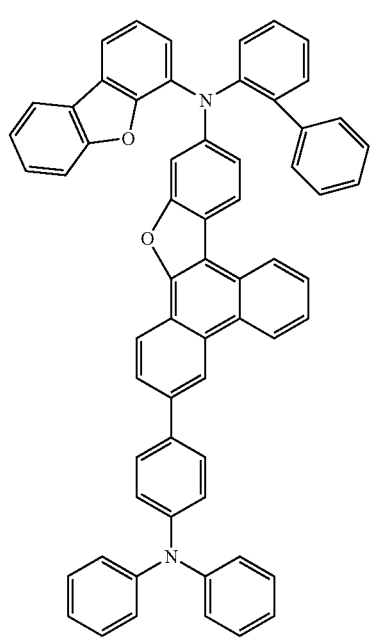
101A
102A
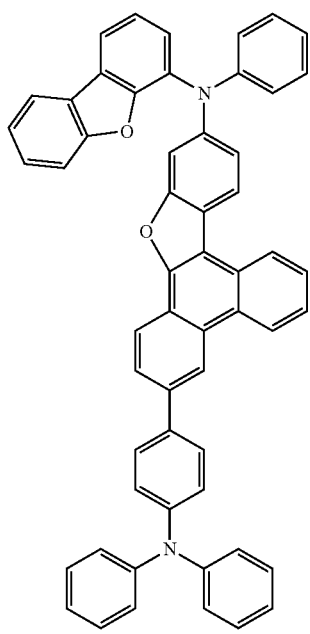
103A
104A

201
-continued
202
-continued
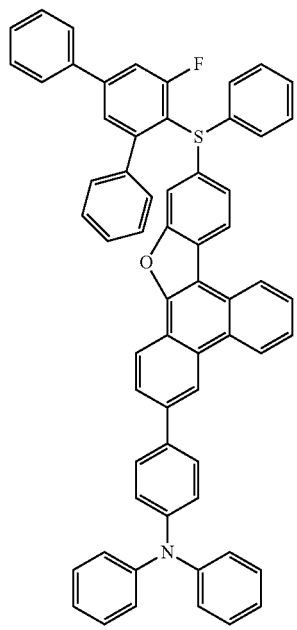
105A
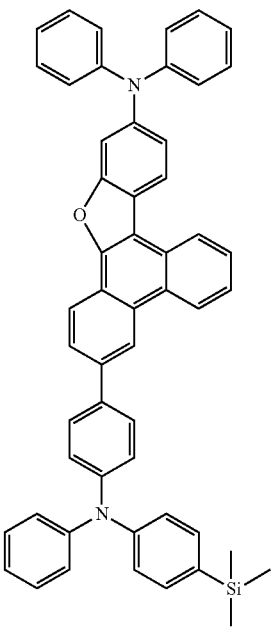
107A
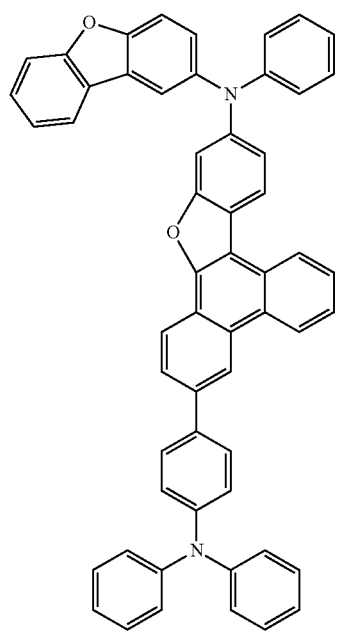
106A
108A 203
-continued
109A
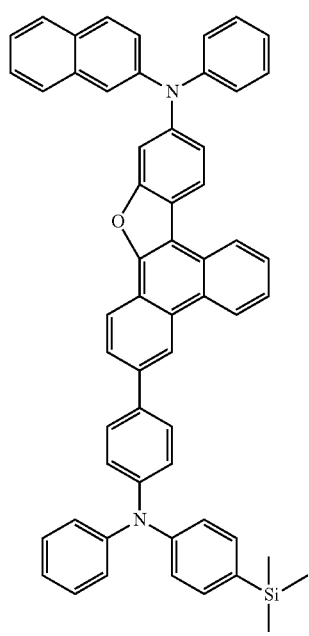
204
-continued
111A
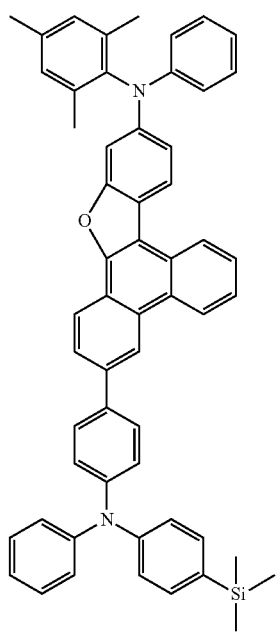
110A
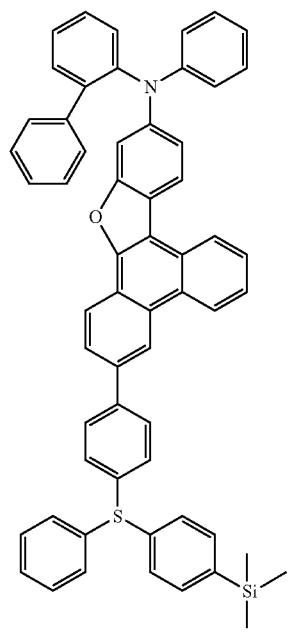
112A
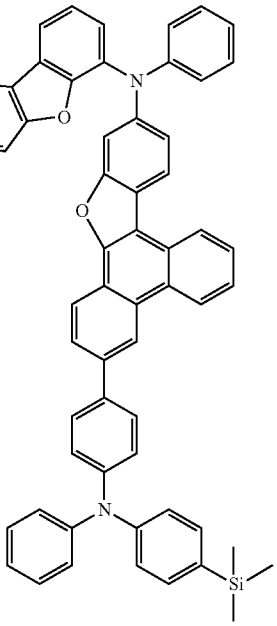

205
-continued
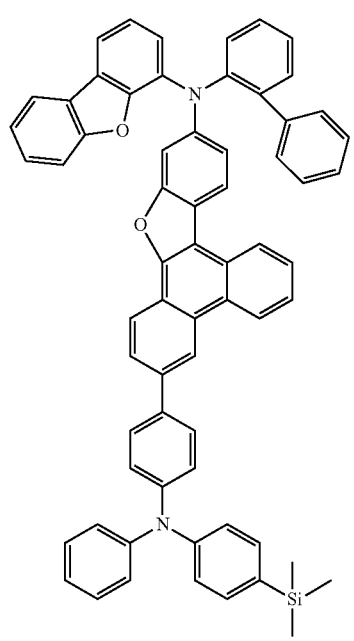
114A
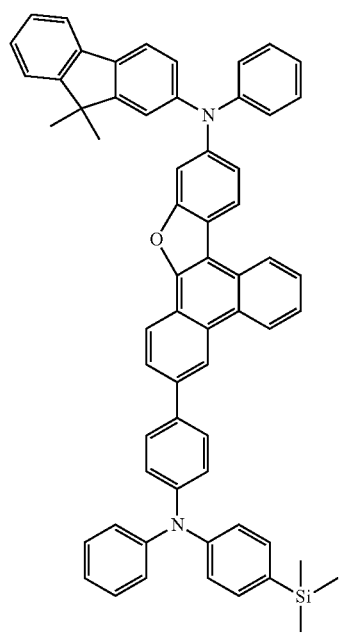
206
-continued
113A
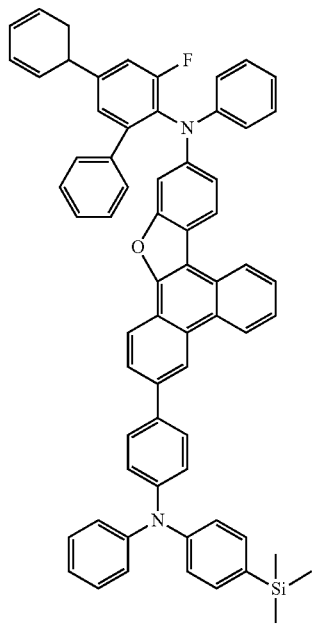
115A
116A
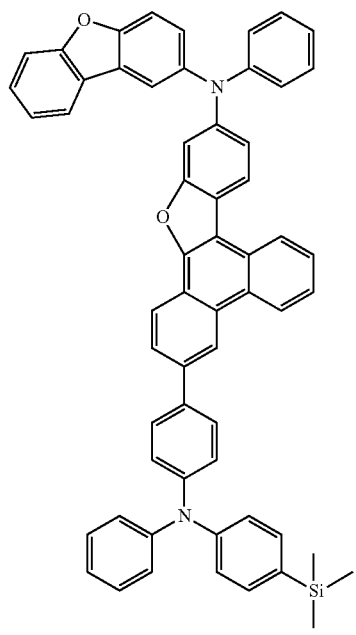

207
-continued
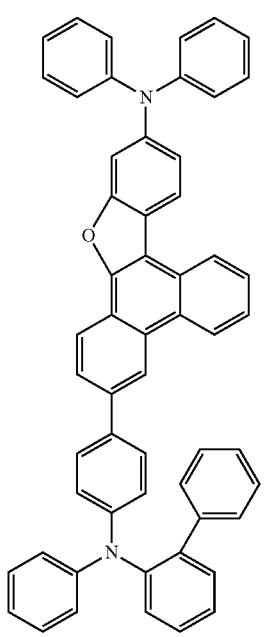
117A
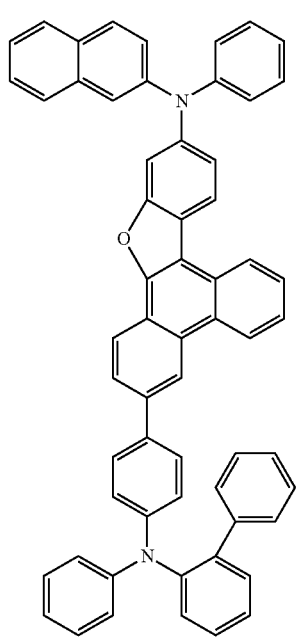
118A
208
-continued
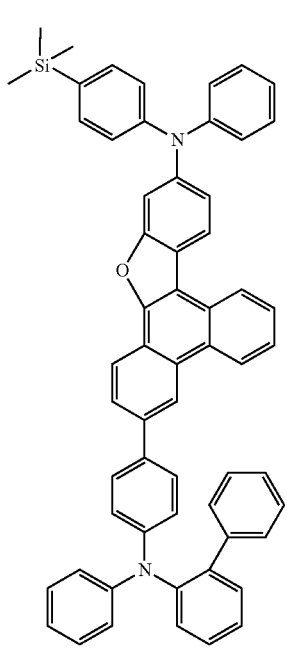
119A
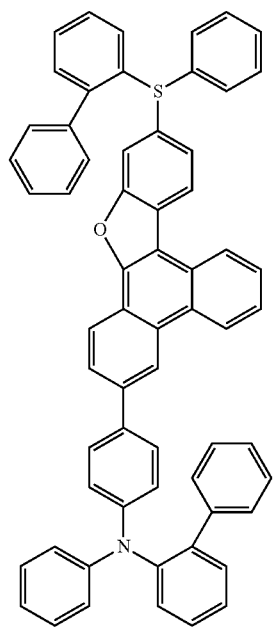
120A 209
-continued
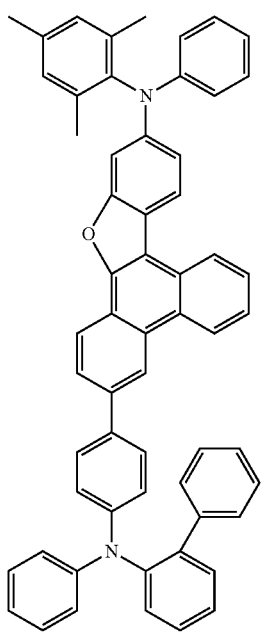
121A
210
-continued
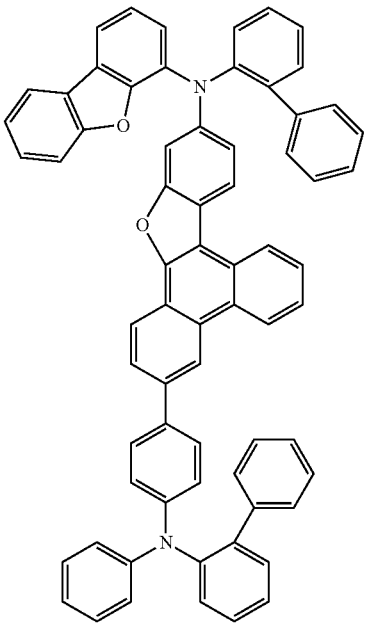
123A
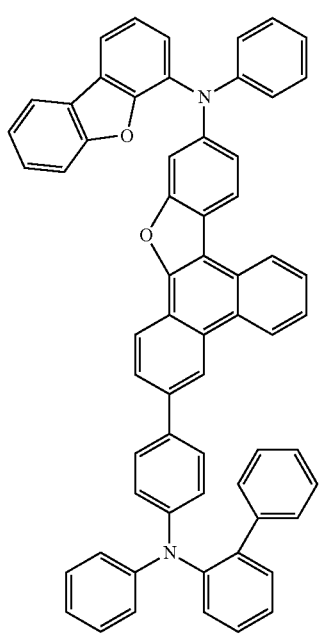
122A
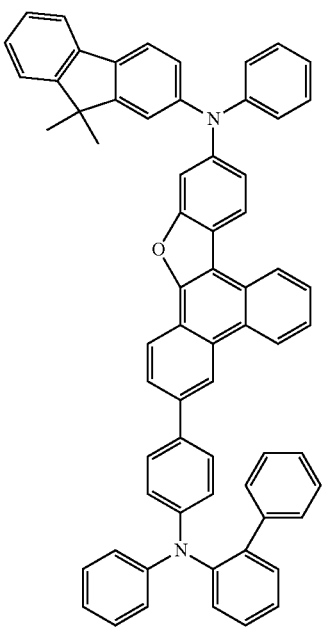
124A 211
-continued
212
-continued
125A 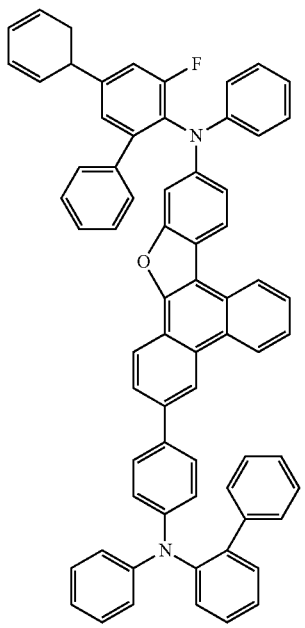
127A 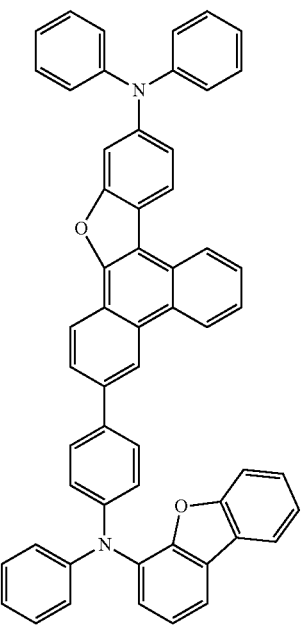
126A 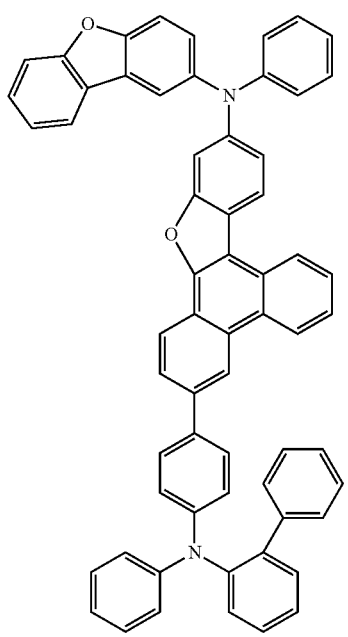
128A 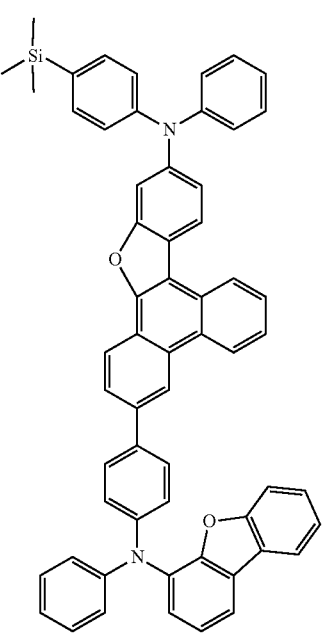

213
-continued
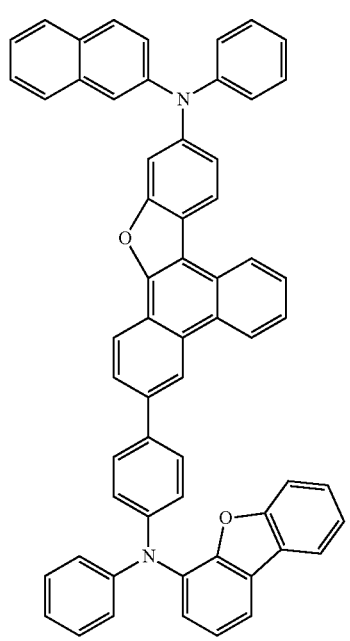
214
-continued
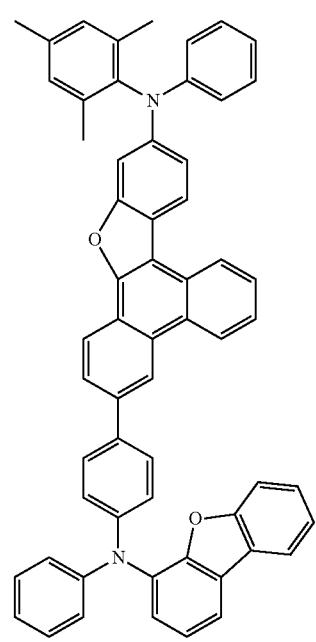
129A
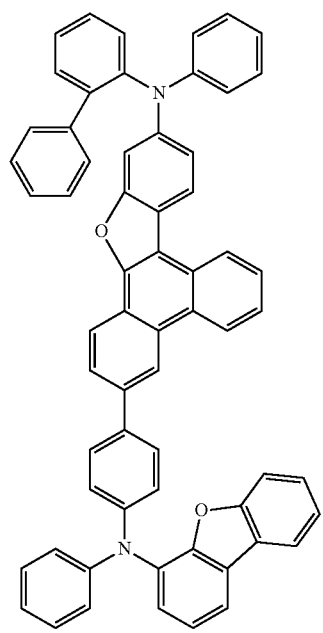
130A
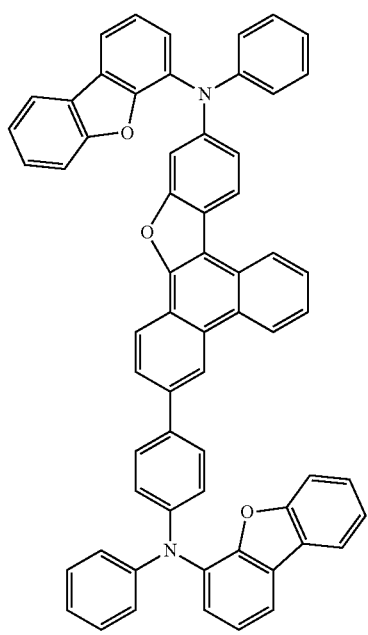
131A
132A 215
-continued
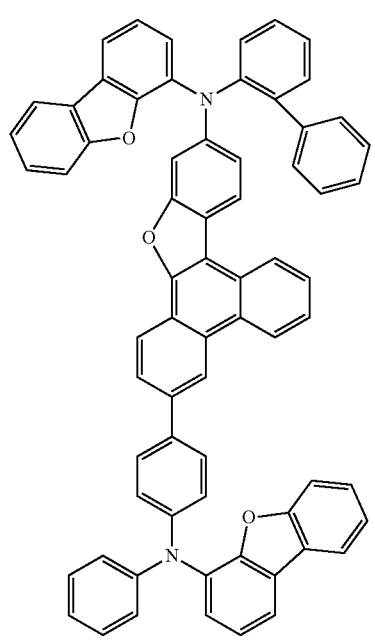
133A
216
-continued
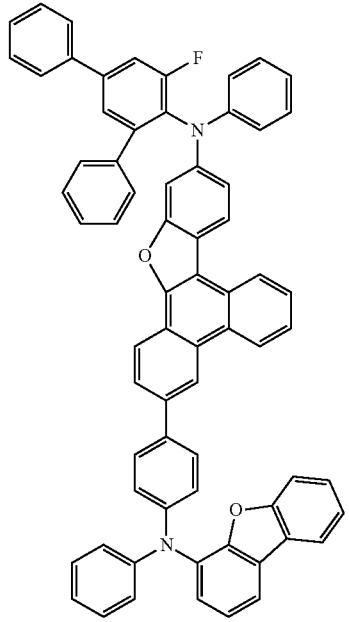
135A
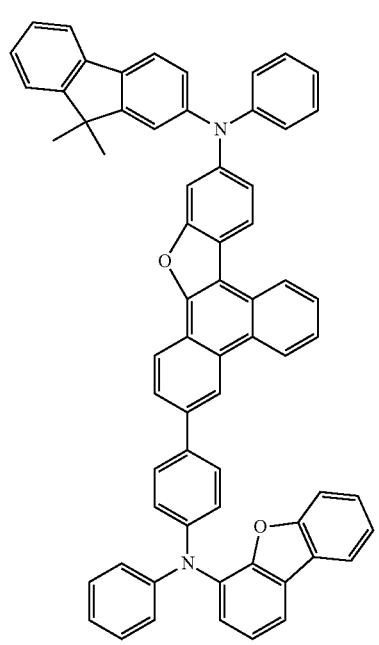
134A
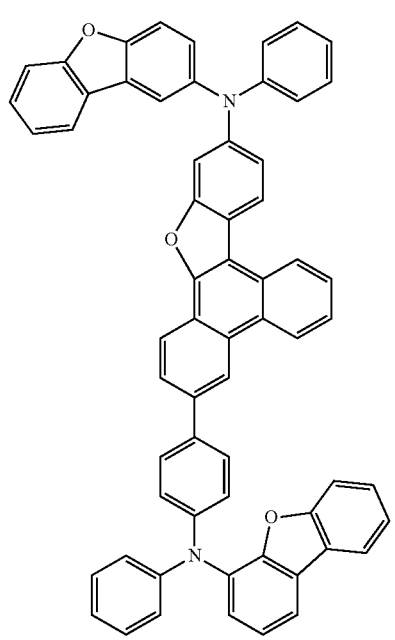
136A 217
-continued
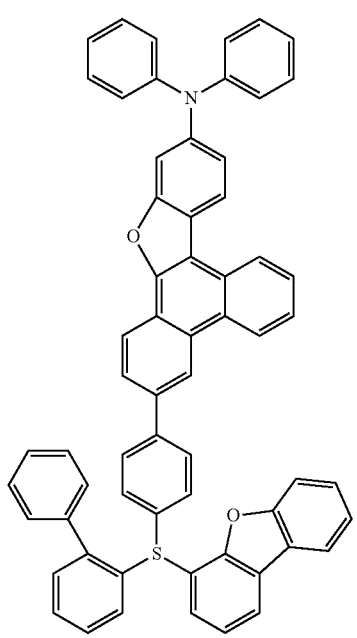
137A
218
-continued
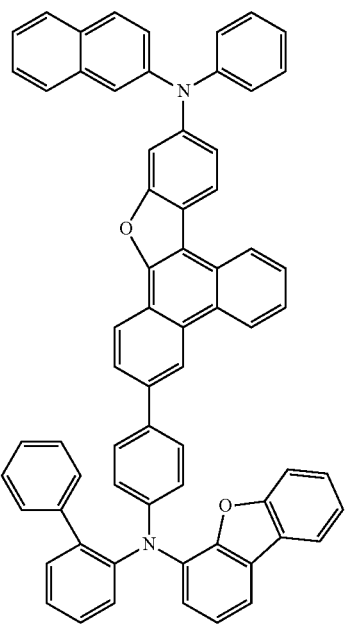
139A
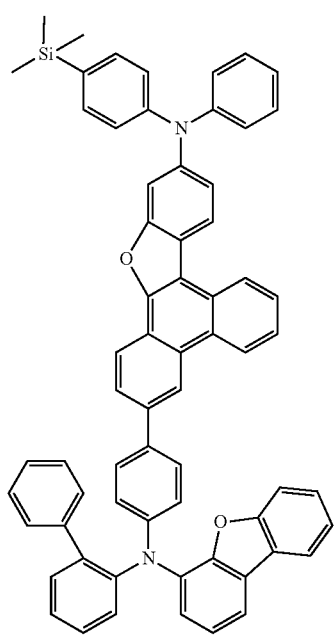
138A
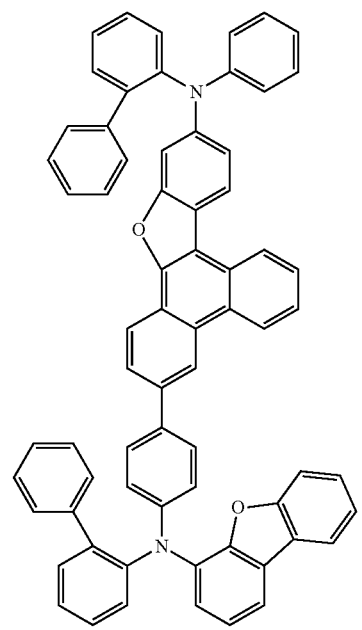
140A 219
-continued
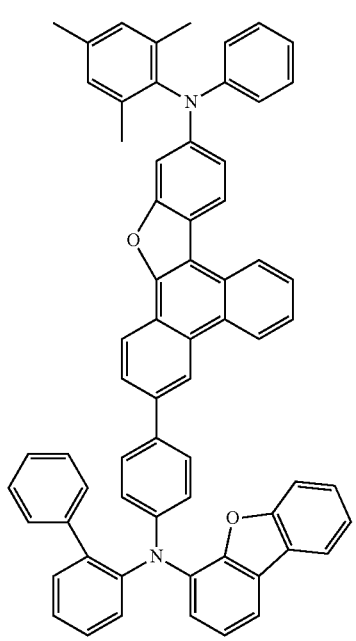
141A
220
-continued
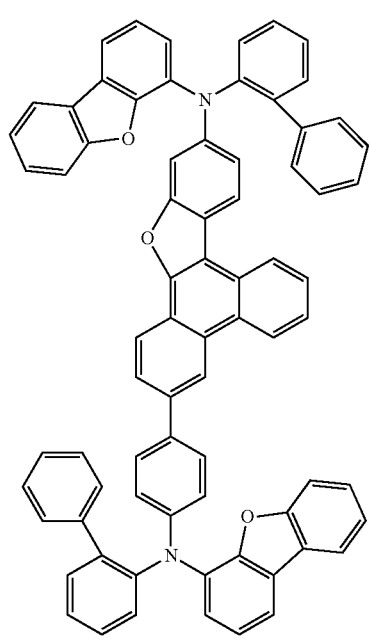
143A
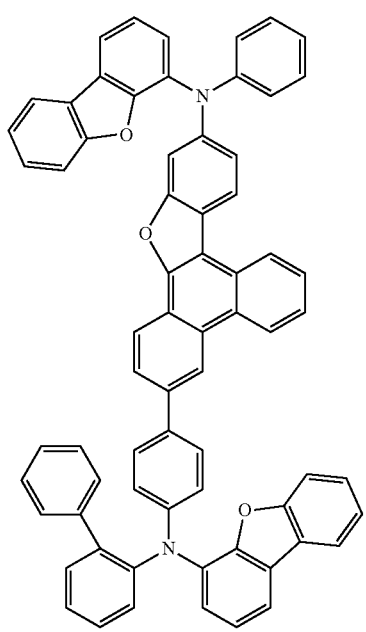
142A
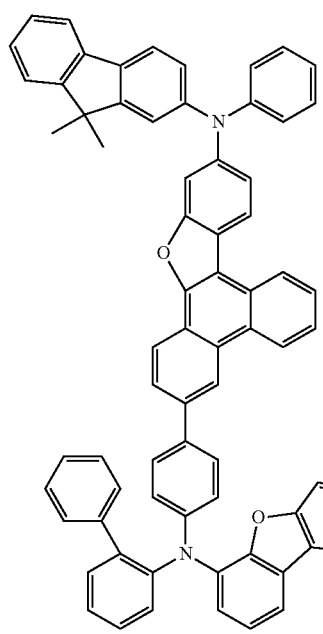
144A 221
-continued
222
-continued
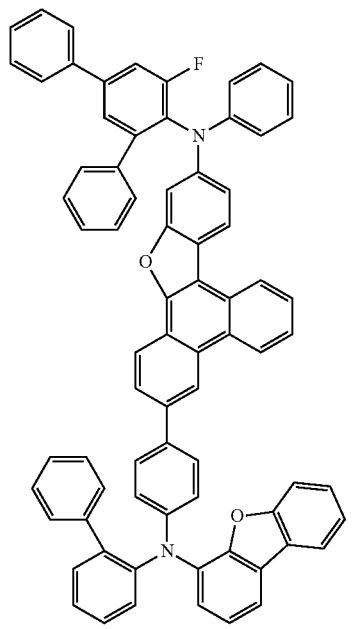
145A
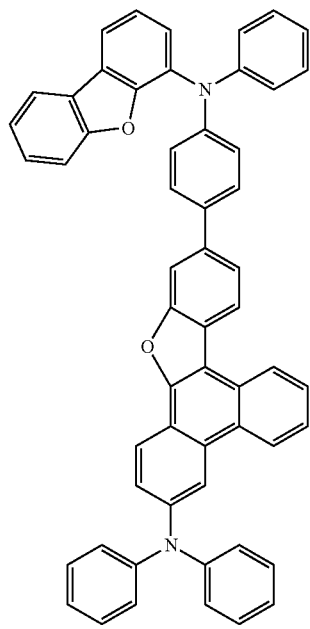
147A
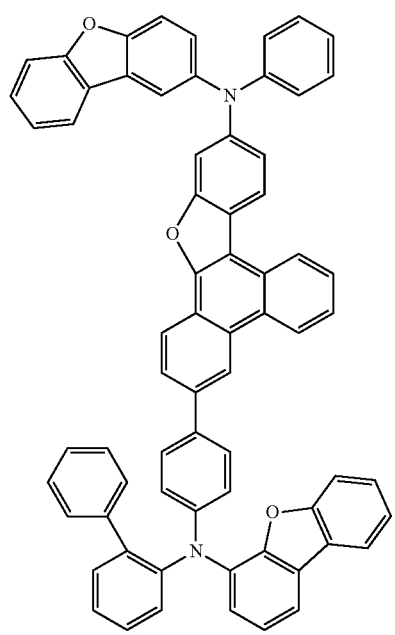
146A
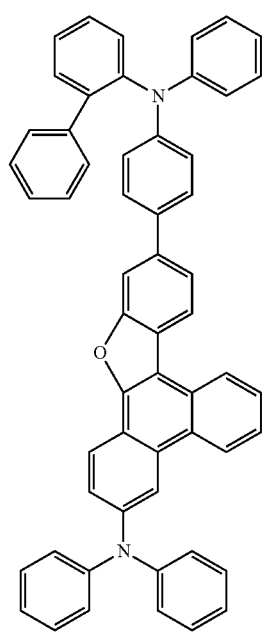
148A -continued
149A
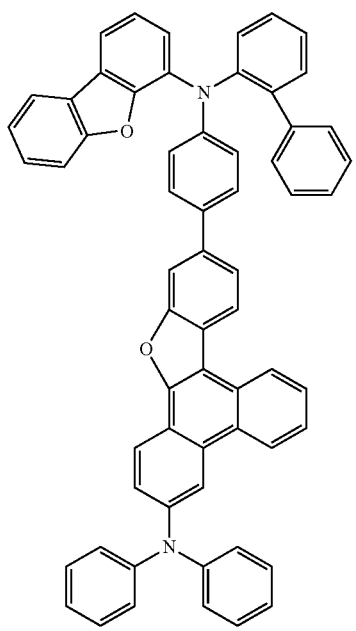
150A
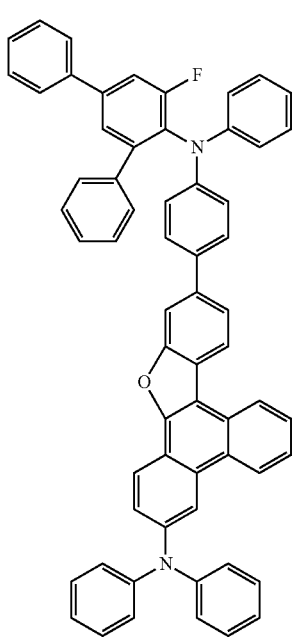
-continued
151A
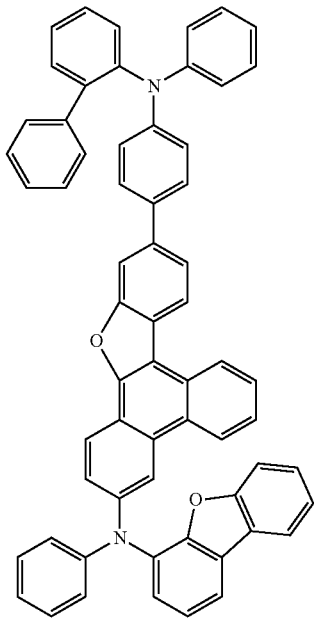
152A
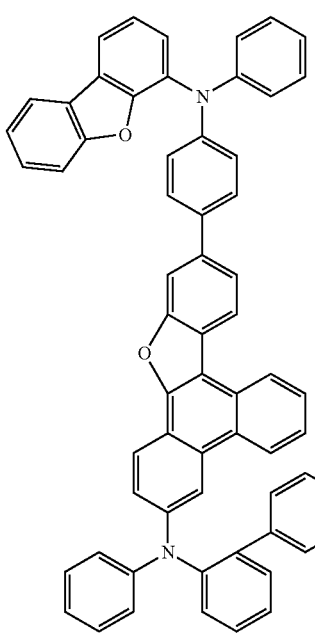

-continued
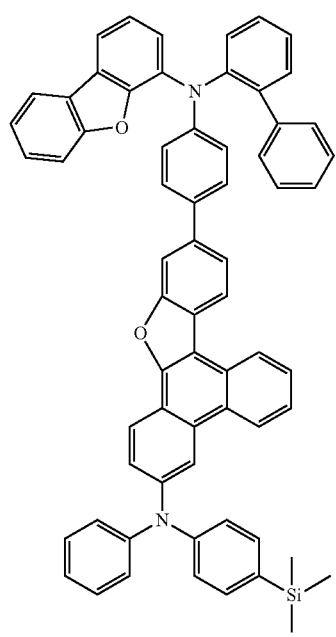
153A
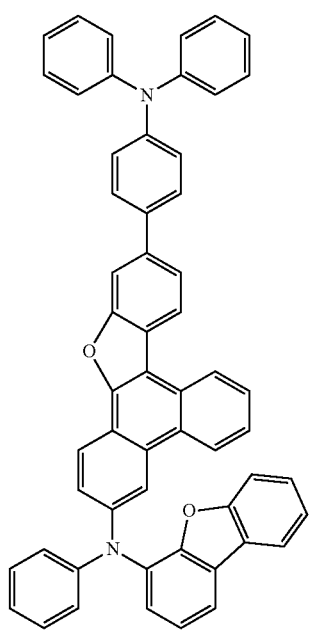
155A
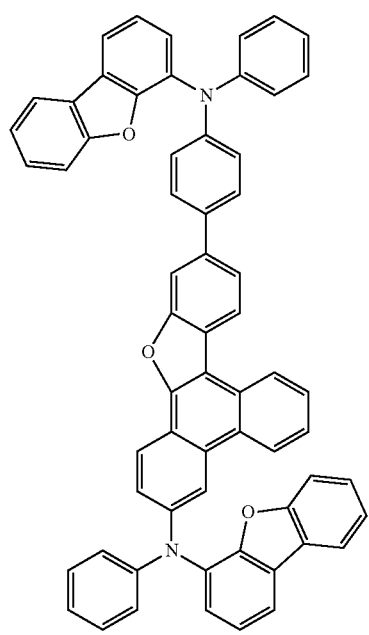
154A
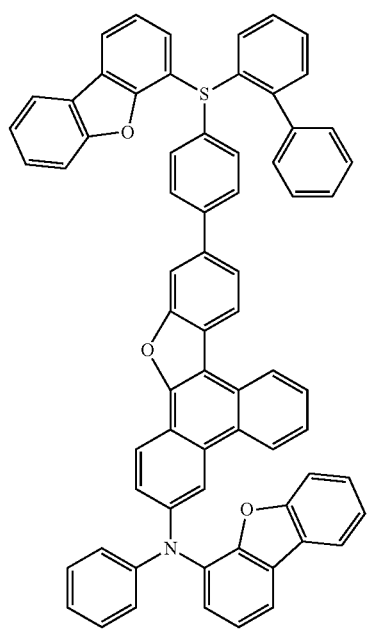
156A

227
-continued
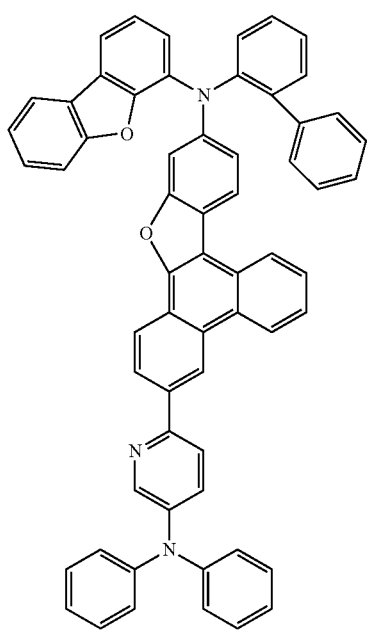
157A
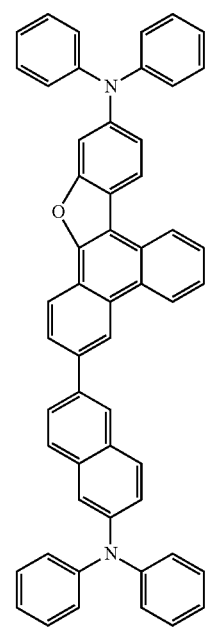
228
-continued
159A
158A
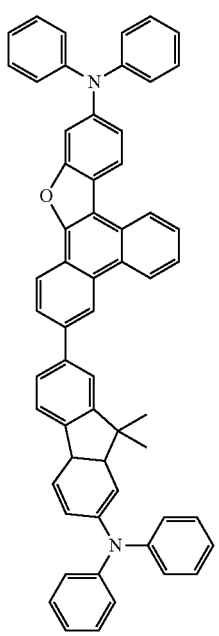
160A
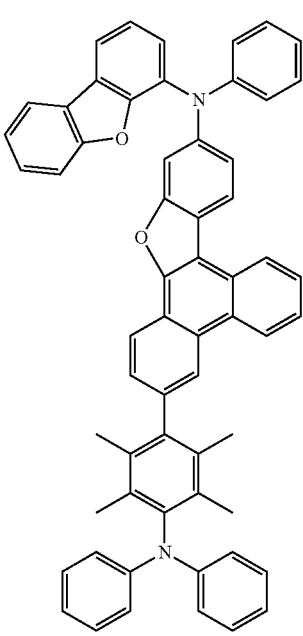

229
-continued
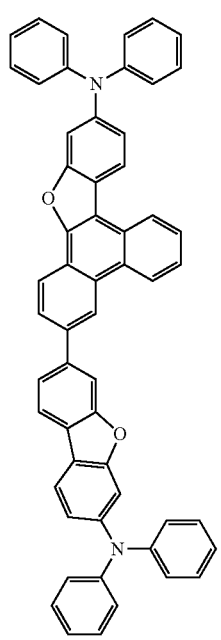
161A
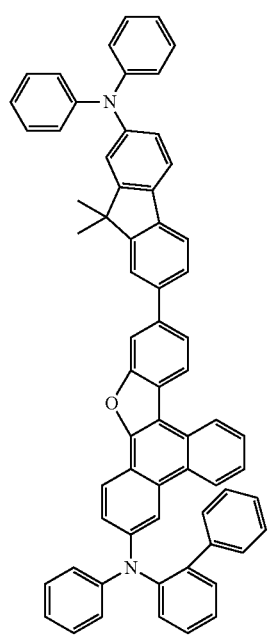
162A
230
-continued
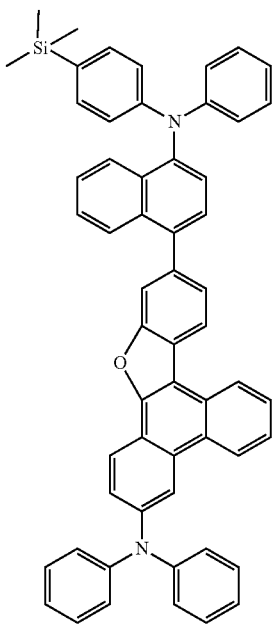
163A
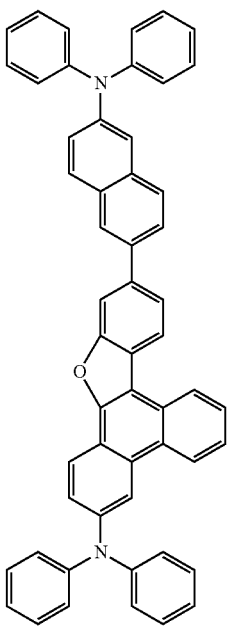
164A 231
-continued
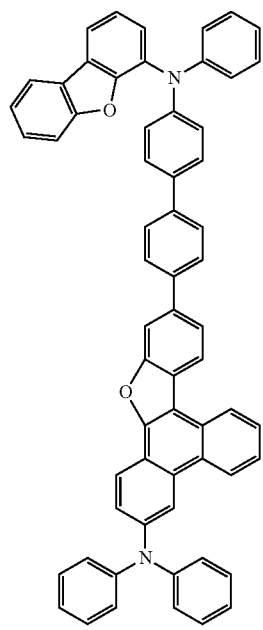
165A
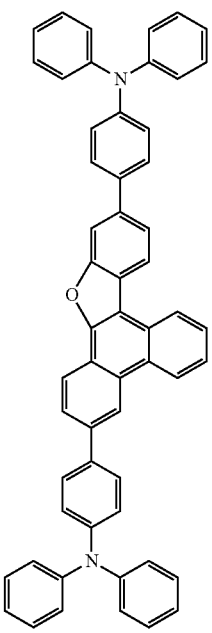
167A
166A
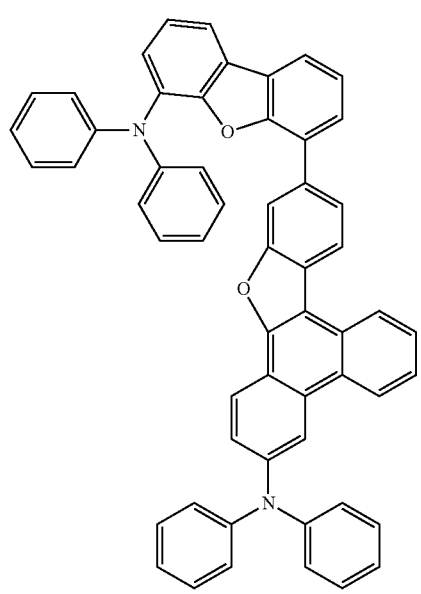
232
-continued
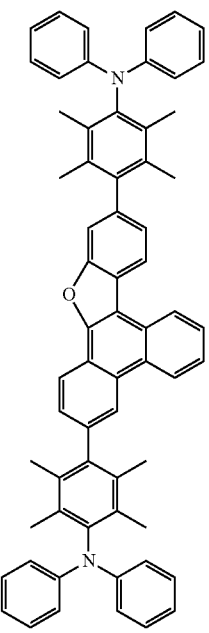
168A 233
-continued
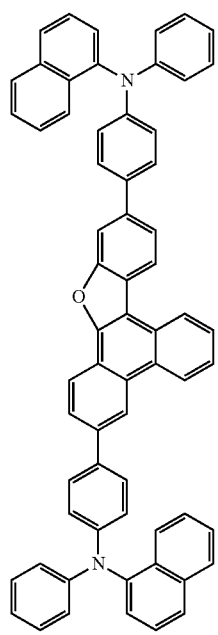
169A
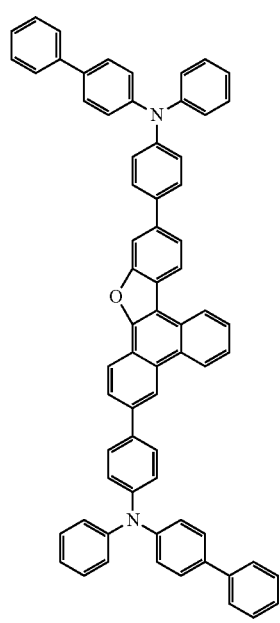
170A
234
-continued
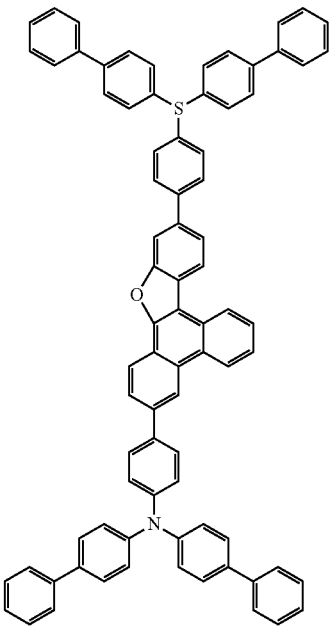
171A
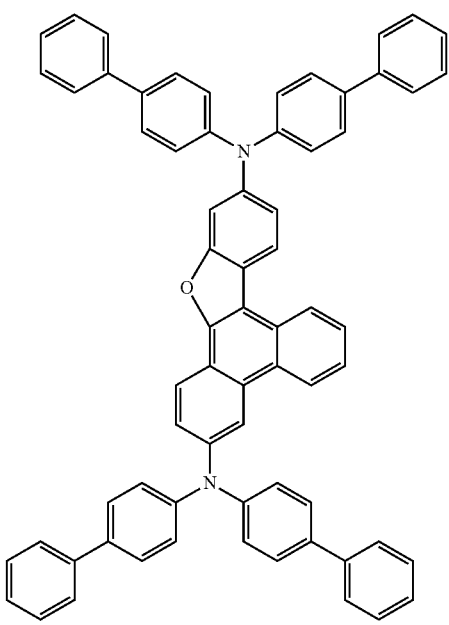
172A 235
-continued
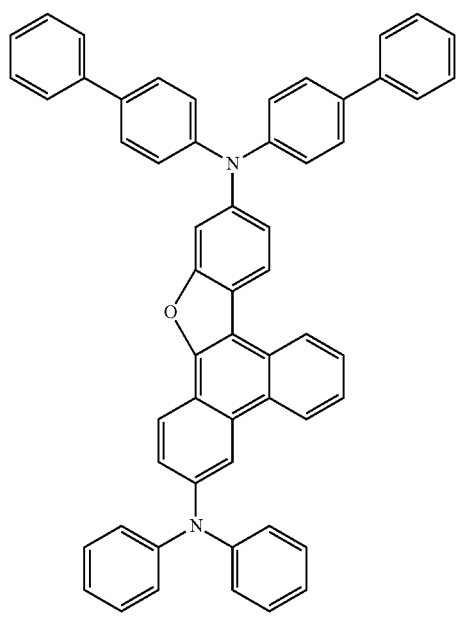
173A
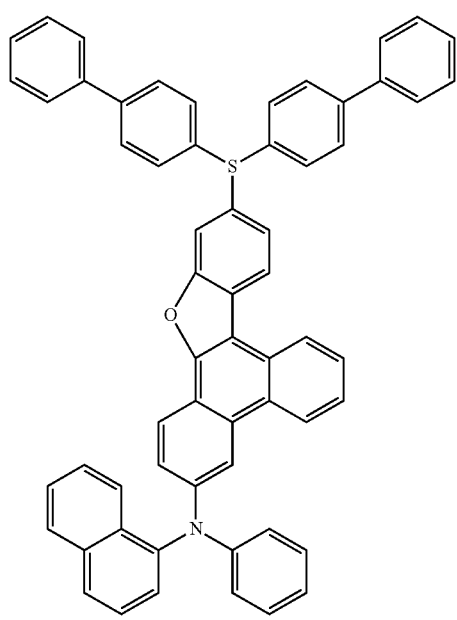
174A
236
-continued
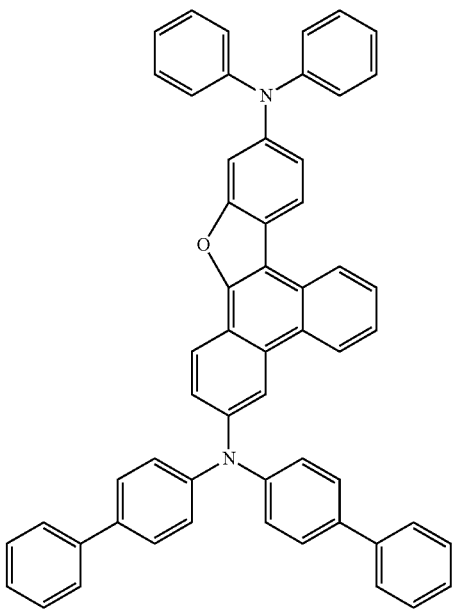
175A
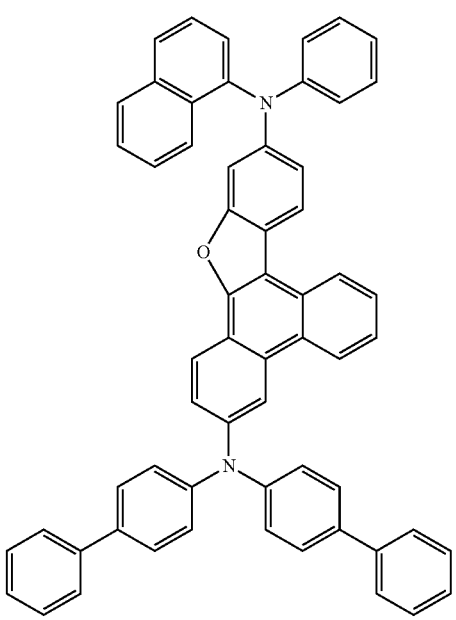
176A 237
-continued
238
-continued
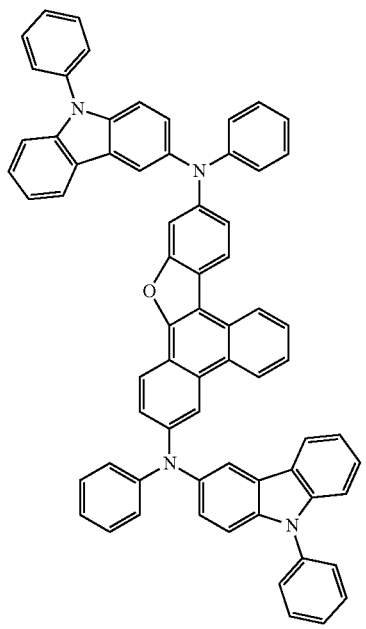
177A
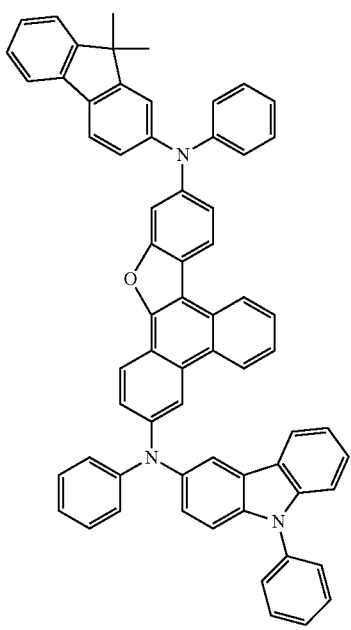
179A
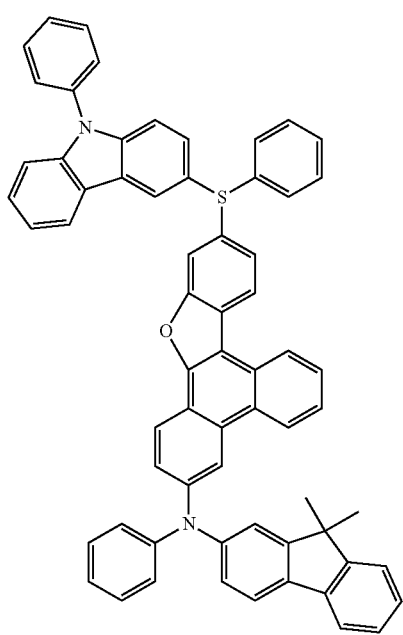
178A
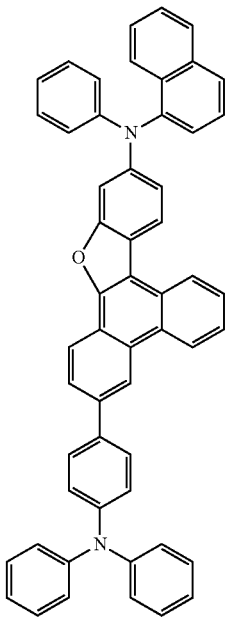
180A 239
-continued
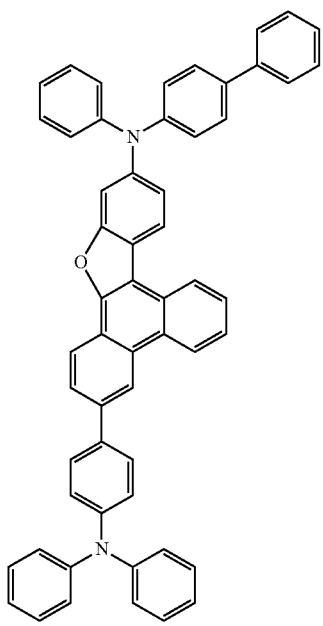
181A
240
-continued
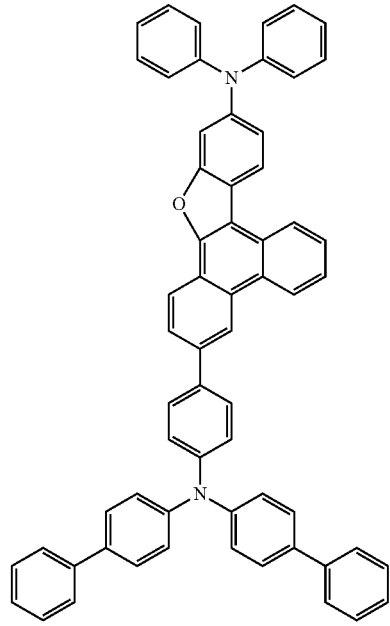
183A
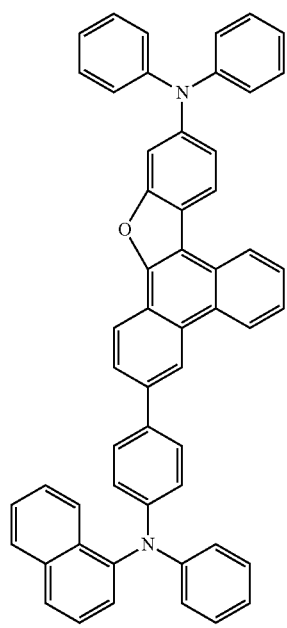
182A
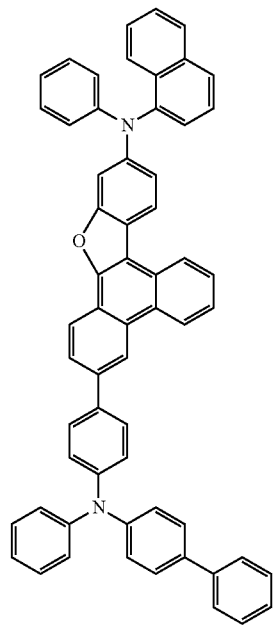
184A

241
-continued
185A
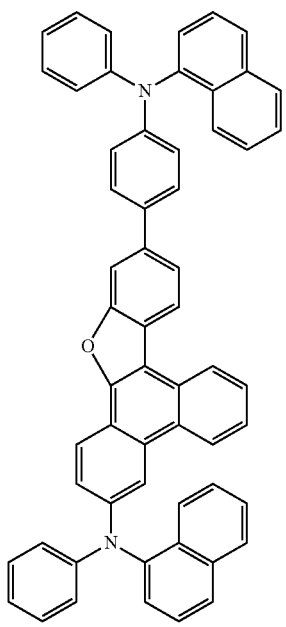
186A
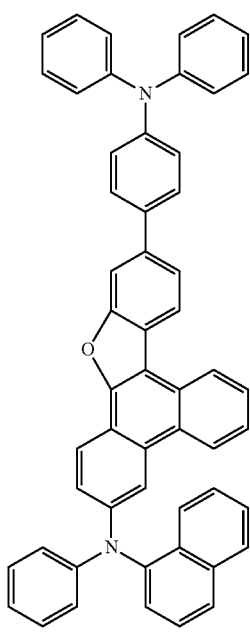
242
-continued
187A
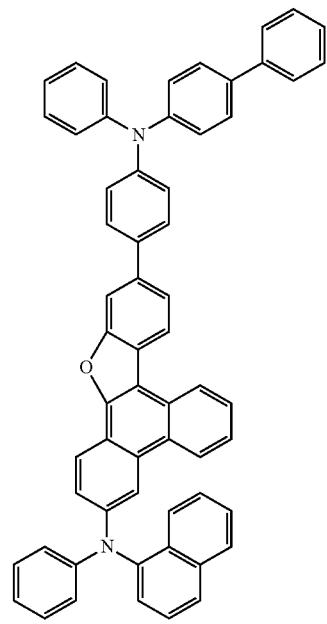
188A
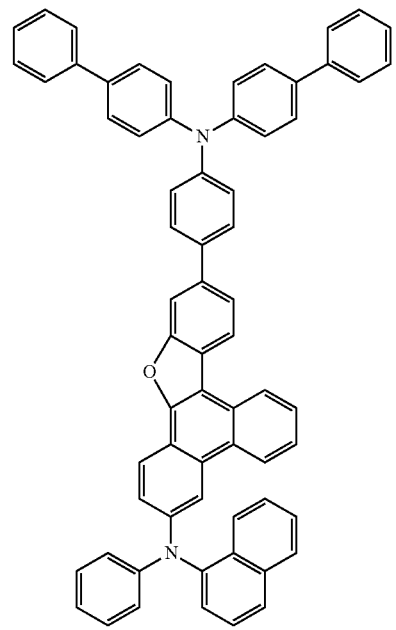

243
-continued
189A
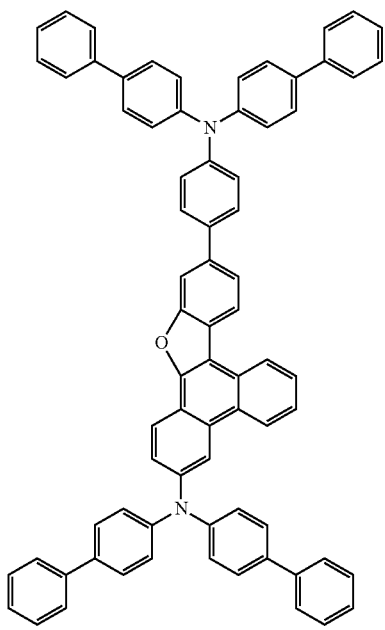
190A
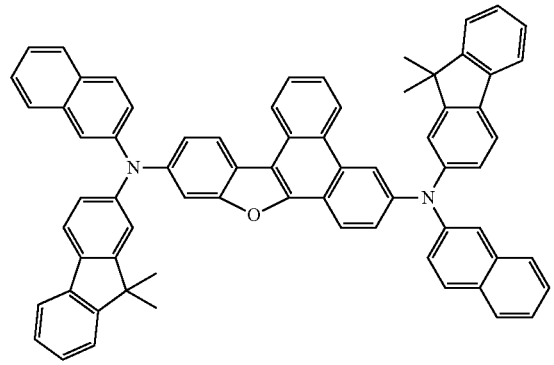
191A
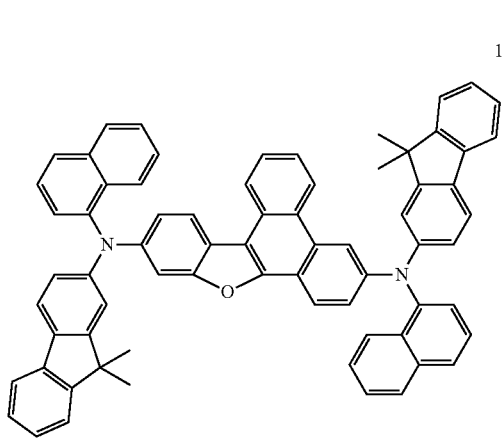
244
-continued
192A
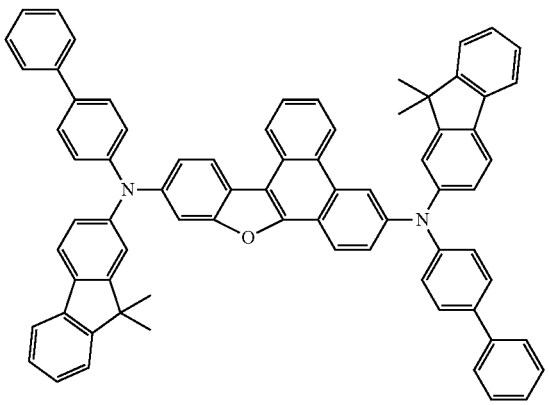
193A
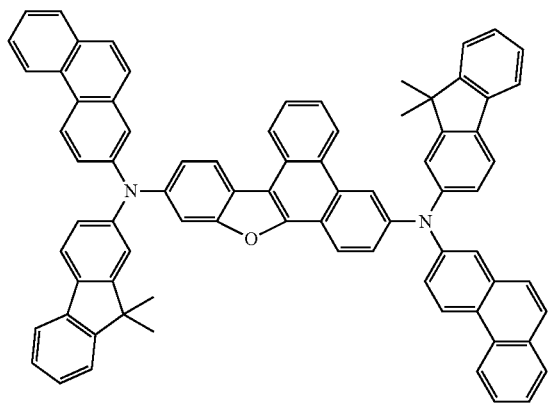
194A
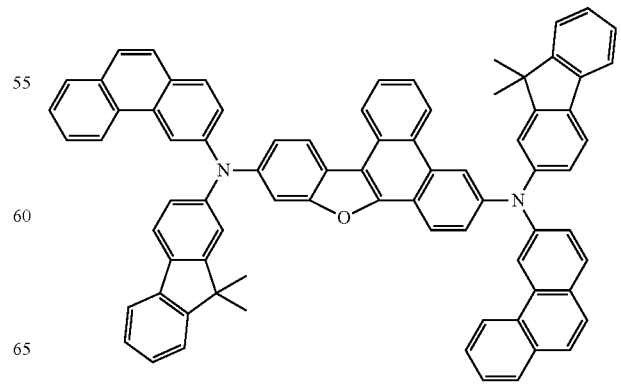

-continued
195A
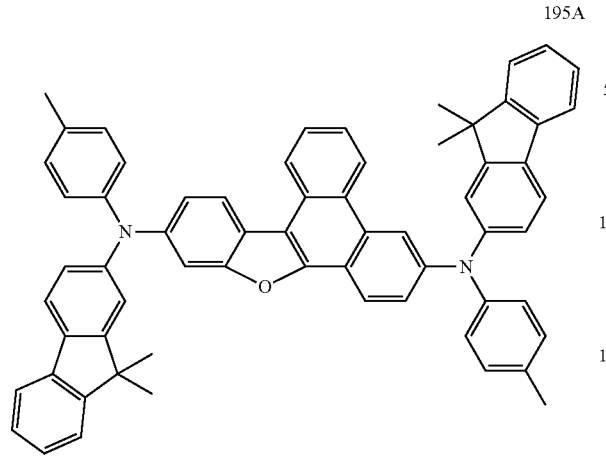
196A
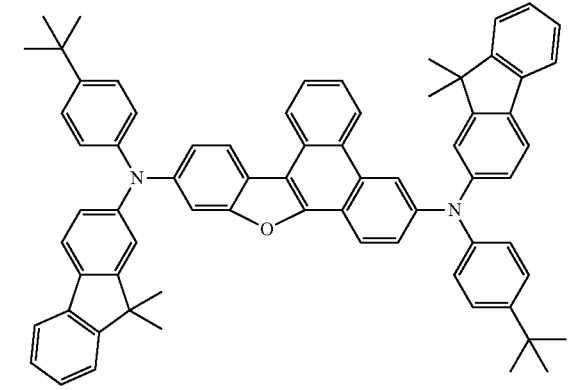
197A
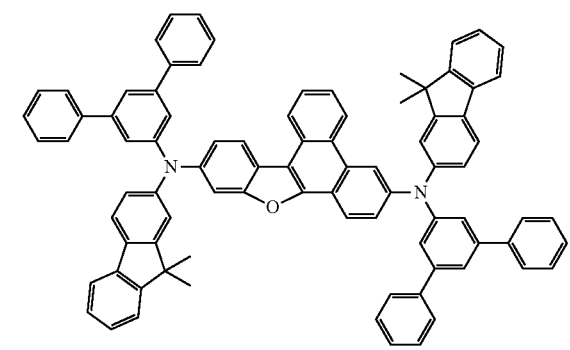
198A
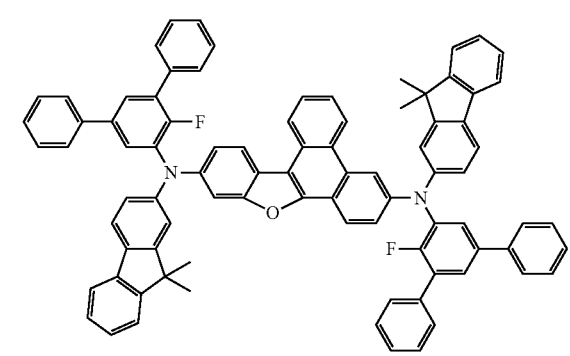
-continued
199A
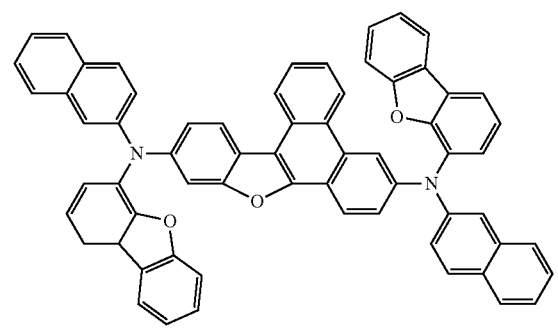
200A
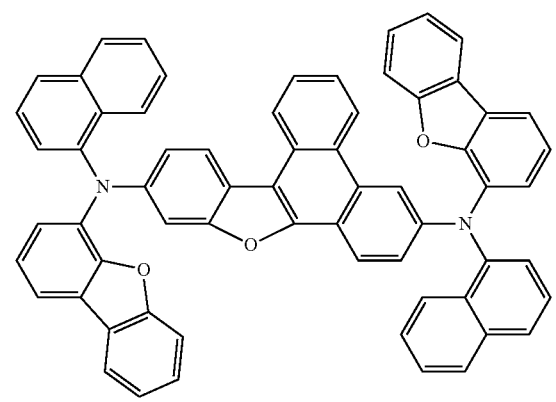
201A
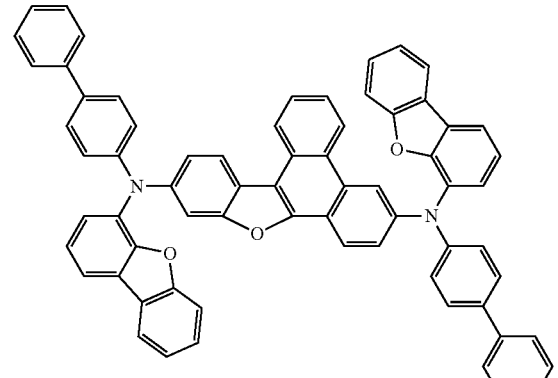
202A
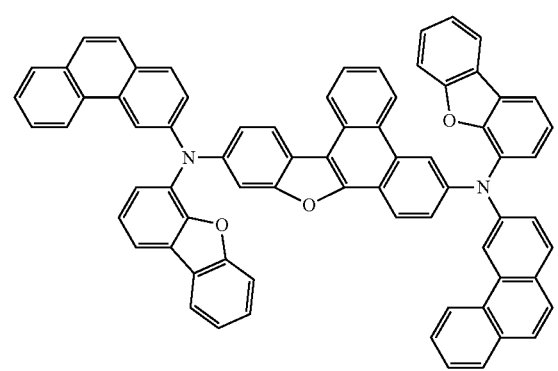

203A
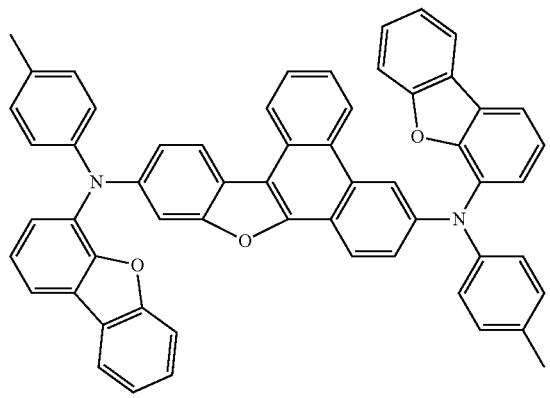
207A
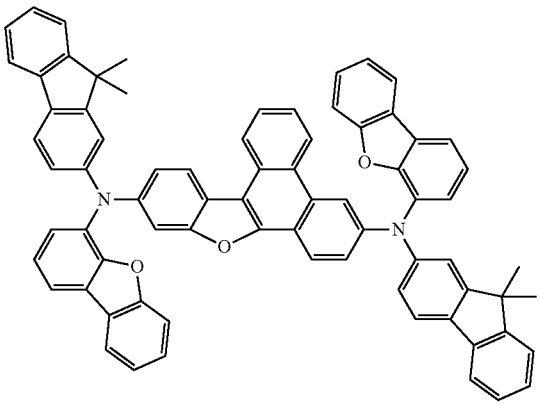
204A
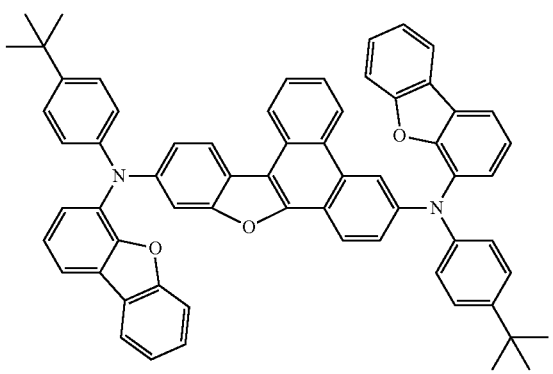
208A
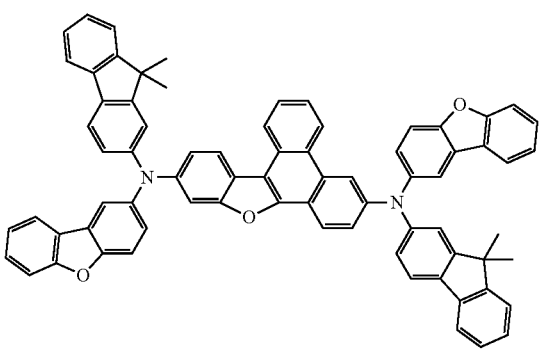
205A
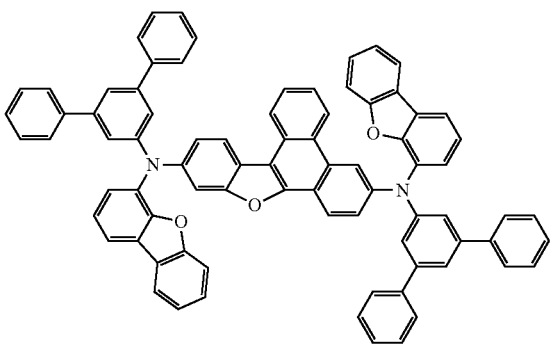
209A
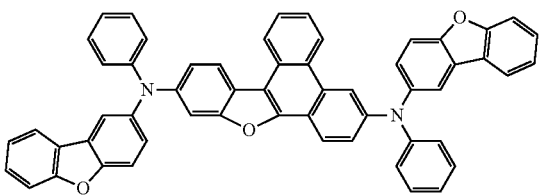
210A
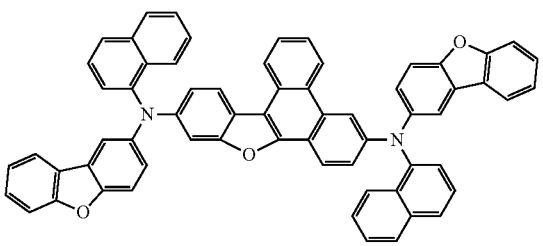
206A
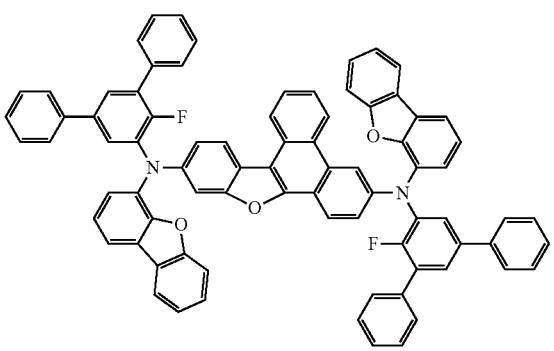
211A
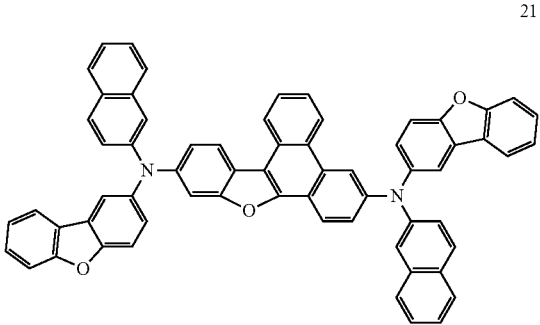

-continued
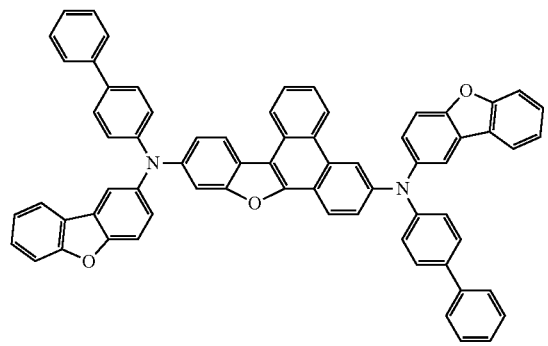
212A
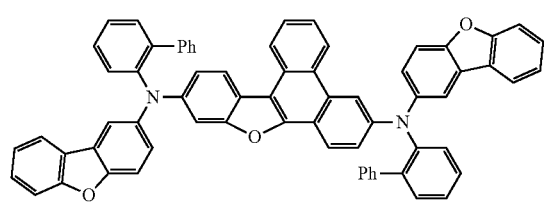
213A
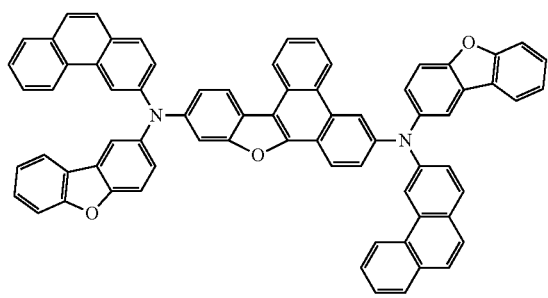
214A
215A
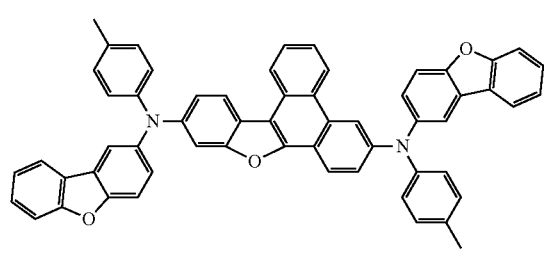
216A
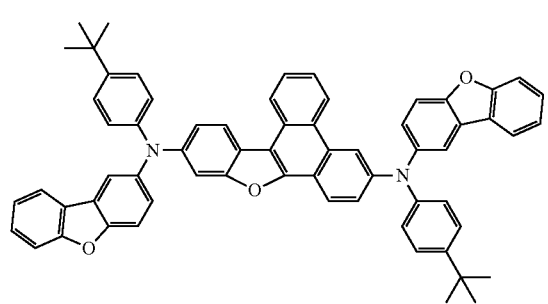
-continued
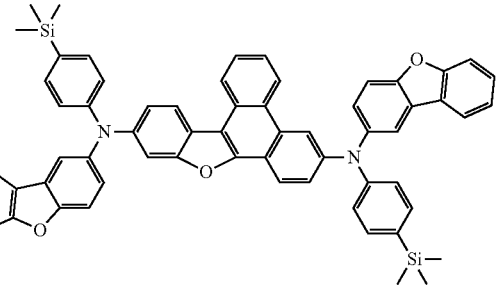
217A
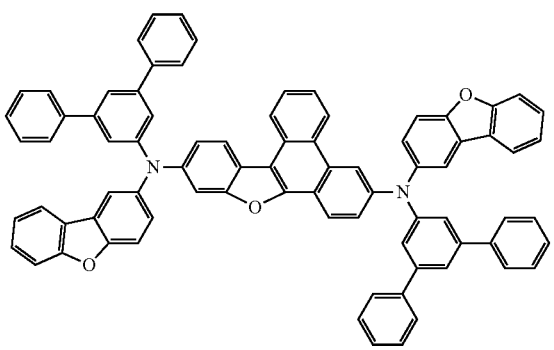
218A
219A
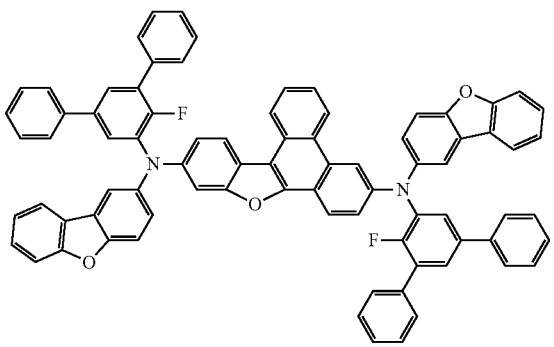
220A
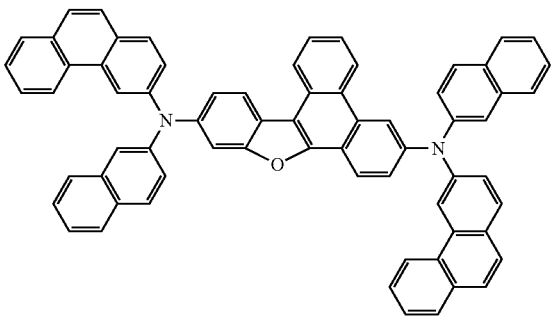

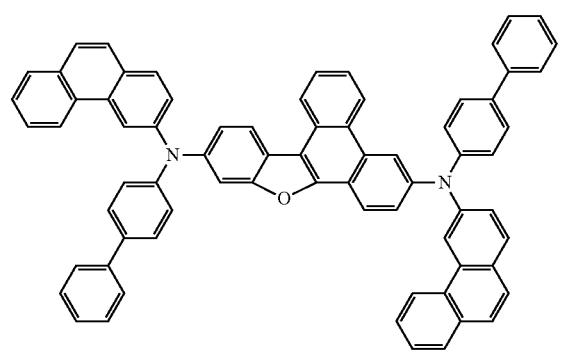
221A
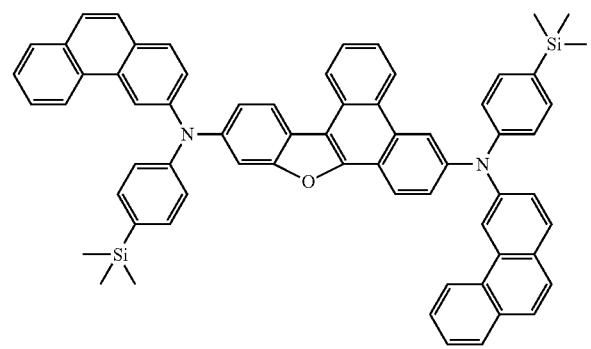
225A
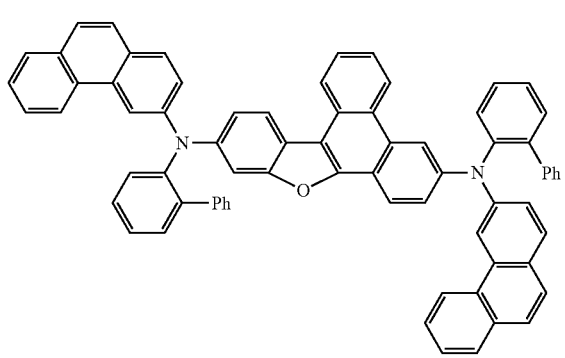
222A
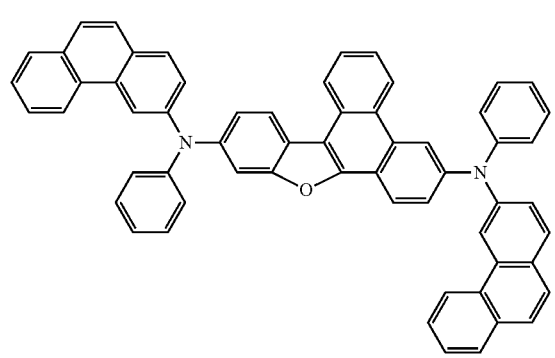
226A
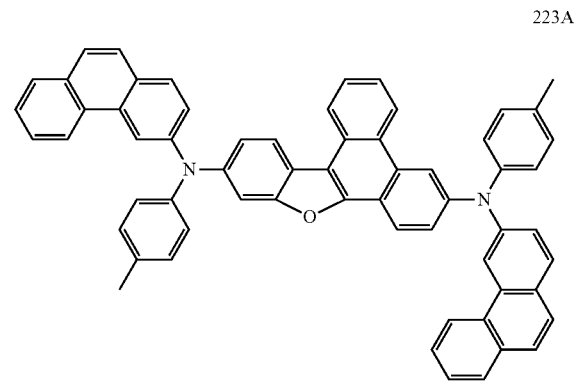
223A
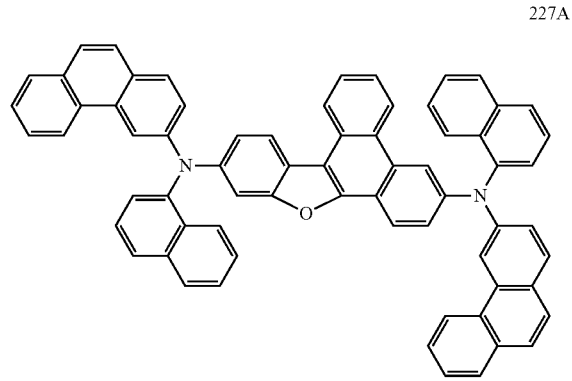
227A
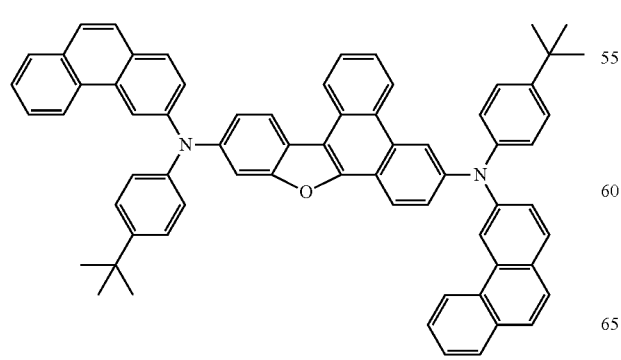
224A
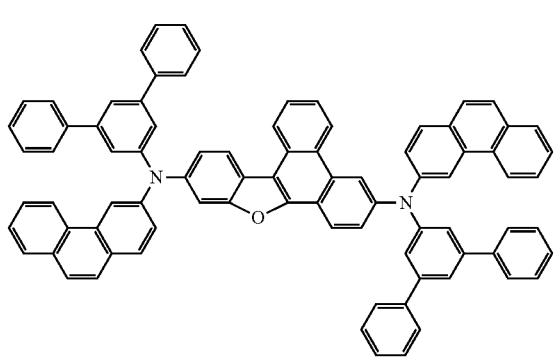
228A 229A
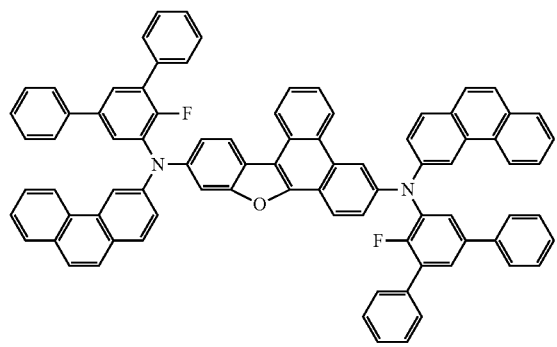
233A
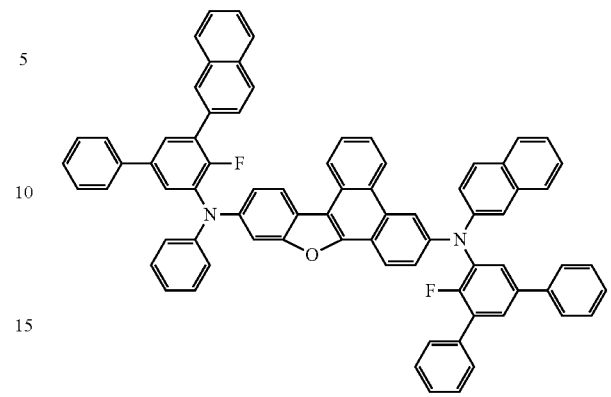
230A
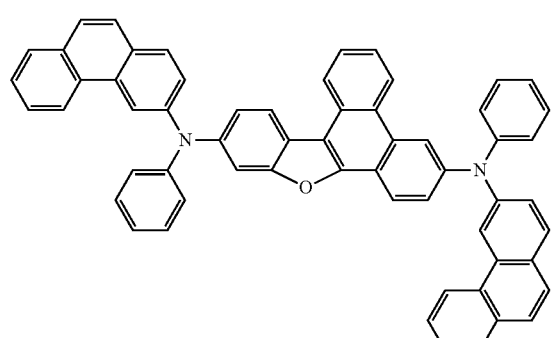
234A
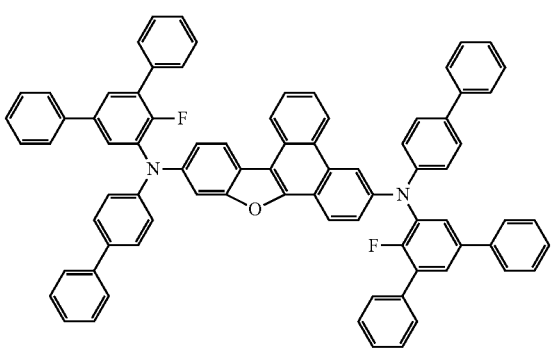
231A
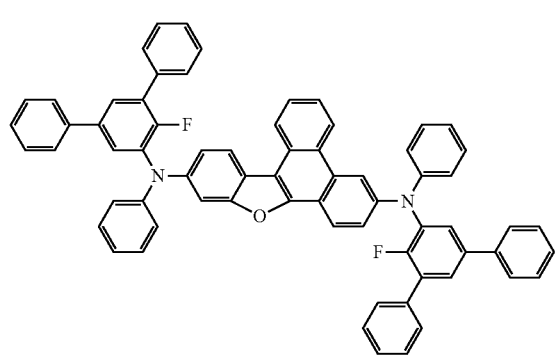
235A
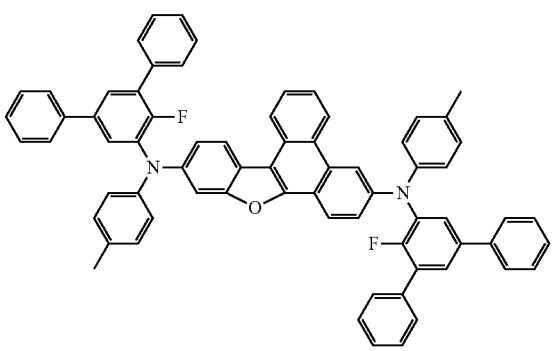
232A
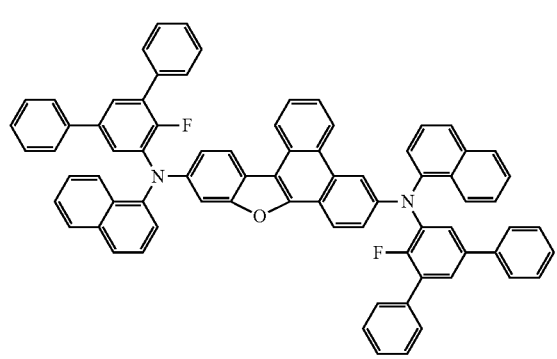
236A
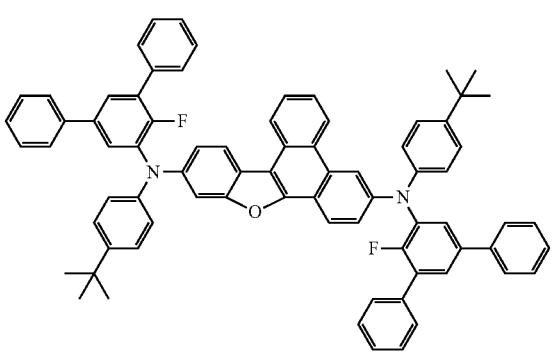

255
-continued
237A
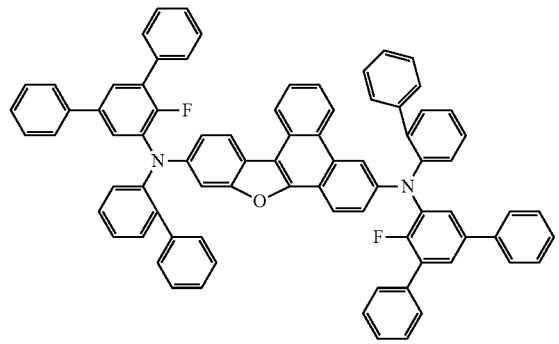
238A
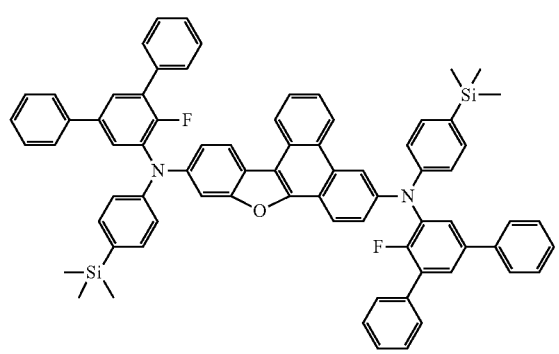
239A
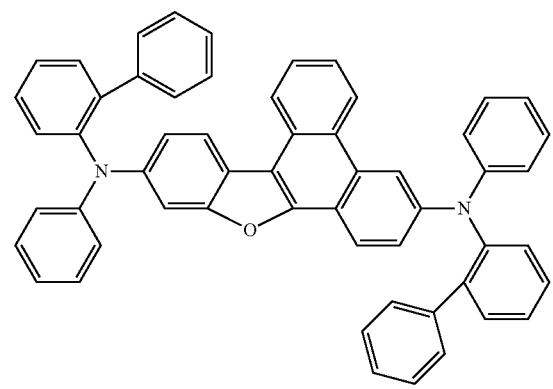
240A
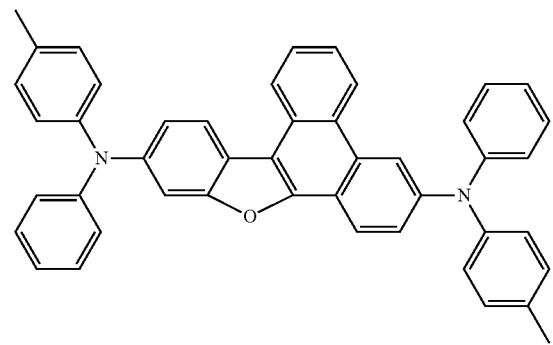
256
-continued
241A
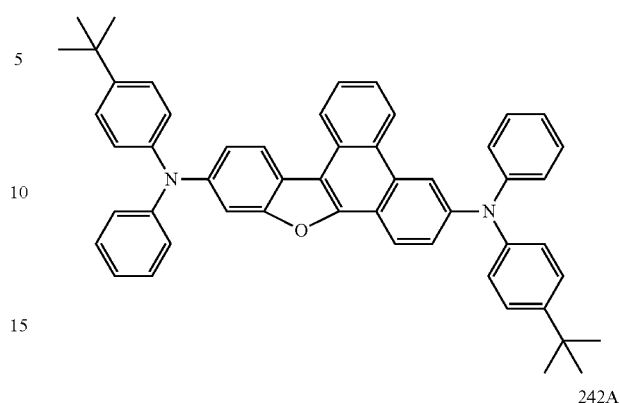
242A
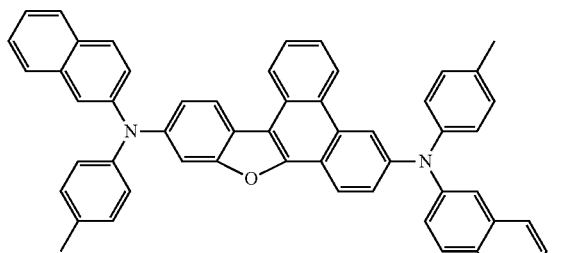
243A
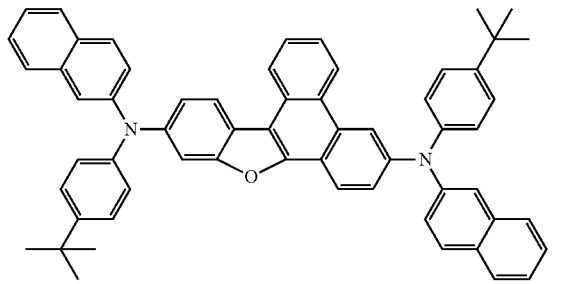
244A
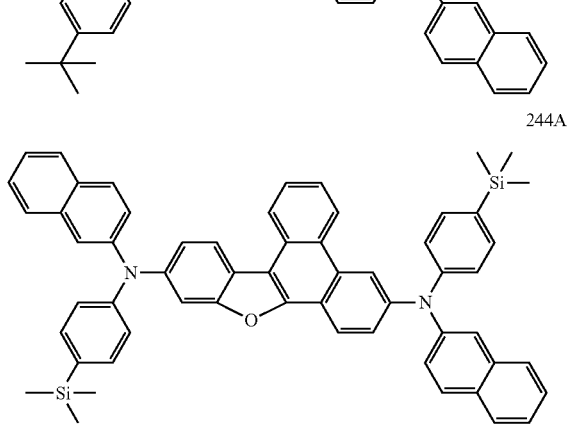
245A
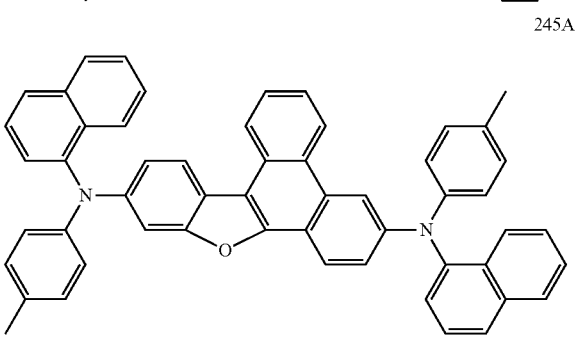

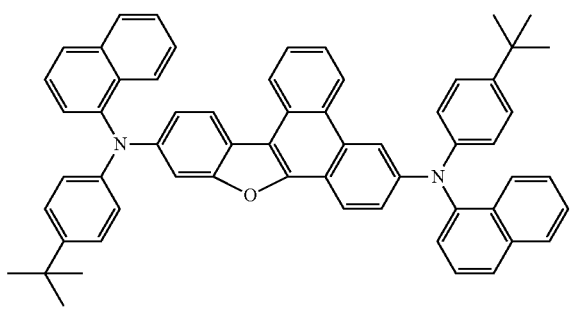

246A

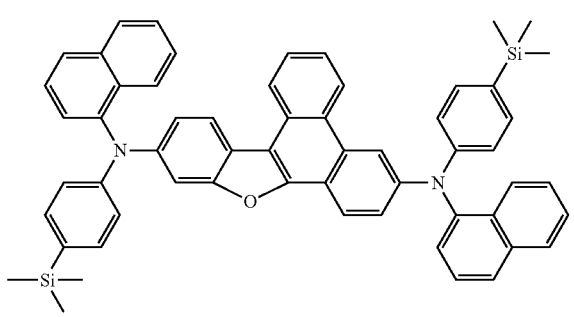

247A

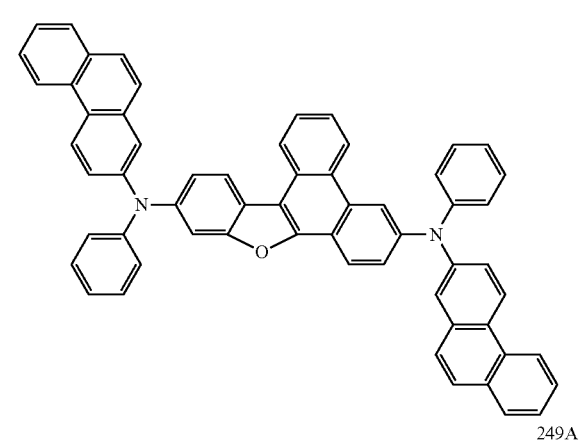

248A

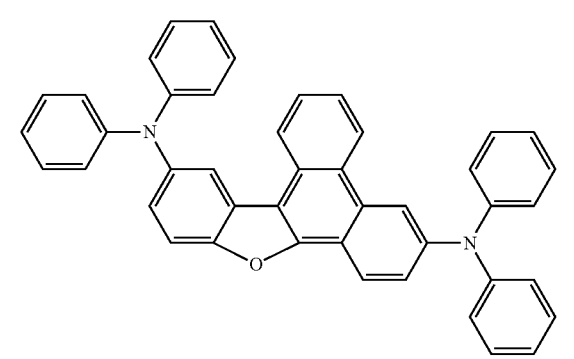

249A

In the condensed cyclic compound of Formula 1, at least two of $R_1$ to $R_{12}$ may be each independently a group represented by Formula 2, and accordingly, an organic light-emitting device employing the condensed cyclic compound of Formula 1 may have excellent efficiency characteristics.

The condensed cyclic compound of Formula 1 may be synthesized according to an organic synthesis method known in the art. The method of synthesizing the condensed cyclic compound of Formula 1 may be understood by referring to Examples described below.

At least one of the condensed cyclic compounds of Formula 1 may be used between a pair of electrodes of the organic light-emitting device. Alternatively, the condensed cyclic compound of Formula 1 may be used as a material for forming a capping layer that is positioned on an outside the pair of electrodes of the organic light-emitting device. For example, the condensed cyclic compound may be included in a hole transport region, e.g., a hole transport layer. Alternatively, the condensed cyclic compound may be included in an emission layer.

Thus, there is provided the organic light-emitting including: a first electrode; a second electrode facing the first electrode; and an organic layer disposed between the first electrode and the second electrode and including an emission layer, wherein the organic layer includes the condensed cyclic compound of Formula 1.

The expression "(an organic layer) includes at least one of the condensed cyclic compound" used herein may be applicable when "(an organic layer) includes one condensed cyclic compound of Formula 1 or two or more different condensed cyclic compound of Formula 1".

For example, the organic layer may include, as the condensed cyclic compound, only Compound 1. In this regard, Compound 1 may exist in a hole transport layer of the organic light-emitting device. Alternatively, the organic layer may include, as the condensed cyclic compound, Compound 1 and Compound 2. In this regard, Compound 1 and Compound 2 may be situated either an identical layer (for example, Compound 1 and Compound 2 all may exist in an emission layer), or different layers (for example, Compound 1 may exist in a hole transport layer and Compound 2 may exist in an emission layer).

The organic layer may include i) a hole transport region that is formed between the first electrode (e.g., an anode) and the emission layer and includes at least one of a hole injection layer, a hole transport layer, a buffer layer, and an electron blocking layer, and ii) an electron transport region that is formed between the emission layer and the second electrode (e.g., a cathode) and includes at least one of a hole blocking layer, an electron transport layer, and an electron injection layer. At least one of the hole transport region and the emission layer may include at least one of the condensed cyclic compounds of Formula 1. For example, the hole transport region may include the hole transport layer, and the hole transport layer may include at least one of the condensed cyclic compounds of Formula 1.

Alternatively, the emission layer included in the organic layer of the organic light-emitting device may include the condensed cyclic compound of Formula 1. In the emission layer, the condensed cyclic compound of Formula 1 may act as a dopant, and the emission layer may further include a host.

Alternatively, the hole transport region (for example, a hole transport layer included in the hole transport region) and emission layer may each include the condensed cyclic compound, wherein the condensed cyclic compound included in the hole transport region (for example, a hole transport layer included in the hole transport region) may be different from the condensed cyclic compound included in the emission layer.

The organic light-emitting device may further include at least one of a first capping layer and a second capping layer, wherein the first capping layer is situated on a path where light generated from the emission layer exits to the outside through the first electrode and the second capping layer is situated on a path where light generated from the emission layer exits to the outside through the second electrode, and wherein at least one of the first capping layer and the second capping layer may include at least one of the condensed cyclic compounds.

For example, the organic light-emitting device may have i) a structure of the first electrode, the organic layer, the second electrode, and the second capping layer, which are sequentially stacked in this stated order, ii) a structure of the first capping layer, the first electrode, the organic layer, and the second electrode, which are sequentially stacked in this stated order, or iii) a structure of the first capping layer, the first electrode, the organic layer, the second electrode, and the second capping layer, which hare sequentially stacked in this stated order, wherein at least one of the first capping layer and the second capping layer may include the condensed cyclic compound.

The term "organic layer" used herein refers to a single layer and/or a plurality of layers disposed between the first electrode and the second electrode of the organic light-emitting device. A material included in the "organic layer" may not be limited to an organic material.

Figure 1:
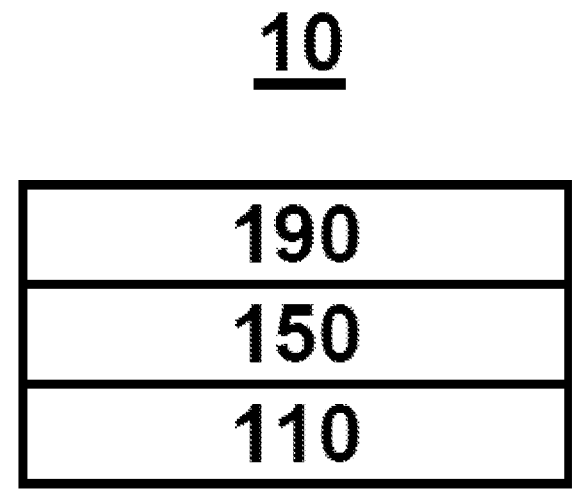

FIG. 1 illustrates a schematic cross-sectional view of an organic light-emitting device 10 according to an embodiment. The organic light-emitting device 10 includes a first electrode 110, an organic layer 150, and a second electrode 190.

Hereinafter, the structure of an organic light-emitting device according to an embodiment and a method of manufacturing an organic light-emitting device according to an embodiment will be described in connection with FIG. 1.

In FIG. 1, a substrate may be additionally disposed under the first electrode 110 or above the second electrode 190. For use as the substrate, any substrate that is used in general organic light-emitting devices may be used, and the substrate may be a glass substrate or transparent plastic substrate, each with excellent mechanical strength, thermal stability, transparency, surface smoothness, ease of handling, and water repellency.

The first electrode 110 may be formed by, for example, depositing or sputtering a material for forming the first electrode 110 on the substrate. When the first electrode 110 is an anode, the material for forming the first electrode 110 may be selected from materials with a high work function to facilitate hole injection. The first electrode 110 may be a reflective electrode, a semi-transmissive electrode, or a transmissive electrode. The material for forming the first electrode 110 may be an indium tin oxide (ITO), indium zinc oxide (IZO), tin oxide ($SnO_2$), or zinc oxide (ZnO), each with transparency and excellent conductivity. Alternatively, in order to form the first electrode 110 such as a semi-transmissive electrode or a transmissive electrode, the material for forming the first electrode 110 may be at least one selected from magnesium (Mg), aluminium (Al), aluminium-lithium (Al—Li), calcium (Ca), magnesium-indium (Mg—In), and magnesium-silver (Mg—Ag).

The first electrode 110 may have a single-layer structure or a multi-layer structure including a plurality of layers. For example, the first electrode 110 may have a triple-layered structure of ITO/Ag/ITO, but the structure of the first electrode 110 is not limited thereto.

An organic layer 150 may be disposed on top of the first electrode 110. The organic layer 150 may include an emission layer.

The organic layer 150 may further include a hole transport region between the first electrode 110 and the emission layer and an electron transport region between the emission layer and the second electrode.

The hole transport region may include at least one of a hole injection layer (HIL), a hole transport layer (HTL), a buffer layer, and an electron blocking layer (EBL), and the electron transport region may include at least one of a hole blocking layer (HBL), an electron transport layer (ETL), and an electron injection layer (EIL), but the layers are not limited thereto.

The hole transport region may have a single-layer structure including a single material, a single-layer structure including a plurality of different materials, or a multi-layer structure including a plurality of different materials.

For example, the hole transport region may have a single-layer structure including a plurality of different materials, or may have a structure of HIL/HTL, a structure of HIL/HTL/buffer layer, a structure of HIL/buffer layer, a structure of HTL/buffer layer, or a structure of HIL/HTL/EBL, each of which layers are sequentially stacked in the stated order form the first electrode 110, but the structure is not limited thereto.

When the hole transport region includes an HIL, the HIL may be formed on top of the first electrode 110 by using various methods, such as vacuum deposition, spin coating, casting, Langmuir-Blodgett (LB) deposition, ink-jet printing, laser-printing, or laser induced thermal imaging (LITI).

When the HIL is formed by vacuum deposition, deposition conditions may vary according to a compound used to form the HIL and a structure of the HIL, and for example, the deposition conditions include a deposition temperature of about 100° C. to about 500° C., a vacuum pressure of about $10^{-8}$ torr to about $10^{-3}$ torr, and a deposition rate of about 0.01 Å/sec to about 100 Å/sec.

When the HIL is formed by spin coating, spin coating conditions may vary according to a compound used to form the HIL and a structure of the HIL, and for example, the spin coating conditions include a coating speed of about 2,000 rpm to about 5,000 rpm, and a temperature at which a heat treatment is performed may be from about 80° C. to about 200° C.

When the hole transport region includes an hole transport layer, the HTL may be formed on top of the first electrode 110 or on the HIL by using various methods, such as vacuum deposition, spin coating, casting, LB deposition, ink-jet printing, laser-printing, or LITI. When the HTL is formed by vacuum deposition and spin coating, deposition and coating conditions for forming the HTL may be determined by referring to the deposition and coating conditions for forming the HIL.

The hole transport region may include the condensed cyclic compound of Formula 1. For example, the hole transport region may include the hole transport layer, and the hole transport layer may include the condensed cyclic compound of Formula 1.

Alternatively, the hole transport region may include at least one selected from m-MTDATA, TDATA, 2-TNATA, NPB, β-NPB, TPD, Spiro-TPD, Spiro-NPB, methylated NPB, TAPC, HMTPD, 4,4',4-tris(N-carbazolyl)triphenylamine (TCTA), polyaniline/dodecylbenzenesulfonic acid:polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), polyaniline/poly(4-styrenesulfonate) (PANI/PSS), a compound represented by Formula 201 below, and a compound represented by Formula 202 below:

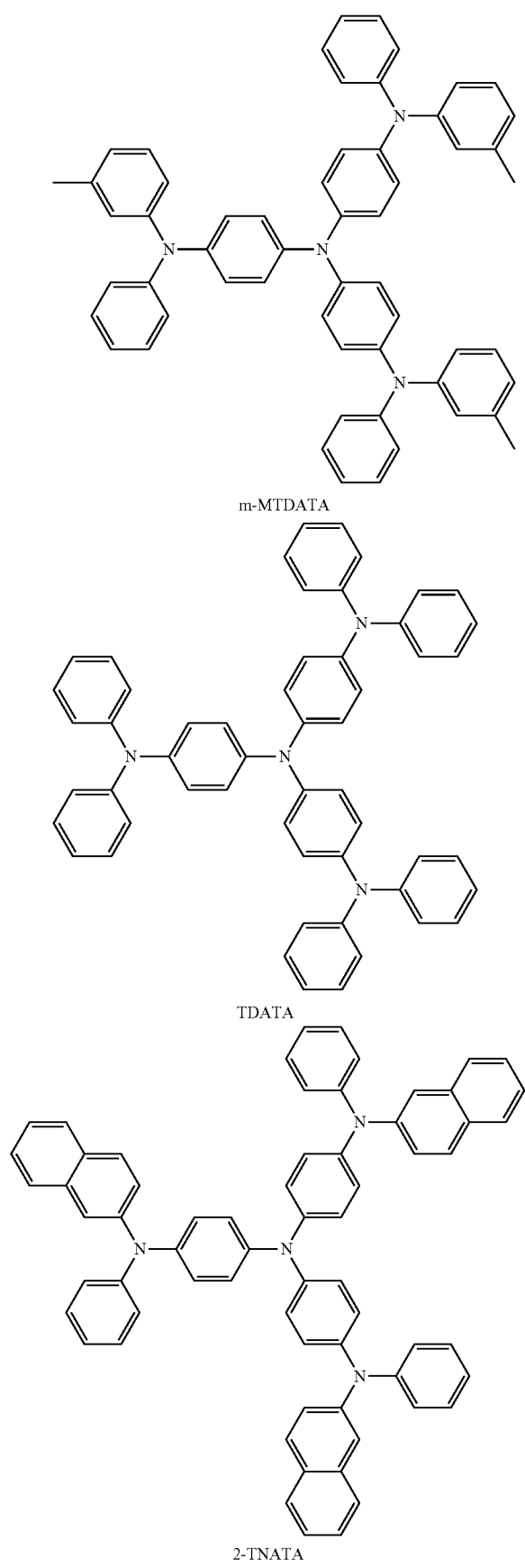
m-MTDATA
TDATA
2-TNATA
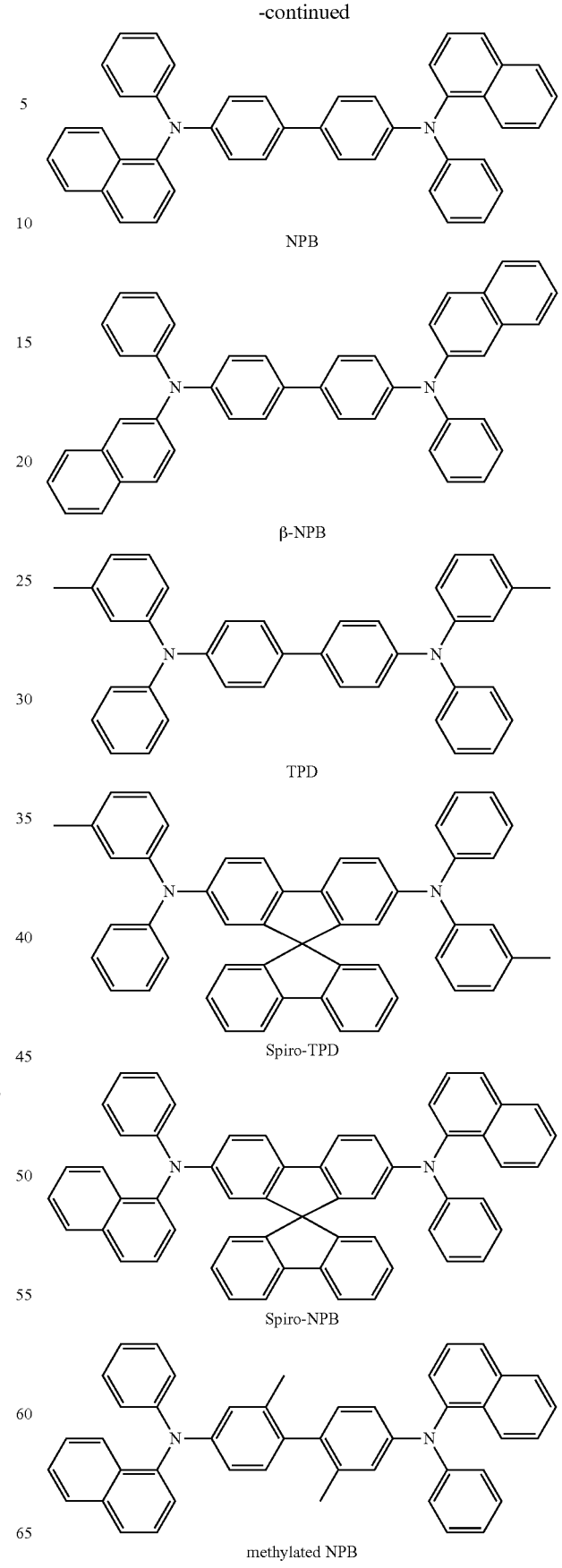
NPB
β-NPB
TPD
Spiro-TPD
Spiro-NPB
methylated NPB

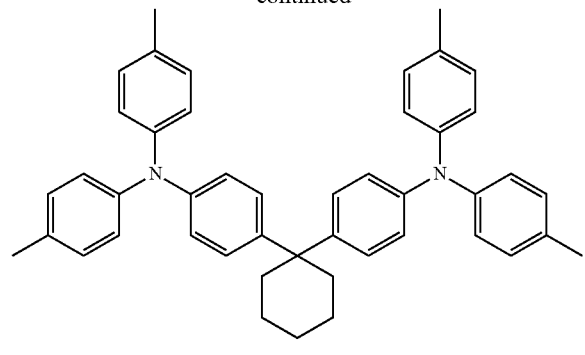

TAPC

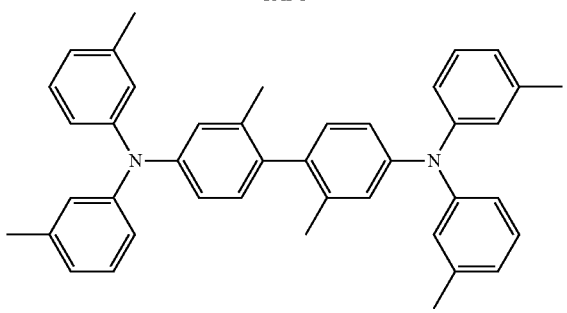

HMTPD

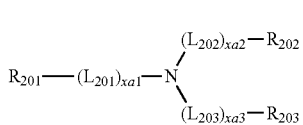

<Formula 201>

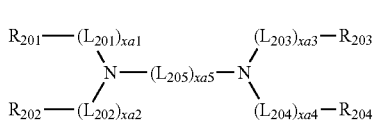

<Formula 202>

In Formulae 201 and 202, $L_{201}$ to $L_{205}$ may be may be each independently understood by referring to the description provided in connection with $L_1$;

xa1 to xa4 may be each independently selected from 0, 1, 2, and 3;

xa5 may be selected from 1, 2, 3, 4, and 5;

$R_{201}$ to $R_{204}$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formulae 201 and 202, $L_{201}$ to $L_{205}$ may be each independently selected from a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently 0, 1, or 2;

xa5 may be 1, 2, or 3; and $R_{201}$ to $R_{204}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl, but $R_{201}$ to $R_{204}$ are not limited thereto.

The compound of Formula 201 may be represented by Formula 201A below:

<Formula 201A>

For example, the compound of Formula 201 may be represented by Formula 201A-1 below, but is not limited thereto:

<Formula 201A-1>

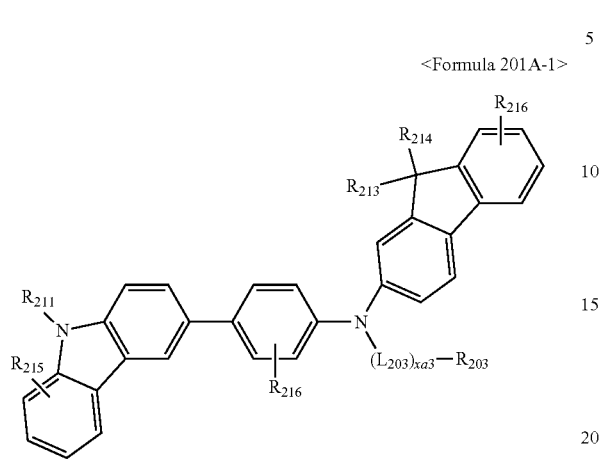

The compound of Formula 202 may be represented by Formula 202A below, but is not limited thereto:

<Formula 202A>

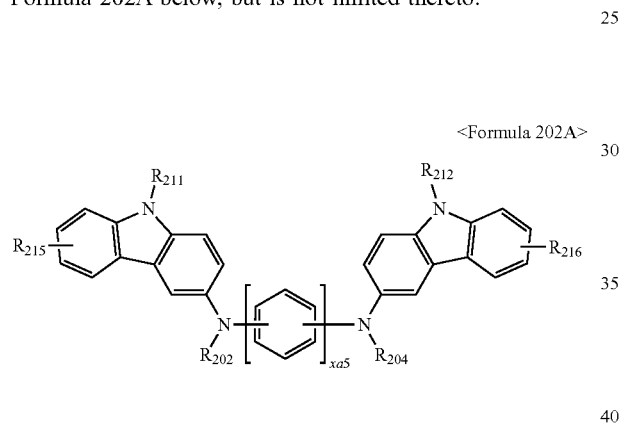

In Formulae 201A, 201A-1, and 202A, $L_{201}$ to $L_{203}$, xa1 to xa3, xa5, and $R_{202}$ to $R_{204}$ may be understood by referring to the description provided herein, $R_{211}$ and $R_{212}$ may be each independently referred to the description provided in connection with $R_{203}$, and $R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

The compound of Formula 201 and the compound of Formula 202 may include Compounds HT1 to HT20, but are not limited thereto:

HT1

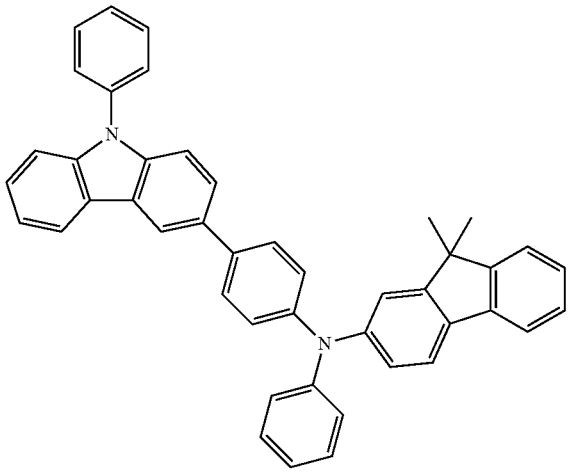

HT2

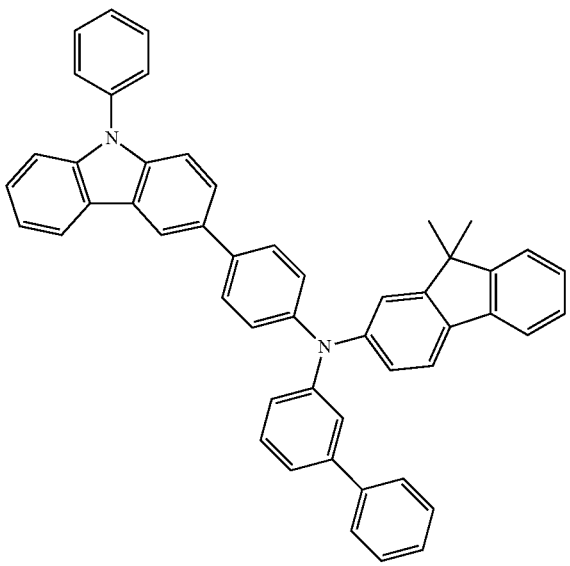

HT3

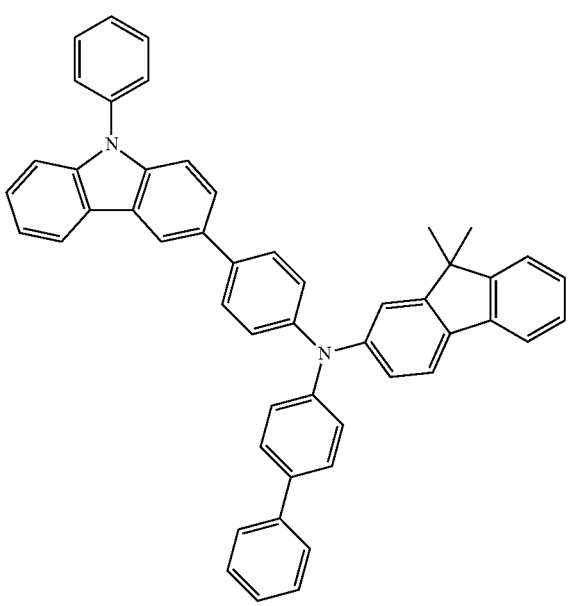

267
-continued
HT4
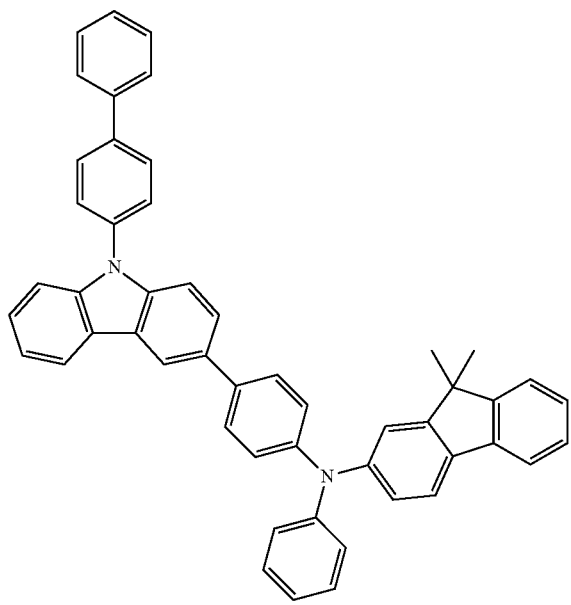
268
-continued
HT6
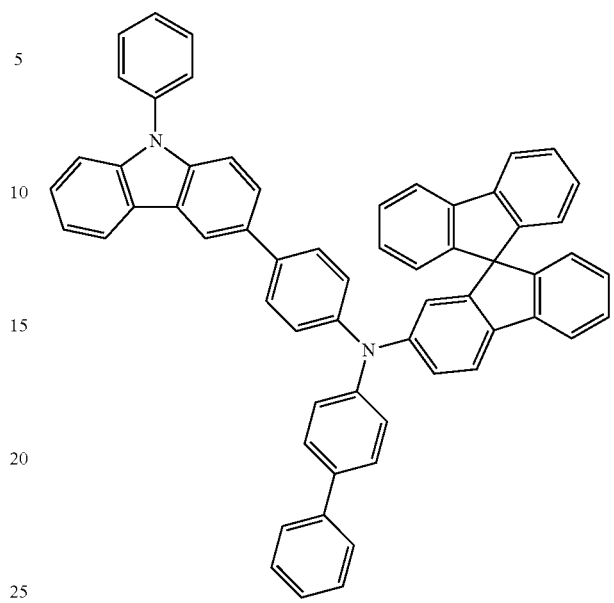
HT5
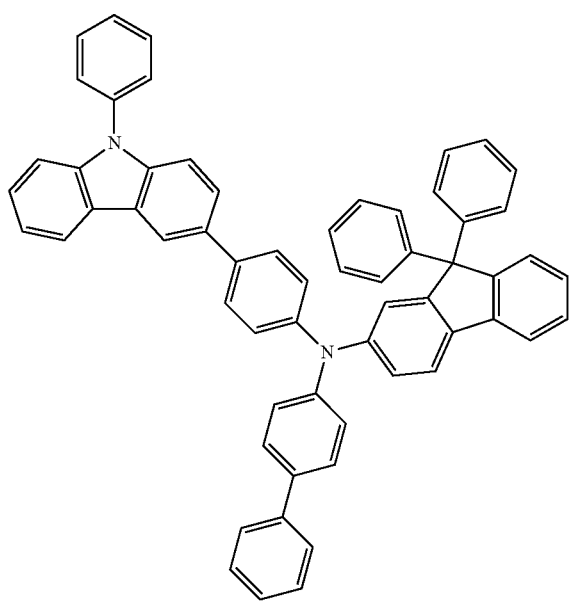
HT7
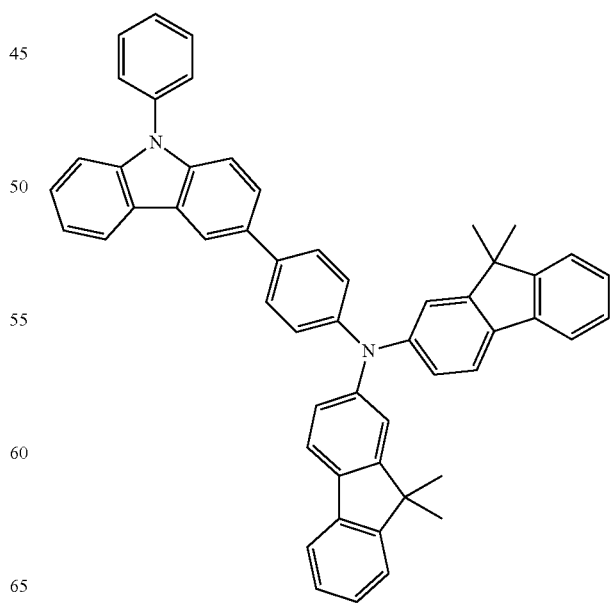

-continued
HT8
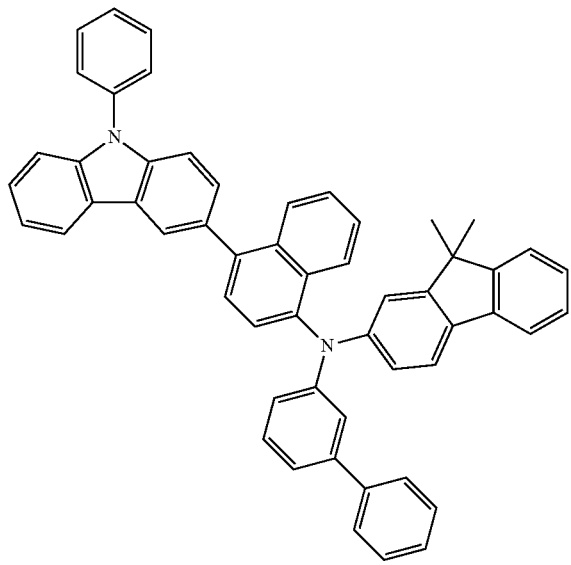
HT9
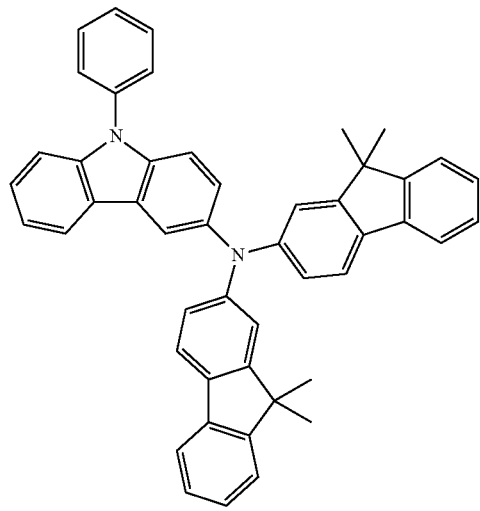
-continued
HT10
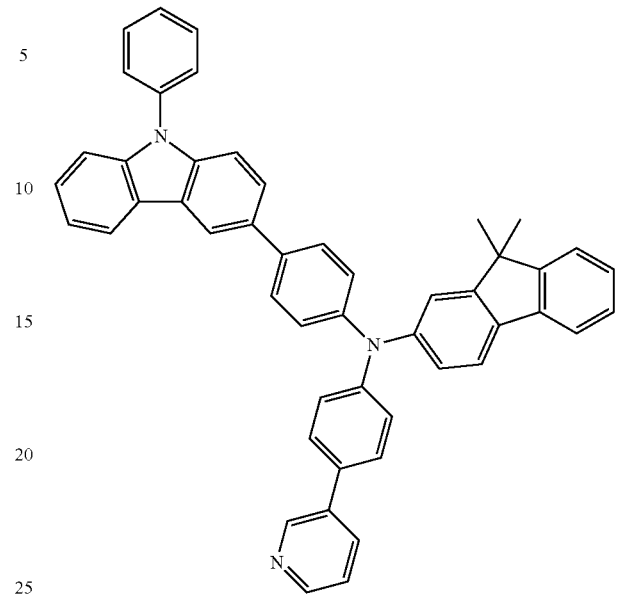
HT11
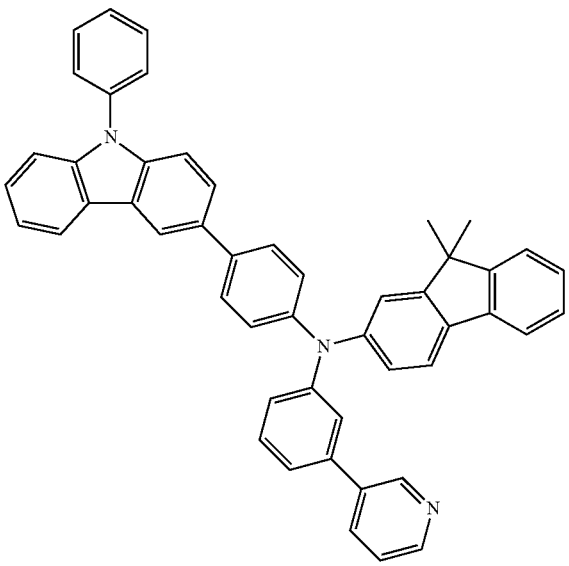

-continued
HT12
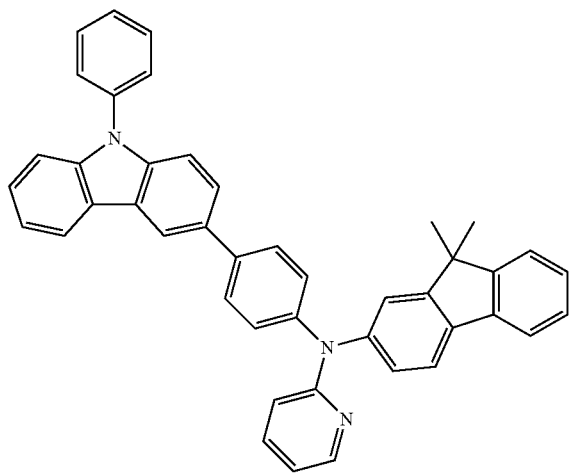
HT13
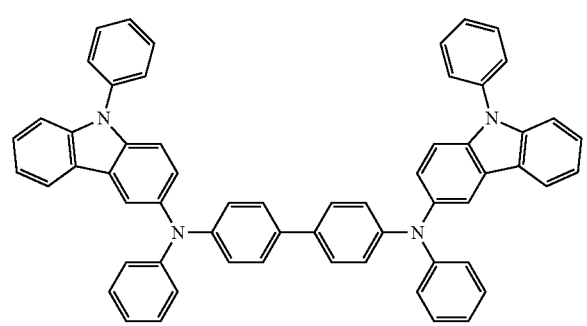
HT14
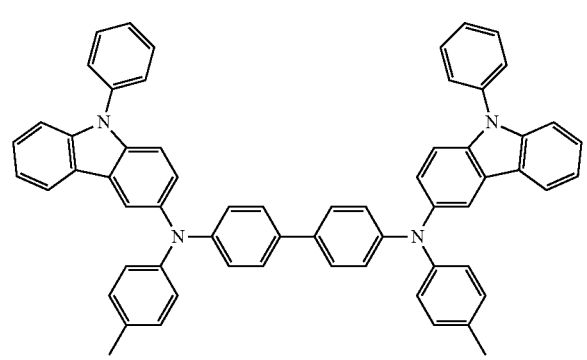
-continued
HT15
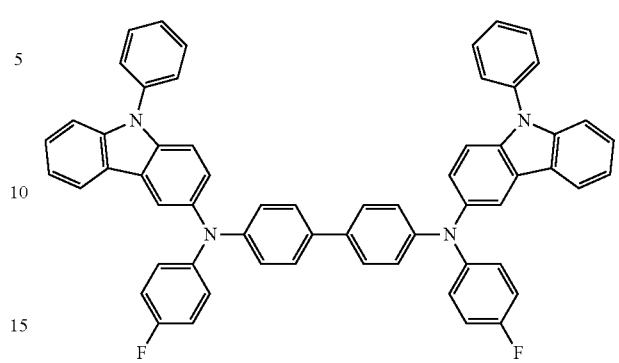
HT16
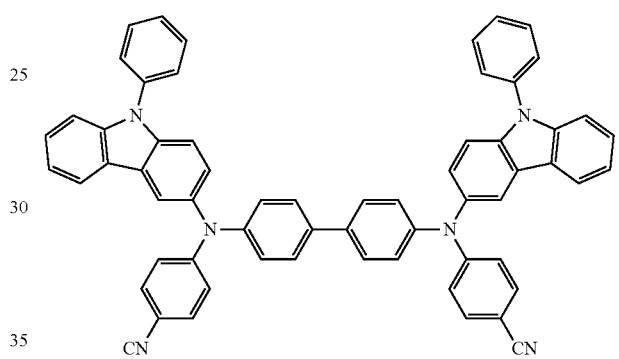
HT17
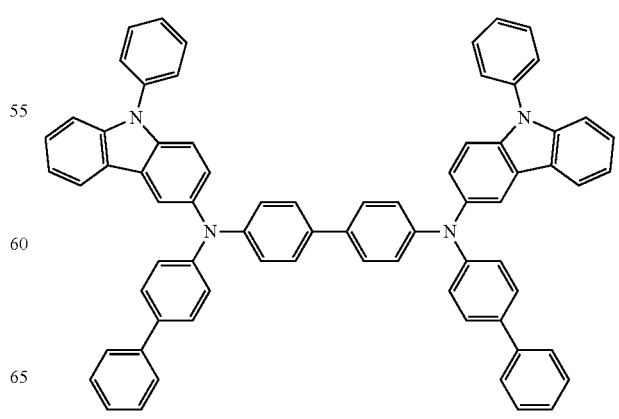
HT18

-continued

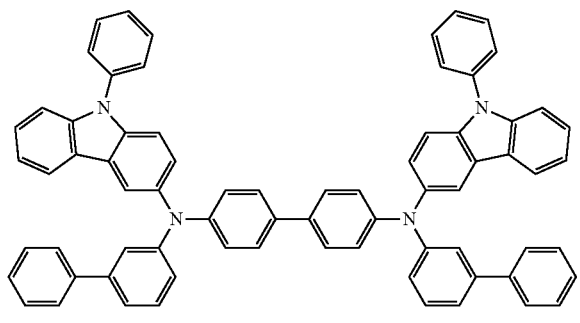

HT19

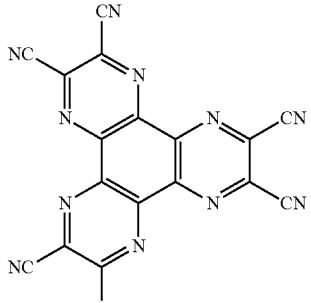

<Compound HT-D1>

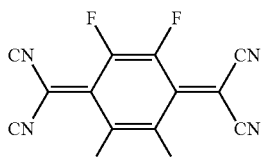

<F4-TCNQ>

HT20

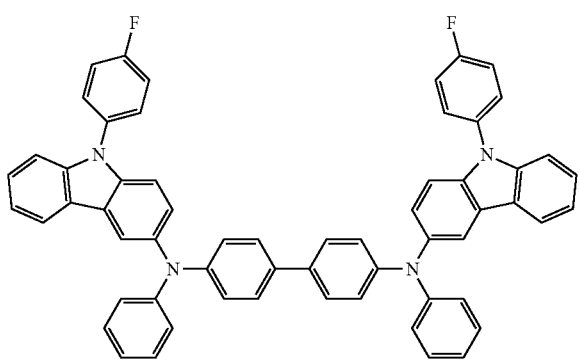

A thickness of the hole transport region may be from about 100 Å to about 10,000 Å, e.g., about 100 Å to about 1,000 Å. When the hole transport region includes both an HIL and an HTL, a thickness of the HIL may be from about 100 Å to about 10,000 Å, e.g., about 100 Å to about 1,000 Å, and a thickness of the HTL may be from about 50 Å to about 2,000 Å, e.g., about 100 Å to about 1,500 Å. When the thicknesses of the hole transport region, the HIL, and the HTL are within these ranges, satisfactory hole transporting characteristics may be obtained without a substantial increase in driving voltage.

In addition to the materials described above, the hole transport region may further include a charge-generation material for the improvement of conductive characteristics. The charge-generation material may be homogeneously or non-homogeneously dispersed in the hole transport region.

The charge-generation material may be, e.g., a p-dopant. The p-dopant may be one of a quinone derivative, a metal oxide, and a cyano group-containing compound, but is not limited thereto. Non-limiting examples of the p-dopant are a quinone derivative such as tetracyanoquinonedimethane (TCNQ) or 2,3,5,6-tetrafluoro-tetracyano-1,4-benzoquinonedimethane (F4-TCNQ); a metal oxide such as a tungsten oxide or a molybdenum oxide; and Compound HT-D1 below, but are not limited thereto.

The hole transport region may further include, in addition to the HIL and the HTL, at least one of a buffer layer and an EBL. The buffer layer may compensate for an optical resonance distance according to a wavelength of light emitted from the emission layer, and thus, a light-emission efficiency of a formed organic light-emitting device may be improved. For use as a material for forming the buffer layer, a material for forming the hole transport region may be used. The EBL may help prevent electron injection from the electron transport region.

An emission layer may be disposed on top of the first electrode 110 or on the hole transport region by using various methods, such as vacuum deposition, spin coating, casting, LB deposition, ink-jet printing, laser-printing, or LITI. When the emission layer is formed by vacuum deposition and spin coating, deposition and coating conditions for forming the emission layer may be determined by referring to the deposition and coating conditions for forming the HIL.

When the organic light-emitting device 10 is a full-color organic light-emitting device, the emission layer may be patterned into a red emission layer, a green emission layer, and a blue emission layer, according to a red subpixel, a green subpixel, and a blue subpixel, respectively. Alternatively, the emission layer may have a structure of a red emission layer, a green emission layer, and a blue emission layer, each of which layers are sequentially stacked in this stated order, or may have a structure where a red light-emitting material, a green light-emitting material, and a blue light-emitting material are mixed regardless of layer division, and accordingly, the emission layer may emit white light.

The emission layer may include a host and a dopant.

The host may include a compound represented by Formula 301 below.

$$Ar_{301}-[(L_{301})_{xb1}-R_{301}]_{xb2}$$ <Formula 301>

In Formula 301,

Ar$_{301}$ may be selected from a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si(Q$_{301}$)(Q$_{302}$)(Q$_{303}$) (wherein Q$_{301}$ to Q$_{303}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

L$_{301}$ may be understood by referring to the description provided in connection with L$_1$;

R$_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3; and xb2 may be selected from 1, 2, 3, and 4.

For example, in Formula 301,

L$_{301}$ may be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and R$_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but L$_{301}$ and R$_{301}$ are not limited thereto.

For example, the host may include a compound represented by Formula 301A below:
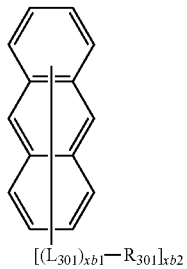
<Formula 301A>
[(L_{301})_{xb1}—R_{301}]_{xb2}
Substituents in Formula 301A may be understood by referring to the description provided herein.
The compound of Formula 301 may include at least one of Compounds H1 to H42 below, but is not limited thereto:
H1
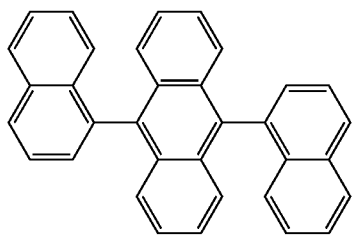
H2
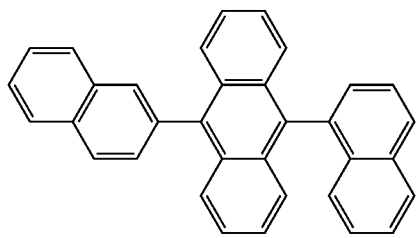
H3
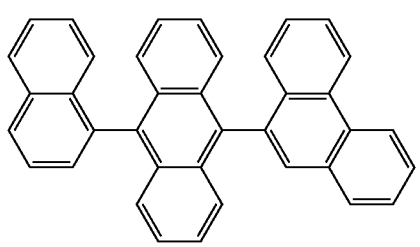
H4
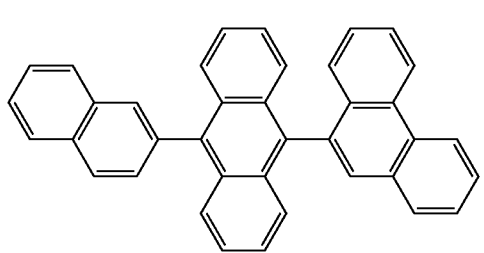
H5
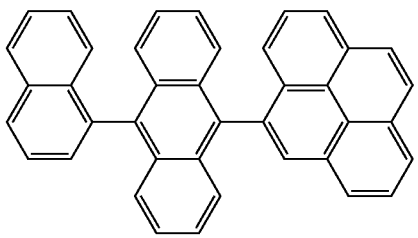
H6
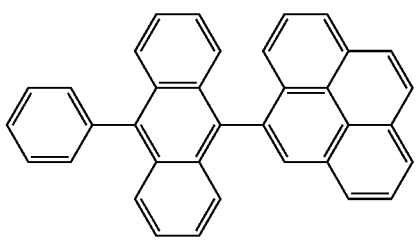
H7
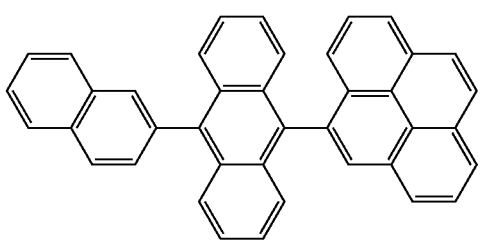
H8
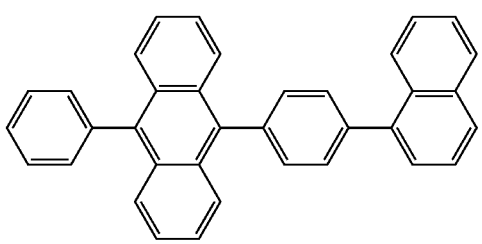
H9
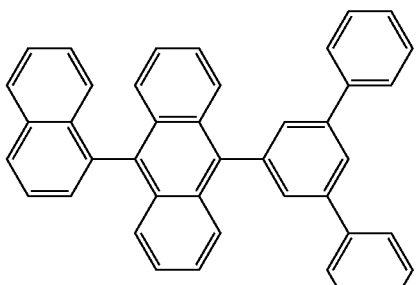
H10
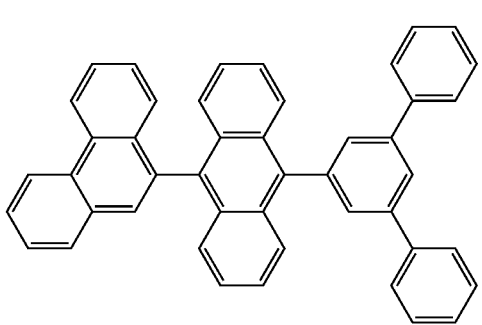

-continued
H11
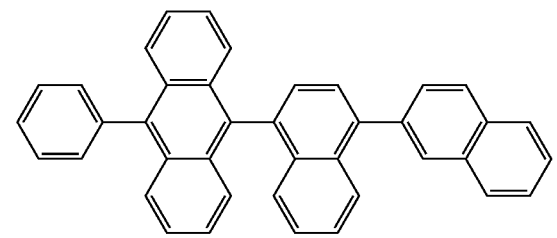
H12
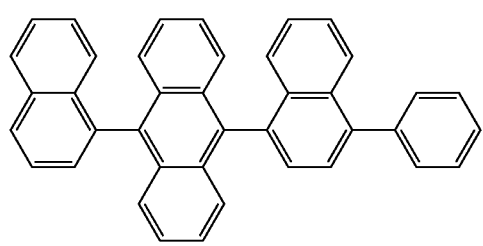
H13
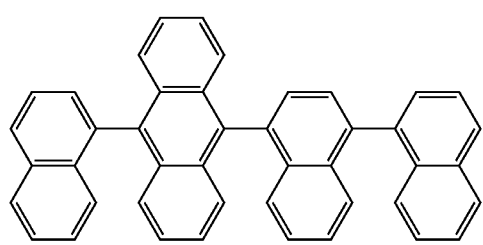
H14
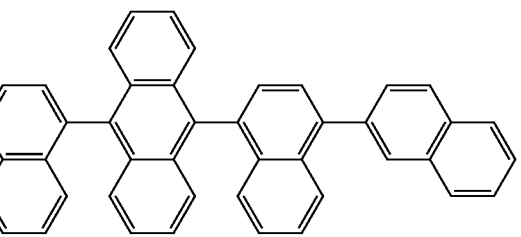
H15
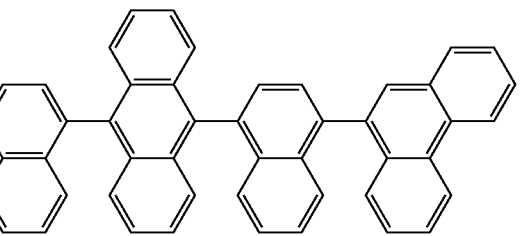
H16
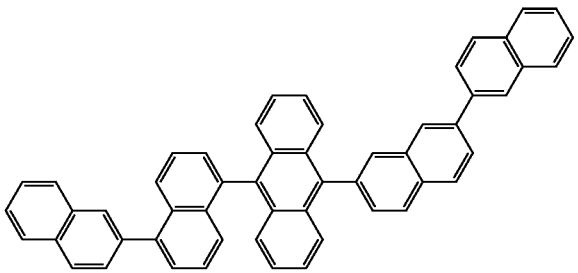
-continued
H17
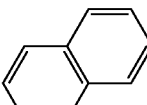
H18
H19
H20
H21

H22
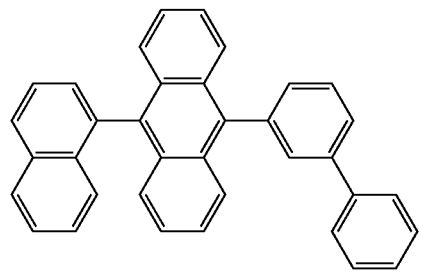
H23
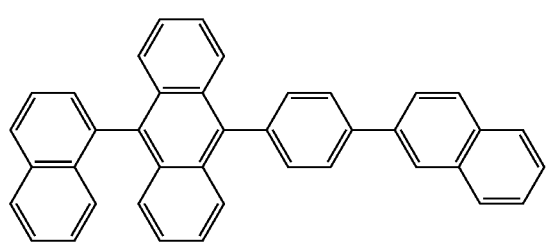
H24
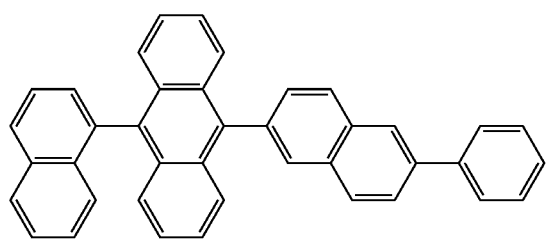
H25
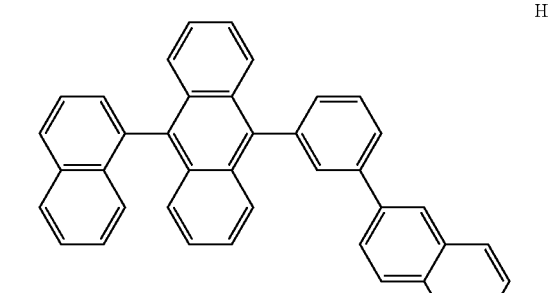
H26
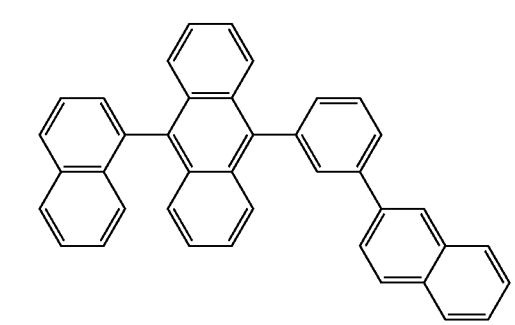
H27
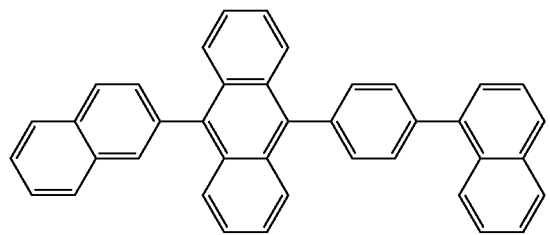
H28
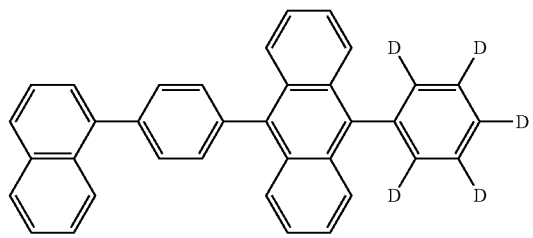
H29
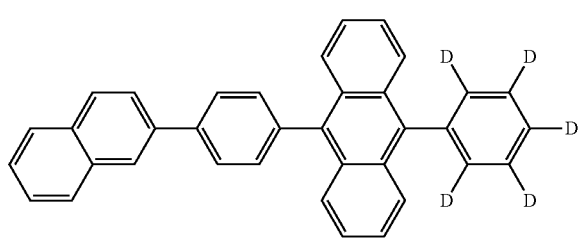
H30
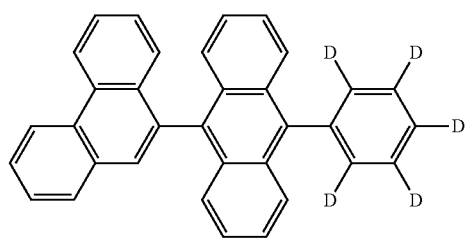
H31
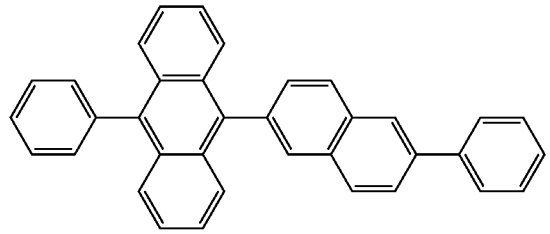
H32
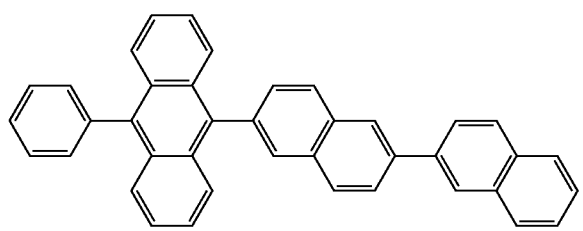

H33
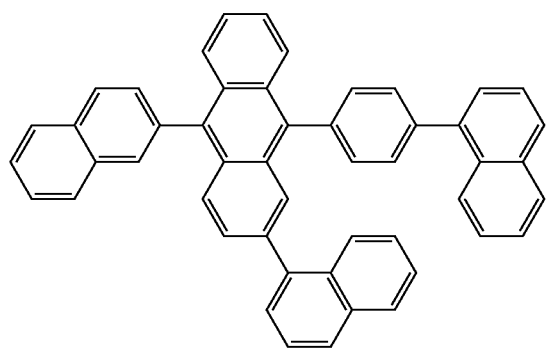
H34
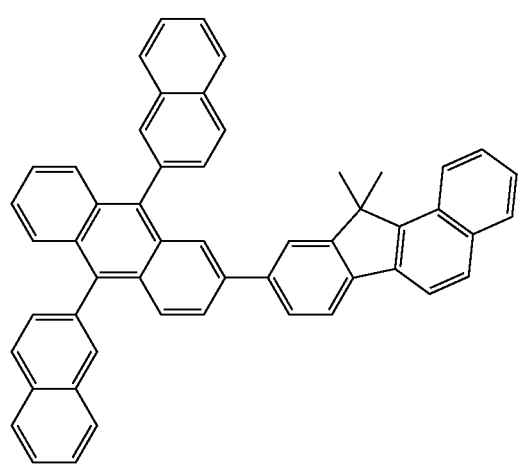
H35
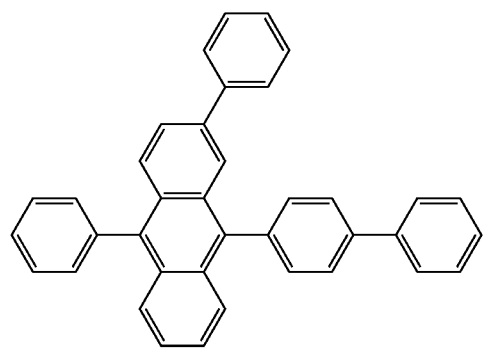
H36
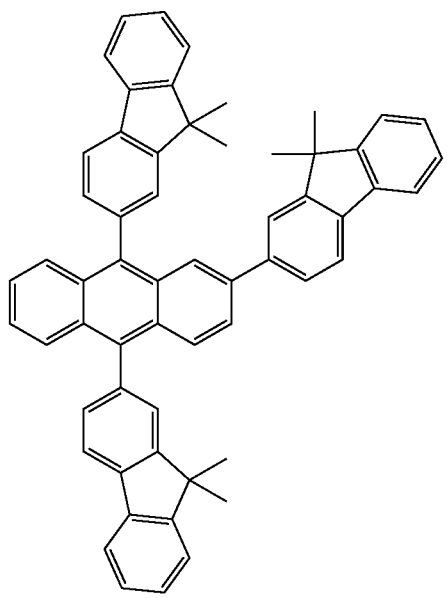
H37
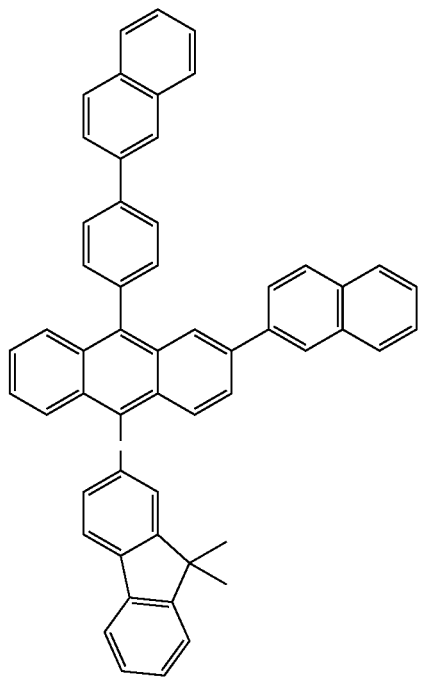
H38
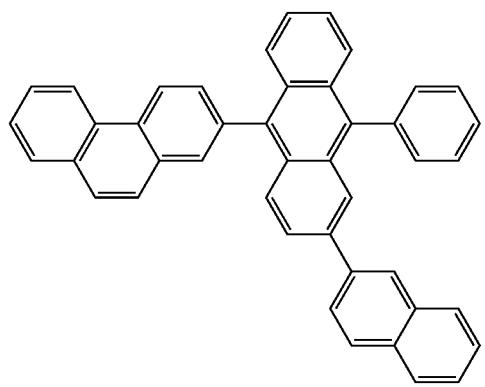

H39
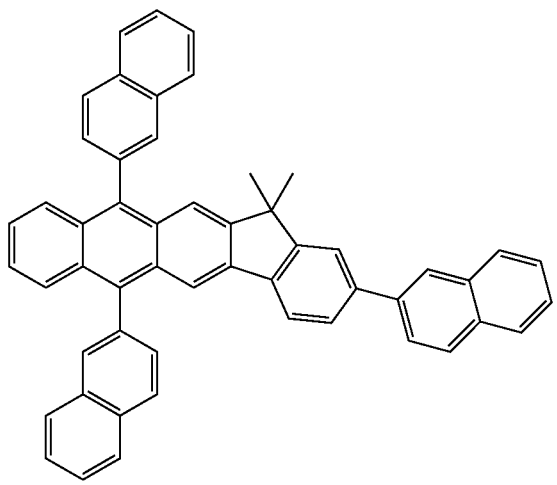
H42
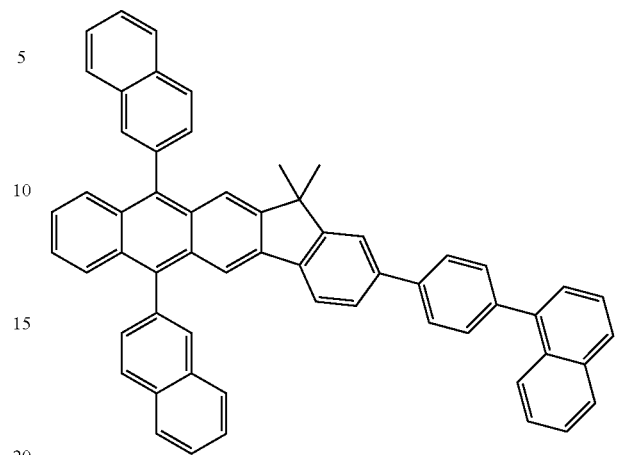
Alternatively, the host may include at least one of Compounds H43 to H49 below, but is not limited thereto:
H40
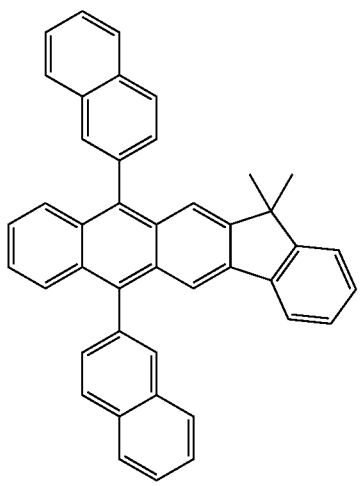
H43
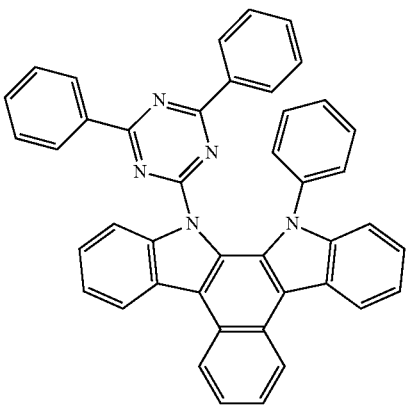
H41
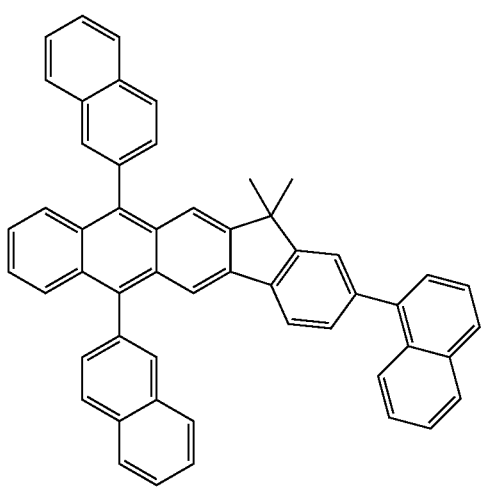
H44
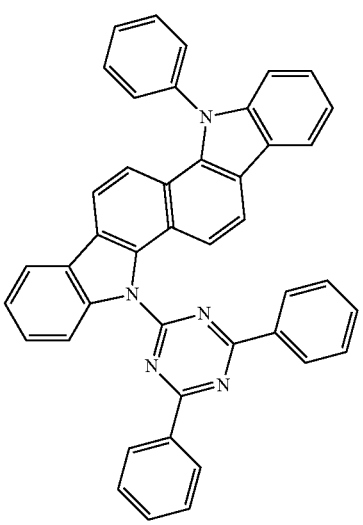

H45

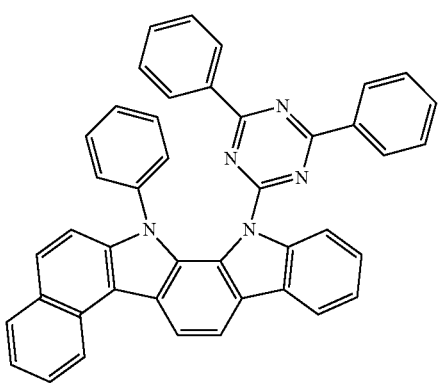

H46

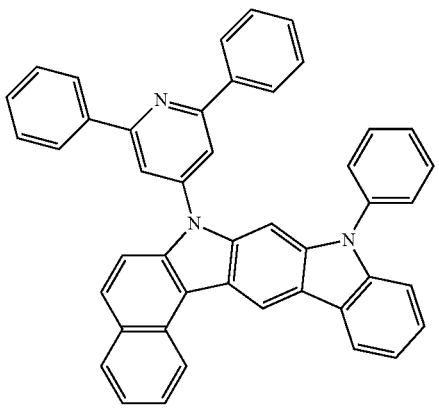

H47

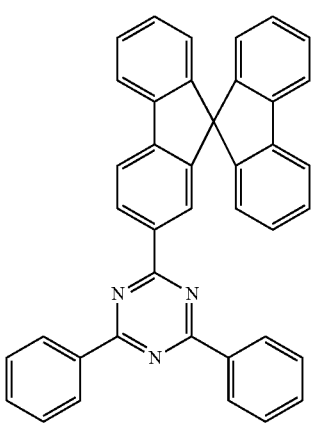

H48

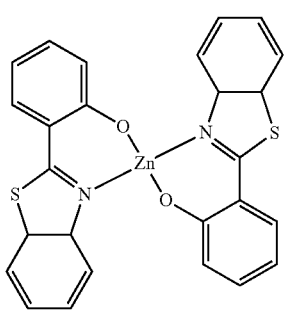

H49

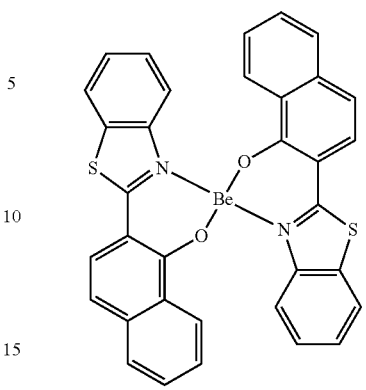

The dopant may include the condensed cyclic compound of Formula 1.

Alternatively, the dopant may include a compound represented by Formula 501 below:

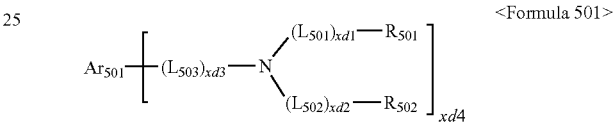

<Formula 501>

In Formula 501, $Ar_{501}$ may be selected from a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) (wherein $Q_{501}$ to $Q_{503}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

$L_{501}$ to $L_{503}$ may be each independently understood by referred to the description provided in connection with $L_1$;

$R_{501}$ and $R_{502}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 may be each independently selected from 0, 1, 2, and 3; and xd4 may be selected from 1, 2, 3, and 4.

The fluorescent dopant may include at least one of Compounds FD1 to FD9 below:

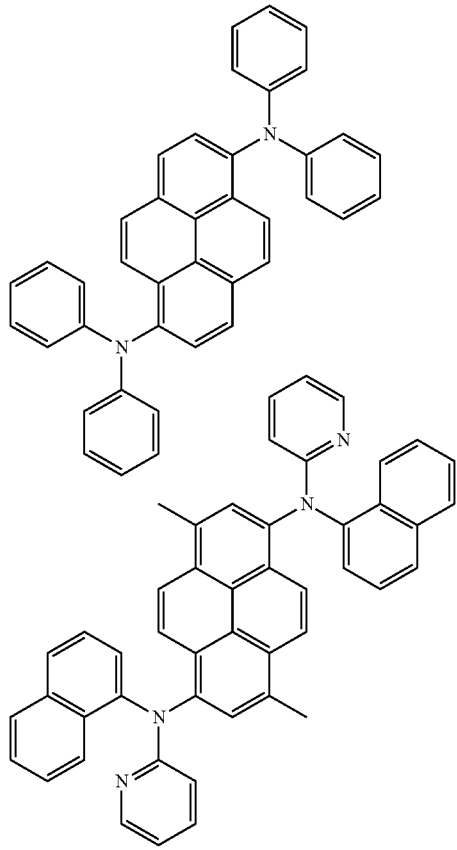

FD1

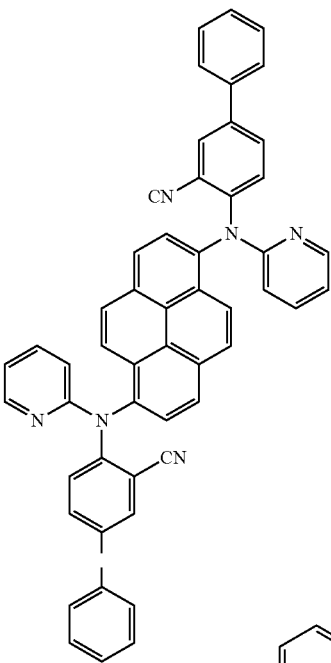

FD2

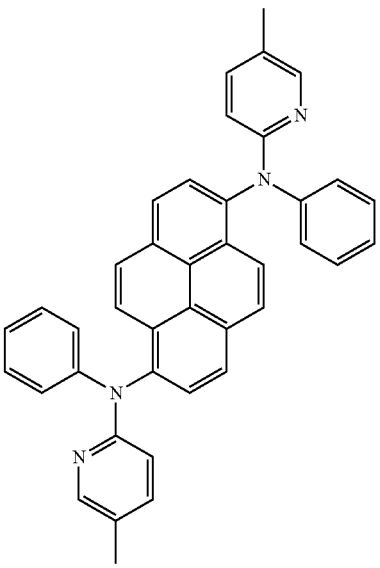

FD3

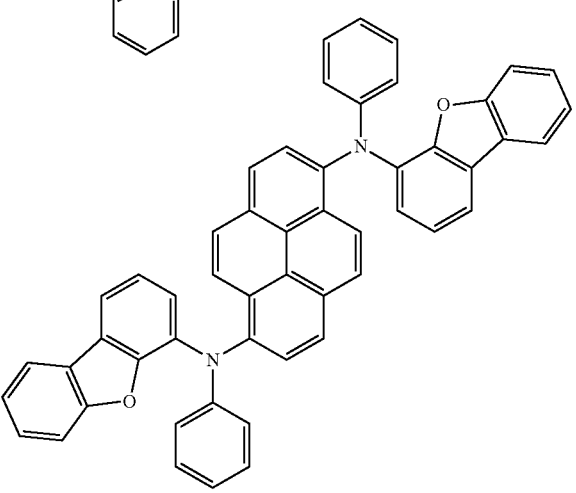

FD4

FD5

-continued

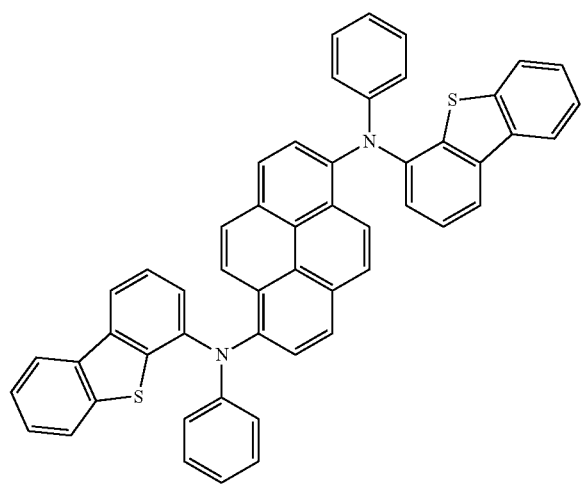
FD6

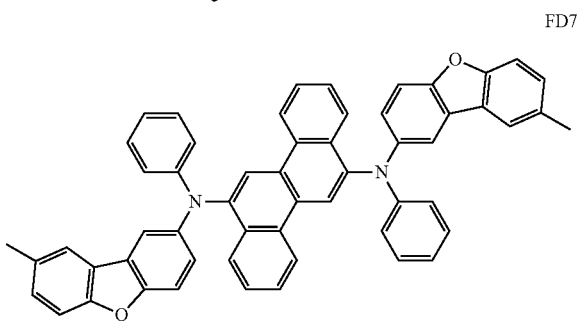
FD7

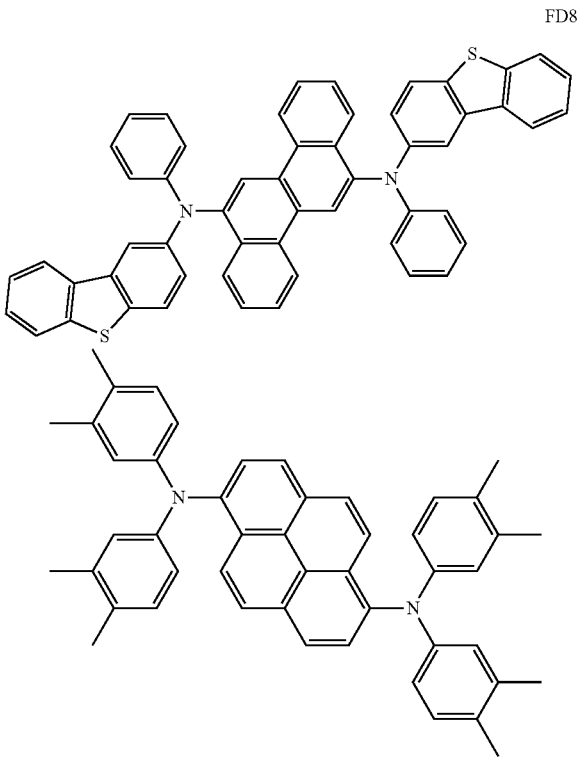
FD8

<Compound FD9>

An amount of the dopant included in the emission layer may be from about 0.01 to about 15 parts by weight, based on 100 parts by weight of the host, but is not limited thereto.

A thickness of the emission layer may be from about 100 Å to about 1,000 Å, e.g., about 200 Å to about 600 Å. When the thickness of the emission layer is within these ranges, excellent emission characteristics may be obtained without a substantial increase in driving voltage.

Next, the electron transport region may be disposed on the emission layer.

The electron transport region may include at least one of an HBL, an ETL, and an EIL, but the layers are not limited thereto.

For example, the electron transport region may have a structure of ETL/EIL or a structure of HBL/ETL/EIL, each of which layers are sequentially stacked in the stated order from the emission layer, but the structure is not limited thereto.

In an embodiment, the organic layer 150 of the organic light-emitting device 10 may include the electron transport region that is formed between the emission layer and the second electrode 190.

When the electron transport region includes an HBL, the HBL may be formed on top of the emission layer by using various methods, such as vacuum deposition, spin coating, casting, LB deposition, ink-jet printing, laser-printing, or LITI. When the HBL is formed by vacuum deposition and spin coating, deposition and coating conditions for forming the HBL may be determined by referring to the deposition and coating conditions for forming the HIL.

The HBL may include, for example, at least one of BCP and Bphen below, but is not limited thereto:

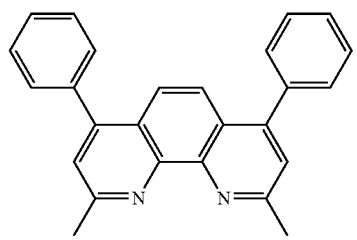
BCP

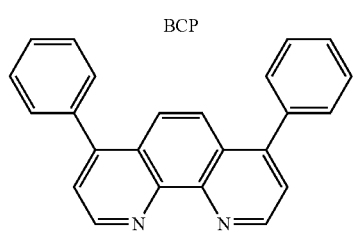
Bphen

A thickness of the HBL may be from about 20 Å to about 1,000 Å, e.g., about 30 Å to about 300 Å. When the thickness of the HBL is within these ranges, excellent hole blocking characteristics may be obtained without a substantial increase in driving voltage.

The electron transport region may include an ETL, and the ETL may be formed on top of the emission layer or on the HBL by using various methods, such as vacuum deposition, spin coating, casting, LB deposition, ink-jet printing, laser-printing, or LITI. When the ETL is formed by vacuum deposition and spin coating, deposition and coating conditions for forming the ETL may be determined by referring to the deposition and coating conditions for forming the HIL.

The ETL may include at least one of a compound represented by Formula 601 below and a compound represented by Formula 602 below:

$Ar_{601}\text{-}[(L_{601})_{xe1}\text{-}E_{601}]_{xe2}$ <Formula 601>

In Formula 601, $Ar_{601}$ may be selected from a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene and an indenoanthracene, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (wherein $Q_{301}$ to $Q_{303}$ may be each independently a hydrogen, a $C_1$-$C_{60}$ alkyl group, a $C_2$-$C_{60}$ alkenyl group, a $C_6$-$C_{60}$ aryl group, or a $C_1$-$C_{60}$ heteroaryl group);

$L_{601}$ may be understood by referring to the description provided in connection with $L_{201}$;

$E_{601}$ may be selected from a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

xe1 may be selected from 0, 1, 2, and 3; and xe2 may be selected from 1, 2, 3, and 4.

<Formula 602>

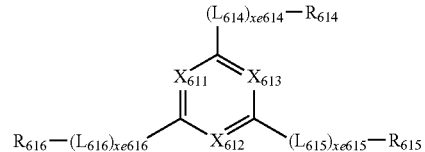

In Formula 602, $X_{611}$ may be N or C-($L_{611}$)$_{xe611}$-$R_{611}$, $X_{612}$ may be N or C-($L_{612}$)$_{xe612}$-$R_{612}$, and $X_{613}$ may be N or C-($L_{613}$)$_{xe613}$-$R_{613}$, wherein at least one of $X_{611}$ to $X_{613}$ may be N;

$L_{611}$ to $L_{616}$ may be each independently understood by referring to the description provided in connection with $L_1$;

$R_{611}$ to $R_{616}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may be each independently selected from 0, 1, 2, and 3.

The compound of Formula 601 and the compound of Formula 602 may be each independently selected from Compounds ET1 to ET15 below:

ET1

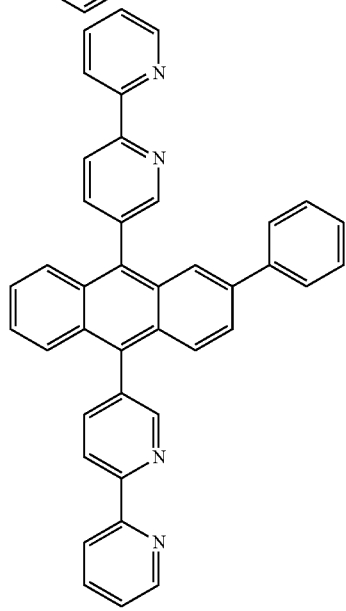

ET2

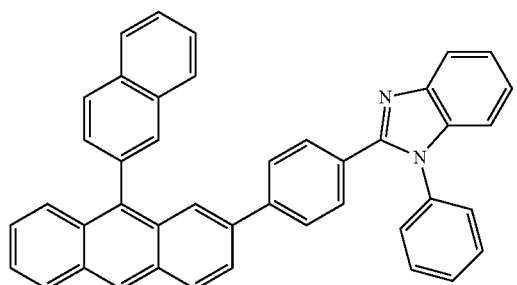

ET3

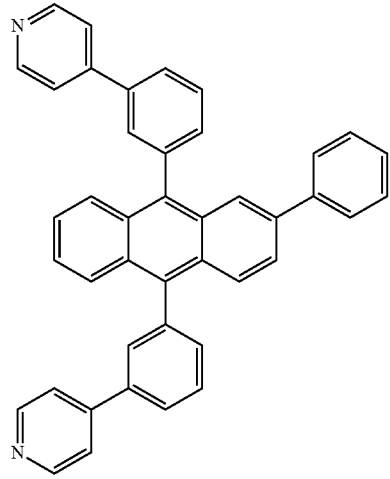

ET4

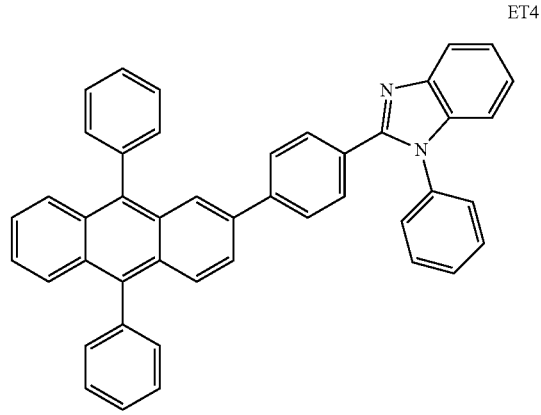

ET5

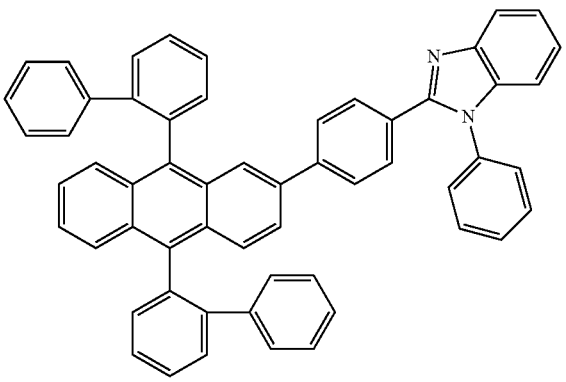

ET6
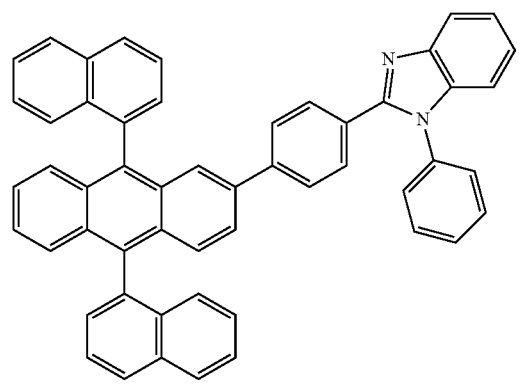
ET7
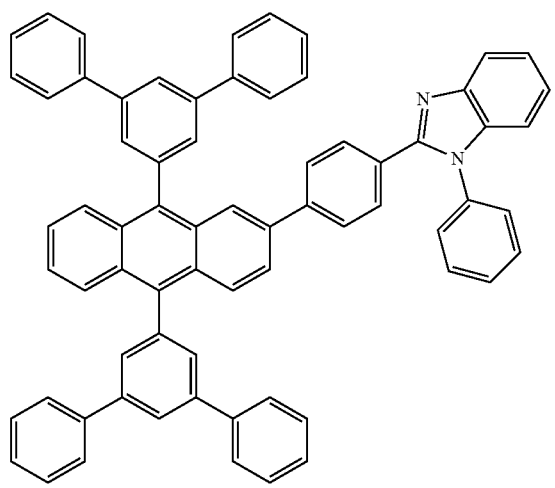
ET8
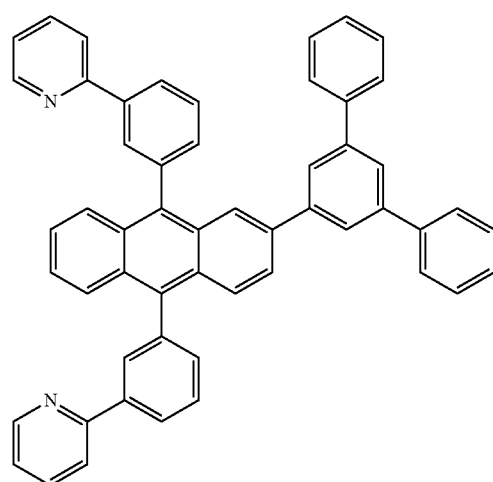
ET9
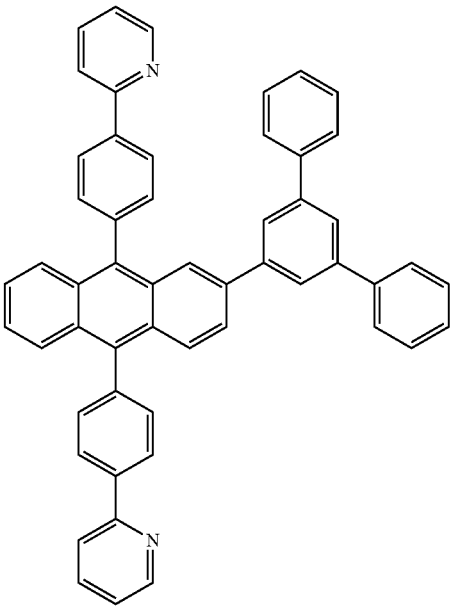
ET10
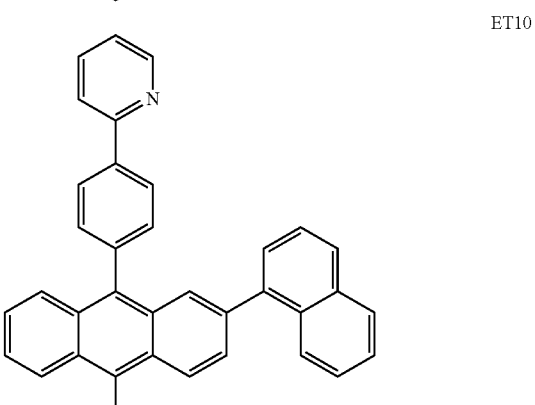
ET11
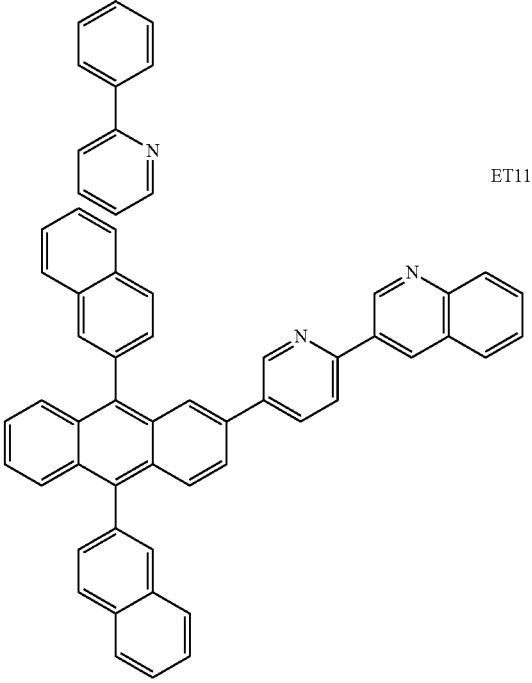

ET12
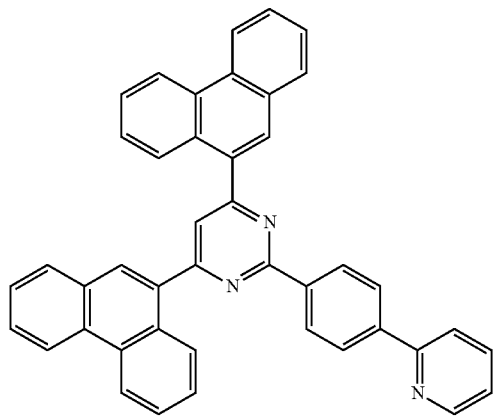
ET15
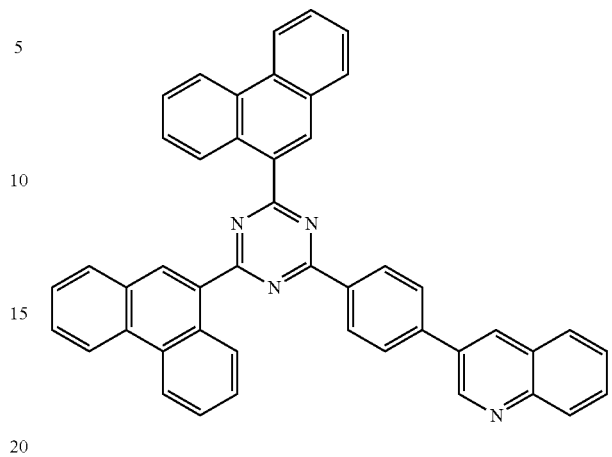
Alternatively, the ETL may include at least one of BCP and Bphen above and Alq₃, Balq, TAZ, and NTAZ below:
ET13
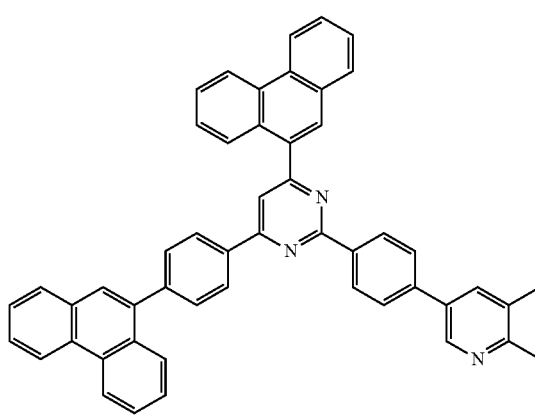
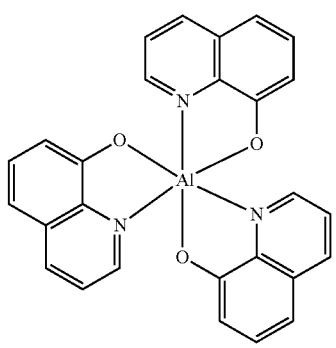
Alq3
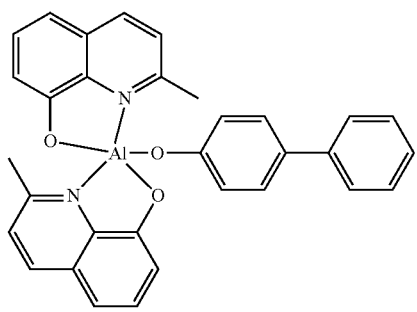
BAlq
ET14
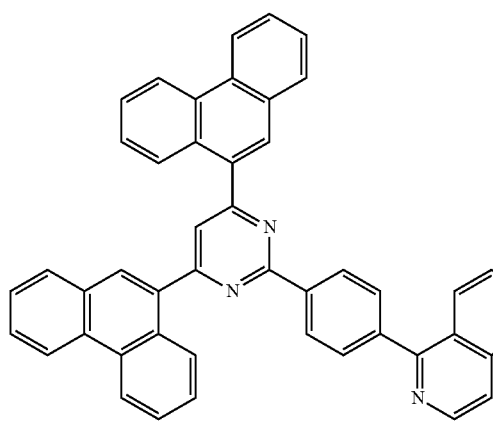
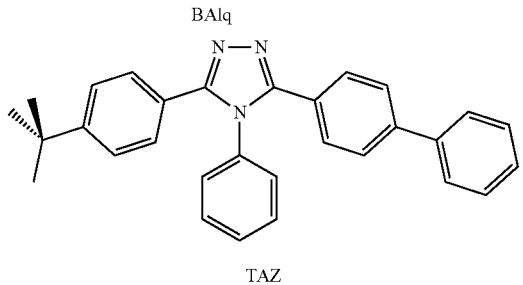
TAZ

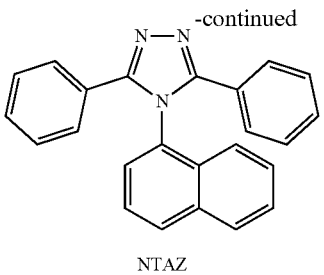

NTAZ

A thickness of the ETL may be from about 100 Å to about 1,000 Å, e.g., about 150 Å to about 500 Å. When the thickness of the ETL is within these ranges, excellent electron transporting characteristics may be obtained without a substantial increase in driving voltage.

In addition to the materials described above, the ETL may further include a metal-containing material.

The metal-containing material may include a Li complex. The Li complex may include, e.g., Compound ET-D1 (e.g., lithium quinolate (LiQ)) or ET-D2 below:

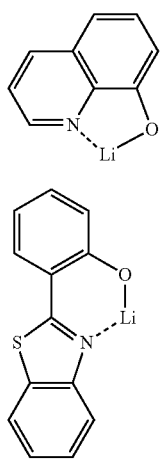

ET-D1

ET-D2

The electron transport region may include an EIL that facilitates electron injection from the second electrode 190.

The EIL may be formed on top of the ETL by using various methods, such as vacuum deposition, spin coating, casting, LB deposition, ink-jet printing, laser-printing, or LITI. When the EIL is formed by vacuum deposition and spin coating, deposition and coating conditions for forming the EIL may be determined by referring to the deposition and coating conditions for forming the HIL.

The EIL may include at least one selected from LiF, NaCl, CsF, $Li_2O$, BaO, and LiQ.

A thickness of the EIL may be from about 1 Å to about 100 Å, e.g., about 3 Å to about 90 Å. When the thickness of the EIL is within these ranges, satisfactory electron injecting characteristics may be obtained without a substantial increase in driving voltage.

The second electrode 190 may be disposed on top of the organic layer 150. The second electrode 190 may be a cathode that is an electron injection electrode, and in this regard, a material for forming the second electrode 190 may be a material having a low work function, such as a metal, an alloy, an electrically conductive compound, or a mixture thereof. Detailed examples of the material for forming the second electrode 190 may include lithium (Li), magnesium (Mg), aluminium (Al), aluminium-lithium (Al—Li), calcium (Ca), magnesium-indium (Mg—In), and magnesium-silver (Mg—Ag). Alternatively, the material for forming the second electrode 190 may be ITO or IZO. The second electrode 190 may be a semi-reflective electrode or a transmissive electrode.

Figure 2:
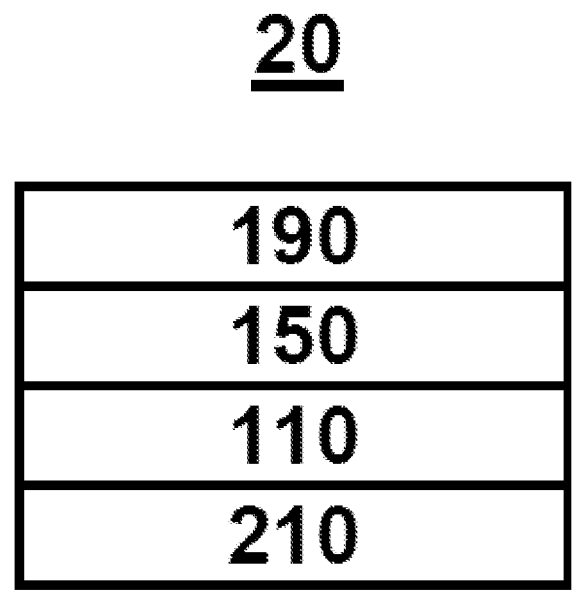
Figure 3:
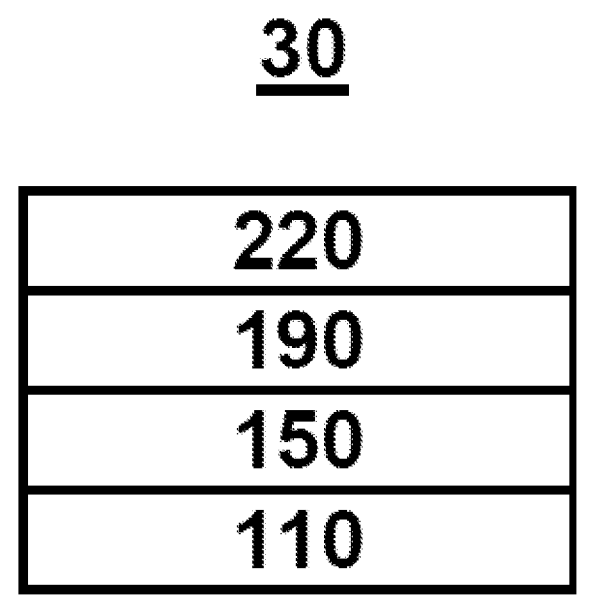
Figure 4:
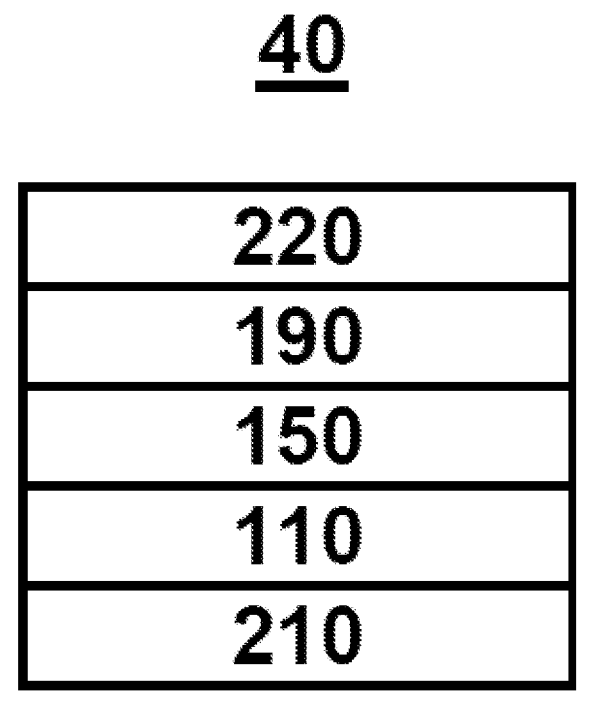

An organic light-emitting device 20 of FIG. 2 has a structure of a first capping layer 210, a first electrode 110, an organic layer 150, and a second electrode 190, which are sequentially stacked in the stated order, an organic light-emitting device 30 of FIG. 3 has a structure of a first electrode 110, an organic layer 150, a second electrode 190, and a second capping layer 220, which are sequentially stacked in the stated order, and an organic light-emitting device 40 of FIG. 4 has a structure of a capping layer 210, a first electrode 110, an organic layer 150, a second electrode 190, and a second capping layer 220, which are sequentially stacked in the stated order.

In FIGS. 2 to 4, the first electrode 110, the organic layer 150, and the second electrode 190 may be understood by referring to the description provided in connection with FIG. 1.

Light generated from the emission layer included in the organic layer 150 of the organic light-emitting devices 20 and 30 may exit to the outside through the first electrode 110, which is a semi-transmissive electrode or a transmissive electrode, and the first capping layer 210. Light generated from the emission layer included in the organic layer 150 of the organic light-emitting devices 30 and 40 may exit to the outside through the second electrode 190, which is a semi-transmissive electrode or a transmissive electrode, and the second capping layer 220.

The first capping layer 210 and the second capping layer 220 may serve to improve efficiency of external light emission based on the constructive interference principle.

The first capping layer 210 of FIG. 2 and the second capping layer 220 of FIG. 3 may include the condensed cyclic compound of Formula 1.

At least one of the first capping layer 210 and the second capping layer 220 of FIG. 4 may include the condensed cyclic compound of Formula 1.

In some embodiments, the organic layer 150 of FIGS. 2 to 4 may not include the condensed cyclic compound of Formula 1.

Hereinbefore, the organic light-emitting device has been described with reference to FIGS. 1 to 4, but is not limited thereto.

A $C_1$-$C_{60}$ alkyl group used herein refers to a linear or branched aliphatic hydrocarbon monovalent group having 1 to 60 carbon atoms, and detailed examples thereof are a methyl group, an ethyl group, a propyl group, an isobutyl group, a sec-butyl group, a ter-butyl group, a pentyl group, an iso-amyl group, and a hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group, and detailed examples thereof are a methoxy group, an ethoxy group, and an isopropyloxy group.

A $C_2$-$C_{60}$ alkenyl group used herein refers to a hydrocarbon group formed by substituting at least one carbon double bond in the middle or terminal of the $C_2$-$C_{60}$ alkyl group, and detailed examples thereof are an ethenyl group, a prophenyl group, and a butenyl group. A $C_2$-$C_{60}$ alkenylene group used herein refers to a divalent group having the same structure as the $C_2$-$C_{60}$ alkenyl group.

A $C_2$-$C_{60}$ alkynyl group used herein refers to a hydrocarbon group formed by substituting at least one carbon triple bond in the middle or terminal of the $C_2$-$C_{60}$ alkyl group, and detailed examples thereof are an ethynyl group and a propynyl group. A $C_2$-$C_{60}$ alkynylene group used herein refers to a divalent group having the same structure as the $C_2$-$C_{60}$ alkynyl group.

A $C_3$-$C_{10}$ cycloalkyl group used herein refers to a monovalent hydrocarbon monocyclic group having 3 to 10 carbon atoms, and detailed examples thereof are a cyclopropyl group, a cyclobutyl group, a cyclopentyl group, a cyclohexyl group, and a cycloheptyl group.

A $C_3$-$C_{10}$ cycloalkylene group used herein refers to a divalent group having the same structure as the $C_3$-$C_{10}$ cycloalkyl group.

A $C_1$-$C_{10}$ heterocycloalkyl group used herein refers to a monovalent monocyclic group having at least one heteroatom selected from N, O, P, and S as a ring-forming atom and 1 to 10 carbon atoms, and detailed examples thereof are a tetrahydrofuranyl group and a tetrahydrothiophenyl group. A $C_1$-$C_{10}$ heterocycloalkylene group used herein refers to a divalent group having the same structure as the $C_1$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromacity, and detailed examples thereof are a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_1$-$C_{10}$ heterocycloalkenyl group used herein refers to a monovalent monocyclic group that has at least one heteroatom selected from N, O, Si, P, and S as a ring-forming atom, 1 to 10 carbon atoms, and at least one double bond in its ring. Detailed examples of the $C_1$-$C_{10}$ heterocycloalkenyl group are a 2,3-hydrofuranyl group and a 2,3-hydrothiophenyl group. A $C_1$-$C_{10}$ heterocycloalkenylene group used herein refers to a divalent group having the same structure as the $C_1$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group used herein refers to a monovalent group having a carbocyclic aromatic system that has at least one heteroatom selected from N, O, Si, P, and S as a ring-forming atom, and 1 to 60 carbon atoms. A $C_1$-$C_{60}$ heteroarylene group used herein refers to a divalent group having a carbocyclic aromatic system that has at least one heteroatom selected from N, O, P, and S as a ring-forming atom, and 1 to 60 carbon atoms. Detailed examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group used herein indicates —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

A monovalent non-aromatic condensed polycyclic group (e.g., a group having 8 to 60 carbon atoms) used herein refers to a monovalent group that has two or more rings condensed to each other, has carbon atoms only as a ring-forming atom, and has non-aromacity in the entire molecular structure. A detailed example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group (e.g., a group having 1 to 60 carbon atoms) used herein refers to a monovalent group that has two or more rings condensed to each other, has heteroatoms as a ring-forming atom selected from N, O, Si, P, and S in addition to C, and has non-aromacity in the entire molecular structure. A detailed example of the monovalent non-aromatic condensed heteropolycyclic group is a carbazolyl group. A divalent non-aromatic condensed heteropolycyclic group used herein refers to a divalent group having the same structure as the monovalent non-aromatic condensed heteropolycyclic group.

At least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group or a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), and —B($Q_{14}$)($Q_{15}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), and —B($Q_{24}$)($Q_{25}$); or —Si($Q_{31}$)($Q_{32}$)($Q_{33}$) or —B($Q_{34}$)($Q_{35}$), wherein $Q_1$ to $Q_5$, $Q_{11}$ to $Q_{15}$, $Q_{21}$ to $Q_{25}$, and $Q_{31}$ to $Q_{35}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

The term "Ph" used herein refers to a phenyl group, the term "Me" used herein refers to a methyl group, the term "Et" used herein refers to an ethyl group, and the term "ter-Bu" or "Bu$^t$" used herein refers to a tert-butyl group.

Hereinafter, the organic light-emitting device according to embodiments is described in detail with reference to Synthesis Example and Examples. The wording "B was used instead of A" used in describing Synthesis Examples means that a molar equivalent of A was identical to a molar equivalent of B.

EXAMPLE

Synthesis Example: Synthesis of Compound 1

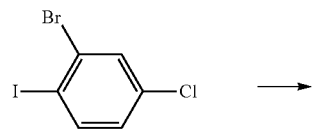

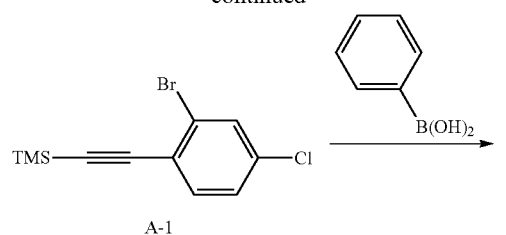

A-1

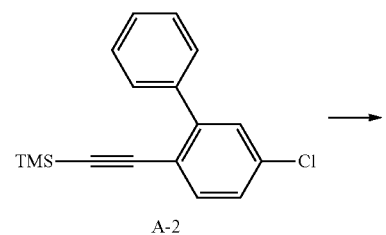

A-2

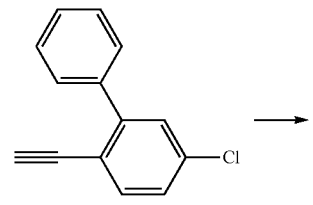

A-3

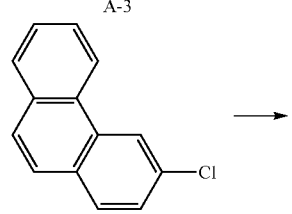

A-4

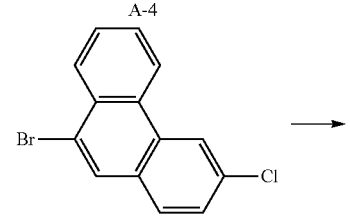

A-5

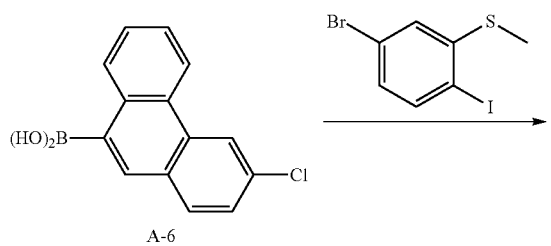

A-6

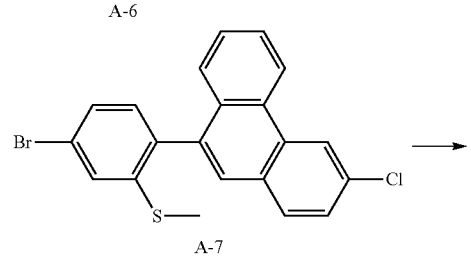

A-7

-continued

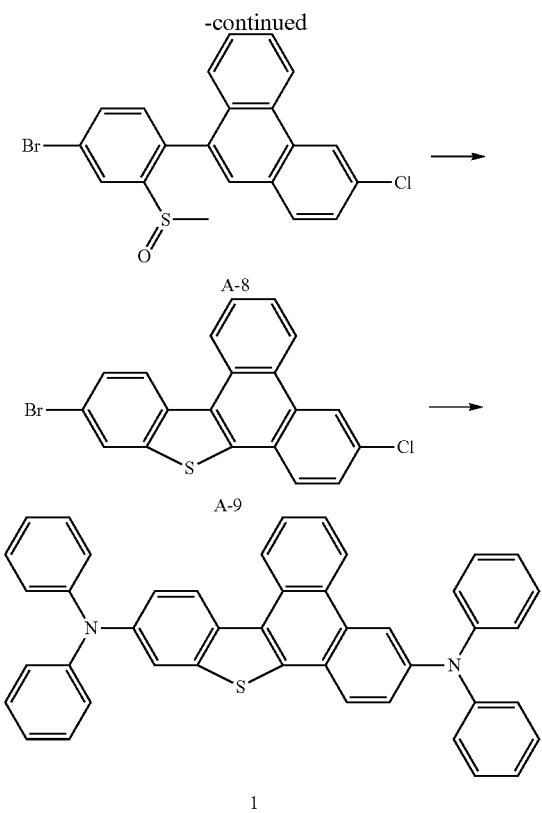

Synthesis of Intermediate A-1

40 g (126.0 mmol) of 2-bromo-4-chloro-1-iodobenzenenzene, 1.41 g (6.3 mmol) of Pd(OAc)$_2$, and 1.6 g (6.3 mmol) of PPh$_3$ were mixed with 800 mL of triethylamine, and then, the mixed solution was stirred for 12 hours under N$_2$ atmosphere at a temperature of 60° C. After the completion of the reaction, the reaction solution was cooled to room temperature, and an organic layer was extracted 5 times therefrom by using water and diethyl ether. The organic layer was dried by using magnesium sulfate to remove a solvent therefrom, and then, the residues were separated and purified by using silica gel column chromatography, so as to obtain 29.0 g (100.8 mmol, yield: 80%) of Intermediate A-1. The synthesized compound was identified by using MS/FAB.

$C_{11}H_{12}BrClSi$ cal. 287.66. found 287.96.

Synthesis of Intermediate A-2

29.0 g (100.8 mmol) of Intermediate A-1, 13.4 g (110.8 mmol) of phenylboronic acid, 11.6 g (10.0 mmol) of Pd(PPh$_3$)$_4$, and 27.8 g (201.2 mmol) of K$_2$CO$_3$ were added to 500 mL of a mixture of THF/H$_2$O (at a volume ratio of 9:1), and then, the mixed solution was stirred for 12 hours at a temperature of 80° C. Afterwards, the reaction solution was cooled to room temperature, and an organic layer was extracted 3 times therefrom by using water and diethyl ether. The organic layer was dried by using magnesium sulfate to remove a solvent therefrom, and then, the residues were separated and purified by using silica gel column chromatography, so as to obtain 20.4 g (71.6 mmol, yield: 71%) of Intermediate A-2. The synthesized compound was identified by using MS/FAB.

$C_{17}H_{17}ClSi$ cal. 284.86. found 284.08.

Synthesis of Intermediate A-3

20.4 g (71.6 mmol) of Intermediate A-2 and 9.8 g (71.6 mmol) of K$_2$CO$_3$ were mixed in 900 ml of a mixture of MeOH/CH$_2$Cl$_2$ (at a volume ratio of 2:1), and then, the mixed solution was stirred for 1 hour at room temperature. Afterwards, the reaction solution was filtered by using a filter paper so that all the organic solvents were evaporated from the filtrate. An organic layer was extracted twice from the filtrate by using water and dichloromethane, and dried by using magnesium sulfate to remove a solvent therefrom. The residues were separated and purified by using silica gel column chromatography, so as to obtain 13.0 g (61.1 mmol, yield: 85%) of Intermediate A-3. The synthesized compound was identified by using MS/FAB.

$C_{14}H_9Cl$ cal. 212.68. found 212.04.

Synthesis of Intermediate A-4

13.0 g (61.1 mmol) of Intermediate A-3 was mixed with 800 mL of dichloromethane, and then, 36 mL (600 mmol) of trifluoroacetic acid was slowly added dropwise thereto at a temperature of 0° C. When the temperature of the mixed solution was raised up to room temperature, 4 mL (60.8 mmol) of methansulfonic acid was added thereto, and the mixed solution was stirred at room temperature. After the completion of the reaction, an organic layer was extracted twice therefrom by using water and diethyl ether. The organic layer was dried by using magnesium sulfate to remove a solvent therefrom, and then, the residues were separated and purified by using silica gel column chromatography, so as to obtain 10.4 g (48.9 mmol, yield: 80%) of Intermediate A-4. The synthesized compound was identified by using MS/FAB.

$C_{14}H_9Cl$ cal. 212.68. found 212.04.

Synthesis of Intermediate A-5

10.4 g (48.9 mmol) of Intermediate A-4 was mixed with 500 mL of methylene chloride, and then, 588 mg (2.4 mmol) of benzoyl peroxide (BPO) and 8.6 g (48.6 mmol) of N-bromosuccinimide (NBS) were slowly added to the mixed solution. The mixed solution was stirred for 24 hours at room temperature. After the completion of the reaction, 500 mL of 5% HCl and 500 mL of water were sequentially added to the reaction solution to remove the remaining NBS, and an organic layer was extracted therefrom by using water and diethyl ether. The organic layer was dried by using magnesium sulfate to remove a solvent therefrom, and then, the residues were separated and purified by using silica gel column chromatography, so as to obtain 11.4 g (39.1 mmol, yield: 80%) of Intermediate A-5. The synthesized compound was identified by using MS/FAB.

$C_{14}H_8BrCl$ cal. 291.57. found 291.95.

Synthesis of Intermediate A-6

11.4 g (39.1 mmol) of Intermediate A-5 was stirred in 500 mL of TFT (having a temperature of −78° C.) for 10 minutes under N$_2$ atmosphere. Then, 15.6 mL of 2.5M n-BuLi was slowly added dropwise thereto by using a dropping funnel, and the mixed solution was stirred for another 30 minutes. Afterwards, 6.09 g (58.7 mmol) of trimethyl borate was slowly added dropwise to the mixed solution by using a dropping funnel, and then, the mixed solution was stirred for another 3 hours at room temperature. 150 mL of an HCl solution was added thereto, and an organic layer was extracted once therefrom. The organic layer was additionally extracted 3 times therefrom by using water and diethyl ether. The organic layer was dried by using magnesium sulfate to remove a solvent, and then, the residues were separated and purified by using silica gel column chromatography, so as to obtain 7.03 g (27.4 mmol, yield: 70%) of Intermediate A-6. The synthesized compound was identified by using MS/FAB.

$C_{14}H_{10}BClO_2$ cal. 256.49. found 256.05.

Synthesis of Intermediate A-7

5.7 g (19.4 mmol) of Intermediate A-6, 7.0 g (21.3 mmol) of (4-bromo-2-iodophenyl)(methyl)sulfane, 2.24 g (1.94 mmol) of $Pd(PPh_3)_4$, and 3.1 g (2.3 mmol) of $K_2CO_3$ were added to 400 mL of a mixture of $THF/H_2O$ (at a volume ratio of 9:1), and then, the mixed solution was stirred for 12 hours at a temperature of 80° C. The reaction solution was cooled to room temperature, and an organic layer was extracted 3 times therefrom by using water and diethyl ether. The organic layer was dried by using magnesium sulfate to remove a solvent therefrom, and then, the residues were separated and purified by using silica gel column chromatography, so as to obtain 7.2 g (17.5 mmol, yield: 90%) of Intermediate A-7. The synthesized compound was identified by using MS/FAB.

$C_{21}H_{14}BrCl_2S$ cal. 413.76. found 413.97.

Synthesis of Intermediate A-8

7.2 g of (17.5 mmol) of Intermediate A-7 was mixed with 100 mL of acetic acid. 2.2 g (19.2 mmol) of hydrogen peroxide (30 wt % in $H_2O$) was added thereto, and then, the mixed solution was stirred for 6 hours at room temperature. After the completion of the reaction, the acetic acid was removed therefrom under reduced pressure, and the residues were separated and purified by using silica gel column chromatography, so as to obtain 5.3 g (12.3 mmol, yield: 70%) of Intermediate A-8. The synthesized compound was identified by using MS/FAB.

$C_{21}H_{14}BrCl_2OS$ cal. 429.76. found 429.96.

Synthesis of Intermediate A-9

5.3 g of Intermediate A-8 (12.3 mmol) was mixed with 100 mL of methylene chloride. 1.8 g (12.3 mmol) of trifluoromethanesulfonic acid was added thereto, and then, the mixed solution was stirred for 24 hours at room temperature. Afterwards, 100 mL of a mixture of water and pyridine (at a volume ratio of 8:1) was added to the reaction solution, and then, the mixed reaction solution was stirred for 1 hour. After the completion of the reaction, an organic layer was extracted twice therefrom by using water and dichloromethane. The organic layer was dried by using magnesium sulfate to remove a solvent therefrom, and then, the residues were separated and purified by using silica gel column chromatography, so as to obtain 3.2 g (8.0 mmol, yield: 80%) of Intermediate A-9. The synthesized compound was identified by using MS/FAB.

$C_{20}H_{10}BrClS$ cal. 397.71. found 395.94.

Synthesis of Compound 1

700 mg (1.76 mmol) of Intermediate A-9, 740 mg (4.4 mmol) of diphenylamine, 156 mg (0.18 mmol) of tris(dibenzylideneacetone)dipalladium(0), 35 mg (0.18 mmol) of tri(tert-butyl)phosphine, and 423 mg (4.4 mmol) of sodium tert-butoxide were added to 20 mL of toluene, and then, the mixed solution was stirred for 2 hours at a temperature of 80° C. After the reaction solution was cooled to room temperature, an organic layer was extracted twice therefrom by using water and diethyl ether. The organic layer was dried by using magnesium sulfate to remove a solvent therefrom, and then, the residues were separated and purified by using silica gel column chromatography, so as to obtain 762 mg (1.2 mmol, yield: 70%) of Compound 1. The synthesized compound was identified by using MS/FAB.

$C_{44}H_{30}N_2S$ cal. 618.80. found 618.21.

Synthesis Example 2: Synthesis of Compound 127

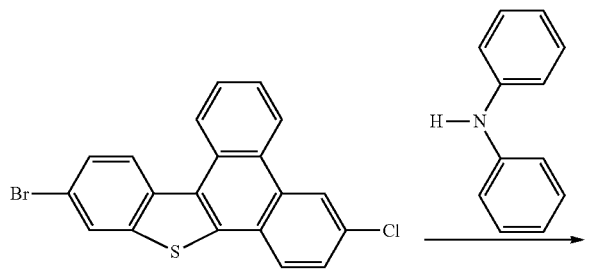

A-9

-continued

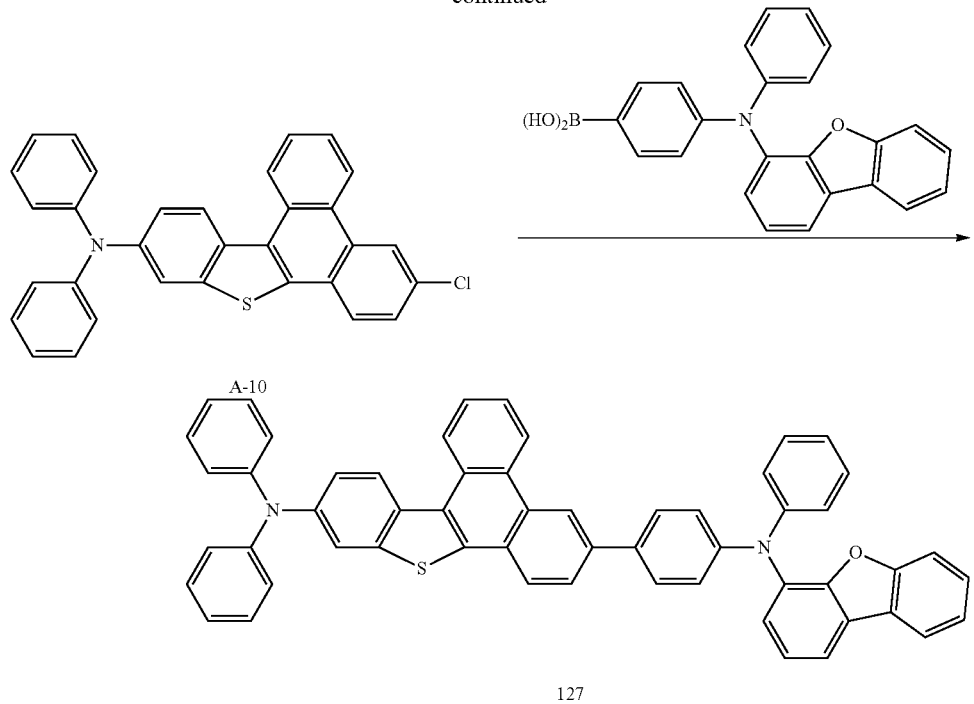

Synthesis of Intermediate A-10

600 mg (1.5 mmol) of Intermediate A-9, 254 mg (1.5 mmol) of diphenylamine, 137 mg (0.15 mmol) of tris(dibenzylideneacetone)dipalladium(0), 30 mg (0.15 mmol) of tri(tert-butyl)phosphine, and 211 mg (2.2 mmol) of sodium tert-butoxide were added to 40 mL of toluene, and then, the mixed solution was stirred for 2 hours at a temperature of 80° C. After the reaction solution was cooled to room temperature, an organic layer was extracted 3 times therefrom by using water and diethyl ether. The organic layer was dried by using magnesium sulfate to remove a solvent therefrom, and then, the residues were separated and purified by using silica gel column chromatography, so as to obtain 656 mg (1.35 mmol, yield: 90%) of Intermediate A-10. The synthesized compound was identified by using MS/FAB.

$C_{32}H_{20}ClNS$ cal. 486.03. found 485.10.

Synthesis of Compound 127

656 mg (1.35 mmol) of Intermediate A-10, 580 mg (1.53 mmol) of (4-(dibenzo[b,d]furan-4-yl(phenyl)amino)phenyl)boronic acid, 173 mg (0.15 mmol) of Pd(PPh$_3$)$_4$, and 304 mg (2.2 mmol) of K$_2$CO$_3$ were added to 40 mL of a mixture of THF/H$_2$O (at a volume ratio of 9/1), and then, the mixed solution was stirred for 12 hours at a temperature of 80° C. After the reaction solution was cooled to room temperature, an organic layer was extracted 3 times therefrom by using water and diethyl ether. The organic layer was dried by using magnesium sulfate to remove a solvent therefrom, and then, the residues were separated and purified by using silica gel column chromatography, so as to obtain 887 mg (1.13 mmol, yield: 84%) of Compound 127. The synthesized compound was identified by using MS/FAB.

$C_{56}H_{36}N_2OS$ cal. 784.98. found 784.25.

Synthesis Example 3: Synthesis of Compound 1A

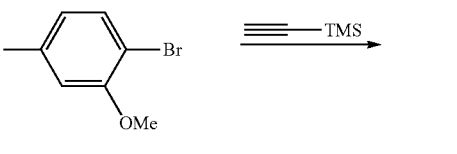

B-1

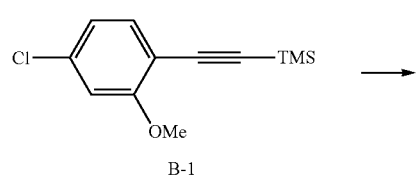

B-2

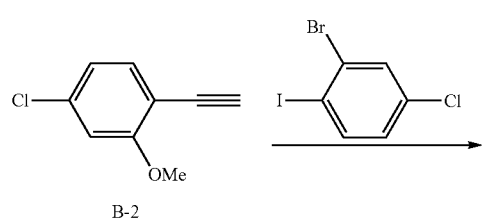

B-3

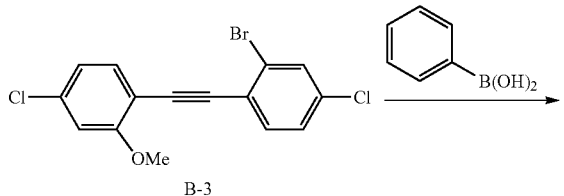

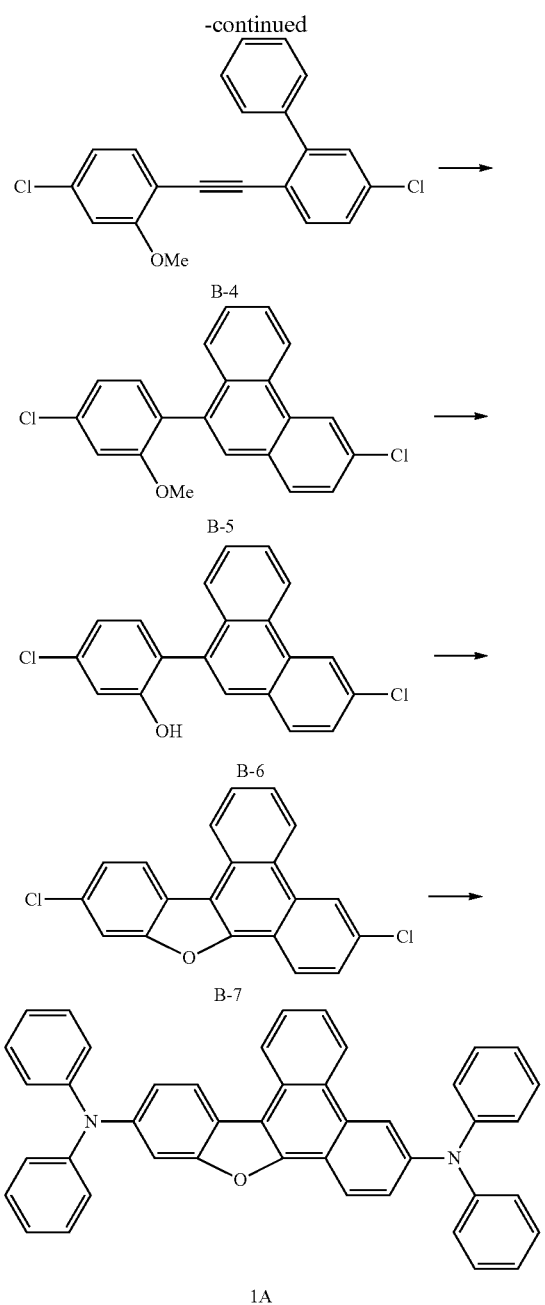

Synthesis of Intermediate B-1

25 g (113 mmol) of bromo-4-chloro-2-methoxybenzene, 19.1 mL (135 mmol) of ethynyltrimethylsilane, 3.96 g (5.6 mmol) of Pd(PPh$_3$)$_2$Cl$_2$, and 2.15 g (11.3 mmol) of CuI were mixed with 100 mL of triethylamine, and then, the mixed solution was stirred for 12 hours under N$_2$ atmosphere at a temperature of 60° C. After the reaction solution was cooled to room temperature, an organic layer was extracted 5 times therefrom by using water and diethyl ether. The organic layer was dried by using magnesium sulfate to remove a solvent therefrom, and then, the residues were separated and purified by using silica gel column chromatography, so as to obtain 22.9 g (96 mmol, yield: 85%) of Intermediate B-1.

The synthesized compound was identified by using MS/FAB.

C$_{12}$H$_{15}$ClOSi cal. 238.79. found 238.06.

Synthesis of Intermediate B-2

22.9 g (96 mmol) of Intermediate B-1 and 13.8 g (100 mmol) of K$_2$CO$_3$ were mixed with 600 mL of a mixture of MeOH/CH$_2$Cl$_2$ (at a volume ratio of 2:1), and then, the mixed solution was stirred for 1 hour at room temperature. Afterwards, the reaction solution was filtered by using a filter paper so that all the organic solvents were evaporated from the filtrate. An organic layer was extracted twice from the filtrate by using water and dichloromethane, and dried by using magnesium sulfate to remove a solvent therefrom. The residues were separated and purified by using silica gel column chromatography, so as to obtain 15.5 g (92.9 mmol, yield: 97%) of Intermediate B-2. The synthesized compound was identified by using MS/FAB.

C$_9$H$_7$ClO cal. 166.60. found 166.02.

Synthesis of Intermediate B-3

15.5 g (92.9 mmol) of Intermediate B-2, 26.8 g (84.4 mmol) of 2-bromo-4-chloro-1-iodobenzene, 5.4 g (4.64 mmol) of Pd(PPh$_3$)$_4$, 1.8 g (9.29 mmol) of CuI, and 52 mL (37.1 mmol) of triethyl amine were dissolved in 500 mL of DMF, and then, the mixed solution was stirred under N$_2$ atmosphere at a temperature 40° C. The reaction solution was cooled to room temperature, and an organic layer was extracted 3 times therefrom by using water and diethyl ether. The organic layer was dried by using magnesium sulfate to remove a solvent therefrom, and then, the residues were separated and purified by using silica gel column chromatography, so as to obtain 22.5 g (63.2 mmol, yield: 68%) of Intermediate B-3. The synthesized compound was identified by using MS/FAB.

C$_{15}$H$_9$BrCl$_2$O cal. 356.04. found 355.92.

Synthesis of Intermediate B-4

8.1 g (22.8 mmol) of Intermediate B-3, 3.0 g (34.1 mmol) of phenylboronic acid, 1.3 g (1.14 mmol) of Pd(PPh$_3$)$_4$, and 12.6 g (91 mmol) of K$_2$CO$_3$ were added to 150 mL of a mixture of THF/H$_2$O (at a volume ratio of 9:1), and then, the mixed solution was stirred for 12 hours at a temperature of 60° C. After the reaction solution was cooled to room temperature, an organic layer was extracted 3 times therefrom by using water and diethyl ether. The organic layer was dried by using magnesium sulfate to remove a solvent therefrom, and then, the residues were separated and purified by using silica gel column chromatography, so as to obtain 13.1 g (37.1 mmol, yield: 81%) of Intermediate B-4. The synthesized compound was identified by using MS/FAB.

C$_{21}$H$_{14}$Cl$_2$O cal. 353.24. found 352.04.

Synthesis of Intermediate B-5

4.0 g (11.3 mmol) of Intermediate B-4 was mixed with 500 mL of dichloromethane, and then, the 12.9 g (113.2 mmol) of trifluoroacetic acid was slowly added dropwise thereto at a temperature of 0° C. When the temperature of the mixed solution was raised to room temperature, 0.74 mL (11.3 mmol) of methansulfonic acid was added thereto, and then, the mixed solution was stirred at room temperature. After the completion of the reaction, an organic layer was extracted twice therefrom by using water and diethyl ether.

The organic layer was dried by using magnesium sulfate to remove a solvent therefrom, and then, the residues were separated and purified by using silica gel column chromatography, so as to obtain 3.14 g (8.6 mmol, yield: 76%) of Intermediate B-5. The synthesized compound was identified by using MS/FAB.

$C_{21}H_{14}Cl_2O$ cal. 353.24. found 352.04.

Synthesis of Intermediate B-6

3.16 g (8.9 mmol) of Intermediate B-5 was mixed with 100 mL of dichloromethane, and then, BBr$_3$ was slowly added dropwise thereto at a temperature of 0° C. After the completion of the reaction, NaHCO$_3$ aqueous solution was added to the reaction solution at a temperature of 0° C. After the completion of the reaction, an organic layer was extracted 3 times therefrom by using water and dichloromethane. The organic layer was dried by using magnesium sulfate to remove a solvent therefrom, and then, the residues were separated and purified by using silica gel column chromatography, so as to obtain 2.72 g (8.0 mmol, yield: 90%) of Intermediate B-6. The synthesized compound was identified by using MS/FAB.

$C_{20}H_{12}Cl_2O$ cal. 339.22. found 338.03.

Synthesis of Intermediate B-7

2.72 g (8.0 mmol) of Intermediate B-6 and 3.4 g (24.0 mmol) of copper(I) oxide were added to 250 mL of nitrobenzene, and then, the mixed solution was heat-stirred for 48 hours at a temperature of 190° C. After the completion of the reaction, the reaction solution was cooled to room temperature, and an organic layer was extracted 4 times therefrom by using water and diethy ether. The organic layer was dried by using magnesium sulfate to remove a solvent therefrom, and then, the residues were separated and purified by using silica gel column chromatography, so as to obtain Intermediate B-7 (1.33 g, 5.6 mmol, yield: 625). The synthesized compound was identified by using MS/FAB.

$C_{20}H_{10}Cl_2O$ cal. 337.20. found 336.01.

Synthesis of Compound 1A 600 mg (1.78 mmol) of Intermediate B-7, 740 mg (4.4 mmol) of diphenylamine, 156 mg (0.18 mmol) of tris(dibenzylideneacetone)dipalladium(0), 35 mg (0.18 mmol) of tri(tert-butyl)phosphine, and 423 mg (4.4 mmol) of sodium tert-butoxide were added to 200 mL of toluene, and then, the mixed solution was stirred for 2 hours at a temperature of 80° C. The reaction solution was cooled to room temperature, and an organic layer was extracted twice therefrom by using water and diethy ether. The organic layer was dried by using magnesium sulfate to remove a solvent therefrom, and then, the residues were separated and purified by using silica gel column chromatography, so as to obtain 858 mg (1.42 mmol, yield: 70%) of Compound 1A. The synthesized compound was identified by using MS/FAB.

$C_{44}H_{30}N_2O$ cal. 602.74. found 602.24.

Synthesis Example 4: Synthesis of Compound 144A

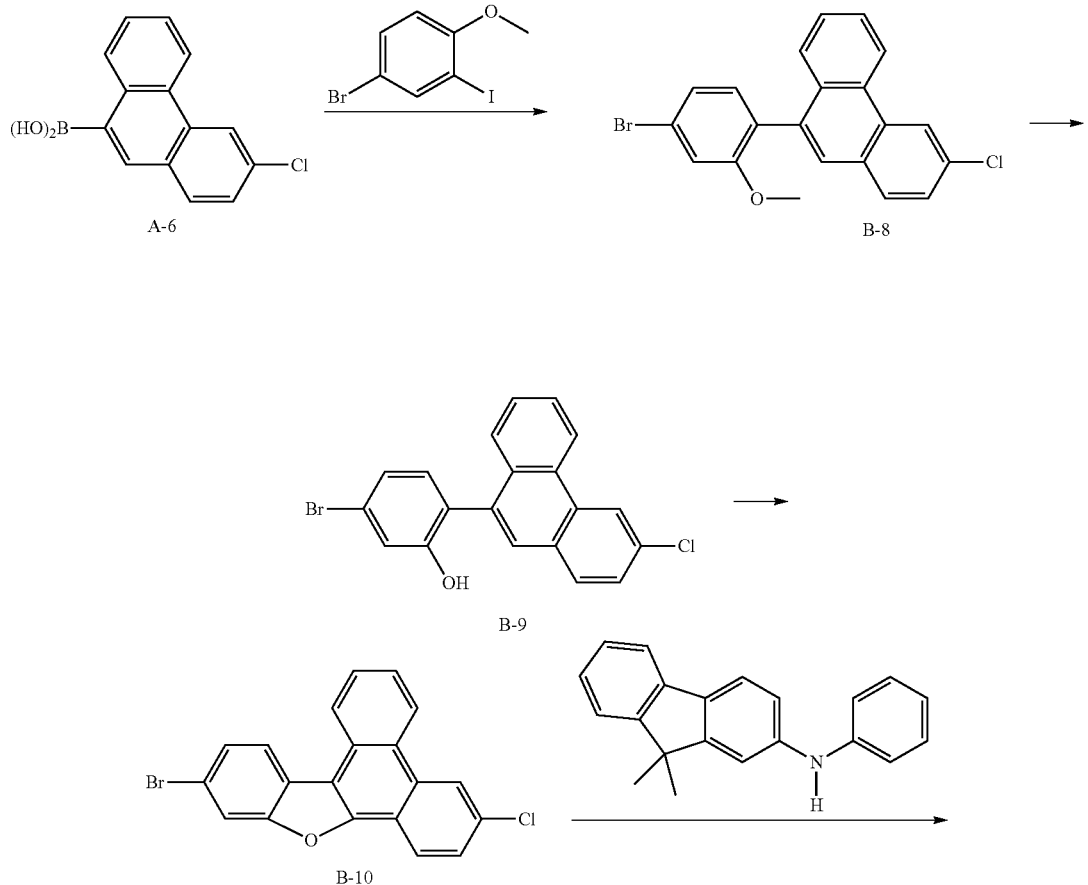

-continued

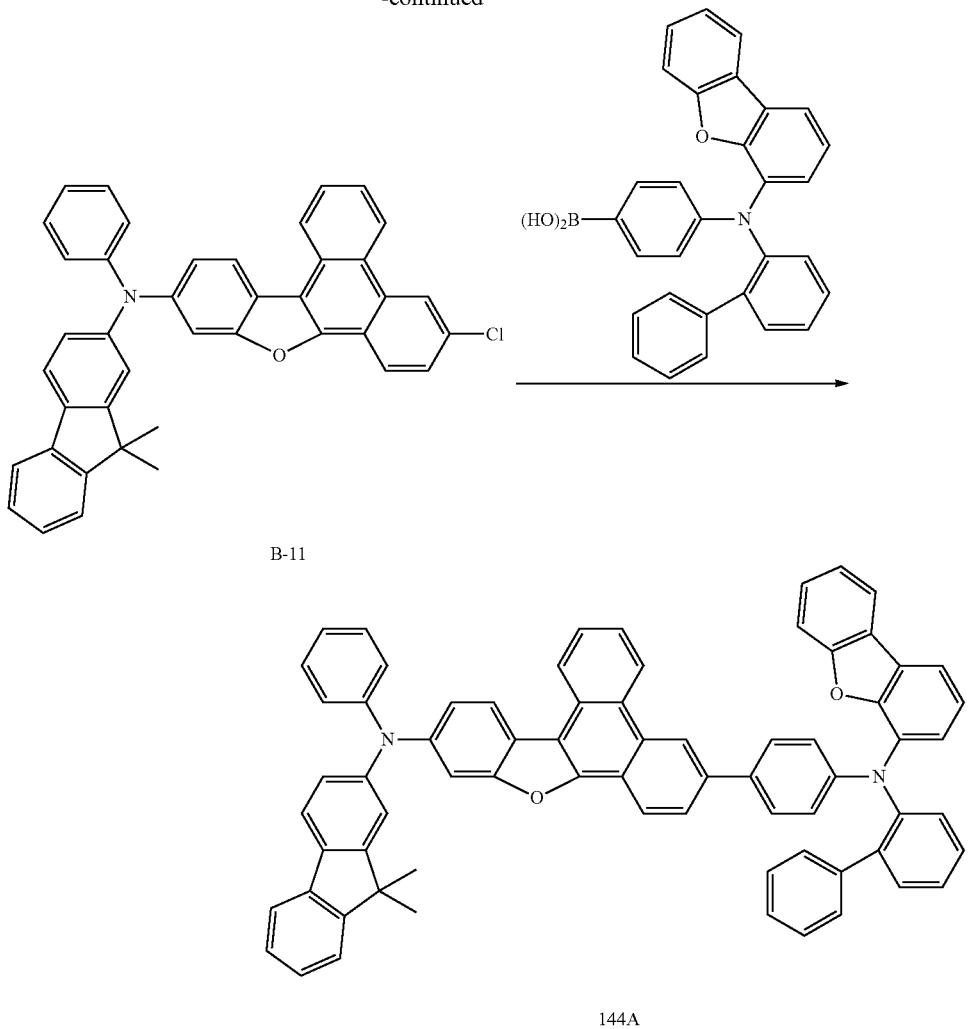

B-11

144A

Synthesis of Intermediate B-8

1.6 g (4 mmol, yield: 84%) of Intermediate B-8 was synthesized in the same manner as in Synthesis of Intermediate A-7 of Synthesis Example 1, except that 4-bromo-2-iodo-1-methoxybenzene was used instead of (4-bromo-2-iodophenyl)(methyl)sulfane. The synthesized compound was identified by using MS/FAB.

$C_{21}H_{14}BrClO$ cal. 397.70. found 395.99.

Synthesis of Intermediate B-9

1.23 g (3.2 mmol, yield: 80%) of Intermediate B-9 was synthesized in the same manner as in Synthesis of Intermediate A-8 of Synthesis Example 1, except that Intermediate B-8 was used instead of Intermediate A-7. The synthesized compound was identified by using MS/FAB.

$C_{20}H_{12}BrClO$ cal. 383.67. found 383.97.

Synthesis of Intermediate B-10

1.04 g (2.7 mmol, yield: 85%) of Intermediate B-10 was synthesized in the same manner as in Synthesis of Intermediate A-9 of Synthesis Example 1, except that Intermediate B-9 was used instead of Intermediate A-8. The synthesized compound was identified by using MS/FAB.

$C_{20}H_{10}BrClO$ cal. 381.65. found 379.96.

Synthesis of Intermediate B-11

1.04 g (1.32 mmol, yield: 84%) of Intermediate B-11 was synthesized in the same manner as in Synthesis of Intermediate A-10 of Synthesis Example 2, except that 600 mg (1.57 mmol) of Intermediate B-10 was used instead of Intermediate A-9 and 9,9-dimethyl-N-phenyl-9H-fluoren-2-amine was used instead of diphenylamine. The synthesized compound was identified by using MS/FAB.

$C_{41}H_{28}ClNO$ cal. 586.13. found 585.19.

Synthesis of Compound 144A 939 mg (0.98 mmol, yield: 74%) of Compound 144A was synthesized in the same manner as in Synthesis of Compound 127 of Synthesis Example 2, except that 1.04 g (1.32 mmol) of Intermediate B-11 was used instead of Intermediate A-10 and 4-([1,1'-biphenyl]-2-yl(dibenzo[b,d]furan-4-yl)amino)phenyl)boronic acid was used instead of 4-(dibenzo[b,d]furan-4-yl(phenyl)amino)phenyl)boronic acid. The synthesized compound was identified by using MS/FAB.

$C_{71}H_{48}N_2O_2$ cal. 961.18. found 960.37.

Synthesis Example 5: Synthesis of Compound 2

753 mg (0.88 mmol, yield: 82%) of Compound 2 was synthesized in the same manner as in Synthesis of Compound 1 of Synthesis Example 1, except that 9,9-dimethyl-N-phenyl-9H-fluoren-2-amine was used instead of diphenylamine. The synthesized compound was identified by using MS/FAB and 1H NMR.

$C_{62}H_{46}N_2S$ cal. 851.12. found 850.34.

Synthesis Example 6: Synthesis of Compound 7

753 mg (0.88 mmol, yield: 82%) of Compound 7 was synthesized in the same manner as in Synthesis of Compound 1 of Synthesis Example 1, except that N-([1,1'-biphenyl]-2-yl)pyridin-3-amine was used instead of diphenylamine. The synthesized compound was identified by using MS/FAB and 1H NMR.

$C_{54}H_{36}N_4S$ cal. 772.97. found 772.27.

Synthesis Example 7: Synthesis of Compound 9

650 mg (0.90 mmol, yield: 79%) of Compound 9 was synthesized in the same manner as in Synthesis Example 1, except that in synthesizing Compound 1, N-phenylnaphthalen-2-amine was used instead of diphenylamine. The synthesized compound was identified by using MS/FAB and 1H NMR.

$C_{52}H_{34}N_2S$ cal. 718.92. found 718.24.

Synthesis Example 8: Synthesis of Compound 10

650 mg (0.65 mmol, yield: 69%) of Compound 10 was synthesized in the same manner as in Synthesis of Compound 1 of Synthesis Example 1, except that 9,9-dimethyl-N-(4-(trimethylsilyl)phenyl)-9H-fluoren-2-amine was used instead of diphenylamine. The synthesized compound was identified by using MS/FAB and 1H NMR.

$C_{68}H_{62}N_2SSi_2$ cal. 995.49. found 994.42.

Synthesis Example 9: Synthesis of Compound 13

782 mg (0.82 mmol, yield: 74%) of Compound 13 was synthesized in the same manner as in Synthesis of Compound 1 of Synthesis Example 1, except that 5'-fluoro-N-phenyl-[1,1':3',1''-terphenyl]-4'-amine was used instead of diphenylamine. The synthesized compound was identified by using MS/FAB and 1H NMR.

$C_{68}H_{44}F_2N_2S$ cal. 959.17. found 958.32.

Synthesis Example 10: Synthesis of Compound 15

485 mg (0.51 mmol, yield: 77%) of Compound 15 was synthesized in the same manner as in Synthesis of Compound 1 of Synthesis Example 1, except that N-([1,1'-biphenyl]-2-yl)dibenzo[b,d]furan-4-amine was used instead of diphenylamine. The synthesized compound was identified by using MS/FAB and 1H NMR.

$C_{68}H_{42}N_2O_2S$ cal. 951.16. found 950.30.

Synthesis Example 11: Synthesis of Compound 16

839 mg (0.76 mmol, yield: 54%) of Compound 16 was synthesized in the same manner as in Synthesis of Compound 1 of Synthesis Example 1, except that N-([1,1'-biphenyl]-2-yl)-6-phenyldibenzo[b,d]furan-4-amine was used instead of diphenylamine. The synthesized compound was identified by using MS/FAB and 1H NMR.

$C_{80}H_{50}N_2O_2S$ cal. 1103.35. found 1102.36.

Synthesis Example 12: Synthesis of Compound 19

535 mg (0.67 mmol, yield: 88%) of Compound 19 was synthesized in the same manner as in Synthesis of Compound 1 of Synthesis Example 1, except that N-phenyldibenzo[b,d]furan-2-amine was used instead of diphenylamine. The synthesized compound was identified by using MS/FAB and 1H NMR.

$C_{56}H_{34}N_2O_2S$ cal. 798.96. found 798.23.

Synthesis Example 13: Synthesis of Compound 26

860 mg (1.77 mmol) of Intermediate A-10, 524 mg (1.95 mmol) of N-phenylphenanthren-2-amine, 156 mg (0.18 mmol) of tris(dibenzylideneacetone)dipalladium(0), 35 mg (0.18 mmol) of tri(tert-butyl)phosphine, and 423 mg (4.4 mmol) of sodium tert-butoxide were mixed with 20 mL of toluene, and then, the mixed solution was stirred for 2 hours at a temperature of 80° C. An organic layer obtained therefrom was dried by using magnesium sulfate to remove a solvent from the organic layer, and then, the residues were separated and purified by using silica gel column chromatography, so as to obtain 1.04 g (1.45 mmol, yield: 82%) of Compound 26. The synthesized compound was identified by using MS/FAB and 1H NMR.

$C_{52}H_{34}N_2S$ cal. 718.92. found 718.24.

Synthesis Example 14: Synthesis of Compound 29

500 mg (1.03 mmol) of Intermediate A-10, 419 mg (1.23 mmol) of 5'-fluoro-N-phenyl-[1,1':3',1''-terphenyl]-4'-amine, 91.6 mg (0.10 mmol) of tris(dibenzylideneacetone) dipalladium(0), 20 mg (0.10 mmol) of tri(tert-butyl)phosphine, and 192 mg (2 mmol) of sodium tert-butoxide were added to 20 mL of toluene, and then, the mixed solution was stirred for 2 hours at a temperature of 80° C. An organic layer obtained therefrom was dried by using magnesium sulfate to remove a solvent therefrom, and then, the residues were separated and purified by using silica gel column chromatography, so as to obtain 560 mg (0.71 mmol, yield: 69%) of Compound 29. The synthesized compound was identified by using MS/FAB and 1H NMR.

$C_{56}H_{37}FN_2S$ cal. 788.98. found 788.27.

Synthesis Example 15: Synthesis of Compound 30

461 mg (0.57 mmol, yield: 55%) of Compound 30 was synthesized in the same manner as in Synthesis of Example 14, except that 4-((5'-fluoro-[1,1':3',1''-terphenyl]-4'-yl)amino)benzonitrile was used instead of 5'-fluoro-N-phenyl-[1,1':3',1''-terphenyl]-4'-amine. The synthesized compound was identified by using MS/FAB and 1H NMR.

$C_{57}H_{36}FN_3S$ cal. 813.99. found 813.26.

Synthesis Example 16: Synthesis of Compound 38

Synthesis of Intermediate A-10(1)

800 mg (2.01 mmol) of Intermediate A-9, 485 mg (2.01 mmol) of N-phenyl-4-(trimethylsilyl)aniline, 156 mg (0.18 mmol) of tris(dibenzylideneacetone)dipalladium(0), 35 mg (0.18 mmol) of tri(tert-butyl)phosphine, and 423 mg (4.4 mmol) of sodium tert-butoxide were added to 20 mL of toluene, and then, the mixed solution was stirred for 2 hours at a temperature of 80° C. After the reaction solution was cooled to room temperature, an organic layer was extracted twice therefrom by using water and diethyl ether. The organic layer was dried by using magnesium sulfate to remove a solvent therefrom, and then, the residues were separated and purified by using silica gel column chromatography, so as to obtain 774 mg (1.39 mmol, yield: 69%) of Intermediate A-10(1) below.

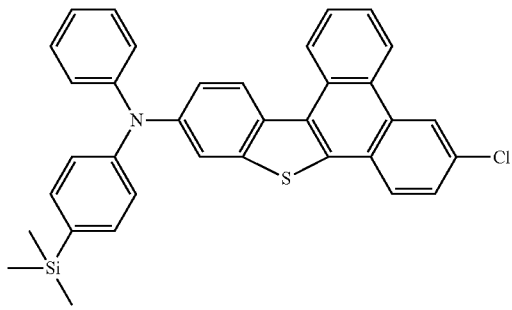

A-10(1)

Synthesis of Compound 38

774 mg (1.39 mmol) of Intermediate A-10(1), 559 mg (1.67 mmol) of N-([1,1'-biphenyl]-2-yl)dibenzo[b,d]furan-4-amine, 91.6 mg (0.10 mmol) of tris(dibenzylideneacetone)dipalladium(0), 20 mg (0.10 mmol) of tri(tert-butyl)phosphine, and 192 mg (2 mmol) of sodium tert-butoxide were added to 20 mL of toluene, and then, the mixed solution was stirred for 2 hours at a temperature of 80° C. An organic layer obtained therefrom was dried by using magnesium sulfate to remove a solvent therefrom, and then, the residues were separated and purified by using silica gel column chromatography, so as to obtain 786 mg (0.92 mmol, yield: 66%) of Compound 38. The synthesized compound was identified by using MS/FAB and 1H NMR.

$C_{59}H_{44}N_2OSSi$ cal. 857.16. found 856.29.

Synthesis Example 17: Synthesis of Compound 54

Synthesis of Intermediate A-10(2)

825 mg (1.47 mmol, yield: 73%) of Intermediate A-10(2) below was synthesized in the same manner as in Synthesis of Intermediate A-10(1) of Synthesis Example 16, except that N-phenyl-[1,1'-biphenyl]-2-amine was used instead of N-phenyl-4-(trimethylsilyl)aniline.

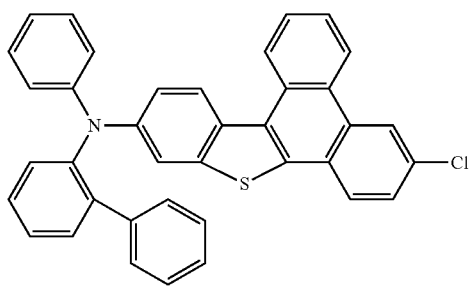

A-10(2)

Synthesis of Compound 54

825 mg (1.47 mmol) of Intermediate A-10(2), 366 mg (1.67 mmol) of N-phenylnaphthalen-2-amine, 91.6 mg (0.10 mmol) of tris(dibenzylideneacetone)dipalladium(0), 20 mg (0.10 mmol) of tri(tert-butyl)phosphine, and 192 mg (2 mmol) of sodium tert-butoxide were added to 20 mL of toluene, and then, the mixed solution was stirred for 2 hours at a temperature of 80° C. An organic layer obtained therefrom was dried by using magnesium sulfate to remove a solvent therefrom, and then, the residues were separated and purified by using silica gel column chromatography, so as to obtain 712 mg (0.96 mmol, yield: 65%) of Compound 54. The synthesized compound was identified by using MS/FAB and 1H NMR.

$C_{54}H_{36}N_2S$ cal. 744.96. found 744.26.

Synthesis Example 18: Synthesis of Compound 57

847 mg (1.51 mmol) of Intermediate A-10(2), 669 mg (1.85 mmol) of N-([1,1'-biphenyl]-2-yl)-9,9-dimethyl-9H-fluoren-2-amine, 183 mg (0.20 mmol) of tris(dibenzylideneacetone)dipalladium(0), 40 mg (0.20 mmol) of tri(tert-butyl)phosphine, and 288 mg (3 mmol) of sodium tert-butoxide were added to 20 mL of toluene, and then, the mixed solution was stirred for 2 hours at a temperature of 80° C. An organic layer obtained therefrom was dried by using magnesium sulfate to remove a solvent therefrom, and then, the residues were separated and purified by using silica gel column chromatography, so as to obtain 1.18 g (1.33 mmol, yield: 88%) of Compound 57. The synthesized compound was identified by using MS/FAB and 1H NMR.

$C_{65}H_{46}N_2S$ cal. 887.16. found 886.34.

Synthesis Example 19: Synthesis of Compound 72

Synthesis of Intermediate A-10(3)

1.00 mg (1.75 mmol, yield: 87%) of Intermediate A-10(3) below was synthesized in the same manner as in Synthesis of Intermediate A-10(1) of Synthesis Example 16, except that N-phenyldibenzo[b,d]furan-4-amine was used instead of N-phenyl-4-(trimethylsilyl)aniline.

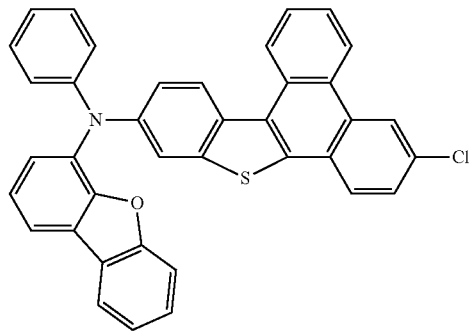

A-10(3)

Synthesis of Compound 72

1.00 g (1.75 mmol) of Intermediate A-10(3), 528 mg (1.85 mmol) of 9,9-dimethyl-N-phenyl-9H-fluoren-2-amine, 183 mg (0.20 mmol) of (dibenzylideneacetone)dipalladium(0), 40 mg (0.20 mmol) of tri(tert-butyl)phosphine, and 288 mg (3 mmol) of sodium tert-butoxide were added to 20 mL of toluene, and then, the mixed solution was stirred for 2 hours at a temperature of 80° C. An organic layer obtained therefrom was dried by using magnesium sulfate to remove a solvent therefrom, and then, the residues were separated and purified by using silica gel column chromatography, so as to obtain 1.27 g (1.54 mmol, yield: 88%) of Compound 72. The synthesized compound was identified by using MS/FAB and 1H NMR.

$C_{59}H_{40}N_2OS$ cal. 825.04. found 824.29.

Synthesis Example 20: Synthesis of Compound 88

Synthesis of Intermediate A-10(4)

1.14 g (1.75 mmol, yield: 87%) of Intermediate A-10(4) below was synthesized in the same manner as in Synthesis of Intermediate A-10(1) of Synthesis Example 16, except that N-([1,1'-biphenyl]-2-yl)dibenzo[b,d]furan-4-amine was used instead of N-phenyl-4-(trimethylsilyl)aniline.

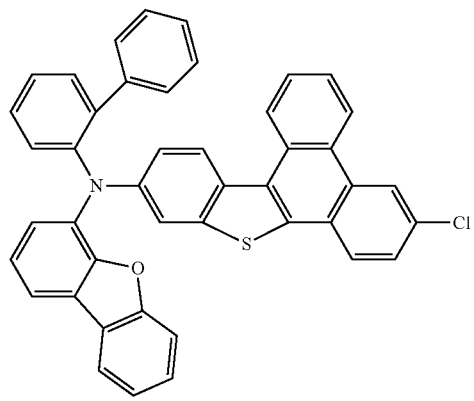

A-10(4)

Synthesis of Compound 88

1.23 g (1.37 mmol, yield: 78%) of Compound 88 was synthesized in the same manner as in Synthesis of Compound 72 of Synthesis Example 19, except that Intermediate A-10(4) was used instead of Intermediate A-10(3). The synthesized compound was identified by using MS/FAB and 1H NMR.

$C_{65}H_{44}N_2OS$ cal. 901.14. found 900.32.

Synthesis Example 21: Synthesis of Compound 90

1.14 g (1.19 mmol, yield: 68%) of Compound 90 was synthesized in the same manner as in Synthesis of Compound 72 of Synthesis Example 19, except that Intermediate A-10(4) was used instead of Intermediate A-10(3) and 5'-fluoro-N-phenyl-[1,1':3',1''-terphenyl]-4'-amine was used instead of 9,9-dimethyl-N-phenyl-9H-fluoren-2-amine. The synthesized compound was identified by using MS/FAB and 1H NMR.

$C_{68}H_{43}FN_2OS$ cal. 955.16. found 954.31.

Synthesis Example 22: Synthesis of Compound 129

Synthesis of Intermediate A-10(5)

916 mg (1.71 mmol, yield: 85%) of Intermediate A-10(5) below was synthesized in the same manner as in Synthesis of Intermediate A-10(1) of Synthesis Example 1, except that N-phenylnaphthalen-2-amine was used instead of N-phenyl-4-(trimethylsilyl)aniline.

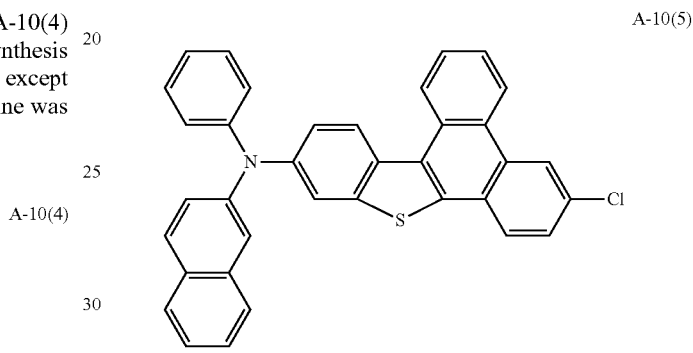

A-10(5)

Synthesis of Compound 129

916 mg (1.71 mmol) of Intermediate A-10(5), 758 mg (2.0 mmol) of (4-(dibenzo[b,d]furan-4-yl(phenyl)amino)phenyl) boronic acid, 196 mg (0.17 mmol) of $Pd(PPh_3)_4$, and 473 mg (3.4 mmol) of $K_2CO_3$ were added to 50 mL of a mixture of $THF/H_2O$ (at a volume ratio of 9/1), and then, the mixed solution was stirred for 12 hours at a temperature of 80° C. After the reaction solution was cooled to room temperature, an organic layer was extracted 3 times therefrom by using water and diethyl ether. The organic layer was dried by using magnesium sulfate to remove a solvent therefrom, and then, the residues were separated and purified by using silica gel column chromatography, so as to obtain 1.20 g (1.44 mmol, yield: 84%) of Compound 129. The synthesized compound was identified by using MS/FAB.

$C_{60}H_{38}N_2OS$ cal. 835.04. found 834.27.

Synthesis Example 23: Synthesis of Compound 134

Synthesis of Intermediate A-10(6)

908 mg (1.50 mmol, yield: 75%) of Intermediate A-10(6) below was synthesized in the same manner as in Synthesis of Intermediate A-10(1) of Synthesis Example 16, except that 9,9-dimethyl-N-phenyl-9H-fluoren-2-amine was used instead of N-phenyl-4-(trimethylsilyl)aniline.

A-10(6)

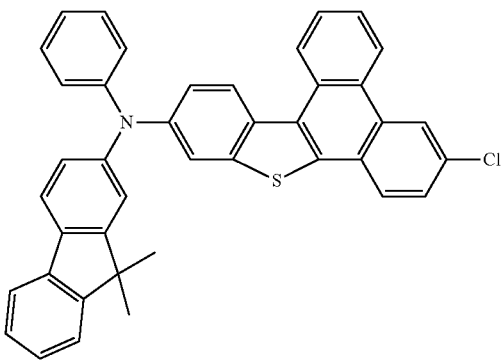

Synthesis of Compound 134

908 mg (1.50 mmol) of Intermediate A-10(6), 758 mg (2.0 mmol) of (4-(dibenzo[b,d]furan-4-yl(phenyl)amino)phenyl)boronic acid, 196 mg (0.17 mmol) of Pd(PPh$_3$)$_4$, and 473 mg (3.4 mmol) of K$_2$CO$_3$ were added to 50 mL of a mixture of THF/H$_2$O (at a volume ratio of 9/1), and then, the mixed solution was stirred for 12 hours at a temperature of 80° C. After the reaction solution was cooled to room temperature, an organic layer was extracted 3 times therefrom by using water and diethyl ether. The organic layer obtained therefrom was dried by using magnesium sulfate to remove a solvent therefrom, and then, the residues were separated and purified by using silica gel column chromatography, so as to obtain 1.08 g (1.40 mmol, yield: 80%) of Compound 134. The synthesized compound was identified by using MS/FAB.

C$_{65}$H$_{44}$N$_2$OS cal. 901.14. found 900.32.

Synthesis Example 24: Synthesis of Compound 140

1.33 g (1.42 mmol, yield: 80%) of Compound 140 was synthesized in the same manner as in Synthesis of Compound 129 of Synthesis Example 22, except that Intermediate A-10(2) was used instead of Intermediate A-10(5) and (4-([1,1'-biphenyl]-2-yl(dibenzo[b,d]furan-4-yl)amino)phenyl)boronic acid was used instead of (4-(dibenzo[b,d]furan-4-yl(phenyl)amino)phenyl)boronic acid. The synthesized compound was identified by using MS/FAB.

C$_{68}$H$_{44}$N$_2$OS cal. 937.17. found 936.32.

Synthesis Example 25: Synthesis of Compound 167

800 mg (2.01 mmol) of Intermediate A-9, 1.45 g (5.0 mmol) of (4-(diphenylamino)phenyl)boronic acid, 231 mg (0.2 mmol) of Pd(PPh$_3$)$_4$, and 5.53 g (4 mmol) of K$_2$CO$_3$ were added to 50 mL of THF/H$_2$O (at a volume ratio of 9/1), and then, the mixed solution was stirred for 12 hours at a temperature of 80° C. After the reaction solution was cooled to room temperature, an organic layer was extracted 3 times therefrom by using water and diethyl ether 3. The organic layer was dried by using magnesium sulfate to remove a solvent therefrom, and then, the residues were separated and purified by using silica gel column chromatography, so as to obtain 1.22 g (1.59 mmol, yield: 79%) of Compound 167. The synthesized compound was identified by using MS/FAB.

C$_{56}$H$_{38}$N$_2$S cal. 770.99. found 770.28.

Synthesis Example 26: Synthesis of Compound 174

Synthesis of Intermediate A-10(7)

1.03 g (1.61 mmol, yield: 80%) of Intermediate A-10(7) below was synthesized in the same manner as in Synthesis of Intermediate A-10(1) of Synthesis Example 16, except that di([1,1'-biphenyl]-4-yl)amine was used instead of N-phenyl-4-(trimethylsilyl)aniline.

A-10(7)

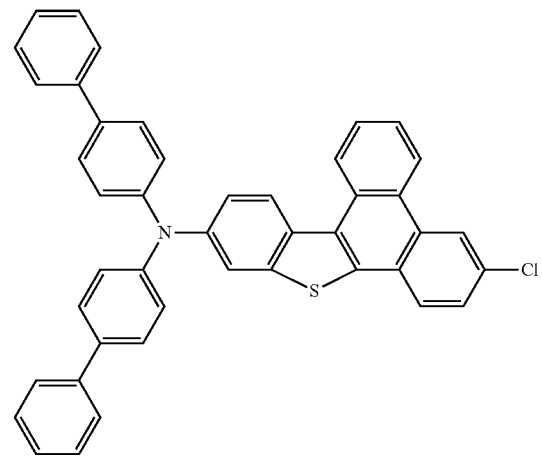

Synthesis of Compound 174

1.03 g (1.61 mmol) of Intermediate A-10(7), 406 mg (1.85 mmol) of N-phenylnaphthalen-1-amine, 183 mg (0.20 mmol) of tris(dibenzylideneacetone)dipalladium(0), 40 mg (0.20 mmol) of tri(tert-butyl)phosphine, and 288 mg (3 mmol) of sodium tert-butoxide were added to 20 mL of toluene, and then, the mixed solution was stirred for 2 hours at a temperature of 80° C. An organic layer obtained therefrom was dried by using magnesium sulfate to remove a solvent therefrom, and then, the residues were separated and purified by using silica gel column chromatography, so as to obtain 1.19 g (1.45 mmol, yield: 90%) of Compound 174. The synthesized compound was identified by using MS/FAB and 1H NMR.

C$_{60}$H$_4$ON$_2$S cal. 821.05. found 820.29.

Synthesis Example 27: Synthesis of Compound 180

Synthesis of Intermediate A-10(8)

981 mg (1.83 mmol, yield: 92%) of Intermediate A-10(8) below was synthesized in the same manner as in Synthesis of Intermediate A-10(1) of Synthesis Example 16, except that N-phenylnaphthalen-1-amine was used instead of N-phenyl-4-(trimethylsilyl)aniline.

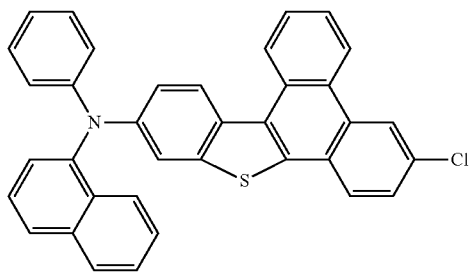

A-10(8)

Synthesis of Compound 180

981 mg (1.83 mmol) of Intermediate A-10(8), 578 mg (2.0 mmol) of (4-(diphenylamino)phenyl)boronic acid, 196 mg (0.17 mmol) of Pd(PPh$_3$)$_4$, and 473 mg (3.4 mmol) of K$_2$CO$_3$ were added to 500 mL of a mixture of THF/H$_2$O (at a volume ratio of 9/1), and then, the mixed solution was stirred for 12 hours at a temperature of 80° C. After the reaction solution was cooled to room temperature, an organic layer was extracted 3 times therefrom by using water and diethyl ether. The organic layer was dried by using magnesium sulfate to remove a solvent therefrom, and then, the residues were separated and purified by using silica gel column chromatography, so as to obtain 1.89 g (1.59 mmol, yield: 87%) of Compound 180. The synthesized compound was identified by using MS/FAB.

$C_{54}H_{36}N_2S$ cal. 744.96. found 744.26.

Synthesis Example 28: Synthesis of Compound 185

Synthesis of Intermediate A-10(9)

800 mg (2.01 mmol) of Intermediate A-9, 682 mg (2.0 mmol) of v(4-(naphthalen-1-yl(phenyl)amino)phenyl)boronic acid, 231 mg (0.2 mmol) of Pd(PPh$_3$)$_4$, and 553 mg (4.0 mmol) of K$_2$CO$_3$ were added to 50 mL of a mixture of THF/H$_2$O (at a volume ratio of 9/1), and then, the mixed solution was stirred for 12 hours at a temperature of 80° C. The reaction solution was cooled to room temperature, and an organic layer was extracted 3 times therefrom by using water and diethyl ether 3. The organic layer was dried by using magnesium sulfate to remove a solvent therefrom, and then, the residues were separated and purified by using silica gel column chromatography, so as to obtain 1.01 g (1.65 mmol, yield: 82%) of Intermediate 10-A(9) below.

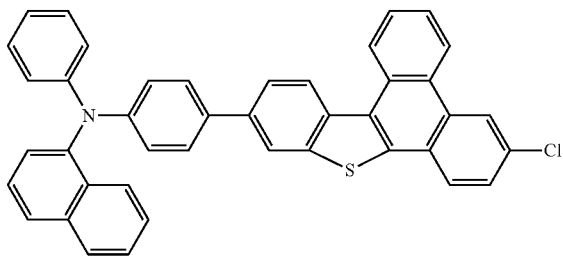

A-10(9)

Synthesis of Compound 185

1.01 g (1.65 mmol) of Intermediate A-10(9), 392 mg (1.8 mmol) of N-phenylnaphthalen-1-amine, 183 mg (0.20 mmol) of tris(dibenzylideneacetone)dipalladium(0), 40 mg (0.20 mmol) of tri(tert-butyl)phosphine, and 384 mg (4.0 mmol) of sodium tert-butoxide were added to 20 mL of toluene, and then, the mixed solution was stirred for 2 hours at a temperature of 80° C. After the reaction solution was cooled to room temperature, an organic layer was extracted twice therefrom by using water and diethyl ether. The organic layer was dried by using magnesium sulfate to remove a solvent therefrom, and then, the residues were separated and purified by using silica gel column chromatography, so as to obtain 1.15 g (1.45 mmol, yield: 88%) of Compound 185. The synthesized compound was identified by using MS/FAB.

$C_{58}H_{38}N_2S$ cal. 795.02. found 794.28.

Synthesis Example 29: Synthesis of Compound 196

596 mg (0.50 mmol, yield: 77%) of Compound 196 was synthesized in the same manner as in Synthesis of Compound 1 of Synthesis Example 1, except that N-(4'-fluoro-[1,1':3',1''-terphenyl]-5'-yl)-9,9-dimethyl-9H-fluoren-2-amine was used instead of diphenylamine. The synthesized compound was identified by using MS/FAB and 1H NMR.

$C_{86}H_{60}F_2N_2S$ cal. 1191.50. found 1190.44.

Synthesis Example 30: Synthesis of Compound 201

675 mg (0.71 mmol, yield: 72%) of Compound 201 was synthesized in the same manner as in Synthesis of Compound 1 of Synthesis Example 1, except that ([1,1'-biphenyl]-4-yl)dibenzo[b,d]furan-4-amine was used instead of diphenylamine. The synthesized compound was identified by using MS/FAB and 1H NMR.

$C_{68}H_{42}N_2O_2S$ cal. 951.16. found 950.30.

Synthesis Example 31: Synthesis of Compound 2A 501 mg (0.60 mmol, yield: 87%) of Compound 2A was synthesized in the same manner as in Synthesis of Compound 1A of Synthesis Example 3, except that 9,9-dimethyl-N-phenyl-9H-fluoren-2-amine was used instead of diphenylamine. The synthesized compound was identified by using MS/FAB and 1H NMR.

$C_{62}H_{46}N_2O$ cal. 835.06. found 834.36.

Synthesis Example 32: Synthesis of Compound 5A 499 mg (0.71 mmol, yield: 92%) of Compound 5A was synthesized in the same manner as in Synthesis of Compound 1A of Synthesis Example 3, except that N-phenylnaphthalen-1-amine was used instead of diphenylamine. The synthesized compound was identified by using MS/FAB and 1H NMR.

$C_{52}H_{34}N_2O$ cal. 702.86. found 702.27.

Synthesis Example 33: Synthesis of Compound 7A 325 mg (0.43 mmol, yield: 62%) of Compound 7A was synthesized in the same manner as in Synthesis of Compound 1A of Synthesis Example 3, except that N-([1,1'-biphenyl]-2-yl)pyridin-3-amine was used instead of diphenylamine. The synthesized compound was identified by using MS/FAB and 1H NMR.

$C_{54}H_{36}N_4O$ cal. 756.91. found 756.29.

Synthesis Example 34: Synthesis of Compound 8A 400 mg (0.53 mmol, yield: 66%) of Compound 8A was synthesized in the same manner as in Synthesis of Compound 1A of Synthesis Example 3, except that N-phenyl-[1,1'-biphenyl]-4-amine was used instead of diphenylamine. The synthesized compound was identified by using MS/FAB and 1H NMR.

$C_{56}H_{38}N_2O$ cal. 754.93. found 754.30.

Synthesis Example 35: Synthesis of Compound 9A 436 mg (0.62 mmol, yield: 89%) of Compound 9A was synthesized in the same manner as in Synthesis of Compound 1A of Synthesis Example 3, except that N-phenyl-naphthalen-2-amine was used instead of diphenylamine. The synthesized compound was identified by using MS/FAB and 1H NMR.

$C_{52}H_{34}N_2O$ cal. 702.86. found 702.27.

Synthesis Example 36: Synthesis of Compound 10A 436 mg (0.62 mmol, yield: 89%) of Compound 10A was synthesized in the same manner as in Synthesis of Compound 1A of Synthesis Example 3, except that 9,9-dimethyl-N-(4-(trimethylsilyl)phenyl)-9H-fluoren-2-amine was used instead of diphenylamine. The synthesized compound was identified by using MS/FAB and 1H NMR.

$C_{68}H_{62}N_2SSi_2$ cal. 995.49. found 994.42.

Synthesis Example 37: Synthesis of Compound 13A 622 mg (0.66 mmol, yield: 72%) of Compound 13A was synthesized in the same manner as in Synthesis of Compound 1A of Synthesis Example 3, except that 5'-fluoro-N-phenyl-[1,1':3',1''-terphenyl]-4'-amine was used instead of diphenylamine. The synthesized compound was identified by using MS/FAB and 1H NMR.

$C_{68}H_{44}F_2N_2O$ cal. 943.11. found 942.34.

Synthesis Example 38: Synthesis of Compound 15A 701 mg (0.75 mmol, yield: 78%) of Compound 15A was synthesized in the same manner as in Synthesis of Compound 1A of Synthesis Example 3, except that N-([1,1'-biphenyl]-2-yl)dibenzo[b,d]furan-4-amine was used instead of diphenylamine. The synthesized compound was identified by using MS/FAB and 1H NMR.

$C_{68}H_{42}N_2O_3$ cal. 935.09. found 934.32.

Synthesis Example 39: Synthesis of Compound 19A 611 mg (0.78 mmol, yield: 88%) of Compound 19A was synthesized in the same manner as in Synthesis of Compound 1A of Synthesis Example 3, except that N-phenyldibenzo[b,d]furan-2-amine was instead of diphenylamine. The synthesized compound was identified by using MS/FAB and 1H NMR.

$C_{56}H_{34}N_2O_3$ cal. 782.90. found 782.26.

Synthesis Example 40: Synthesis of Compound 26A

Synthesis of Intermediate B-11(1)

763 mg (2.0 mmol) of Intermediate B-10, 338 mg (2.0 mmol) of diphenylamine, 183 mg (0.20 mmol) of tris(dibenzylideneacetone)dipalladium(0), 40 mg (0.20 mmol) of tri(tert-butyl)phosphine, and 384 mg (4.0 mmol) of sodium tert-butoxide were added to 20 mL of toluene, and then, the mixed solution was stirred for 2 hours at a temperature of 80° C. The reaction solution was cooled to room temperature, and an organic layer was extracted twice therefrom by using water and diethy ether. The organic layer was dried by using magnesium sulfate to remove a solvent therefrom, and then, the residues were separated and purified by using silica gel column chromatography, so as to obtain 818 mg (1.74 mmol, yield: 63%) of Intermediate B-11(1) below.

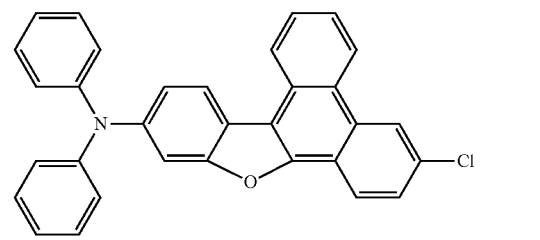

B-11(1)

Synthesis of Compound 26A 818 mg (1.74 mmol) of Intermediate B-11(1), 498 mg (1.85 mmol) of N-phenylphenanthren-2-amine, 156 mg (0.17 mmol) of tris(dibenzylideneacetone)dipalladium(0), 34 mg (0.17 mmol) of tri(tert-butyl)phosphine, and 288 mg (3 mmol) of sodium tert-butoxide were added to 20 mL of toluene 20 mL, and then, the mixed solution was stirred for 2 hours at a temperature of 80° C. An organic layer obtained therefrom was dried by using magnesium sulfate to remove a solvent therefrom, and then, the residues were separated and purified by using silica gel column chromatography, so as to obtain 1.14 g (1.62 mmol, yield: 93%) of Compound 26A. The synthesized compound was identified by using MS/FAB and 1H NMR.

$C_{52}H_{34}N_2O$ cal. 702.86. found 702.27.

Synthesis Example 41: Synthesis of Compound 29A 982 mg (1.27 mmol, yield: 73%) of Compound 29A was synthesized in the same manner as in Synthesis of Compound 26A of Synthesis Example 40, except that 5'-fluoro-N-phenyl-[1,1':3',1''-terphenyl]-4'-amine was used instead of N-phenylphenanthren-2-amine. The synthesized compound was identified by using MS/FAB and 1H NMR.

$C_{56}H_{37}FN_2O$ cal. 772.92. found 772.29.

Synthesis Example 42: Synthesis of Compound 30A 958 mg (1.20 mmol, yield: 69%) of Compound 30A was synthesized in the same manner as in Synthesis of Compound 26A of Synthesis Example 40, except that 5'-fluoro-6'-(phenylamino)-[1,1':3',1''-terphenyl]-4-carbonitrile was used instead of N-phenylphenanthren-2-amine. The synthesized compound was identified by using MS/FAB and 1H NMR.

$C_{57}H_{36}FN_3O$ cal. 797.93. found 797.28.

Synthesis Example 43: Synthesis of Compound 38A

Synthesis of Intermediate B-11(2)

650 mg (1.20 mmol, yield: 60%) of Intermediate B-11(2) below was synthesized in the same manner as in Synthesis of Intermediate B-11(1) of Synthesis Example 40, except that N-phenyl-4-(trimethylsilyl)aniline was used instead of diphenylamine.

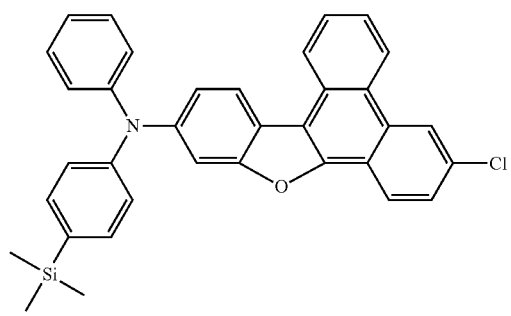

B-11(2)

Synthesis of Compound 38A 650 mg (1.20 mmol) of Intermediate B-11(2), 469 mg (1.4 mmol) of N-([1,1'-biphenyl]-2-yl)dibenzo[b,d]furan-4-amine, 110 mg (0.12 mmol) of tris(dibenzylideneacetone)dipalladium(0), 24.3 mg (0.12 mmol) of tri(tert-butyl)phosphine, and 240 mg (2.5 mmol) of sodium tert-butoxide were added to 20 mL of toluene, and then, the mixed solution was stirred for 2 hours at a temperature of 80° C. An organic layer obtained therefrom was dried by using magnesium sulfate to remove a solvent therefrom, and then, the residues were separated and purified by using silica gel column chromatography, so as to obtain 689 mg (0.82 mmol, yield: 68%) of Compound 38A. The synthesized compound was identified by using MS/FAB and 1H NMR.

$C_{59}H_{44}N_2O_2Si$ cal. 841.10. found 840.32.

Synthesis Example 44: Synthesis of Compound 54A

Synthesis of Intermediate B-11(3)

852 mg (1.56 mmol, yield: 78%) of Intermediate B-11(3) below was synthesized in the same manner as in Synthesis of Intermediate B-11(1) of Synthesis Example 40, except that N-phenyl-4-(trimethylsilyl)aniline was used instead of diphenylamine.

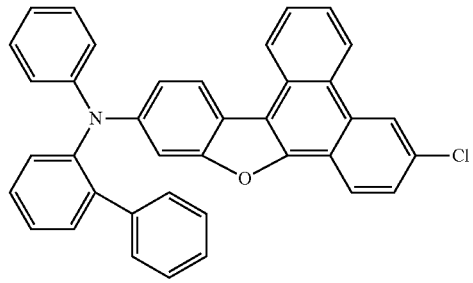

B-11(3)

Synthesis of Compound 54A 852 mg (1.56 mmol) of Intermediate B-11(3), 372 mg (1.7 mmol) of N-phenylnaphthalen-2-amine, 146 mg (0.16 mmol) of tris(dibenzylideneacetone)dipalladium(0), 32.4 mg (0.16 mmol) of tri(tert-butyl)phosphine, and 288 mg (3.0 mmol) of sodium tert-butoxide were added to 20 mL of toluene, and then, the mixed solution was stirred for 2 hours at a temperature of 80° C. An organic layer obtained therefrom was dried by using magnesium sulfate to remove a solvent therefrom, and then, the residues were separated and purified by using silica gel column chromatography, so as to obtain 1.00 g (1.32 mmol, yield: 88%) of Compound 54A. The synthesized compound was identified by using MS/FAB and 1H NMR.

$C_{54}H_{36}N_2O$ cal. 728.89. found 728.28.

Synthesis Example 45: Synthesis of Compound 57A 1.01 g (1.16 mmol, yield: 77%) of Compound 57A was synthesized in the same manner as in Synthesis of Compound 54A of Synthesis Example 44, except that N-([1,1'-biphenyl]-2-yl)-9,9-dimethyl-9H-fluoren-2-amine was used instead of N-phenylnaphthalen-2-amine. The synthesized compound was identified by using MS/FAB and 1H NMR.

$C_{65}H_{46}N_2O$ cal. 871.10. found 870.36.

Synthesis Example 46: Synthesis of Compound 72A

Synthesis of Intermediate B-11(4)

1.01 g (1.8 mmol, yield: 90%) of Intermediate B-11(4) below was synthesized in the same manner as in Synthesis of Intermediate B-11(1) of Synthesis Example 40, except that N-phenyl-4-(trimethylsilyl)aniline was used instead of diphenylamine.

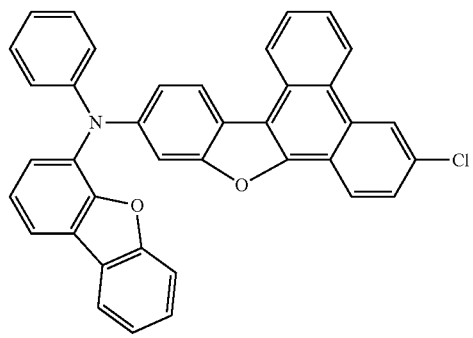

B-11(4)

Synthesis of Compound 72A 1.01 g (1.8 mmol) of Intermediate B-11(4), 542 mg (1.9 mmol) of 9,9-dimethyl-N-phenyl-9H-fluoren-2-amine, 183 mg (0.2 mmol) of tris(dibenzylideneacetone)dipalladium(0), 40 mg (0.2 mmol) of tri(tert-butyl)phosphine, and 336 mg (3.5 mmol) of sodium tert-butoxide were added to 20 mL of toluene, and then, the mixed solution was stirred for 2 hours at a temperature of 80° C. An organic layer obtained therefrom was dried by using magnesium sulfate to remove a solvent therefrom, and then, the residues were separated and purified by using silica gel column chromatography, so as to obtain 1.20 g (1.48 mmol, yield: 82%) of Compound 72A. The synthesized compound was identified by using MS/FAB and 1H NMR.

$C_{59}H_{40}N_2O_2$ cal. 808.98. found 808.31.

Synthesis Example 47: Synthesis of Compound 88A

Synthesis of Intermediate B-11(5)

891 mg (1.4 mmol, yield: 70%) of Intermediate B-11(5) below was synthesized in the same manner as in Synthesis of Intermediate B-11(1) of Synthesis Example 40, except that N-([1,1'-biphenyl]-2-yl)dibenzo[b,d]furan-4-amine was used instead of diphenylamine.

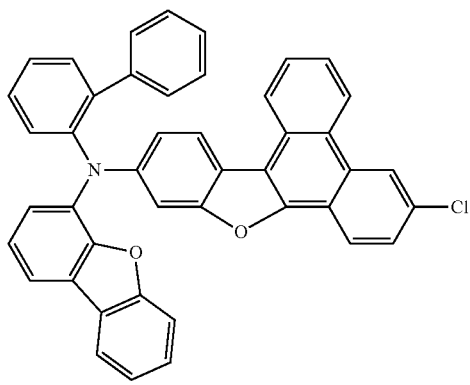

B-11(5)

Synthesis of Compound 88A 891 mg (1.4 mmol) of Intermediate B-11(5), 457 mg (1.6 mmol) of 9,9-dimethyl-N-phenyl-9H-fluoren-2-amine, 183 mg (0.2 mmol) of tris(dibenzylideneacetone)dipalladium(0), 40 mg (0.2 mmol) of tri(tert-butyl)phosphine, and 336 mg (3.5 mmol) of sodium tert-butoxide were added to 20 mL of toluene, and then, the mixed solution was stirred for 2 hours at a temperature of 80° C. An organic layer obtained therefrom was dried by using magnesium sulfate to remove a solvent therefrom, and then, the residues were separated and purified by using silica gel column chromatography, so as to obtain 1.08 g (1.22 mmol, yield: 87%) of Compound 88A. The synthesized compound was identified by using MS/FAB and 1H NMR.

$C_{65}H_{44}N_2O_2$ cal. 885.08. found 884.34.

Synthesis Example 48: Synthesis of Compound 90A 882 mg (0.94 mmol, yield: 67%) of Compound 90A was synthesized in the same manner as in Synthesis of Compound 88A of Synthesis Example 47, except that 5'-fluoro-N-phenyl-[1,1':3',1''-terphenyl]-4'-amine was used instead of 9,9-dimethyl-N-phenyl-9H-fluoren-2-amine. The synthesized compound was identified by using MS/FAB and 1H NMR.

$C_{68}H_{43}FN_2O_2$ cal. 939.10. found 938.33.

Synthesis Example 49: Synthesis of Compound 129A

Synthesis of Intermediate B-11(6)

957 mg (1.84 mmol, yield: 92%) of Intermediate B-11(6) below was synthesized in the same manner as in Synthesis of Intermediate B-11(1) of Synthesis Example 40, except that N-phenylnaphthalen-2-amine was used instead of diphenylamine.

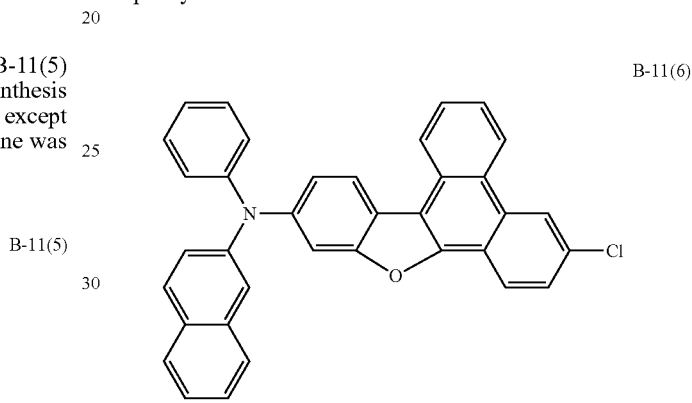

B-11(6)

Synthesis of Compound 129A 957 mg (1.84 mmol) of Intermediate B-11(6), 758 mg (2.0 mmol) of (4-(dibenzo[b,d]furan-4-yl(phenyl)amino)phenyl)boronic acid, 208 mg (0.18 mmol) of Pd(PPh$_3$)$_4$, and 497 mg (3.6 mmol) of K$_2$CO$_3$ were added to 50 mL of a mixture of THF/H$_2$O (at a volume ratio of 9/1), and then, the mixed solution was stirred for 12 hours at a temperature of 80° C. The reaction solution was cooled to room temperature, and an organic layer was extracted 3 times therefrom by using water and diethyl ether. The organic layer was dried by using magnesium sulfate to remove a solvent therefrom, and then, the residues were separated and purified by using silica gel column chromatography, so as to obtain 1.05 g (1.29 mmol, yield: 70%) of Compound 129A. The synthesized compound was identified by using MS/FAB.

$C_{60}H_{38}N_2O_2$ cal. 818.98. found 818.29.

Synthesis Example 50: Synthesis of Compound 134A

Synthesis of Intermediate B-11(7)

1.03 g (1.76 mmol, yield: 88%) of Intermediate B-11(7) below was synthesized in the same manner as in Synthesis of Intermediate B-11(1) of Synthesis Example 40, except that 9,9-dimethyl-N-phenyl-9H-fluoren-2-amine was used instead of diphenylamine.

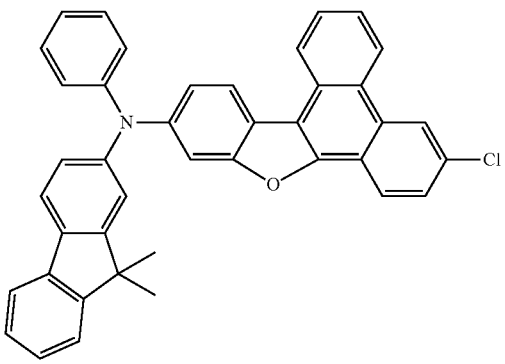

B-11(7)

Synthesis of Compound 134A 1.03 g (1.76 mmol) of Intermediate B-11(7), 758 mg (2.0 mmol) of (4-(dibenzo[b,d]furan-4-yl(phenyl)amino)phenyl)boronic acid, 208 mg (0.18 mmol) of Pd(PPh$_3$)$_4$, and 497 mg (3.6 mmol) of K$_2$CO$_3$ were added to 50 mL of a mixture of THF/H$_2$O (at a volume ratio of 9/1), and then, the mixed solution was stirred for 12 hours at a temperature of 80° C. The reaction solution was cooled to room temperature, and an organic layer was extracted therefrom 3 times by using water and diethyl ether. The organic layer was dried by using magnesium sulfate to remove a solvent therefrom, and then, the residues were separated and purified by using silica gel column chromatography, so as to obtain 1.07 g (1.21 mmol, yield: 71%) of Compound 134A. The synthesized compound was identified by using MS/FAB.

C$_{65}$H$_{44}$N$_2$O$_2$ cal. 885.08. found 884.34.

Synthesis Example 51: Synthesis of Compound 144A 1.04 g (1.08 mmol, yield: 635) of Compound 144A was synthesized in the same manner as in Synthesis of Compound 134A of Synthesis Example 50, except that (4-([1,1'-biphenyl]-2-yl(dibenzo[b,d]furan-4-yl)amino)phenyl)boronic acid was used instead of (4-(dibenzo[b,d]furan-4-yl(phenyl)amino)phenyl)boronic acid. The synthesized compound was identified by using MS/FAB.

C$_{71}$H$_{48}$N$_2$O$_2$ cal. 961.18. found 960.37.

Synthesis Example 52: Synthesis of Compound 167A 800 mg (2.01 mmol) of Intermediate B-10, 1.45 g (5.0 mmol) of (4-(diphenylamino)phenyl)boronic acid, 231 mg (0.2 mmol) of Pd(PPh$_3$)$_4$, and 5.53 g (4 mmol) of K$_2$CO$_3$ were added to 50 mL of a mixture of THF/H$_2$O (at a volume ratio of 9/1), and then, the mixed solution was stirred for 12 hours at a temperature of 80. The reaction solution was cooled to room temperature, and an organic layer was extracted therefrom 3 times by using water and diethyl ether. The organic layer was dried by using magnesium sulfate to remove a solvent therefrom, and then, the residues were separated and purified by using silica gel column chromatography, so as to obtain 1.23 g (1.63 mmol, yield: 81%) of Compound 167A. The synthesized compound was identified by using MS/FAB.

C$_{56}$H$_{38}$N$_2$O cal. 754.93. found 754.30.

Synthesis Example 53: Synthesis of Compound 174A

Synthesis of Intermediate B-11(8)

958 mg (1.54 mmol, yield: 77%) of Intermediate B-11(8) below was synthesized in the same manner as in Synthesis of Intermediate B-11(1) of Synthesis Example 40, except that di([1,1'-biphenyl]-4-yl)amine was used instead of diphenylamine.

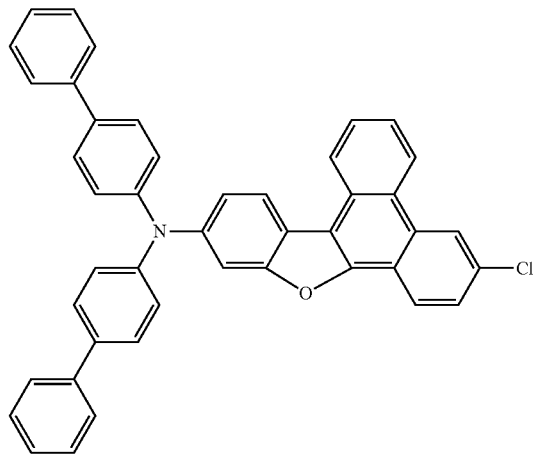

B-11(8)

Synthesis of Compound 174A 958 mg (1.54 mmol) of Intermediate B-11(8), 373 mg (1.7 mmol) of N-phenylnaphthalen-1-amine, 183 mg (0.2 mmol) of tris(dibenzylideneacetone)dipalladium(0), 40 mg (0.2 mmol) of tri(tert-butyl)phosphine, 336 mg (3.5 mmol) of sodium tert-butoxide were added to 20 mL of toluene, and then, the mixed solution was stirred for 2 hours at a temperature of 80° C. An organic layer obtained therefrom was dried by using magnesium sulfate to remove a solvent therefrom, and then, the residues were separated and purified by using silica gel column chromatography, so as to obtain 882 mg (0.94 mmol, yield: 67%) of Compound 174A. The synthesized compound was identified by using MS/FAB and 1H NMR.

C$_{60}$H$_{40}$N$_2$O cal. 804.99. found 804.31.

Synthesis Example 54: Synthesis of Compound 183A 874 mg (1.86 mmol) of Intermediate B-11(1), 730 mg (2.0 mmol) of di([1,1'-biphenyl]-4-yl)boramidic acid, 208 mg (0.18 mmol) of Pd(PPh$_3$)$_4$, and 497 mg (3.6 mmol) of K$_2$CO$_3$ were added to 50 mL of a mixture of THF/H$_2$O (at a volume ratio of 9/1), and then, the mixed solution was stirred for 12 hours at a temperature of 80° C. The reaction solution was cooled to room temperature, and an organic layer was extracted therefrom 3 times by using water and diethyl ether. The organic layer obtained therefrom was dried by using magnesium sulfate to remove a solvent therefrom, and then, the residues were separated and purified by using silica gel column chromatography, so as to obtain 1.19 g (1.43 mmol, yield: 77%) of Compound 184A. The synthesized compound was identified by using MS/FAB.

$C_{62}H_{42}N_2O$ cal. 831.03. found 830.33.

Synthesis Example 55: Synthesis of Compound 185A

Synthesis of Intermediate B-11(9)

990 mg (1.66 mmol, yield: 83%) of Intermediate B-11(9) below was synthesized in the same manner as in Synthesis of Intermediate B-11(1) of Synthesis Example 40, except that (4-(naphthalen-1-yl(phenyl)amino)phenyl)boronic acid was used instead of diphenylamine.

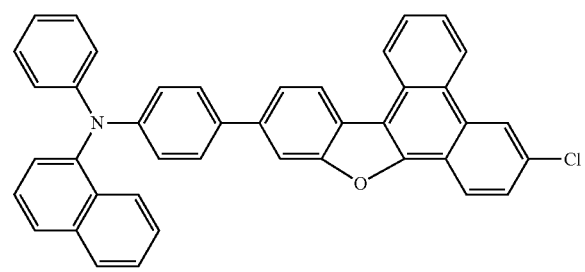

B-11(9)

Synthesis of Compound 185A 990 mg (1.66 mmol) of Intermediate B-11(9), 439 mg (2.0 mmol) of N-phenylnaphthalen-1-amine, 183 mg (0.20 mmol) of tris(dibenzylideneacetone)dipalladium(0), 40 mg (0.20 mmol) of tri(tert-butyl)phosphine, and 384 mg (4.0 mmol) of sodium tert-butoxide were added to 20 mL of toluene, and then, the mixed solution was stirred for 2 hours at a temperature of 80° C. The reaction solution was cooled to room temperature, and an organic layer was extracted therefrom twice by using water and diethy ether. The organic layer was dried by using magnesium sulfate to remove a solvent therefrom, and then, the residues were separated and purified by using silica gel column chromatography, so as to obtain 1.16 g (1.49 mmol, yield: 90%) of Compound 185A. The synthesized compound was identified by using MS/FAB.

$C_{58}H_{38}N_2O$ cal. 778.95. found 778.30.

Synthesis Example 56: Synthesis of Compound 196A 611 mg (0.78 mmol, yield: 88%) of Compound 196A was synthesized in the same manner as in Synthesis of Compound 1A of Synthesis Example 3, except that N-([1,1'-biphenyl]-2-yl)-9,9-dimethyl-9H-fluoren-2-amine was used instead of diphenylamine. The synthesized compound was identified by using MS/FAB and 1H NMR.

$C_{70}H_{62}N_2O$ cal. 947.28. found 946.49.

Synthesis Example 57: Synthesis of Compound 201A 823 mg (0.88 mmol, yield: 91%) of Compound 201A was synthesized in the same manner as in Synthesis of Compound 1A of Synthesis Example 3, except that N-([1,1'-biphenyl]-4-yl)dibenzo[b,d]furan-4-amine was used instead of diphenylamine. The synthesized compound was identified by using MS/FAB and 1H NMR.

$C_{68}H_{42}N_2O_3$ cal. 935.09. found 934.32.

The NMR and MS data with respect to Compounds synthesized in Synthesis Examples above are shown in Table 1 below:

TABLE 1

| Compound | $^1$H NMR (CDCl$_3$, 400 MHz) | MS/FAB calc. | found |
|---|---|---|---|
| 1 | δ = 8.46(m, 1H), 8.12(m, 1H), 8.04(d, 1H), 8.02-7.96(m, 1H), 7.66-7.60(m, 2H), 7.35(m, 1H), 7.17(m, 1H), 7.10-7.02(m, 8H), 6.70-7.55(m, 6H), 6.35-6.28(m, 4H), 6.25-6.20(m, 4H) | 618.80 | 618.21 |
| 2 | δ = 8.37(d, 1H), 8.04-7.97(m, 4H), 7.78(d, 1H), 7.76(d, 1H), 7.75-7.69(m, 2H), 7.54(d, 1H), 7.48-7.42(m, 2H), 7.30-7.21(m, 8H), 7.02-6.85(m, 7H), 6.80-6.77(m, 1H), 6.68(d, 1H), 6.66(d, 1H), 1.65(dd, 2H), 6.65(m, 1H), 2.93(s, 12H) | 851.12 | 850.34 |
| 7 | δ = 8.46(m, 1H), 8.34-8.30(m, 2H), 8.13-8.10(m, 1H), 8.09-8.03(m, 2H), 8.02-9-7.96(m, 1H), 7.80-7.76(m, 1H), 7.64-7.52(m, 6H), 7.50-7.42(m, 6H), 7.38-7.30(m, 3H), 7.29-7.16(m, 6H), 7.12-7.06(m, 1H), 67.02-6.93(m, 3H), 6.90-6.87(m, 1H), 6.52-6.40(m, 2H) | 772.97 | 772.27 |
| 9 | δ = 8.35(d, 1H), 8.10-0.08(m, 1H), 8.01(d, 1H), 7.98-7.94(m, H), 7.9-7.86(m, 2H), 7.74-7.57(m, 8H), 7.55-7.44(m, 6H), 7.38-7.28(m, 3H), 7.26-7.18(m, 4H), 6.93-6.80(m, 4H), 6.68-6.62(m, 2H), 6.62-6.58(m, 2H), | 718.92 | 718.24 |
| 10 | δ = 8.49-8.45 (m, 1H), 8.07-7.86(m, 2H), 7.74-7.70(m, 3H), 7.67-7.62(m, 2H), 7.47-7.43(m, 2H), 7.40-7.30(m, 7H), 7.20-7.09(m, 5H), 6.83-6.78(m, 2H), 6.77-6.70 (m, 4H), 6.65-6.60 (m, 3H), 6.53-6.49(m, 1H), 1.61 (s, 12H), 0.24 (s, 18H) | 995.49 | 994.42 |
| 13 | δ = 8.35(d, 1H), 8(d, 1H), 7.97(ddd, 1H), 7.84(dd, 1H), 7.74-7.66(m, 9H), 7.62-7.54(m, 10H), 7.52-7.42(m, 6H), 7.3-7.20(m, 7H), 6.90-6.86(m, 2H), 6.71(dd, 1H), 6.62(dd, 1H), 6.60-6.56(m, 2H), 6.54-6.51(m, 2H), | 959.17 | 958.32 |

TABLE 1-continued

| Compound | ¹H NMR (CDCl₃, 400 MHz) | MS/FAB calc. | MS/FAB found |
|---|---|---|---|
| 15 | δ = 8.28-8.24(m, 1H), 7.94(d, 1H), 7.84(dd, 1H), 7.72-7.66(m, 2H), 7.61-7.51(m, 5H), 7.51-7.48(m, 2H), 7.48-7.42(m, 8H), 7.36-7.29(m, 6H), 7.27(ddd, 1H), 7.11-7.04(m, 4H), 7.02-6.87(m, 9H), 6.65(dd, 1H), 6.28-6.25(m, 1H) | 951.16 | 950.30 |
| 16 | δ = 8.48-8.44 (m, 1H), 8.03-7.96(m, 2H), 7.86-7.80 (m, 4H), 7.77-7.73 (m, 2H), 7.68-7.60 (m, 7H), 7.58-7.52 (m, 8H), 7.48-7.44 (m, 2H), 7.40-7.36 (m, 4H), 7.35-7.32 (m, 3H), 7.25-7.21 (m, 2H), 7.16-7.10 (m, 4H), 7.09-7.02 (m, 3H), 7.10-6.94 (m, 4H), 6.85-6.81 (m, 2H), 6.69-6.65 (m, 1H), 6.25-6.22 (m, 1H) | 1103.35 | 1102.36 |
| 19 | δ = 8.28-8.25(m, 1H), 8.08-8.04(m, 1H), 7.89(d, 1H), 7.86-7.81(m, 1H), 7.72-7.66(m, 2H), 7.63-7.49(m, 3H), 7.45-7.39(m, 4H), 7.34-7.22(m, 6H), 7.09(d, 1H), 7.06-6.99(m, 4H), 6.91(dd, 1H), 6.88(dd, 1H), 6.72(dd, 1H), 6.66-6.62(m, 3H), 6.47-6.42(m, 2H), 6.4-6.36(m, 2H) | 798.96 | 798.23 |
| 26 | δ = 8.29-8.24(m, 2H), 8.08-8.02(m, 1H), 7.99-7.94(m, 1H), 7.89(d, 1H), 7.87-7.82(m, 1H), 7.73-7.68(m, 1H), 7.60-7.51(m, 3H), 7.48-7.42(m, 4H), 7.27(dd, 1H), 7.1(dd, 1H), 7.06-6.98(m, 6H), 6.95(dd, 1H), 6.66(dd, 1H), 6.64(d, 1H), 6.64(dd, 1H), 6.63(dd, 1H), 6.62(dd, 1H), 6.36-6.26(m, 6H) | 718.92 | 718.24 |
| 29 | δ = 8.29-8.24(m, 1H), 7.89(d, 1H), 7.87-7.83(m, 1H), 7.69(d, 1H), 7.58-7.49(m, 5H), 7.45-7.37(m, 5H), 7.34-7.22(m, 4H), 7.1(dd, 1H), 7.05(dd, 1H), 7.02-6.95(m, 6H), 6.68-6.57(m, 4H), 6.37-6.29(m, 5H), 6.23-6.18(m, 2H) | 788.98 | 788.27 |
| 30 | δ = 8.52-8.47(m, 1H), 8.1(d, 1H), 8.08-7.99(m, 2H), 7.79-7.68(m, 5H), 7.65-7.56(m, 5H), 7.54-7.41(m, 6H), 7.29(dd, 1H), 7.23(dd, 1H), 7.21-7.15(m, 4H), 6.87-6.77(m, 5H), 6.58(dd, 1H), 6.53-6.47(m, 4H) | 813.99 | 813.26 |
| 38 | δ = 8.50-8.45(m, 1H), 8.10-8.02(m, 2H), 7.88(dd, 1H), 7.78-7.66(m, 5H), 5.80-5.74(m, 4H), 7.58-7.43(m, 6H), 7.30-7.21(m, 3H), 7.20-7.05(m, 6H), 6.90-6.83(m, 4H), 6.54(dd, 1H), 6.54(dd, 1H), 6.41(dd, 1H), 0.83(s, 9H) | 857.16 | 856.29 |
| 54 | δ = 8.4-8.36(m, 1H), 8.07(dd, 1H), 7.97(dd, 1H), 7.94(dd, 1H), 7.83(ddd, 1H), 7.66(ddd, 1H), 7.64-7.51(m, 5H), 7.51-7.41(m, 6H), 7.40-7.33(m, 2H), 7.21(ddd, 1H), 7.2(d, 1H), 7.16(ddd, 1H), 7.11(ddd, 1H), 7.11-7.05(m, 4H), 7.02-6.89(m, 2H), 6.70-6.65(m, 2H), 6.6(ddd, 1H), 6.38-6.31(m, 2H), 6.3-6.24(m, 2H) | 744.96 | 744.26 |
| 57 | δ = 8.60-8.56(m, 1H), 8.17(d, 1H), 8.14(dd, 1H), 7.96-7.85(m, 2H), 7.83-7.71(m, 6H), 7.70-7.58(m, 7H), 7.57-7.51(m, 2H), 7.43-7.30(m, 6H), 7.29-7.13(m, 6H), 6.90-6.85(m, 2H), 6.71-6.63(m, 3H), 6.5-6.45(m, 3H), 2.21(s, 6H) | 887.16 | 886.34 |
| 72 | δ = 8.6-8.56(m, 1H), 8.22-8.12(m, 3H), 7.98(dd, 1H), 7.93(dd, 1H), 7.88-7.80(m, 4H), 7.68-7.57(m, 3H), 7.57-7.51(m, 2H), 7.36-7.25(m, 8H), 7.21(dd, 1H), 6.99-6.85(m, 5H), 6.74(dd, 1H), 6.64(dd, 1H), 6.64(dd, 1H), 6.56(ddd, 1H), 6.55(ddd, 1H), 2.21(s, 6H) | 825.04 | 824.29 |
| 88 | δ = 8.61-8.57(m, 1H), 8.23-8.14(m, 3H), 8(dd, 1H), 7.94(dd, 1H), 7.9-7.81(m, 4H), 7.78-7.72(m, 4H), 7.69-7.59(m, 4H), 7.58-7.52(m, 2H), 7.38-7.16(m, 9H), 6.98(dd, 1H), 6.93(ddd, 1H), 6.91(dd, 1H), 6.9(dd, 1H), 6.75(dd, 1H), 6.57(dd, 1H), 6.57(dd, 1H), 2.22(s, 6H) | 888.12 | 887.31 |
| 90 | δ = 8.43-8.39(m, 1H), 8.04-7.95(m, 2H), 7.82-7.79(m, 2H), 7.72-7.6(m, 7H), 7.59-7.48(m, 9H), 7.48(, H), 7.49-7.32(m, 7H), 7.19-7.04(m, 8H), 7.02(dd, 1H), 6.97(d, 1H), 6.71(dd, 1H), 6.66(ddd, 1H), 6.41-6.34(m, 1H), 6.26-6.22(m, 2H) | 955.16 | 954.31 |
| 127 | δ = 8.43-8.40 (m, 1H), 8.33-8.30 (m, 1H), 8.27-8.22 (m, 1H), 8.16-8.12 (m, 1H), 8.06-8.00 (m, 2H), 7.84-7.80 (m, 1H), 7.70-7.59 (m, 3H), 7.51-7.45 (m, 3H), 7.42-7.38 (m, 1H), 7.36-7.34 (m, 1H), 7.19-7.16 (m, 1H), 7.08-7.03 (m, 6H), 6.99-6.95 (m, 2H), 6.70-6.61 (m, 4H), 6.56-6.53 (m, 2H), 6.33-6.22 (m, 6H) | 784.98 | 784.25 |
| 129 | δ = 8.42-8.38(m, 1H), 8.28-8.24(m, 1H), 8.2(dd, 1H), 8.1(dd, 1H), 8(ddd, 1H), 7.99-7.97(m, 2H), 7.87-7.78(m, 2H), 7.68-7.52(m, 5H), 7.52-7.41(m, 5H), 7.41-7.33(m, 3H), 7.21(dd, 1H), 7.16(d, 1H), 7.13-7.02(m, 3H), 6.99(dd, 1H), 6.98(dd, 1H), 6.7-6.64(m, 3H), 6.61-6.54(m, 2H), 6.44-6.36(m, 2H), 6.33-6.26(m, 2H) | 835.04 | 834.27 |
| 134 | δ = 8.38-8.36(m, 1H), 8.27(dd, 1H), 8.21(d, 1H), 8.11(dd, 1H), 8.03-7.98(m, 2H), 7.75(d, 1H), 7.69-7.59(m, 3H), 7.51-7.39(m, 5H), 7.39-7.31(m, 2H), 7.19(dd, 1H), 7.15-7.05(m, 6H), 7.03-6.75(m, 4H), 6.71-6.61(m, 3H), 6.61-6.56(m, 2H), 6.42(d, 1H), 6.41(d, 1H), 6.34-6.27(m, 2H), 1.9(s, 6H) | 888.12 | 887.31 |

TABLE 1-continued

| Compound | $^1$H NMR (CDCl$_3$, 400 MHz) | MS/FAB calc. | MS/FAB found |
|---|---|---|---|
| 140 | δ = 8.43-8.40 (m, 1H), 8.33-8.31 (m, 1H), 8.26-8.24 (m, 1H), 8.15-8.13 (m, 1H), 8.85-8.00 (m, 2H), 7.84-7.80 (m, 1H), 7.70-7.63 (m, 2H), 7.63-7.52 (m, 7H), 7.50-7.44 (m, 7H), 7.42-7.33 (m, 2H), 7.2-7.10 (m, 4H), 7.06-6.90 (m, 9H), 6.65-6.61 (m, 1H), (6.45-6.37 (m, 3H), 6.23-6.16 (m, 2H) | 937.17 | 936.32 |
| 167 | δ = 8.49 (s, 1H), 8.43-8.40 (m, 1H), 8.33-8.20 (m, 3H), 8.16-8.12 (m, 1H), 8.04-8.00 (m, 1H), 7.63-7.60 (m, 1H), 7.56-7.43 (m, 5H), 7.37-7.33 (m, 1H), 7.08-7.04 (m, 8H), 6.85-6.80 (m, 2H), 6.67-6.55 (m, 6H), 6.18-6.12 (m, 8H) | 770.99 | 770.28 |
| 174 | δ = 8.48-8.44 (m, 1H), 8.15-8.11 (m, 1H), 8.05-7.98 (m, 2H), 7.89-7.85 (m, 1H), 7.73-7.70 (m, 1H), 7.66-7.65 (m, 1H), 7.59-7.50 (m, 5H), 7.48-7.42 (m, 10H), 7.39-7.33 (m, 3H), 7.27-7.28 (m, 1H), 7.24-7.21 (m, 1H), 7.15-7.13 (m, 1H), 7.08-7.03 (m, 2H), 6.85-6.84 (m, 1H), 6.75-6.70 (m, 5H), 6.63-6.35 (m, 2H), 6.15-6.11 (m, 2H) | 821.05 | 820.29 |
| 180 | δ = 8.45 (s, 1H), 8.33-8.30 (m, 1H), 8.27-8.24 (m, 1H), 8.16-8.10 (m, 2H), 8.05-8.03 (m, 2H), 7.89-7.85 (m, 1H), 7.63-7.60 (m, 1H), 7.55-7.48 (m, 3H), 7.46-7.43 (m, 1H), 3.37-7.27 (m, 2H), 7.25-7.21 (m, 1H), 7.12-7.03 (m, 7H), 6.85-6.81 (m, 2H), 6.74-6.70 (m, 1H), 6.70-6.63 (m, 3H), 6.21-6.10 (m, 6H) | 744.96 | 744.26 |
| 185 | δ = 8.41(d, 1H), 8.38(d, 1H), 8.2(s, 1H), 8.16(dd, 1H), 8.12(dd, 1H), 8.01(d, 1H), 7.91(d, 2H), 7.79(d, 1H), 7.72(t, 1H), 7.66-7.63(m, 3H), 7.6-7.56(m, 5H), 7.52-7.37(m, 5H), 7.28-7.23(m, 4H), 7.0(t, 2H), 6.93(t, 2H), 6.77(dd, 2H), 6.68(dd, 1H), 6.53-6.47(m, 4H) | 795.02 | 794.28 |
| 196 | δ = 8.28-8.25(m, 1H), 7.92-7.84(m, 3H), 7.67-7.59(m, 3H), 7.56-7.47(m, 5H), 7.44-7.4(m, 4H), 7.37-7.28(m, 14H), 7.28-7.21(m, 5H), 7.18-7.00(m, 5H), 6.88-6.52(m, 3H), 6.69-6.62(m, 3H), 6.55(d, 1H), 6.46(dd, 1H), 1.8(s, 6H), 1.79(s, 6H) | 1191.5 | 1190.44 |
| 201 | δ = 8.38-8.35(m, 1H), 8.18-8.15(m, 1H), 8(dd, 1H), 7.96(ddd, 1H), 7.83-7.78(m, 2H), 7.71-7.59(m, 6H), 7.58-7.53(m, 4H), 7.51-7.43(m, 11H), 7.42-7.32(m, 5H), 7.08(dd, 1H), 7.04-6.98(m, 3H), 6.79(dd, 1H), 6.76-6.61(m, 5H) | 951.16 | 950.30 |
| 1A | δ = 8.72-8.68(m, 1H), 8.37-8.32(m, 1H), 8.23-8.19(m, 1H), 7.92(dd, 1H), 7.71(d, 1H), 7.67-7.54(m, 2H), 7.11-7.06(m, 8H), 6.86-6.74(m, 3H), 6.71-6.67(m, 4H), 6.37-6.26(m, 8H) | 602.74 | 602.24 |
| 2A | δ = 8.76-8.73(m, 1H), 8.40-8.36(m, 1H), 8.02(d, 1H), 7.82-7.73(m, 3H), 7.65-7.55(m, 3H), 7.45(d, 1H), 7.43(d, 1H), 7.36-7.30(m, 2H), 7.21-7.03(m, 8H), 6.91-6.77(m, 3H), 6.77-6.47(m, 6H), 6.37-6.28(m, 4H), 1.73(s, 6H), 1.71(s, 6H) | 835.06 | 834.36 |
| 5A | δ = 8.95-8.91(m, 1H), 8.6-8.54(m, 1H), 8.34-8.28(m, 2H), 8.15(ddd, 1H), 8.09-8.03(m, 2H), 7.98(dd, 1H), 7.87-7.71(m, 5H), 7.68-7.6(m, 2H), 7.53-7.41(m, 4H), 7.3-7.22(m, 4H), 6.97-6.77(m, 7H), 6.45-6.31(m, 4H) | 702.86 | 702.27 |
| 7A | δ = 8.75-8.7(m, 1H), 8.39-8.35(m, 1H), 8.31-8.27(m, 2H), 8.08-7.96(m, 3H), 7.79-7.74(m, 1H), 7.67-7.55(m, 7H), 7.5-7.44(m, 6H), 7.34(dd, 1H), 7.32(dd, 1H), 7.26(dd, 1H), 7.25(dd, 1H), 7.23-7.15(m, 3H), 7.11-6.81(m, 5H), 6.81-6.7(m, 3H) | 756.91 | 758.29 |
| 8A | δ = 8.66-8.62(m, 1H), 8.3-8.26(m, 1H), 8.22-8.18(m, 1H), 7.84(d, 1H), 7.63(d, 1H), 7.55-7.44(m, 6H), 7.38-7.32(m, 8H), 7.3-7.25(m, 2H), 7.01-6.94(m, 4H), 6.79-6.67(m, 3H), 6.61-6.47(m, 6H), 6.3-6.21(m, 4H) | 754.93 | 754.30 |
| 9A | δ = 8.75-8.71(m, 1H), 8.39-8.34(m, 1H), 8.01(d, 1H), 8.01(d, 1H), 7.86(dd, 1H), 7.85(dd, 1H), 7.79(d, 1H), 7.65-7.50(m, 8H), 7.48-7.38(m, 4H), 7.2(dd, 1H), 7.11-7.06(m, 4H), 6.9(dd, 1H), 6.84-6.65(m, 5H), 6.41-6.29(m, 4H) | 702.86 | 702.27 |
| 13A | δ = 8.36-8.32(m, 1H), 7.94-8.84(m, 2H), 7.71(d, 1H), 7.60-7.50(m, 9H), 7.45-7.38(m, 10H), 7.33-7.21(m, 6H), 7.06-6.94(m, 7H), 6.57-6.50(m, 2H), 6.33(dd, 1H), 6.22(dd, 1H), 6.19-6.16(m, 1H), 6.12-6.08(m, 1H) | 943.110 | 942.34 |
| 15A | δ = 8.85-8.81(m, 1H), 8.49-8.44(m, 1H), 8.03-7.87(m, 5H), 7.81-7.60 (m, 14H), 7.6-7.48(m, 6H), 7.26-7.19(m, 4H), 7.11-7.02(m, 8H), 6.77(dd, 1H), 6.72(dd, 1H), 6.68(dd, 1H) | 935.09 | 934.32 |
| 19A | δ = 8.65-8.61(m, 1H), 8.29-8.24(m, 2H), 7.93-7.86(m, 1H), 7.74-7.64(m, 3H), 7.54-7.40(m, 6H), 7.32-7.25(m, 6H), 7.01-6.52(m, 9H), 6.52-6.23 (m, 6H) | 782.90 | 782.26 |
| 26A | δ = 8.67-7.75(m, 1H), 8.36-8.26(m, 2H), 8.19(dd, 1H), 8.1(dd, 1H), 7.93-7.89(m, 1H), 7.77-7.73(m, 1H), 7.63(d, 1H), 7.58-7.52(m, 2H), 7.50-7.40(m, 5H), 7.01-6.95(m, 6H), 6.91(dd, 1H), 6.72-6.56(m, 6H), 6.23-6.19(m, 6H) | 702.86 | 702.27 |

TABLE 1-continued

| Compound | $^1$H NMR (CDCl$_3$, 400 MHz) | MS/FAB calc. | MS/FAB found |
|---|---|---|---|
| 29A | δ = 8.75-8.71(m, 1H), 8.39-8.34(m, 1H), 8.01-7.96(m, 1H), 7.74-7.55(m, 8H), 7.55-7.45(m, 5H), 7.42-7.30(m, 2H), 7.16-7.06(m, 7H), 7.01-6.58(m, 6H), 6.35-6.19(m, 6H) | | |
| 30A | δ = 8.56-8.52(m, 1H), 8.13(d, 1H), 8.09-8.04(m, 2H), 7.80-7.70(m, 5H), 7.65-7.56(m, 6H), 7.52-7.42(m, 5H), 7.28(dd, 1H), 7.22(dd, 1H), 7.19-7.15(m, 4H), 6.82-6.74(m, 5H), 6.52(dd, 1H), 6.47-6.42 (m, 4H) 6.42(, H), | 797.93 | 797.28 |
| 38A | δ = 8.56-8.53(m, 1H), 8.20-8.15(m, 1H), 7.74-7.50(m, 4H), 7.55-7.30(m, 8H), 7.29-7.15(m, 5H), 6.96-6.86(m, 4H), 6.83-6.32(m, 10H), 6.17-6.13(m, 2H), 0.19(s, 9H) | 841.10 | 840.32 |
| 54A | δ = 8.66-6.63(m, 1H), 8.30-8.18(m, 2H), 7.94-7.89(m, 1H), 7.76(dd, 1H), 7.58-7.40(m, 8H), 7.40-7.28(m, 5H), 7.16-7.05(m, 3H), 7.03-6.86(m, 5H), 6.76-6.69(m, 2H), 6.60-6.52(m, 3H), 6.57(d, 1H), 6.22-6.08(m, 4H) | 728.89 | 728.26 |
| 57A | δ = 8.46-8.42(m, 1H), 8.03(d, 1H), 7.99-7.94(m, 1H), 7.79-7.53(m, 8H), 7.50-7.43(m, 6H), 7.43-7.04(m, 11H), 7.01-6.91(m, 4H), 6.67-6.62(m, 2H), 6.47-6.37(m, 3H), 6.25-6.20(m, 3H), 1.73(s, 6H) | 871.10 | 870.36 |
| 72A | δ = 8.85-8.81(m, 1H), 8.49-8.45(m, 1H), 8.13-8.09(m, 1H), 7.99-7.84(m, 3H), 7.79-7.64(m, 5H), 7.60-7.45(m, 4H), 7.26-7.06(m, 6H), 6.97-6.63(m, 6H), 6.63-6.38(m, 5H), 1.88(s, 6H) | 808.98 | 808.31 |
| 88A | δ = 8.65-8.61(m, 1H), 8.29-8.25(m, 1H), 7.89-7.63(m, 3H), 7.55-7.44(m, 7H), 7.4-7.29(m, 7H), 7.25-6.99(m, 5H), 6.97-6.67(m, 5H), 6.60-6.48(m, 5H), 6.38(dd, 1H), 6.19-6.09(m, 3H), 1.69(s, 6H) | 885.08 | 884.34 |
| 90A | δ = 8.66-8.62(m, 1H), 8.30-8.26(m, 1H), 7.91-7.87(m, 1H), 7.73-7.67(m, 2H), 7.61-7.51(, 8H), 7.51-7.35(m, 12H), 7.33-7.27(m, 2H), 7.25(dd, 1H), 7.06-7.00(m, 3H), 6.99-6.95(m, 2H), 6.91-6.81(m, 4H), 6.71-6.42(m, 4H), 6.12-6.08(m, 2H) | 939.10 | 938.33 |
| 129A | δ = 8.79-8.74(m, 1H), 8.25-8.20(m, 2H), 8.06-7.96(m, 2H), 7.87-7.67(m, 3H), 7.59-7.28(, 13H), 7.03-6.82(m, 6H), 6.82-6.53(m, 5H), 6.48-6.19(m, 6H) | 818.98 | 818.29 |
| 134A | δ = 8.99-8.94(m, 1H), 8.45-8.40(m, 2H), 8.28-8.23(m, 1H), 8.18(dd, 1H), 7.93-7.84(m, 3H), 7.79-7.66(m, 4H), 7.60-7.41(m, 6H), 7.26-7.14(m, 6H), 7.11-7.07(m, 2H), 7.12-6.24(m, 5H), 6.68-6.58(m, 3H), 6.48-6.45(m, 4H), 1.89(s, 6H) | 885.08 | 884.34 |
| 144A | δ = 8.88-8.84(m, 1H), 8.34-8.31(m, 2H), 8.16-8.06(m, 2H), 7.83-7.73(m, 3H), 7.69-7.52(m, 8H), 7.5-7.34(m, 7H), 7.16-6.87(m, 12H), 6.74(d, 1H), 6.67-6.53(m, 1H), 6.49-6.34(m, 4H), 1.79(s, 6H) | 961.18 | 960.37 |
| 167A | δ = 8.72-8.62(m, 1H), 8.17-8.08(m, 2H), 7.99-7.95(m, 1H), 7.88(dd, 1H), 7.75(d, 1H), 7.55(dd, 1H), 7.42-7.30(m, 4H), 7.25-7.20(m, 3H), 6.90-6.82(m, 8H), 6.7-6.61(m, 4H), 6.50-6.42(m, 4H), 6.01-5.93(m, 8H) | 754.93 | 754.30 |
| 174A | δ = 76-8.73(m, 1H), 8.40-8.36(m, 1H), 8.12(dd, 1H), 7.99-7.95(m, 1H), 7.86(dd, 1H), 7.78(d, 1H), 7.73(d, 1H), 7.65-7.50(m, 7H), 7.48-7.42(m, 9H), 7.39-7.34(m, 2H), 7.31-7.24(m, 2H), 7.1-(m, 2H), 6.89(dd, 1H), 6.82(dd, 1H), 6.77-6.71(m, 5H), 6.67-6.62(m, 2H), 6.17-6.12(m, 2H) | 804.99 | 804.31 |
| 183A | δ = 8.89-8.85(m, 1H), 8.37-8.31(m, 2H), 8.18-8.16(m, 1H), 8.08(dd, 1H), 7.72(d, 1H), 7.65-7.55(m, 6H), 7.52-7.35(m, 12H), 7.09-6.66(m, 10H), 6.66-6.59(m, 4H), 6.34-6.28(m, 4H) | 831.03 | 830.33 |
| 185A | δ = 8.76-8.73(m, 1H), 8.12(dd, 1H), 8.12(dd, 1H), 8.13(d, 1H), 7.97(d, 1H), 7.86(dd, 1H), 7.85(dd, 1H), 7.78(d, 1H), 7.75(dd, 1H), 7.73-7.58(m, 2H), 7.66(dd, 1H), 7.6(d, 1H), 7.55-7.50(m, 3H), 7.46-7.38(m, 3H), 7.32-7.21(m, 4H), 7.10-7.03(m, 4H), 6.85(dd, 1H), 6.8(dd, 1H), 6.74(dd, 1H), 6.73(dd, 1H), 6.67-6.60(m, 3H), 6.22-6.11(m, 4H) | 778.95 | 778.3 |
| 192A | δ = 8.86-8.82(m, 1H), 8.50-8.46(m, 1H), 8.12(d, 1H), 7.89(d, 1H), 7.85(dd, 1H), 7.84(dd, 1H), 7.76-7.65(m, 7H), 7.58-7.53(m, 10H), 7.50-7.40(m, 4H), 7.26-7.17(m, 4H), 7.02-6.84(m, 5H), 6.79-6.62(m, 6H), 6.28(s, 6H), 6.28(s, 6H) | 987.26 | 986.42 |
| 196A | δ = 8.67-8.63(m, 1H), 8.30-8.26(m, 1H), 7.92(dd, 1H), 7.69(d, 1H), 7.65(dd, 1H), 7.65(dd, 1H), 7.55-7.48(m, 3H), 7.35(d, 1H), 7.34(d, 1H), 7.25-7.16(m, 6H), 7.06-6.99(m, 4H), 6.83-6.76(m, 3H), 6.71-6.40(m, 8H), 1.65(s, 6H), 1.63(s, 6H), 1.52(s, 9H), 1.52(s, 9H) | 947.28 | 946.49 |
| 201A | δ = 8.46-8.42(m, 1H), 8.79-8.17(m, 1H), 8.02(d, 1H), 7.98(dd, 1H), 7.83-7.79(m, 2H), 7.70-7.62(m, 6H), 7.59-7.55(m, 5H), 7.50-7.43(m, 10H), 7.42-7.33(m, 5H), 7.07(d, | 935.09 | 934.32 |

TABLE 1-continued

| Compound | $^1$H NMR (CDCl$_3$, 400 MHz) | MS/FAB calc. | found |
|---|---|---|---|
| | 1H), 7.02-6.97(m, 3H), 6.77(dd, 1H), 6.74-6.67(m, 3H), 6.65-6.60(m, 2H) | | |

Example 1

A glass substrate on which an ITO anode was formed (available by Corning company) having a surface resistance of 15 Ω/cm$^2$ (1,200 Å) was cut to a size of 50 mm×50 mm×0.7 mm, sonicated by using isopropyl alcohol and pure water each for 15 minutes, and cleansed by the exposure to UV ozone for 30 minutes. Then, the ITO glass substrate was equipped with a vacuum deposition apparatus.

2-TNATA was vacuum deposited on the ITO anode of the glass substrate to form a hole injection layer having a thickness of 600 Å. Compound 1 was vacuum deposited on the hole injection layer to form a hole transport layer having a thickness of 300 Å, thereby forming a hole transport region.

A host, e.g., 9,10-di-naphthalene-2-yl-anthracene (ADN), and a dopant, e.g., N,N,N',N'-tetraphenyl-pyrene-1,6-di-amine (TPD) were co-deposited on the hole transport region at a weight ratio of 98:2 to form an emission layer having a thickness of 300 Å.

Alq$_3$ was vacuum deposited on the emission layer form an electron transport layer having a thickness of 300 Å. LiF was deposited on the electron transport layer to form an electron injection layer having a thickness of 10 Å, thereby forming an electron transport region.

Al was vacuum deposited on the electron transport region to form a cathode having a thickness of 3,000 Å, thereby manufacturing an organic light-emitting device.

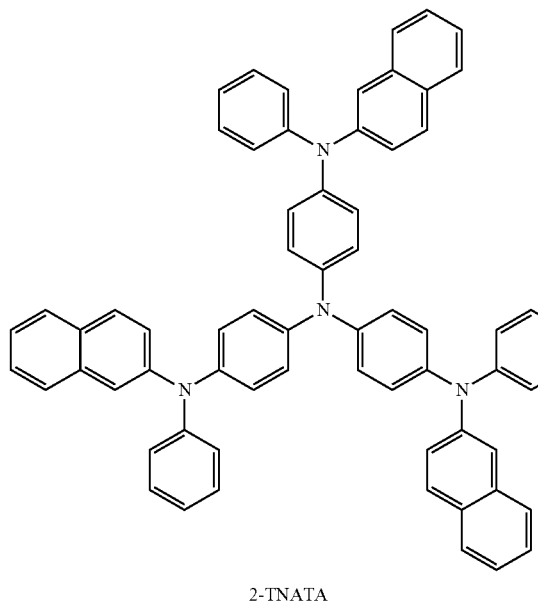

2-TNATA

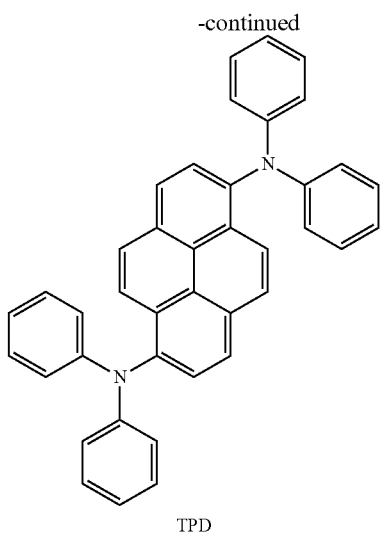

TPD

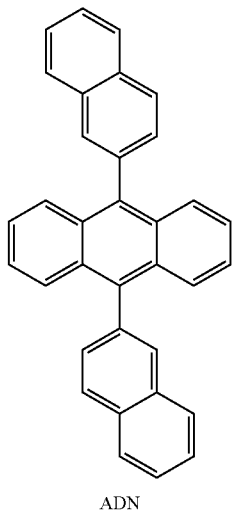

ADN

Examples 2 to 10

An organic light-emitting device was manufactured in the same manner as in Example 1, except that in forming the host transport layer, Compounds 7, 10, 16, 127, 140, 167, 174, 180, and 185 were used respectively instead of Compound 1.

Comparative Example 1

An organic light-emitting device was manufactured in the same manner as in Example 1, except that in forming the host transport layer, NPB below was used instead of Compound 1.

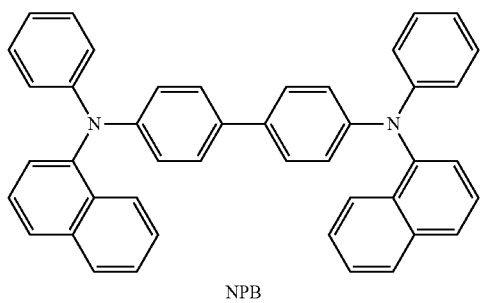

NPB

Comparative Example 2

An organic light-emitting device was manufactured in the same manner as in Example 1, except that in forming the host transport layer, Compound B was used instead of Compound 1.

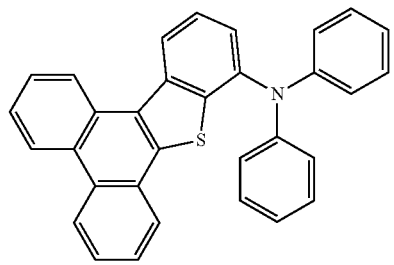

<Compound B>

Evaluation Example 1

The organic light-emitting devices of Examples 1 to 10 and Comparative Examples 1 and 2 were evaluated in terms of driving voltage, current density, brightness, efficiency, and half-lifespan characteristics, and obtained data were analyzed by an measuring device (Kethley SMU 236) and an luminance meter (PR650). The results are shown in Table 2 below. Half-lifespan data were obtained, upon operation, when brightness of the organic light-emitting device reached 50% with respect to initial brightness 100%.

TABLE 2

|  | Hole transport layer | Driving voltage (V) | Current density (mA/cm$^2$) | Brightness (cd/m$^2$) | Efficiency (cd/A) | Emission color | Half-lifespan (hr @100 mA/cm$^2$) |
| --- | --- | --- | --- | --- | --- | --- | --- |
| Example 1 | Compound 1 | 5.82 | 50 | 3211 | 6.43 | blue | 378 |
| Example 2 | Compound 7 | 5.67 | 50 | 3329 | 6.62 | blue | 351 |
| Example 3 | Compound 10 | 5.71 | 50 | 3163 | 6.33 | blue | 299 |
| Example 4 | Compound 16 | 5.78 | 50 | 3343 | 6.66 | blue | 354 |
| Example 5 | Compound 127 | 5.88 | 50 | 3212 | 6.42 | blue | 332 |
| Example 6 | Compound 140 | 5.65 | 50 | 3288 | 6.57 | blue | 362 |
| Example 7 | Compound 167 | 5.63 | 50 | 3391 | 6.72 | blue | 385 |
| Example 8 | Compound 174 | 5.60 | 50 | 3383 | 6.73 | blue | 390 |
| Example 9 | Compound 180 | 5.70 | 50 | 3332 | 6.69 | blue | 363 |
| Example 10 | Compound 185 | 5.65 | 50 | 3269 | 6.51 | blue | 360 |
| Comparative Example 1 | NPB | 7.01 | 50 | 2645 | 5.29 | blue | 258 |
| Comparative Example 2 | Compound B | 6.50 | 50 | 2954 | 5.50 | blue | 243 |

<Compound B>

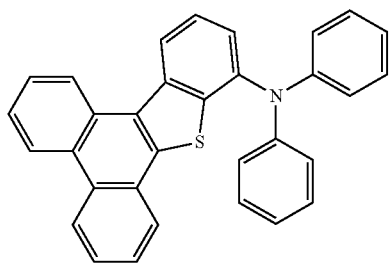

Referring to Table 2, it was confirmed that the organic light-emitting devices of Examples 1 to 10 had excellent driving voltage, brightness, efficiency, and half-lifespan characteristics as compared with those of the organic light-emitting devices of Comparative Examples 1 and 2.

Example 11

An organic light-emitting device was manufactured in the same manner as in Example 1, except in forming the hole transport layer, NPB was used instead of Compound 1, and in forming the emission layer, Compound 2 was used instead of TPD as a dopant.

Examples 12 to 28

Organic light-emitting devices were manufactured in the same manner as in Example 11, except that in forming the emission layer, Compounds 9, 13, 15, 19, 26, 29, 30, 38, 54, 57, 72, 88, 90, 129, 134, 196, and 201 were each used respectively instead of Compound 2 as a dopant.

Example 29

An organic light-emitting device was manufactured in the same manner as in Example 1, except that in forming the host transport layer, Compound 174 was used instead of NPB, and in forming the emission layer, Compound 2 was used instead of Compound 1 as a dopant.

Examples 30 to 33

Organic light-emitting devices were manufactured in the same manner as in Example 29, except that in forming the emission layer, Compounds 13, 38, 57, and 88 were each used instead of Compound 2 as a dopant.

Comparative Example 3

An organic light-emitting device was manufactured in the same manner as in Example 11, except that in forming the emission layer, TPD was used instead of Compound 2 as a dopant.

Comparative Example 4

An organic light-emitting device was manufactured in the same manner as in Example 11, except that in forming the emission layer, Compound A below was used instead of Compound 2 as a dopant.

<Compound A>

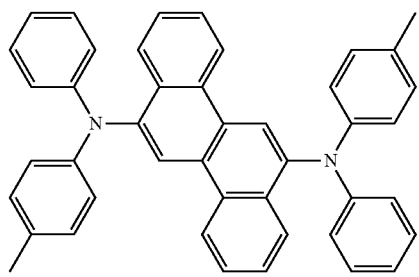

Evaluation Example 2

The organic light-emitting devices of Examples 11 to 33 and Comparative Examples 3 and 4 were evaluated in terms of driving voltage, current density, brightness efficiency, and half-lifespan characteristics, and obtained data were analyzed by an measuring device (Kethley SMU 236) and an luminance meter (PR650). The results are shown in Table 3 below. Half-lifespan data were obtained, upon operation, when brightness of the organic light-emitting device reached 50% with respect to initial brightness 100%.

TABLE 3

| | Hole transport layer | Dopant | Driving voltage (V) | Current density (mA/cm$^2$) | Brightness (cd/m$^2$) | Efficiency (cd/A) | Emission color | Half-lifespan (hr @100 mA/cm$^2$) |
|---|---|---|---|---|---|---|---|---|
| Example 11 | NPB | Compound 2 | 6.82 | 50 | 3550 | 7.21 | blue | 335 |
| Example 12 | NPB | Compound 9 | 6.85 | 50 | 3485 | 6.99 | blue | 349 |
| Example 13 | NPB | Compound 13 | 6.85 | 50 | 3505 | 7.52 | blue | 350 |
| Example 14 | NPB | Compound 15 | 6.86 | 50 | 3565 | 7.34 | blue | 332 |
| Example 15 | NPB | Compound 19 | 6.90 | 50 | 3498 | 7.22 | blue | 345 |
| Example 16 | NPB | Compound 26 | 6.80 | 50 | 3557 | 7.01 | blue | 365 |
| Example 17 | NPB | Compound 29 | 6.86 | 50 | 3515 | 6.90 | blue | 335 |
| Example 18 | NPB | Compound 30 | 6.83 | 50 | 3350 | 6.89 | blue | 328 |

TABLE 3-continued

| | Hole transport layer | Dopant | Driving voltage (V) | Current density (mA/cm$^2$) | Brightness (cd/m$^2$) | Efficiency (cd/A) | Emission color | Half-lifespan (hr @100 mA/cm$^2$) |
|---|---|---|---|---|---|---|---|---|
| Example 19 | NPB | Compound 38 | 6.82 | 50 | 3560 | 7.15 | blue | 320 |
| Example 20 | NPB | Compound 54 | 6.85 | 50 | 3485 | 6.89 | blue | 354 |
| Example 21 | NPB | Compound 57 | 6.83 | 50 | 3589 | 7.22 | blue | 362 |
| Example 22 | NPB | Compound 72 | 6.86 | 50 | 3523 | 7.13 | blue | 363 |
| Example 23 | NPB | Compound 88 | 6.87 | 50 | 3515 | 7.25 | blue | 345 |
| Example 24 | NPB | Compound 90 | 6.87 | 50 | 3567 | 7.33 | blue | 361 |
| Example 25 | NPB | Compound 129 | 6.83 | 50 | 3484 | 6.90 | blue | 350 |
| Example 26 | NPB | Compound 134 | 6.82 | 50 | 3465 | 6.70 | blue | 342 |
| Example 27 | NPB | Compound 196 | 6.80 | 50 | 3572 | 6.81 | blue | 357 |
| Example 28 | NPB | Compound 201 | 6.89 | 50 | 3557 | 7.10 | blue | 330 |
| Example 29 | Compound 174 | Compound 2 | 5.58 | 50 | 3688 | 7.48 | blue | 399 |
| Example 30 | Compound 174 | Compound 13 | 5.54 | 50 | 3715 | 7.40 | blue | 387 |
| Example 31 | Compound 174 | Compound 38 | 5.57 | 50 | 3739 | 7.48 | blue | 325 |
| Example 32 | Compound 174 | Compound 57 | 5.53 | 50 | 3747 | 7.51 | blue | 413 |
| Example 33 | Compound 174 | Compound 88 | 5.52 | 50 | 3780 | 7.55 | blue | 402 |
| Comparative Example 3 | NPB | TPD | 7.01 | 50 | 2645 | 5.29 | blue | 258 |
| Comparative Example 4 | NPB | Compound A | 6.95 | 50 | 2420 | 4.84 | blue | 250 |

Referring to Table 3, it was confirmed that the organic light-emitting devices of Examples 11 to 33 had excellent driving voltage, brightness, efficiency and half-lifespan characteristics as compared with those of the organic light-emitting devices of Comparative Examples 3 and 4.

Examples 1A to 10A

Organic light-emitting devices of Examples 1A to 10A were manufactured in the same manner as in Example 1, except in forming the hole transport layer, Compounds 1A, 5A, 7A, 8A, 144A, 167A, 174A, 183A, 185A, and 192A were each used instead of Compound 1.

Evaluation Example 3

The organic light-emitting devices of Examples 1A to 10A were evaluated in terms of driving voltage, current density, brightness, efficiency, and half-lifespan characteristics, and obtained data were analyzed by an measuring device (Kethley SMU 236) and an luminance meter (PR650). The results are shown in Table 4 below. Half-lifespan data were obtained, upon operation, when brightness of the organic light-emitting device reached 50% with respect to initial brightness 100%.

TABLE 4

| | Hole transport layer | Driving voltage (V) | Current density (mA/cm$^2$) | Brightness (cd/m$^2$) | Efficiency (cd/A) | Emission color | Half-lifespan (hr @100 mA/cm$^2$) |
|---|---|---|---|---|---|---|---|
| Example 1A | Compound 1A | 5.80 | 50 | 3203 | 6.46 | blue | 372 |
| Example 2A | Compound 5A | 5.65 | 50 | 3303 | 6.71 | blue | 354 |
| Example 3A | Compound 7A | 5.77 | 50 | 3166 | 6.37 | blue | 284 |
| Example 4A | Compound 8A | 5.71 | 50 | 3311 | 6.73 | blue | 361 |
| Example 5A | Compound 144A | 5.69 | 50 | 3203 | 6.46 | blue | 312 |
| Example 6A | Compound 167A | 5.74 | 50 | 3270 | 6.63 | blue | 363 |
| Example 7A | Compound 174A | 5.62 | 50 | 3357 | 6.84 | blue | 385 |

TABLE 4-continued

| | Hole transport layer | Driving voltage (V) | Current density (mA/cm$^2$) | Brightness (cd/m$^2$) | Efficiency (cd/A) | Emission color | Half-lifespan (hr @100 mA/cm$^2$) |
|---|---|---|---|---|---|---|---|
| Example 8A | Compound 183A | 5.64 | 50 | 3307 | 6.72 | blue | 363 |
| Example 9A | Compound 185A | 5.71 | 50 | 3353 | 6.86 | blue | 351 |
| Example 10A | Compound 192A | 5.69 | 50 | 3268 | 6.59 | blue | 372 |
| Comparative Example 1 | NPB | 7.01 | 50 | 2645 | 5.29 | blue | 258 |
| Comparative Example 2 | Compound B | 6.50 | 50 | 2954 | 5.50 | blue | 243 |

Referring to Table 4, it was confirmed that the organic light-emitting devices of Example 1A to 10A had excellent driving voltage, brightness, efficiency and half-lifespan characteristics as compared with those of the organic light-emitting devices of Comparative Examples 1 and 2.

Example 12A

An organic light-emitting device was manufactured in the same manner as in Example 1A, except in forming the hole transport layer, NPB was used instead of Compound 1A, and in forming the emission layer, Compound 2A was used instead of TPD as a dopant.

Examples 13A to 29A

Organic light-emitting devices of Examples 13A to 29A were manufactured in the same manner as in Example 12A, except in forming the emission layer, Compounds 9A, 13A, 15A, 19A, 26A, 29A, 30A, 38A, 54A, 57A, 72A, 88A, 90A, 129A, 134A, 196A, and 201A were each used instead of Compound 2A as a dopant.

Example 30A

An organic light-emitting device was manufactured in the same manner as in Example 1A, except in forming the hole transport layer, Compound 192A was used instead of NPB, and in forming emission layer, Compound 2A was used instead of Compound 1A as a dopant.

Examples 31A to 33A

Organic light-emitting devices of Examples 31A to 33A were manufactured in the same manner as in Example 30A, except in forming the emission layer, Compounds 13A, 38A, and 57A were each used instead of Compound 2A as a dopant.

Evaluation Example 4

The organic light-emitting devices of Examples 12A to 33A were evaluated in terms of driving voltage, current density, brightness, efficiency, and half-lifespan characteristics, and obtained data were analyzed by an measuring device (Kethley SMU 236) and an luminance meter (PR650). The results are shown in Table 5 below. Half-lifespan data were obtained, upon operation, when brightness of the organic light-emitting device reached 50% with respect to initial brightness 100%. For the comparison, data obtained with respect to the organic light-emitting devices of Comparative Examples 3 and 4 are also shown in Table 5.

TABLE 5

| | Hole transport layer | Dopant | Driving voltage (V) | Current density (mA/cm$^2$) | Brightness (cd/m$^2$) | Efficiency (cd/A) | Emission color | Half-lifespan (hr @100 mA/cm$^2$) |
|---|---|---|---|---|---|---|---|---|
| Example 12A | NPB | Compound 2A | 6.87 | 50 | 3455 | 7.13 | blue | 336 |
| Example 13A | NPB | Compound 9A | 6.83 | 50 | 3460 | 6.92 | blue | 349 |
| Example 14A | NPB | Compound 13A | 6.84 | 50 | 3575 | 7.15 | blue | 346 |
| Example 15A | NPB | Compound 15A | 6.87 | 50 | 3465 | 7.11 | blue | 358 |
| Example 16A | NPB | Compound 19A | 6.83 | 50 | 3575 | 7.05 | blue | 339 |
| Example 17A | NPB | Compound 26A | 6.86 | 50 | 3525 | 7.09 | blue | 348 |
| Example 18A | NPB | Compound 29A | 6.81 | 50 | 3545 | 7.01 | blue | 329 |
| Example 19A | NPB | Compound 30A | 6.89 | 50 | 3360 | 6.72 | blue | 333 |
| Example 20A | NPB | Compound 38A | 6.81 | 50 | 3565 | 7.14 | blue | 318 |
| Example 21A | NPB | Compound 54A | 6.86 | 50 | 3505 | 6.93 | blue | 356 |
| Example 22A | NPB | Compound 57A | 6.89 | 50 | 3498 | 7.12 | blue | 366 |

TABLE 5-continued

| | Hole transport layer | Dopant | Driving voltage (V) | Current density (mA/cm$^2$) | Brightness (cd/m$^2$) | Efficiency (cd/A) | Emission color | Half-lifespan (hr @100 mA/cm$^2$) |
|---|---|---|---|---|---|---|---|---|
| Example 23A | NPB | Compound 72A | 6.85 | 50 | 3555 | 7.1 | blue | 359 |
| Example 24A | NPB | Compound 88A | 6.84 | 50 | 3570 | 7.15 | blue | 342 |
| Example 25A | NPB | Compound 90A | 6.88 | 50 | 3575 | 7.13 | blue | 363 |
| Example 26A | NPB | Compound 129A | 6.87 | 50 | 3550 | 6.92 | blue | 347 |
| Example 27A | NPB | Compound 134A | 6.86 | 50 | 3565 | 6.91 | blue | 338 |
| Example 28A | NPB | Compound 196A | 6.79 | 50 | 3560 | 6.95 | blue | 367 |
| Example 29A | NPB | Compound 201A | 6.81 | 50 | 3460 | 7.19 | blue | 348 |
| Example 30A | Compound 192A | Compound 2A | 5.56 | 50 | 3690 | 7.38 | blue | 397 |
| Example 31A | Compound 192A | Compound 13A | 5.55 | 50 | 3725 | 7.45 | blue | 389 |
| Example 32A | Compound 192A | Compound 38A | 5.56 | 50 | 3755 | 7.51 | blue | 328 |
| Example 33A | Compound 192A | Compound 57A | 5.55 | 50 | 3765 | 7.53 | blue | 415 |
| Comparative Example 3 | NPB | TPD | 7.01 | 50 | 2645 | 5.29 | blue | 258 |
| Comparative Example 4 | NPB | Compound A | 6.95 | 50 | 2420 | 4.84 | blue | 250 |

Referring to Table 5, it was confirmed that the organic light-emitting devices of Examples 12A to 33A had excellent driving voltage, brightness, efficiency, and half-lifespan characteristics as compared with those of the organic light-emitting devices of Comparative Examples 3 and 4.

As described above, according to the one or more of the above example embodiments, an organic light-emitting device including a condensed cyclic compound has low driving voltage, high efficiency, high brightness, and long lifespan.

It should be understood that the example embodiments described therein should be considered in a descriptive sense only and not for purposes of limitation. Descriptions of features or aspects within each example embodiment should typically be considered as available for other similar features or aspects in other example embodiments.

While one or more example embodiments have been described with reference to the figures, it will be understood by those of ordinary skill in the art that various changes in form and details may be made therein without departing from the spirit and scope as defined by the following claims.

What is claimed is:

1. A condensed cyclic compound represented by one of Formulae 1-1 to 1-4 below:

<Formula 1-1>

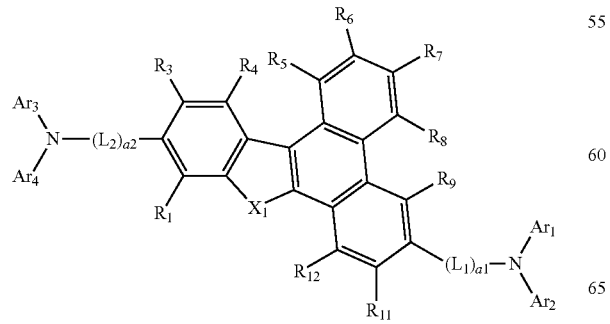

<Formula 1-2>

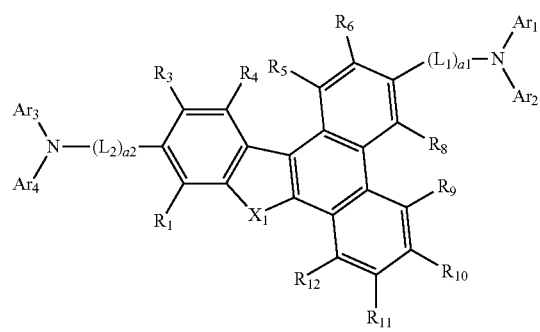

<Formula 1-3>

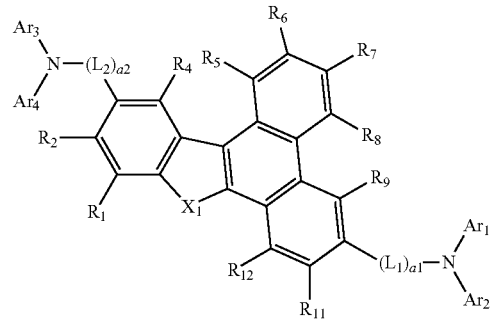

-continued

<Formula 1-4>

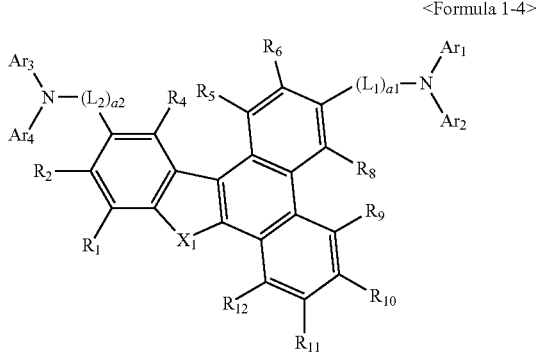

wherein $X_1$ is O or S;

L1 is selected from a substituted or unsubstituted C3-C10 cycloalkylene group, a substituted or unsubstituted C1-C10 heterocycloalkylene group, a substituted or unsubstituted C3-C10 cycloalkenylene group, a substituted or unsubstituted C1-C10 heterocycloalkenylene group, a substituted or unsubstituted C6-C60 arylene group, a substituted or unsubstituted C1-C60 heteroarylene group, a substituted or unsubstituted divalent non-aromatic condensed polycyclic group, and a substituted or unsubstituted divalent non-aromatic condensed heteropolycyclic group;

a1 is selected from 0, 1, 2, and 3, and when a1 is 2 or more, 2 or more L1s are identical to or different from each other;

Ar1 and Ar2 are each independently selected from a substituted or unsubstituted C3-C10 cycloalkyl group, a substituted or unsubstituted C1-C10 heterocycloalkyl group, a substituted or unsubstituted C3-C10 cycloalkenyl group, a substituted or unsubstituted C1-C10 heterocycloalkenyl group, a substituted or unsubstituted C6-C60 aryl group, a substituted or unsubstituted C1-C60 heteroaryl group, a substituted or unsubstituted monovalent non-aromatic condensed polycyclic group, and a substituted or unsubstituted monovalent non-aromatic condensed heteropolycyclic group;

$R_1$ to $R_{12}$ are each independently selected from a hydrogen, a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, and —B$(Q_4)(Q_5)$; and at least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si$(Q_{11})(Q_{12})(Q_{13})$, and —B$(Q_{14})(Q_{15})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si$(Q_{21})(Q_{22})(Q_{23})$, and —B$(Q_{24})(Q_{25})$; and —Si(Q$_{31}$)(Q$_{32}$)(Q$_{33}$) and —B(Q$_{34}$)(Q$_{35}$), wherein Q$_1$ to Q$_5$, Q$_{11}$ to Q$_{15}$, Q$_{21}$ to Q$_{25}$, and Q$_{31}$ to Q$_{35}$ are each independently selected from a hydrogen, a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_1$-C$_{60}$ heteroaryl group, a monovalent non-aromatic condensed polycyclic group, and a monovalent non-aromatic condensed heteropolycyclic group.

2. The condensed cyclic compound of claim 1, wherein L$_1$ in Formula 2 is selected from a phenylene group, a pentalenylene group, an indenylene group, a naphthylene group, an naphthylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one of a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a C$_1$-C$_{20}$ alkyl group, a C$_1$-C$_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

3. The condensed cyclic compound of claim 1, wherein L$_1$ in Formula 2 is selected from groups represented by Formulae 3-1 to 3-35 below:

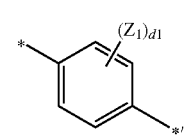

Formula 3-1

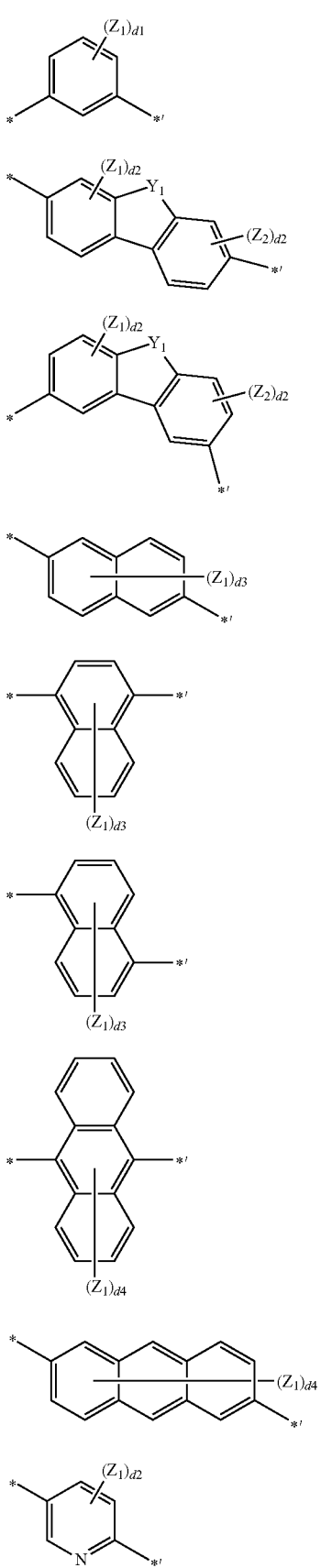
Formula 3-2
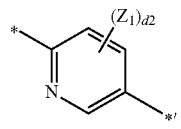
Formula 3-11
Formula 3-3
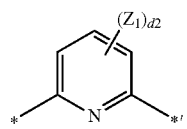
Formula 3-12
Formula 3-4
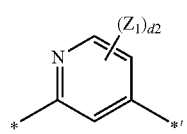
Formula 3-13
Formula 3-14
Formula 3-5
Formula 3-15
Formula 3-6
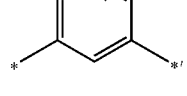
Formula 3-16
Formula 3-7
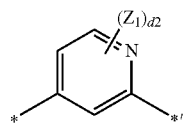
Formula 3-17
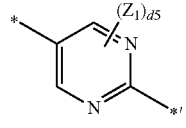
Formula 3-18
Formula 3-8
Formula 3-19
Formula 3-9
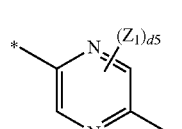
Formula 3-20
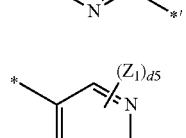
Formula 3-10
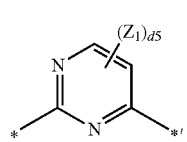
Formula 3-21

-continued

Formula 3-22
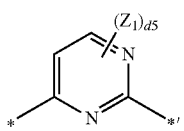

Formula 3-23
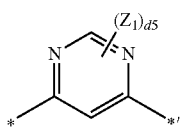

Formula 3-24
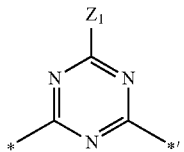

Formula 3-25
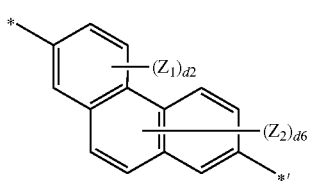

Formula 3-26
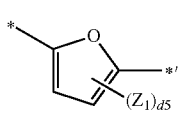

Formula 3-27
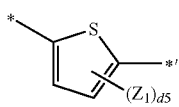

Formula 3-28
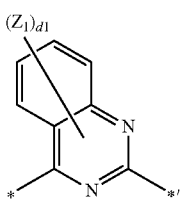

Formula 3-29
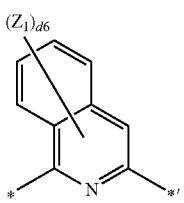

Formula 3-30
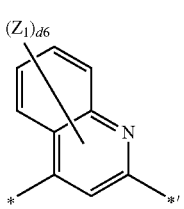

-continued

Formula 3-31
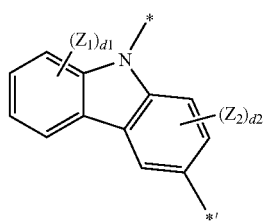

Formula 3-32
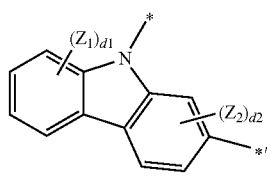

Formula 3-33
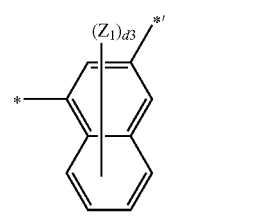

Formula 3-34
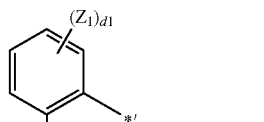

Formula 3-35
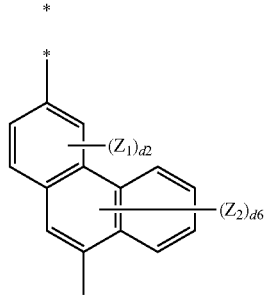

wherein in Formulae 3-1 to 3-35, $Y_1$ is O, S, $C(Z_3)(Z_4)$, $N(Z_5)$, or $Si(Z_6)(Z_7)$;

$Z_1$ to $Z_7$ are each independently selected from a hydrogen, a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, d1 is selected from integers of 1 to 4, d2 is selected from integers of 1 to 3, d3 is selected from integers of 1 to 6, d4 is selected from integers of 1 to 8, d5 is 1 or 2, and d6 is selected from integers of 1 to 5, and * and *' indicate a binding site to a neighboring atom.

4. The condensed cyclic compound of claim 1, wherein L₁ in Formula 2 is selected from groups represented by Formulae 4-1 to 4-28 below:
Formula 4-1
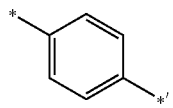
Formula 4-2
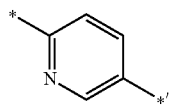
Formula 4-3
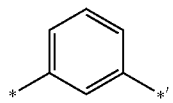
Formula 4-4
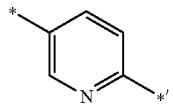
Formula 4-5
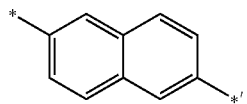
Formula 4-6
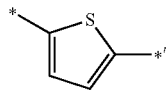
Formula 4-7
Formula 4-8
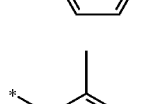
Formula 4-9
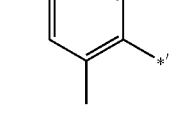
Formula 4-10
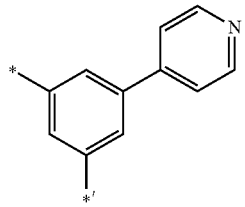
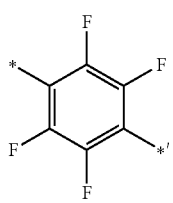
-continued
Formula 4-11
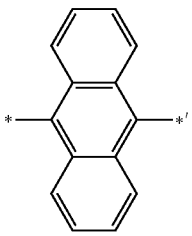
Formula 4-12
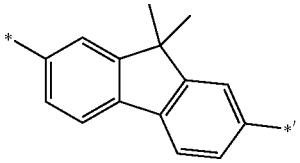
Formula 4-13
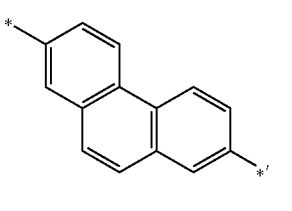
Formula 4-14
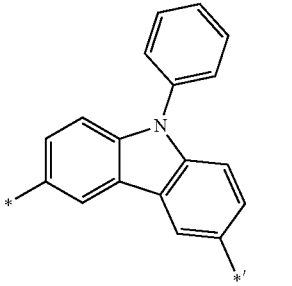
Formula 4-15
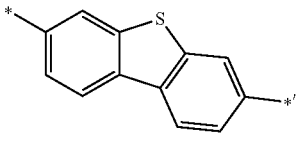
Formula 4-16
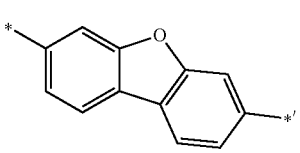
Formula 4-17
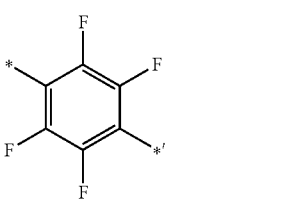
Formula 4-18
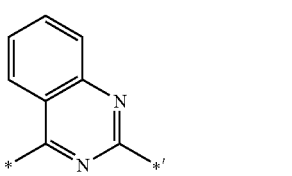

-continued

Formula 4-19

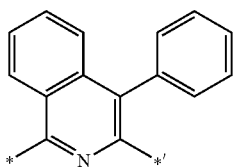

Formula 4-20

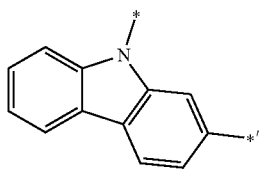

Formula 4-21

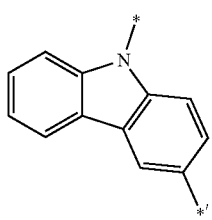

Formula 4-22

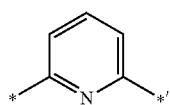

Formula 4-23

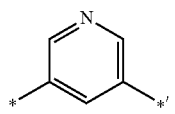

Formula 4-24

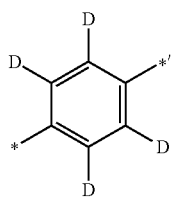

Formula 4-25

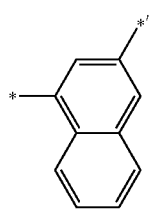

Formula 4-26

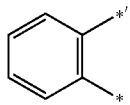

Formula 4-27

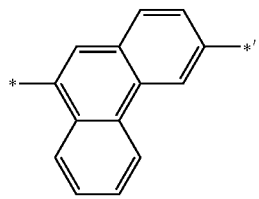

-continued

Formula 4-28

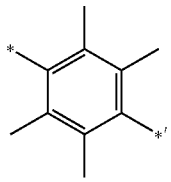

wherein in Formulae 4-1 and 4-28, * and *' indicate a binding site to a neighboring atom.

5. The condensed cyclic compound of claim 1, wherein a1 is 0 or 1.

6. The condensed cyclic compound of claim 1, wherein $Ar_1$ and $Ar_2$ are each independently selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group, each substituted with at least one of a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzooxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group.

7. The condensed cyclic compound of claim 1, wherein $Ar_1$ and $Ar_2$ in Formula 2 are each independently selected from a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, and an imidazopyrimidinyl group; and a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, and an imidazopyrimidinyl group, each substituted with at least one of a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$), wherein $Q_{31}$ to $Q_{33}$ are each independently a $C_1$-$C_{10}$ alkyl group, a $C_1$-$C_{10}$ alkoxy group, a phenyl group, and a naphthyl group.

8. The condensed cyclic compound of claim 1, wherein $Ar_1$ and $Ar_2$ in Formula 2 are each independently selected from a phenyl group, a naphthyl group, a fluorenyl group, a phenanthrenyl group, a pyridinyl group, a pyrimidinyl group, a triazinyl group, a dibenzofuranyl group, and a dibenzothiophenyl group; and a phenyl group, a naphthyl group, a fluorenyl group, a phenanthrenyl group, a pyridinyl group, a pyrimidinyl group, a triazinyl group, a dibenzofuranyl group, and a dibenzothiophenyl group, each substituted with at least one of a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a phenanthrenyl group, a pyridinyl group, a pyrimidinyl group, a triazinyl group, a dibenzofuranyl group, a dibenzothiophenyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, and a naphthyl group.

9. The condensed cyclic compound of claim 1, wherein $R_1$ to $R_{12}$ are each independently selected from a hydrogen, a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, and an imidazopyrimidinyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, and an imidazopyrimidinyl group, each substituted with at least one of a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzooxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, and a naphthyl group.

10. The condensed cyclic compound of claim 1, wherein $R_1$ to $R_{12}$ in Formula 1 are each independently selected from a hydrogen, a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a $C_1$-$C_{10}$ alkyl group, and a $C_1$-$C_{10}$ alkoxy group;

a phenyl group, a naphthyl group, a pyridinyl group, a pyrimidinyl group, and a triazinyl group;

a phenyl group, a naphthyl group, a pyridinyl group, a pyrimidinyl group, and a triazinyl group, each substituted with at least one of a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, and a naphthyl group.

11. The condensed cyclic compound of claim 1, wherein $Ar_1$ and $Ar_2$ in Formula 2 are each independently selected from groups represented by Formulae 5-1 to 5-43 below, and $R_1$ to $R_{12}$ in Formula 1 are each independently selected from a hydrogen, a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_1$)($Q_2$)($Q_3$) and groups represented by Formulae 5-1 to 5-43 below, wherein $Q_1$ to $Q_3$ are each independently selected from a $C_1$-$C_{10}$ alkyl group, a $C_1$-$C_{10}$ alkoxy group, a phenyl group, and a naphthyl group:

373
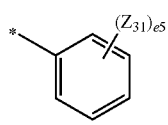
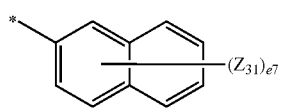
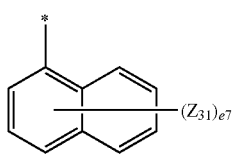
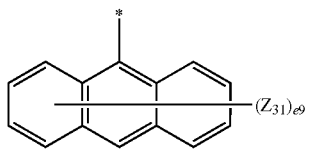
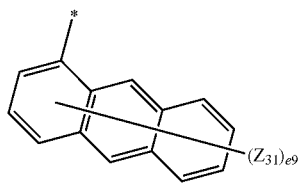
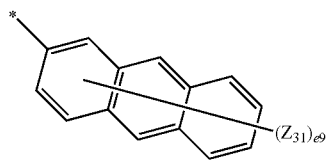
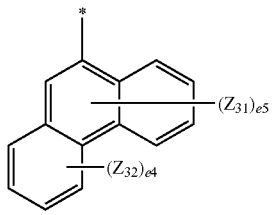
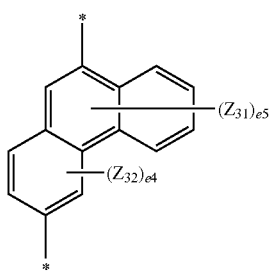
374
-continued
Formula 5-1
Formula 5-2
Formula 5-3
Formula 5-4
Formula 5-5
Formula 5-6
Formula 5-7
Formula 5-8
Formula 5-9
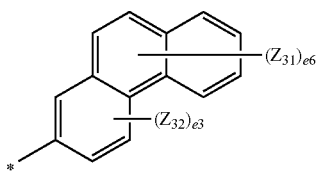
Formula 5-10
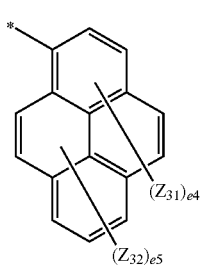
Formula 5-11
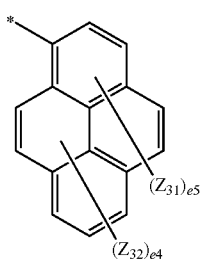
Formula 5-12
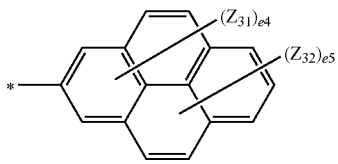
Formula 5-13
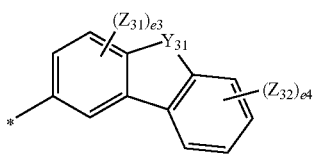
Formula 5-14
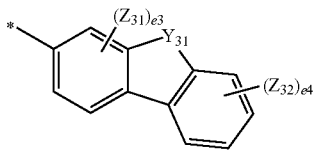
Formula 5-15
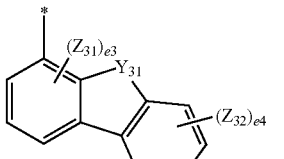
Formula 5-16
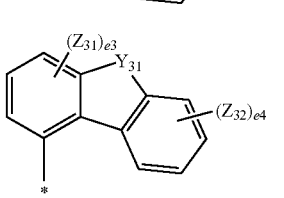

-continued
Formula 5-17
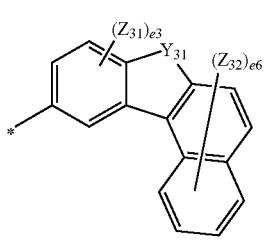
Formula 5-18
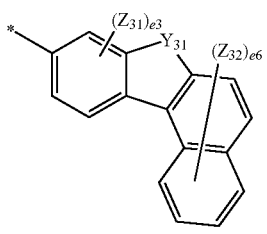
Formula 5-19
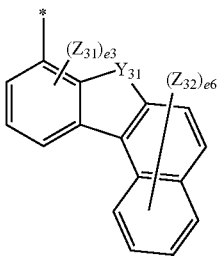
Formula 5-20
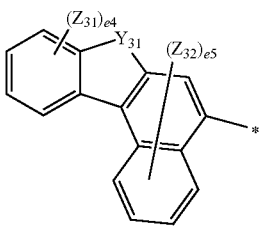
Formula 5-21
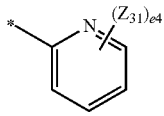
Formula 5-22
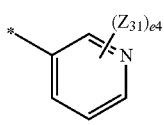
Formula 5-23
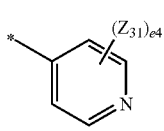
Formula 5-24
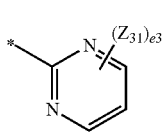
Formula 5-25
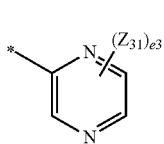
-continued
Formula 5-26
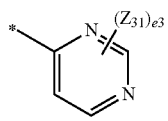
Formula 5-27
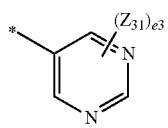
Formula 5-28
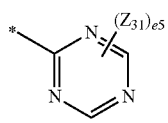
Formula 5-29
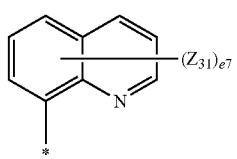
Formula 5-30
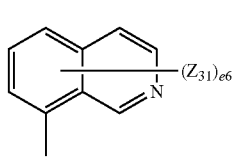
Formula 5-31
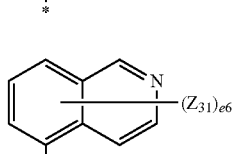
Formula 5-32
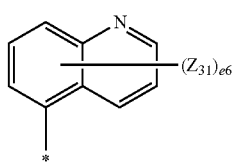
Formula 5-33
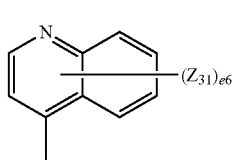
Formula 5-34
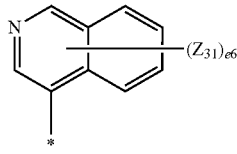
Formula 5-35
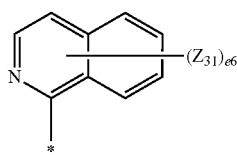

-continued

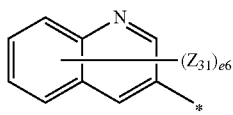 Formula 5-36

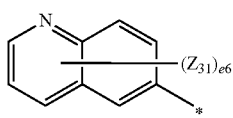 Formula 5-37

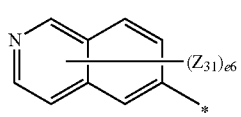 Formula 5-38

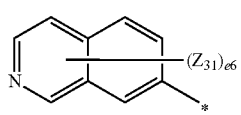 Formula 5-39

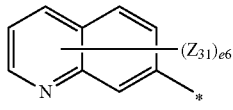 Formula 5-40

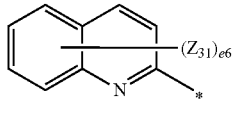 Formula 5-41

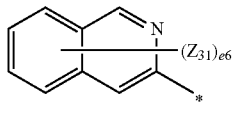 Formula 5-42

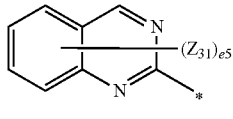 Formula 5-43 wherein in Formulae 5-1 to 5-43, $Y_{31}$ is O, S, C($Z_{33}$)($Z_{34}$), N($Z_{35}$), or Si($Z_{36}$)($Z_{37}$);

$Z_{31}$ to $Z_{37}$ are each independently selected from a hydrogen, a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, e3 is selected from integers of 1 to 3, e4 is selected from integers of 1 to 4, e5 is selected from integers of 1 to 5, e6 is selected from integers of 1 to 6, e7 is selected from integers of 1 to 7, e8 is selected from integers of 1 to 8, and e9 is selected from integers of 1 to 9, and * indicates a binding site to a neighboring atom.

12. The condensed cyclic compound of claim 1, wherein $Ar_1$ and $Ar_2$ in Formula 2 are each independently selected from groups represented by Formulae 6-1 to Formula 6-41 below, and $R_1$ to $R_{12}$ in Formula 1 are each independently selected from a hydrogen, a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_1$)($Q_2$)($Q_3$), a phenyl group, a naphthyl group, a pyridinyl group, a pyrimidinyl group, and a triazinyl group, wherein $Q_1$ to $Q_3$ are each independently selected from a $C_1$-$C_{10}$ alkyl group, a $C_1$-$C_{10}$ alkoxy group, a phenyl group, and a naphthyl group:

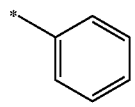 Formula 6-1

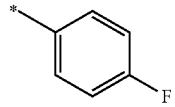 Formula 6-2

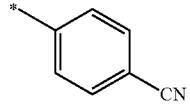 Formula 6-3

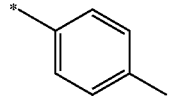 Formula 6-4

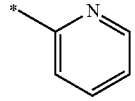 Formula 6-5

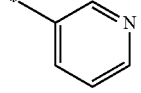 Formula 6-6

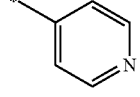 Formula 6-7

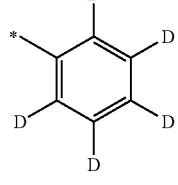 Formula 6-8

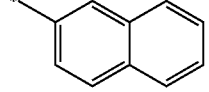 Formula 6-9

-continued
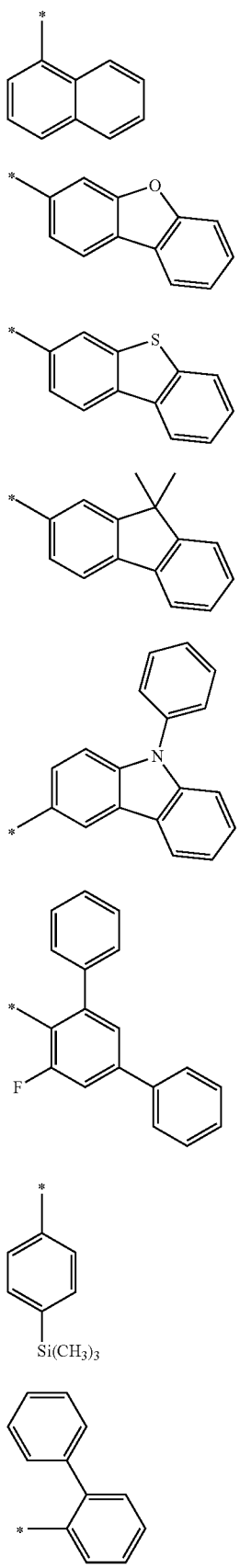
Formula 6-10
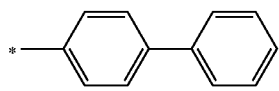
Formula 6-11
Formula 6-12
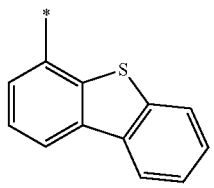
Formula 6-13
Formula 6-14

Formula 6-15
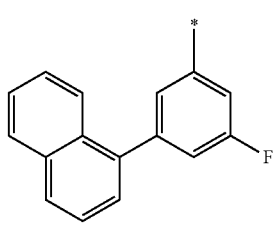
Formula 6-16
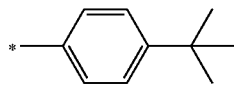
Formula 6-17
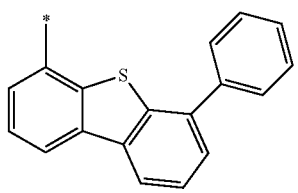
Formula 6-18
Formula 6-19
Formula 6-20
Formula 6-21
Formula 6-22
Formula 6-23
Formula 6-24
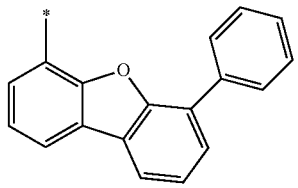
Formula 6-25
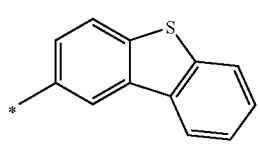
Formula 6-26

Formula 6-27
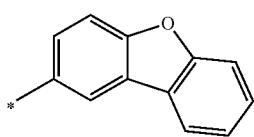
Formula 6-28
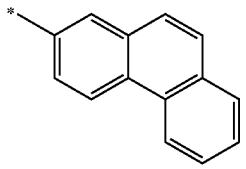
Formula 6-29
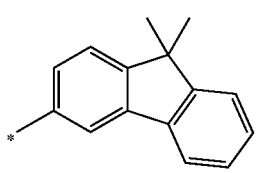
Formula 6-30
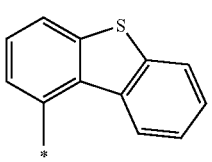
Formula 6-31
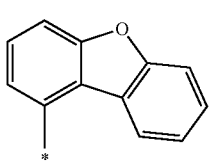
Formula 6-32
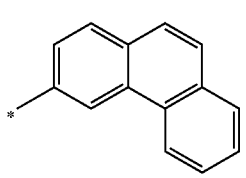
Formula 6-33
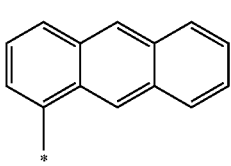
Formula 6-34
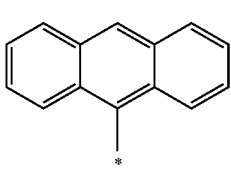
Formula 6-35
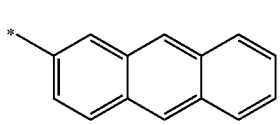
Formula 6-36
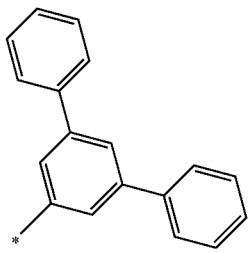
Formula 6-37
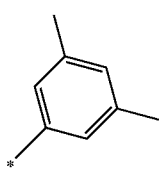
Formula 6-38
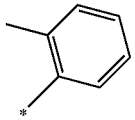
Formula 6-39
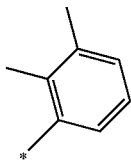
Formula 6-40
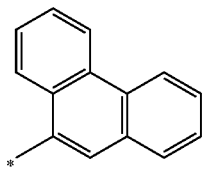
Formula 6-41
wherein in Formula 6-1 to 6-41, * indicates a binding site to a neighboring atom.
13. The condensed cyclic compound of claim 1, wherein the condensed cyclic compound is represented by one of Formulae 1-1(1) to 1-1(4) below:

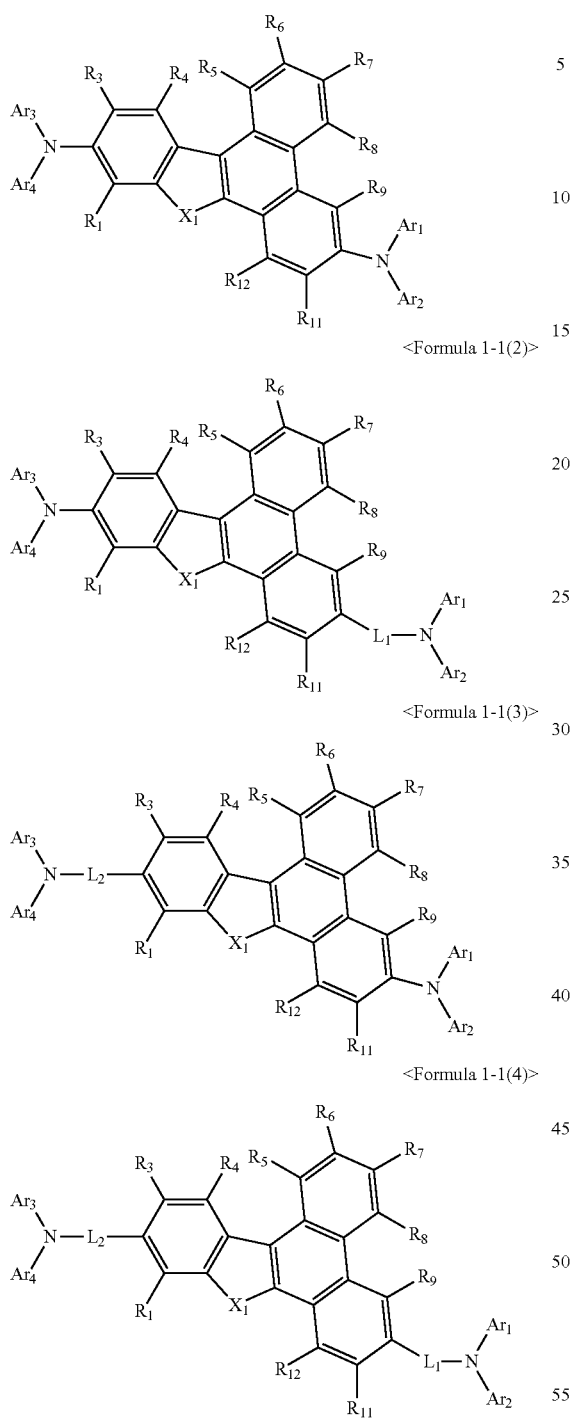

<Formula 1-1(1)>

<Formula 1-1(2)>

<Formula 1-1(3)>

<Formula 1-1(4)> wherein in Formulae 1-1(1) to 1-1(4), $X_1$, $L_1$, a1, $Ar_1$, $Ar_2$, $R_1$, $R_3$, $R_5$ to $R_7$, and $R_9$ to $R_{12}$ are defined the same as those in claim 1, and $L_2$, $a_2$, $Ar_3$, and $Ar_4$ are each the same as defined with respect to $L_1$, a1, $Ar_1$, and $Ar_2$.

14. The condensed cyclic compound of claim 1, wherein $R_1$ to $R_4$ and $R_6$ to $R_{12}$ in Formulae 1-1 to 1-4 are a hydrogen, $R_5$ in Formulae 1-1 to 1-4 is selected from a hydrogen, a deuterium, —F, —Cl, —Br, —I, a hydroxyl group, a cyano group, a nitro group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group, $L_1$ and $L_2$ in Formulae 1-1 to 1-4 are each independently selected from groups represented by Formulae 4-1 to 4-28 below, a1 and a2 in Formulae 1-1 to 1-4 are each independently 0 or 1, and $Ar_1$ to $Ar_4$ in Formulae 1-1 to 1-4 are each independently selected from groups represented by Formulae 6-1 to 6-41 below:

Formula 4-1

Formula 4-2

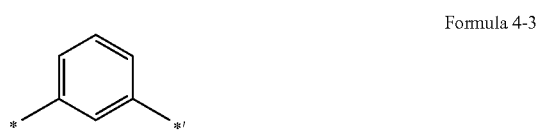

Formula 4-3

Formula 4-4


Formula 4-5

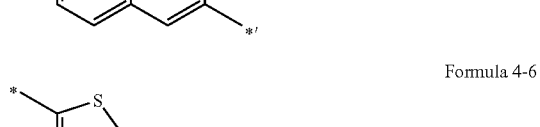

Formula 4-6

Formula 4-7

Formula 4-8

-continued
Formula 4-9
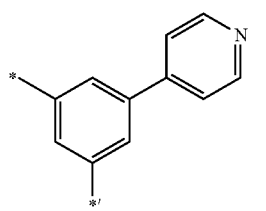
Formula 4-10
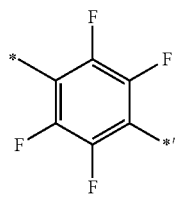
Formula 4-11
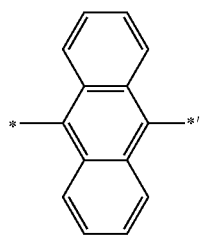
Formula 4-12
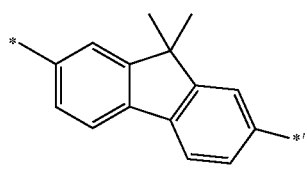
Formula 4-13
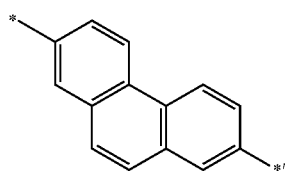
Formula 4-14
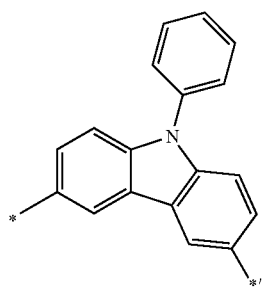
Formula 4-15
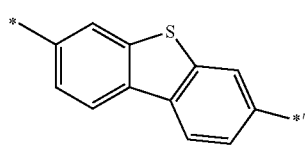
Formula 4-16
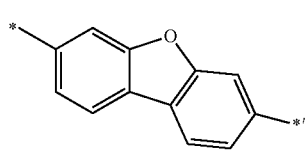
-continued
Formula 4-17
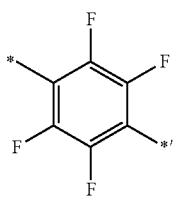
Formula 4-18
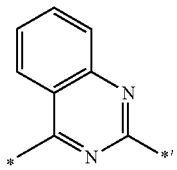
Formula 4-19
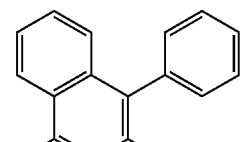
Formula 4-20
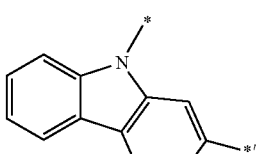
Formula 4-21
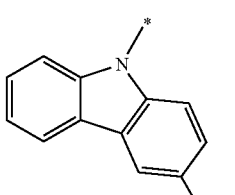
Formula 4-22
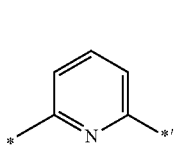
Formula 4-23
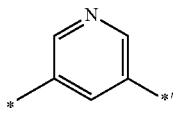
Formula 4-24
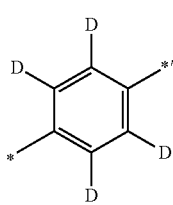

-continued
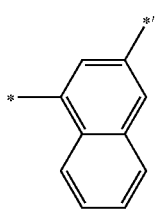
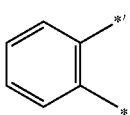
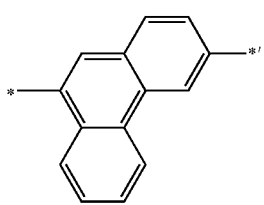
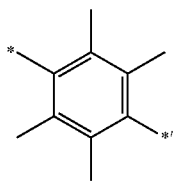
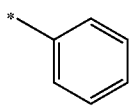
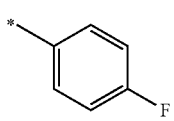
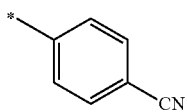
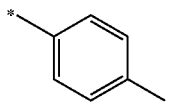
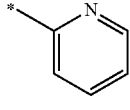
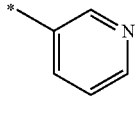
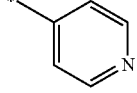
-continued
Formula 4-25
Formula 4-26
Formula 4-27
Formula 4-28
Formula 6-1
Formula 6-2
Formula 6-3
Formula 6-4
Formula 6-5
Formula 6-6
Formula 6-7
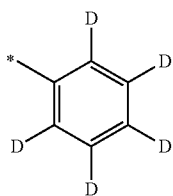
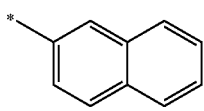
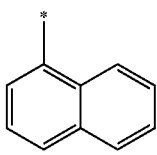
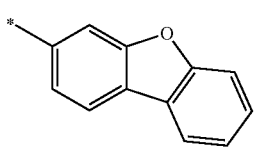
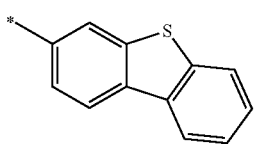
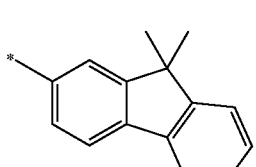
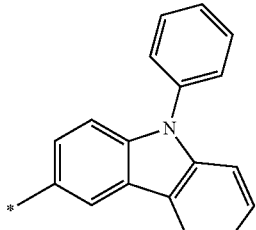
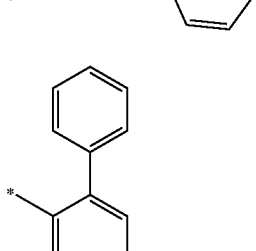
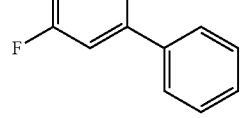
Formula 6-8
Formula 6-9
Formula 6-10
Formula 6-11
Formula 6-12
Formula 6-13
Formula 6-14
Formula 6-15

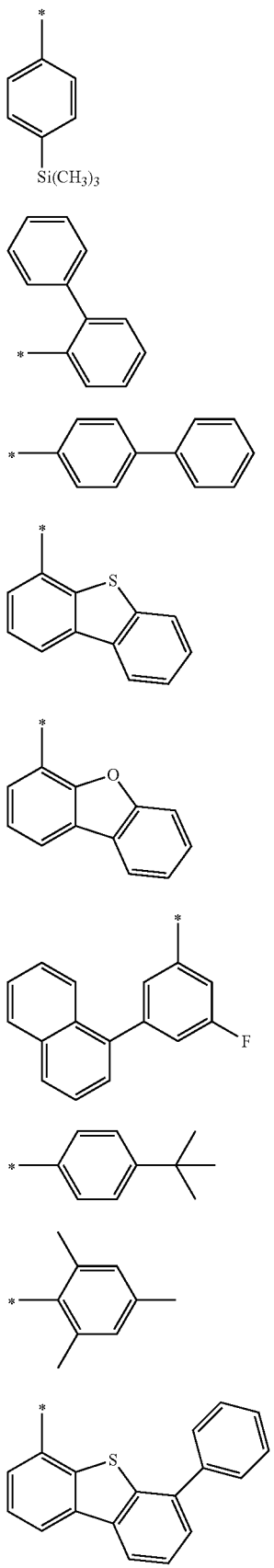
Formula 6-16
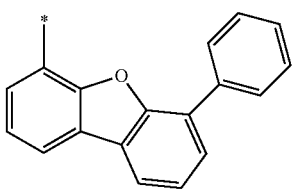
Formula 6-25
Formula 6-17
Formula 6-26
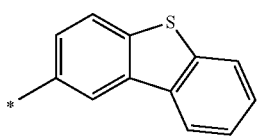
Formula 6-18
Formula 6-27
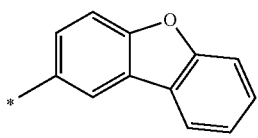
Formula 6-19
Formula 6-28
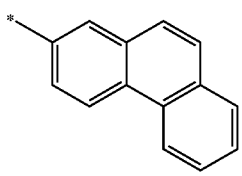
Formula 6-20
Formula 6-29
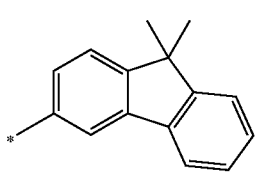
Formula 6-21
Formula 6-30
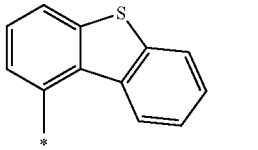
Formula 6-22
Formula 6-31
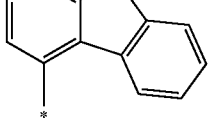
Formula 6-23
Formula 6-32
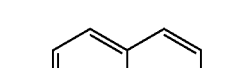
Formula 6-24
Formula 6-33
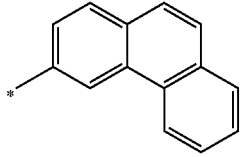
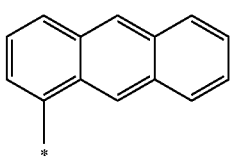

-continued
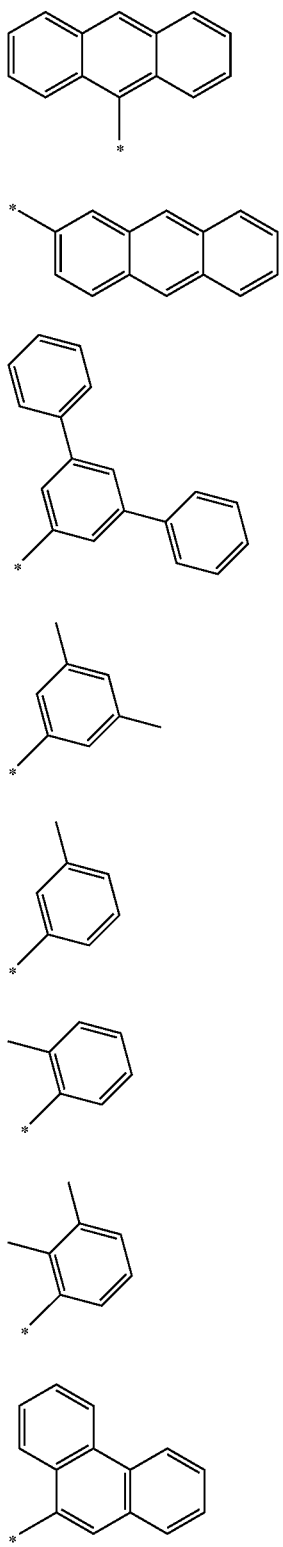
15. The condensed cyclic compound of claim 1, wherein the condensed cyclic compound is one of Compounds 1 to 248 and 1A to 249A below:
Formula 6-34
Formula 6-35
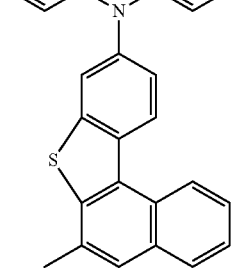
Formula 6-36
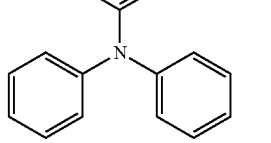
Formula 6-37
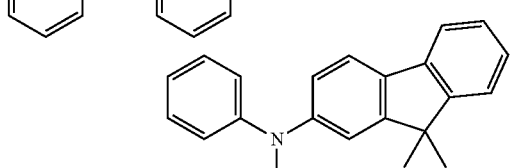
Formula 6-38
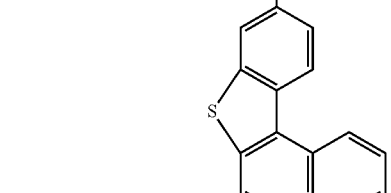
Formula 6-39
Formula 6-40
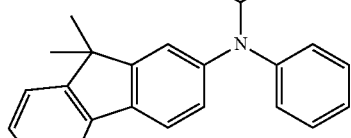
Formula 6-41
1
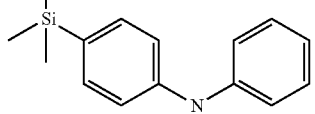
2
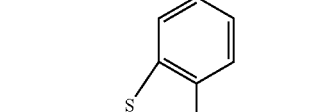
3
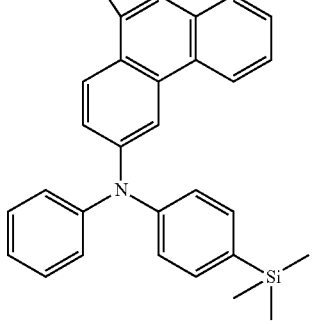

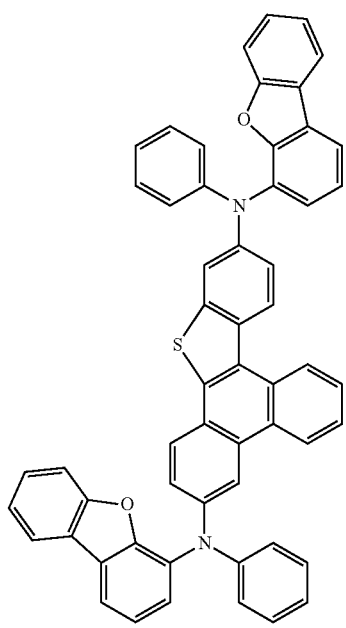
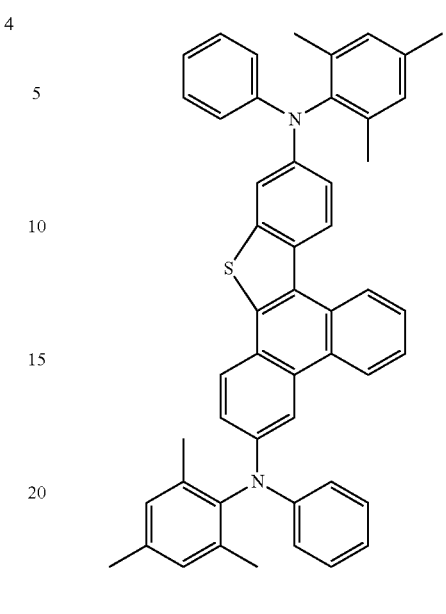
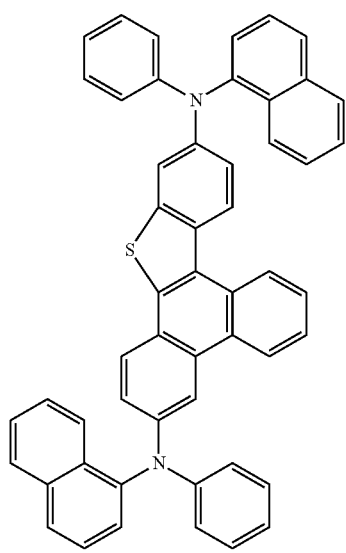
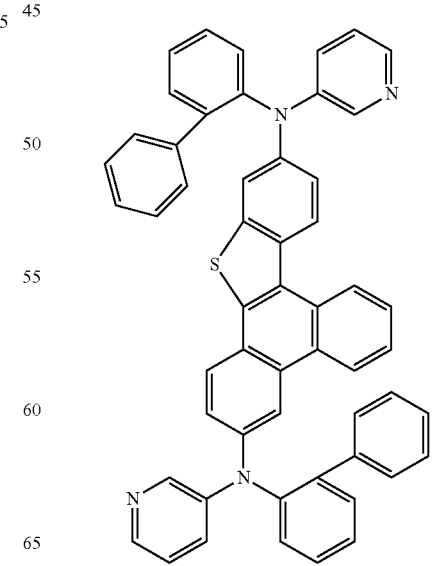

395
-continued
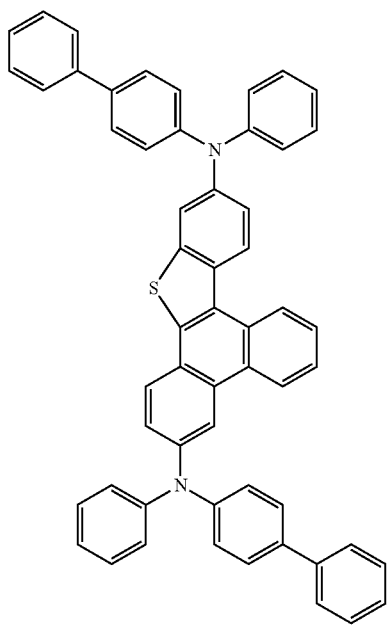
8
396
-continued
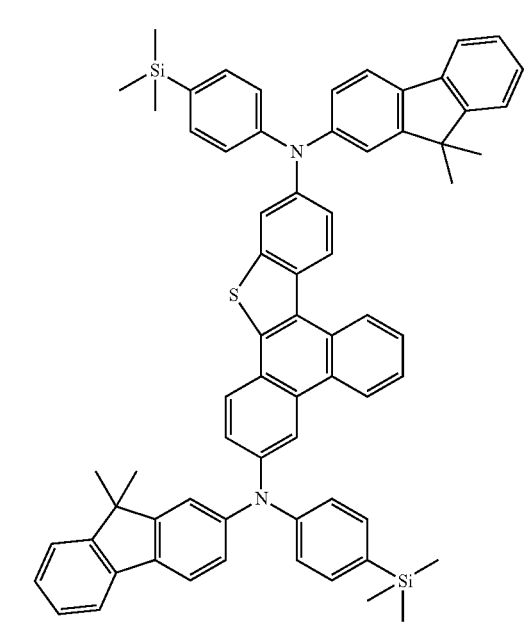
10
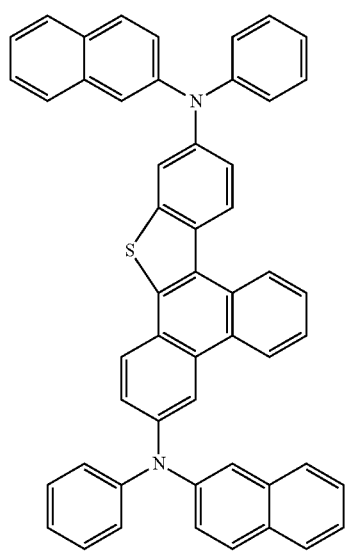
9
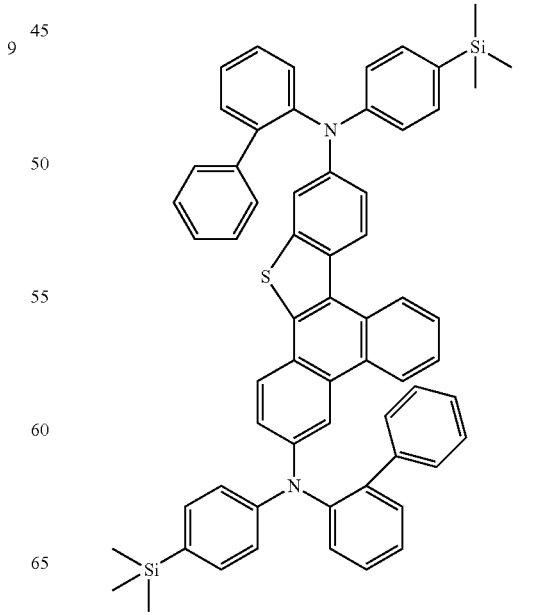
11

397
-continued
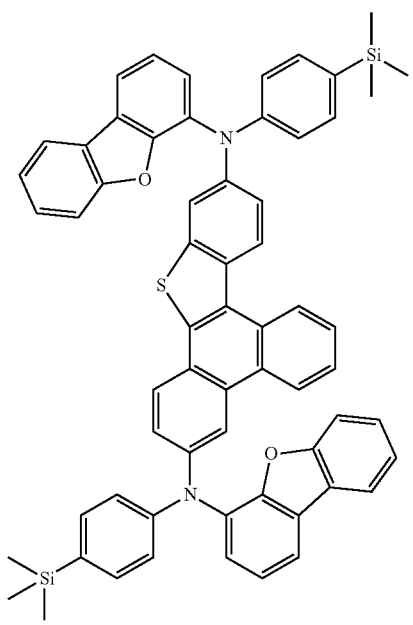
398
-continued
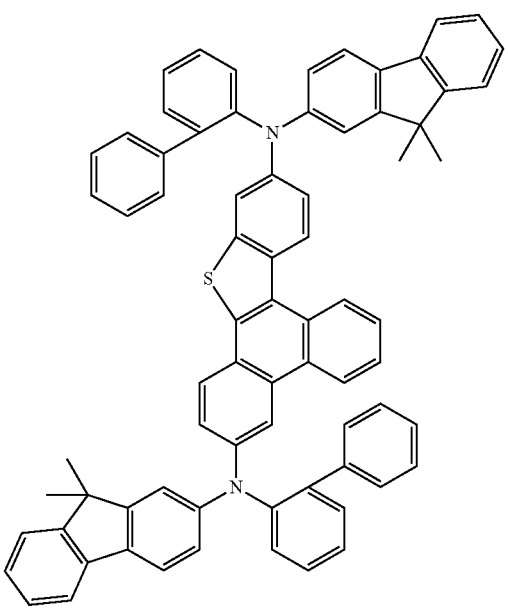
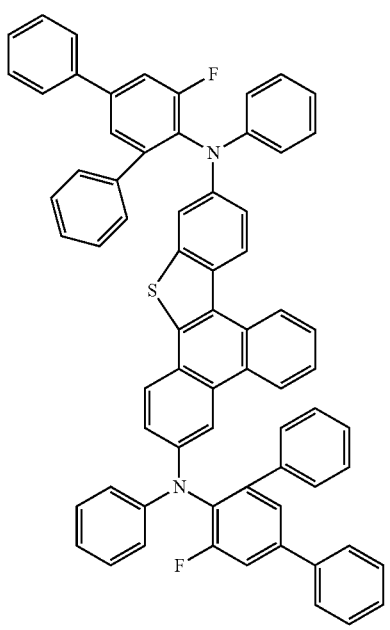
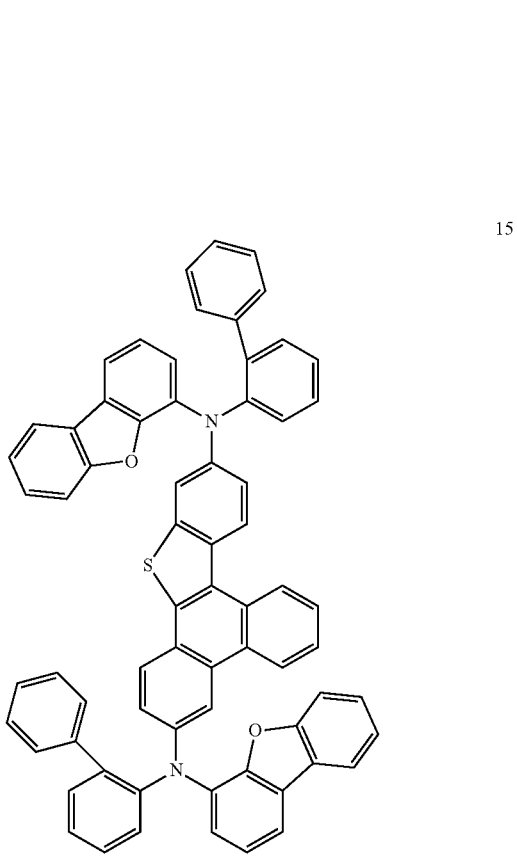

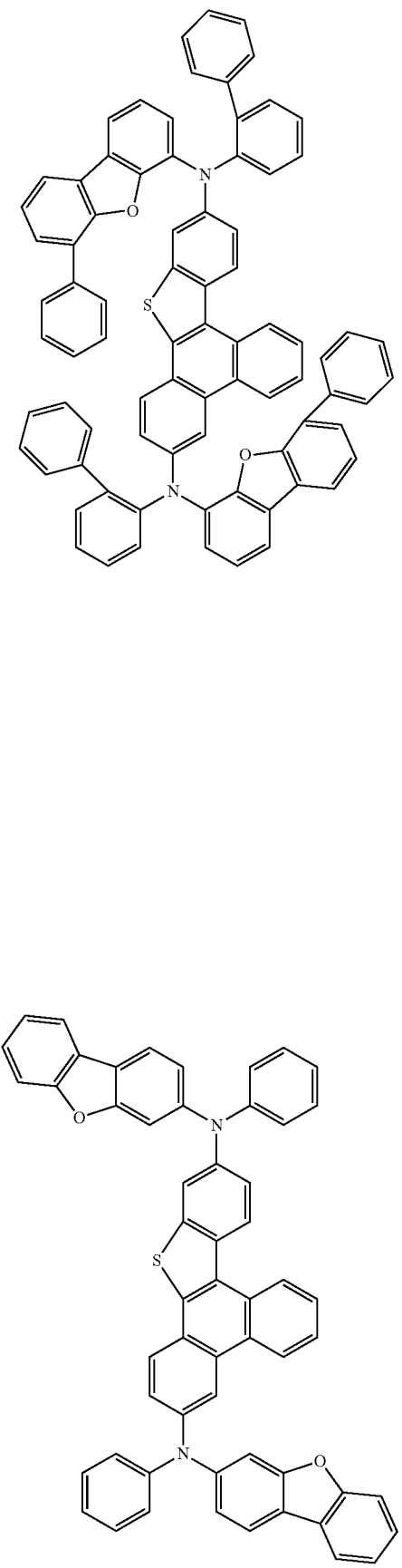
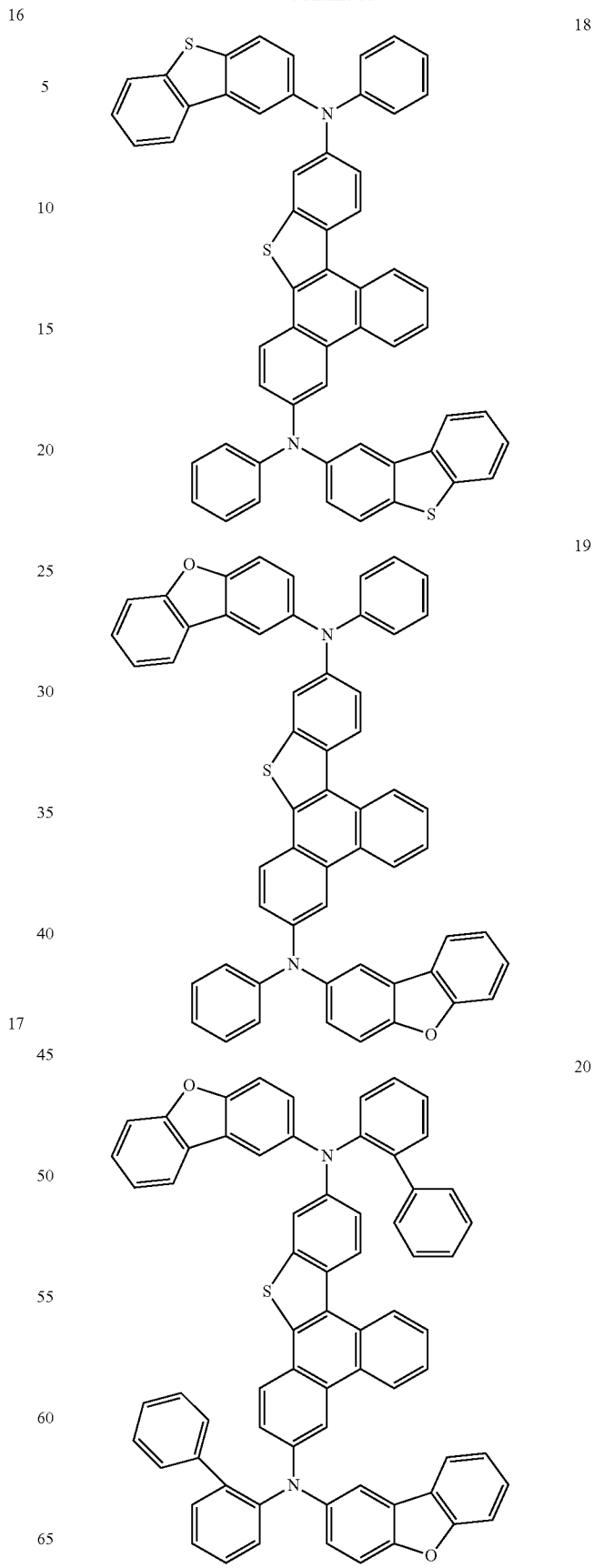

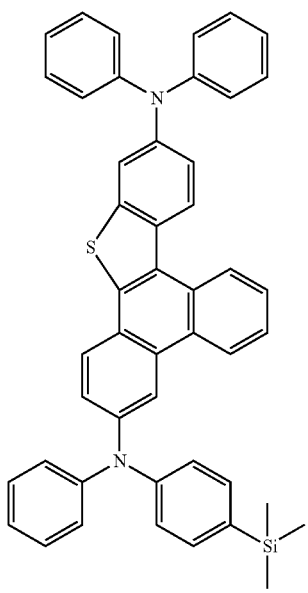
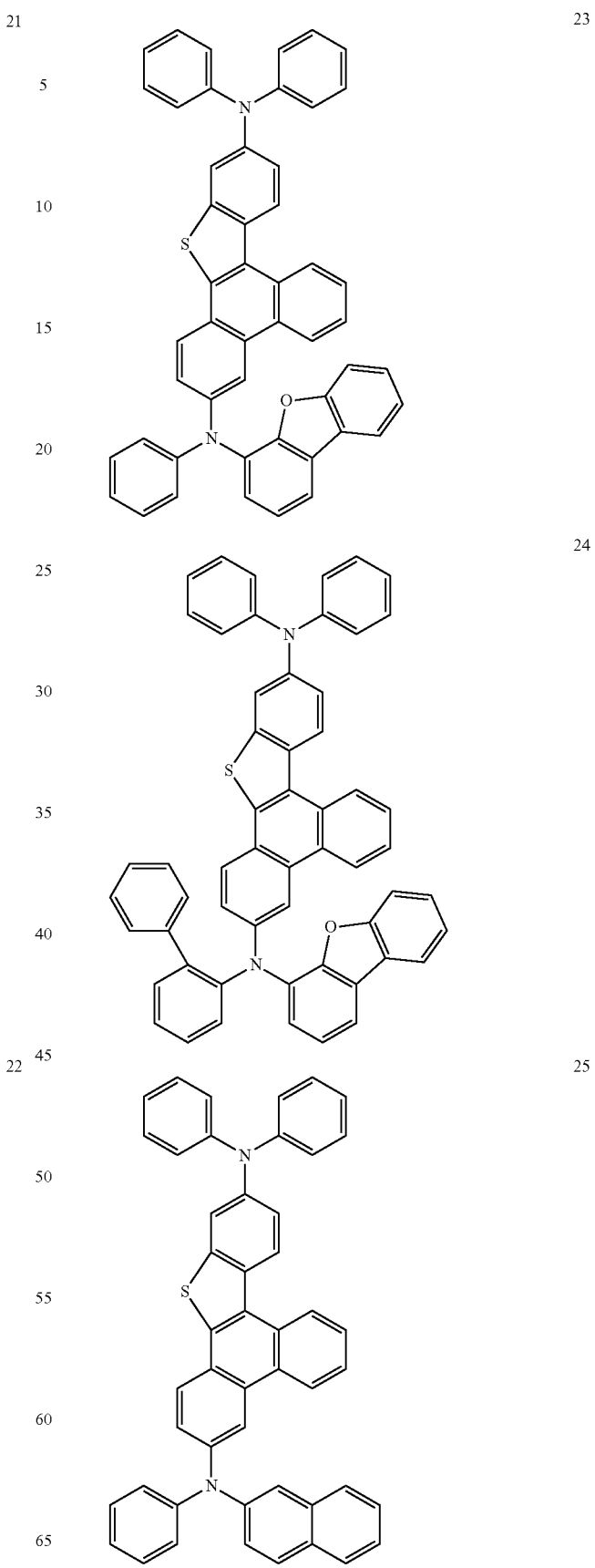

403
-continued
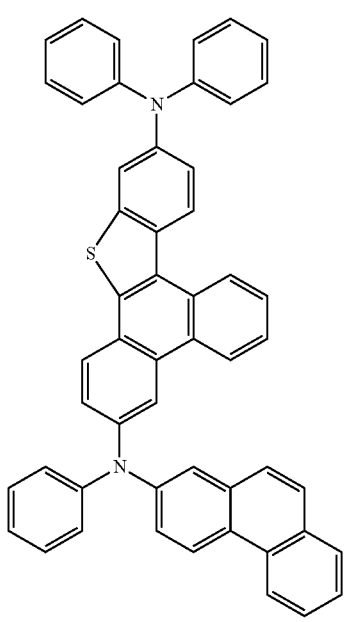
26
404
-continued
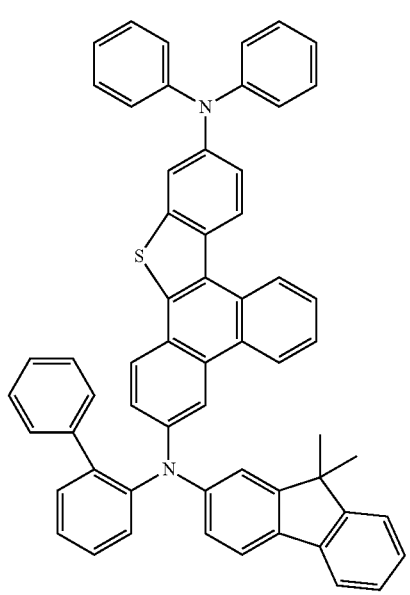
28
27
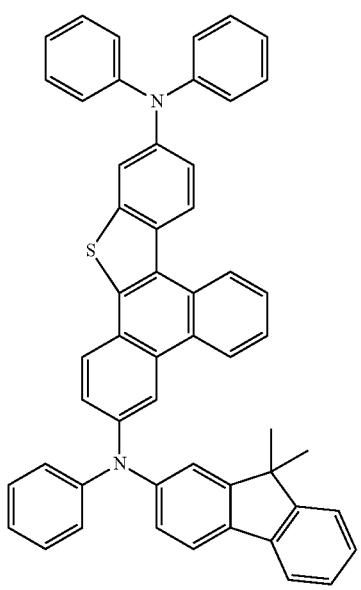
29
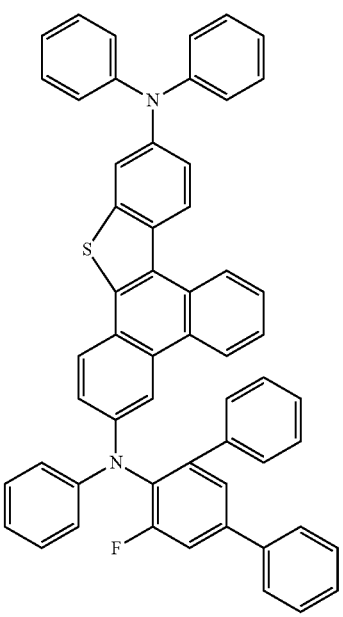

405
-continued
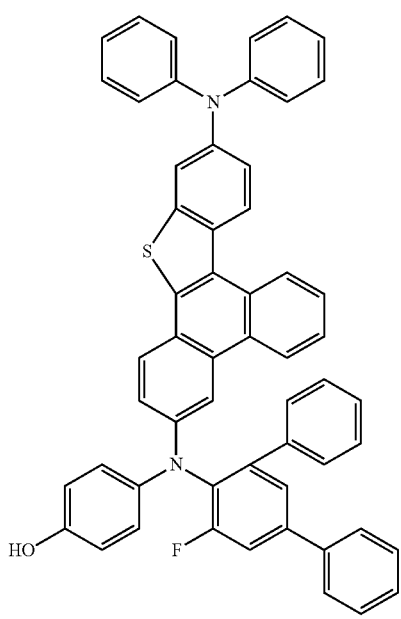
30
406
-continued
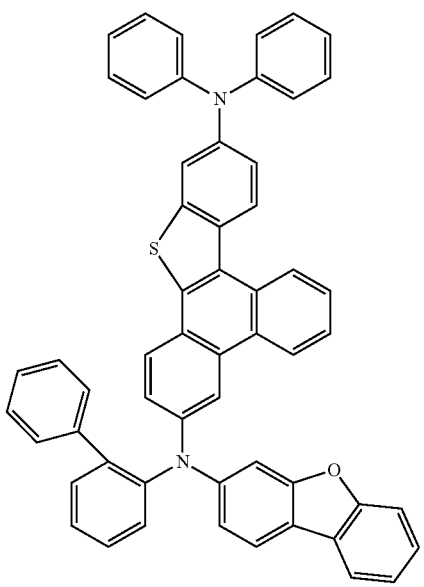
31
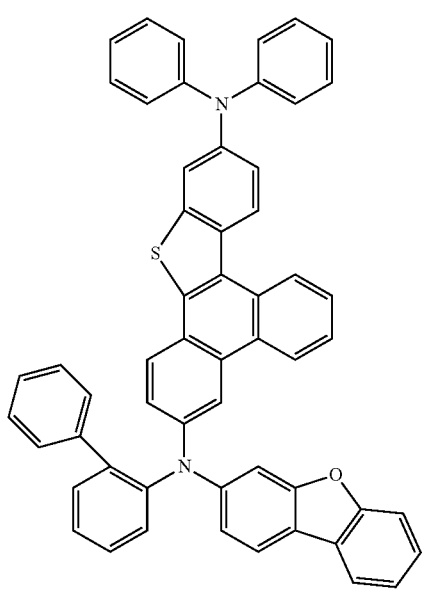
32
33
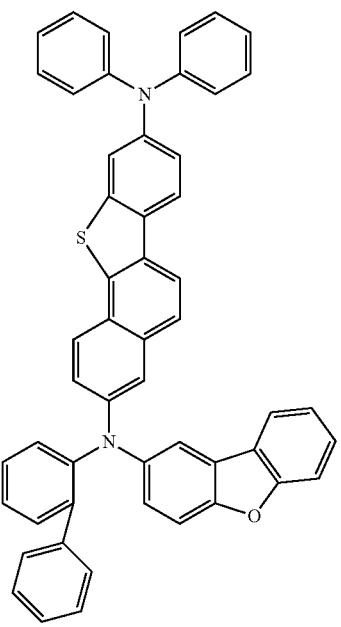

407
-continued
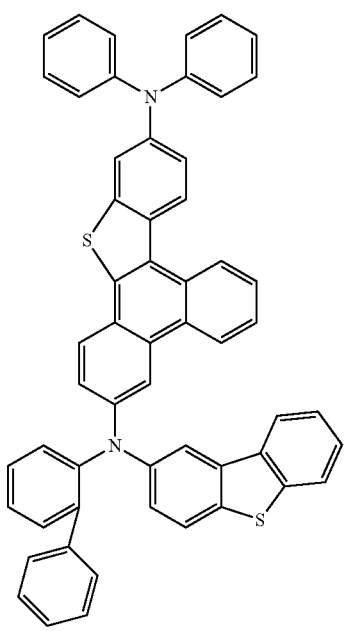
34
408
-continued
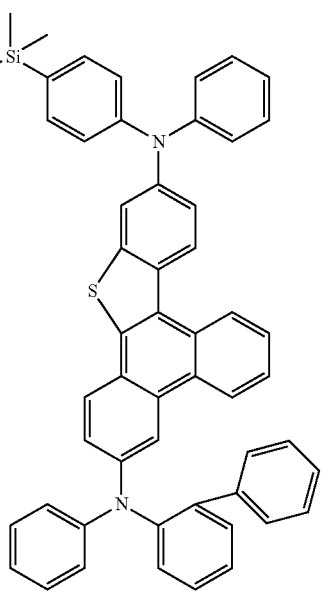
36
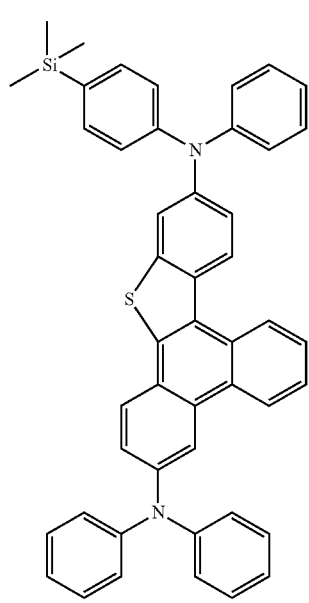
35
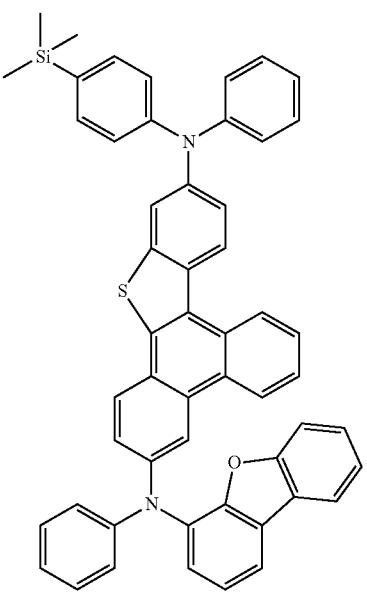
37

409
-continued
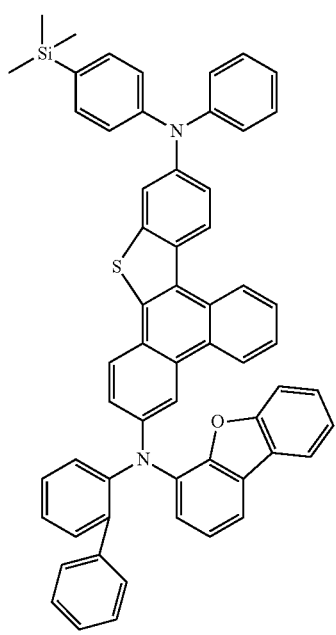
38
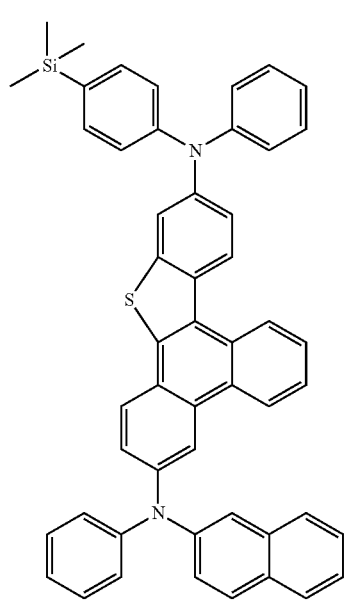
39
410
-continued
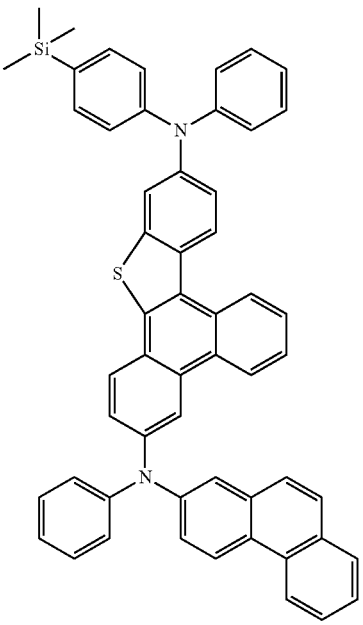
40
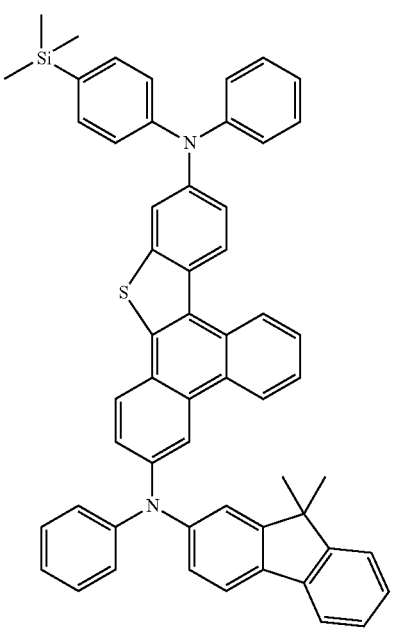
41

411
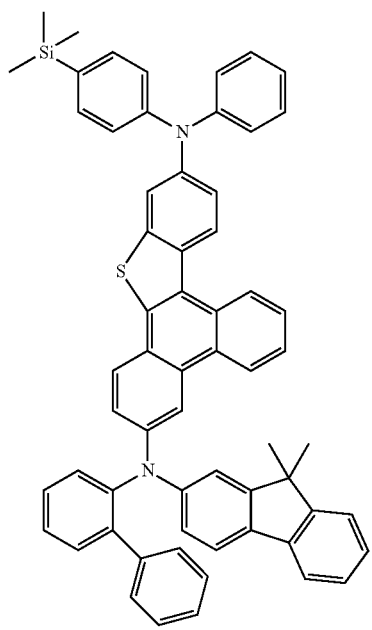
412
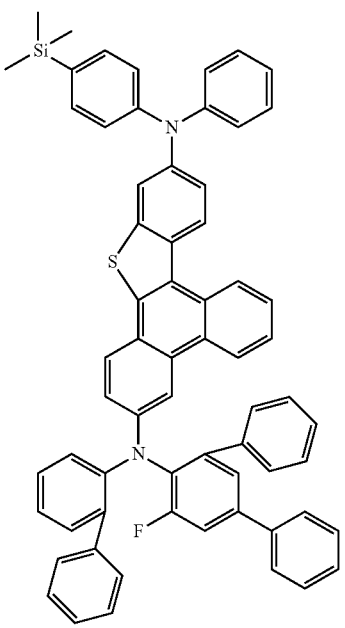
43
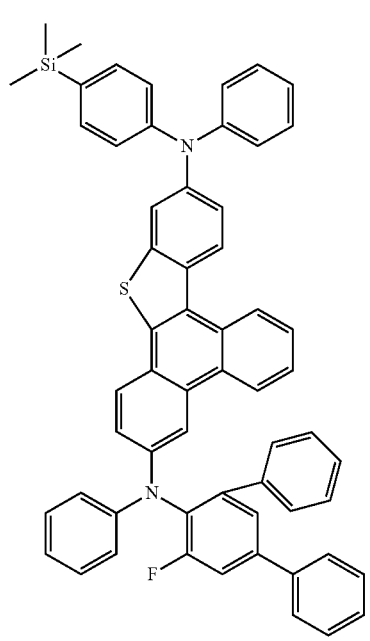
45
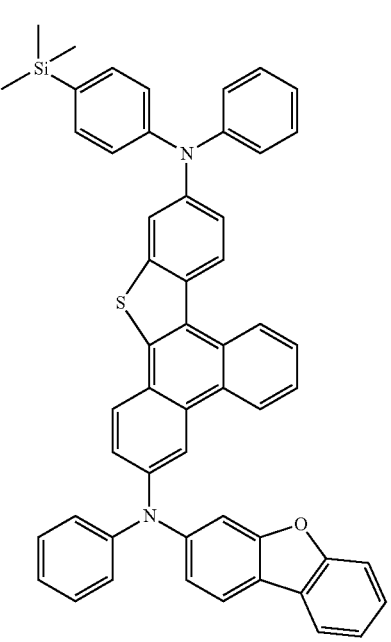

413
-continued
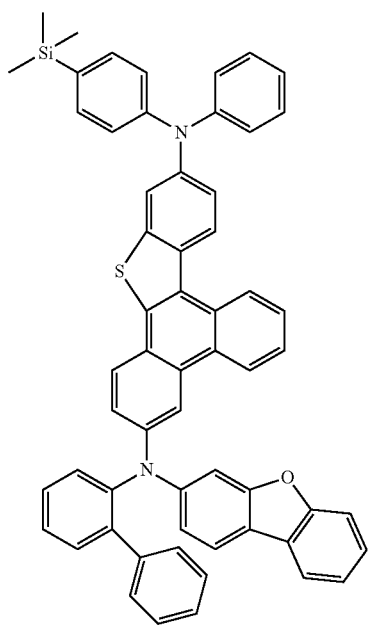
46
414
-continued
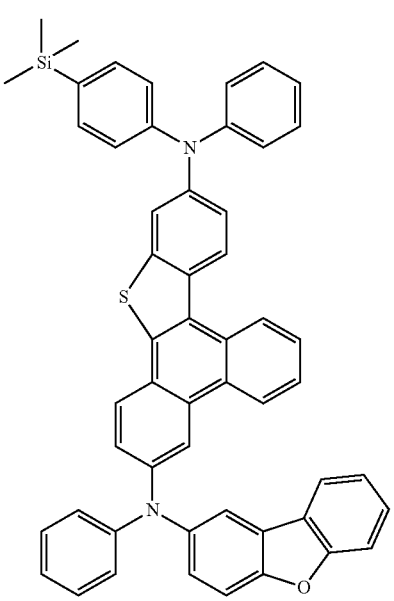
48
47
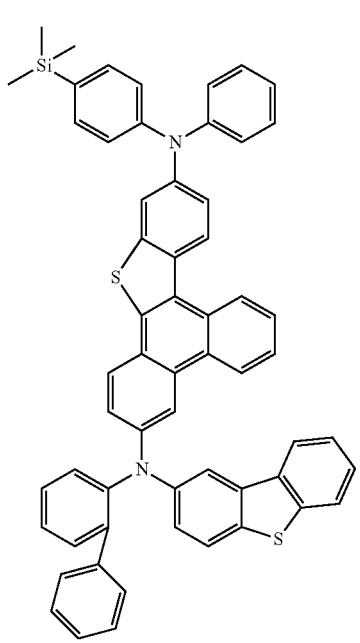
49
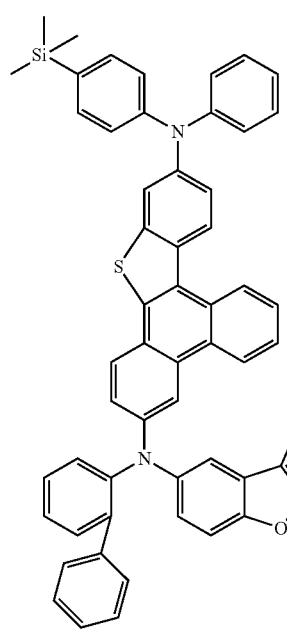

415
-continued
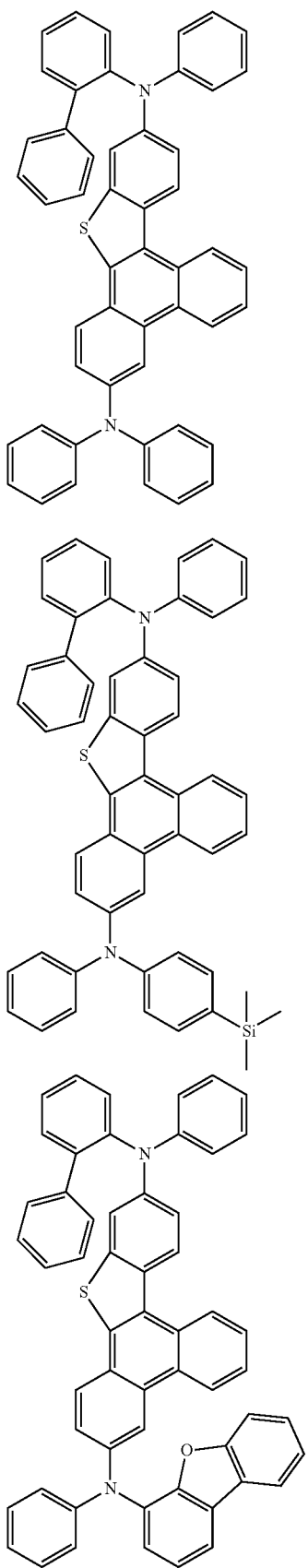
416
-continued
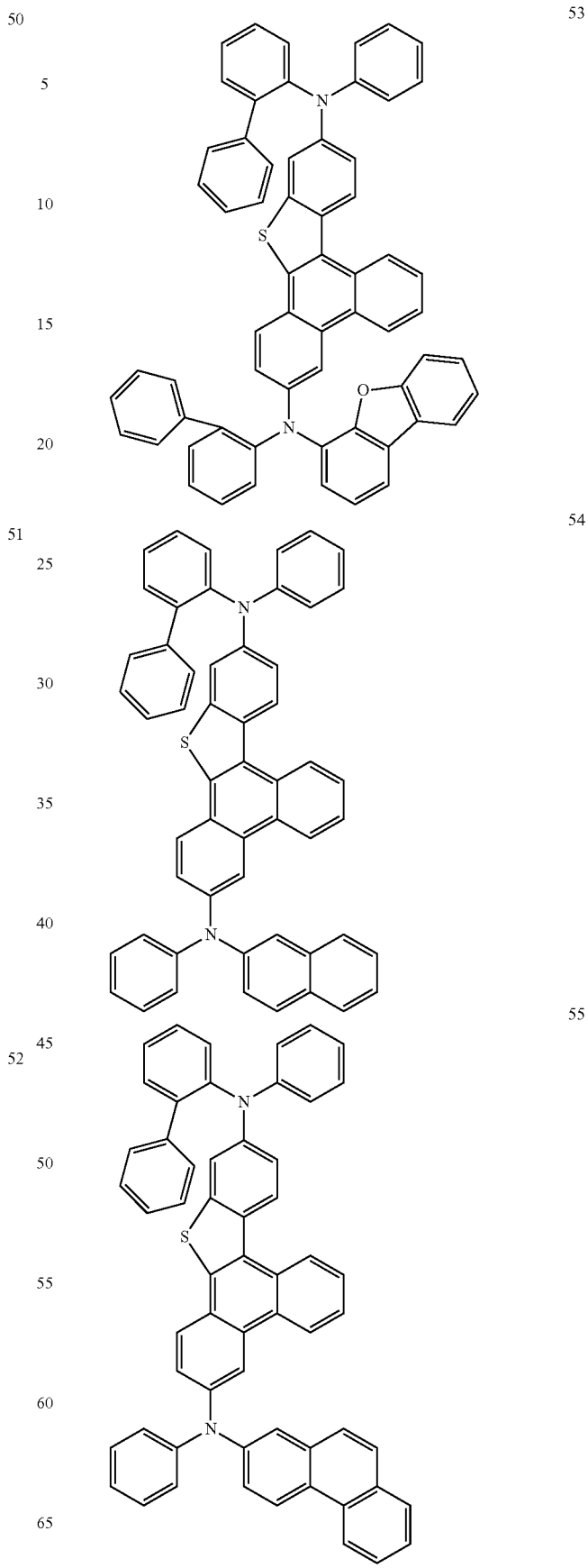

417
-continued
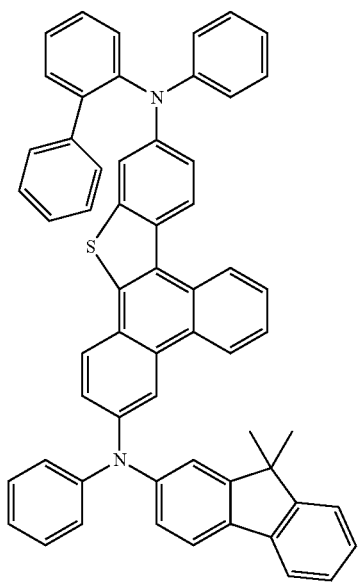
418
-continued
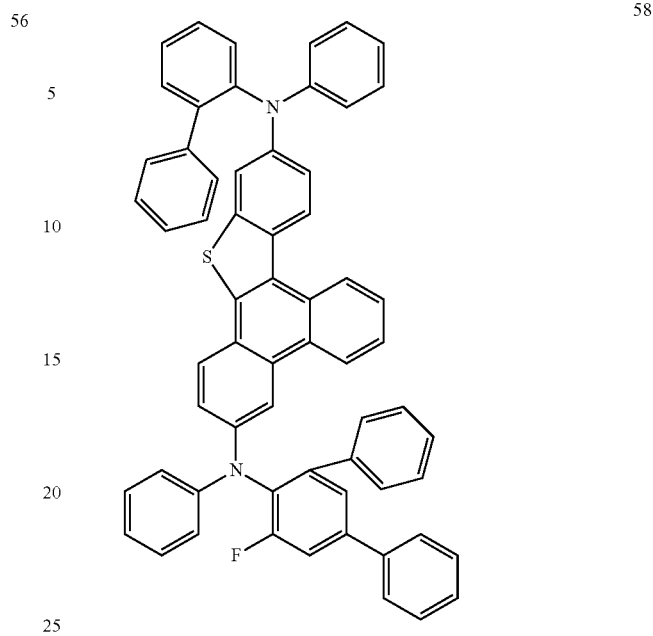
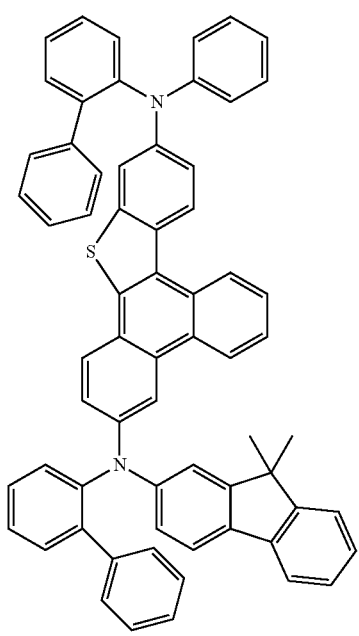
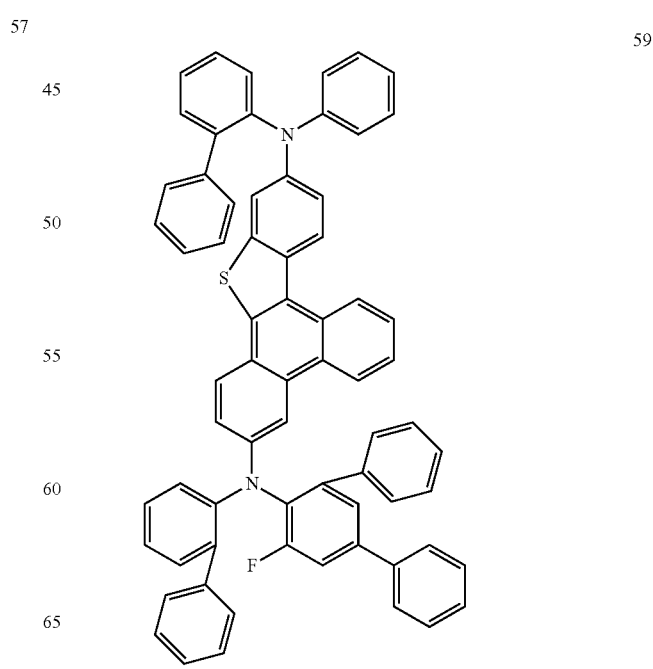

419
-continued
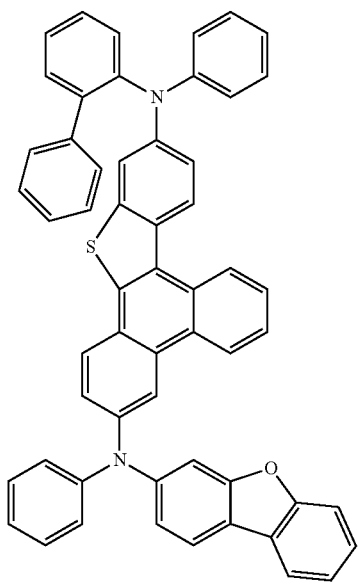
420
-continued
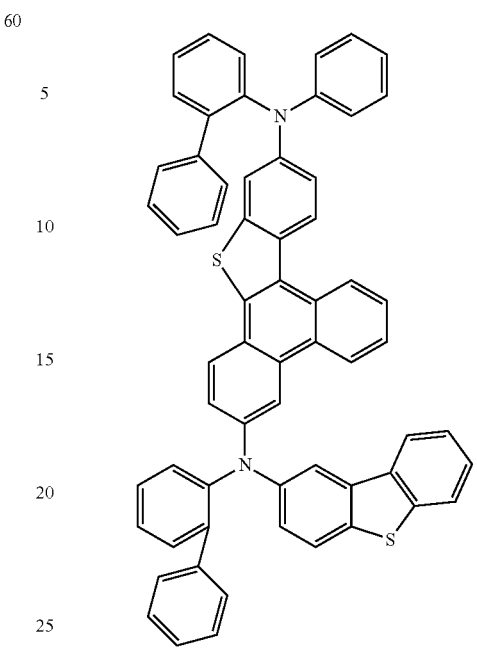
61
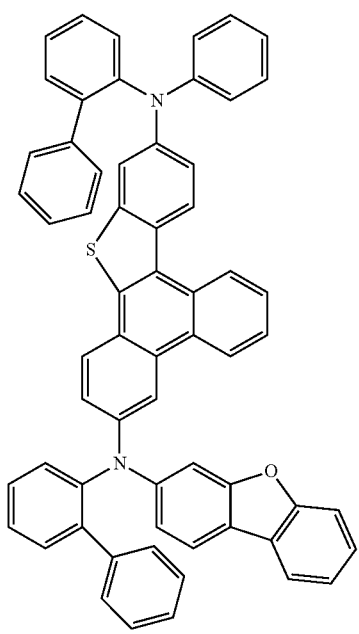
62
63
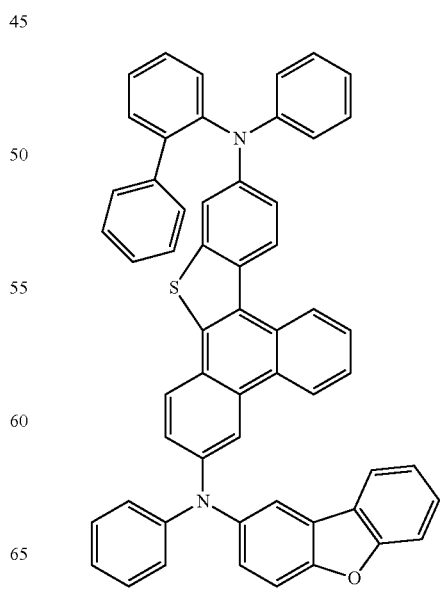

421
-continued
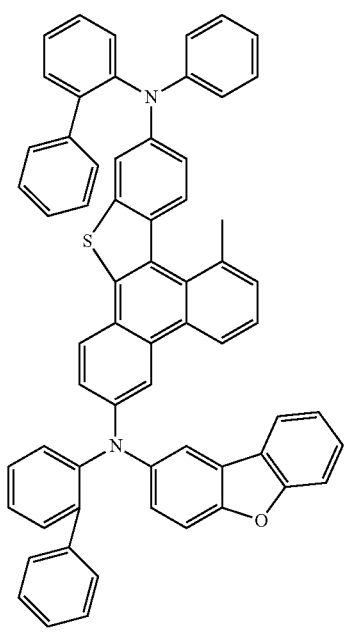
422
-continued
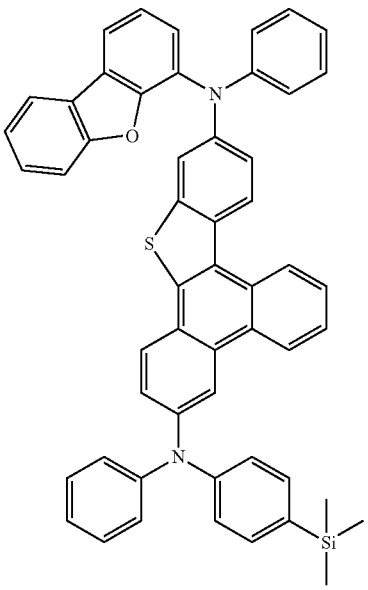
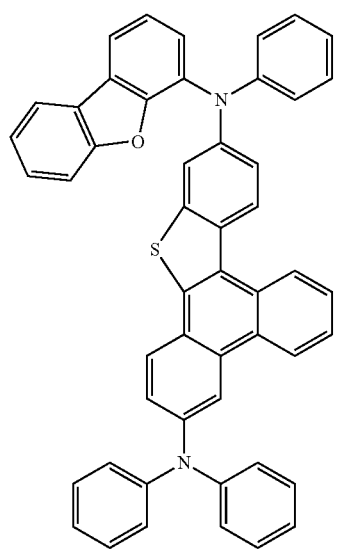
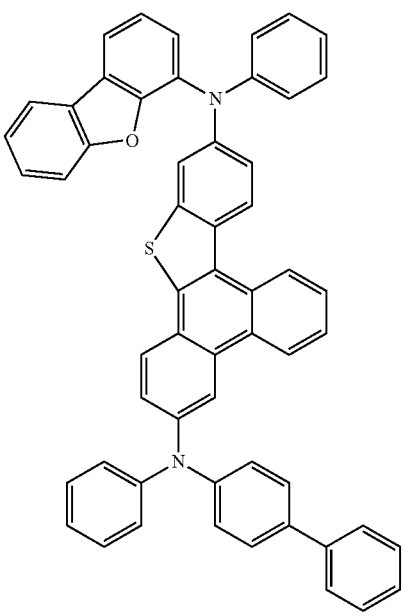

423
-continued
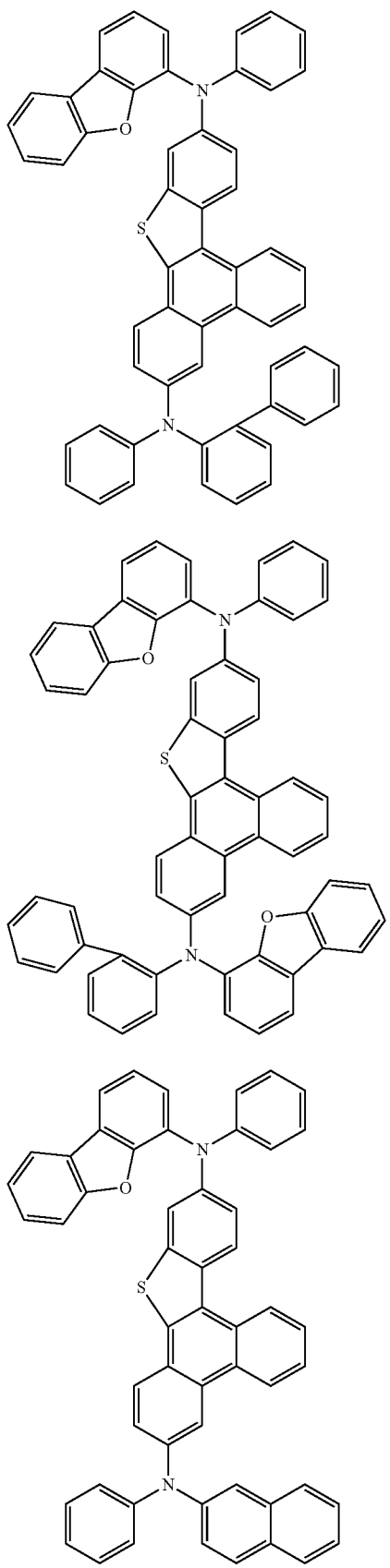
424
-continued
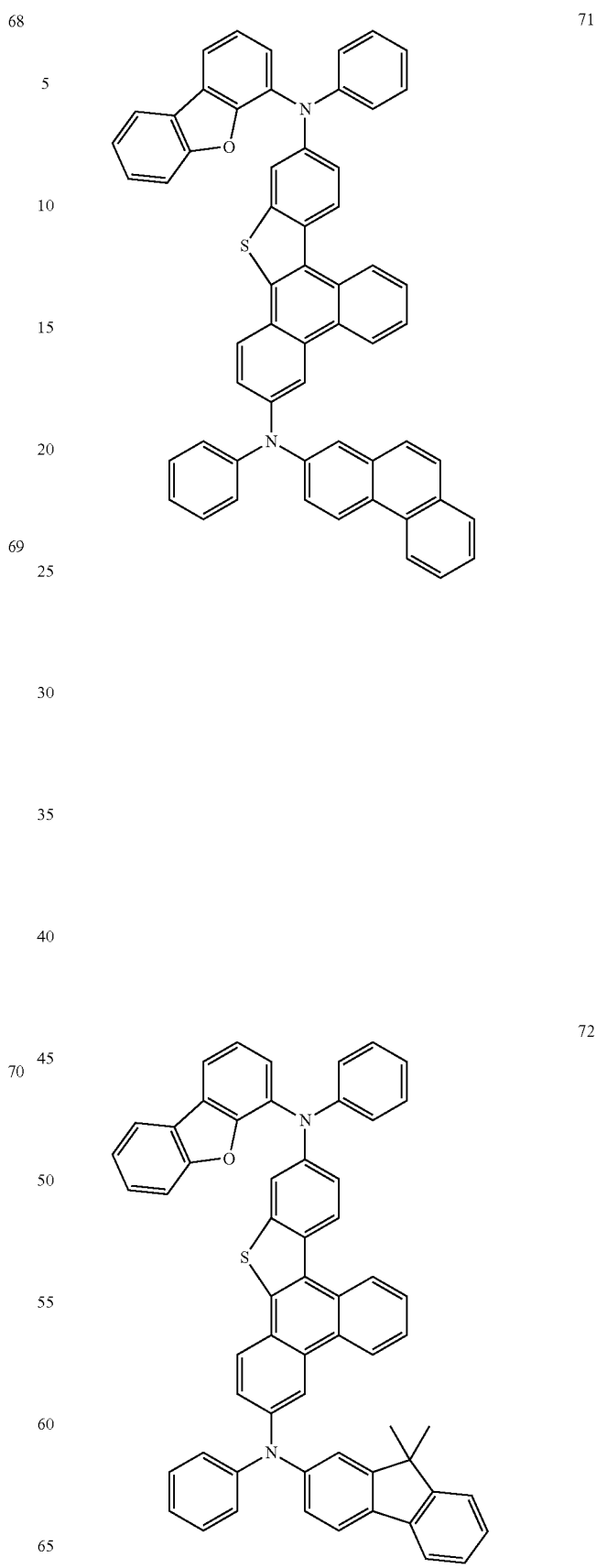

425
-continued
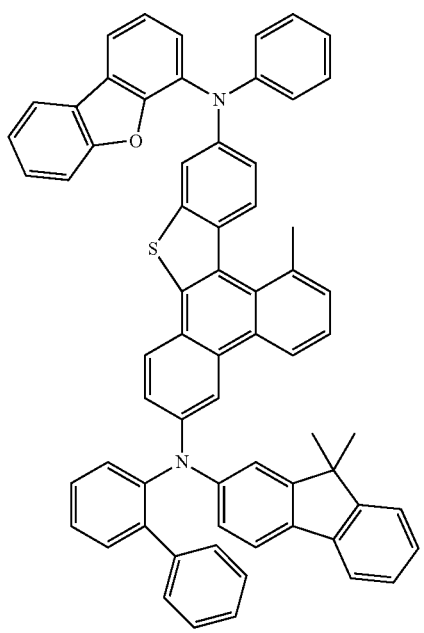
426
-continued
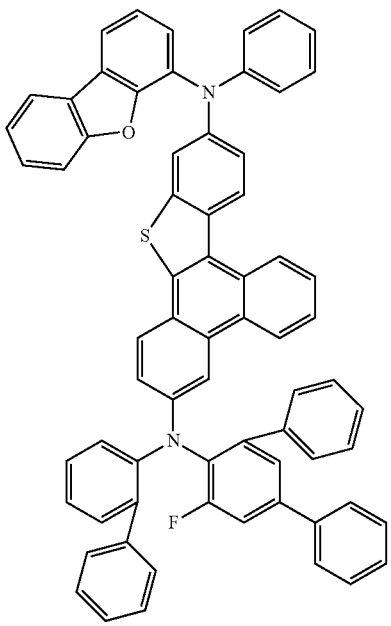
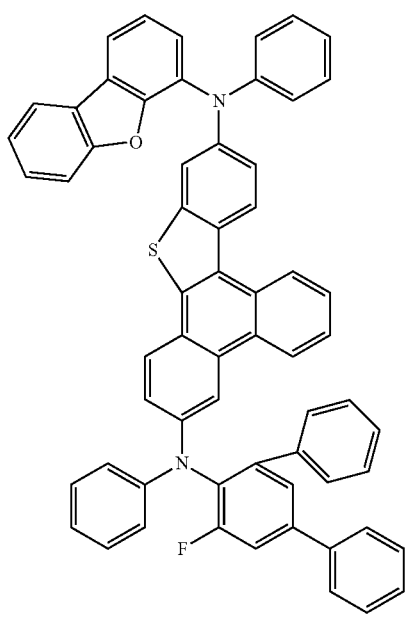
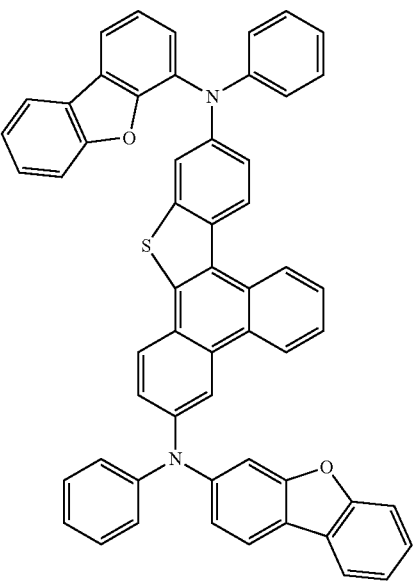

427
-continued
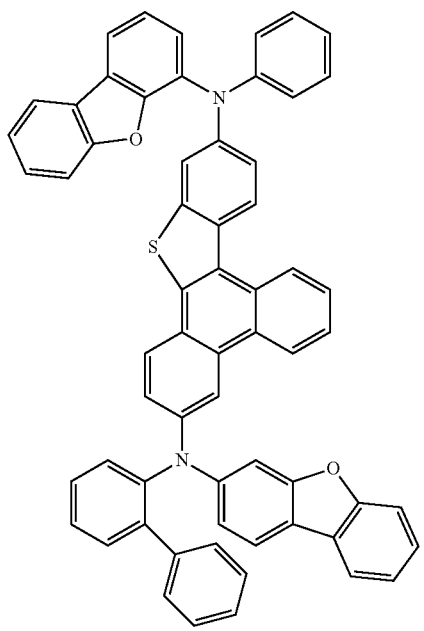
77
428
-continued
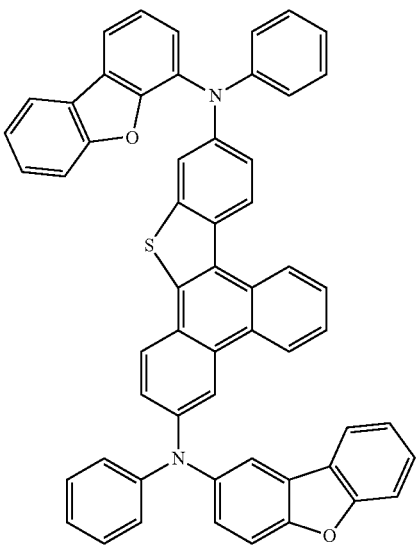
79
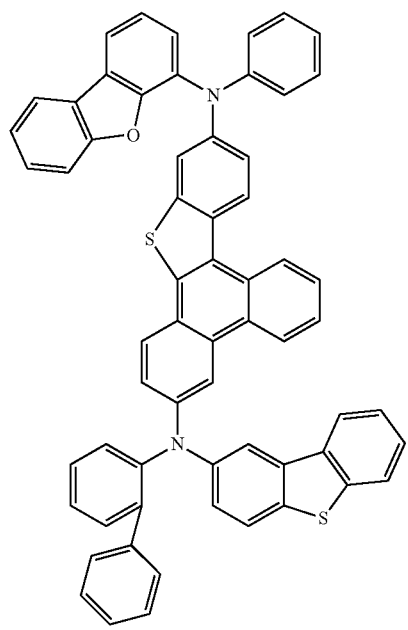
78
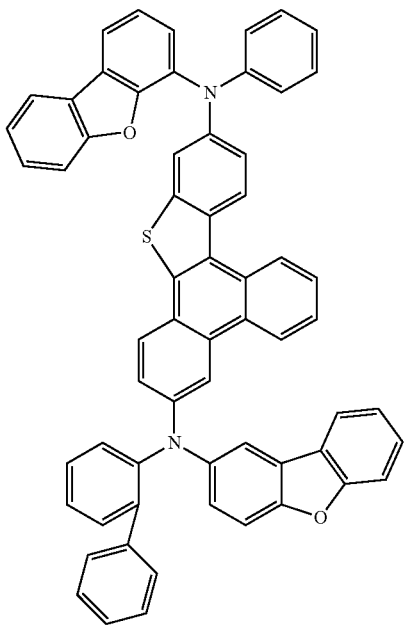
80

429
-continued
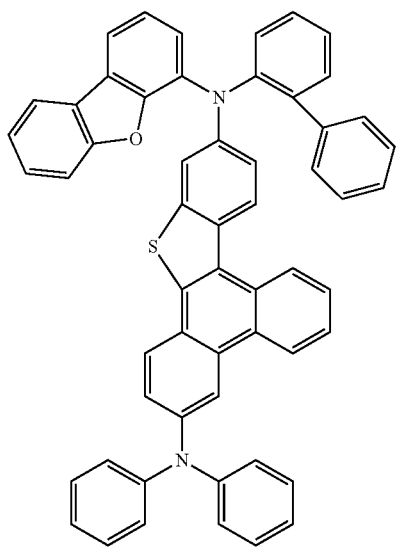
81
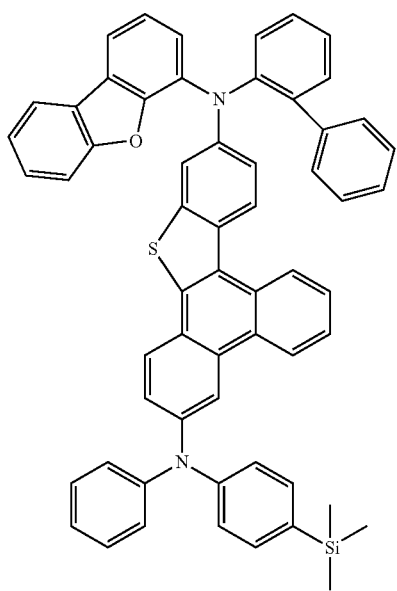
82
430
-continued
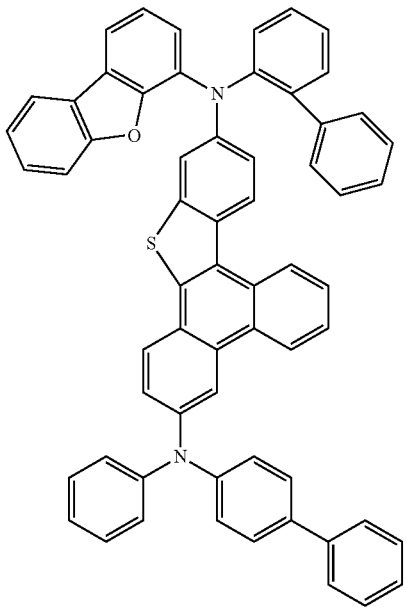
83
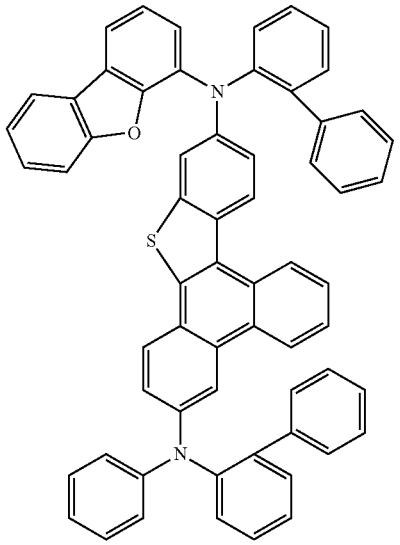
84

431
-continued
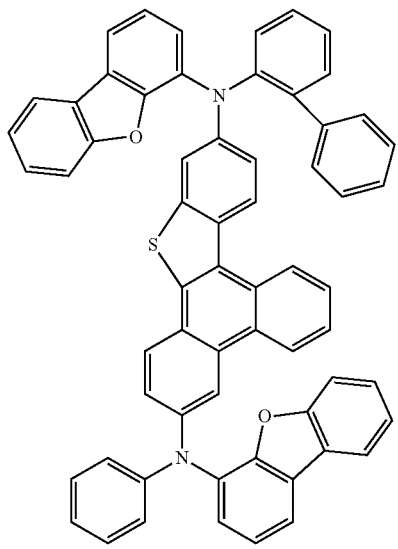
432
-continued
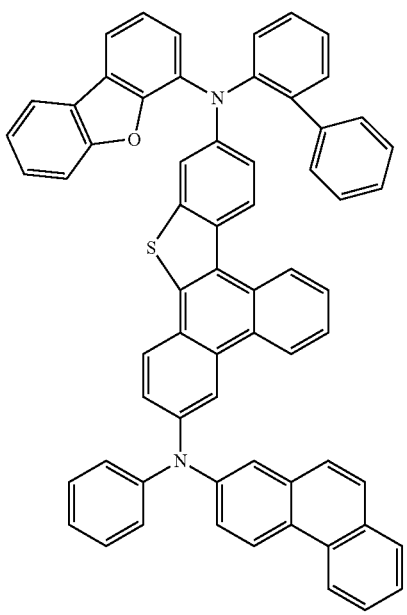
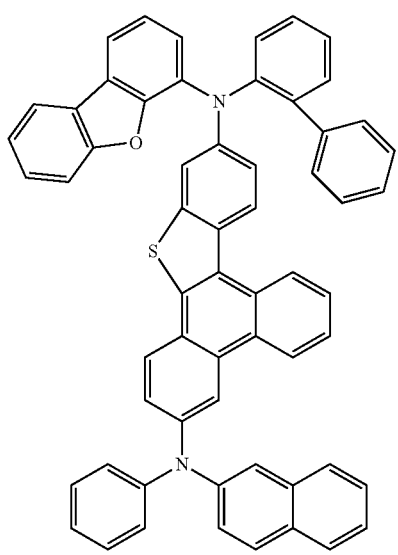
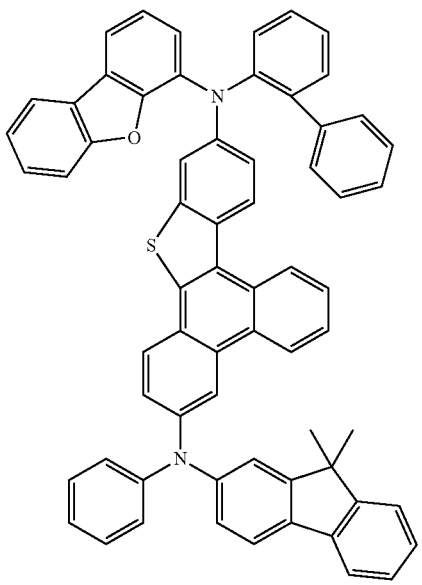

433
-continued
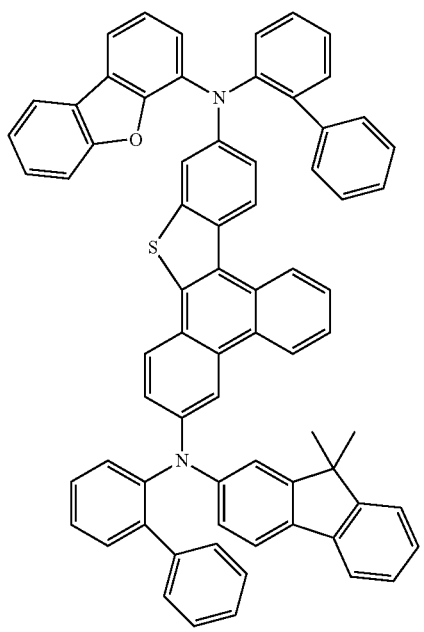
89
434
-continued
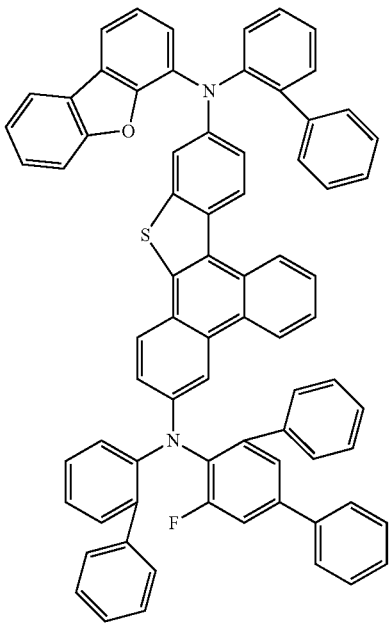
91
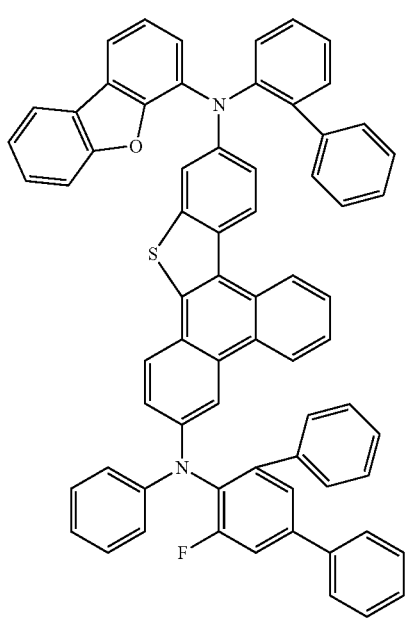
90
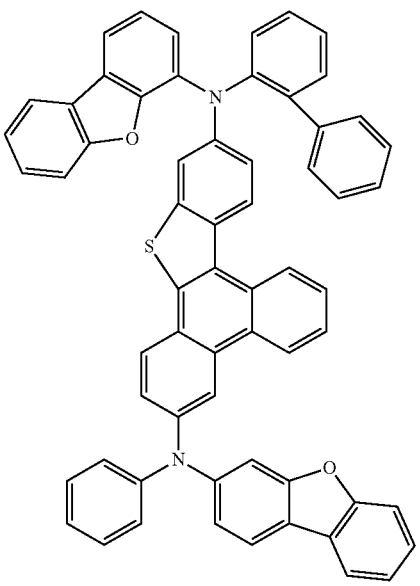
92

435
-continued
93
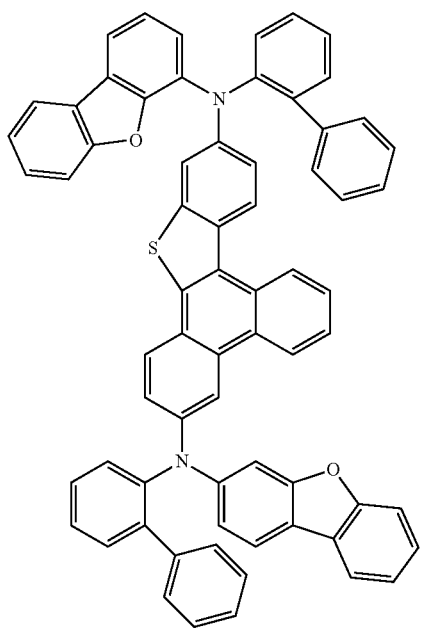
94
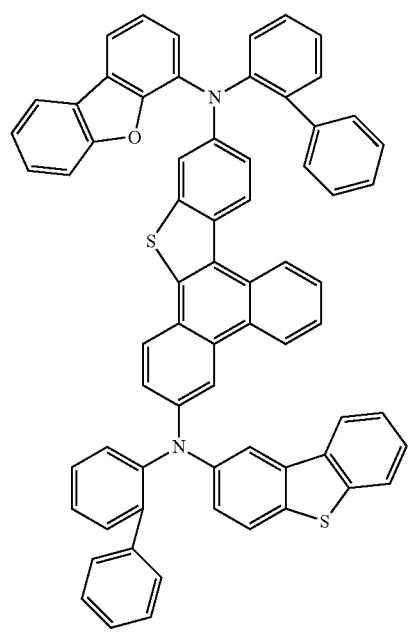
436
-continued
95
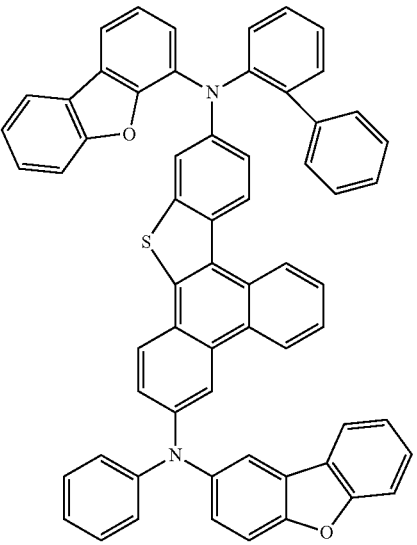
96
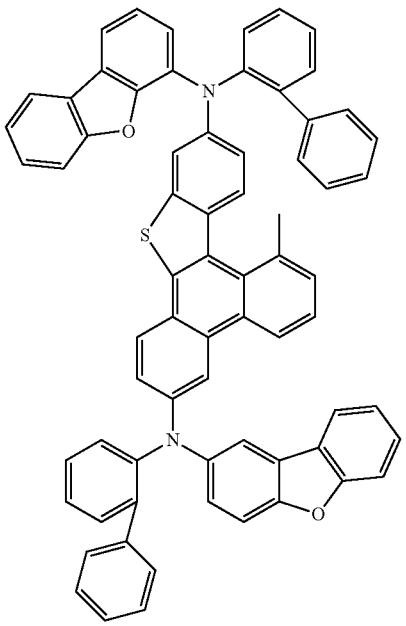

-continued
437
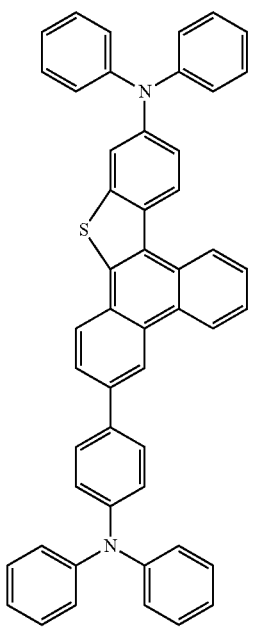
438
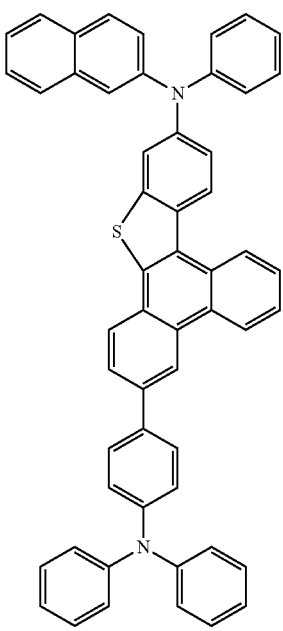
-continued
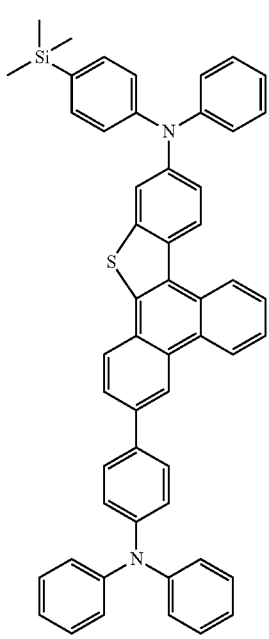
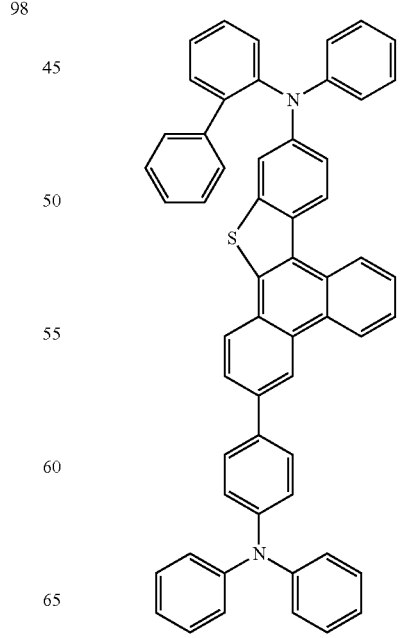

439
-continued
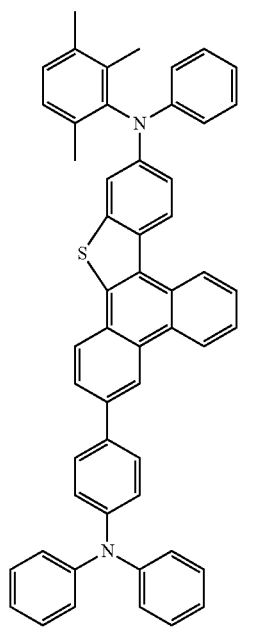
440
-continued
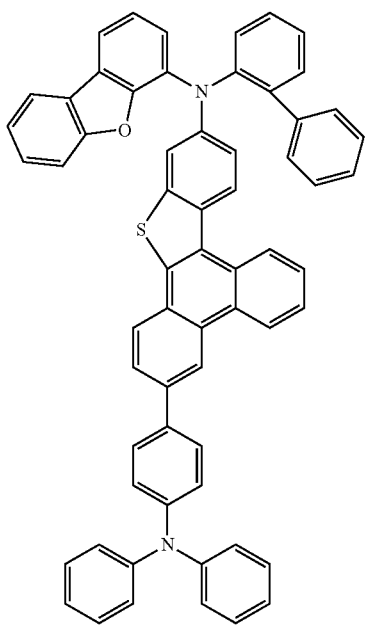
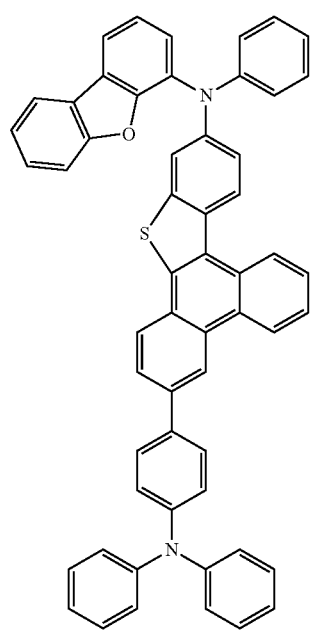
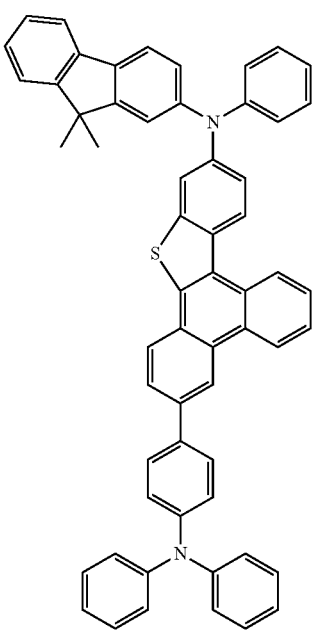

-continued
441
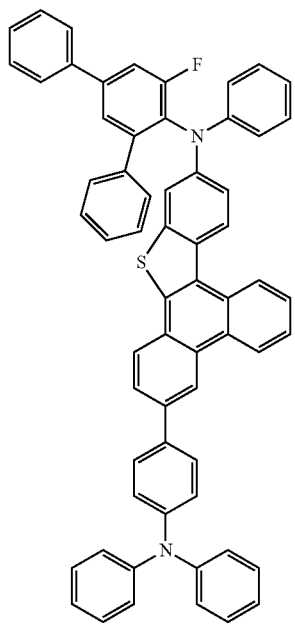
105
442
-continued
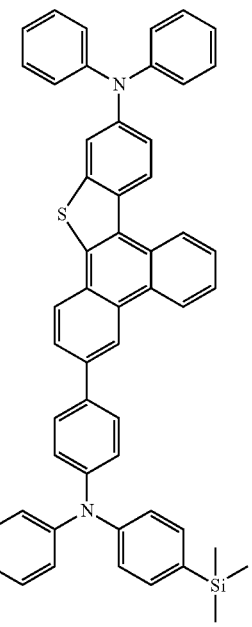
107
106
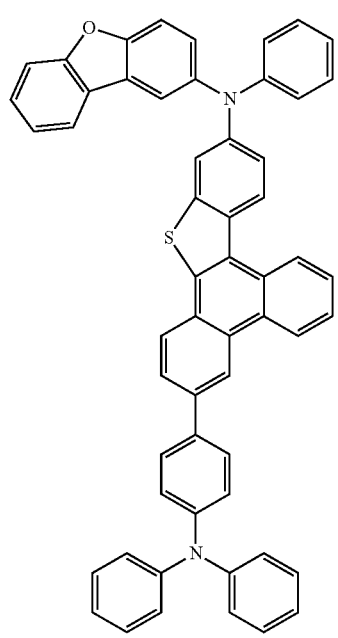
108
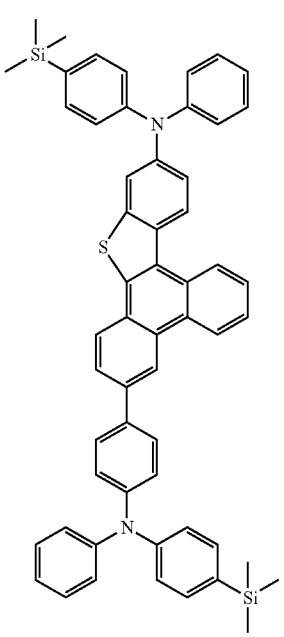

443
-continued
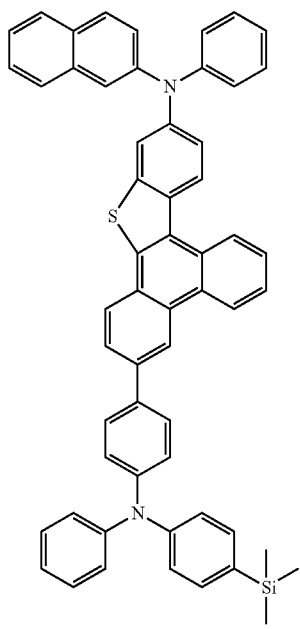
109
444
-continued
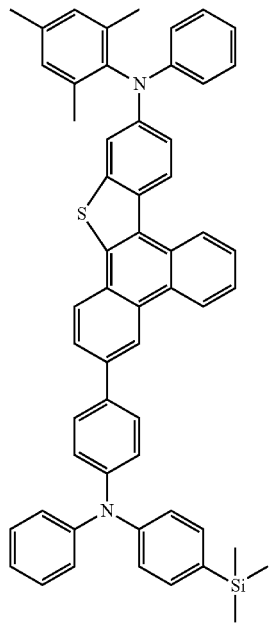
111
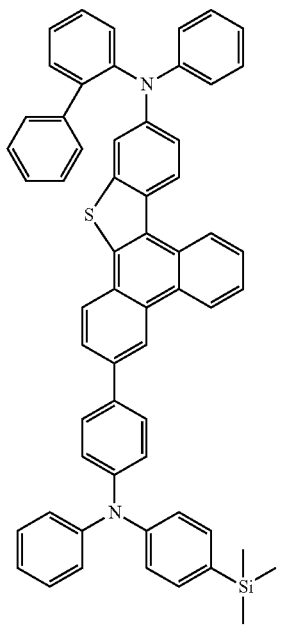
110
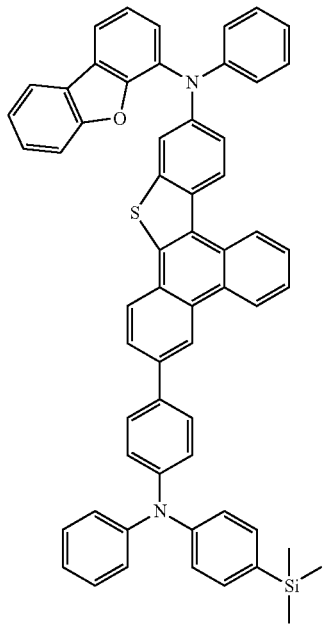
112

445
-continued
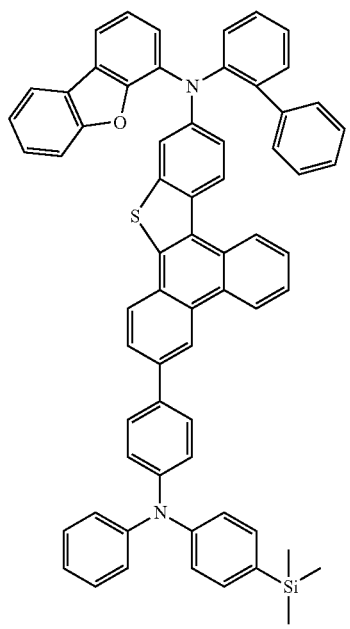
113
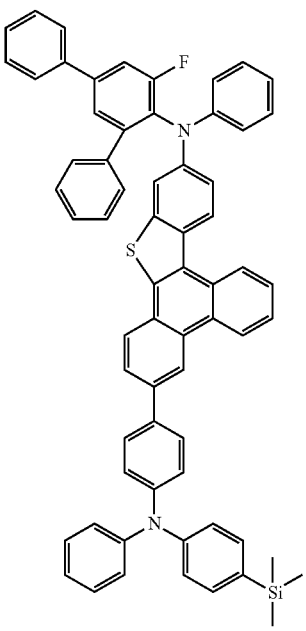
115
446
-continued
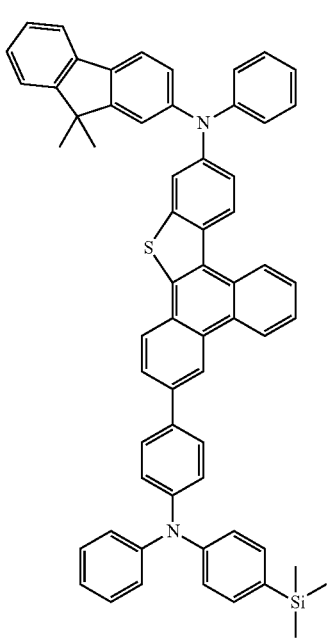
114
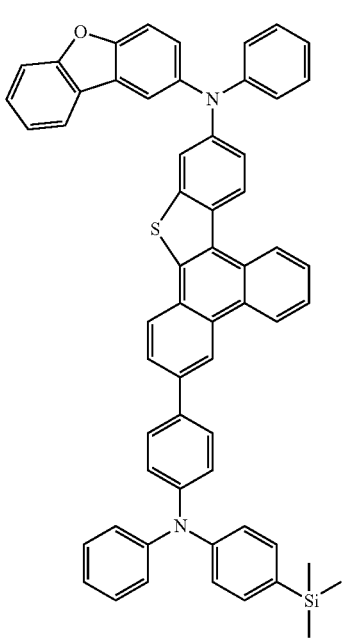
116

447
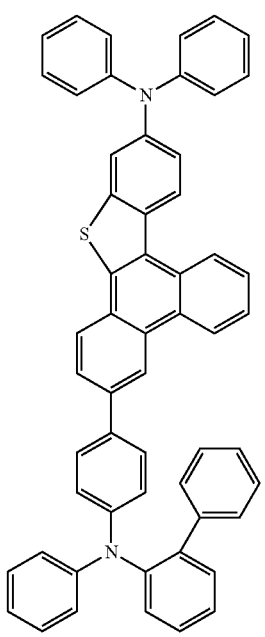
448
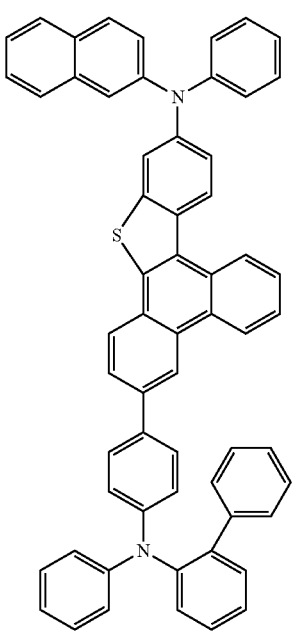
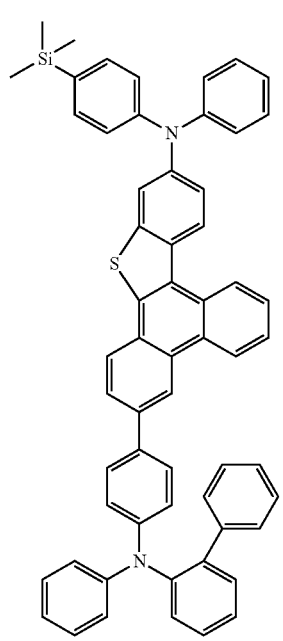
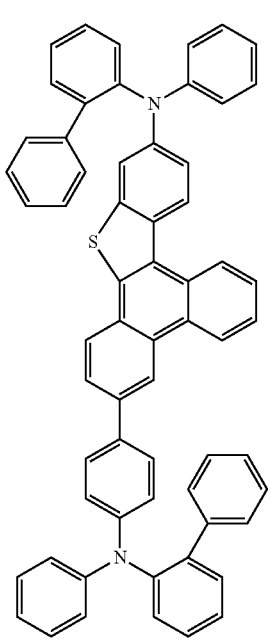

449
-continued
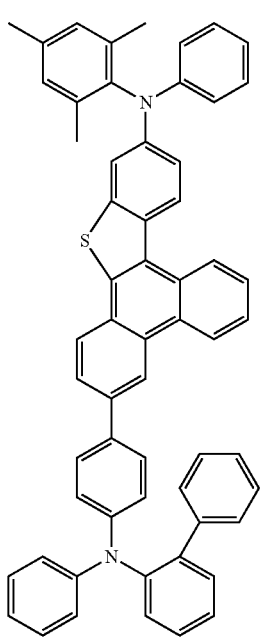
121
450
-continued
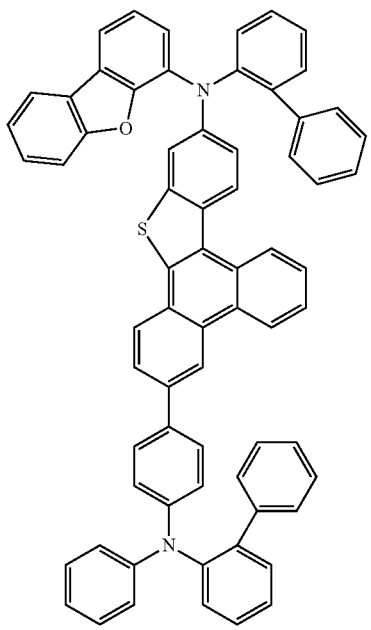
123
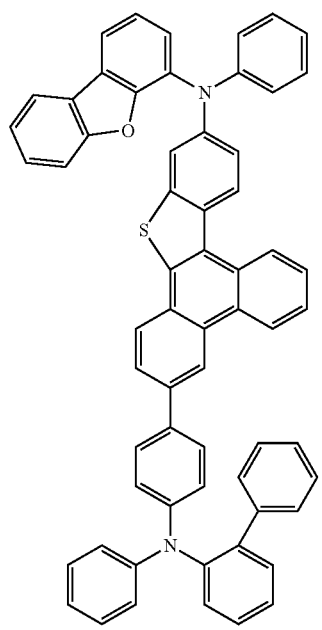
122

451
-continued
125
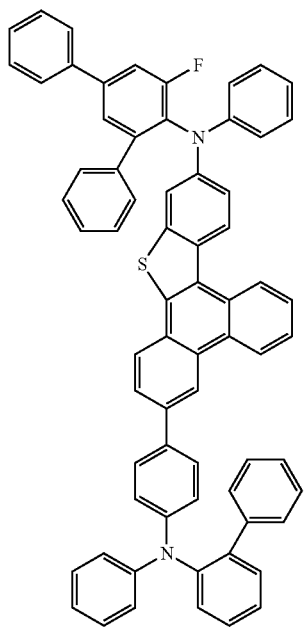
127
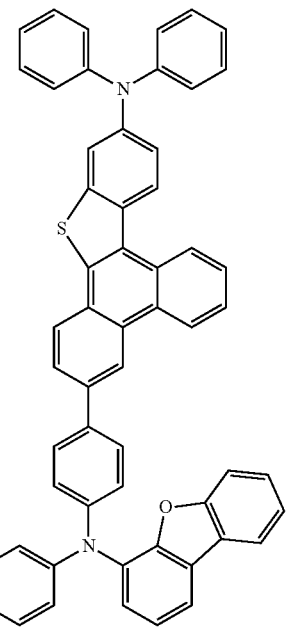
452
-continued
126
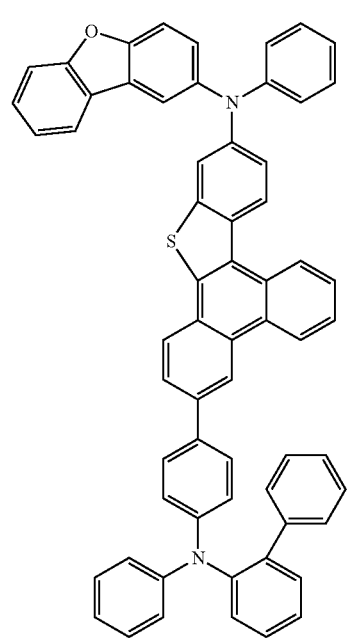
128
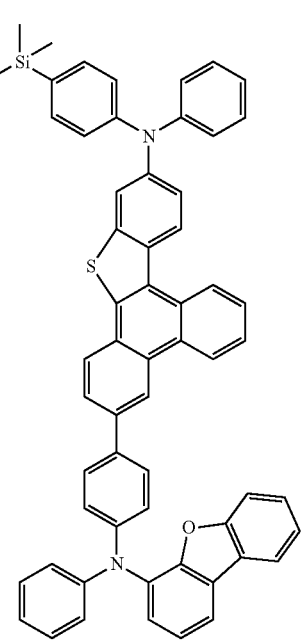

453
-continued
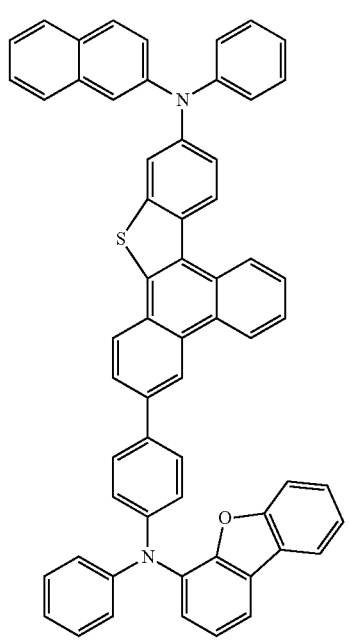
454
-continued
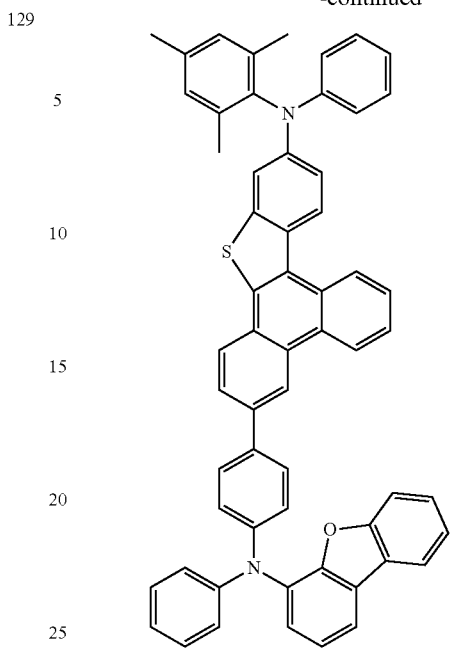
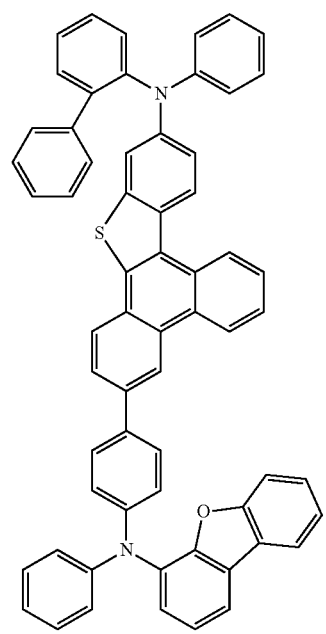
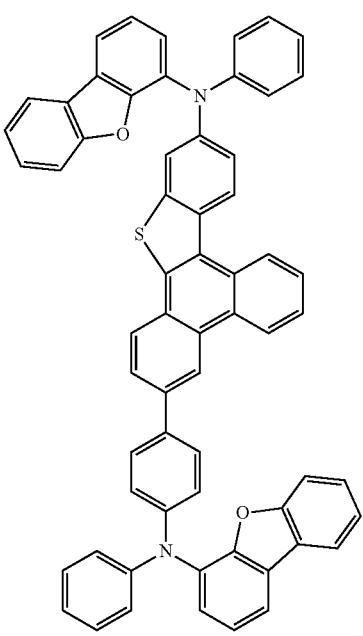

455
-continued
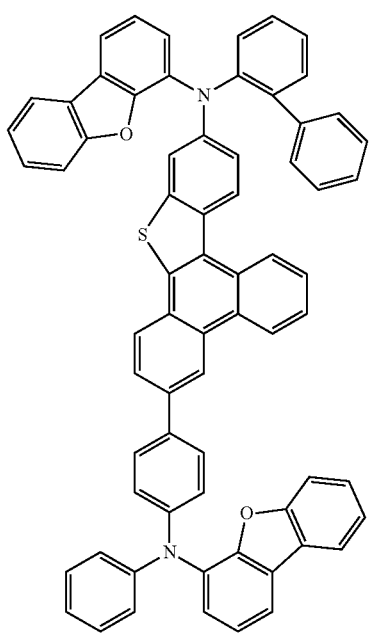
133
456
-continued
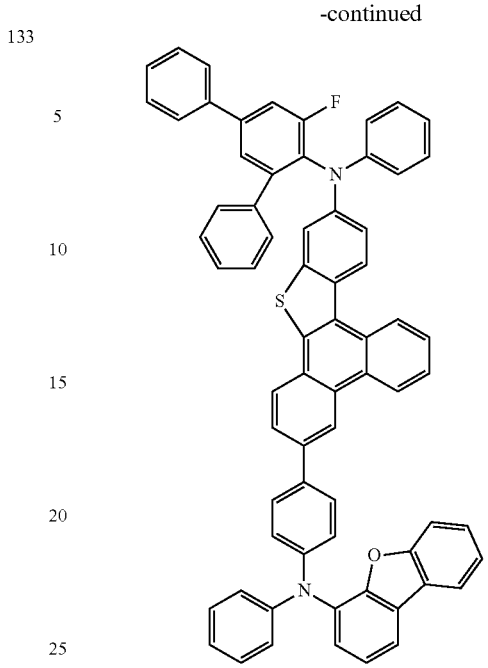
135
134
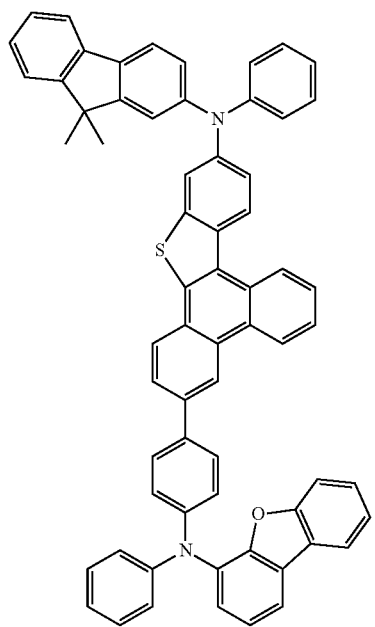
136
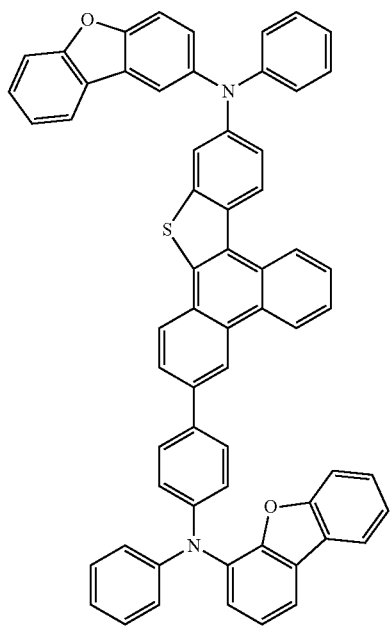

457
-continued
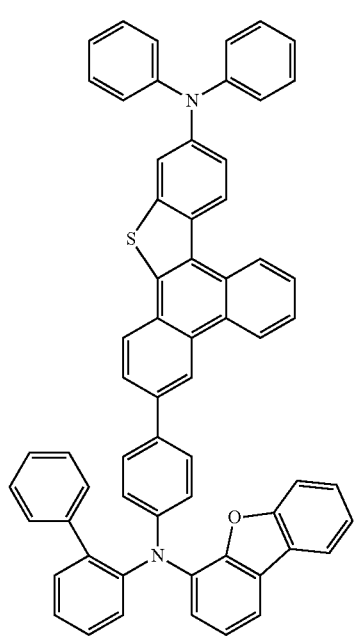
458
-continued
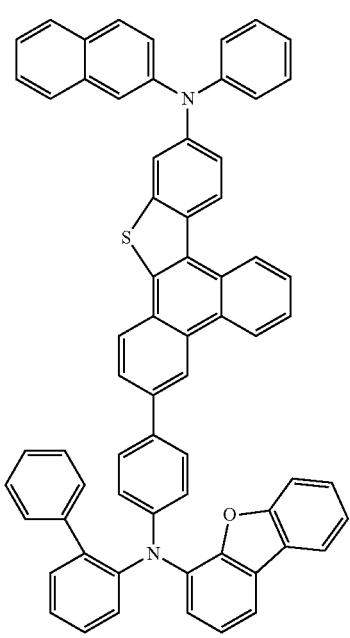
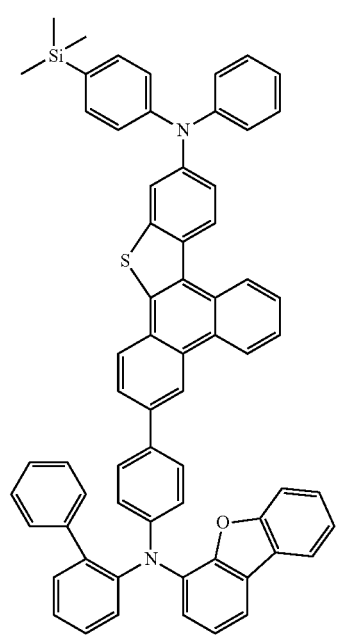
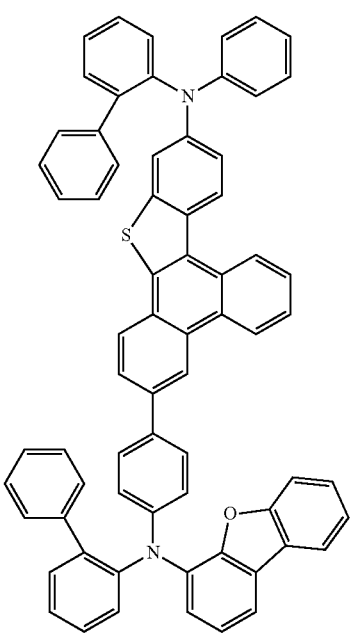

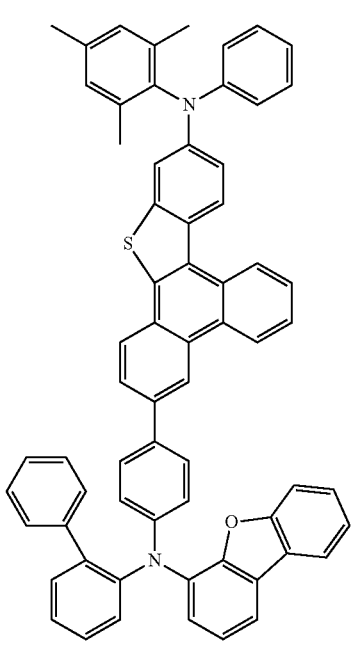
459
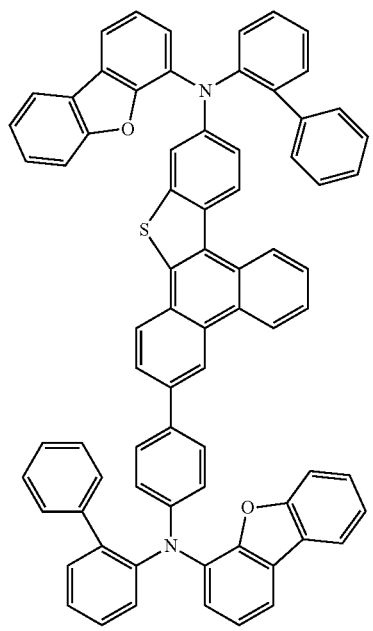
460
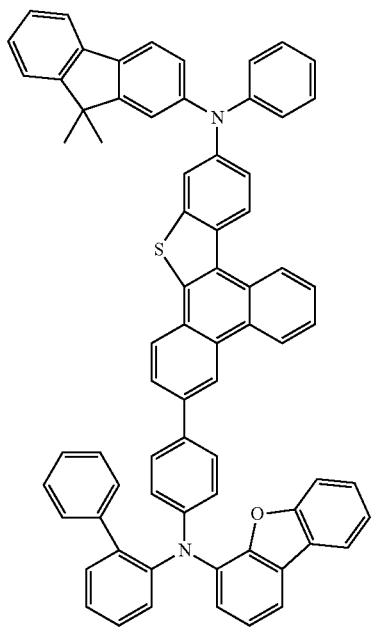

461
-continued
145
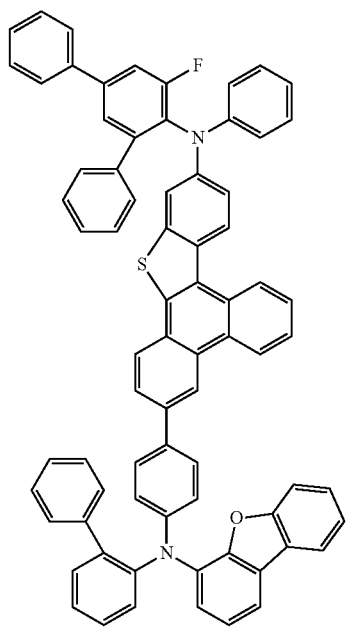
147
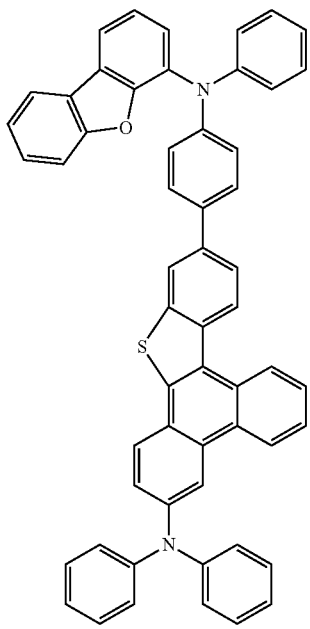
462
-continued
146
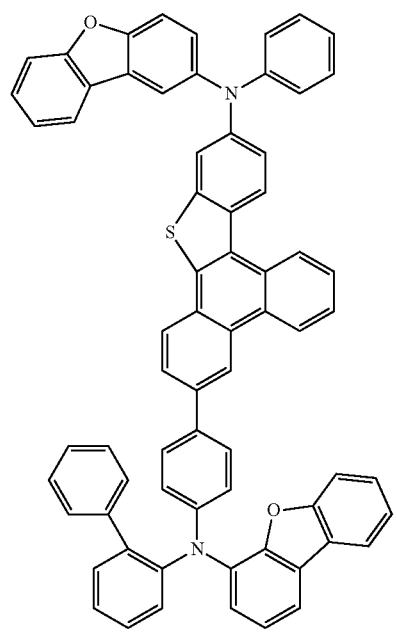
148
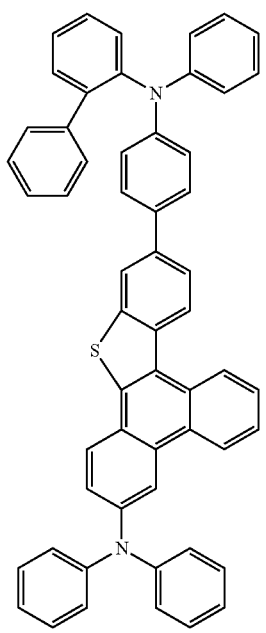

463
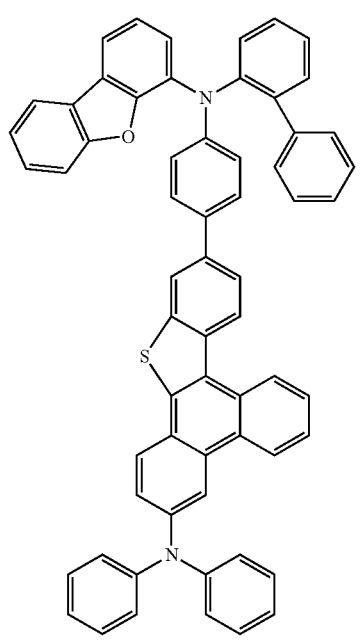
464
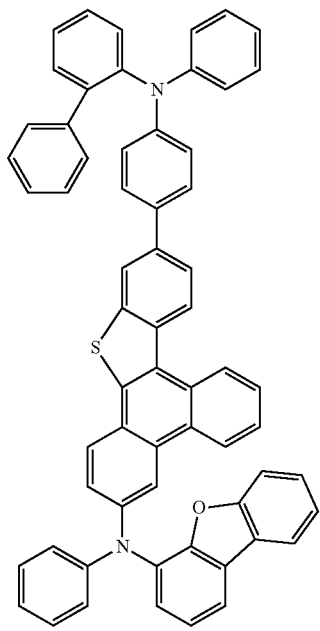
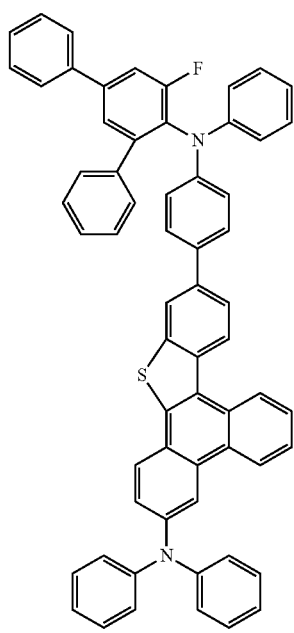
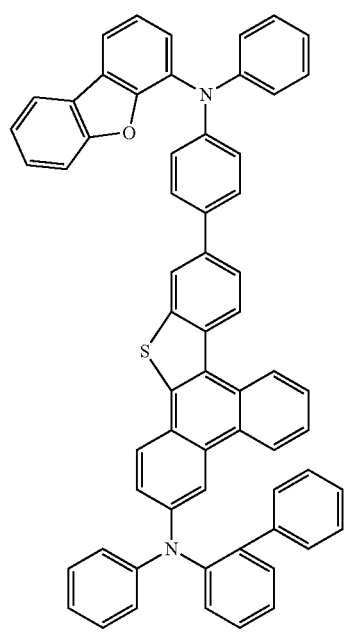

-continued
153
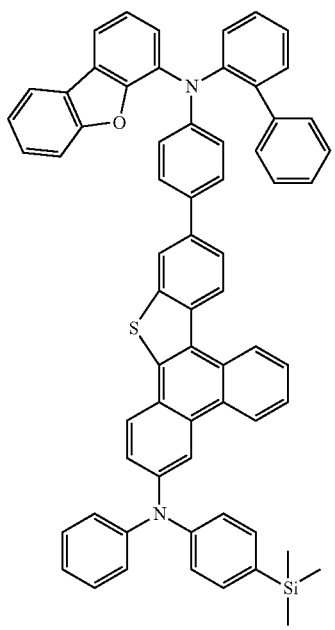
-continued
155
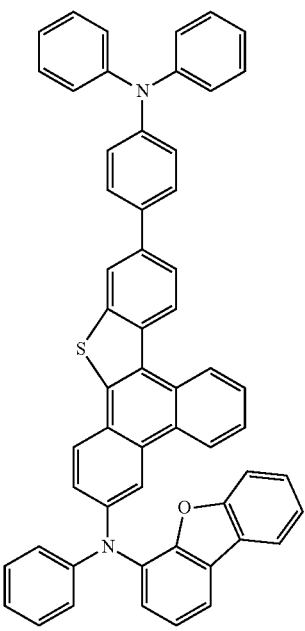
154
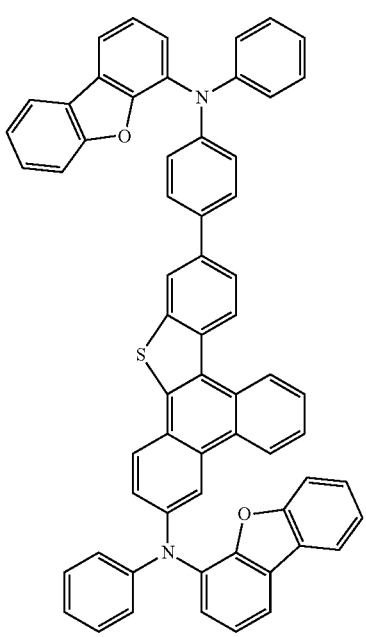
156
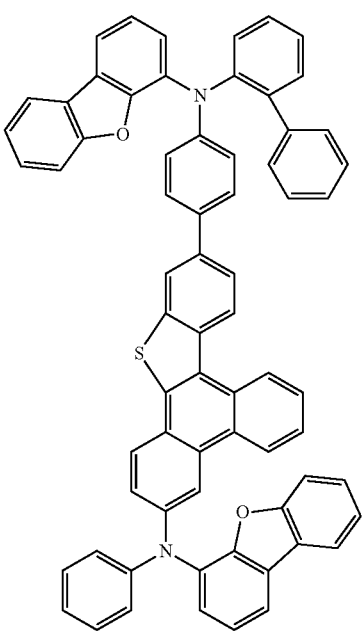

467
-continued
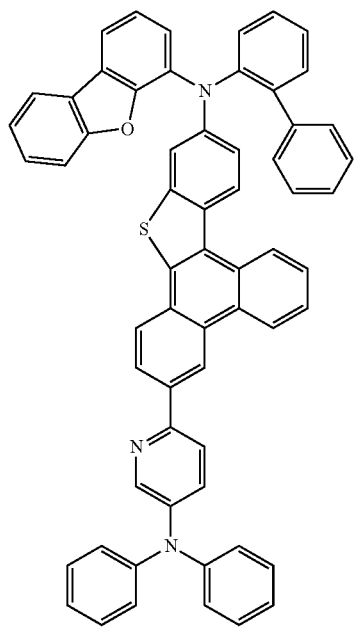
468
-continued
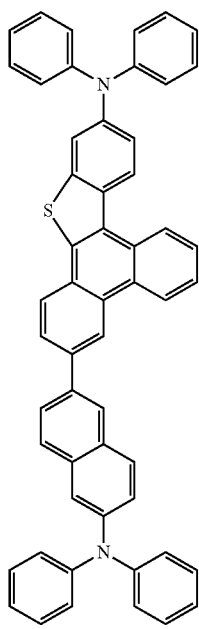
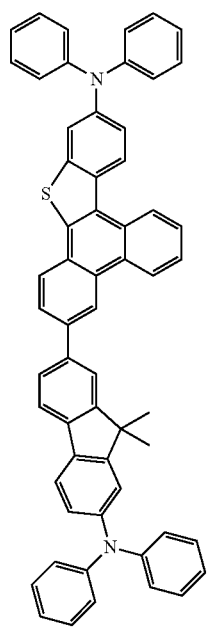
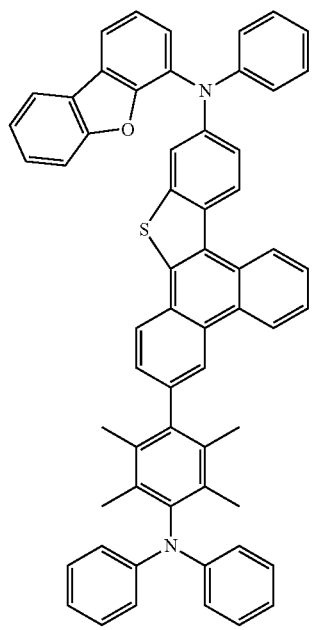

469 470
-continued -continued
161 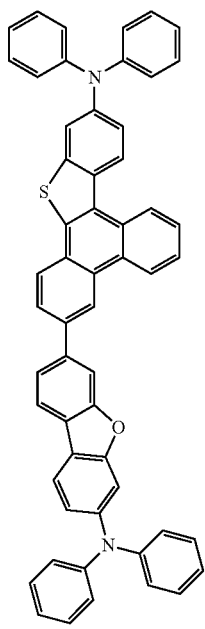 163 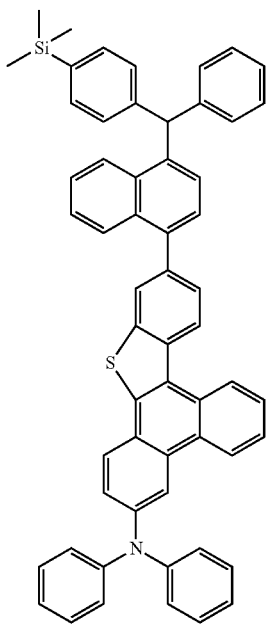
162 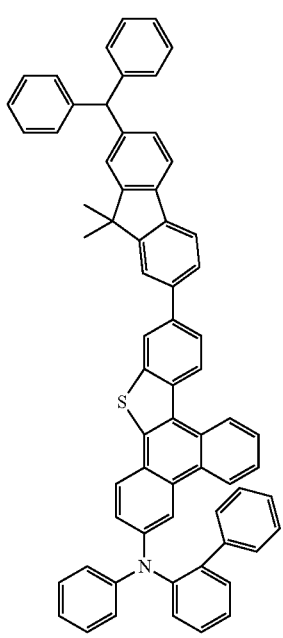 164 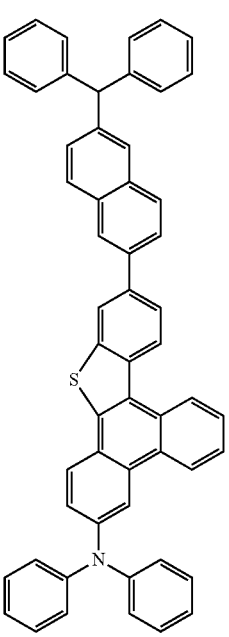

471
-continued
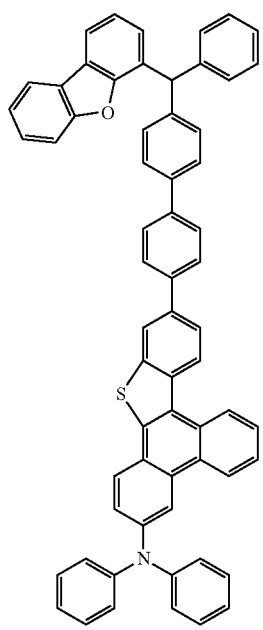
166
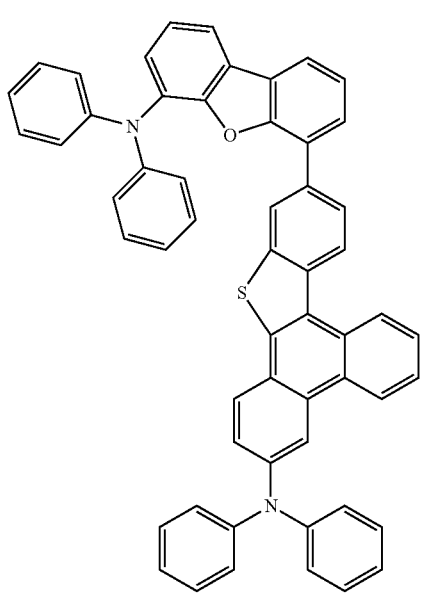
472
-continued
165
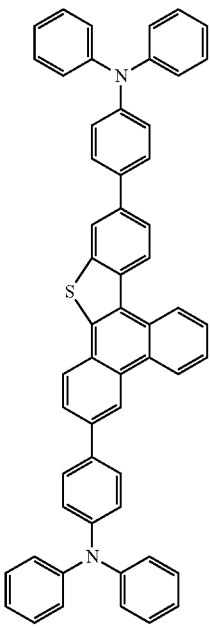
167
168
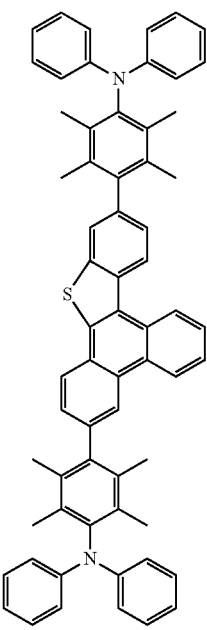

473
-continued
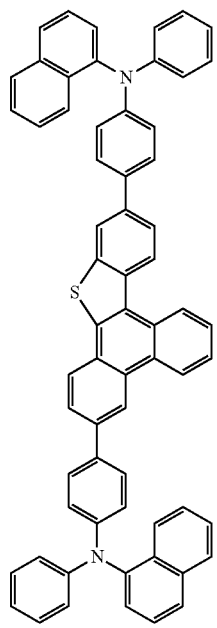
474
-continued
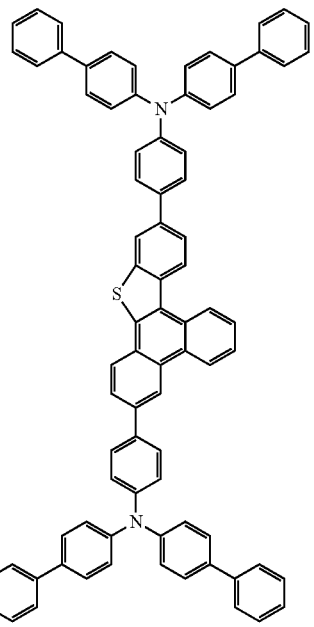
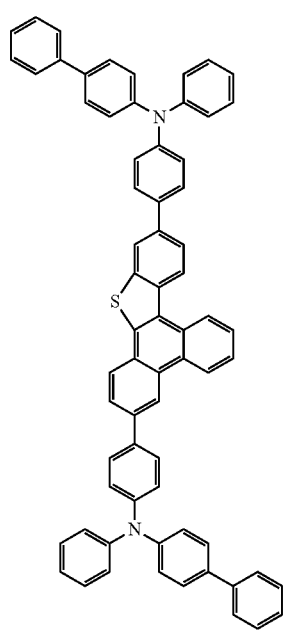
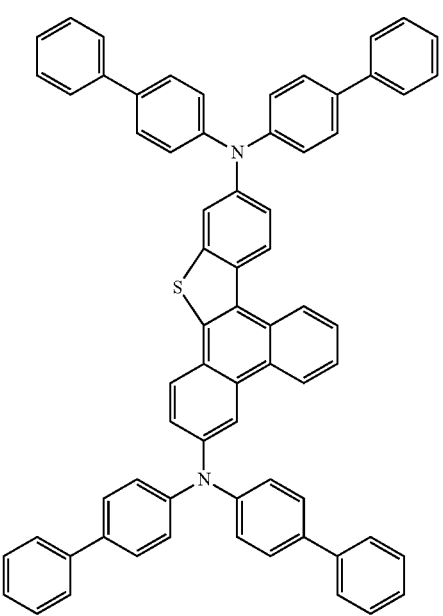

475
-continued
476
-continued
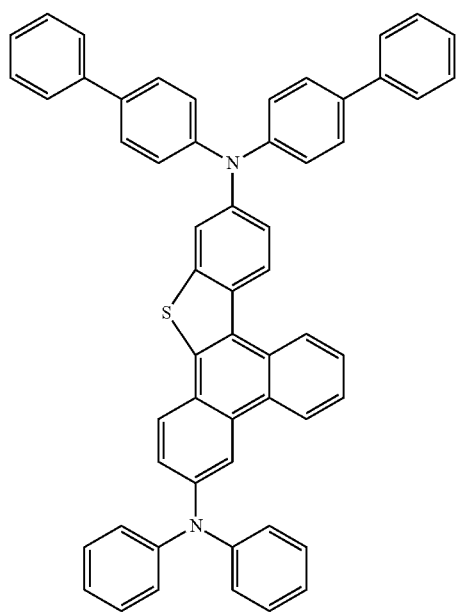
173
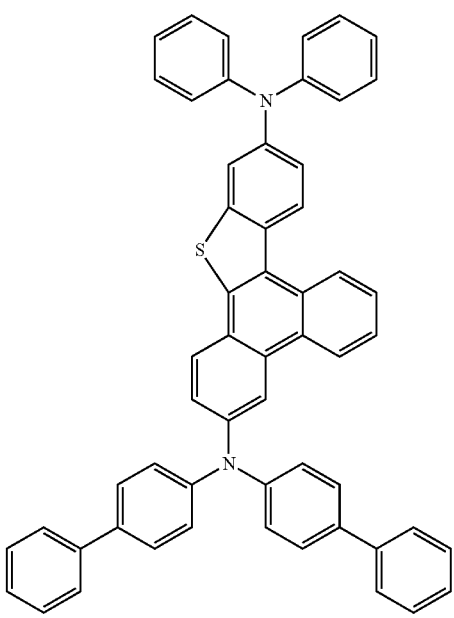
175
174
176

477
-continued
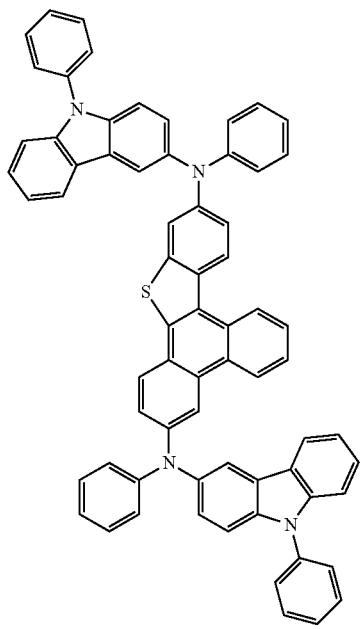
177
478
-continued
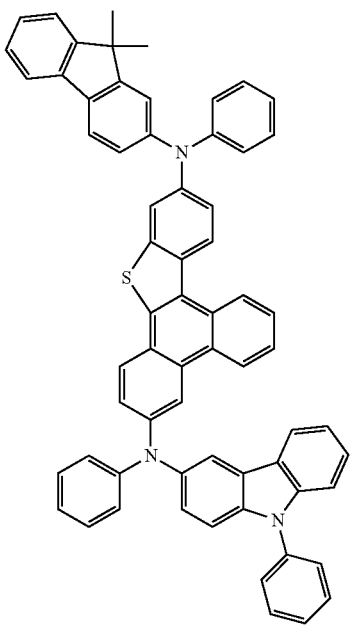
179
178
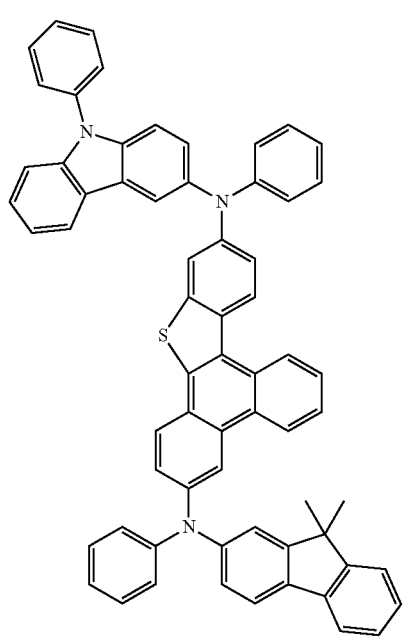
180

479
-continued
181
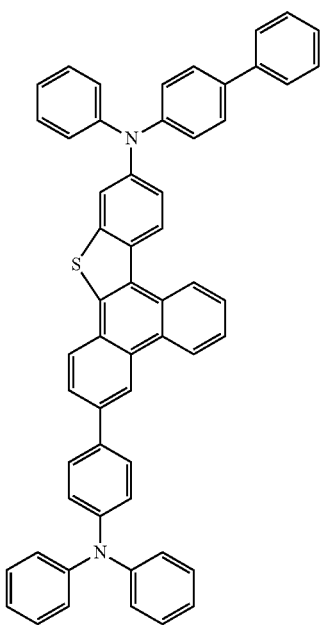
182
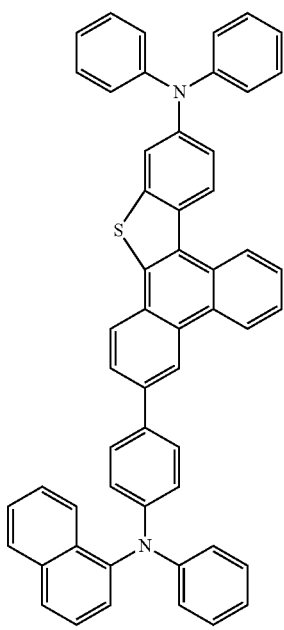
480
-continued
183
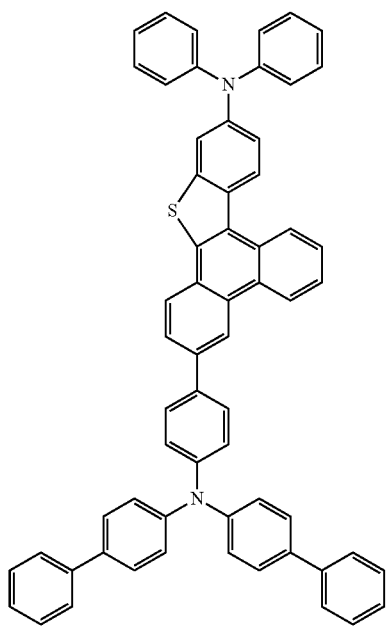
184
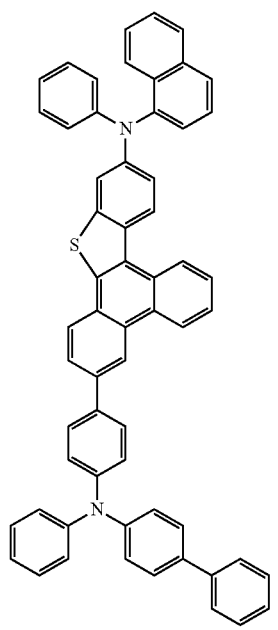

481
-continued
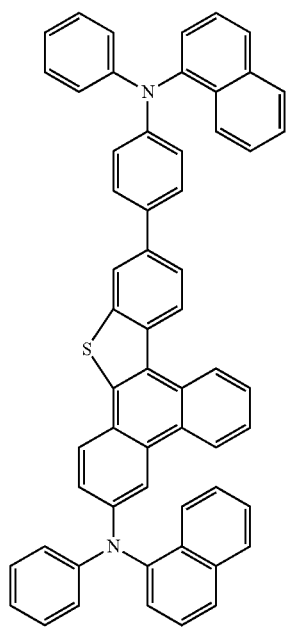
185
186
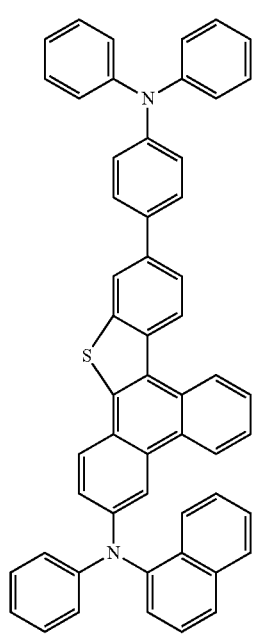
482
-continued
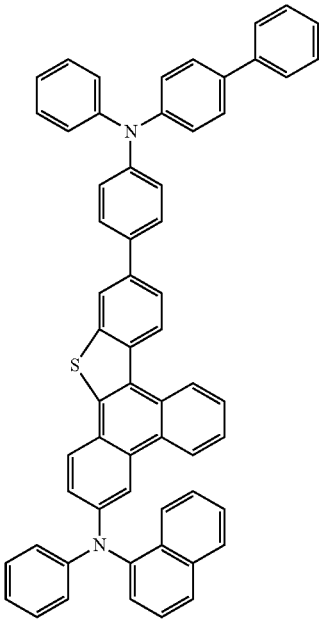
187
188
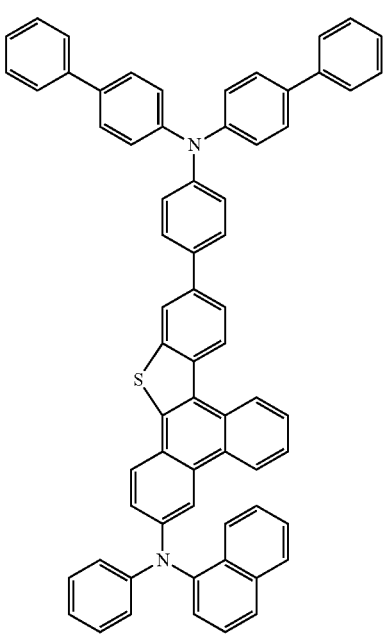

483
-continued
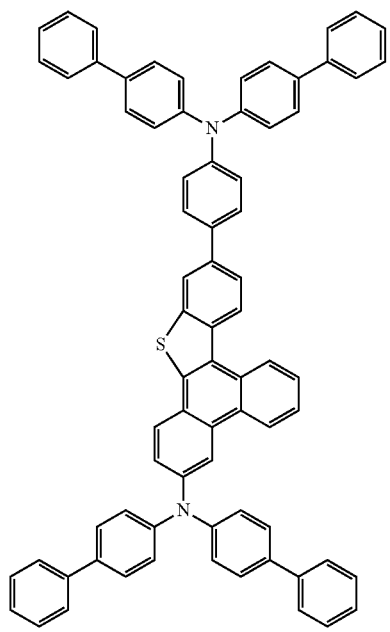
484
-continued
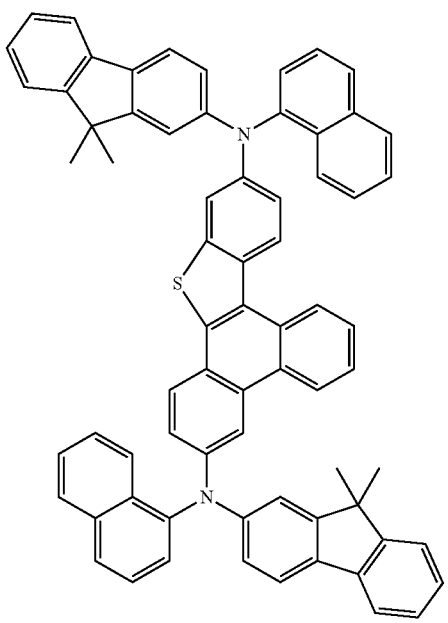
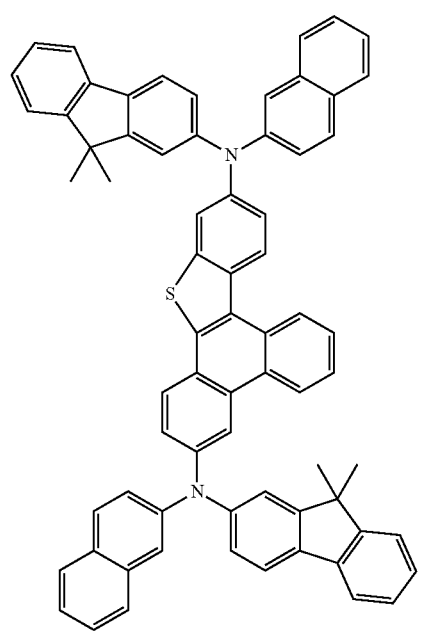
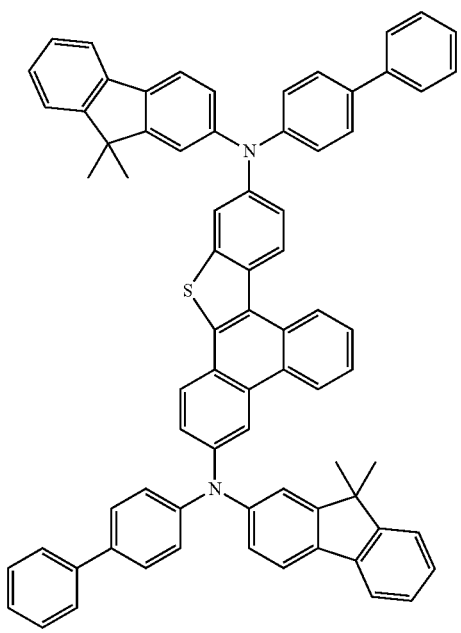

-continued
485
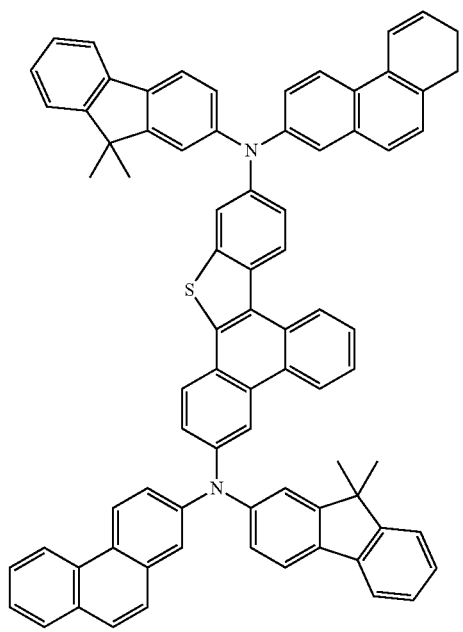
486
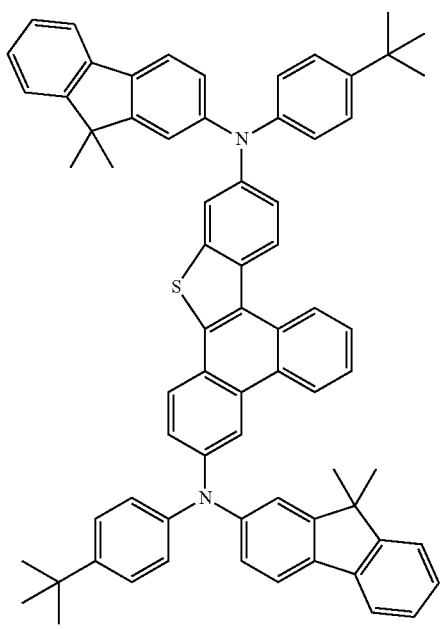
194
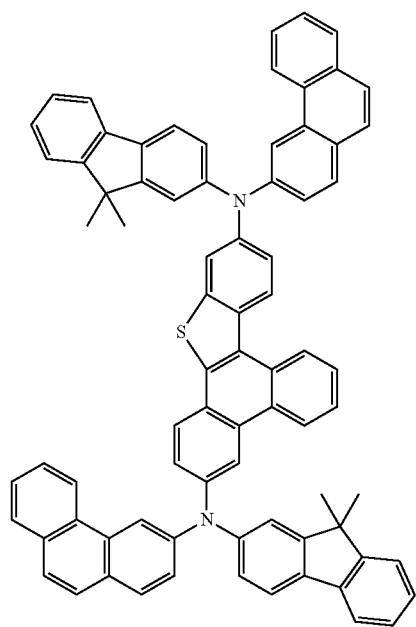
196
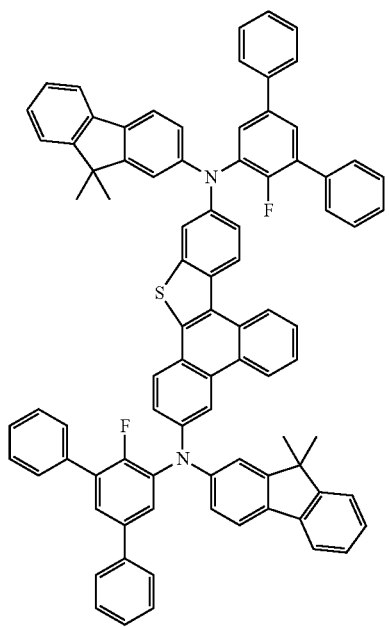

487
-continued
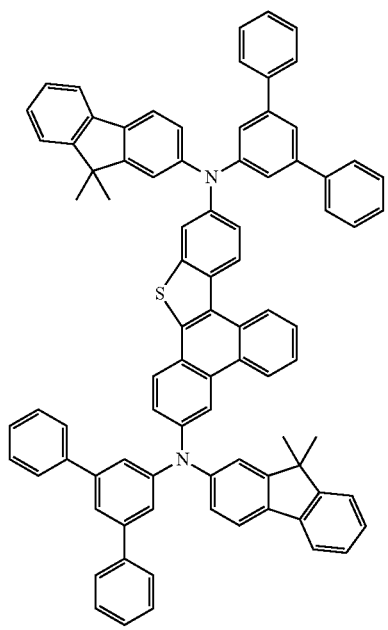
197
488
-continued
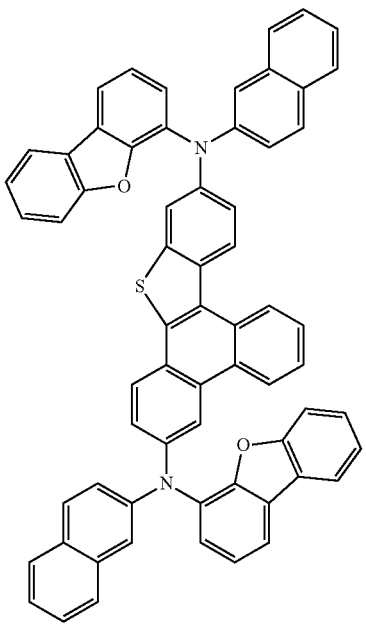
199
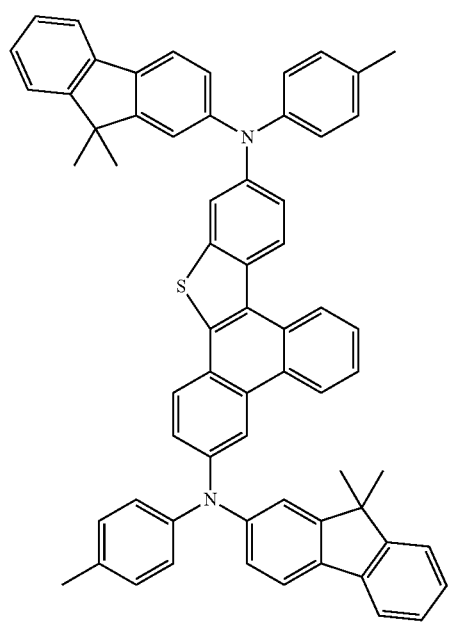
198
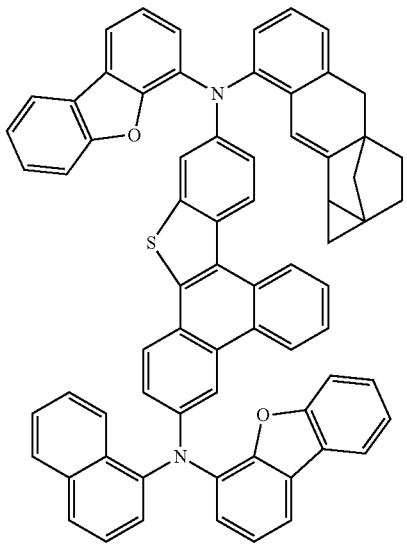
200

489
-continued
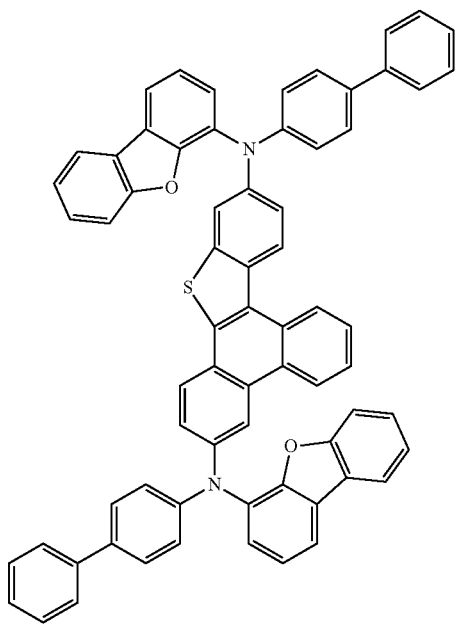
490
-continued
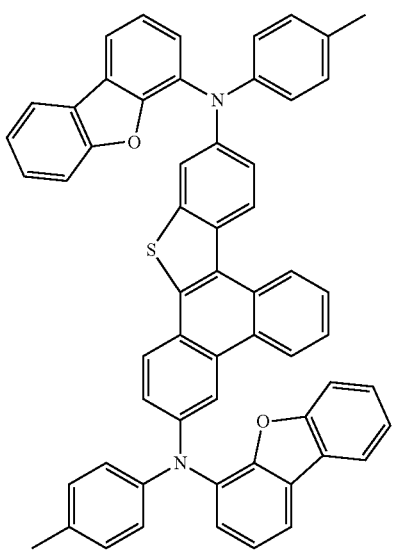
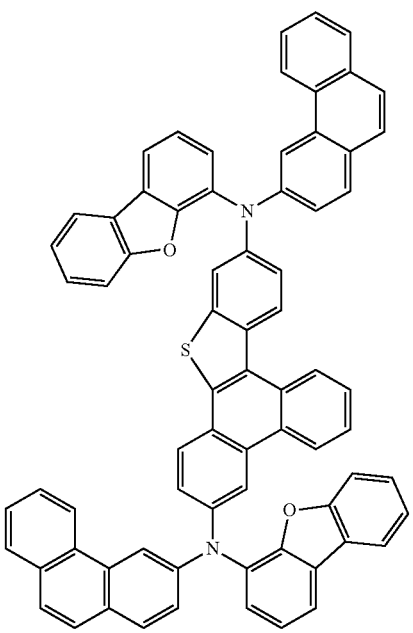
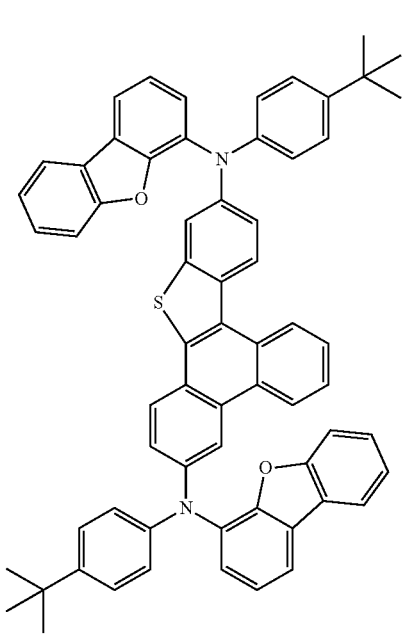

491
-continued
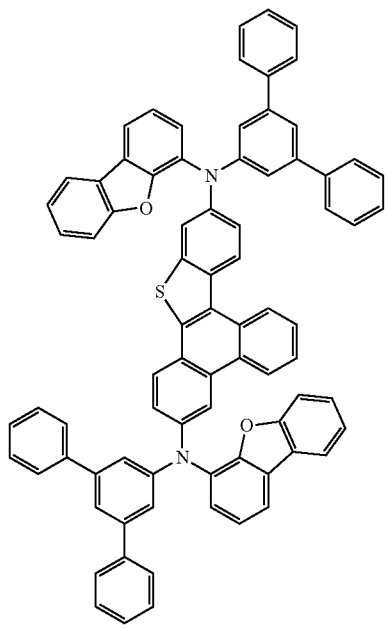
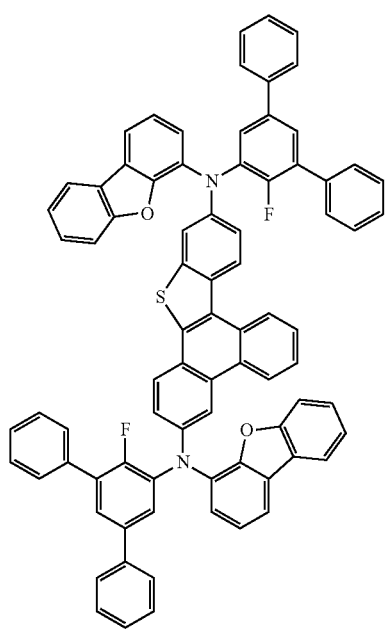
492
-continued
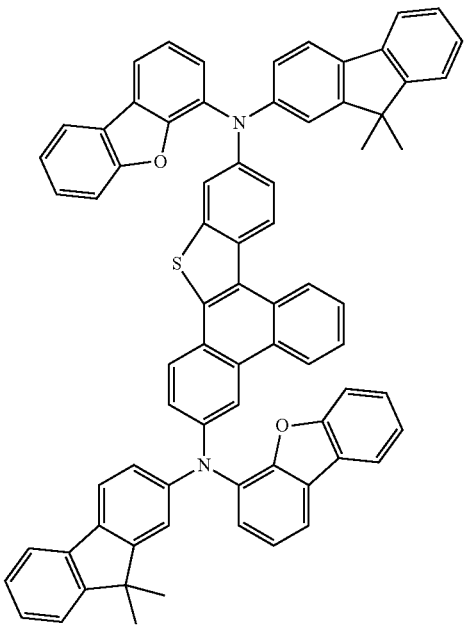
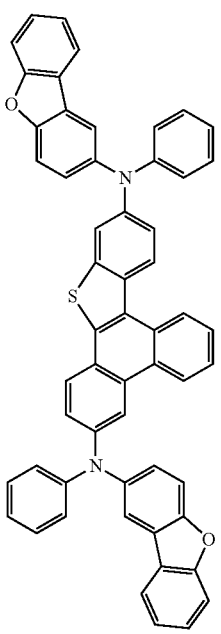

493
-continued
494
-continued
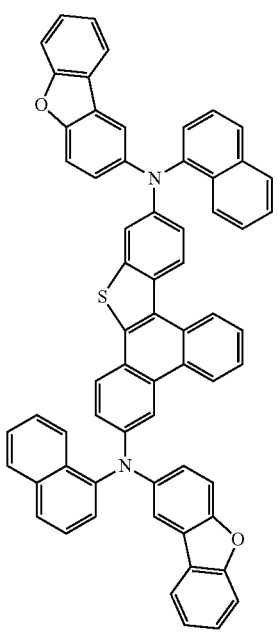
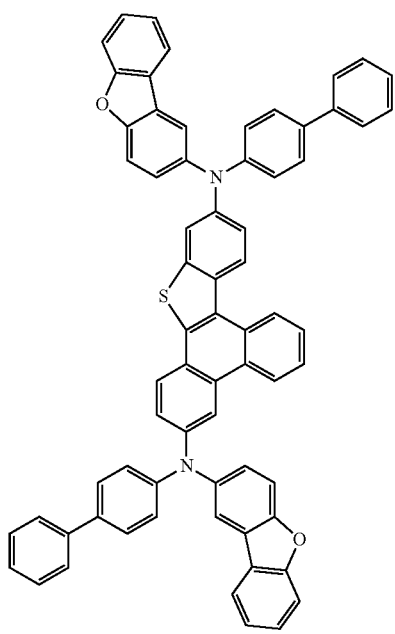

495
-continued
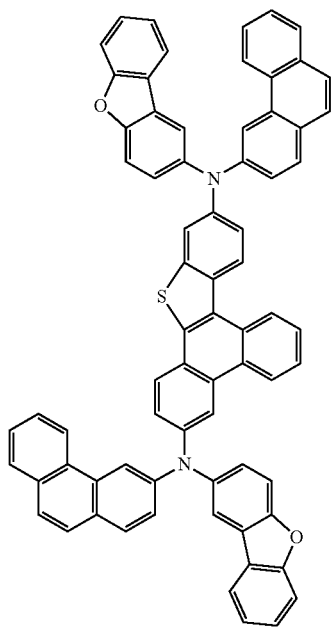
213
496
-continued
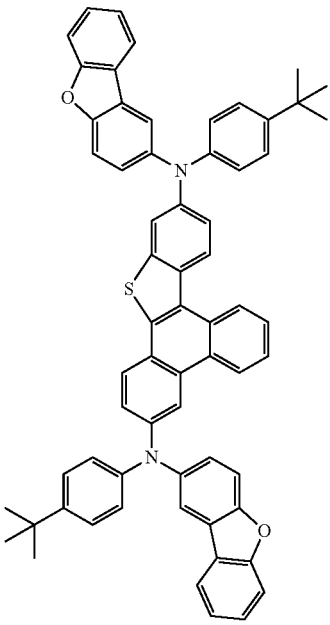
215
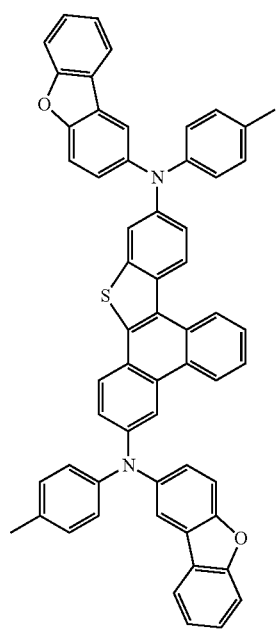
214
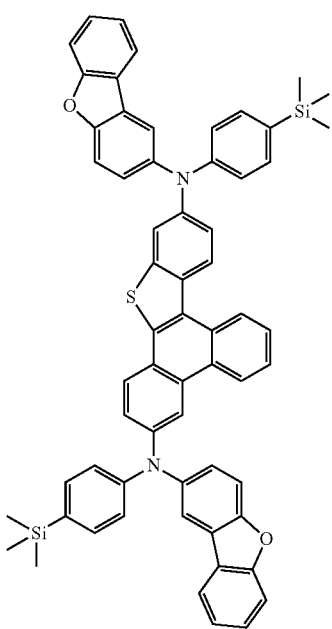
216

497
-continued
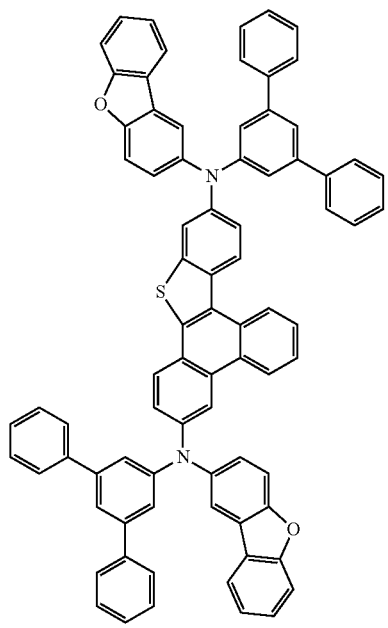
218
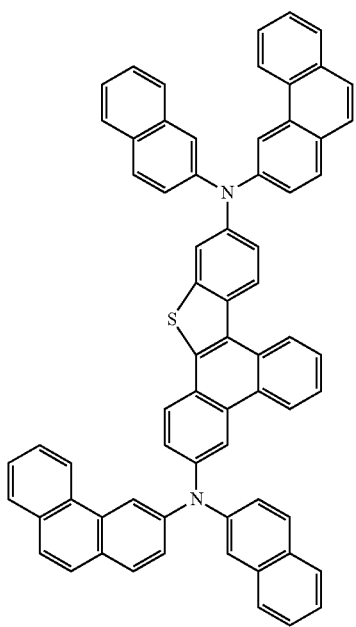
498
-continued
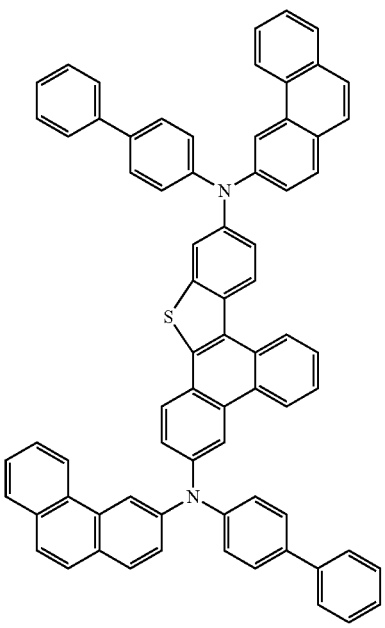
220
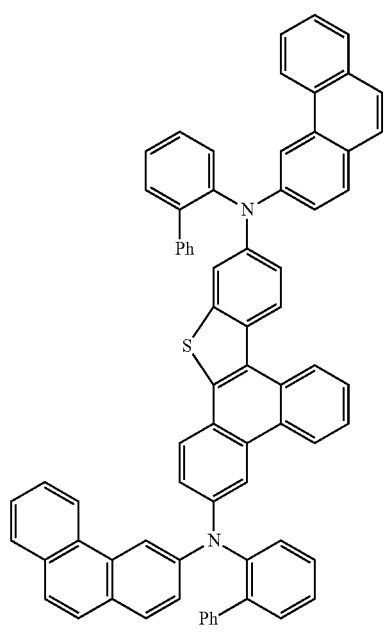

499
-continued
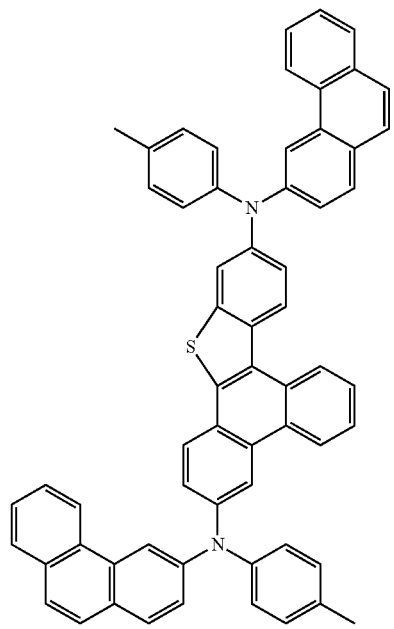
221
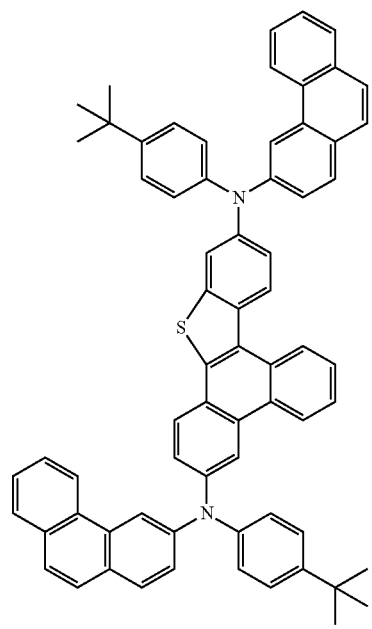
222
500
-continued
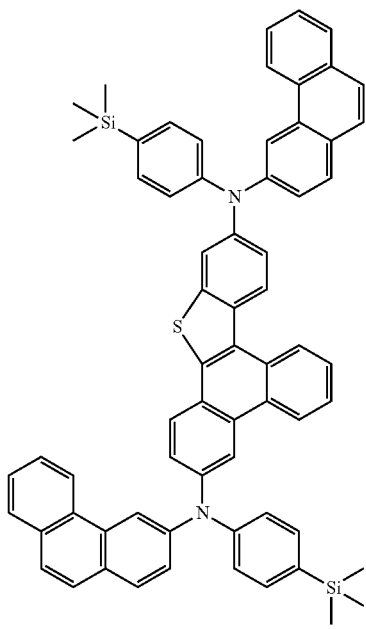
223
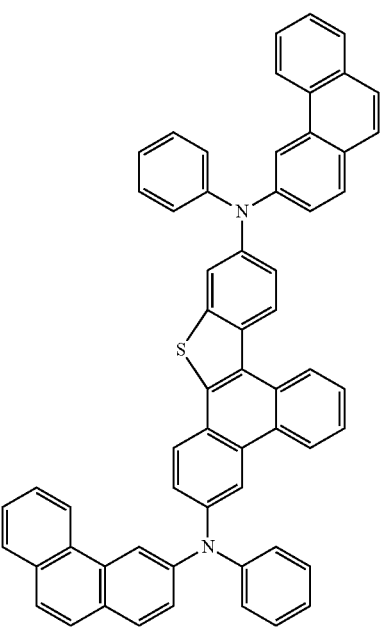
224

501
-continued
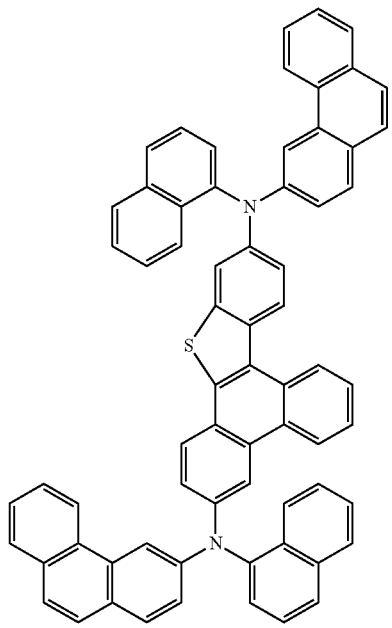
225
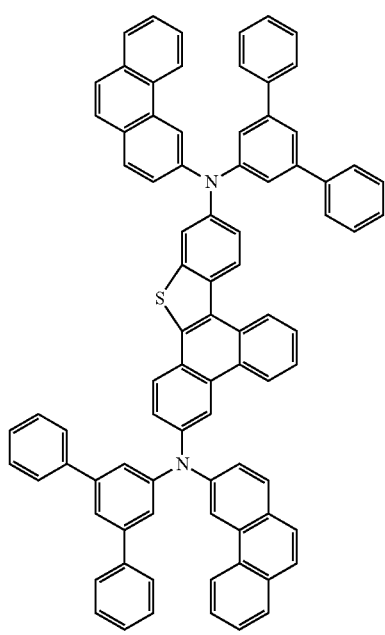
226
502
-continued
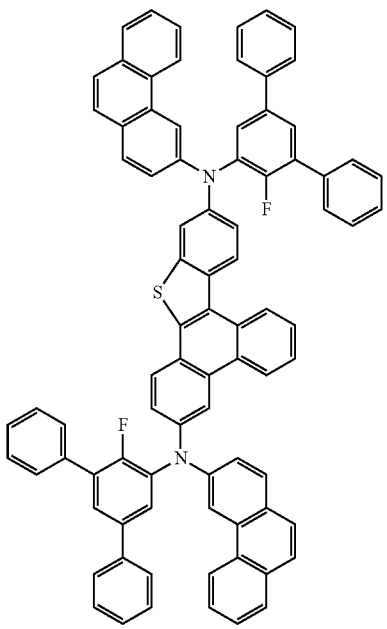
227
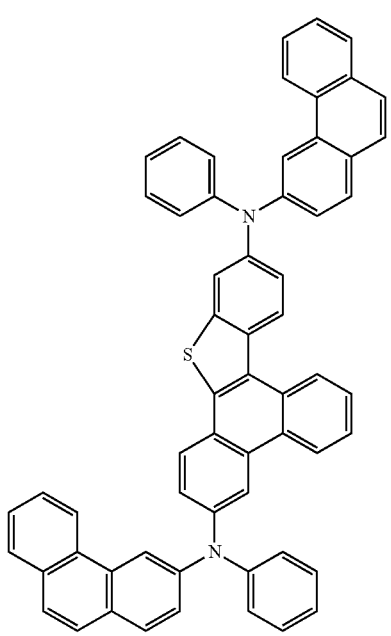
228

503
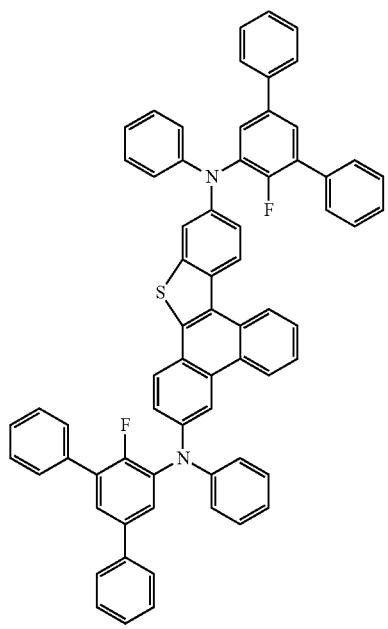
504
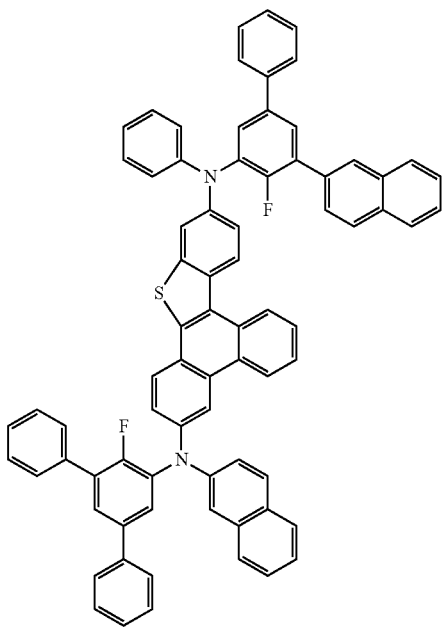
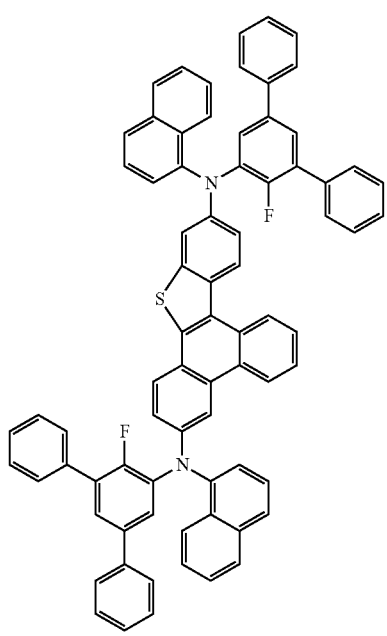
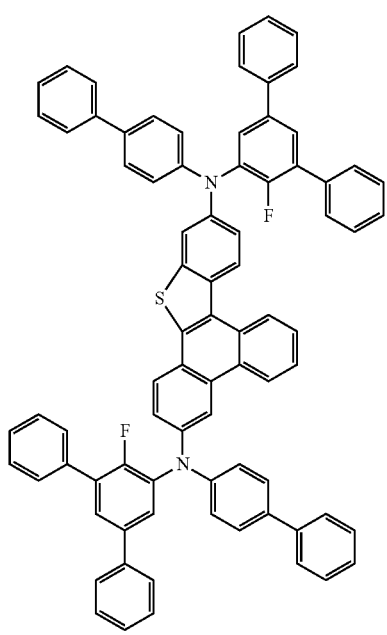

505
-continued
233
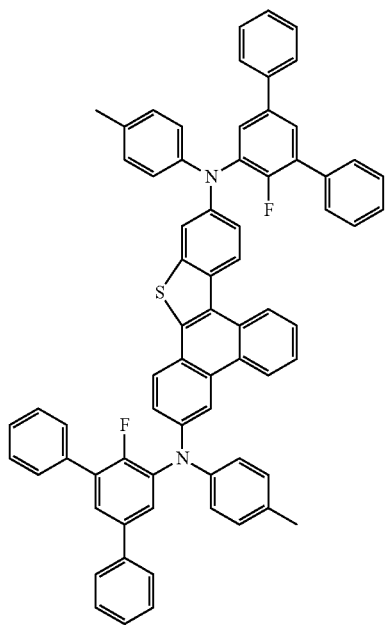
234
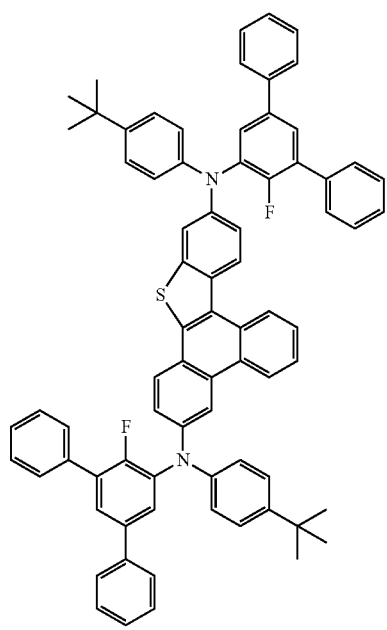
506
-continued
235
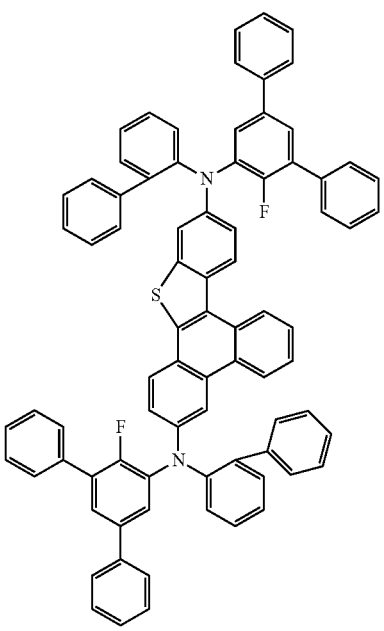
236
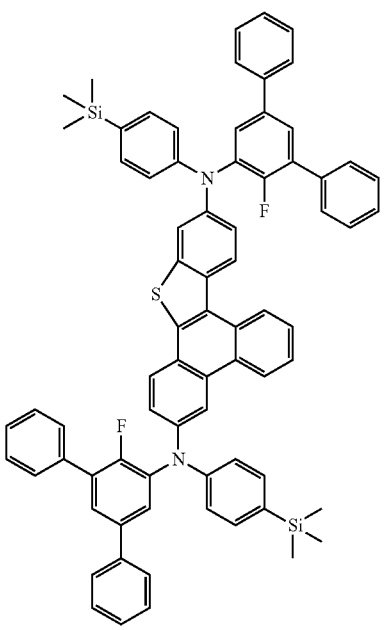

507
-continued
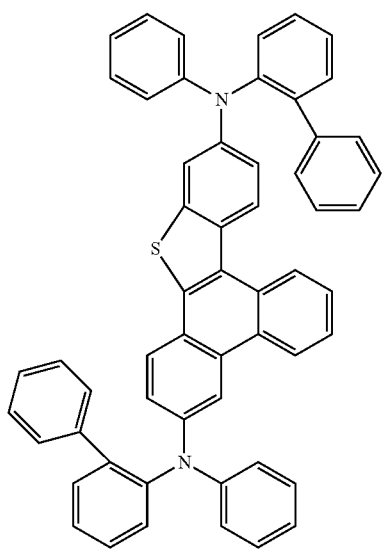
237
508
-continued
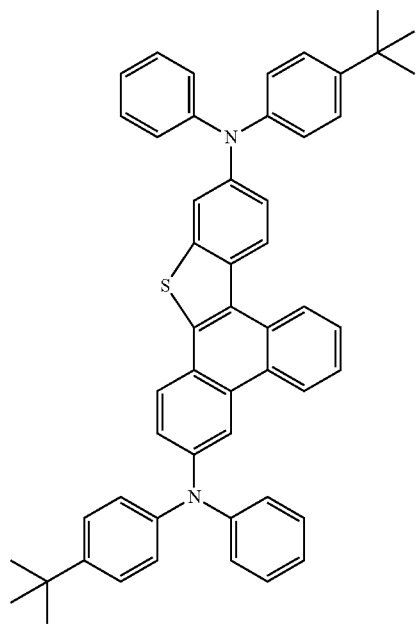
239
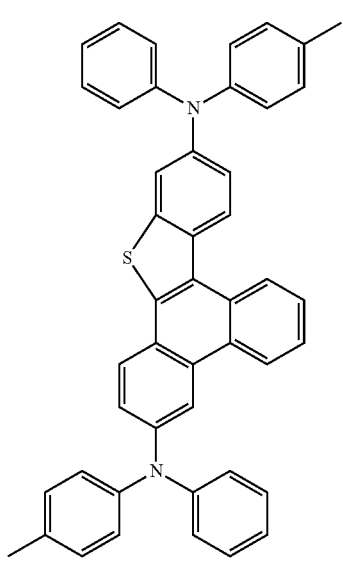
238
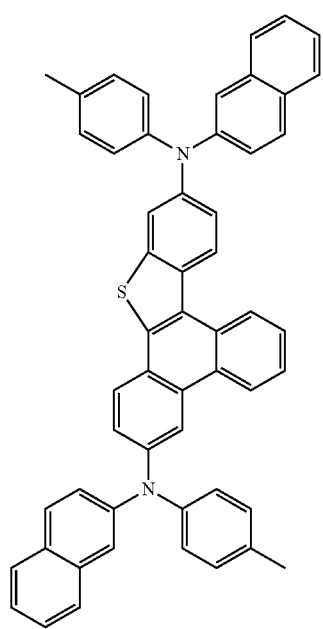
240

509
-continued
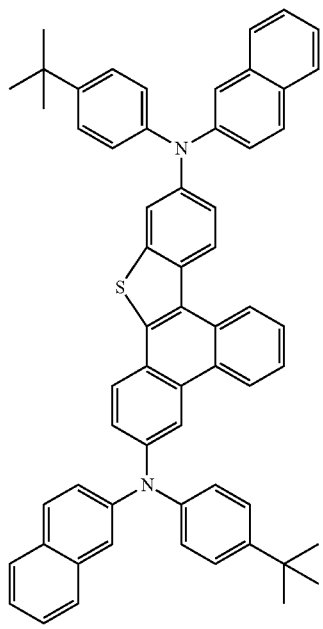
241
510
-continued
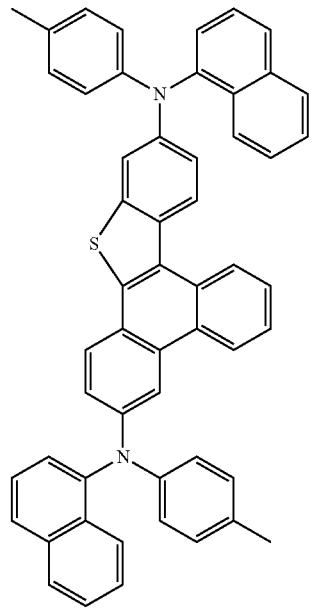
243
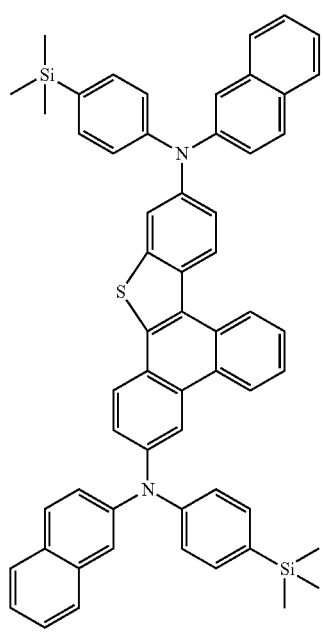
242
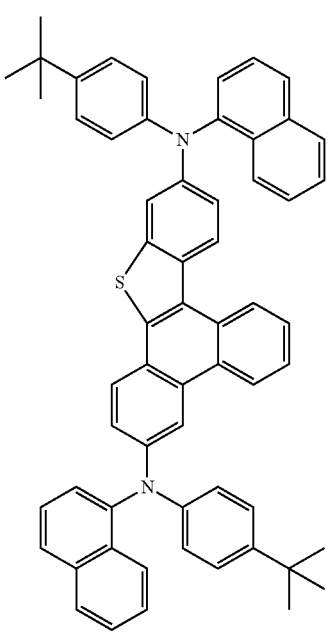
244

511
-continued
512
-continued
245
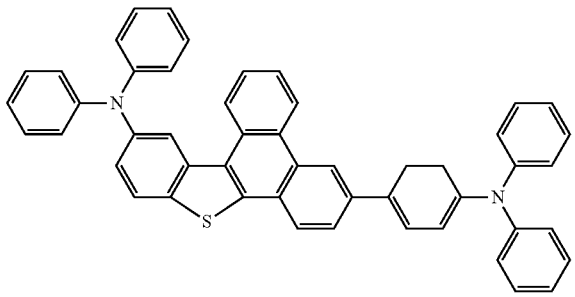
246
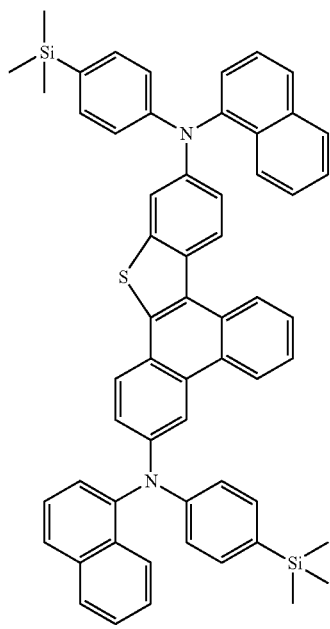
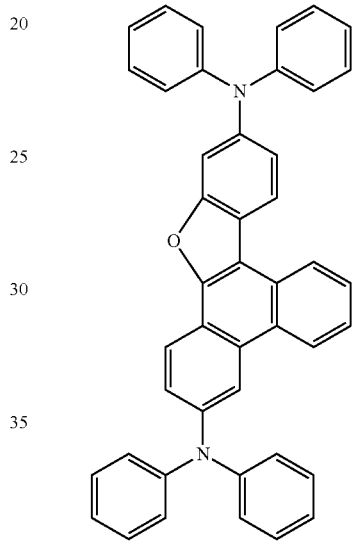
1A
247
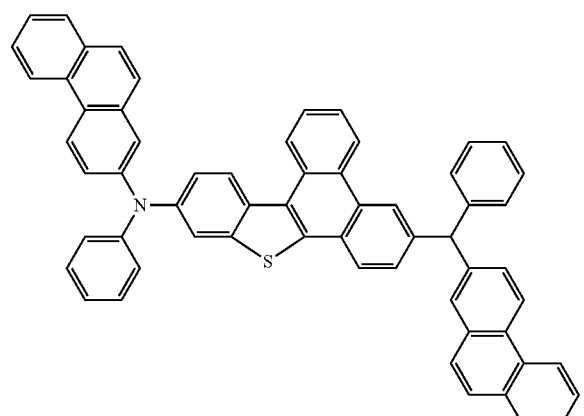
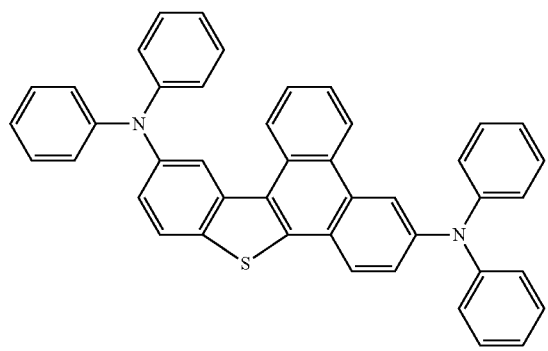
248
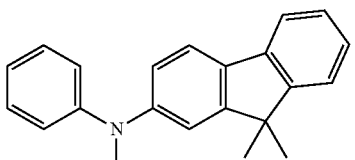
2A
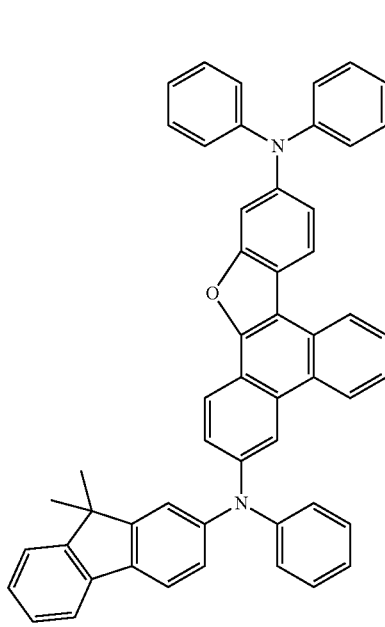

513
-continued
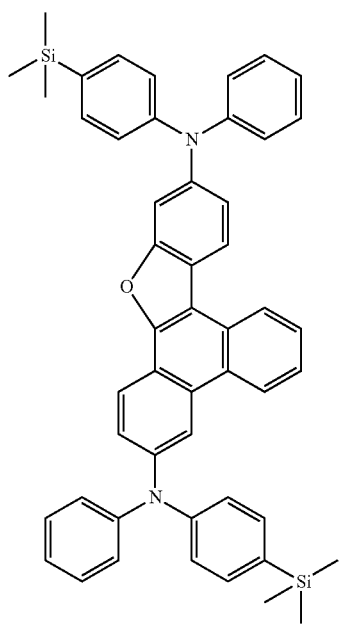
514
-continued
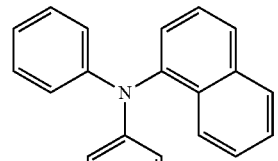
3A
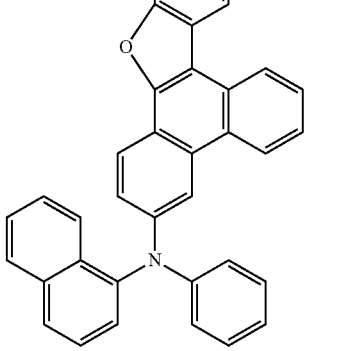
5A
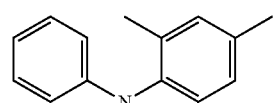
6A
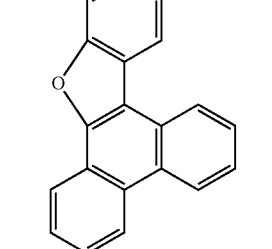
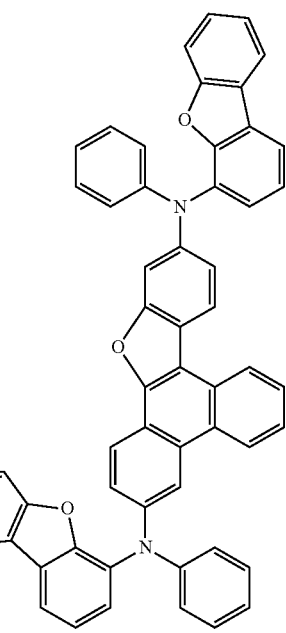
4A
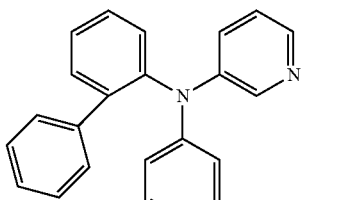
7A
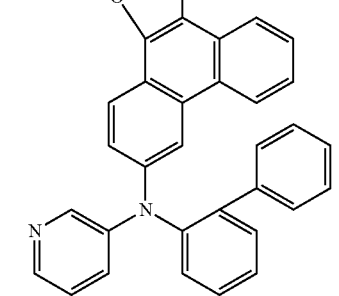

515
-continued
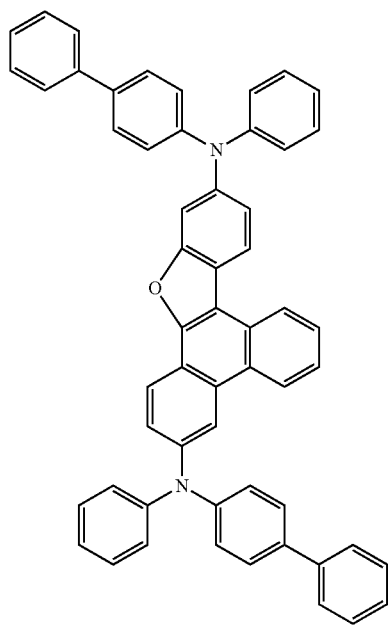
8A
516
-continued
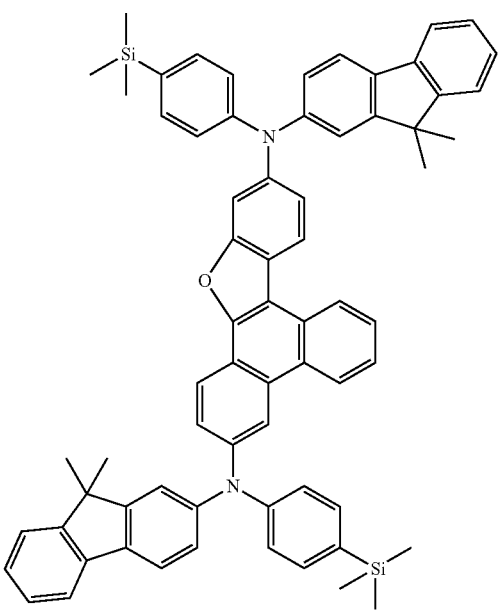
10A
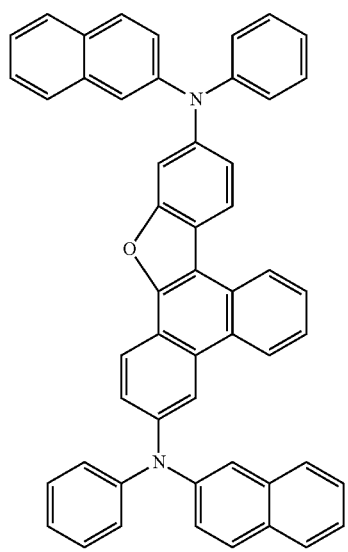
9A
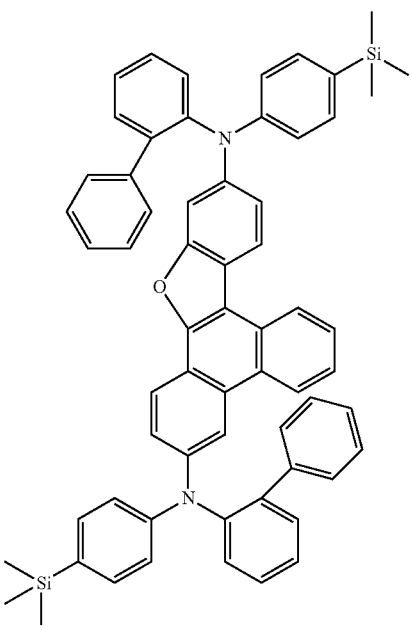
11A 517
-continued
518
-continued
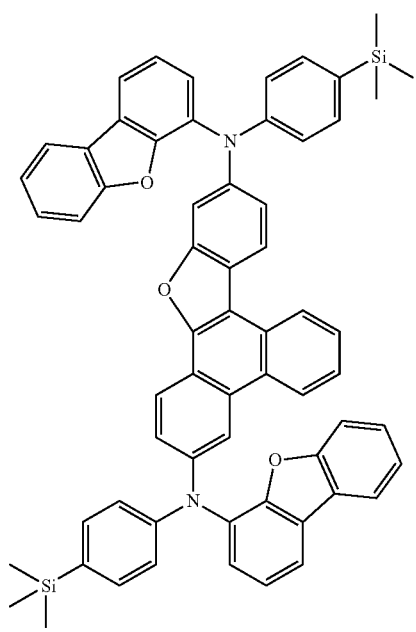
12A
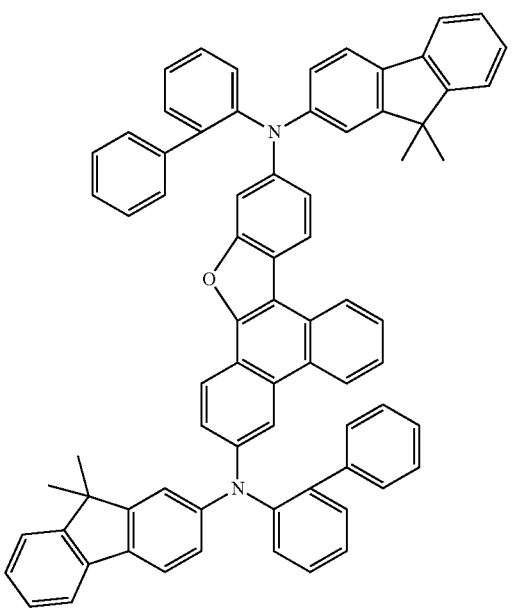
14A
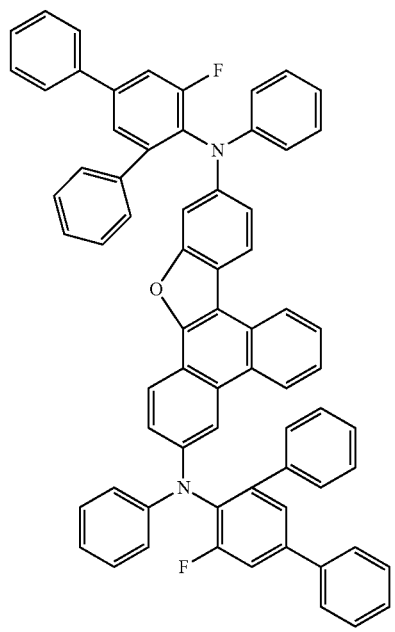
13A
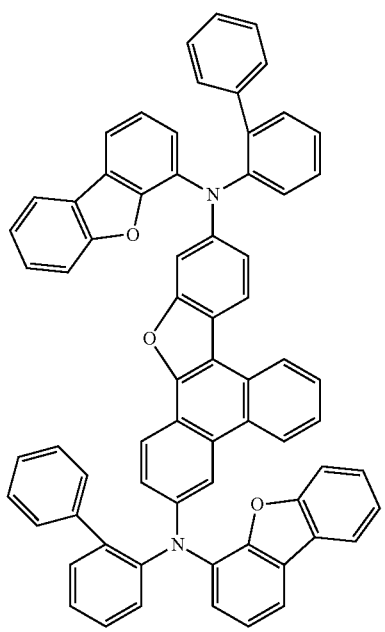
15A 519
-continued
520
-continued
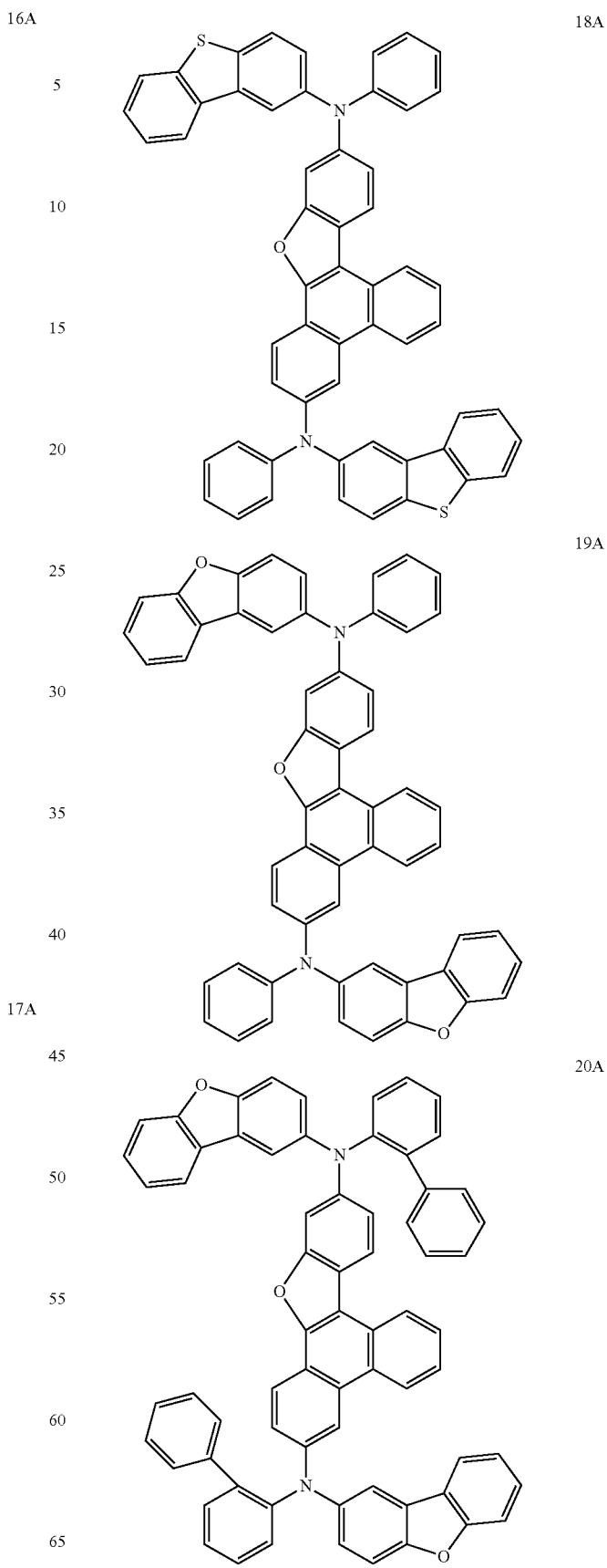

521
-continued
522
-continued
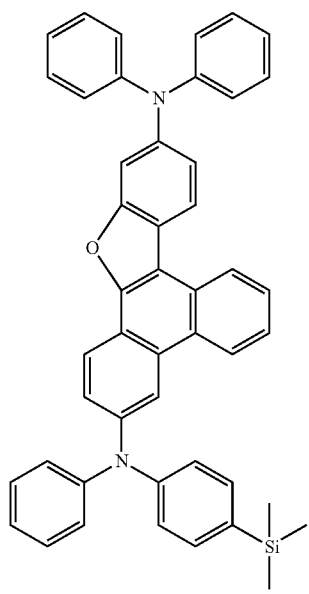
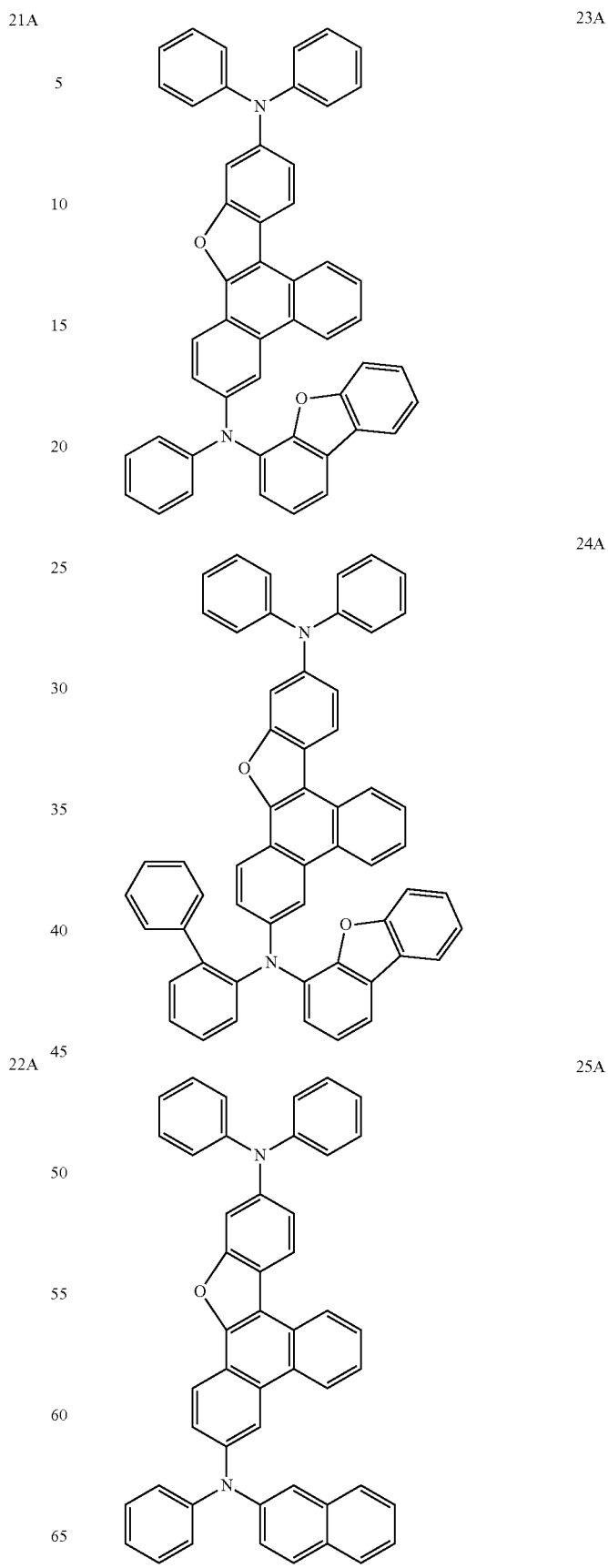

523
-continued
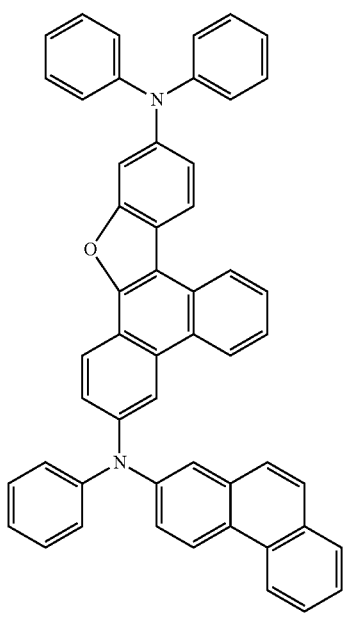
26A
524
-continued
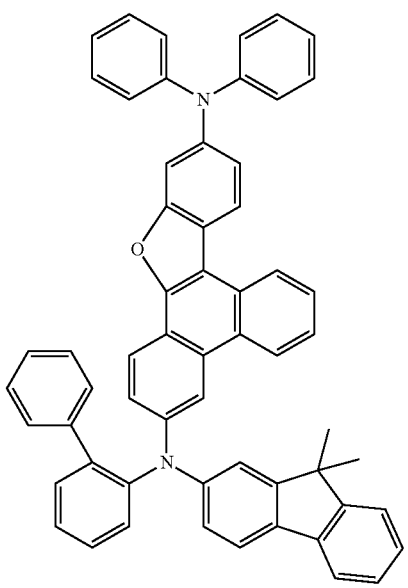
28A
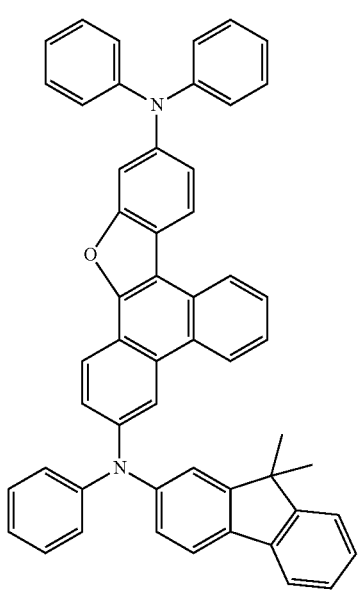
27A
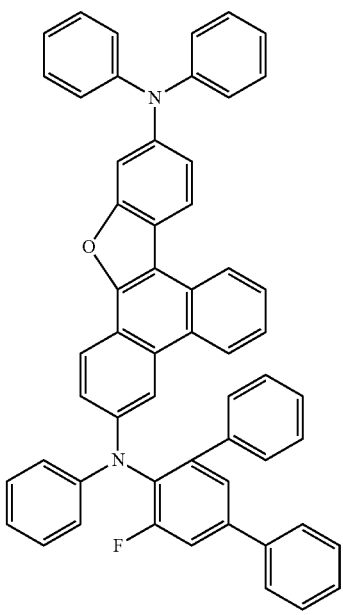
29A 525
-continued
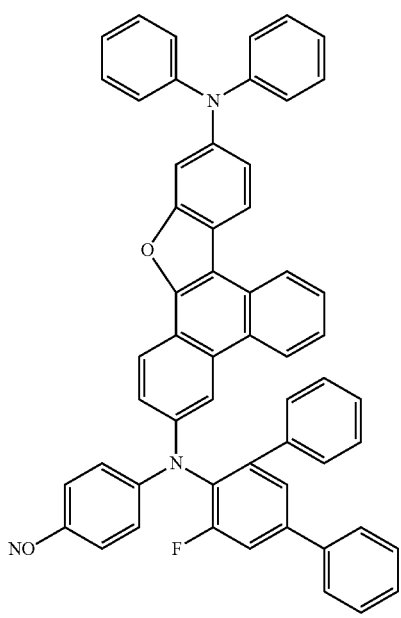
30A
526
-continued
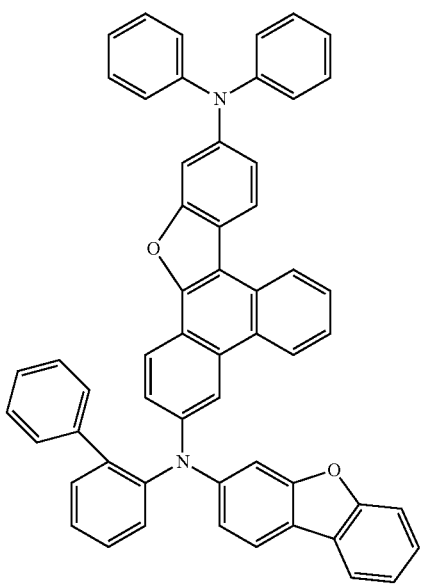
32A
31A
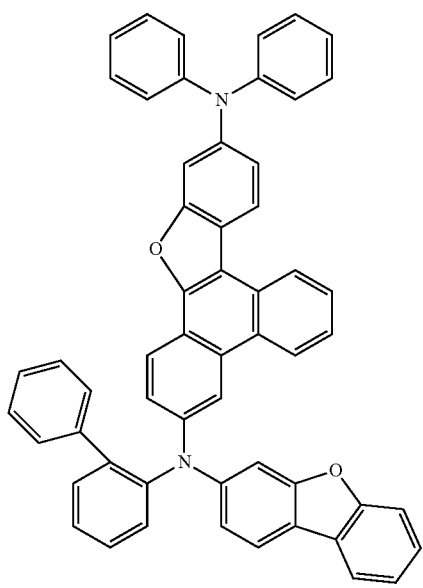
33A
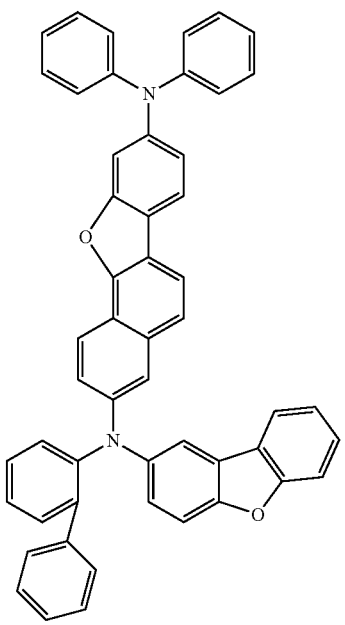

527
-continued
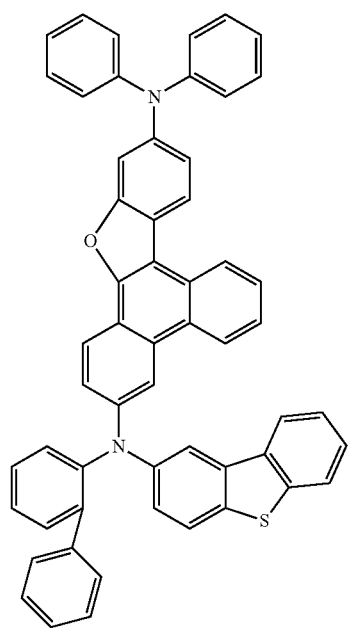
528
-continued
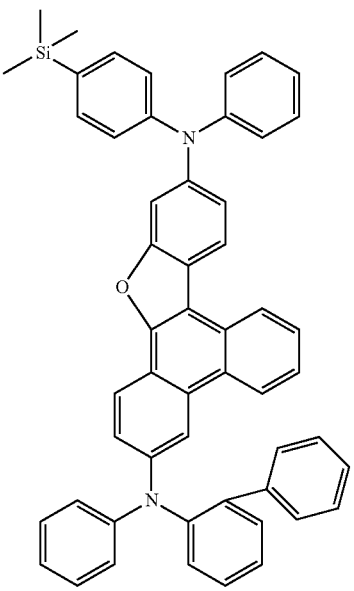
34A
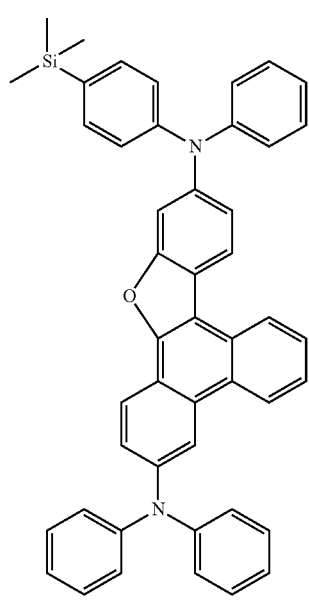
35A
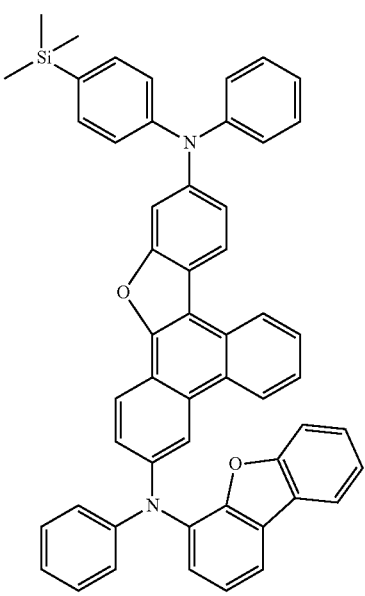
36A
37A 529
-continued
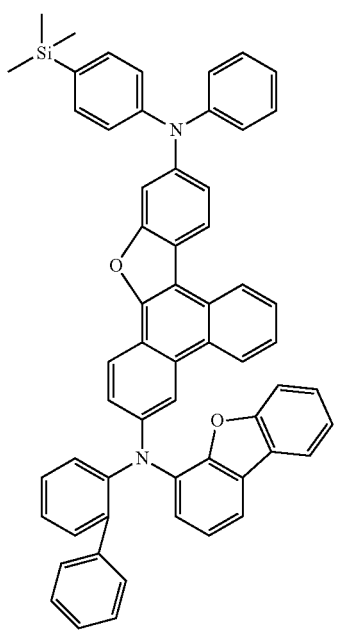
38A
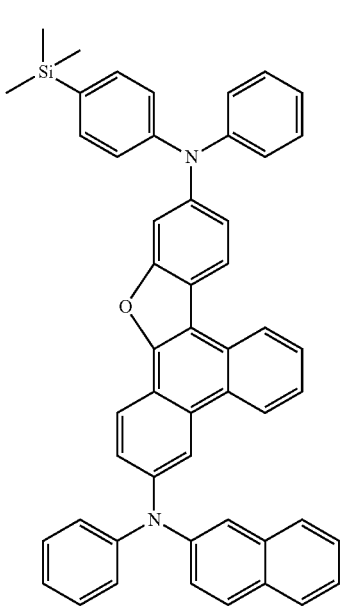
39A
530
-continued
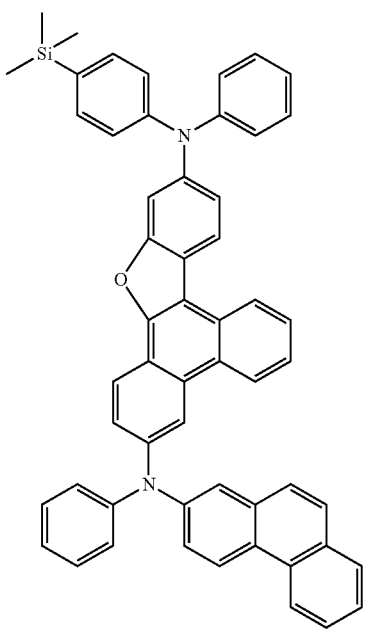
40A
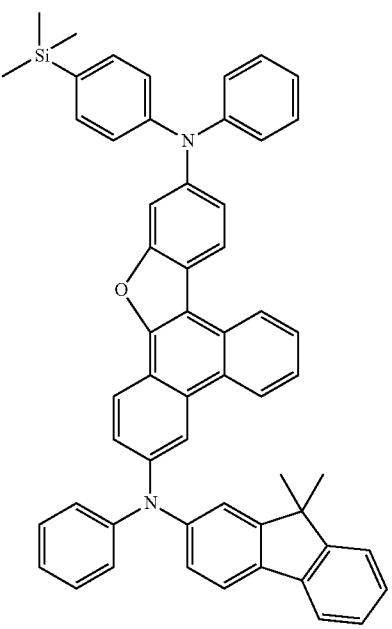
41A

531
-continued
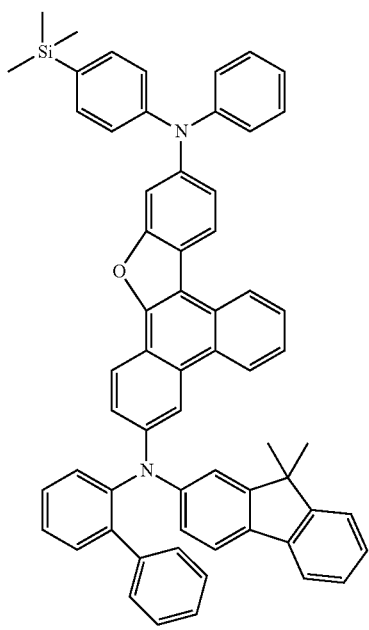
532
-continued
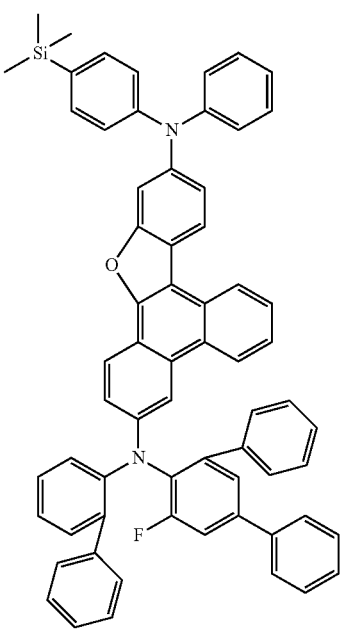
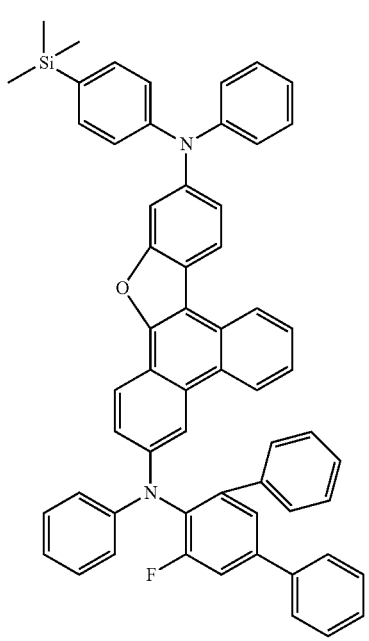
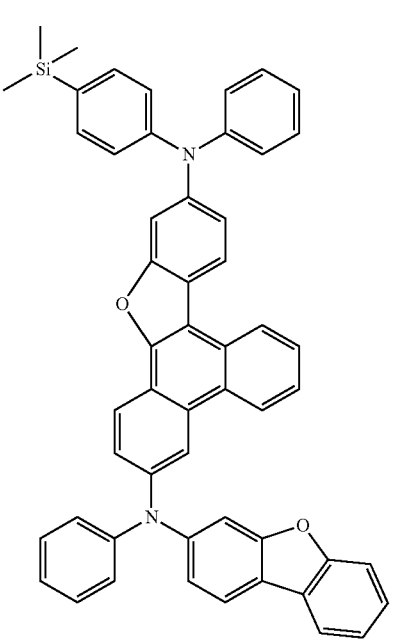

533
-continued
46A
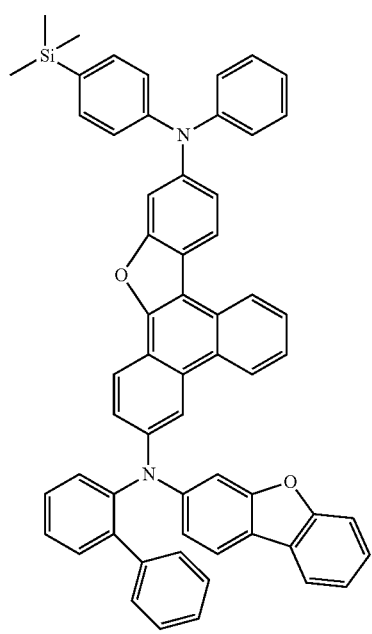
534
-continued
48A
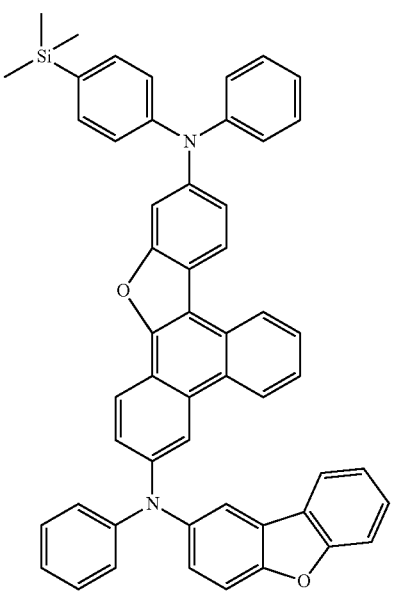
47A
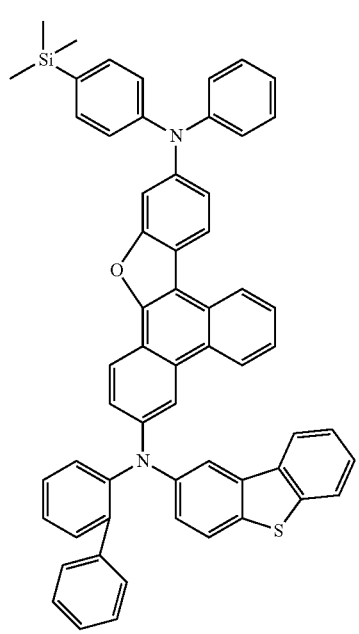
49A
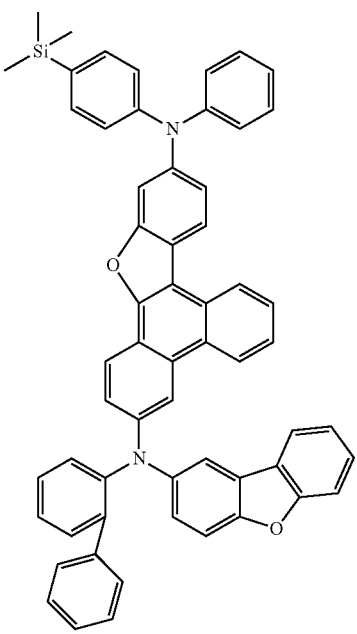

535
-continued
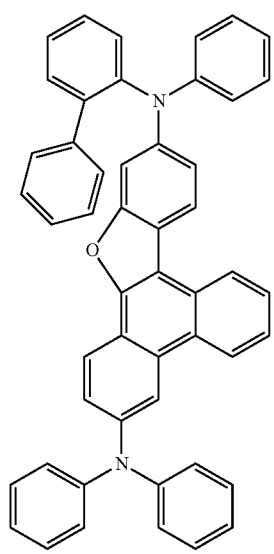
536
-continued
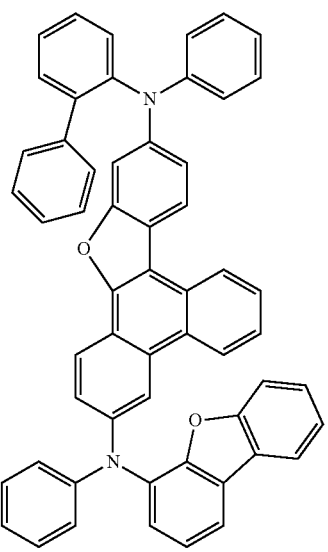
50A
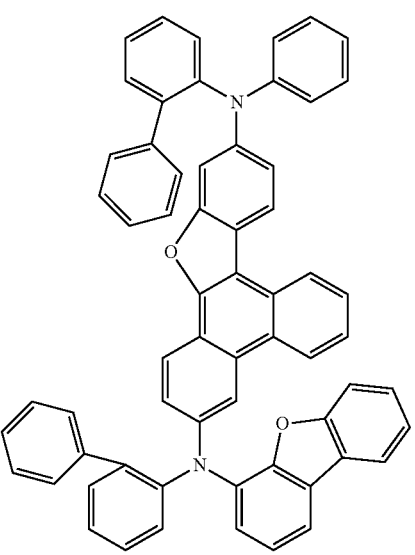
51A
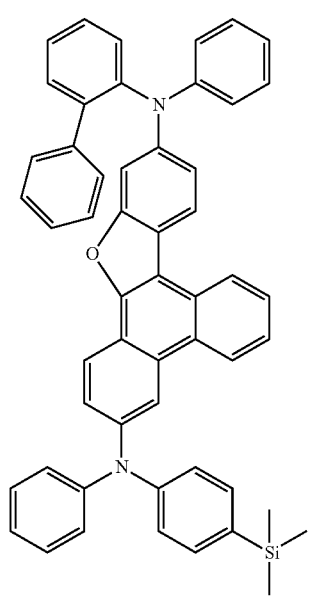
52A
53A
54A 537
-continued
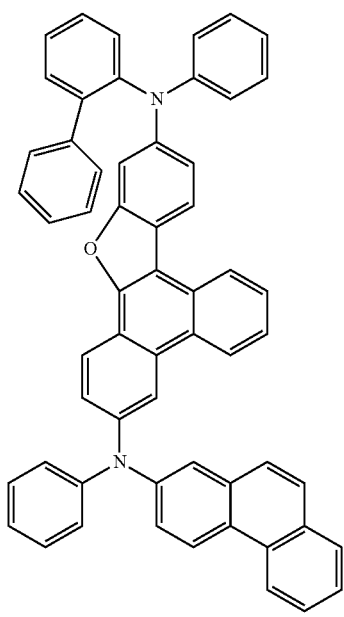
55A
538
-continued
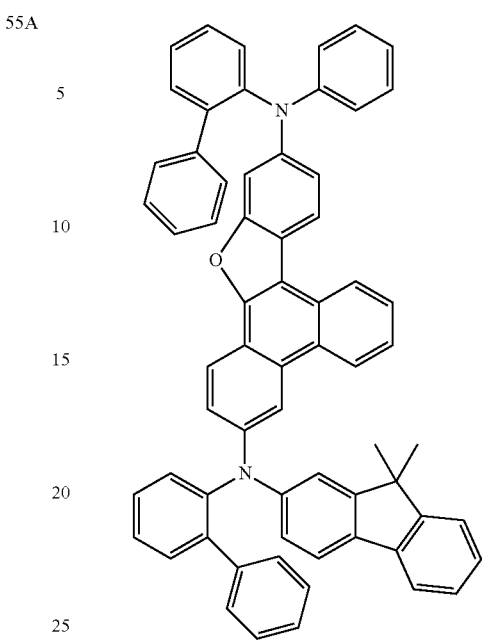
57A
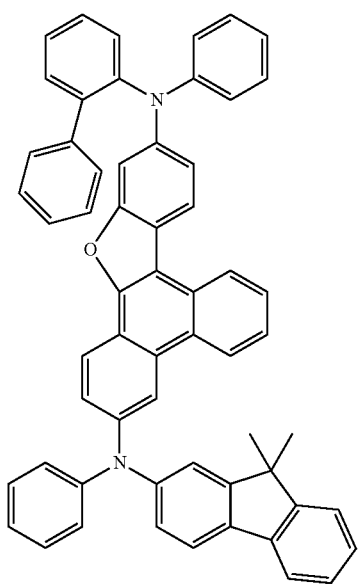
56A
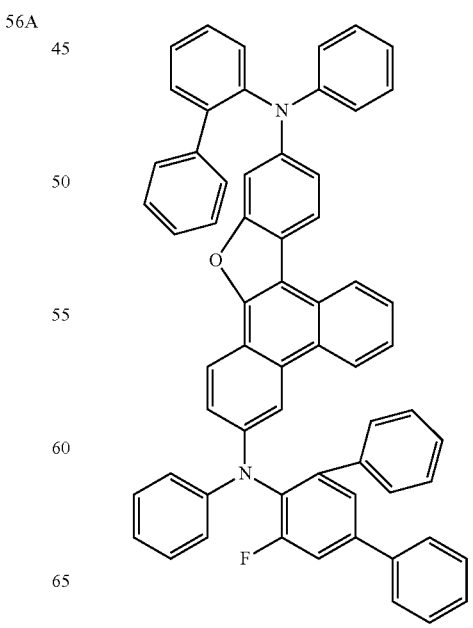
58A 539
-continued
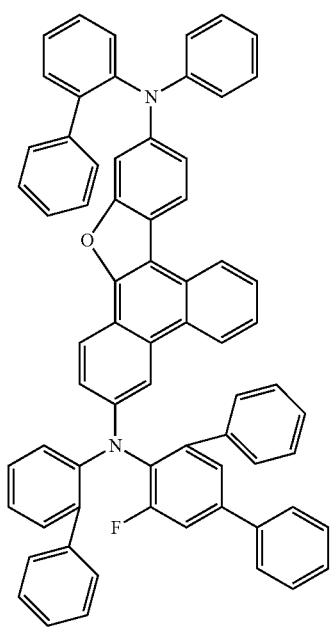
540
-continued
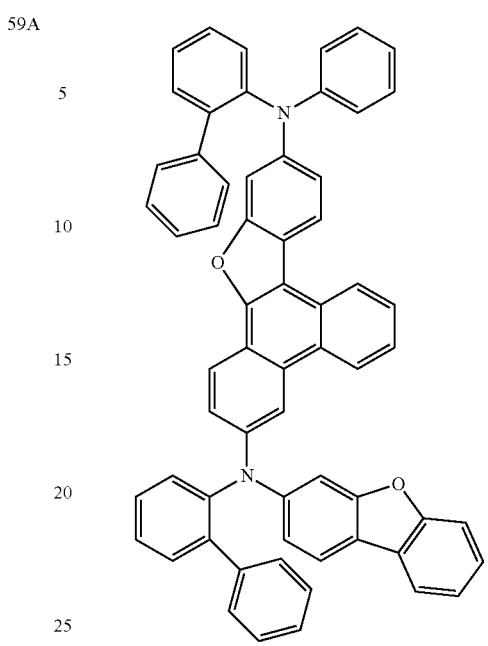
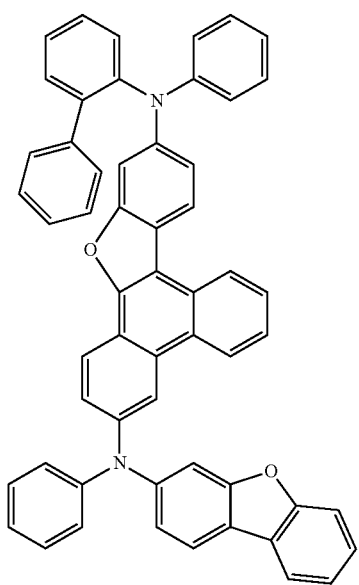
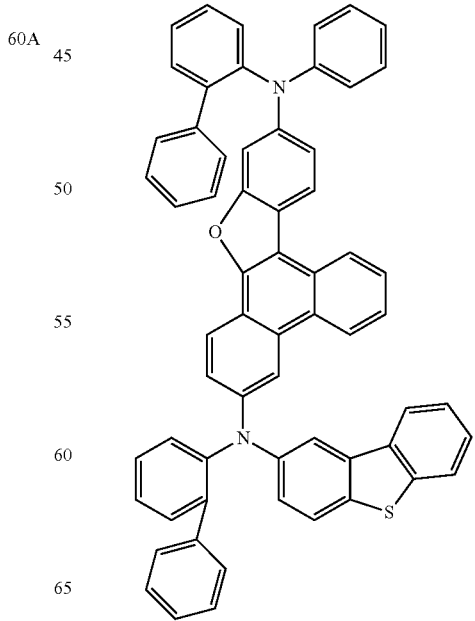

541
-continued
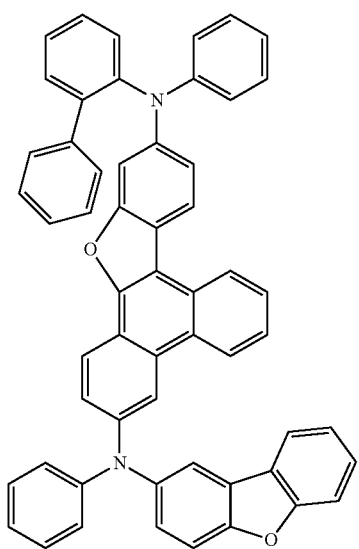
63A
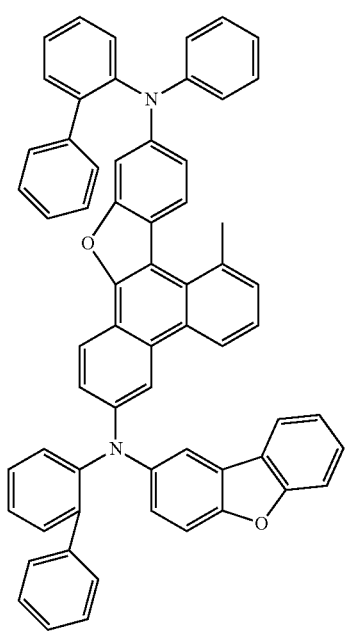
64A
542
-continued
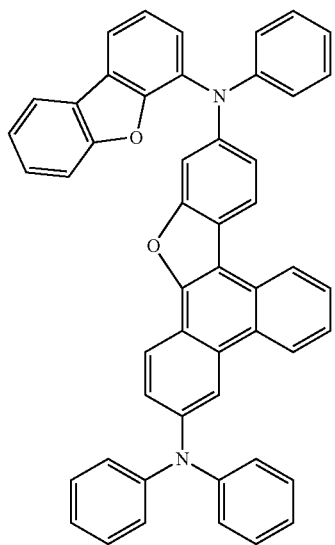
65A
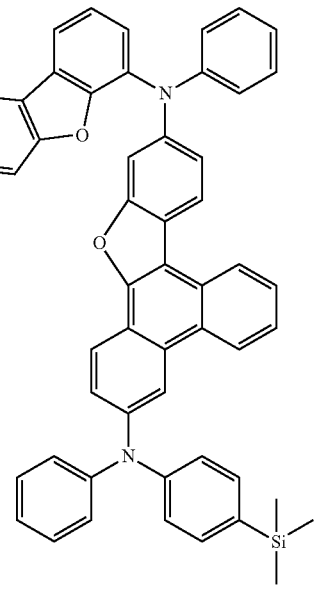
66A 543
-continued
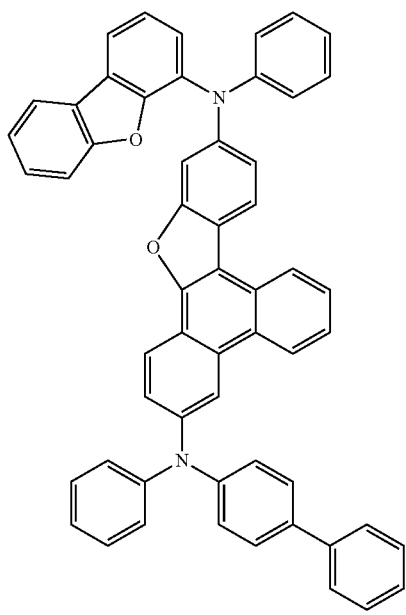
67A
544
-continued
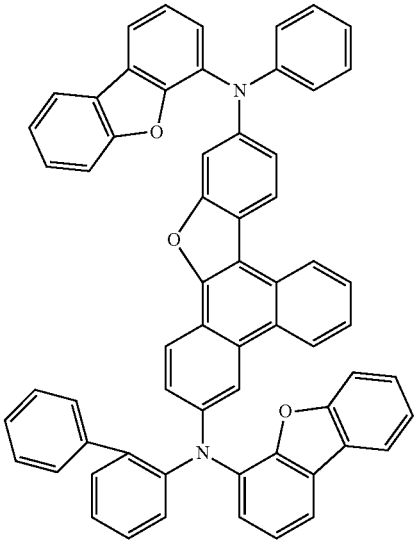
69A
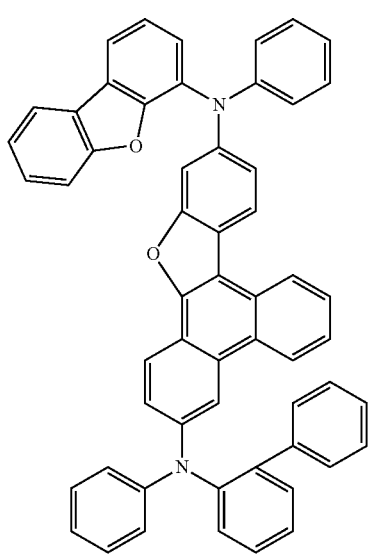
68A
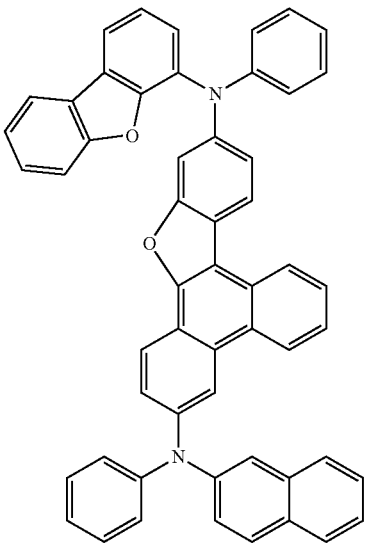
70A 545
-continued
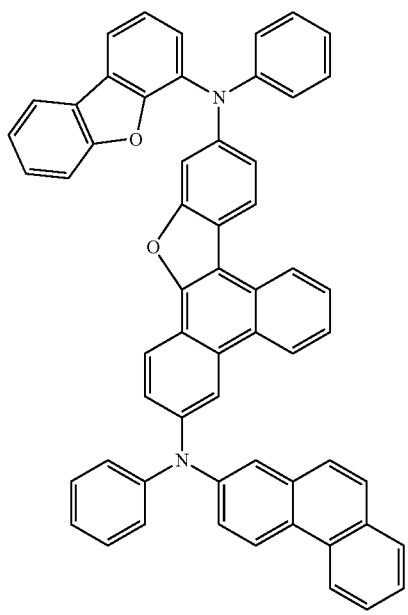
71A
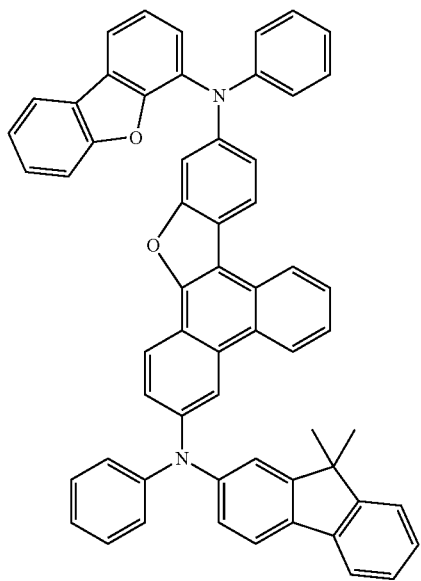
72A
546
-continued
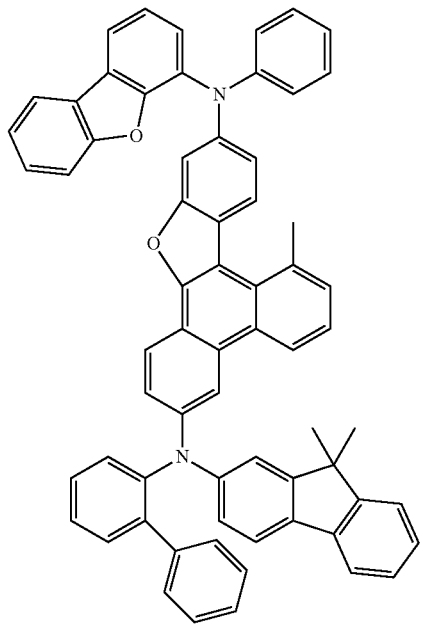
73A
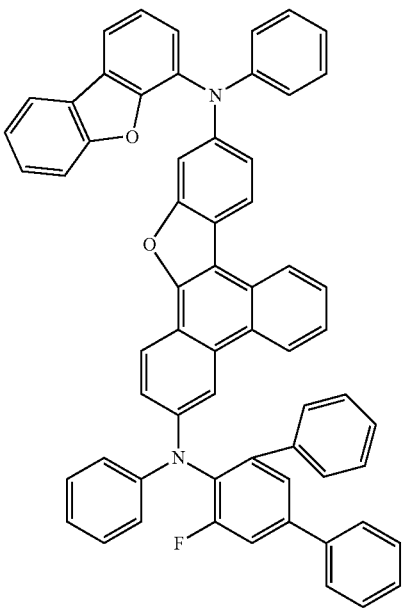
74A 547
-continued
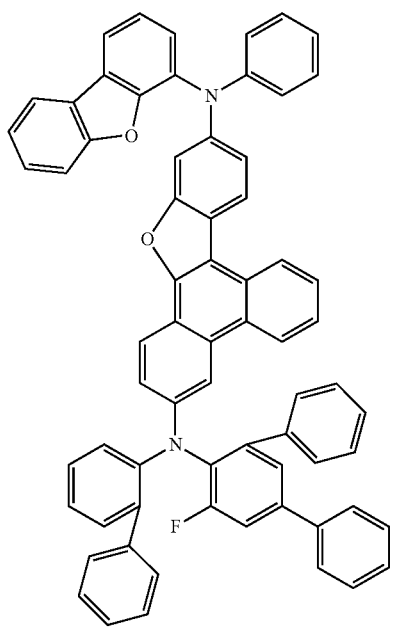
75A
548
-continued
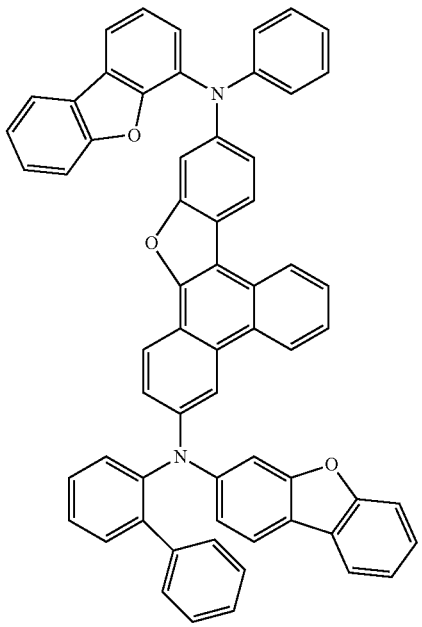
77A
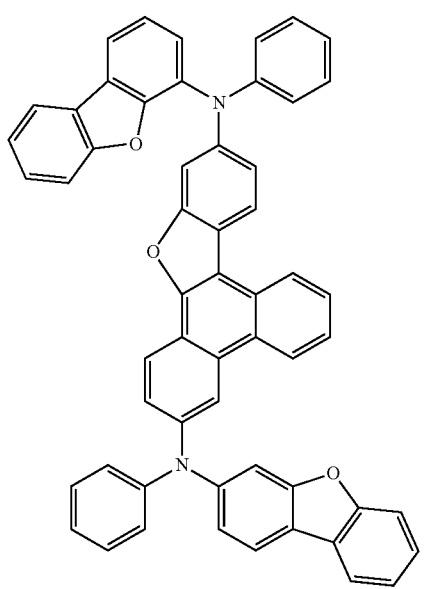
76A
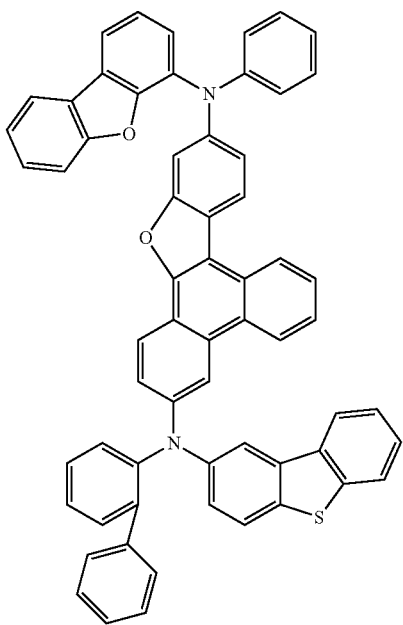
78A

549
-continued
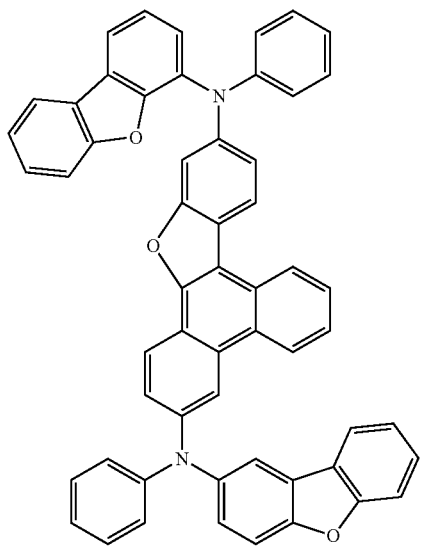
79A
550
-continued
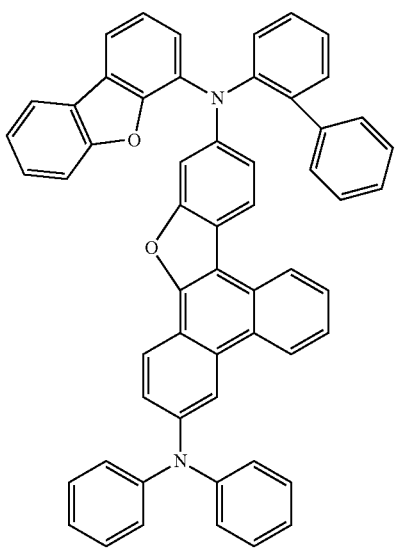
81A
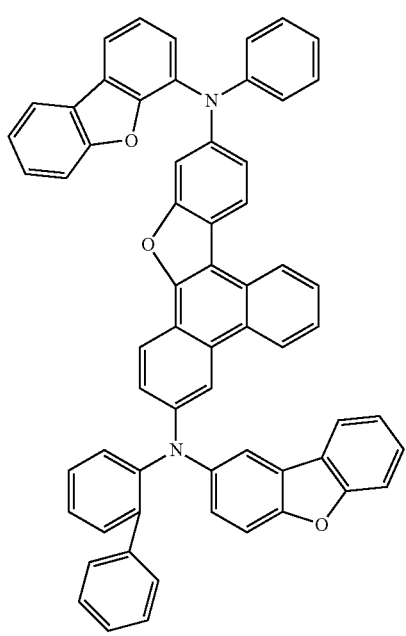
80A
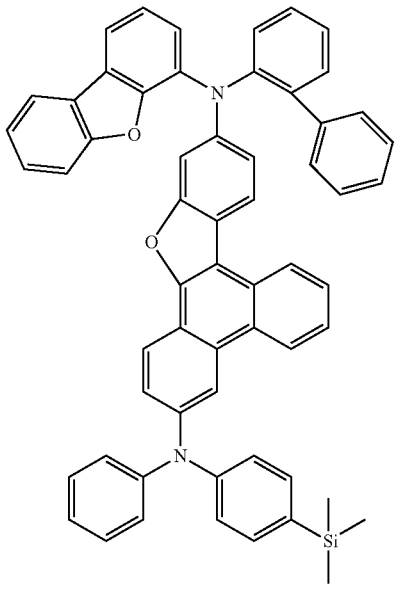
82A 551
-continued
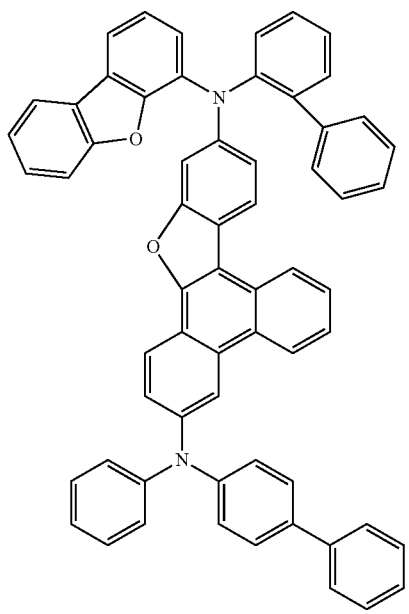
83A
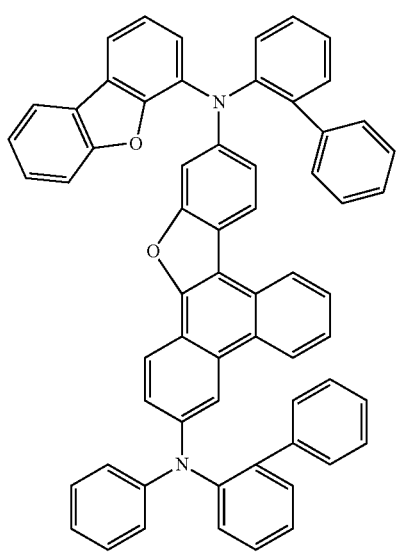
84A
552
-continued
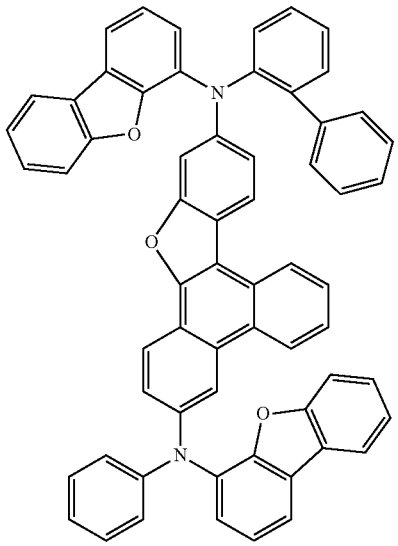
85A
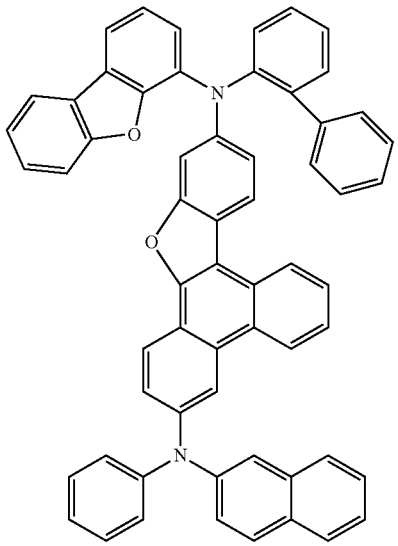
86A 553
-continued
554
-continued
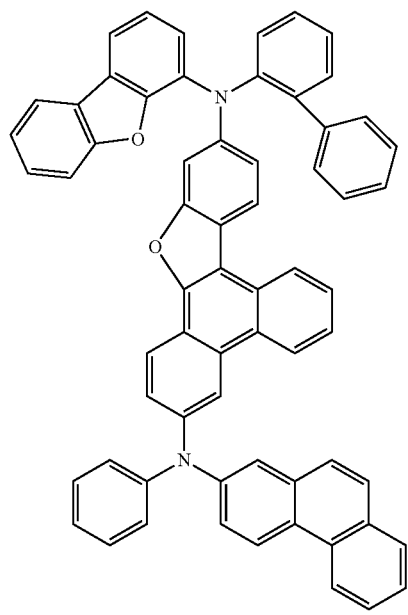
87A
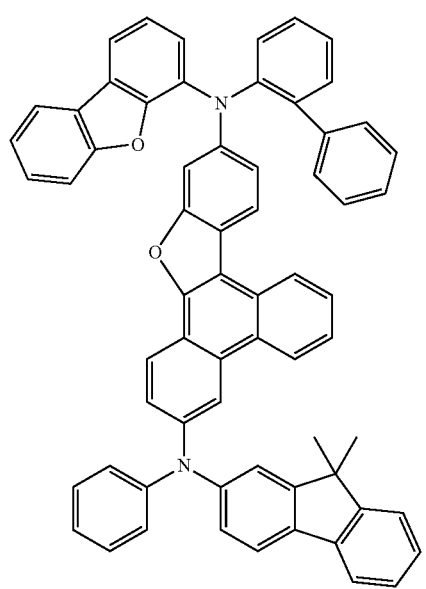
88A
89A
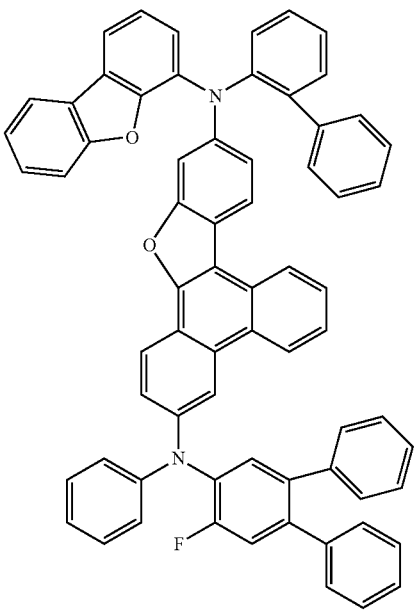
90A 555
-continued
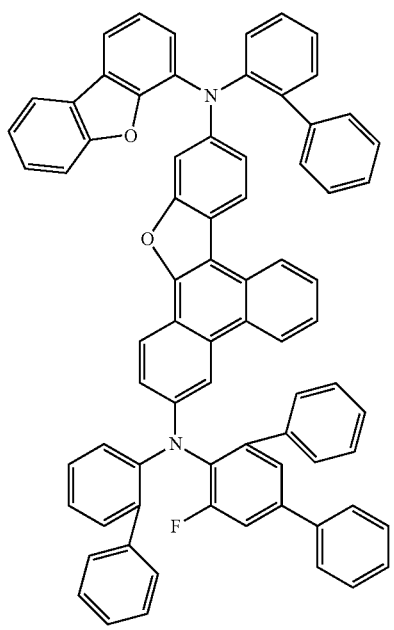
91A
556
-continued
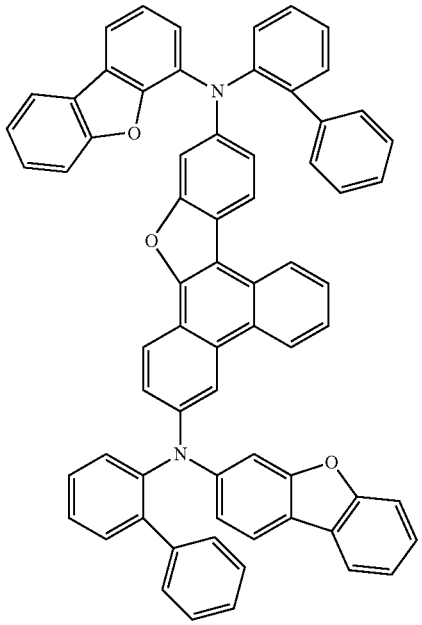
93A
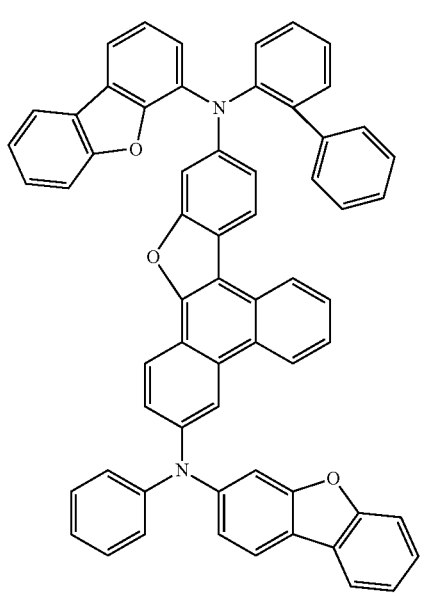
92A
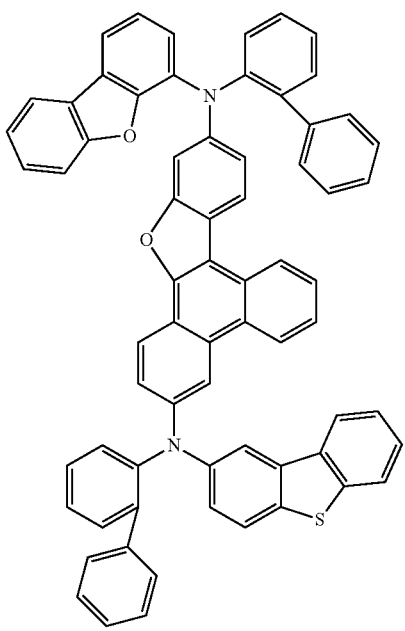
94A 557
-continued
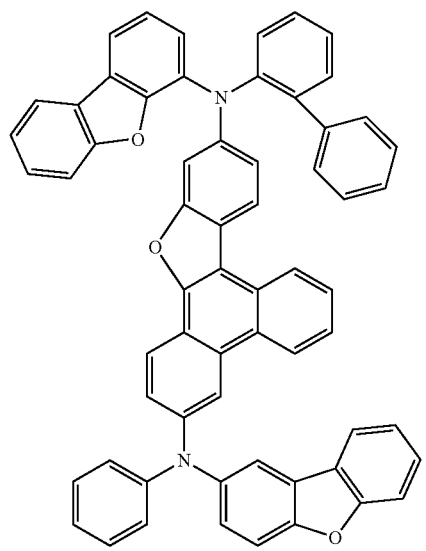
95A
558
-continued
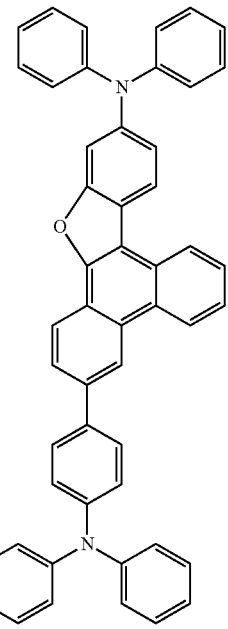
97A
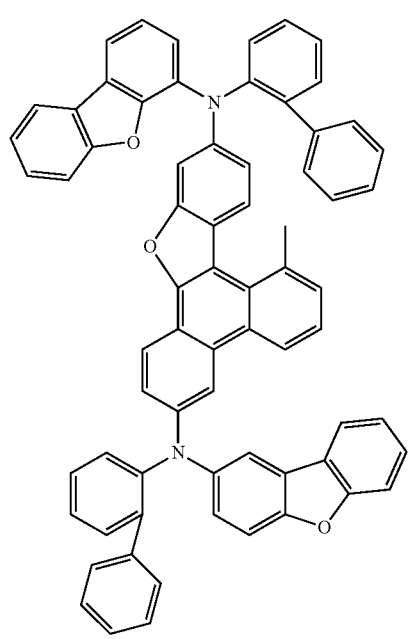
96A
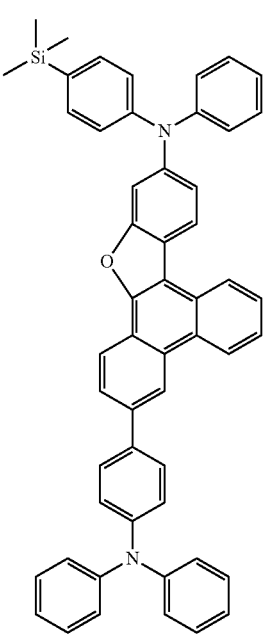
98A 559  
-continued
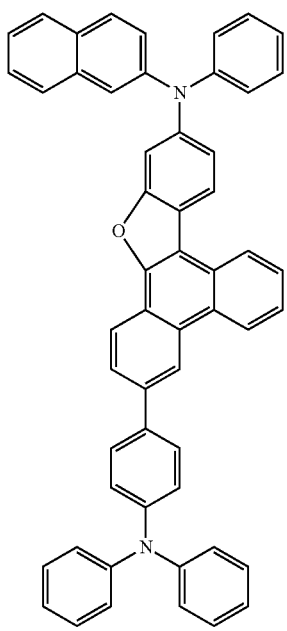
99A
560  
-continued
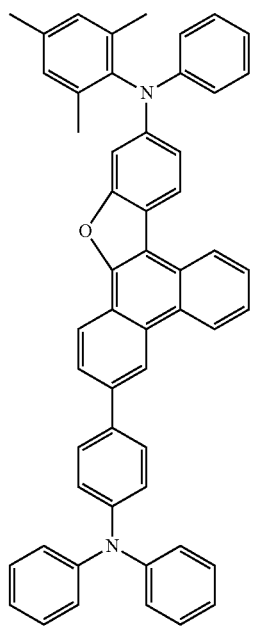
101A
100A
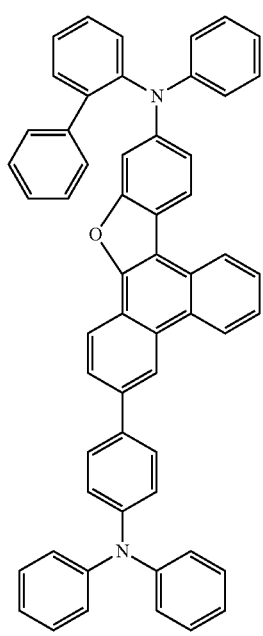
102A
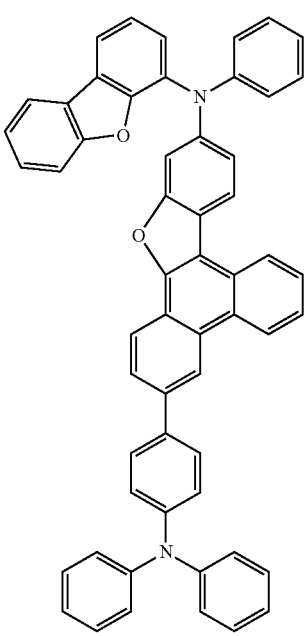

561
-continued
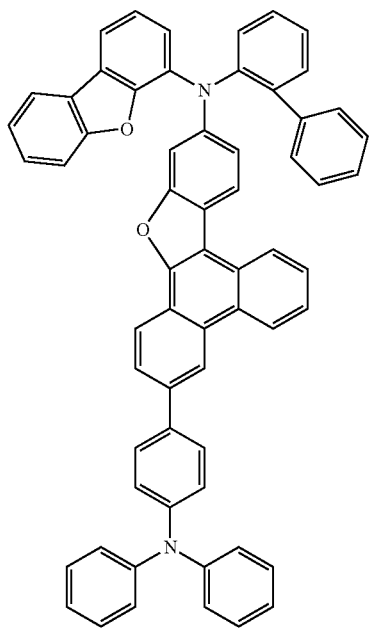
103A
562
-continued
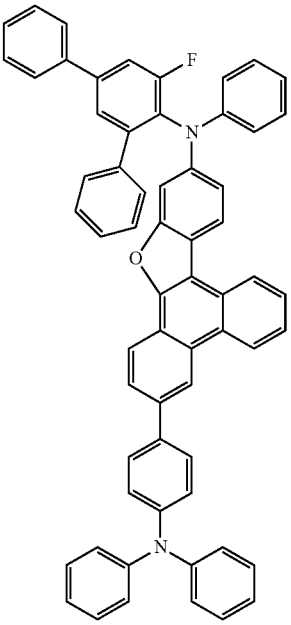
105A
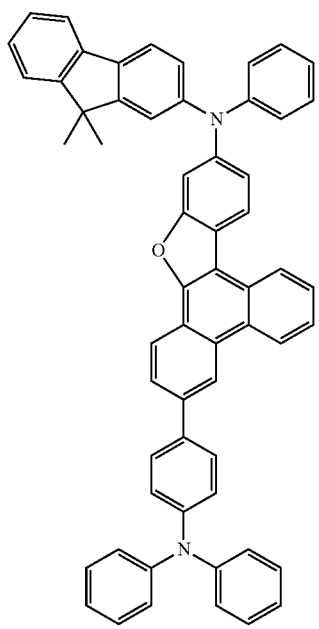
104A
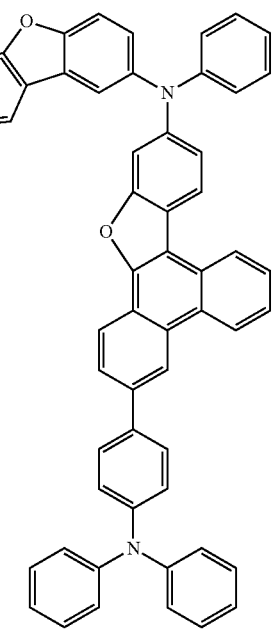
106A 563
-continued
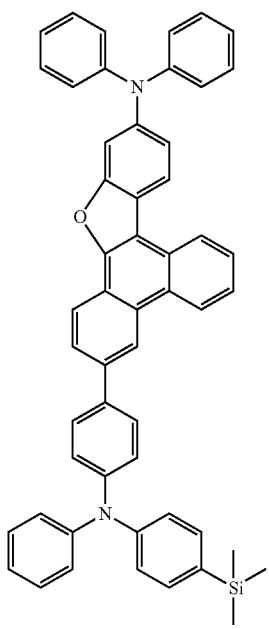
107A
564
-continued
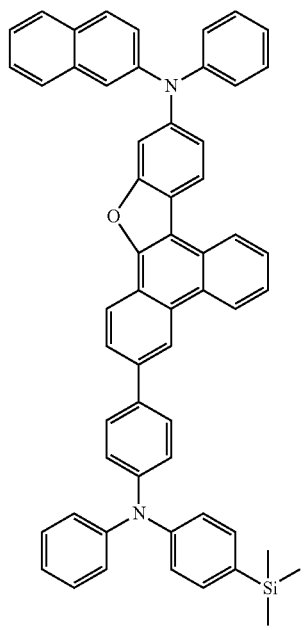
109A
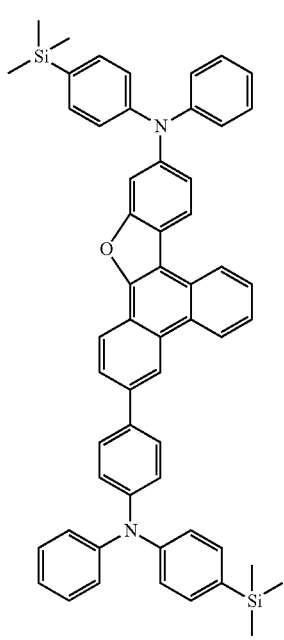
108A
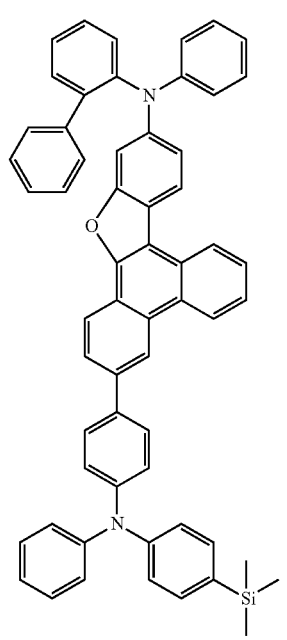
110A 565
-continued
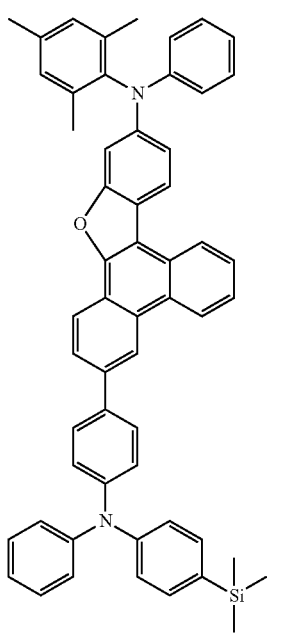
566
-continued
111A
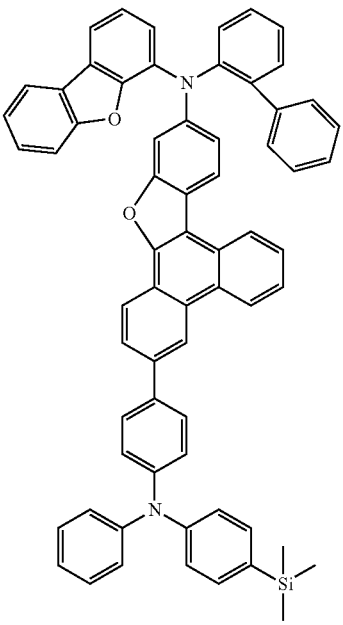
113A
112A
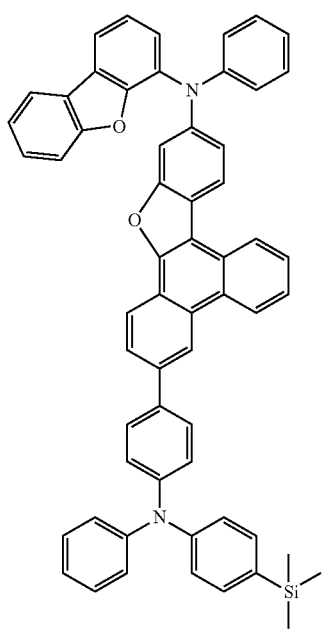
114A
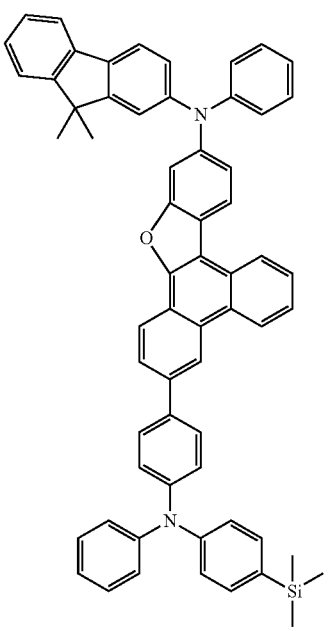

567
-continued
568
-continued
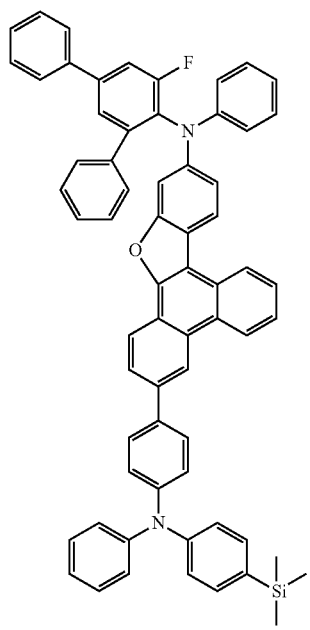
115A
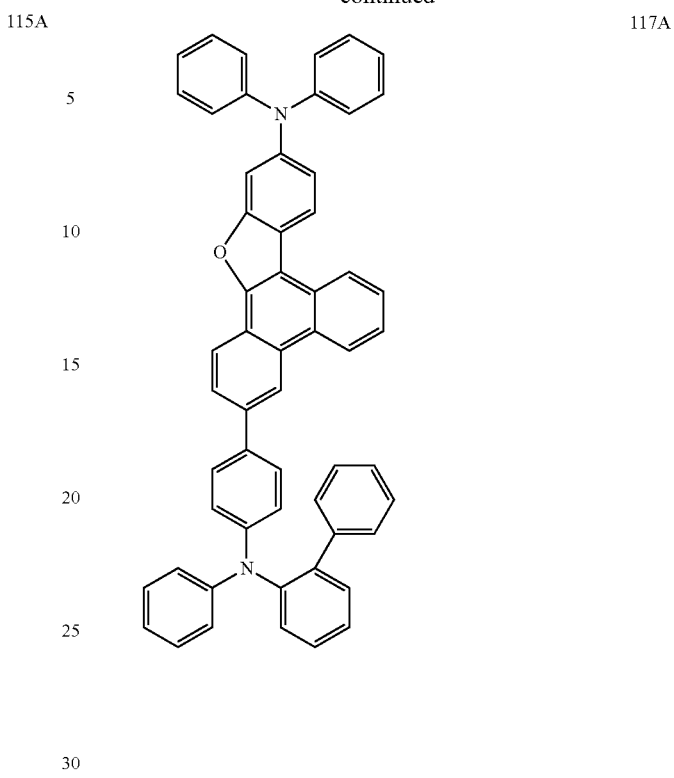
117A
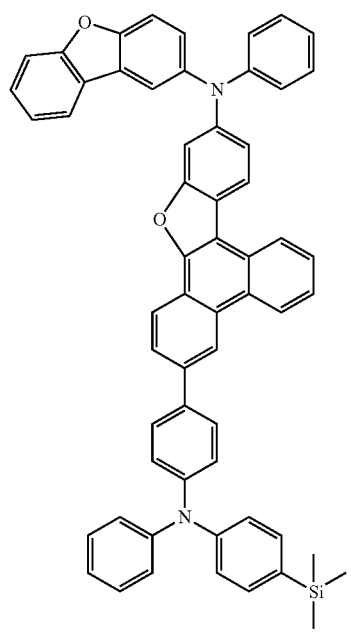
116A
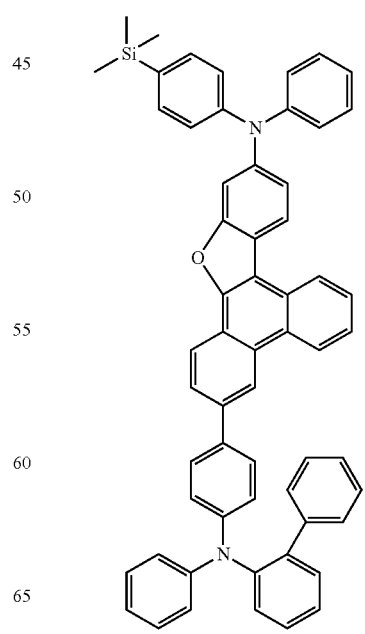
118A

569
-continued
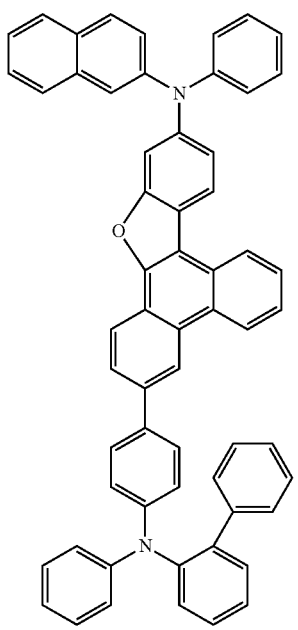
570
-continued
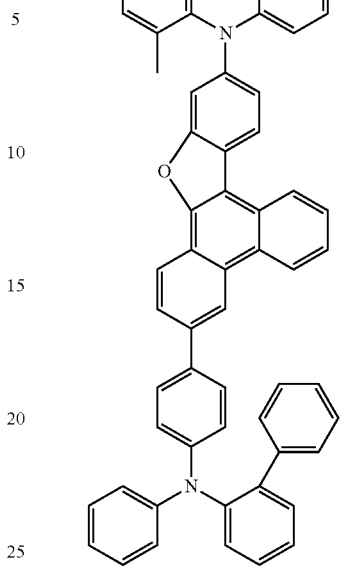
119A
121A
120A
122A
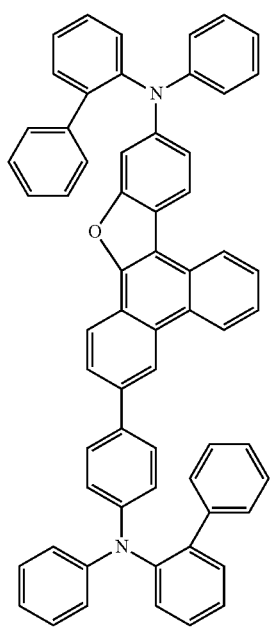
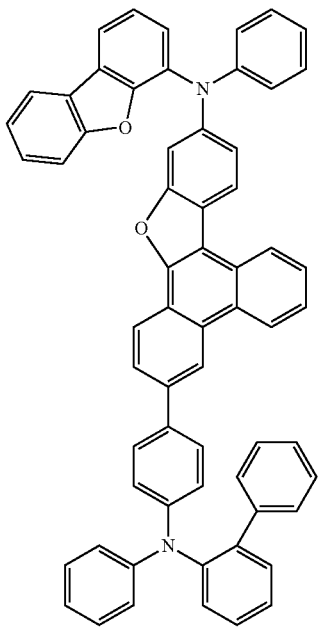

571
-continued
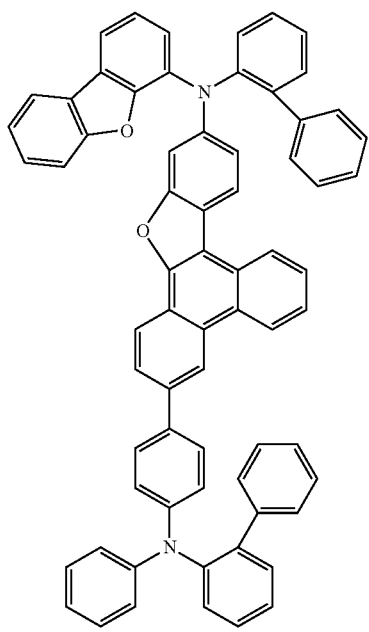
123A
572
-continued
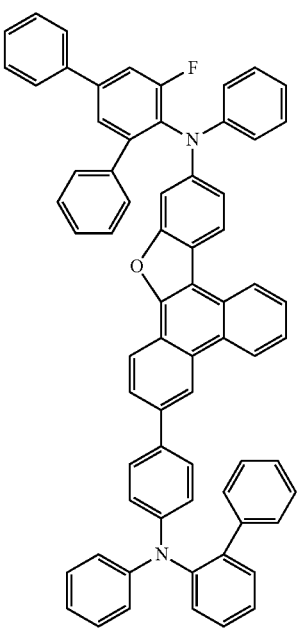
125A
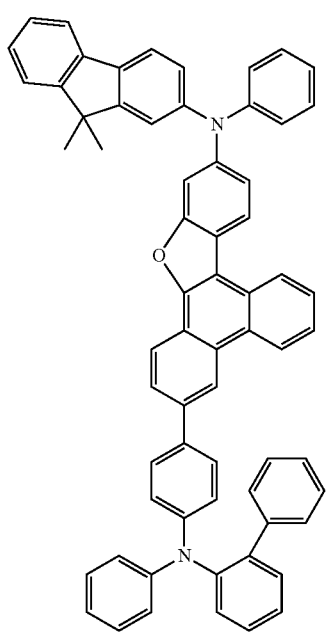
124A
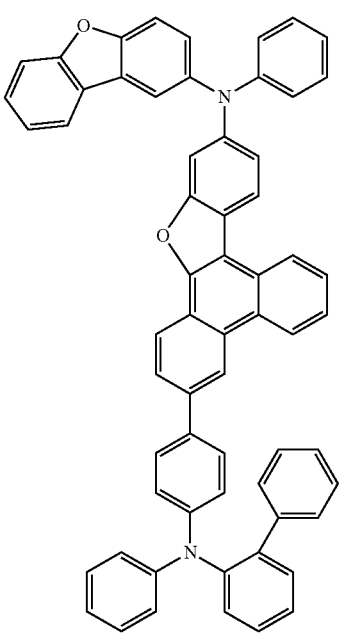
126A 573
-continued
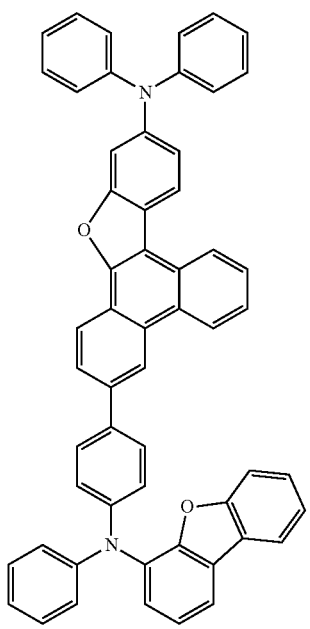
127A
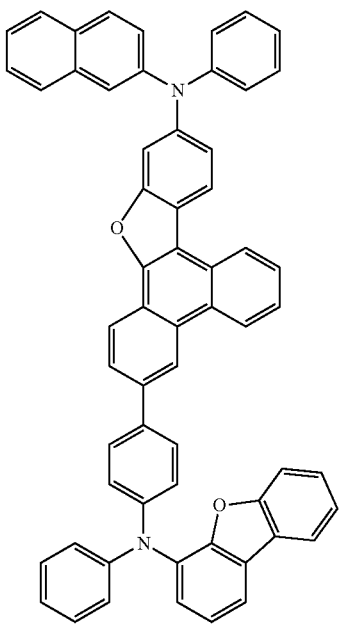
129A
574
-continued
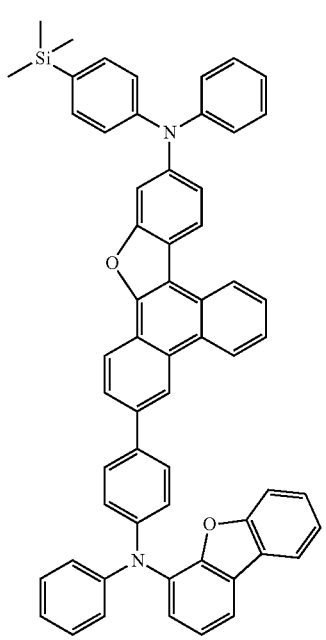
128A
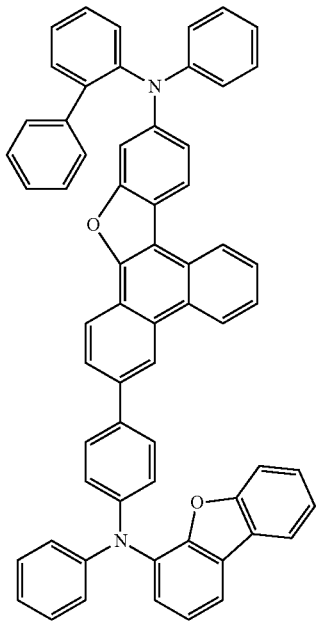
130A 575
-continued
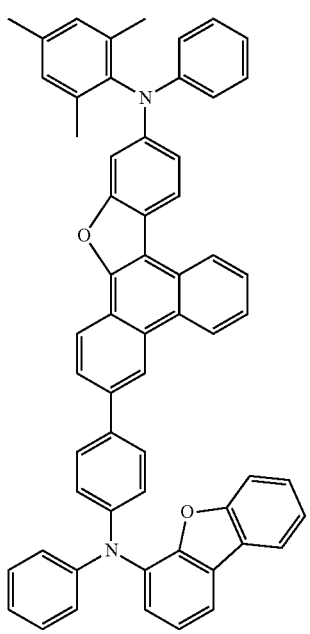
131A
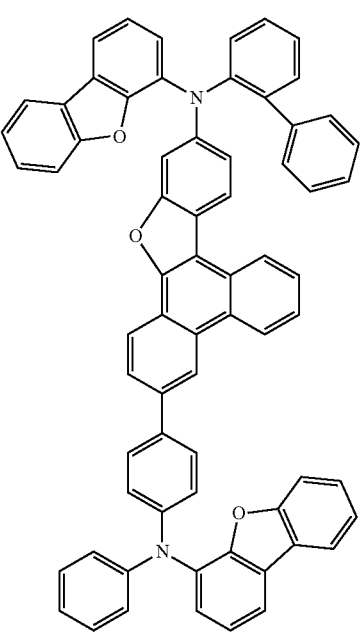
133A
576
-continued
132A
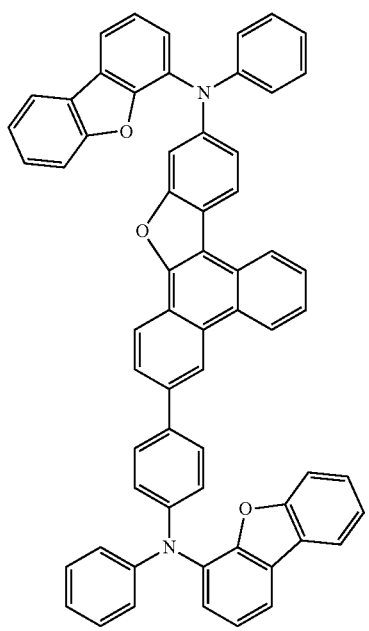
134A
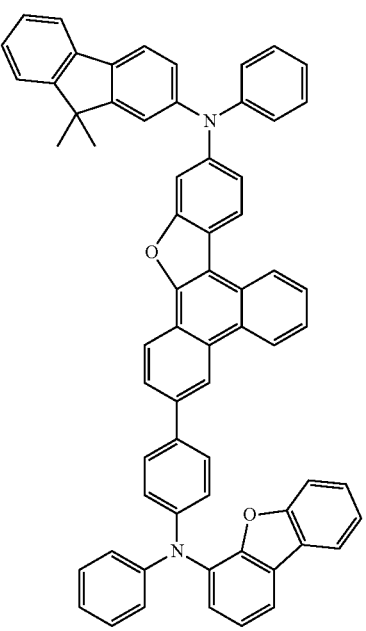

577
-continued
135A
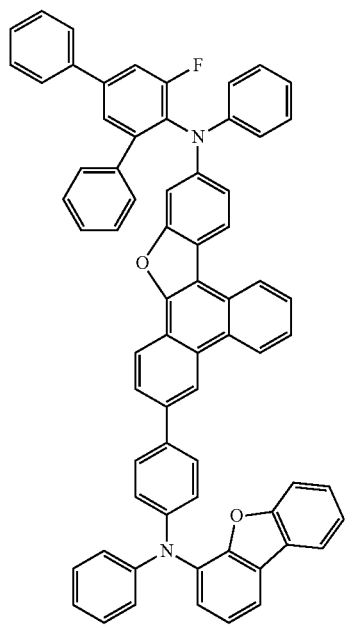
578
-continued
137A
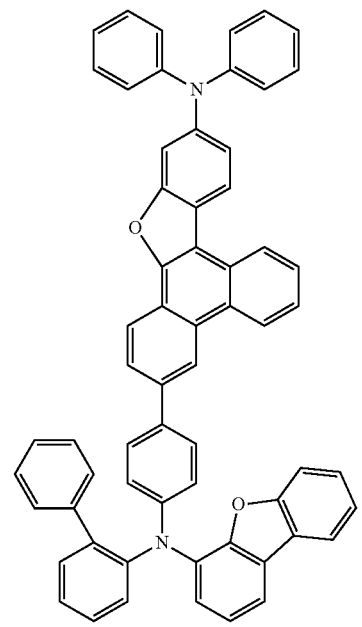
136A
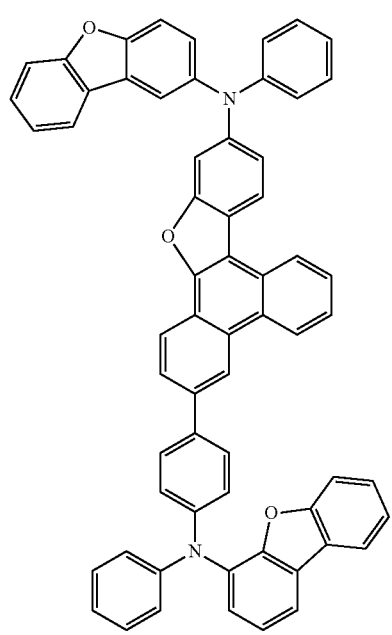
138A
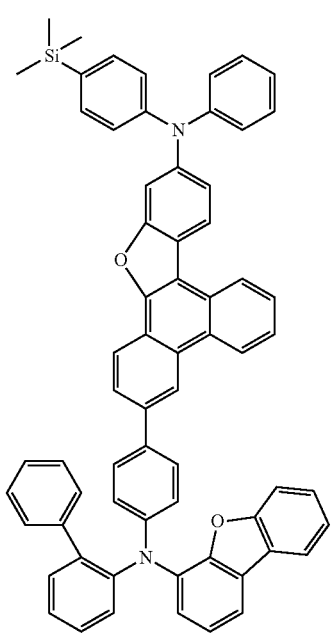

579
-continued
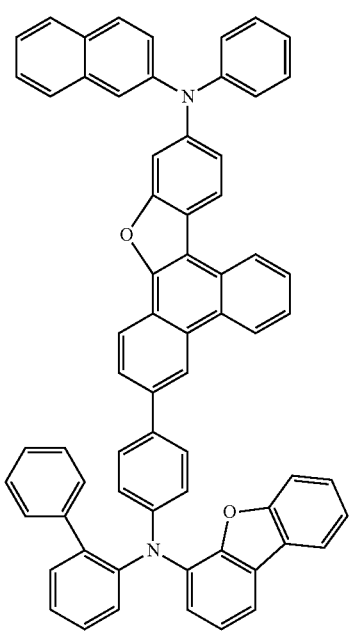
139A
580
-continued
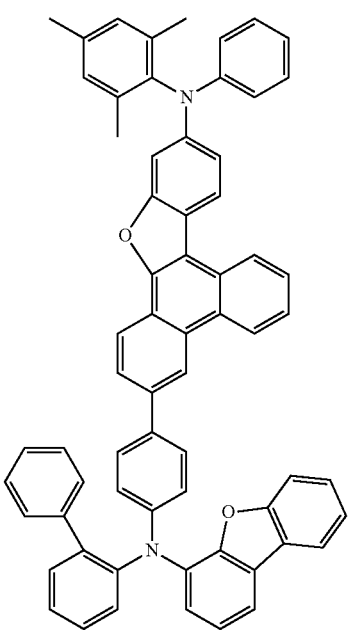
141A
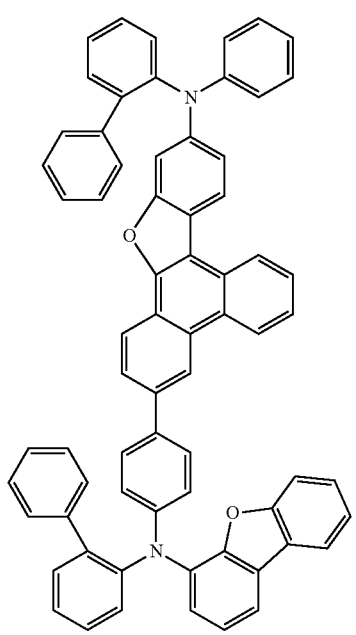
140A
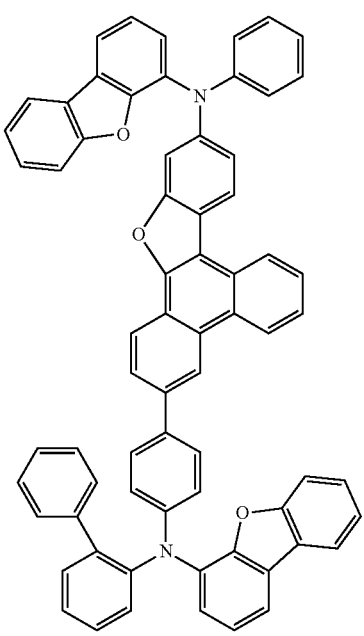
142A

581
-continued
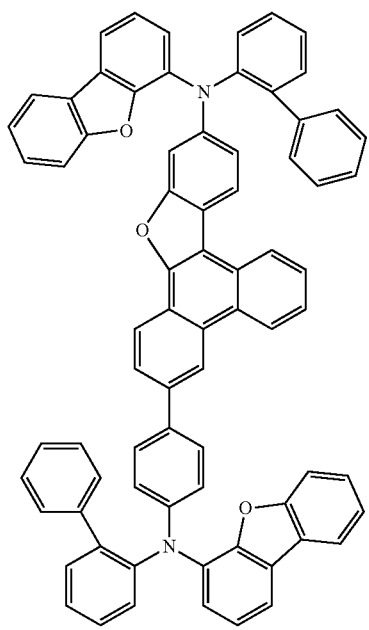
143A
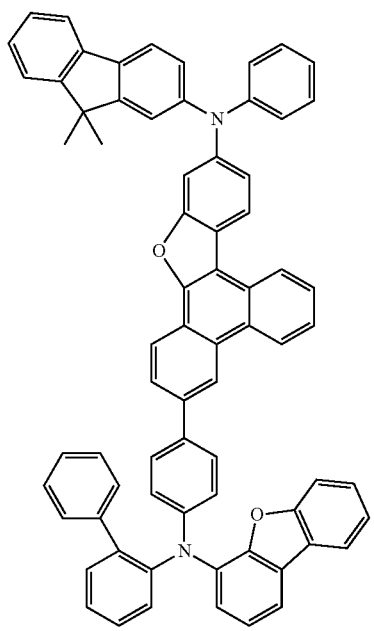
144A
582
-continued
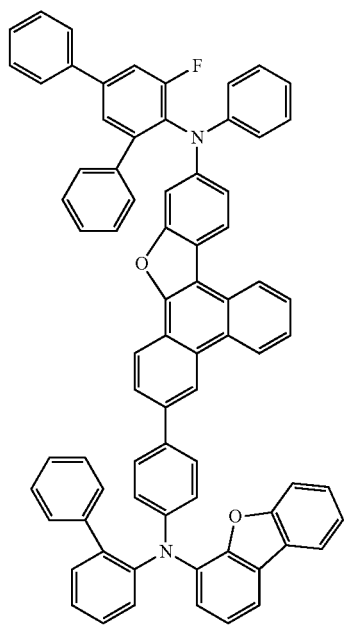
145A
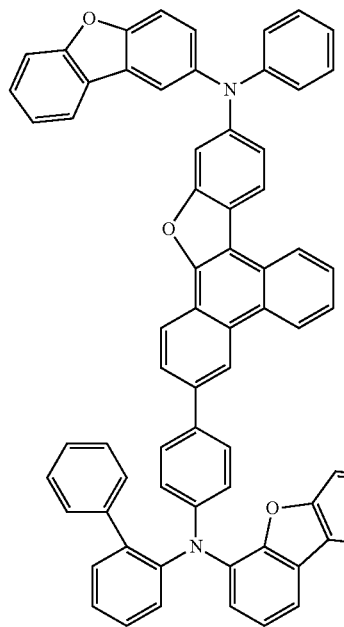
146A 583
-continued
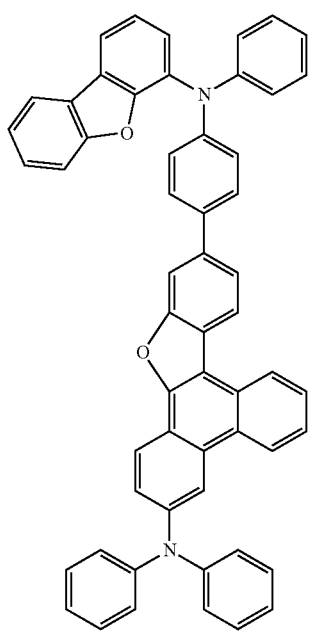
147A
584
-continued
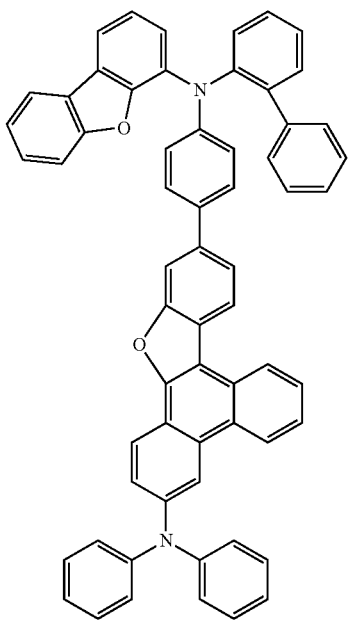
149A
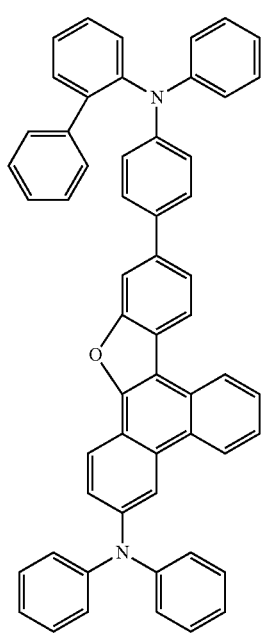
148A
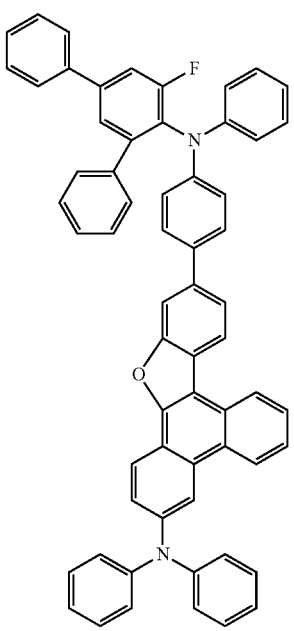
150A 585
-continued
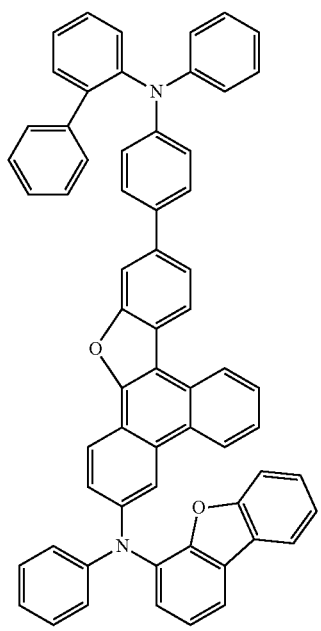
151A
586
-continued
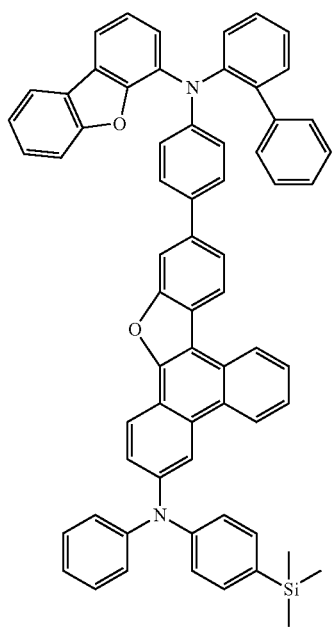
153A
152A
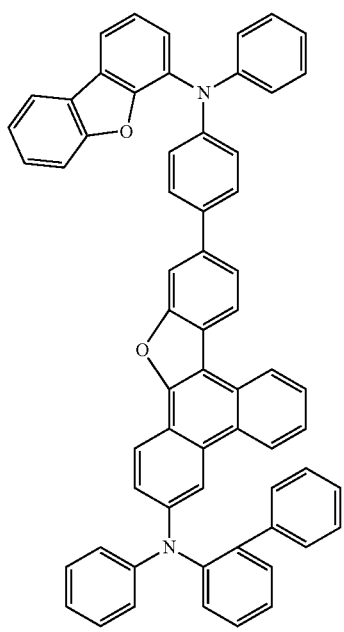
154A
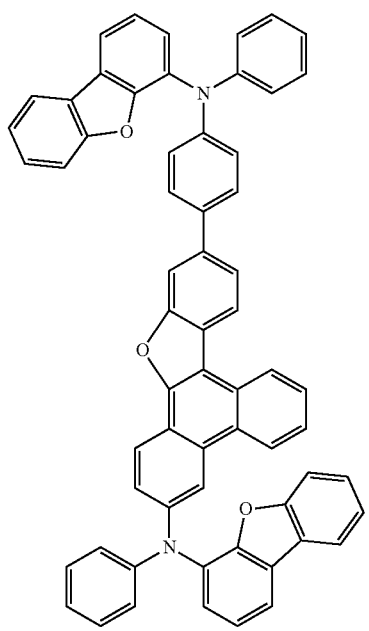

587
-continued
155A
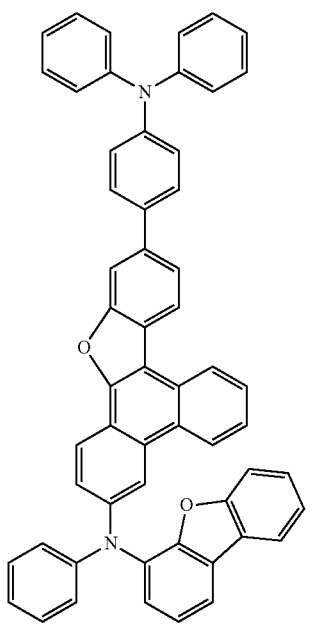
156A
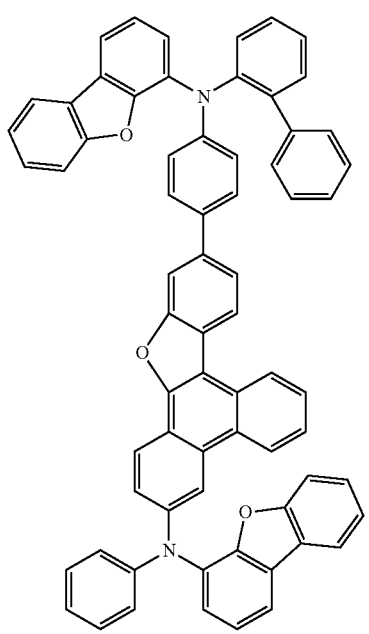
588
-continued
157A
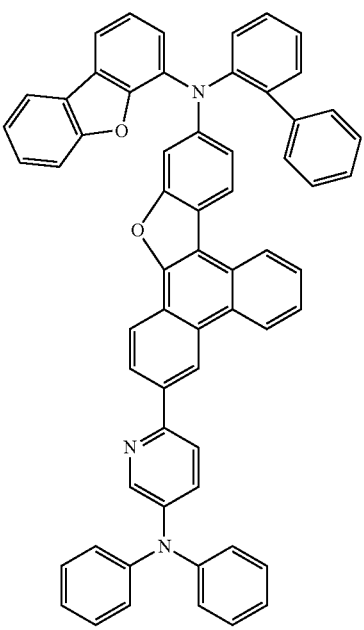
158A
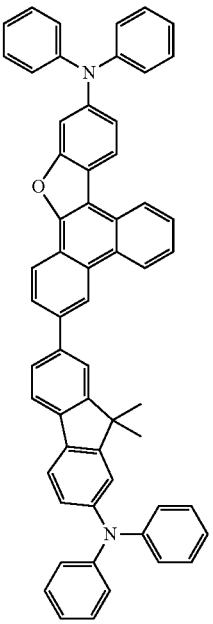

589
-continued
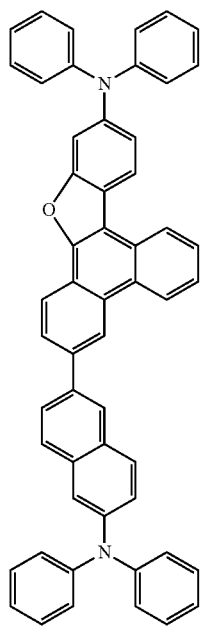
159A
590
-continued
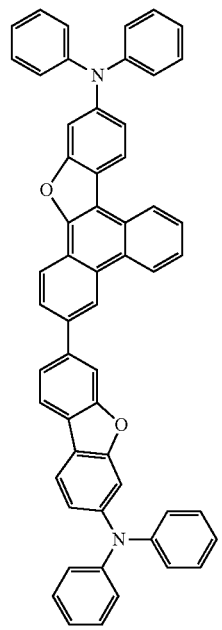
161A
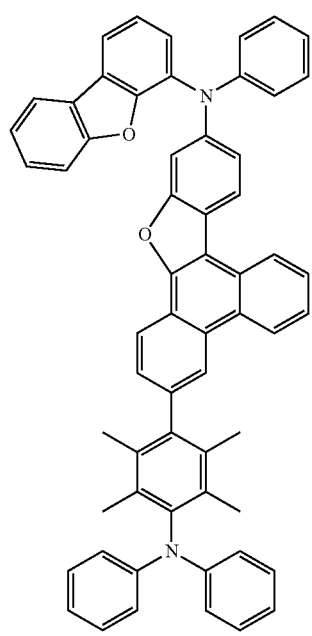
160A
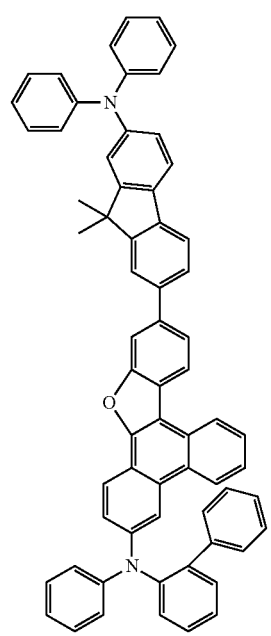
162A 591
-continued
163A
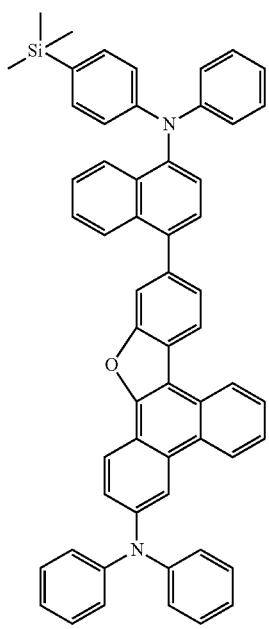
164A
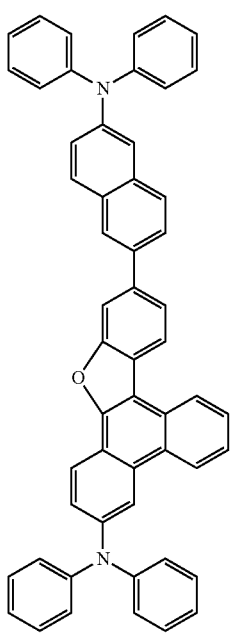
592
-continued
165A
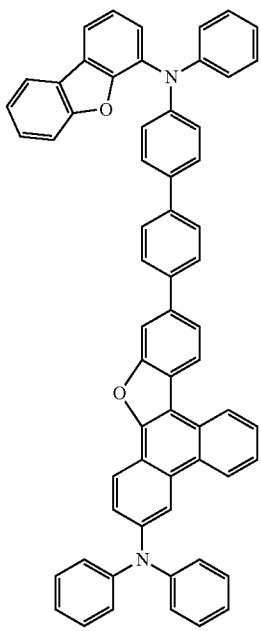
166A
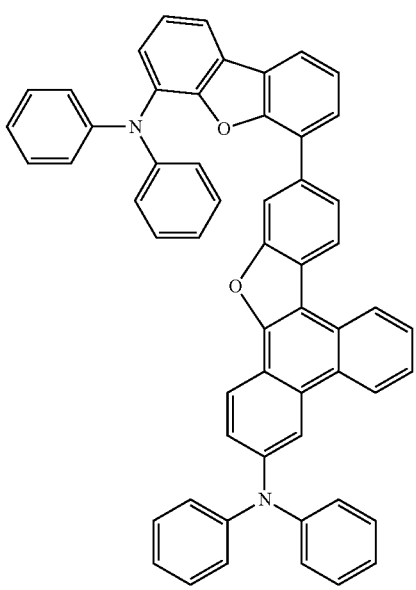

593
-continued
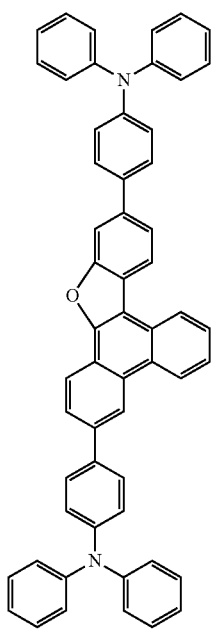
167A
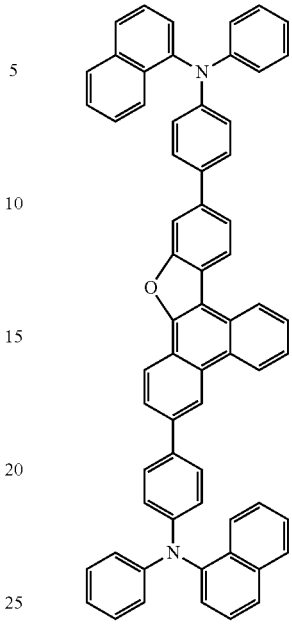
169A
594
-continued
168A
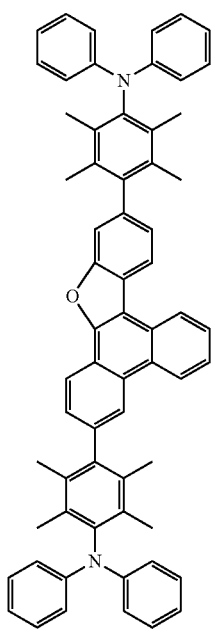
170A
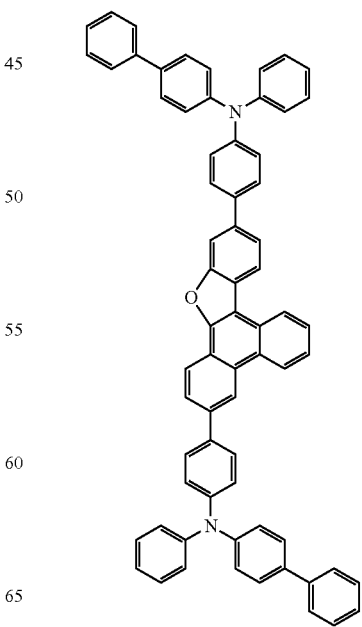

595
-continued
596
-continued
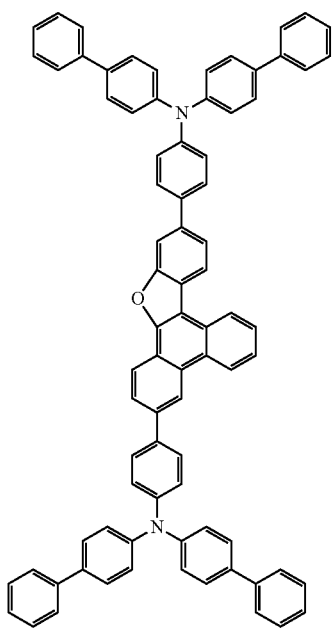
171A
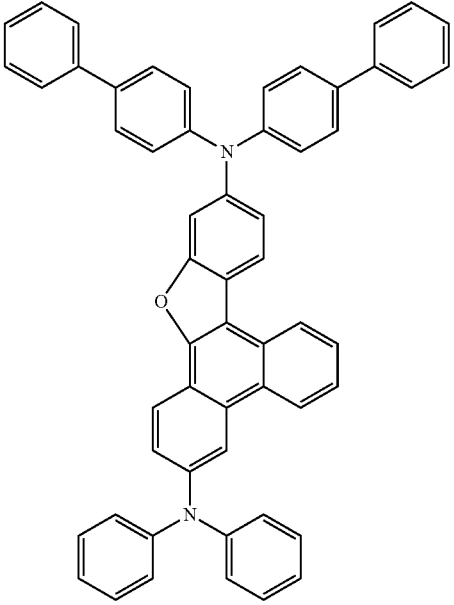
173A
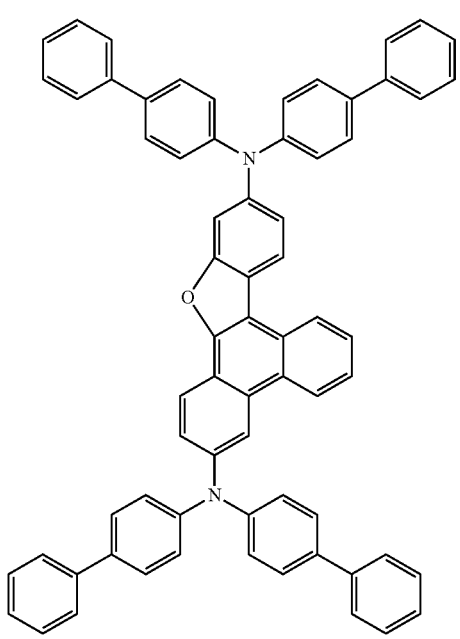
172A
174A 597
-continued
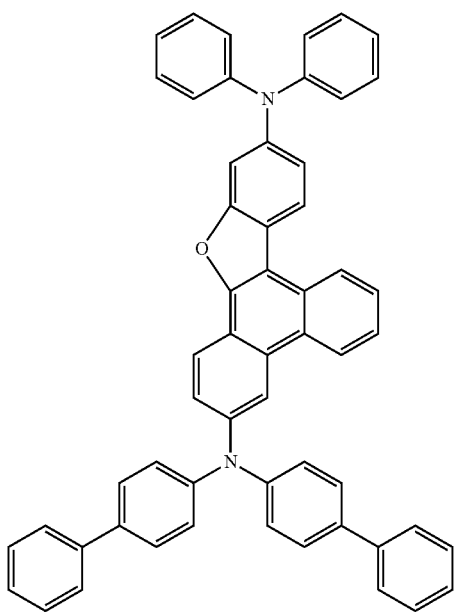
175A
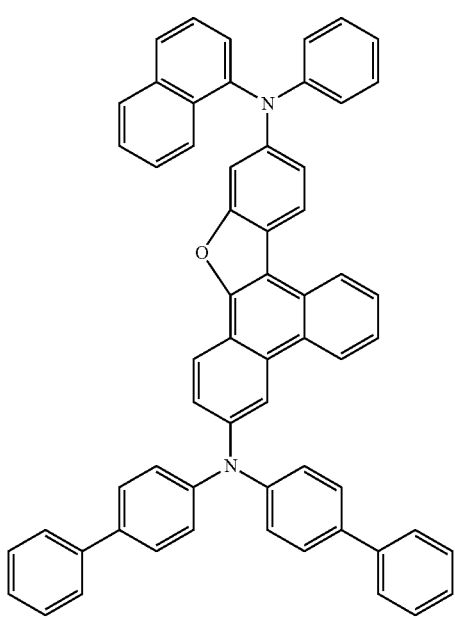
176A
598
-continued
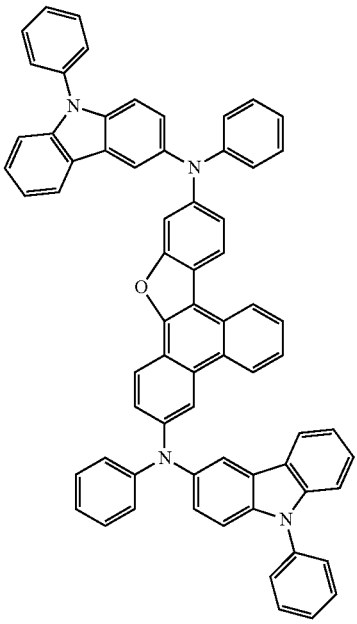
177A
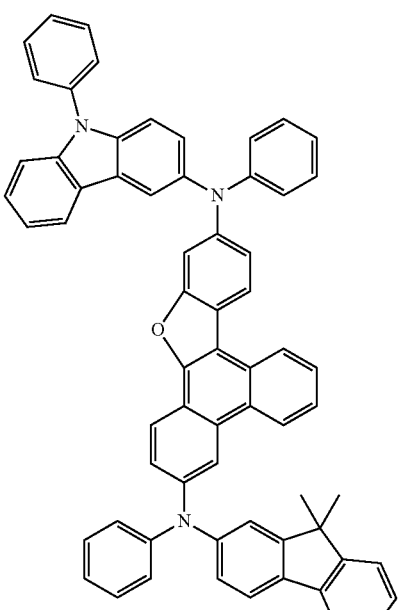
178A 599
-continued
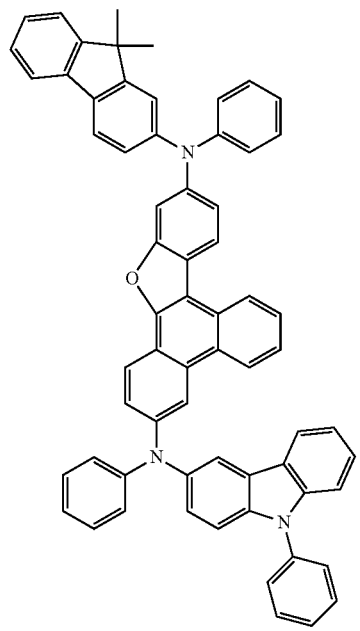
600
-continued
179A
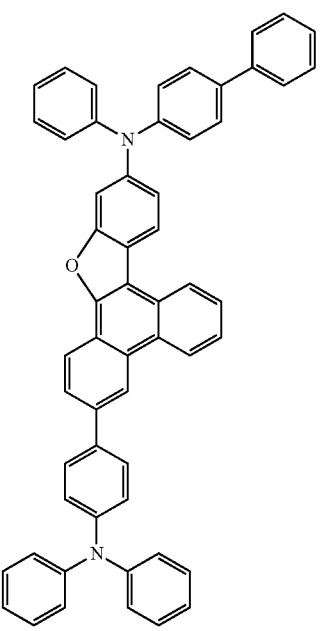
180A
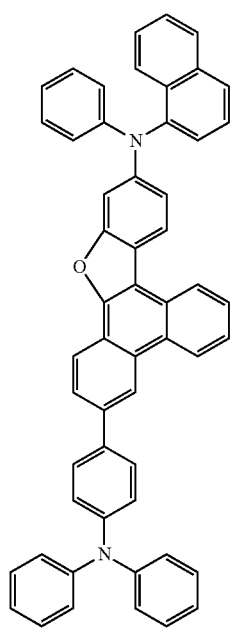
181A
182A
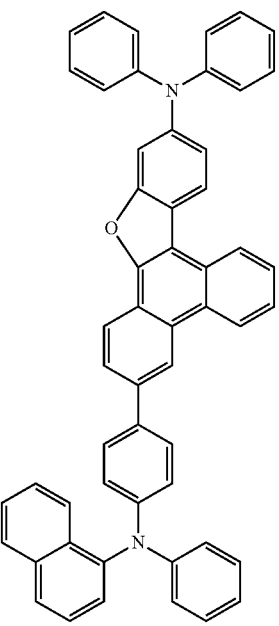

601
-continued
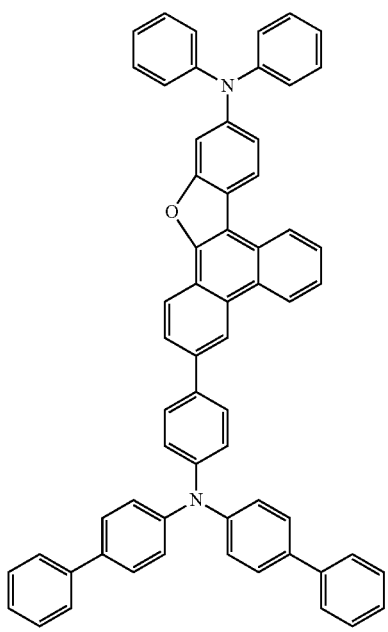
183A
602
-continued
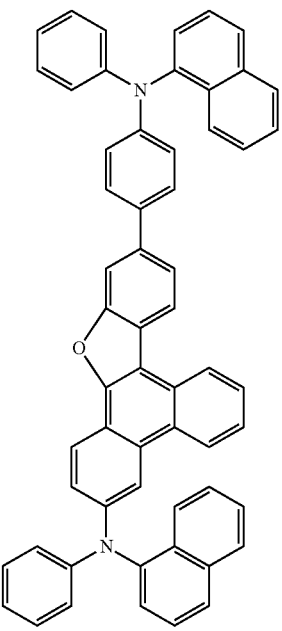
185A
184A
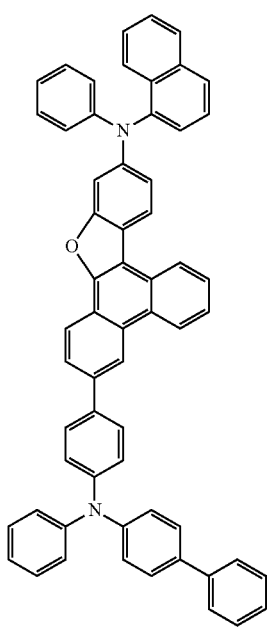
186A
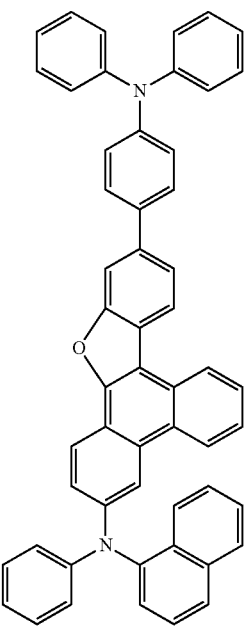

603
187A
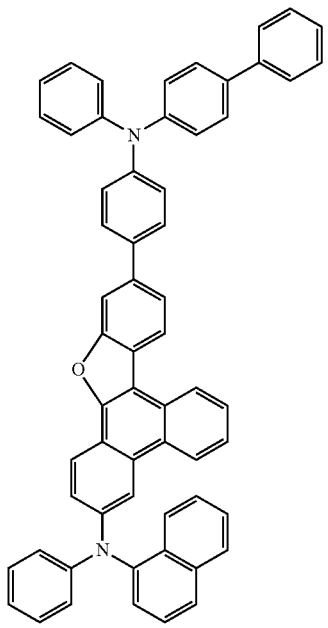
188A
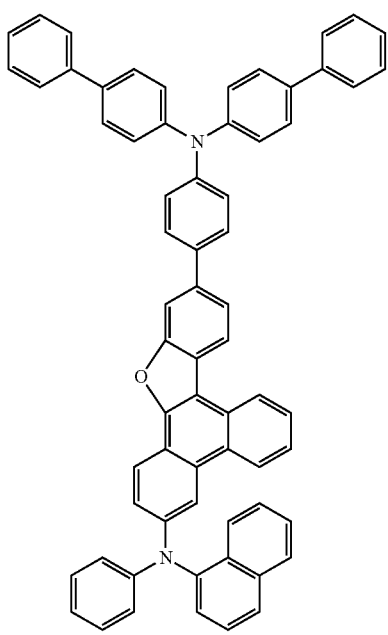
604
189A
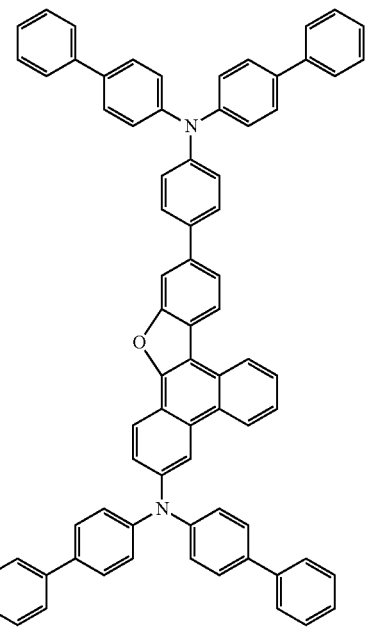
190A
191A
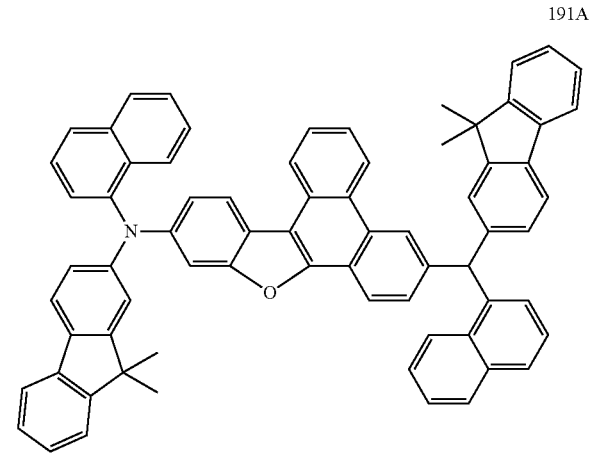

-continued
192A
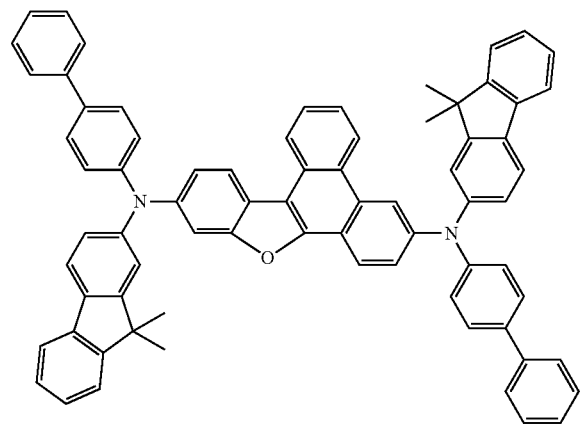
193A
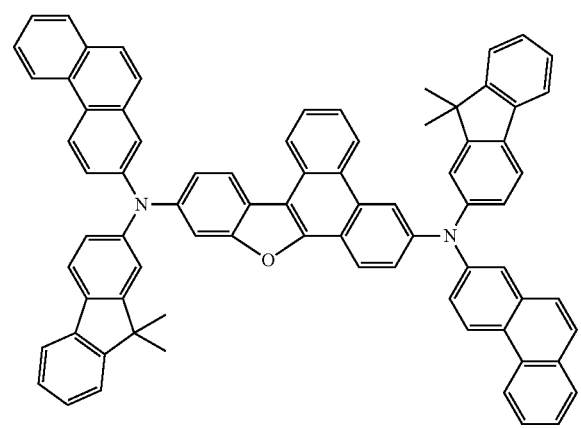
194A
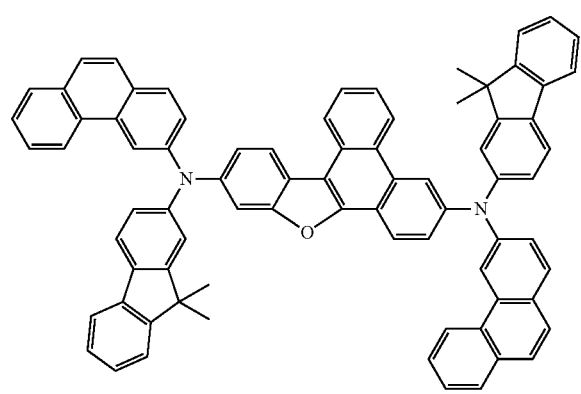
-continued
195A
196A
197A
198A
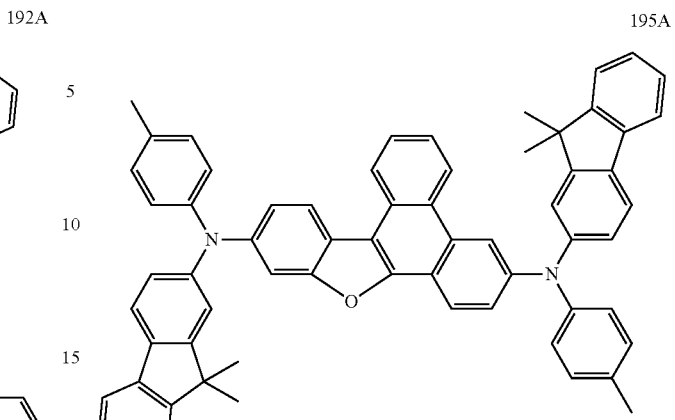

199A
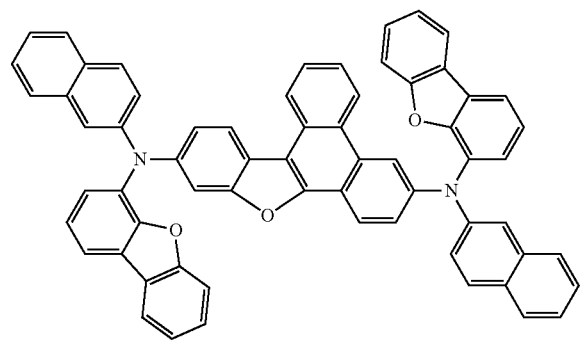
200A
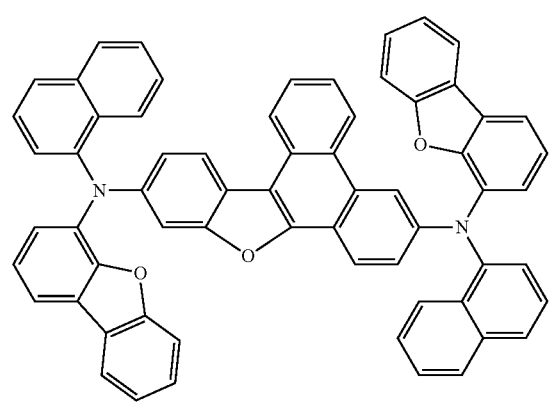
201A
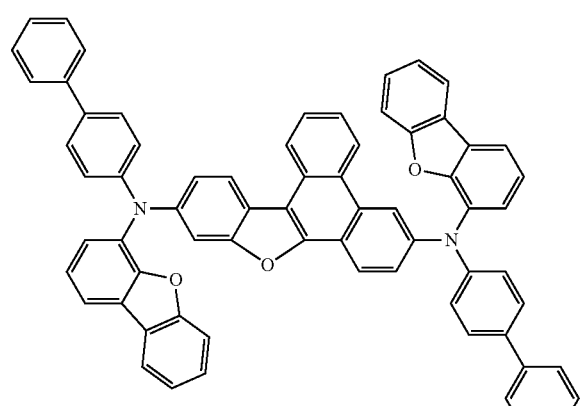
202A
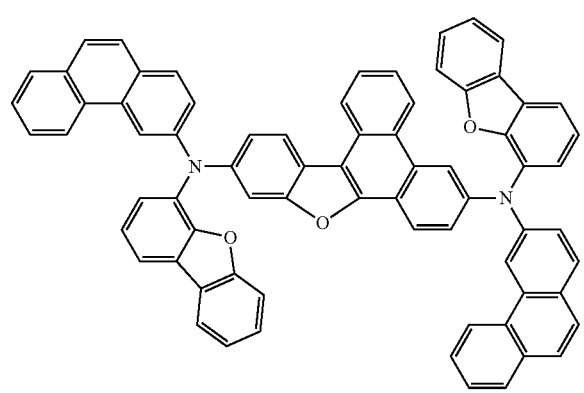
203A
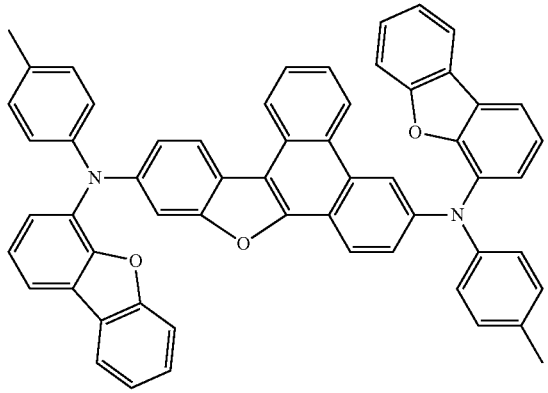
204A
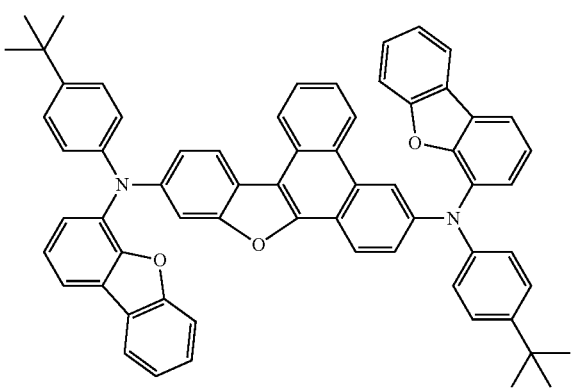
205A
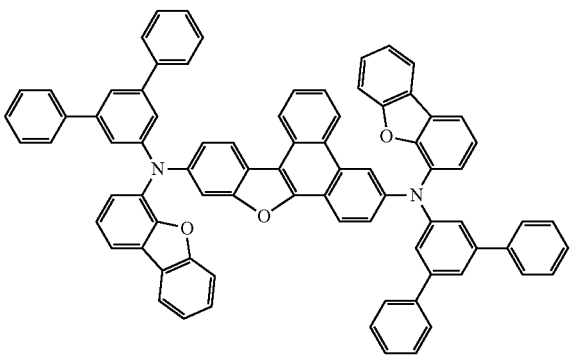
206A
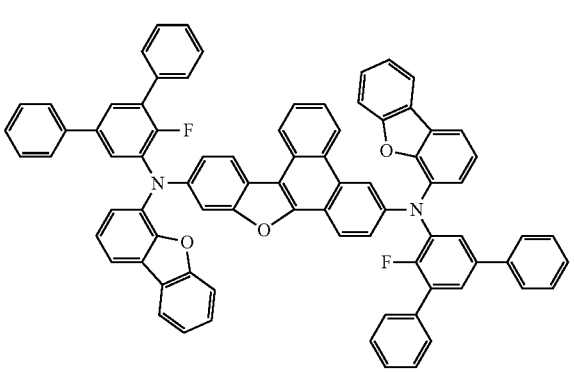

207A
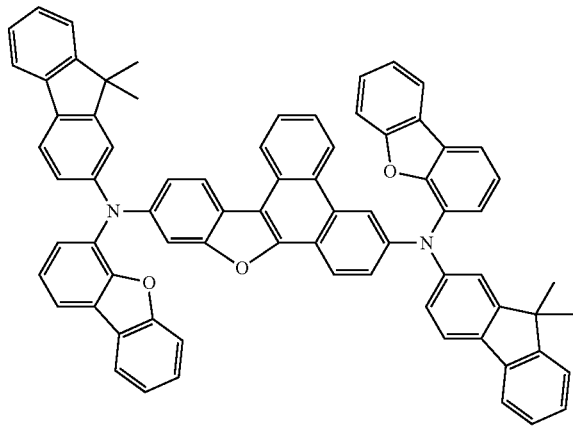
211A
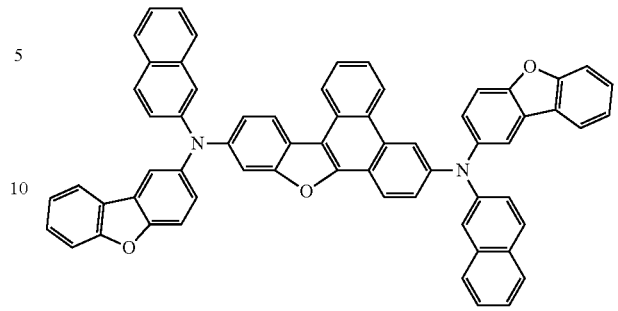
208A
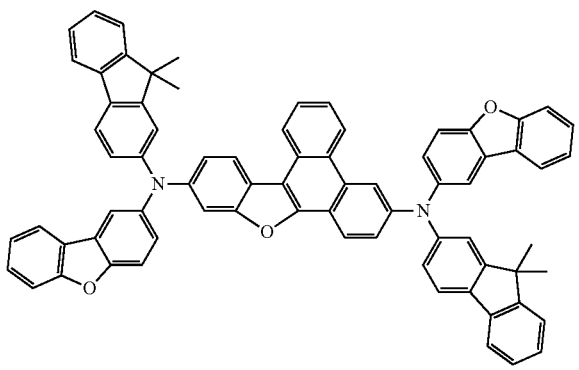
212A
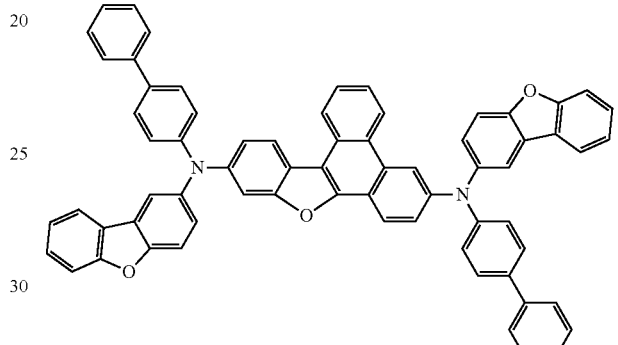
213A
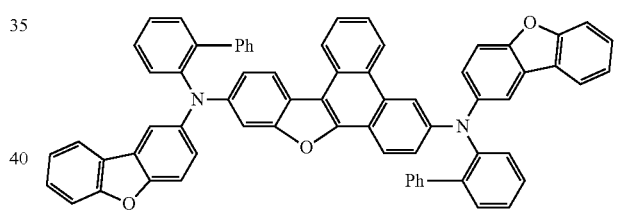
209A
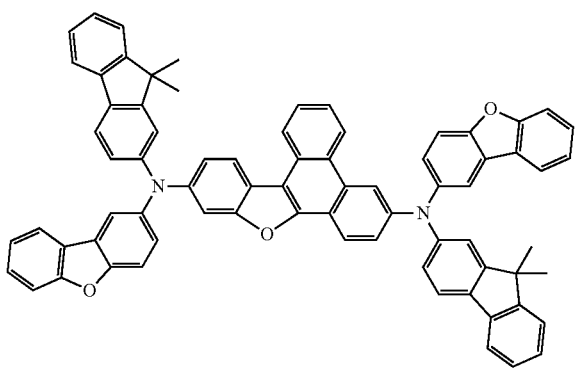
214A
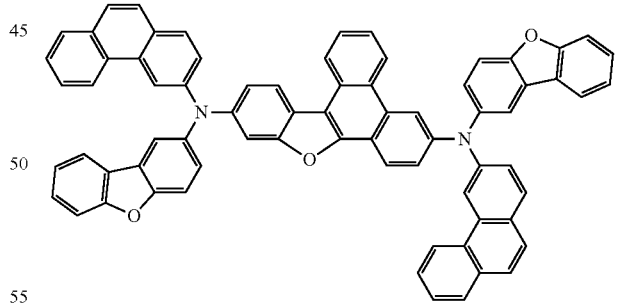
210A
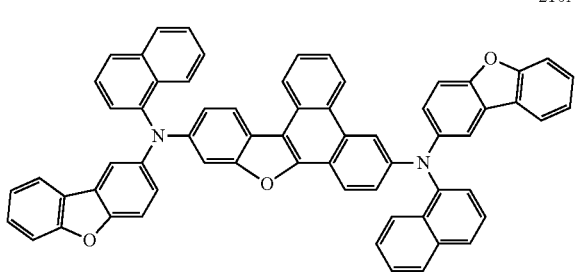
215A
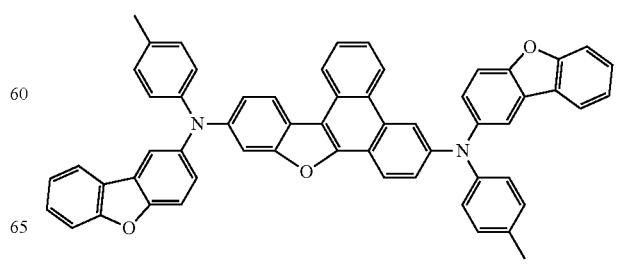

611
-continued
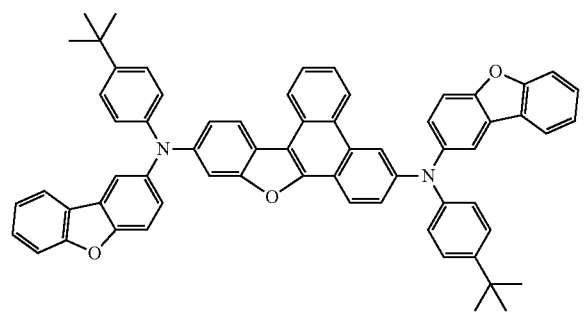
216A
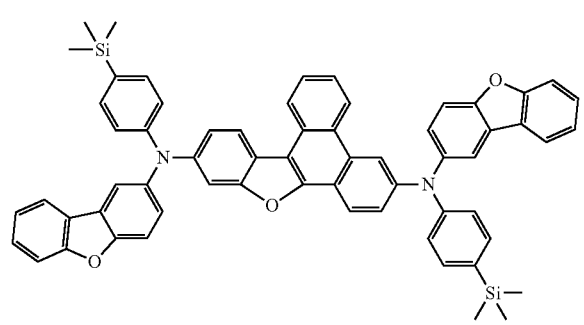
217A
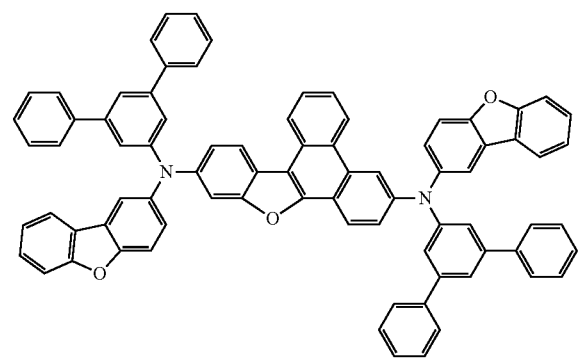
218A
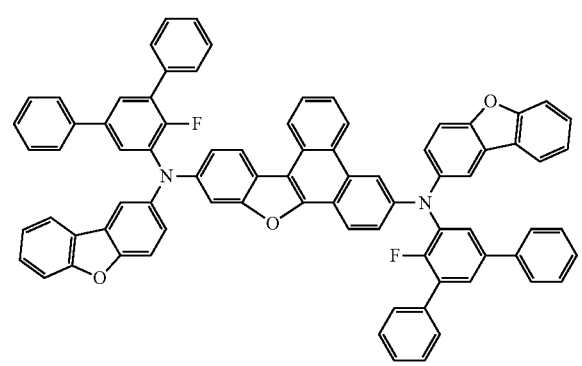
219A
612
-continued
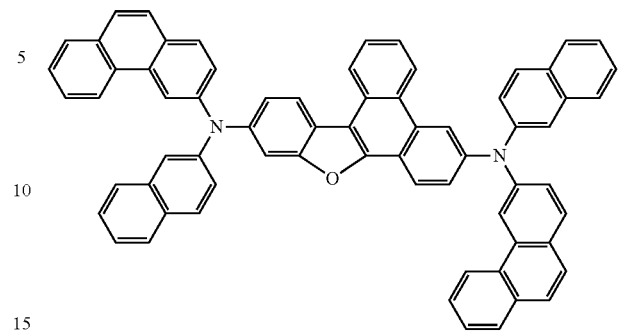
220A
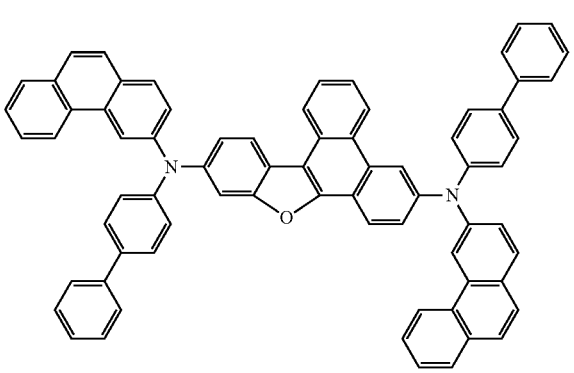
221A
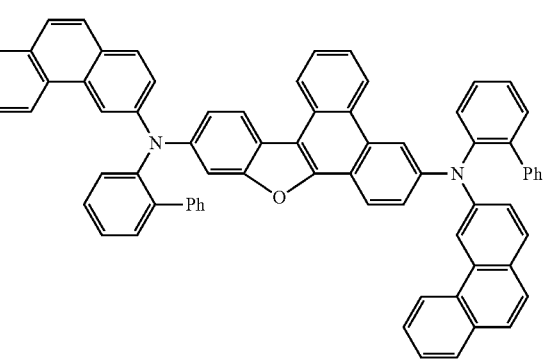
222A
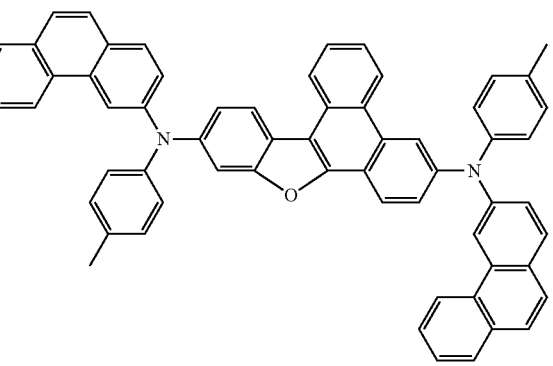
223A 224A
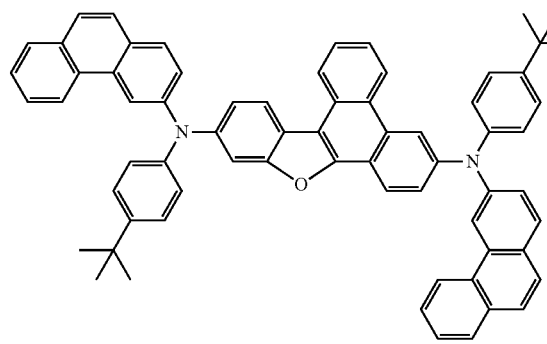
228A
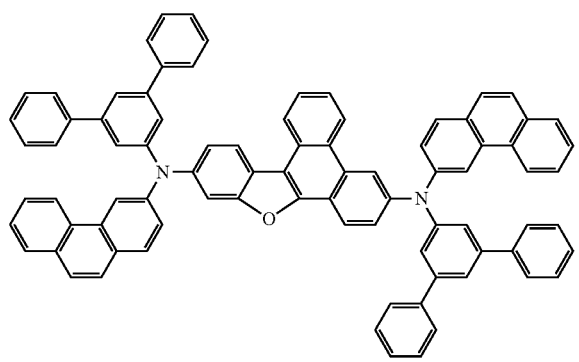
225A
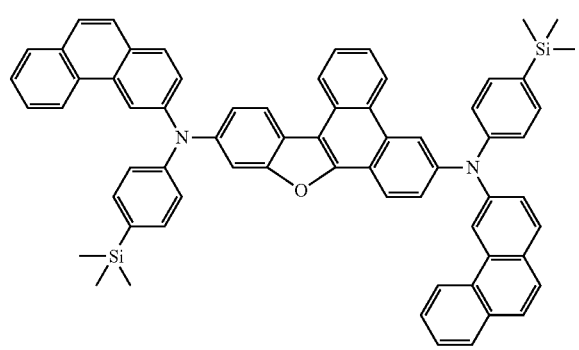
229A
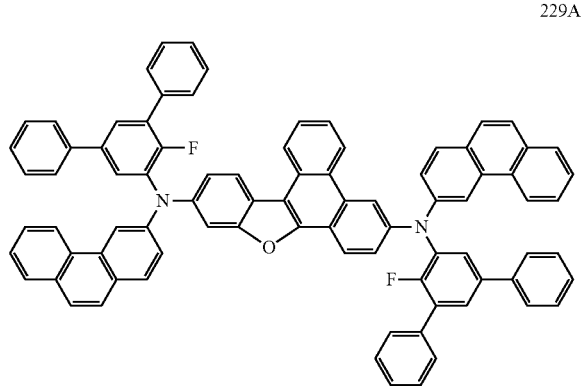
226A
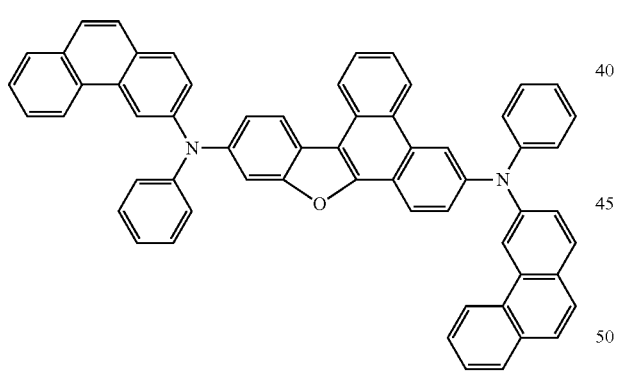
230A
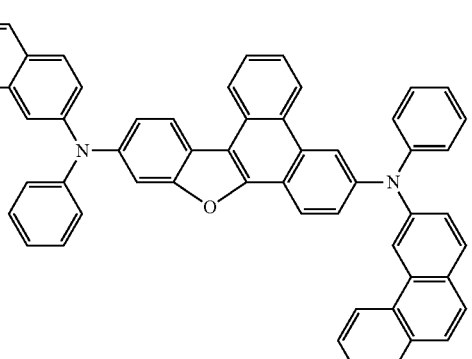
227A
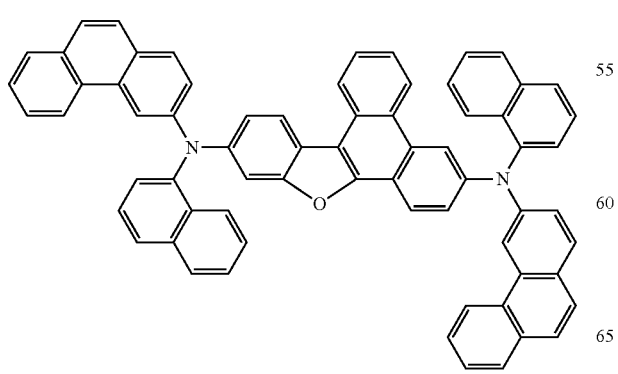
231A
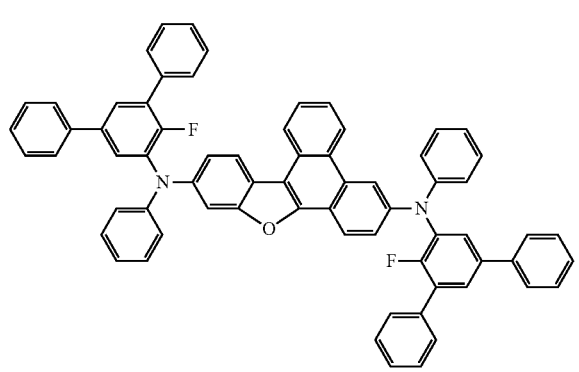

232A
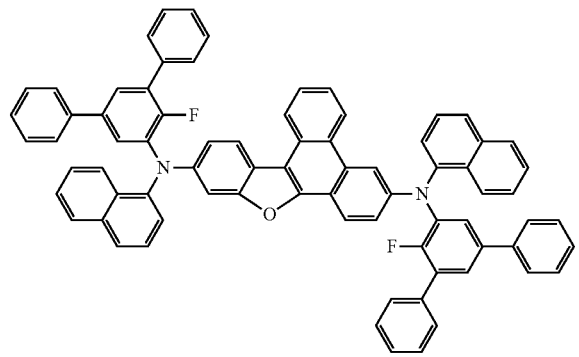
233A
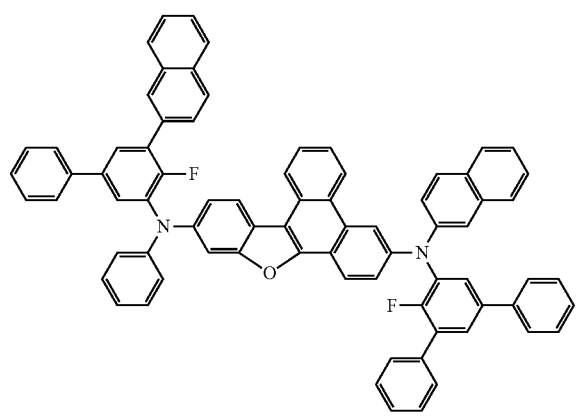
234A
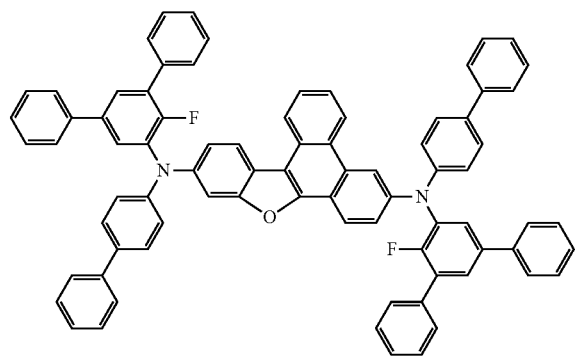
235A
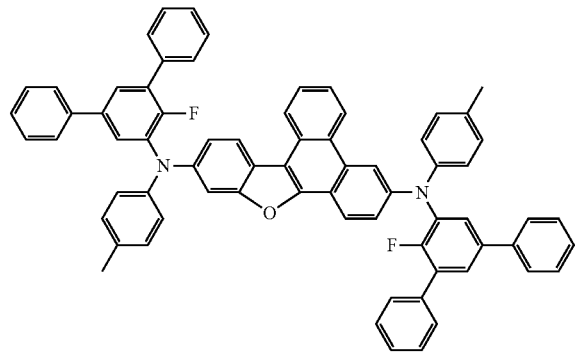
236A
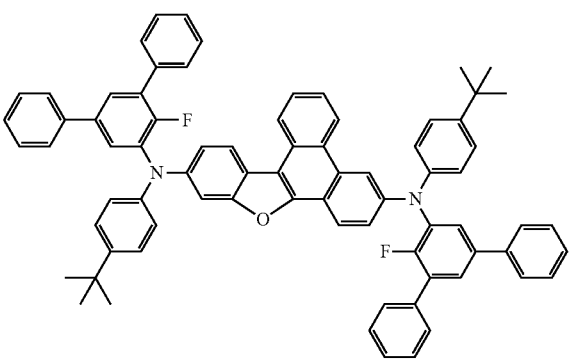
237A
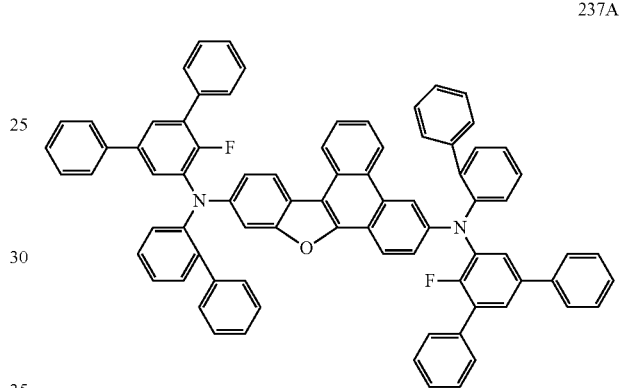
238A
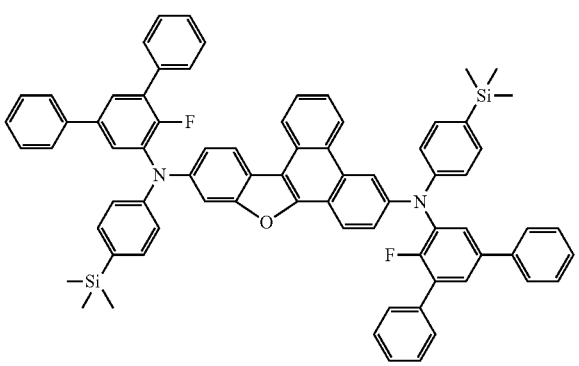
239A
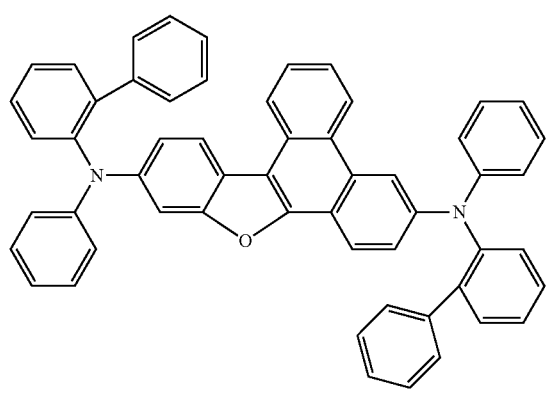

617
-continued
240A
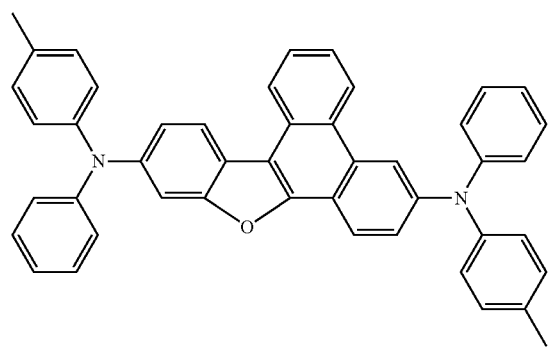
241A
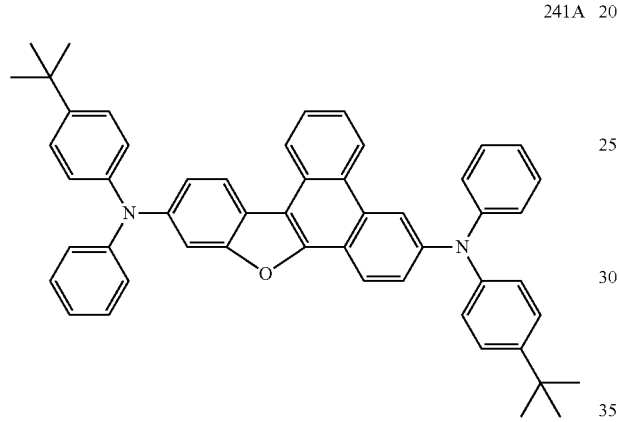
242A
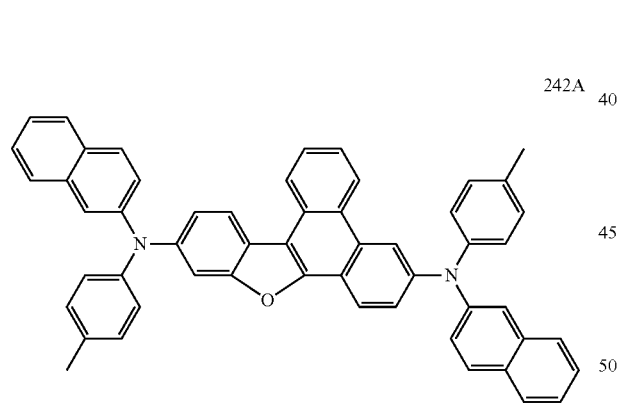
243A
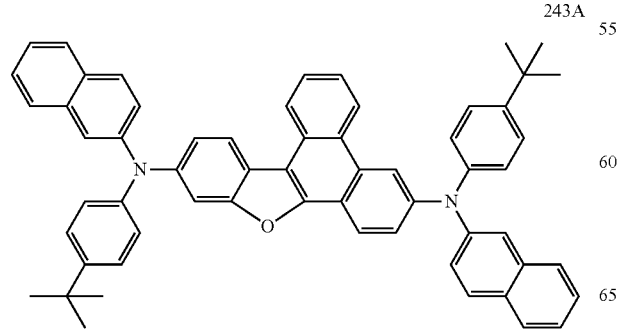
618
-continued
244A
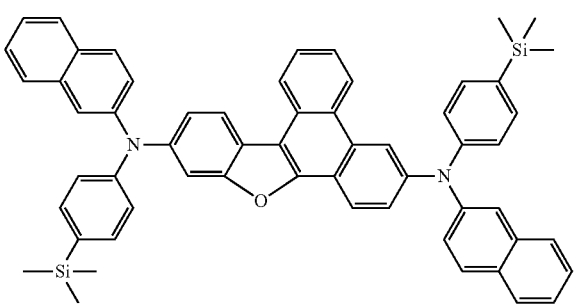
245A
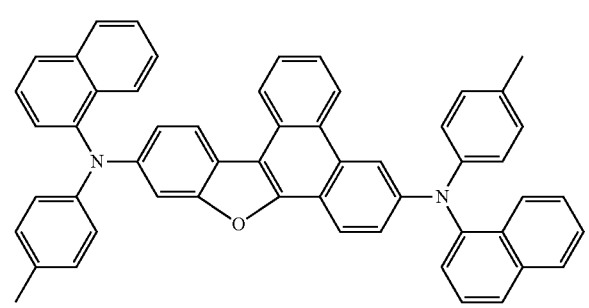
246A
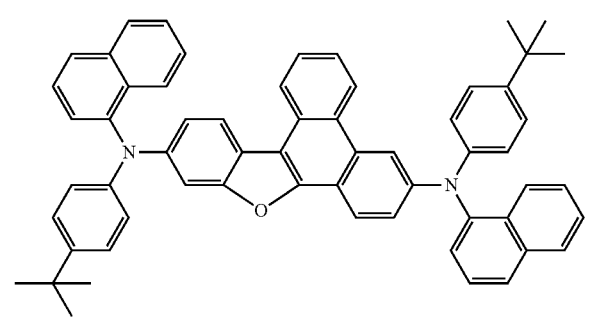
247A
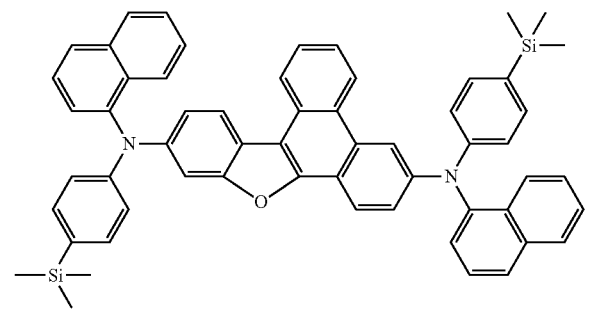

-continued

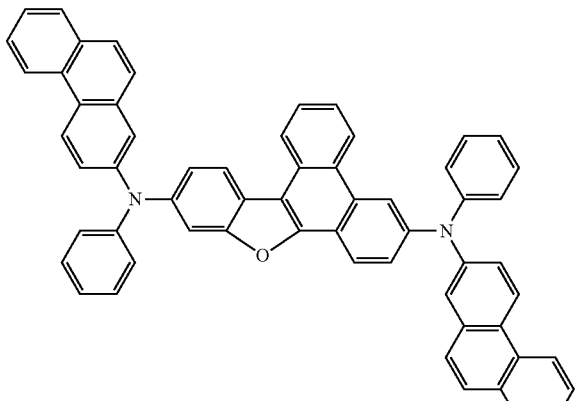
248A

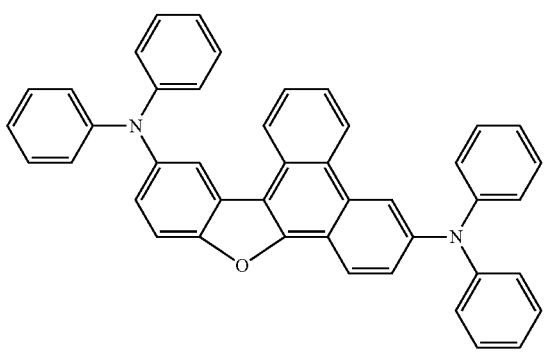
249A

16. An organic light-emitting device comprising:
   a first electrode;
   a second electrode facing the first electrode; and
   an organic layer disposed between the first electrode and the second electrode and comprising an emission layer, wherein the organic layer comprises at least one of the condensed cyclic compounds of claim 1.

17. The organic light-emitting device of claim 16, wherein
   the first electrode is an anode,
   the second electrode is a cathode,
   the organic layer comprises i) a hole transport region that is formed between the first electrode and the emission layer and that comprises at least one of a hole injection layer, a hole transport layer, a buffer layer, and an electron blocking layer, and ii) an electron transport region that is formed between the emission layer and the second electrode and comprises at least one of a hole blocking layer, an electron transport layer, and an electron injection layer, and
   the emission layer comprises the condensed cyclic compound.

18. The organic light-emitting device of claim 17, wherein the emission layer further comprises a host.

19. The organic light-emitting device of claim 17, wherein the hole transport region comprises a hole transport layer and the hole transport layer and the emission layer each comprises the condensed cyclic compound,
   wherein the condensed cyclic compound comprised in the hole transport layer is different from the condensed cyclic compound included in the emission layer.

* * * * *